US 7,858,642 B2

(12) United States Patent
John et al.

(10) Patent No.: US 7,858,642 B2
(45) Date of Patent: *Dec. 28, 2010

(54) SUBSTITUTED HYDROXYETHYLAMINE ASPARTYL PROTEASE INHIBITORS

(75) Inventors: Varghese John, San Francisco, CA (US); Michel Maillard, Redwood City, CA (US); John Tucker, San Diego, CA (US); Jose Aquino, Daly City, CA (US); Barbara Jagodzinska, Redwood City, CA (US); Louis Brogley, Santa Cruz, CA (US); Jay S. Tung, Belmont, CA (US); Simeon Bowers, Oakland, CA (US); Darren Dressen, Fremont, CA (US); Gary Probst, San Francisco, CA (US); Neerav Shah, San Mateo, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/396,989

(22) Filed: Mar. 3, 2009

(65) Prior Publication Data
US 2009/0270367 A1 Oct. 29, 2009

Related U.S. Application Data

(63) Continuation of application No. 11/075,312, filed on Mar. 9, 2005, now abandoned.

(60) Provisional application No. 60/619,918, filed on Oct. 20, 2004, provisional application No. 60/591,918, filed on Jul. 29, 2004, provisional application No. 60/575,977, filed on Jun. 2, 2004, provisional application No. 60/551,052, filed on Mar. 9, 2004.

(51) Int. Cl.
*A61K 31/427* (2006.01)
*A61K 31/4709* (2006.01)
*C07D 215/58* (2006.01)
*C07D 285/04* (2006.01)

(52) U.S. Cl. .................. 514/314; 514/362; 546/159; 548/128

(58) Field of Classification Search ............. 514/362, 514/314; 548/128; 546/159
See application file for complete search history.

(56) References Cited

U.S. PATENT DOCUMENTS

| 4,522,811 | A | 6/1985 | Eppstein et al. |
|---|---|---|---|
| 5,095,006 | A | 3/1992 | Bender et al. |
| 5,132,400 | A | 7/1992 | Gammill et al. |
| 5,145,684 | A | 9/1992 | Liversidge et al. |
| 5,254,595 | A | 10/1993 | Guzzi et al. |
| 5,362,912 | A | 11/1994 | Sowin et al. |
| 5,387,742 | A | 2/1995 | Cordell |
| 5,441,870 | A | 8/1995 | Seubert et al. |
| 5,593,846 | A | 1/1997 | Schenk et al. |
| 5,604,102 | A | 2/1997 | McConlogue et al. |
| 5,612,486 | A | 3/1997 | McConlogue et al. |
| 5,696,270 | A | 12/1997 | Kempf et al. |
| 5,720,936 | A | 2/1998 | Wadsworth et al. |
| 5,721,130 | A | 2/1998 | Seubert et al. |
| 5,744,346 | A | 4/1998 | Chrysler et al. |
| 5,766,846 | A | 6/1998 | Schlossmacher et al. |
| 5,811,633 | A | 9/1998 | Wadsworth et al. |
| 5,850,003 | A | 12/1998 | McLonlogue et al. |
| 5,877,015 | A | 3/1999 | Hardy et al. |
| 5,877,399 | A | 3/1999 | Hsiao et al. |
| 5,892,052 | A | 4/1999 | Kempf et al. |
| 5,912,410 | A | 6/1999 | Cordell |
| 5,942,400 | A | 8/1999 | Anderson et al. |
| 6,045,829 | A | 4/2000 | Liversidge et al. |
| 6,150,530 | A | 11/2000 | Kempf et al. |
| 6,191,166 | B1 | 2/2001 | Audia et al. |
| 6,379,666 | B1 | 4/2002 | Tobinick |
| 7,109,217 | B2 | 9/2006 | Coburn et al. |
| 2002/0019403 | A1 | 2/2002 | Hom et al. |
| 2003/0096864 | A1 | 5/2003 | Fang et al. |
| 2004/0044072 | A1 | 3/2004 | Tenbrink et al. |
| 2005/0043290 | A1 | 2/2005 | Cumming et al. |
| 2005/0119227 | A1 | 6/2005 | Cumming et al. |
| 2006/0014737 | A1 | 1/2006 | John et al. |
| 2007/0225372 | A1 | 9/2007 | Bueno Melendo et al. |

FOREIGN PATENT DOCUMENTS

| EP | 0 279 707 A2 | 8/1988 |
|---|---|---|
| EP | 0 375 560 B1 | 6/1990 |
| WO | WO 98/22597 A2 | 5/1998 |
| WO | WO 99/64001 A2 | 12/1999 |

(Continued)

OTHER PUBLICATIONS

Ajay, et al., "Designing libraries with CNS activity," J. Med. Chem., (1999) 42, 4942-4951.
Albright, J.D., "Synthesis of 1,4,5,6,-Tetrahydropyrazolo[3,4-d]pyrido[3,2-b]azepine," J. Heterocycl. Chem., (2000), 37, 41-46.
Alexakis et al., "A practical, solvent free, one-pot synthesis of C2-symmetrical secondary amines," Tet. Lett. 2004, 45: 1449-1451.
Alvarez, A., et al., "Synthesis of 3-Arylpyrroles and 3-Pyrrolylacetylenes by Palladium-Catalyzed Coupling Reactions", J. Org. Chem., (1992), 57, 1653-1656.
Anderson, G.W., et al., "Studies in Chemotherapy. X. Antithyroid Compounds. Synthesis of 5- and 6- Substituted 2-Thiouracils from b-Oxoesters and Thiourea," J. Am. Chem. Soc., (1945), 67, 2197-2200.

(Continued)

*Primary Examiner*—Taofiq A Solola
(74) *Attorney, Agent, or Firm*—Finnegan, Henderson, Farabow, Garrett & Dunner, L.L.P.

(57) ABSTRACT

The invention relates to novel compounds and also to methods of treating at least one disease, disorder, or condition associated with amyloidosis using such compounds. Amyloidosis refers to a collection of diseases, disorders, and conditions associated with abnormal deposition of A-beta protein.

24 Claims, No Drawings

FOREIGN PATENT DOCUMENTS

| WO | WO 00/17369 A2 | 3/2000 |
|---|---|---|
| WO | WO 00/47618 A2 | 8/2000 |
| WO | WO 01/10387 A2 | 2/2001 |
| WO | WO 01/23533 A2 | 4/2001 |
| WO | WO 02/02512 A2 | 1/2002 |
| WO | WO 02/05804 A1 | 1/2002 |
| WO | WO 02/09760 A2 | 2/2002 |
| WO | WO 02/085877 A2 | 10/2002 |
| WO | WO 02/098849 A2 | 12/2002 |
| WO | WO 02/100399 A1 | 12/2002 |
| WO | WO 02/100820 A1 | 12/2002 |
| WO | WO 03/002122 A1 | 1/2003 |
| WO | WO 03/006021 A1 | 1/2003 |
| WO | WO 03/006423 A1 | 1/2003 |
| WO | WO 03/029169 A2 | 4/2003 |
| WO | WO 03/040096 A2 | 5/2003 |
| WO | WO 03/050073 A1 | 6/2003 |
| WO | WO 03/072535 A2 | 9/2003 |
| WO | WO 2004/024081 A2 | 3/2004 |
| WO | WO 2004/029019 A2 | 4/2004 |
| WO | WO 2004/043916 A1 | 5/2004 |
| WO | WO 2004/050609 A1 | 6/2004 |
| WO | WO 2004/050619 A1 | 6/2004 |
| WO | WO 2004/069793 A2 | 8/2004 |
| WO | WO 2004/094384 A2 | 11/2004 |
| WO | WO 2004/094413 A1 | 11/2004 |
| WO | WO 2005/014517 A2 | 2/2005 |
| WO | WO 2005/014540 A1 | 2/2005 |
| WO | WO 2005/016876 A2 | 2/2005 |
| WO | WO 2005/058915 A1 | 6/2005 |
| WO | WO 2005/087714 A2 | 9/2005 |
| WO | WO 2005/108358 A2 | 11/2005 |
| WO | WO 2005/108391 A1 | 11/2005 |

OTHER PUBLICATIONS

Anzalone, L. and Hirsch, J.A., "Substituent Effects on Hydrogenation of Aromatic Rings: Hydrogenation vs. Hydrogenolysis in Cyclic Analogues of Benzyl Ethers," J. Org. Chem., (1985), 50, 2128-2133.

Beam, C.F., et al., "Preparation of Pyrazoles from the C($\alpha$)NN-Trianion of Hyrdrazones having an $\alpha$-Hydrogen Atom," J. Chem. Soc., Section C: Organic (1971), 9, 1658-1660.

Becker, D.P. & Flynn, D.L., "A Short Synthesis of 1-Azaadamantan-4-one and the 4r and 4s Isomers of 4-Amino-l-azaadamantane," Synthesis, (1992), 1080-1082.

Benedetti, et al., "Versatile and Stereoselective Synthesis of Diamino Diol Dipeptide Isosteres, Core Units of Psuedopeptide HIV Protease Inhibitors," J. Org. Chem., (1997), 62, 9348-9353.

Boeckman, R. K., Jr.; Liu, X., "Controllable Monoaddition of Carbon Nucleophiles to 1,2,3,4-Diepoxybutane: Two-directional Chain Extension of a C2 Symmetric Four Carbon Diepoxide as a Route to Differentiated Syn 1,2-Diols," Synthesis, (2002), 14, 2138-2142.

Castro, B., et al., "Reactifs de Couplage Peptidique IV (1)—L'Hexaflourophosphate De Benzotriazolyl N-Oxytrisdimethylamino Phosphonium (B.O.P.)," Tet. Letters, (1975), 14, 1219-1222.

Cerri, A., et al., "17beta-O-Aminoalkyloximes of 5beta-androstane-3beta,14beta-diol with digitalis-like activity: synthesis, cardiotonic activity, structure-activity relationships, and molecular modeling of the Na(+),K(+)-ATPase receptor.," J. Med. Chem.; 2000, 43, 2332-2349.

Citron, et al., "Mutation of the B-amyloid precursor protein in familial Alzheimer's disease increases B-protein production," Nature, (1992), 360:672-674.

Copending U.S. Appl. No. 11/038,790, filed Jan. 21, 2005, published Jan. 19, 2006.

U.S. Appl. No. 11/074,828, filed Mar. 9, 2005, published Oct. 27, 2005.

U.S. Appl. No. 11/075,292, filed Mar. 9, 2005, published Nov. 24, 2005.

Copending U.S. Appl. No. 11/075,294, filed Mar. 9, 2005, published Oct. 27, 2005.

Copending U.S. Appl. No. 11/075,445, filed Mar. 9, 2005, published Jan. 19, 2006.

U.S. Appl. No. 11/177,324, filed Jul. 11, 2005, published Jun. 22, 2006, issued as U.S. Patent No. 7,385,085.

Copending U.S. Appl. No. 11/177,348, filed Jul. 11, 2005, published Jun. 15, 2006.

Copending U.S. Appl. No. 11/211,484, filed Aug. 26, 2005, published Apr. 6, 2006.

Copending U.S. Appl. No. 11/546,347, filed Oct. 12, 2006, published Jun. 28, 2007.

Copending U.S. Appl. No. 11/659,788, filed Aug. 21, 2007, published Jul. 10, 2008.

Copending U.S. Appl. No. 12/117,094, filed May 8, 2008, published Feb. 12, 2009.

Coria F. and Rubio, I., "Cerebral amyloid angiopathies," Neuropath Appl. Neurobiol., (1996) 22, 216-227.

Cornelius, L.A.M.; Combs, D.W., "A Convenient Synthesis of Mono- and Polyhalogenated Benzocyclanones," Synthetic Communications, (1994), 24, 2777-2788.

Dai, C. and Fu, G.J., "The first general method for palladium-catalyzed Negishi cross-coupling of aryl and vinyl chlorides: use of commercially available Pd(P(t-Bu)(3))(2) as a catalyst," J. Am. Chem. Soc., (2001), 123, 2719-2724.

Dantzig, A.H., et al., "Reversal of P-glycoprotein-mediated multidrug resistance by a potent cyclopropyldibenzosuberane modulator, LY335979," Cancer Research, (1996), 56, 4171-4179.

Dovey, et al., "Functional gamma-secretase inhibitors reduce beta-amyloid peptide levels in brain," J. Neurochemistry, (2001), 76:173-181.

Emilien, G., et al., "Prospects for Pharmacological Intervention in Alzheimer Disease," Arch. Neurol. (2000), 57:454-459.

Ertl, P., et al., "Fast calculation of molecular polar surface area as a sum of fragment-based contributions and its application to the prediction of drug transport properties," J. Med. Chem., (2000), 43:3714-3717.

Fujita, T., et al., "A new substituent constant, pie-derived from partition coefficient" J. Am. Chem. Soc., (1964), 86, 5175-5183.

Games, et al., "Alzheimer-type neuropathology in transgenic mice overexpressing V717F beta-amyloid precursor protein," Nature, (1995), 373:523-527.

Gibaldi, M. and Perrier, D., "Noncompartmental Analysis Based on Statistical Moment Theory," Pharmacokinetics, 2nd Ed., 1982, Marcel Dekker Inc., New York, NY, pp. 409-418.

Gilzinsky, A.G., et al., "On the relative power of electophilic fluorinating reagents of the N-F class," J. Fluorine Chemistry, 59, (1992), 157-162.

Greene, T.W., and Wuts, D.G.H., Protecting Groups in Organic Chemistry, 3d Ed., John, Wiley and Sons, 1999.

Hall, J.H., Gisler, M., "A simple method for converting nitriles to amides. Hydrolysis with potassium hydroxide in tert-butyl alcohol," J. Org Chem. (1976), 41, 3769-3770.

Hansch, C., "Substitutent Constants for Correlation Analysis in Chemistry and Biology," Wiley, New York (1979).

Hardy, J., "Framing beta-amyloid," Nature Genetics, (1992) 1:233-234.

Harnden, M.R., et al., "Synthesis and antiviral activity of 9-alkoxypurines. 1. 9-(3-Hydroxypropoxy)- and 9-[3-hydroxymethyl)propoxy]purines," J. Med. Chem., (1990), 33, 187-196.

Hegedus, L.S., "Transition Metals in the Synthesis of Complex Organic Molecules," Second Edition, University Science Books, 1999.

Holy, A., et al., "6-[2-Phosphonomethoxy) alkoxy]pyrimidines with antiviral activity," J. Med. Chem., (2002), 45, 1918-1929.

Huo, S., "Highly efficient, general procedure for the preparation of alkylzinc reagents from unactivated alkyl bromides and chlorides," Org. Lett., (2003), 5, 423-425.

Hussain, et al., "Identification of a novel aspartic protease (Asp 2) as beta-secretase," Mol. Cell. Neurosci. (1999), 14:419-427.

Hyafil, F., et al., "In vitro and in vivo reversal of multidrug resistance by GF120918, an acridonecarboxamide derivative," Cancer Research, (1993), 53, 4595-4602.

Jones, T.K., et al., "An asymmetric synthesis of MK-0417. Observations on Oxazaborolidine-catalyzed reductions," J. Org. Chem. (1991), 56, 763-769.

Kabalka, G.W., et al., "Tosylation of alcohols," J. Org. Chem., (1986), 51, 2386-2388.

Kaiho, T., et al., "Cardiotonic agents. 1-Methyl-7-(4-pyridyl)-5,6,7,8-tetrahydro-3 (2H)-isoquinolinones and related compounds. Synthesis and activity," J. Med. Chem., (1989), 32(2), 351-357.

Kang, et al., "Synthesis of 1,4-Diaminocyclitols from L-serine Methyl Ester," J. Org. Chem., (1996), 61, 5528-5531.

Kang, et al., "The precursor of Alzheimer's disease amyloid A4 protein resembles a cell-surface receptor," Nature (1987), 325:733-736.

Katritzky, A.R. et al., "Comprehensible Heterocyclic Chemistry: The Structure, Reactions and Synthesis and Use of Heterocyclic Compounds," vol. 1-8, New York: Pergamon Press, 1984.

Kempf, et al., "Symmetry-based inhibitors of HIV protease. Structure-activity studies of acylated 2,4-diamino-1,5-diphenyl-3-hydroxypentane and 2,5-diamino-1,6-diphenylhexane-3,4-diol," J. Med. Chem., (1993), 36, 320-330.

Kikugawa, Y., et al., "N-Methoxydiacetamide: A New Selective Acetylating Agent," Tet. Letters, (1990), 31, 243-246.

Kim, J.T. and Gevorgyan, V., "Double cycloisomerization as a novel and expeditious route to tricyclic heteroaromatic compounds: short and highly diastereoselective synthesis of (+/−)-tetraponerine T6," Org. Lett., (2002), 4, 4697-4669.

Kimura, T., et al., "Strategy for the synthesis of large peptides: an application to the total synthesis of human parathyroid hormone [hPTH (1-84)]," Biopolymers, (1981), 20, 1823-1832.

King, "Bioisosteres, Conformational Restriction, and Prodrugs—Case History: An Example of a Conformational Restriction Approach," Chapter 14, Principles and Practice, 1994, 206-208.

Kitaguchi, et al., "Novel precursor of Alzheimer's disease amyloid protein shows protease inhibitory activity," Nature (1981), 331:530-532.

Knight, S.D. and Overman, L.E., "Preparation of Spirocyclic Polyethers by Intramolecular Heck Reactions," Heterocycles, (1994), 39, 497-501.

Knochel, P., et al., "Organozinc Mediated Reactions," Tetrahedron, (1998), 54, 8275-8319.

Kocieski, P.J., Protecting Groups, Stuttgart, FRG: G. T. Verlag 1994.

Kurihara, M., et al., "Stereoselective Synthesis of an Erythro N-protected alpha-Amino Epoxide Derivative," Tetrahedron Letters (1999), 40, 3183-3184.

Lang, F., et al., "Amination of aryl halides using copper catalysis," Tet. Letters; (2001), 42, 3251-3254.

Larock, R.C., "Comprehensive Organic Transformations," VCH Publishers, 1989, p. 981, 979 & 972.

Larock, R.C., "Comprehensive Organic Transformations," Wiley-VCH Publishers, 1999, 2d Ed. pp. 1942-1943, 1952-1953, 1955.

Lee, et al., "Development of a New Type of Protease Inhibitors, Efficacious against FIV and HIV Variants," J. Am. Chem. Soc., (1999), 121, 1145-1155.

Lin, et al., "Human aspartic protease memapsin 2 cleaves the beta-secretase site of beta-amyloid precursor protein," Proceedings Nat'l Acad. Sciences USA (2000) 97:1456-1460.

Lipinski, C.A., et al., "Experimental and computational approaches to estimate solubility and permeability in drug delivery and development settings," Adv. Drug Deliv. Reviews, (1997) 23:3-25.

Liu, G., et al., "Synthesis of Enantiomerically Pure N-tert-Butanesulfinyl Imines (tert-Butanesulfinimines) by the Direct Condensation of tert-Butanesulfinamide with Aldehydes and Ketones," J. Org. Chem., (1999), 64, 1278-1284.

Luly, J.R., et al., "A synthesis of protected aminoalkyl epoxides from a-amino acids," J. Org. Chem., (1987), 52, 1487-1492.

Mauleon et al., "Synthesis and β-Adrenergic Antagonism of 2-(Aryloxy)-1-(2-piperidyl)ethanols," J. Med. Chem. (1988), 31, 2122-2126.

McMahon, J.P. and Ellman, J.A., "Highly stereoselective addition of organometallic reagents to N-tert-butanesulfinyl imines derived from 3- and 4-substituted cyclohexanones," Org. Lett. (2004), 6, 1645-1647.

McOmie, J.F.W., ed., "Protecting Groups in Organic Chemistry," Plenum Press, New York, 1973, Ch. 2, 43-93.

Negishi, E.I., et al., "A convenient synthesis of unsymmetrical bibenzyls, homoallylarenes, and homopropargylarenes via palladium-catalyzed cross coupling," Tet. Letters, (1983), 24, 3823-3824.

Njar, V.C.O.; "High-Yield Synthesis of Novel Imidazoles and Triazoles from Alcohols and Phenols," Synthesis; (2000); 14; 2019-2028.

Orito, K., et al., "Synthesis of 5-Iodobenzofurans and 6-Iodobenzopyrans via Direct Iodination with Mercury(II) Oxide-Iodine Reagent," Synthesis, (1997), 23-25.

Ornstein, P.L., et al., "4-(Tetrazolylalkyl)piperidine-2-carboxylic acids. Potent and selective N-methyl-D-aspartic acid receptor antagonists with a short duration of action," J. Med. Chem. (1991), 34, 90-97.

Padhy, A., et al. "Synthesis and anti-microbial activity of some pyrimidine derivatives," Indian J. Pharm., Section B, 42B, 910-915, (2003).

Pirttila, et al., "Longitudinal study of cerebrospinal fluid amyloid proteins and apolipoprotein E in patients with probable Alzheimer's disease," Neuro. Lett. (1998) 249:21-24.

"Protection for the Amino Group," Chapter 7, Protecting Groups in Organic Synthesis, John Wiley and Sons, New York, N.Y., 1981, Ch. 7, 218-287.

Rekker, R.F., "The Hydrophobic Fragmental Constant," Elsevier, Amsterdam (1977).

Rogers, G.A. and Bruice, T.C., "Control of Model of Intramolecular Imidazole Catalysis ofEster Hydrolysis by Steric and Electronic effects," J. Am. Chem. Soc., (1974), 96, 2463-2472.

Rover, S., et al., "High-affinity, non-peptide agonists for the ORL1 (orphanin FQ/nociceptin) receptor,"J. Med. Chem., (2000), 43, 1329-1338.

Saito, M., et al., "Synthesis and immunological activity of 5,6,6a,8,9,11a-hexahydronaphth[1',2':4,5]imidazo[2,1-b]thiazoles and 5,6,6a,9,10,11a-hexahydroanaphth[2',1':4,5]imidazo[2,1-b]thiazoles," J. Med. Chem., (1980), 23, 1364-1372.

Satoh, Y. and Marcopulos, N., "Application of 5-Lithiotetrazoles in Organic Synthesis," Tet. Letters (1995), 36, 1759-1762.

Scott, W.J., et al., "Palladium-catalyzed coupling of vinyl triflates with organostannanes: 4-tert-Butyl-1-Vinylcyclohexene and 1-(4-tert-Butylcyclohexen-1-YL)-2-Propen-1-one," Org. Syn.; (1983) Wiley: New York; Coll. vol. 8; 97-103.

Selkoe, "The molecular pathology of Alzheimer's disease," Neuron (1991), 6:487-498.

Seubert, et al., "Isolation and quantification of soluble Alzheimer's beta-peptide from biological fluids," Nature (1992), 359:325-327.

Sinha, et al., "Purification and cloning of amyloid precursor protein -secretase from human brain," Nature (1999), 402, 537-554.

Smith et al., "March's Advanced Organic Chemistry: Reactions, Mechanisms, and Structure," $5^{th}$ Ed., Wiley: New York (2001).

Stahl et al., "Handbook of Pharmaceutical Salts: Properties, Selection and Use," Wiley-VCH; 1st Edition (2002).

Takechi, H., et al., "Screening Search for Organic Fluorophores: Syntheses and Fluorescence Properties of 3-Azolyl-7-diethylaminocoumarin Derivatives," Chem. Pharm. Bull. (2000), 48, 1702-1710.

Tao, B. and Timberlake, J.W., "Synthesis of Conformationally Constrained Spirohydantoins with a Dibenzo[a,d]heptadiene Ring," Synthesis; (2000); 10; 1449-1453.

Tucker, T.J., et al., "A series of potent HIV-1 protease inhibitors containing a hydroxyethyl secondary amine transition state isostere: synthesis, enzyme inhibition, and antiviral activity," J. Med. Chem., (1992), 35, 2525-2533.

Vassar, et al., "Beta-Secretase Cleavage of Alzheimer's Amyloid Precursor Protein by the Transmembrane Aspartic Protease BACE," Science, (1999), 286:735-741.

Witherspoon, S.M., et al., "Flow Cytometric Assay of Modulation of P-Glycoprotein Function in Whole Blood by the Multidrug Resistance Inhibitor GG918," Clin. Cancer Res., (1996), 2, 7-12.

Xiao-Yi et al., "Solid-Phase Synthesis of Alkyl Aryl Ethers via the Ullmann Condensation," J. Comb. Chem. (2002), 4, 536-539.

Yan, et al., "Membrane-anchored aspartyl protease with Alzheimer's disease beta-secretase activity," Nature, (1999), 402:533-537.

Zuccarello, et al., "HIV-1 Protease Inhibitors Based on Acyclic Carbohydrates," J. Org. Chem., (1998), 63, 4898-4906.

Copending U.S. Appl. No. 11/546,453, filed Oct. 12, 2006, published Jun. 28, 2007.

U.S. Appl. No. 11/075,312, filed Mar. 9, 2005, published Oct. 27, 2005.

Office Action (Notice of Allowability) dated Jan. 31, 2008, in copending U.S. Appl. No. 11/177,324.

Office Action dated Nov. 9, 2009, in copending U.S. Appl. No. 11/075,294.

Office Action dated Apr. 10, 2009, in copending U.S. Appl. No. 11/075,294.

Office Action dated Aug. 11, 2008, in copending U.S. Appl. No. 11/075,294.

Office Action dated Jan. 30, 2008, in copending U.S. Appl. No. 11/038,790.

Office Action dated Jul. 27, 2007, in copending U.S. Appl. No. 11/177,324.

Office Action dated Jul. 30, 2009, in copending U.S. Appl. No. 11/211,484.

Office Action dated Jul. 31, 2009, in copending U.S. Appl. No. 11/546,453.

Office Action dated Jun. 11, 2009, in copending U.S. Appl. No. 11/177,348.

Office Action dated Jun. 19, 2009, in copending U.S. Appl. No. 11/546,347.

Office Action dated Jun. 9, 2009, in copending U.S. Appl. No. 11/038,790.

Office Action dated Nov. 7, 2008, in copending U.S. Appl. No. 11/211,484.

Office Action dated Oct. 15, 2008, in copending U.S. Appl. No. 11/177,348.

Office Action dated Sep. 3, 2008, in copending U.S. Appl. No. 11/075,312.

Office Action dated Sep. 3, 2009, in copending U.S. Appl. No. 11/075,445.

Scarpini et al., "Treatment of Alzheimer's disease: current status and new perspectives," The Lancet Neurology, vol. 2, pp. 539-547, 2003.

ically relat cognitive activities. These regions include, for example, the hippocampus and cerebral cortex. A-beta is a neurotoxin that may be causally related to neuronal death observed in Alzheimer's disease patients. See, for example, Selkoe, *Neuron,* 6 (1991) 487. Since A-beta peptide accumulates as a result of APP processing by beta-secretase, inhibiting beta-secretase's activity is desirable for the treatment of Alzheimer's disease.

SUBSTITUTED HYDROXYETHYLAMINE ASPARTYL PROTEASE INHIBITORS

CROSS-REFERENCE TO RELATED APPLICATIONS

This is a continuation of application Ser. No. 11/075,312, filed Mar. 9, 2005 now abandoned, and claims the benefit of priority under 35 U.S.C. §119(e) to U.S. Provisional Application No. 60/619,918, filed Oct. 20, 2004, U.S. Provisional Application No. 60/591,918, filed Jul. 29, 2004, U.S. Provisional Application No. 60/575,977, filed Jun. 2, 2004, and U.S. Provisional Application No. 60/551,052, filed Mar. 9, 2004, all of which are expressly incorporated herein by reference in their entirety.

FIELD of THE PRESENT INVENTION

The present invention is directed to novel compounds and also to methods of treating at least one condition, disorder, or disease associated with amyloidosis using such compounds.

BACKGROUND of THE PRESENT INVENTION

Amyloidosis refers to a collection of conditions, disorders, and diseases associated with abnormal deposition of amyloidal protein. For instance, Alzheimer's disease is believed to be caused by abnormal deposition of amyloidal protein in the brain. These amyloidal protein deposits, otherwise known as amyloid-beta peptide, A-beta, or betaA4, are the result of proteolytic cleavage of the amyloid precursor protein (APP).

The majority of APP molecules that undergo proteolytic cleavage are cleaved by the aspartyl protease alpha-secretase. Alpha-secretase cleaves APP between Lys687 and Leu688 producing a large, soluble fragment, alpha-sAPP, which is a secreted form of APP that does not result in beta-amyloid plaque formation. The alpha-secretase cleavage pathway precludes the formation of A-beta, thus providing an alternate target for preventing or treating amyloidosis.

Some APP molecules, however, are cleaved by a different aspartyl protease known as beta-secretase, which is also referred to in the literature as BACE, BACE1, Asp2, and Memapsin2. Beta-secretase cleaves APP after Met671, creating a C-terminal fragment. See, for example, Sinha et at., *Nature,* (1999), 402:537-554 and published PCT application WO 00/17369. After cleavage of APP by beta-secretase, an additional aspartyl protease, gamma-secretase, may then cleave the C-terminus of this fragment, at either Val711 or Ile713, found within the APP transmembrane domain, generating an A-beta peptide. The A-beta peptide may then proceed to form beta-amyloid plaques. A detailed description of the proteolytic processing of APP fragments is found, for example, in U.S. Pat. Nos. 5,441,870, 5,721,130, and 5,942,400.

The amyloidal disease Alzheimer's is a progressive degenerative disease that is characterized by two major pathologic observations in the brain which are (1) neurofibrillary tangles, and (2) beta-amyloid (or neuritic) plagues. A major factor in the development of Alzheimer's disease is A-beta deposits in regions of the brain responsible for cognitive activities. These regions include, for example, the hippocampus and cerebral cortex. A-beta is a neurotoxin that may be causally related to neuronal death observed in Alzheimer's disease patients. See, for example, Selkoe, *Neuron,* 6 (1991) 487. Since A-beta peptide accumulates as a result of APP processing by beta-secretase, inhibiting beta-secretase's activity is desirable for the treatment of Alzheimer's disease.

Dementia-characterized disorders also arise from A-beta accumulation in the brain including accumulation in cerebral blood vessels (known as vasculary amyloid angiopathy) such as in the walls of meningeal and parenchymal arterioles, small arteries, capillaries, and venules. A-beta may also be found in cerebrospinal fluid of both individuals with and without Alzheimer's disease. Additionally, neurofibrillary tangles similar to the ones observed in Alzheimer's patients can also be found in individuals without Alzheimer's disease. In this regard, a patient exhibiting symptoms of Alzheimer's due to A-beta deposits and neurofibrillary tangles in their cerebrospinal fluid may in fact be suffering from some other form of dementia. See, for example, Seubert et al., *Nature,* 359 (1992) 325-327. Examples of other forms of dementia where A-beta accumulation generates amyloidogenic plaques or results in vascular amyloid angiopathy include Trisomy 21 (Down's Syndrome), Hereditary Cerebral Hemorrhage with amyloidosis of the Dutch-Type (HCHWA-D), and other neurodegenerative disorders. Consequently, inhibiting beta-secretase is not only desirable for the treatment of Alzheimer's, but also for the treatment of other conditions associated with amyloidosis.

Amyloidosis is also implicated in the pathophysiology of stroke. Cerebral amyloid angiopathy is a common feature of the brains of stroke patients exhibiting symptoms of dementia, focal neurological syndromes, or other signs of brain damage. See, for example, Corio et al., *Neuropath Appl. Neurobiol.,* 22 (1996) 216-227. This suggests that production and deposition of A-beta may contribute to the pathology of Alzheimer's disease, stroke, and other diseases and conditions associated with amyloidosis. Accordingly, the inhibition of A-beta production is desirable for the treatment of Alzheimer's disease, stroke, and other diseases and conditions associated with amyloidosis.

Presently there are no known effective treatments for preventing, delaying, halting, or reversing the progression of Alzheimer's disease and other conditions associated with amyloidosis. Consequently, there is an urgent need for methods of treatment capable of preventing and treating conditions associated with amyloidosis including Alzheimer's disease.

Likewise, there is a need for methods of treatment using compounds that inhibit beta-secretase-mediated cleavage of APP. There is also a need for methods of treatment using compounds that are effective inhibitors of A-beta production, and/or are effective at reducing A-beta deposits or plaques, as well as methods of treatment capable of combating diseases and conditions characterized by amyloidosis, or A-beta deposits, or plaques.

There is also a need for methods of treating conditions associated with amyloidosis using compounds that are efficacious, bioavailable and/or selective for beta-secretase. An increase in efficacy, selectivity, and/or oral bioavailability may result in preferred, safer, less expensive products that are easier for patients to use.

There is also a need for methods of treating conditions associated with amyloidosis using compounds with characteristics that would allow them to cross the blood-brain-barrier. Desirable characteristics include a low molecular weight and a high log P (increased log P=increased lipophilicity). Generally, known aspartyl protease inhibitors are either incapable of crossing the blood-brain barrier or do so with great difficulty. These compounds are unsuitable for the treatment of the conditions described herein. Accordingly, there is a need for methods of treating conditions associated with amyloidosis using compounds that can readily cross the blood-brain barrier and inhibit beta-secretase.

There is also a need for a method of finding suitable compounds for inhibiting beta-secretase activity, inhibiting cleavage of APP, inhibiting production of A-beta, and/or reducing A-beta deposits or plaques.

The present invention is directed to novel compounds and also to methods of treating conditions, disorders, and diseases associated with amyloidosis using such compounds. An embodiment of the present invention is administering at least one compound of formula (I) wherein $R_1$, $R_2$, and $R_C$ are defined below for treating at least one condition, disorder, or disease associated with amyloidosis. Another embodiment of the present invention is a method of administering at least one compound of formula (I) wherein $R_1$, $R_2$, and $R_C$ are defined below in treating conditions, disorders, and diseases associated with amyloidosis. Another embodiment of the present invention is directed to methods of treatment comprising administering at least one compound of formula (I) wherein $R_1$, $R_2$, and $R_C$ are defined below useful in preventing, delaying, halting, or reversing the progression of Alzheimer's disease.

Another embodiment of the present invention is directed to uses of beta-secretase inhibitors of at least one compound of formula (I) wherein $R_1$, $R_2$, and $R_C$ are defined below in treating or preventing conditions, disorders, and diseases associated with amyloidosis.

Another embodiment of the present invention is to administer beta-secretase inhibitors of at least one compound of formula (I) wherein $R_1$, $R_2$, and $R_C$ are defined below, exhibiting at least one property chosen from improved efficacy, oral bioavailability, selectivity, and blood-brain barrier penetrating properties. The present invention accomplishes one or more of these objectives and provides further related advantages.

BRIEF SUMMARY of THE PRESENT INVENTION

The present invention is directed to novel compounds and also to methods of treating at least one condition, disorder, or disease associated with amyloidosis using such compounds. As previously noted, amyloidosis refers to a collection of diseases, disorders, and conditions associated with abnormal deposition of A-beta protein.

Properties contributing to viable pharmaceutical compositions of beta-secretase inhibitors are incorporated into the present invention. These properties include improved efficacy, bioavailability, selectivity, and/or blood-brain barrier penetrating properties. They can be inter-related, though an increase in any one of them correlates to a benefit for the compound and its corresponding method of treatment. For example, an increase in any one of these properties may result in preferred, safer, less expensive products that are easier for patients to use.

In an embodiment, the present invention provides a method of preventing or treating conditions which benefit from inhibition of at least one aspartyl-protease, comprising administering to a host a composition comprising a therapeutically effective amount of at least one compound of formula (I),

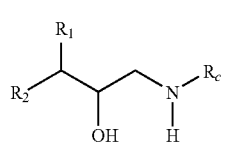

(I)

or pharmaceutically acceptable salts thereof, and wherein $R_1$, $R_2$, and $R_C$ are as defined below.

In an embodiment, the present invention provides a method of preventing or treating conditions which benefit from inhibition of at least one aspartyl-protease, comprising administering to a host a composition comprising a therapeutically effective amount of at least one compound of formula (I), or pharmaceutically acceptable salts thereof, wherein the inhibition is at least 10% for a dose $\leq 100$ mg/kg, and wherein $R_1$, $R_2$, and $R_C$ are as defined below.

In another embodiment, the present invention provides a method for preventing or treating conditions associated with amyloidosis, comprising administering to a host a therapeutically effective amount of at least one compound of formula (I), or a pharmaceutically acceptable salt thereof, the compound having an F value of at least 10%, wherein $R_1$, $R_2$, and $R_C$ are as defined below.

In another embodiment, the present invention provides a method of preventing or treating conditions associated with amyloidosis, comprising administering to a host a composition comprising a therapeutically effective amount of at least one selective beta-secretase inhibitor of formula (I), or pharmaceutically acceptable salt thereof, wherein $R_1$, $R_2$, and $R_C$ are as defined below.

In another embodiment, the present invention provides a method of preventing or treating Alzheimer's disease by administering to a host an effective amount of at least one compound of formula (I), or a pharmaceutically acceptable salt thereof, wherein $R_1$, $R_2$, and $R_C$ are as defined below.

In another embodiment, the present invention provides a method of preventing or treating dementia by administering to a host an effective amount of at least one compound of formula (I), or pharmaceutically acceptable salt thereof, wherein $R_1$, $R_2$, and $R_C$ are as defined below.

In another embodiment, the present invention provides a method of inhibiting beta-secretase activity in a host, the method comprising administering to the host an effective amount of at least one compound of formula (I), or a pharmaceutically acceptable salt thereof, wherein $R_1$, $R_2$, and $R_C$ are as defined below.

In another embodiment, the present invention provides a method of inhibiting beta-secretase activity in a cell, the method comprising administering to the cell an effective amount of at least one compound of formula (I), or a pharmaceutically acceptable salt thereof, wherein $R_1$, $R_2$, and $R_C$ are as defined below.

In another embodiment, the present invention provides a method of inhibiting beta-secretase activity in a host, the method comprising administering to the host an effective amount of at least one compound of formula (I), or a pharmaceutically acceptable salt thereof, wherein the host is a human, wherein $R_1$, $R_2$, and $R_C$ are as defined below.

In another embodiment, the present invention provides a method of affecting beta-secretase-mediated cleavage of amyloid precursor protein in a patient, comprising administering a therapeutically effective amount of at least one compound of formula (I), or a pharmaceutically acceptable salt thereof, wherein $R_1$, $R_2$, and $R_C$ are as defined below.

In another embodiment, the present invention provides a method of inhibiting cleavage of amyloid precursor protein at a site between Met596 and Asp597 (numbered for the APP-695 amino acid isotype), or at a corresponding site of an isotype or mutant thereof, comprising administering a therapeutically effective amount of at least one compound of formula (I), or a pharmaceutically acceptable salt thereof, wherein $R_1$, $R_2$, and $R_C$ are as defined below.

In another embodiment, the present invention provides a method of inhibiting production of A-beta, comprising administering to a patient a therapeutically effective amount of at least one compound of formula (I), or a pharmaceutically acceptable salt thereof, wherein $R_1$, $R_2$, and $R_C$ are as defined below.

In another embodiment, the present invention provides a method of preventing or treating deposition of A-beta, comprising administering a therapeutically effective amount of at least one compound of formula (I), or a pharmaceutically acceptable salt thereof, wherein $R_1$, $R_2$, and $R_C$ are as defined below.

In another embodiment, the present invention provides a method of preventing, delaying, halting, or reversing a disease characterized by A-beta deposits or plaques, comprising administering a therapeutically effective amount of at least one compound of formula (I), or a pharmaceutically acceptable salt thereof, wherein $R_1$, $R_2$, and $R_C$ are as defined below.

In another embodiment, the A-beta deposits or plaques are in a human brain.

In another embodiment, the present invention provides a method of inhibiting the activity of at least one aspartyl protease in a patient in need thereof, comprising administering a therapeutically effective amount of at least one compound of formula (I), or a pharmaceutically acceptable salt thereof, wherein $R_1$, $R_2$, and $R_C$ are as defined below.

In another embodiment, the at least one aspartyl protease is beta-secretase.

In another embodiment, the present invention provides a method of interacting an inhibitor with beta-secretase, comprising administering to a patient in need thereof a therapeutically effective amount of at least one compound of formula (I), or a pharmaceutically acceptable salt thereof, wherein $R_1$, $R_2$, and $R_C$ are as defined below, and wherein the at least one compound interacts with at least one beta-secretase subsite such as S1, S1', or S2'.

In another embodiment, the present invention provides an article of manufacture, comprising (a) at least one dosage form of at least one compound of formula (I), or pharmaceutically acceptable salt thereof, wherein $R_1$, $R_2$, and $R_C$ are defined below, (b) a package insert providing that a dosage form comprising a compound of formula (I) should be administered to a patient in need of therapy for disorders, conditions or diseases associated with amyloidosis, and (c) at least one container in which at least one dosage form of at least one compound of formula (I) is stored.

In another embodiment, the present invention provides a packaged pharmaceutical composition for treating conditions related to amyloidosis, comprising (a) a container which holds an effective amount of at least one compound of formula (I), or a pharmaceutically acceptable salt thereof wherein $R_1$, $R_2$, and $R_C$ are as defined below, and (b) instructions for using the pharmaceutical composition.

Definitions

Throughout the specification and claims, including the detailed description below, the following definitions apply.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple groups are indicated as being attached to a structure, it is to be understood that the groups can be the same or different.

APP, amyloid precursor protein, is defined as any APP polypeptide, including APP variants, mutations, and isoforms, for example, as disclosed in U.S. Pat. No. 5,766,846.

Beta-amyloid peptide (A-beta peptide) is defined as any peptide resulting from beta-secretase mediated cleavage of APP, including, for example, peptides of 39, 40, 41, 42, and 43 amino acids, and extending from the beta-secretase cleavage site to amino acids 39, 40, 41, 42, or 43.

Beta-secretase is an aspartyl protease that mediates cleavage of APP at the N-terminus of A-beta, Human beta-secretase is described, for example, in WO 00/17369.

The term "complex" as used herein refers to an inhibitor-enzyme complex, wherein the inhibitor is a compound of formula (I) described herein, and wherein the enzyme is beta-secretase or a fragment thereof.

The term "host" as used herein refers to a cell or tissue, in vitro or in vivo, an animal, or a human.

The term "treating" refers to administering a compound or a composition of formula (I) to a host having at least a tentative diagnosis of disease or condition. The methods of treatment and compounds of the present invention will delay, halt, or reverse the progression of the disease or condition thereby giving the host a longer and/or more functional life span.

The term "preventing" refers to administering a compound or a composition of formula (I) to a host who has not been diagnosed as having the disease or condition at the time of administration, but who could be expected to develop the disease or condition or be at increased risk for the disease or condition. The methods of treatment and compounds of the present invention may stow the development of disease symptoms, delay the onset of the disease or condition, halt the progression of disease development, or prevent the host from developing the disease or condition at all. Preventing also includes administration of a compound or a composition of the present invention to those hosts thought to be predisposed to the disease or condition due to age, familial history, genetic or chromosomal abnormalities, due to the presence of one or more biological markers for the disease or condition, such as a known genetic mutation of APP or APR cleavage products in brain tissues or fluids, and/or due to environmental factors.

The term "halogen" in the present invention refers to fluorine, bromine, chlorine, or iodine.

The term "alkyl" in the present invention refers to straight or branched chain alkyl groups having 1 to 20 carbon atoms. An alkyl group may optionally comprise at least one double bond and/or at least one triple bond. The alkyl groups herein are unsubstituted or substituted in one or more positions with various groups. For example, such alkyl groups may be optionally substituted with alkyl, alkoxy, —C(O)H, carboxy, alkoxycarbonyl, cycloalkyl, heterocycloalkyl, aryl, heteroaryl, amido, alkanoylamino, amidino, alkoxycarbonylamino, N-alkyl amidino, N-alkyl amido, N,N'-dialkylamido, aralkoxycarbonylamino, halogen, alkyl thio, alkylsulfinyl, alkylsulfonyl, hydroxy, cyano, nitro, amino, monoalkylamino, dialkylamino, halo alkyl, halo alkoxy, aminoalkyl, monoalkylaminoalkyl, dialkylaminoalkyl, and the like. Additionally, at least one carbon within any such alkyl may be optionally replaced with —C(O)—.

Examples of alkyls include methyl, ethyl, ethenyl, ethynyl, propyl, 1-ethyl-propyl, propenyl, propynyl, isopropyl, n-butyl, isobutyl, sec-butyl, tert-butyl, 2-methylbutyl, 3-methylbutyl, 1-but-3-enyl, butynyl, pentyl, 2-pentyl, isopentyl, neopentyl, 3-methylpentyl, 1-pent-3-enyl, 1-pent-4-enyl, pentyn-2-yl, hexyl, 2-hexyl, 3-hexyl, 1-hex-5-enyl, formyl, acetyl, acetylamino, trifluoromethyl, propionic acid ethyl ester, trifluoroacetyl, methylsulfonyl, ethylsulfonyl, 1-hydroxy-1-methylethyl, 2-hydroxy-1,1,-dimethyl-ethyl, 1,1-dimethyl-propyl, cyano-dimethyl-methyl, propylamine and the like.

In an embodiment, alkyls may be selected from the group comprising sec-butyl, isobutyl, ethynyl, 1-ethyl-propyl, pentyl, 3-methyl-butyl, pent-4-enyl, isopropyl, tert-butyl, 2-methylbutane, and the like.

In another embodiment, alkyls may be selected from formyl, acetyl, acetylamino, trifluoromethyl, propionic acid ethyl ester, trifluoroacetyl, methylsulfonyl, ethylsulfonyl, 1-hydroxy-1-methylethyl, 2-hydroxy-1,1-dimethyl-ethyl, 1,1-dimethyl-propyl, cyano-dimethyl-methyl, propylamine, and the like.

The term "alkoxy" in the present invention refers to straight or branched chain alkyl groups, wherein an alkyl group is as defined above, and having 1 to 20 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexyloxy, heptyloxy, allyloxy, 2-(2-methoxy-ethoxy)-ethoxy, benzyloxy, 3-methylpentoxy, and the like.

In an embodiment, alkoxy groups may be selected from the group comprising allyloxy, hexyloxy, heptyloxy, 2-(2-methoxy-ethoxy)-ethoxy, benzyloxy, and the like.

The term "—C(O)-alkyl" or "alkanoyl" refers to an acyl radical derived from an alkylcarboxylic acid, a cycloalkylcarboxylic acid, a heterocycloalkylcarboxylic acid, an arylcarboxylic acid, an arylalkylcarboxylic acid, a heteroarylcarboxylic acid, or a heteroarylalkylcarboxylic acid, examples of which include formyl, acetyl, 2,2,2-trifluoroacetyl, propionyl, butyryl, valeryl, 4-methylvaleryl, and the like.

The term "cycloalkyl" refers to an optionally substituted carbocyclic ring system of one or more 3, 4, 5, 6, 7, or 8 membered rings. A cycloalkyl can further include 9, 10, 11, 12, 13, and 14 membered fused ring systems. A cycloalkyl can be saturated or partially unsaturated. The cycloalkyl may be monocyclic, bicyclic, tricyclic, and the like. Bicyclic and tricyclic as used herein are intended to include both fused ring systems, such as adamantyl, octahydroindenyl, decahydronaphthyl, and the like, substituted ring systems, such as cyclopentylcyclohexyl and the like, and spirocycloalkyls such as spiro[2.5]octane, spiro[4.5]decane, 1,4-dioxa-spiro[4.5]decane, and the like. A cycloalkyl may optionally be a benzo fused ring system which is optionally substituted as defined herein with respect to the definition of aryl. At least one —CH$_2$— group within any such cycloalkyl ring system may be optionally replaced with —C(O)—, —C(S)—, —C(=N—OH)—, —C(=N-alkyl)- (optionally substituted as defined herein with respect to the definition of alkyl), or —C(=N—O-alkyl)- (optionally substituted as defined herein with respect to the definition of alkyl).

Further examples of cycloalkyl radicals include cyclopropyl, cyclobutyl, cyclopentyl, cyclohexyl, octahydronaphthyl, 2,3-dihydro-1H-indenyl, and the like.

In one embodiment, a cycloalkyl may be selected from the group comprising cyclopentyl, cyclohexyl, cycloheptyl, adamantenyl, bicyclo[2.2.1]-heptyl, and the like.

The cycloalkyl groups herein are unsubstituted or substituted in at least one position with various groups. For example, such cycloalkyl groups may be optionally substituted with alkyl, alkoxy, —C(O)H, carboxy, alkoxycarbonyl, cycloalkyl, heterocycloalkyl, aryl, heteroaryl, amido, alkanoylamino, amidino, alkoxycarbonylamino, N-alkyl amidino, N-alkyl amido, N,N'-dialkylamido, aralkoxycarbonylamino, halogen, alkylthio, alkylsulfinyl, alkylsulfonyl, hydroxy, cyano, nitro, amino, monoalkylamino, dialkylamino, haloalkyl, haloalkoxy, aminoalkyl, monoalkylaminoalkyl, dialkylaminoalkyl, and the like.

The term "cycloalkylcarbonyl" refers to an acyl radical of the formula cycloalkyl-C(O)— in which the term "cycloalkyl" has the significance given above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl, and the like.

The term "heterocycloalkyl", "heterocycle", or "heterocyclyl", refers to a monocyclic, bicyclic, or tricyclic heterocycle radical, containing at least one nitrogen, oxygen or sulfur atom ring member and having 3 to 8 ring members in each ring, wherein at least one ring in the heterocycloalkyl ring system may optionally contain at least one double bond. At least one —CH$_2$— group within any such heterocycloalkyl ring system may be optionally replaced with —C(O)—, —C(S)—, —C(=N—H)—, —C(=N—OH)—, —C(=N=alkyl)- (optionally substituted as defined herein with respect to the definition of alkyl), or —C(=N—O-alkyl) (optionally substituted as defined herein with respect to the definition of alkyl).

The term "bicyclic" and "tricyclic" as used herein are intended to include both fused ring systems, such as 2,3-dihydro-1H-indole, and substituted ring systems, such as bicyclohexyl. At least one —CH$_2$— group within any such heterocycloalkyl ring system may be optionally replaced with a —C(O)—, —C(N)— or —C(S)—. Heterocycloalkyl is intended to include sulfones, sulfoxides, N-oxides of tertiary nitrogen ring members, and carbocyclic fused and benzo fused ring systems wherein the benzo fused ring system is optionally substituted as defined herein with respect to the definition of aryl. Such heterocycloalkyl radicals may be optionally substituted on one or more carbon atoms by halogen, alkyl, alkoxy, cyano, nitro, amino, alkylamino, dialkylamino, monoalkylaminoalkyl, dialkylaminoalkyl, haloalkyl, haloalkoxy, aminohydroxy, oxo, aryl, aralkyl, heteroaryl, heteroaralkyl, amidino, N-alkylamidino, alkoxycarbonylamino, alkylsulfonylamino, and the like, and/or on a secondary nitrogen atom (i.e., —NH—) by hydroxy, alkyl, aralkoxycarbonyl, alkanoyl, heteroaralkyl, phenyl, phenylalkyl, and the like.

Examples of a heterocycloalkyl include morpholinyl, thiomorpholinyl, thiomorpholinyl S-oxide, thiomorpholinyl S,S-dioxide, piperazinyl, homopiperazinyl, pyrrolidinyl, pyrrolinyl, 2,5-dihydro-pyrrolyl, tetrahydropyranyl, pyranyl, thiopyranyl, piperidinyl, tetrahydrofuranyl, tetrahydrothienyl, imidazolidinyl, homopiperidinyl, 1,2-dihydro-pyridinyl, homomorpholinyl, homothiomorpholinyl, homothiomorpholinyl S,S-dioxide, oxazolidinonyl, dihydropyrazolyl, dihydropyrrolyl, 1,4-dioxa-spiro[4.5]decyl, dihydropyrazinyl, dihydropyridinyl, dihydropyrimidinyl, dihydrofuryl, dihydropyranyl, tetrahydrothienyl S-oxide, tetrahydrothienyl S,S-dioxide, homothiomorpholinyl S-oxide, 2-oxo-piperidinyl, 5-oxo-pyrrolidinyl, 2-oxo-1,2-dihydro-pyridinyl, 6-oxo-6H-pyranyl, 1,1-dioxo-hexahydro-thiopyranyl, 1-acetyl-piperidinyl, 1-methanesulfonylpiperidinyl, 1-ethanesulfonylpiperidinyl, 1-oxo-hexahydro-thiopyranyl, 1-(2,2,2-trifluoroacetyl)-piperidinyl, 1-formyl-piperidinyl, and the like.

In an embodiment, a heterocycloalkyl may be selected from pyrrolidinyl, 2,5-dihydro-pyrrolyl, piperidinyl, 1,2-dihydro-pyridinyl, pyranyl, piperazinyl, imidazolidinyl, thiopyranyl, tetrahydropyranyl, 1,4-dioxa-spiro[4.5]decyl, and the like.

In another embodiment, a heterocycloalkyl may be selected from 2-oxo-piperidinyl, 5-oxo-pyrrolidinyl, 2-oxo- 1,2-dihydro-pyridinyl, 6-oxo-6H-pyranyl, 1,1-dioxo-hexahydro-thiopyranyl, 1-acetyl-piperidinyl, 1-methanesulfonyl piperidinyl, 1-ethanesulfonylpiperidinyl, 1-oxo-hexahydro-thiopyranyl, 1-(2,2,2-trifluoroacetyl)-piperidinyl, 1-formyl-piperidinyl, and the like.

The term "aryl" refers to an aromatic carbocyclic group having a single ring (e.g., phenyl) or multiple condensed rings in which at least one ring is aromatic. The aryl may be monocyclic bicyclic, tricyclic, etc. Bicyclic and tricyclic as used herein are intended to include both fused ring systems, such as naphthyl and β-carbolinyl, and substituted ring systems, such as biphenyl, phenylpyridyl, diphenylpiperazinyl, tetrahydronaphthyl, and the like. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. The aryl groups herein are unsubstituted or substituted in one or more positions with various groups. For example, such aryl groups may be optionally substituted with alkyl, alkoxy, —C(O)H, carboxy, alkoxycarbonyl, aryl, heteroaryl, cycloalkyl, heterocyclalkyl, amido, alkanoylamino, amidino, alkoxycarbonylamino, N-alkyl amidino, N-alkyl amido, N,N'-dialkylamido, aralkoxycarbonylamino, halogen, alkyl thio, alkylsulfinyl, alkylsulfonyl, hydroxy, cyano, nitro, amino, monoalkylamino, dialkylamino, aralkoxycarbonylamino, halo alkyl, halo alkoxy, aminoalkyl, monoalkylaminoalkyl, dialkylaminoalkyl, and the like.

Examples of aryl radicals are phenyl, p-tolyl, 4-methoxyphenyl, 4-(tert-butoxy)phenyl, 3-methyl-4-methoxyphenyl, 4-$CF_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl, and the like.

Further examples of aryl radicals include 3-tert-butyl-1-fluoro-phenyl, 1,3-difluoro-phenyl, (1-hydroxy-1-methyl-ethyl)-phenyl, 1-fluoro-3-(2-hydroxy-1,1-dimethyl-ethyl)-phenyl, (1,1-dimethyl-propyl)-phenyl, cyclobutyl-phenyl, pyrrolidin-2-yl-phenyl, (5-oxo-pyrrolidin-2-yl)-phenyl, (2,5-dihydro-1H-pyrrol-2-yl)-phenyl, (1H-pyrrol-2-yl)-phenyl, (cyano-dimethyl-methyl)-phenyl, tert-butyl-phenyl, 1-fluoro-2-hydroxy-phenyl, 1,3-difluoro-4-propylamino-phenyl, 1,3-difluoro-4-hydroxy-phenyl, 1,3-difluoro-4-ethylamino-phenyl, 3-isopropyl-phenyl, (3H-[1,2,3]triazol-4-yl)-phenyl, [1,2,3]triazol-1-yl-phenyl, [1,2,4]triadiazol-3-yl-phenyl, [1,2,4]thiadiazol-5-yl-phenyl, (4H-[1,2,4]triazol-3-yl)-phenyl, [1,2,4]oxadial-3-yl-phenyl, imidazol-1-yl-phenyl, (3H-imidazol-4-yl)-phenyl, [1,2,4]triazol-4-yl-phenyl, [1,2,4]oxadiazol-5-yl-phenyl, isoxazol-3-yl-phenyl, (1-methyl-cyclopropyl)-phenyl, isoxazol-4-yl-phenyl, isoxazol-5-yl-phenyl, 1-cyano-2-tert-butyl-phenyl, 1-trifluoromethyl-2-tert-butyl-phenyl, 1-chloro-2-tert-butyl-phenyl, 1-acetyl-2-tert-butyl-phenyl, 1-tert-butyl-2-methyl-phenyl, 1-tert-butyl-2-ethyl-phenyl, 1-cyano-3-tert-butyl-phenyl, 1-trifluoromethyl-3-tert-butyl-phenyl, 1-chloro-3-tert-butyl-phenyl, 1-acetyl-3-tert-butyl-phenyl, 1-tert-butyl-3-methyl-phenyl, 1-tert-butyl-3-ethyl-phenyl, 4-tert-butyl-1-imidazol-1-yl-phenyl, ethylphenyl, isobutylphenyl, isopropylphenyl, 3-allyloxy-1-fluoro-phenyl, (2,2-dimethyl-propyl)-phenyl, ethynylphenyl, 1-fluoro-3-heptyloxy-phenyl, 1-fluoro-3-[2-(2-methoxy-ethoxy)-ethoxy]-phenyl, 1-benzyloxy-3-fluoro-phenyl, 1-fluoro-3-hydroxy-phenyl, 1-fluoro-3-hexyloxy-phenyl, (4-methyl-thiophen-2-yl)-phenyl, (5-acetyl-thiophen-2-yl)-phenyl, furan-3-yl-phenyl, thiophen-3-yl-phenyl, (5-formyl-thiophen-2-yl)-phenyl, (3-formyl-furan-2-yl)-phenyl, acetylamino-phenyl, trifluoromethylphenyl, sec-butyl-phenyl, pentylphenyl, (3-methyl-butyl)-phenyl, (1-ethyl-propyl)-phenyl, cyclopentyl-phenyl, 3-pent-4-enyl-phenyl, phenyl propionic acid ethyl ester, pyridin-2-yl-phenyl, (3-methyl-pyridin-2-yl)-phenyl, thiazol-2-yl-phenyl, (3-methyl-thiophen-2-yl)-phenyl, fluoro-phenyl, adamantan-2-yl-phenyl, 1,3-difluoro-2-hydroxy-phenyl, cyclopropyl-phenyl, 1-bromo-3-tert-butyl-phenyl, (3-bromo-[1,2,4]thiadiazol-5-yl)-phenyl, (1-methyl-1H-imidazol-2-yl)-phenyl, (3,5-dimethyl-3H-pyrazol-4-yl)-phenyl, (3,6-dimethyl-pyrazin-2-yl)-phenyl, (3-cyano-pyrazin-2-yl)-phenyl, thiazol-4-yl-phenyl, (4-cyano-pyridin-2-yl)-phenyl, pyrazin-2-yl-phenyl, (6-methyl-pyridazin-3-yl)-phenyl, (2-cyano-thiophen-3-yl)-phenyl, (2-chloro-thiophen-3-yl)-phenyl, (5-acetyl-thiophen-3-yl)-phenyl, cyano-phenyl, and the like.

The term "heteroaryl" refers to an aromatic heterocycloalkyl radical as defined above. The heteroaryl groups herein are unsubstituted or substituted in at least one position with various groups. For example, such heteroaryl groups may be optionally substituted with, for example, alkyl, alkoxy, halogen, hydroxy, cyano, nitro, amino, monoalkylamino, dialkylamino, haloalkyl, haloalkoxy, —C(O)H, carboxy, alkoxycarbonyl, cycloalkyl, heterocyclalkyl, aryl, heteroaryl, amido, alkanoylamino, amidino, alkoxycarbonylamino, N-alkyl amidino, N-alkyl amido, N,N'-dialkylamido, alkyl thio, alkylsulfinyl, alkylsulfonyl, aralkoxycarbonylamino, aminoalkyl, monoalkylaminoalkyl, dialkylaminoalkyl, and the like.

Examples of heteroaryl groups include Benzo[4,5]thieno[3,2-d]pyrimidin-4-yl, pyridyl, pyrimidyl, furanyl, imidazolyl, thienyl, oxazolyl, thiazolyl, pyrazinyl, 3-methyl-thienyl, 4-methyl-thienyl, 3-propyl-thienyl, 2-chloro-thienyl, 2-chloro-4-ethyl-thienyl, 2-cyano-thienyl, 5-acetyl-thienyl, 5-formyl-thienyl, 3-formyl-furanyl, 3-methyl-pyridinyl, 3-bromo-[1,2,4]thiadiazolyl, 1-methyl-1H-imidazole, 3,5-dimethyl-3H-pyrazolyl, 3,6-dimethyl-pyrazinyl, 3-cyano-pyrazinyl, 4-tert-butyl-pyridinyl, 4-cyano-pyridinyl, 6-methyl-pyridazinyl, 2-tert-butyl-pyrimidinyl, 4-tert-butyl-pyrimidinyl, 6-tert-butyl-pyrimidinyl, 5-tert-butyl-pyridazinyl, 6-tert-butyl-pyridazinyl, quinolinyl, benzothienyl, indolyl, indolinyl, pyridazinyl, isoindolyl, isoquinolyl, quinazolinyl, quinoxalinyl, phthalazinyl, imidazolyl, isoxazolyl, pyrazolyl, indolizinyl, indazolyl, benzothiazolyl, benzimidazolyl, benzofuranyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazotinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, tetrahydrocarbazole, tetrahydrobetacarboline, and the like.

In an embodiment, a heteroaryl group may be selected from pyridyl, pyrimidyl, furanyl, imidazolyl, thienyl, oxazolyl, thiazolyl, pyrazinyl, and the like.

In another embodiment, a heteroaryl group may be selected from 3-methyl-thienyl, 4-methyl-thienyl, 3-propyl-thienyl, 2-chloro-thienyl, 2-chloro-4-ethyl-thienyl, 2-cyano-thienyl, 5-acetyl-thienyl, 5-formyl-thienyl, 3-formyl-furanyl, 3-methyl-pyridinyl, 3-bromo-[1,2,4]thiadiazolyl, 1-methyl-1H-imidazole, 3,5-dimethyl-3H-pyrazolyl, 3,6-dimethyl-pyrazinyl, 3-cyano-pyrazinyl, 4-tert-butyl-pyridinyl, 4-cyano-pyridinyl, 6-methyl-pyridazinyl, 2-tert-butyl-pyrimidinyl, 4-tert-butyl-pyrimidinyl, 6-tert-butyl-pyrimidinyl, 5-tert-butyl-pyridazinyl, 6-tert-butyl-pyridazinyl, and the like.

Further examples of heterocycloalkyls and heteraryls may be found in Katritzky, A. R. et al., *Comprehensive Heterocyclic Chemistry: The Structure, Reactions, Synthesis and Use of Heterocyclic Compounds*, Vol. 1-8, New York: Pergamon Press, 1984.

The term "aralkoxycarbonyl" refers to a radical of the formula aralkyl-O—C(O)— in which the term "aralkyl" is encompassed by the definitions above for aryl and alkyl. Examples of an aralkoxycarbonyl radical include benzyloxycarbonyl, 4-methoxyphenylmethoxycarbonyl, and the like.

The term "aryloxy" refers to a radical of the formula —O-aryl in which the term aryl is as defined above.

The term "aralkanoyl" refers to an acyl radical derived from an aryl-substituted alkanecarboxylic acid such as phenylacetyl, 3-phenylpropionyl(hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like.

The term "aroyl" refers to an acyl radical derived from an arylcarboxylic acid, "aryl" having the meaning given above. Examples of such aroyl radicals include substituted and unsubstituted benzoyl or naphthoyl such as benzoyl, 4-chlorobenzoyl, 4-carboxybenzoyl, 4-(benzyloxycarbonyl)benzoyl, 1-naphthoyl, 2-naphthoyl, 6-carboxy-2naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "haloalkyl" refers to an alkyl radical having the meaning as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl, and the like.

The term "epoxide" refers to chemical compounds or reagents comprising a bridging oxygen wherein the bridged atoms are also bonded to one another either directly or indirectly. Examples of epoxides include epoxyalkyl (e.g., ethylene oxide and 1,2-epoxybutane), epoxycycloalkyl (e.g., 1,2-epoxycyclohexane and 1,2-epoxy-1-methylcyclohexane), and the like.

The term "structural characteristics" refers to chemical moieties, chemical motifs, and portions of chemical compounds. These include R groups, such as those defined herein, ligands, appendages, and the like. For example, structural characteristics may be defined by their properties, such as, but not limited to, their ability to participate in intermolecular interactions including Van der Waal's interactions (e.g., electrostatic interactions, dipole-dipole interactions, dispersion forces, hydrogen bonding, and the like). Such characteristics may impart desired pharmacokinetic properties and thus have an increased ability to cause the desired effect and thus prevent or treat the targeted diseases or conditions.

Compounds of formula (I) also comprise structural moieties that participate in inhibitory interactions with at least one subsite of beta-secretase. For example, moieties of the compounds of formula (I) may interact with at least one of the S1, S1', and S2' subsites, wherein S1 comprises residues Leu30, Tyr71, Phe108, Ile110, and Trp115, S1' comprises residues Tyr198, Ile226; Val227, Ser 229, and Thr231, and S2' comprises residues Ser35, Asn37, Pro70, Tyr71, Ile118, and Arg128. Such compounds and methods of treatment may have an increased ability to cause the desired effect and thus prevent or treat the targeted diseases or conditions.

The term "pharmaceutically acceptable" refers to those properties and/or substances that are acceptable to the patient from a pharmacological/toxicological point of view, and to the manufacturing pharmaceutical chemist from a physical/chemical point of view regarding composition, formulation, stability, patient acceptance, and bioavailability.

The term "effective amount" as used herein refers to an amount of a therapeutic agent administered to a host, as defined herein, necessary to achieve a desired effect.

The term "therapeutically effective amount" as used herein refers to an amount of a therapeutic agent administered to a host to treat or prevent a condition treatable by administration of a composition of the invention. That amount is the amount sufficient to reduce or lessen at least one symptom of the disease being treated or to reduce or delay onset of one or more clinical markers or symptoms of the disease.

The term "therapeutically active agent" refers to a compound or composition that is administered to a host, either alone or in combination with another therapeutically active agent, to treat or prevent a condition treatable by administration of a composition of the invention.

The terms "pharmaceutically acceptable salt" and "salts thereof" refer to acid addition salts or base addition salts of the compounds in the present invention. A pharmaceutically acceptable salt is any salt which retains the activity of the parent compound and does not impart any deleterious or undesirable effect on the subject to whom it is administered and in the context in which it is administered. Pharmaceutically acceptable salts include salts of both inorganic and organic acids. Pharmaceutically acceptable salts include acid salts such as acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolylarsanilic, hexamic, hexylresorcinoic, hydrabamic, hydrobromic, hydrochloric, hydroiodic, hydroxynapythoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic, toluenesulfonic, and the like. Other acceptable salts may be found, for example, in Stahl et al., *Pharmaceutical Salts: Properties, Selection, and Use*, Wiley-VCH; 1st edition (Jun. 15, 2002).

In an embodiment of the present invention, a pharmaceutically acceptable salt is selected from the group comprising hydrochloric, hydrobromic, hydroiodic, nitric, sulfuric, phosphoric, citric, methanesulfonic, $CH_3—(CH_2)_{0-4}—COOH$, $HOOC—(CH_2)_{0-4}—COOH$, $HOOC—CH=CH—COOH$, phenyl-COOH, and the like.

The term "unit dosage form" refers to physically discrete units suitable as unitary dosages for human subjects or other mammals, each unit containing a predetermined quantity of active material calculated to produce the desired therapeutic effect, in association with a suitable pharmaceutical vehicle. The concentration of active compound in the drug composition will depend on absorption, inactivation, and/or excretion rates of the active compound, the dosage schedule, the amount administered and medium and method of administration, as well as other factors known to those of skill in the art.

The term "modulate" refers to a chemical compound's activity of either enhancing or inhibiting a functional property of biological activity or process.

The terms "interact" and "interactions" refer to a chemical compound's association and/or reaction with another chemical compound, such as an interaction between an inhibitor and beta-secretase. Interactions include, but are not limited to, hydrophobic, hydrophilic, lipophilic, lipophobic, electrostatic, and van der Waal's interactions including hydrogen bonding.

An "article of manufacture" as used herein refers to materials useful for the diagnosis, prevention or treatment of the disorders described above, such as a container with a label. The label can be associated with the article of manufacture in a variety of ways including, for example, the label may be on the container or the label may be in the container as a package insert. Suitable containers include, for example, blister packs, bottles, bags, vials, syringes, test tubes, and the like. The containers may be formed from a variety of materials such as glass, metal, plastic, rubber, and/or paper, and the like. The container holds a composition as described herein which is effective for diagnosing, preventing, or treating a condition treatable by a compound or composition of the present invention.

The article of manufacture may contain bulk quantities or less of a composition as described herein. The label on, or associated with, the container may provide instructions for the use of the composition in diagnosing, preventing, or treating the condition of choice, instructions for the dosage amount and for the methods of administration. The label may further indicate that the composition is to be used in combination with one or more therapeutically active agents wherein the therapeutically active agent is selected from an antioxidant, an anti-inflammatory, a gamma-secretase inhibitor, a neurotrophic agent, an acetyl cholinesterase inhibitor, a statin, an A-beta, an anti-A-beta antibody, and/or a beta-secretase complex or fragment thereof. The article of manufacture may further comprise multiple containers, also referred to herein as a kit, comprising a therapeutically active agent or a pharmaceutically-acceptable buffer, such as phosphate-buffered saline, Ringer's solution and/or dextrose solution. It may further include other materials desirable from a commercial and user standpoint, including other buffers, diluents, filters, needles, syringes, and/or package inserts with instructions for use.

The compounds of formula (I), their compositions, and methods of treatment employing them, can be enclosed in multiple or single dose containers. The enclosed compounds and/or compositions can be provided in kits, optionally including component parts that can be assembled for use. For example, a compound inhibitor in lyophilized form and a suitable diluent may be provided as separated components for combination prior to use. A kit may include a compound inhibitor and at least one additional therapeutic agent for co-administration. The inhibitor and additional therapeutic agents may be provided as separate component parts.

A kit may include a plurality of containers, each container holding at least one unit dose of the compound of the present invention. The containers are preferably adapted for the desired mode of administration, including, for example, pill, tablet, capsule, powder, gel or gel capsule, sustained-release capsule, or elixir form, and/or combinations thereof, and the like, for oral administration, depot products, pre-filled syringes, ampoules, vials, and the like, for parenteral administration, and patches, medipads, creams, and the like, for topical administration.

The term "$C_{max}$" refers to the peak plasma concentration of a compound in a host.

The term "$T_{max}$" refers to the time at peak plasma concentration of a compound in a host.

The term "half-life" refers to the period of time required for the concentration or amount of a compound in a host to be reduced to exactly one-half of a given concentration or amount.

DETAILED DESCRIPTION OF THE PRESENT INVENTION

The present invention is directed to novel compounds and also to methods of treating conditions, disorders, and diseases associated with amyloidosis using such compounds. Amyloidosis refers to a collection of diseases, disorders, and conditions associated with abnormal deposition of amyloidal protein.

Accordingly, an embodiment of the present invention is to provide a method of preventing or treating conditions which benefit from inhibition of at least one aspartyl-protease, comprising administering to a host a composition comprising a therapeutically effective amount of at least one compound of formula (I),

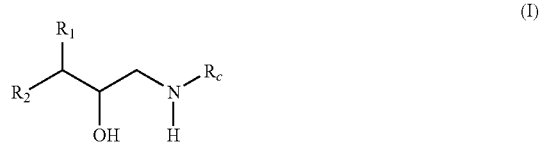

(I)

or pharmaceutically acceptable salts thereof, wherein $R_1$ is selected from

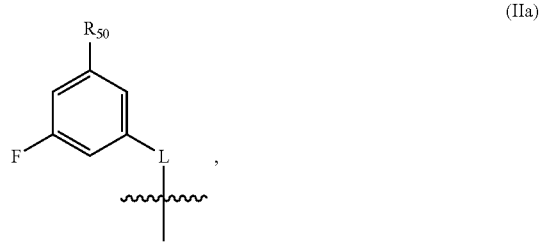

(IIa)

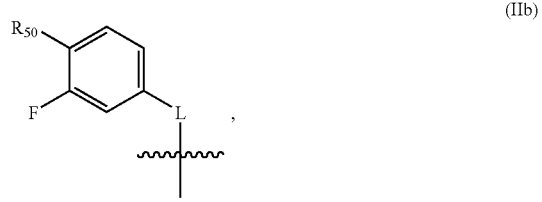

(IIb)

-continued

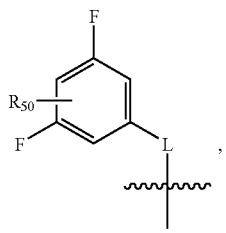
(IIc)

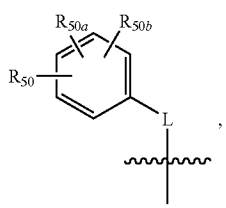
(IId)

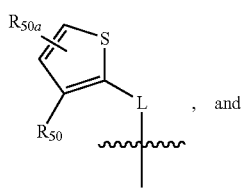
(IIe)
, and

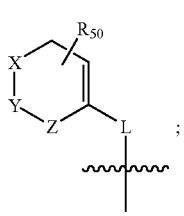
(IIf)

wherein
X, Y, and Z are independently, selected from —C(H)$_{0-2}$—, —O—, —C(O)—, —NH—, and —N—, wherein at least one bond of the (IIf) ring may optionally be a double bond;

L is selected from —O—, —SO$_2$—, —C(O)—, —C(R$_{55}$)(R$_{60}$)—, and —CH(NR$_{55}$R$_{60}$)—;
R$_{55}$ and R$_{60}$ are each independently selected from hydrogen and alkyl;

R$_{50}$, R$_{50a}$, and R$_{50b}$ are independently selected from —H, -halogen, —OH, —C(O)H, —C(O)CH$_3$, —CH$_2$OH, —SH, —S(O)$_{0-2}$CH$_3$, —CN, —NO$_2$, —NH$_2$, —NHCH$_3$, —N(CH$_3$)$_2$ —C$_1$—C$_2$ alkyl, —OCH$_3$, —OCF$_3$, and —CF$_3$;

R$_2$ is selected from —H, —OH, —O-alkyl (optionally substituted with at least one group independently selected from R$_{200}$), —O-aryl, (optionally substituted with at least one group independently selected from R$_{200}$), -alkyl (optionally substituted with at least one group independently selected from R$_{200}$). —NH-alkyl, (optionally substituted with at least one group independently selected from R$_{200}$), -heterocycloalkyl, (wherein at least one carbon is optionally replaced with a group independently selected from —(CR$_{245}$R$_{250}$)—, —O—, —C(O)—, —C(O)C(O)—, —N(R$_{200}$)$_{0-1}$—,and —S(O)$_{0-2}$—, and wherein the heterocycloalkyl is optionally substituted with at least one group independently selected from R$_{200}$). —NH— heterocycloalkyl, (wherein at least one carbon is optionally replaced with a group independently selected from —(CR$_{245}$R$_{250}$)—, —O—, —C(O)—, —C(O)C(O)—, —N(R$_{200}$)$_{0-2}$—, and —S(O)$_{0-2}$—, and wherein the heterocycloalkyl is optionally substituted with at least one group independently selected from R$_{200}$), —C(O)—N(R$_{315}$)(R$_{320}$), —O—C(O)—N(R$_{315}$)(R$_{320}$), —NH—R$_{400}$, —R$_{400}$, —NH—R$_{500}$, —R$_{500}$, —NH—R$_{600}$, —R$_{600}$, and —NH—R$_{700}$;
wherein R$_{315}$ and R$_{320}$ are each independently selected from —H, -alkyl, and phenyl;

R$_{400}$ is

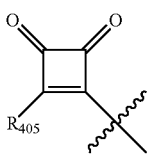

wherein R$_{405}$ is selected from —H, —N(R$_{515}$)$_2$, and O-alkyl;
R$_{500}$ is a heteroaryl selected from III(a) and III(b),

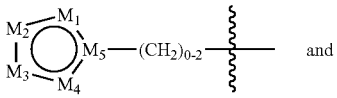
(IIIa)
and

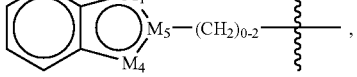
(IIIb)
, wherein
M$_1$ and M$_4$ are independently selected from —C(R$_{505}$)—, —N—, —N(R$_{515}$)—, —S—, and —O—;
M$_2$ and M$_3$ are independently selected from —C(R$_{510}$)—, —N—, —N(R$_{520}$)—, —S—, and —O—;
M$_5$ is selected from —C— and —N—;
R$_{505}$ is independently selected from —H, -alkyl, -halogen, —NO$_2$, —CN, —R$_{200}$, and -phenyl;
R$_{510}$ is independently selected from —H, -alkyl, -halogen, -amino, —CF$_3$, —R$_{200}$, and -phenyl;
R$_{515}$ is independently selected from —H, -alkyl, and -phenyl;
R$_{520}$ is independently selected from —H, -alkyl, —(CH$_2$)$_{0-2}$-phenyl, and —C(Ph)$_3$;
R$_{600}$ is a monocyclic, bicyclic, or tricyclic heteroaryl ring system of 6, 7, 8, 9, 10, 11, 12, 13, or 14 atoms, optionally substituted with at least one group independently selected from R$_{505}$;
R$_{605}$ is selected from -hydrogen, -halogen, -alkyl, —phenyl, alkyl-O—C(O)—, —nitro, —CN, -amino, —NR$_{220}$R$_{225}$, -thioalkyl, —CF$_3$, —OH, —O-alkyl, and -heterocycloalkyl;
R$_{700}$ is aryl optionally substituted with at least one R$_{205}$;
R$_C$ is selected from
—(CH$_2$)$_{0-3}$-cycloalkyl wherein the cycloalkyl is optionally substituted with at least one group independently selected from —R$_{205}$ and —CO$_2$-(alkyl),
-alkyl optionally substituted with at least one group independently selected from R$_{205}$.
—(CR$_{245}$R$_{250}$)$_{0-4}$—R$_x$, wherein at least one —(CR$_{245}$R$_{250}$)— is optionally replaced with a group independently selected from —O—, —N(R$_{215}$)—, —C(O)$_{1-2}$—, —C(O)N(R$_{215}$)— and —S(O)$_{0-2}$—, and -formulae (IVa), (IVb), (IVc), (IVd), (IVe), (IVf), and (IVg);

$R_X$ is selected from -hydrogen, -aryl, -heteroaryl, -cycloalkyl, -heterocycloalkyl, and —$R_{Xa}$—$R_{Xb}$, wherein $R_{Xa}$ and $R_{Xb}$ are independently selected from aryl, heteroaryl, cycloalkyl, and heterocycloalkyl;

wherein each aryl or heteroaryl group attached directly or indirectly to —$(CR_{245}R_{250})_{0-4}$— is optionally substituted with at least one group independently selected from $R_{200}$;

wherein each cycloalkyl or heterocycloalkyl group attached directly or indirectly to —$(CR_{245}R_{250})_{0-4}$— is optionally substituted with at least one group independently selected from $R_{210}$ and —$(CR_{245}R_{250})_{0-4}$—$R_{200}$;

wherein at least one atom of the heteroaryl or heterocycloalkyl group attached directly or indirectly to —$(CR_{245}R_{250})_{0-4}$— is independently optionally replaced with a group selected from —O—, —C(O)—, —N$(R_{215})_{0-1}$—, and —$S(O)_{0-2}$—;

wherein at least one heteroatom of the heteroaryl or heterocycloalkyl group attached directly or indirectly to —$(CR_{245}R_{250})_{0-4}$— is independently optionally substituted with a group selected from —$(CO)_{0-1}R_{215}$, —$(CO)_{0-1}R_{220}$, —$S(O)_{0-2}R_{200}$, and —$N(R_{200})$—$S(O)_{0-2}R_{200}$;

$R_{245}$ and $R_{250}$ at each occurrence are independently selected from —H, —$(CH_2)_{0-4}C(O)$—OH, —$(CH_2)_{0-4}C(O)$—O-alkyl, —$(CH_2)_{0-4}C(O)$-alkyl, -alkyl, -hydroxyalkyl, —O-alkyl; -haloalkoxy; —$(CH_2)_{0-4}$-cycloalkyl, —$(CH_2)_{0-4}$-aryl, —$(CH_2)_{0-4}$-heteroaryl, and —$(CH_2)_{0-4}$-heterocycloalkyl; or $R_{245}$ and $R_{250}$ are taken together with the carbon to which they are attached to form a monocyclic or bicyclic ring system of 3, 4, 5, 6, 7, 8, 9, or 10 carbon atoms, wherein at least one bond in the monocyclic or bicyclic ring system is optionally a double bond, wherein the bicyclic ring system is optionally a fused or spiro ring system, wherein at least one carbon atom in the monocyclic or bicyclic ring system is optionally replaced by a group independently selected from —O—, —C(O)—, —$S(O)_{0-2}$—, —C(=N—$R_{255}$)—, —N—, —$NR_{220}$—, —$N((CO)_{0-1}R_{200})$—, and —$N(SO_2R_{200})$—;

wherein the aryl, heteroaryl, and heterocycloalkyl groups included in $R_{245}$ and $R_{250}$ are optionally substituted with at least one group independently selected from -halogen, -alkyl, —$N(R_{220})(R_{225})$, —CN, and —OH;

wherein the monocyclic and bicyclic groups included in $R_{245}$ and $R_{250}$ are optionally substituted with at least one group independently selected from halogen, —$(CH_2)_{0-2}$—OH, —O-alkyl, alkyl, —$(CH_2)_{0-2}$-alkyl, —$CF_3$, aryl, —$N(R_{220}R_{225})$, —CN, —$(CH_2)_{0-2}$—$NH_2$, —$(CH_2)_{0-2}$—NH(alkyl), —NHOH, —NH—O-alkyl, —N(alkyl)(alkyl), —NH-heteroaryl, —NH—C(O)-alkyl, and —$NHS(O_2)$-alkyl;

formula (IVa) is

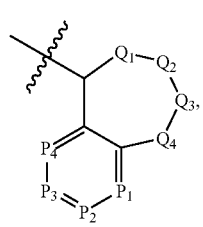

(IVa)

wherein $Q_1$ is selected from (—$CH_2$)$_{0-1}$, —$CH(R_{200})$—, —$C(R_{200})_2$—, and —C(O)—;

$Q_2$ and $Q_3$ each are independently selected from (—$CH_2$—)$_{0-1}$, —$CH(R_{200})$—, —$C(R_{200})_2$—, —O—, —C(O)—, —S—, —$S(O)_2$—, —NH—, and —$N(R_7)$—;

$Q_4$ is selected from a bond, (—$CH_2$—)$_{0-1}$, —$CH(R_{200})$—, —$C(R_{200})_2$—, —O—, —C(O)—, —S—, —$S(O)_2$—, —NH—, and —$N(R_7)$—; and $P_1$, $P_2$, $P_3$, and $P_4$ each are independently selected from —CH—, —$C(R_{200})$—, and —N—; formula (IVb) is

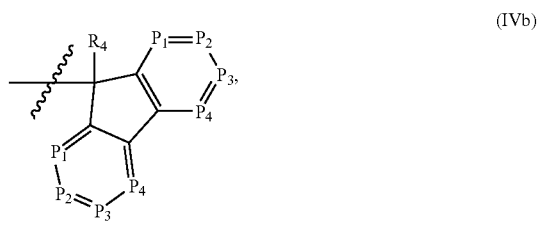

(IVb)

wherein $R_4$ is selected from —H and -alkyl; and $P_1$, $P_2$, $P_3$, and $P_4$ at each occurrence are independently selected from —CH—, —$C(R_{200})$—, and —N—;

formula (IVc) is

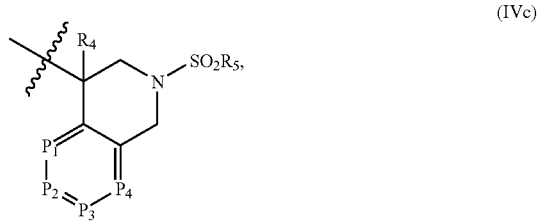

(IVc)

wherein $R_4$ is selected from —H and -alkyl; and $P_1$, $P_2$, and $P_4$ at each occurrence are independently selected from —CH—, —$CR_{200}$—, and —N—;

formula (IVd) is

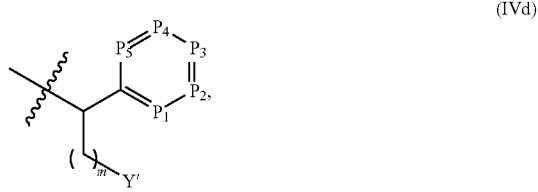

(IVd)

wherein m is 0, 1, 2, 3, 4, 5, or 6;

Y' is selected from —H, —CN, —OH, —O-alkyl, —$C(O)_2$H, —$C(O)OR_{215}$, -amino, -aryl, and -heteroaryl; and $P_1$ and $P_2$ at each occurrence are independently selected from —CH—, —$C(R_{200})$—, and —N—, or $P_1$ and $P_2$ are optionally taken together to form a monocyclic or bicyclic ring system of 3, 4, 5, 6, 7, 8, 9, or 10 carbon atoms, $P_3$ and $P_4$ at each occurrence are independently selected from —CH—, —$C(R_{200})$—, and —N—, or $P_3$ and $P_4$ are optionally taken together to form a monocyclic or bicyclic ring system of 3, 4, 5, 6, 7, 8, 9, or 10 carbon atoms, $P_5$ at each occurrence is independently selected from —CH—, —C($R_{200}$)—, and —N—, wherein at least one bond in the monocyclic or bicyclic ring system included in $P_1$ and $P_2$ or $P_3$ and $P_4$ is optionally a double bond, wherein the bicyclic ring system included in $P_1$ and $P_2$ or $P_3$ and $P_4$ is optionally a fused or spiro ring system, wherein at least one carbon atom in the monocyclic or bicyclic ring system included in $P_1$ and $P_2$ or $P_3$ and $P_4$ is optionally replaced by a group independently selected from —O—,
—C(O)—,
—S(O)$_{0-2}$—,
—C(=N—$R_{255}$)—,
—N—,
—N$R_{220}$—,
—N((CO)$_{0-1}$($R_{200}$))—, and
—N(SO$_2$$R_{200}$)—;

formula (IVe) is

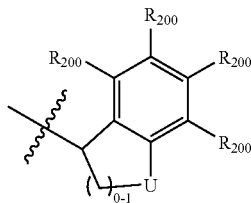

(IVe)

wherein

U is selected from —CH$_2$—C$R_{100}$$R_{101}$, —CH$_2$—S—, —CH$_2$—S(O)—, —CH$_2$—S(O)$_2$—, —CH$_2$—N($R_{100}$)—, CH$_2$—C(O)—, —CH$_2$—O—, —C(O)—C($R_{100}$)($R_{101}$)—, —SO$_2$—N($R_{100}$)—, —C(O)—N($R_{55}$)—, —N($R_{55}$)—C(O)—N($R_{55}$)—, —O—C(O)—O—, —N($R_{55}$)—C(O)—O—, and —C(O)—O—;

wherein $R_{100}$ and $R_{101}$ at each occurrence are independently selected from —H, -alkyl, -aryl, —C(O)-alkyl, —(CO)$_{0-1}$$R_{215}$, —(CO)$_{0-1}$$R_{220}$, and —S(O)$_2$-alkyl;

formula (IVf) is

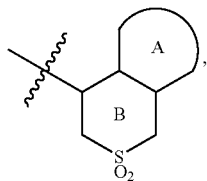

(IVf)

wherein the B ring is optionally substituted with at least one group independently selected from -alkyl, -halogen, —OH, —SH, —CN, —CF$_3$, —O-alkyl, —N($R_5$)C(O)H, —C(O)H, —C(O)N($R_5$)($R_6$), —N$R_5$$R_6$, —$R_{280}$, —$R_{285}$, -aryl, and -heteroaryl;

wherein $R_{280}$ and $R_{285}$, and the carbon to which they are attached form a $C_3$—$C_7$ spirocycle which is optionally substituted with at least one group independently selected from -alkyl, —O-alkyl, -halogen, —CF$_3$, and —CN;

wherein the A ring is aryl or heteroaryl, each optionally substituted with at least one group independently selected from $R_{290}$ and $R_{295}$, wherein $R_{290}$ and $R_{295}$ at each occurrence are independently selected from -alkyl (optionally substituted with at least one group independently selected from -alkyl, -halogen, —OH, —SH, —CN, —CF$_3$, —O-alkyl, and —N$R_5$$R_6$), —OH, —NO$_2$, -halogen, —CO$_2$H, —CN, —(CH$_2$)$_{0-4}$—C(O)—N$R_{21}$$R_{22}$, —(CH$_2$)$_{0-4}$—CO$_2$$R_{20}$, —(CH$_2$)$_{0-4}$—SO$_2$—N$R_{21}$$R_{22}$, —(CH$_2$)$_{0-4}$—S(O)-(alkyl), —(CH$_2$)$_{0-4}$—S(O)$_2$-(alkyl), —(CH$_2$)$_{0-4}$—S(O)$_2$-(cycloalkyl), —(CH$_2$)$_{0-4}$—N(H or $R_{20}$)—C(O)—O—$R_{20}$, —(CH$_2$)$_{0-4}$—N(H or $R_{20}$)—C(O)—N($R_{20}$)$_2$, —(CH$_2$)$_{0-4}$—N—C(S)—N($R_{20}$)$_2$, —(CH$_2$)$_{0-4}$—N(H or $R_{20}$)—CO—$R_{21}$), —(CH$_2$)$_{0-4}$—N$R_{21}$$R_{22}$, —(CH$_2$)$_{0-4}$—$R_{11}$, —(CH$_2$)$_{0-4}$—O—C(O)-(alkyl), —(CH$_2$)$_{0-4}$—O—P(O)—(O$R_5$)$_2$, —(CH$_2$)$_{0-4}$—O—C(O)—N($R_{20}$)$_2$, —(CH$_2$)$_{0-4}$—O—C(S)—N($R_{20}$)$_2$, —(CH$_2$)$_{0-4}$—O—($R_{20}$)$_2$, —(CH$_2$)$_{0-4}$—O—($R_{20}$)—CO$_2$H, —(CH$_2$)$_{0-4}$—S—($R_{20}$), —(CH$_2$)$_{0-4}$—O-(alkyl optionally substituted with at least one halogen), -cycloalkyl, —(CH$_2$)$_{0-4}$—N(H or $R_{20}$)—S(O)$_2$—$R_{21}$, and —(CH$_2$)$_{0-4}$-cycloalkyl;

formula (IVg) is

wherein a is 0 or 1;
b is 0 or 1;
S' is selected from —C(O)— and —CO$_2$—;
T' is —(CH$_2$)$_{0-4}$—;
U' is —(C$R_{245}$$R_{250}$)—;
V' is selected from -aryl- and -heteroaryl-;
W' is selected from a bond, -alkyl- (optionally substituted with at least one group independently selected from $R_{205}$), —(CH$_2$)$_{0-4}$—(CO)$_{0-1}$—N($R_{220}$)—, —(CH$_2$)$_{0-4}$—(CO)$_{0-1}$—, —(CH$_2$)$_{0-4}$—CO$_2$—, —(CH$_2$)$_{0-4}$—SO$_2$—N($R_{220}$)—, —(CH$_2$)$_{0-4}$—N(H or $R_{215}$)—CO$_2$—, —(CH$_2$)$_{0-4}$—N(H or $R_{215}$)—SO$_2$—, —(CH$_2$)$_{0-4}$—N(H or $R_{215}$)—C(O)—N($R_{215}$)—, —(CH$_2$)$_{0-4}$—N(H or $R_{215}$)—C(O)—, —(CH$_2$)$_{0-4}$—N($R_{220}$)—, —(CH$_2$)$_{0-4}$—O—, and —(CH$_2$)$_{0-4}$—S—;
X' is selected from aryl and heteroaryl;

wherein each cycloalkyl included in formula (IVg) is optionally substituted with at least one group independently selected from $R_{205}$;

wherein each aryl or heteroaryl group included in formula (IVg) is optionally substituted with at least one group independently selected from $R_{200}$;

wherein at least one heteroatom of the heteroaryl group included in formula (IVg) is optionally substituted with a group selected from —(CO)$_{0-1}$$R_{215}$, —(CO)$_{0-1}$$R_{220}$, and —S(O)$_{0-2}$$R_{200}$;

$R_{21}$ and $R_{22}$ each independently are selected from —H, -alkyl (optionally substituted with at least one group independently selected from —OH, -amino, -halogen, -alkyl, -cycloalkyl, -(alkyl)-(cycloalkyl), -(alkyl)-O-(alkyl), —$R_{17}$, and —$R_{18}$), —(CH$_2$)$_{0-4}$—C(O)-(alkyl), —(CH$_2$)$_{0-4}$—C(O)-(cycloalkyl), —$(CH_2)_{0-4}$—C(O)—$R_{17}$, —$(CH_2)_{0-4}$—C(O)—$R_{18}$, —$(CH_2)_{0-4}$—C(O)—$R_{19}$, and —$(CH_2)_{0-4}$—C(O)—$R_{11}$;

$R_{17}$ at each occurrence is aryl optionally substituted with at least one group independently selected from -alkyl (optionally substituted with at least one group independently selected from -alkyl, -halogen, —OH, —SH, —$NR_5R_6$, —CN, —$CF_3$, and —O-alkyl), -halogen, —O-alkyl (optionally substituted with at least one group independently selected from halogen, —$NR_{21}R_{22}$, —OH, and —CN), cycloalkyl (optionally substituted with at least one group independently selected from halogen, —OH, —SH, —CN, —$CF_3$, —O-alkyl, and —$NR_5R_6$), —C(O)-(alkyl), —$S(O)_2$—$NR_5R_6$, —C(O)—$NR_5R_6$, and —$S(O)_2$-(alkyl);

$R_{18}$ at each occurrence is heteroaryl optionally substituted with at least one group independently selected from -alkyl (optionally substituted with at least one group independently selected from alkyl, halogen, —OH, —SH, —CN, —$CF_3$, —O-alkyl, and —$NR_5R_6$), halogen, —O-alkyl (optionally substituted with at least one group independently selected from -halogen, —$NR_{21}R_{22}$, —OH, and —CN), -cycloalkyl (optionally substituted with at least one group independently selected from -halogen, —OH, —SH, —CN, $CF_3$, —O-alkyl, and —$NR_5R_6$), —C(O)-(alkyl), —$S(O)_2$—$NR_5R_6$, —C(O)—$NR_5R_6$, and —$S(O)_2$-(alkyl);

$R_{19}$ at each occurrence is heterocycloalkyl wherein at least one carbon is optionally replaced with —C(O)—, —S(O)—, and —$S(O)_2$—, wherein the heterocycloalkyl is optionally substituted with at least one group independently selected from alkyl (optionally substituted with at least one group independently selected from -alkyl, -halogen, —OH, —SH, —CN, —$CF_3$, —O-alkyl, and —$NR_5R_6$), -halogen, —O-alkyl (optionally substituted with at least one group independently selected from -halogen, —OH, —CN, —$NR_{21}R_{22}$, and -cycloalkyl optionally substituted with at least one group independently selected from -halogen, —OH, —SH, —CN, —$CF_3$, —O-alkyl, and —$NR_5R_6$), —C(O)-(alkyl), —$S(O)_2$—$NR_5R_6$, —C(O)—$NR_5R_6$,and —$S(O)_2$-(alkyl);

$R_{11}$ at each occurrence is heterocycloalkyl wherein at least one carbon of the heterocycloalkyl is optionally replaced with —C(O)—, —S(O)—, and —$S(O)_2$—,
wherein the heterocycloalkyl is optionally substituted with at least one group independently selected from -alkyl, —O-alkyl, and -halogen;

$R_{20}$ is selected from -alkyl, -cycloalkyl, —$(CH_2)_{0-2}$—($R_{17}$), and —$(CH_2)_{0-2}$—$R_{18}$);

$R_{200}$ at each occurrence is independently selected from -alkyl (optionally substituted with at least one group independently selected from $R_{205}$), —OH, —$NO_2$, —$NH_2$, -halogen, —CN, —$CF_3$, —$OCF_3$, —$(CH_2)_{0-4}$—C(O)H, —$(CO)_{0-1}R_{215}$, —$(CO)_{0-1}R_{220}$, $(CH_2)_{0-4}$—C(O)—$NR_{220}R_{225}$, —$(CH_2)_{0-4}$—$(C(O))_{0-1}$—$R_{215}$, —$(CH_2)_{0-4}$—$(C(O))_{0-1}$—$R_{220}$, $(CH_2)_{0-4}$—C(O)-alkyl, —$(CH_2)_{0-4}$—$(C(O))_{0-1}$-cycloalkyl, —$(CH_2)_{0-4}$—$(C(O))_{0-1}$-heterocycloalkyl, —$(CH_2)_{0-4}$—$(C(O))_{0-1}$-aryl, —$(CH_2)_{0-4}$—$(C(O))_{0-1}$heteroaryl, $(CH_2)_{0-4}$—C(O)—O—$R_{215}$, —$(CH_2)_{0-4}$—$S(O)_{0-2}$—$NR_{220}R_{225}$, —$(CH_2)_{0-4}$—S$(O)_{0-2}$-alkyl, $(CH_2)_{0-4}$—$S(O)_{0-2}$-cycloalkyl, —$(CH_2)_{0-4}$—N(H or $R_{215}$—C(O)—O—$R_{215}$, —$(CH_2)_{0-4}$—N(H or $R_{215}$)—$S(O)_{1-2}$—$R_{220}$, —$(CH_2)_{0-4}$—N(H or $R_{215}$)—C(O)—$N(R_{215})_2$, —$(CH_2)_{0-4}$—N(H or $R_{215}$)—C(O)—$R_{220}$, —$(CH_2)_{0-4}$—$NR_{220}R_{225}$, —$(CH_2)_{0-4}$—O—C(O)-alkyl, $(CH_2)_{0-4}$—O—($R_{215}$), —$(CH_2)_{0-4}$—S—($R_{215}$), —$(CH_2)_{0-4}$—C(O)H, —$(CH_2)_{0-4}$—O-alkyl optionally substituted with at least one halogen, and -adamantane, wherein each aryl and heteroaryl group included within $R_{200}$ is optionally substituted with at least one group independently selected from —$R_{205}$, —$R_{210}$, and -alkyl optionally substituted with at least one group independently selected from $R_{205}$ and $R_{210}$;

wherein each cycloalkyl or heterocycloalkyl group included within $R_{200}$ is optionally substituted with at least one group independently selected from —$R_{205}$, —$R_{210}$, and -alkyl optionally substituted with at least one group independently selected from $R_{205}$ and $R_{210}$;

$R_{205}$ at each occurrence is independently selected from -alkyl, -heteroaryl, -heterocycloalkyl, -aryl, haloalkoxy, —$(CH_2)_{0-3}$-cycloalkyl, -halogen, —$(CH_2)_{0-6}$—OH, —O-phenyl, —SH, —$(CH_2)_{0-4}$—C(O)$CH_3$, —$(CH_2)_{0-4}$—C(O)H, —$(CH_2)_{0-4}$—$CO_2H$, —$(CH_2)_{0-6}$—CN, —$(CH_2)_{0-6}$—C(O)—$NR_{235}R_{240}$, —$(CH_2)_{0-6}$—C(O)—$R_{235}$, —$(CH_2)_{0-4}$—N(H or $R_{215}$)—$SO_2$—$R_{235}$, —$CF_3$, —CN, —$OCF_3$, —$C(O)_2$-benzyl, —O-alkyl, —$C(O)_2$-alkyl, and —$NR_{235}R_{240}$;

$R_{210}$ at each occurrence is independently selected from —OH, —CN —$(CH_2)_{0-4}$—C(O)H, -alkyl (wherein a carbon atom is optionally replaced with —C(O)—, and wherein a carbon atom is optionally substituted with at least one group independently selected from $R_{205}$), —S-alkyl, -halogen, —O-alkyl, -haloalkoxy, —$NR_{220}R_{225}$, -cycloalkyl (optionally substituted with at least one group independently selected from $R_{205}$), —C(O)-alkyl, —$S(O)_2$—$NR_{235}R_{240}$, —C(O)—$NR_{235}R_{240}$, and —$S(O)_2$-alkyl;

$R_{215}$ at each occurrence is independently selected from -alkyl, —$(CH_2)_{0-2}$-aryl, —$(CH_2)_{0-2}$-cycloalkyl, —$(CH_2)_{0-2}$-heteroaryl, and —$(CH_2)_{0-2}$-heterocycloalkyl,
wherein the aryl groups included within $R_{215}$ are optionally substituted with at least one group independently selected from $R_{205}$ and $R_{210}$,
wherein the heterocycloalkyl and heteroaryl groups included within $R_{215}$ are optionally substituted with at least one group independently selected from $R_{210}$;

$R_{220}$ and $R_{225}$ at each occurrence are independently selected from —H, —OH, -alkyl, —$(CH_2)_{0-4}$—C(O)H, —$(CH_2)_{0-4}$—C(O)$CH_3$, -alkyl-OH, —$(CH_2)_{0-4}$—$CO_2$-alkyl, (wherein alkyl is optionally substituted with at least one group independently selected from $R_{205}$), -aminoalkyl, —$S(O)_2$-alkyl, —$(CH_2)_{0-4}$—C(O)-alkyl, (wherein alkyl is optionally substituted with at least one group independently selected from $R_{205}$), —$(CH_2)_{0-4}$—C(O)—$NH_2$, —$(CH_2)_{0-4}$—C(O)—NH(alkyl), (wherein alkyl is optionally substituted with at least one group independently selected from $R_{205}$), —$(CH_2)_{0-4}$—C(O)—N(alkyl)(alkyl), -haloalkyl, —$(CH_2)_{0-2}$-cycloalkyl, -alkyl-O-alkyl, —O-alkyl, -aryl, -heteroaryl, and -heterocycloalkyl,
wherein the aryl, heteroaryl and heterocycloalkyl groups included within $R_{220}$ and $R_{225}$ are each optionally substituted with at least one group independently selected from $R_{270}$;

$R_{270}$ at each occurrence is independently selected from —$R_{205}$, -alkyl (optionally substituted with at least one group independently selected from $R_{205}$), -phenyl, -halogen, —O-alkyl, -haloalkoxy, —$NR_{235}R_{240}$, —OH, —CN, -cycloalkyl (optionally substituted with at least one group independently selected from $R_{205}$), —C(O)-alkyl, —S(O)$_2$—$NR_{235}R_{240}$, —CO—$NR_{235}R_{240}$, —S(O)$_2$-alkyl, and —(CH$_2$)$_{0-4}$—C(O)H;

$R_{235}$ and $R_{240}$ at each occurrence are independently selected from —H, -alkyl, —C(O)-alkyl, —OH, —CF$_3$, —OCH$_3$, —NH—CH$_3$, —N(CH$_3$)$_2$, —(CH$_2$)$_{0-4}$—C(O)—(H or alkyl), —SO$_2$-alkyl, and -phenyl;

$R_{255}$ is selected from -hydrogen, —OH, —N($R_{220}$)($R_{225}$), and —O-alkyl;

$R_5$ and $R_6$ are independently selected from —H and -alkyl, or $R_5$ and $R_6$, and the nitrogen to which they are attached, form a 5 or 6 membered heterocycloalkyl ring; and $R_7$ is independently selected from —H, -alkyl (optionally substituted with at least one group independently selected from —OH, amino, and halogen), -cycloalkyl, and -alkyl-O-alkyl.

Exemplary $R_{600}$ substituents of monocyclic, bicyclic, or tricyclic heteroaryls include Benzo[4,5]thieno[3,2-d]pyrimidin-4-yl, 4,6-Diamino-[1,3,5]triazin-2-yl, 3-nitro-pyridin-2-yl, 5-trifluoromethyl-pyridin-2-yl, 8-trifluoromethyl-quinolin-4-yl, 4-trifluoromethyl-pyrimidin-2-yl, 2-phenyl-quinazolin-4-yl, 6-Chloro-pyrazin-2-yl, pyrimidin-2-yl, quinolin-2-yl, 3-Chloro-pyrazin-2-yl, 6-Chloro-2,5-diphenyl-pyrimidin-4-yl, 3-Chloro-quinoxalin-2-yl, 5-ethyl-pyrimidin-2-yl, 6-Chloro-2-methylsulfanyl-5-phenyl-pyrimidin-4-yl, quinolin-4-yl, 3-ethoxycarbonyl-pyridin-2yl, 5-Cyano-pyridin-2-yl, 2-phenyl-quinolin-4-yl, 7H-purin-6-yl, 3-Cyano-pyridin-2-yl, 4,6-dimethoxy-[1,3,5]triazin-2-yl, 3-Cyano-pyrazin-2-yl, 9-(tetrahydro-pyran-2-yl)-9H-purin-6-yl, 2-Chloro-7H-purin-6-yl, 2-Amino-6-chloro-pyrimidin-4-yl, 2-Chloro-6-methyl-pyrimidin-4-yl, 2-Amino-6-methyl-pyrimidin-4-yl, 4-Chloro-pyrimidin-2-yl, 2-Amino-7H-purin-6-yl, and 4-trifluoromethyl-pyrimidin-2-yl, and the like.

Exemplary $R_2$ substituents include 3-Allyl-5-benzyl-2-oxo-imidazolidin-1-yl, 6-Benzyl-3,3-dimethyl-2-oxo-piperazin-1-yl, 3-Allyl-5-benzyl-2-oxo-pyrrolidin-1-yl, 5-Benzyl-3-isobutyl-2-oxo-imidazolidin-1-yl, 3-Benzyl-5-methyl-1,1-dioxo-1$\lambda^6$-[1,2,5]thiadiazolidin-2-yl, 3-Benzyl-1,1-dioxo-1$\lambda^6$-isothiazolidin-2-yl, 2-Benzyl-5-oxo-pyrrolidin-1-yl, 5-Benzyl-3-ethyl-2-oxo-pyrrolidin-1-yl, 3-Amino-5-benzyl-2-oxo-pyrrolidin-1-yl, 3-Acetylamino-5-benzyl-2-oxo-pyrrolidin-1-yl, 5-Benzyl-3-[1,3]dioxolan-4-ylmethyl-2-oxo-pyrrolidin-1-yl, 3-Benzyl-5-oxo-morpholin-4-yl, 2-Benzyl-6-oxo-piperazin-1-yl, 8-Benzyl-6-methyl-10-oxo-6,9-diaza-spiro[4,5]dec-9-yl, 5-Benzyl-3-furan-2-ylmethylene-2-oxo-pyrrolidin-1-yl, 3-acetylamino-3-(sec-butyl)-2-oxo-pyrrolidin-1-yl, 3-acetylamino-3-(cyclopropylmethyl)-2-oxo-pyrrolidin-1-yl, 3-(2-amino-5-carboxypentanoylamino)-3-(sec-butyl)-2-oxo-pyrrolidin-1-yl, 3-(2-methoxy-acetylamino)-3-(sec-butyl)-2-oxo-pyrrolidin-1-yl, 3-ethoxycarbonylamino-3-(sec-butyl)-2-oxo-pyrrolidin-1-yl, 3-ethylureido-3-(sec-butyl)-2-oxo-pyrrolidin-1-yl, and 3-hydroxypropionylamino-3-(sec-butyl)-2-oxo-pyrrolidin-1-yl.

In another embodiment, compounds of formula (I) are used to prevent or treat conditions associated with amyloidosis, wherein $R_C$, $R_1$, and $R_2$ are defined herein, excluding the combinations wherein, $R_C$ is 3-methoxy-benzyl, $R_1$ is 3,5-difluorobenzyl, and $R_2$ is 4,6-Diamino-[1,3,5]triazin-2-ylamino, 3-nitro-pyridin-2-ylamino, 5-trifluoromethyl-pyridin-2-ylamino, 8-trifluoromethyl-quinolin-4-ylamino, 4-trifluoromethyl-pyrimidin-2-ylamino, 2-phenyl-quinazolin-4-ylamino, 6-Chloro-pyrazin-2-ylamino, pyrimidin-2-ylamino, quinolin-2-ylamino, 3-Chloro-pyrazin-2-ylamino, 6-Chloro-2,5-diphenyl-pyrimidin-4-ylamino, 3-Chloro-quinoxalin-2-ylamino, 5-ethyl-pyrimidin-2-ylamino, 6-Chloro-2-methylsulfanyl-5-phenyl-pyrimidin-4-ylamino, quinolin-4-ylamino, 3-ethoxycarbonyl-pyridin-2ylamino, 5-Cyano-pyridin-2-ylamino, 2-phenyl-quinolin-4-ylamino, 7H-purin-6-ylamino, 3-Cyano-pyridin-2-ylamino, 4,6-dimethoxy-[1,3,5]triazin-2-ylamino, 3-Cyano-pyrazin-2-ylamino, 9-(tetrahydro-pyran-2-yl)-9H-purin-6-ylamino, 2-Chloro-7H-purin-6-ylamino, 2-Amino-6-chloro-pyrimidin-4-ylamino, 2-Chloro-6-methyl-pyrimidin-4-ylamino, 2-Amino-6-methyl-pyrimidin-4-ylamino, 4-Chloro-pyrimidin-2-ylamino, 2-Amino-7H-purin-6-ylamino, and the like.

In another embodiment, compounds of formula (I) are used to prevent or treat conditions associated with amyloidosis, wherein RC, $R_1$, and $R_2$ are defined herein, excluding the combinations wherein $R_C$ is 6-ethyl-2,2-dioxo-2$\lambda^6$-isothiochroman-4-yl, $R_1$ is 3,5-difluorobenzyl, and $R_2$ is 4-trifluoromethyl-pyrimidin-2-ylamino.

In another embodiment, $R_1$ is selected from —CH$_2$-phenyl, wherein the phenyl ring is optionally substituted with at least one group independently selected from -halogen, —C$_1$-C$_2$ alkyl, —O-methyl, and —OH.

In another embodiment, $R_1$ is selected from 4-hydroxybenzyl, 3-hydroxy-benzyl, 5-chloro-thiophen-2-yl-methyl, 5-chloro-3-ethyl-thiophen-2-yl-methyl, 3,5-difluoro-2-hydroxy-benzyl, piperidin-4-yl-methyl, 2-oxo-piperidin-4-yl-methyl, 2-oxo-1,2-dihydro-pyridin-4-yl-methyl, 5-hydroxy-6-oxo-6H-pyran-2-yl-methyl, 3,5-difluoro-4-hydroxy-benzyl, 3,5-difluoro-benzyl, 3-fluoro-4-hydroxy-benzyl, 3-fluoro-5-hydroxy-benzyl, and 3-fluoro-benzyl.

In another embodiment, $R_C$ is —C($R_{245}R_{250}$)—$R_X$, wherein $R_{245}$ and $R_{250}$ are taken together with the carbon to which they are attached to form a monocyclic or bicyclic ring system of 3, 4, 5, 6, 7, 8, 9, or 10 carbon atoms, wherein at least one bond in the monocyclic or bicyclic ring system is optionally a double bond, wherein the bicyclic ring system is optionally a fused or spiro ring system, and wherein at least one atom within the monocyclic or bicyclic ring system is optionally replaced by a group independently selected from —O—, —C(O)—, —S(O)$_{0-2}$—, —C(=N—$R_{255}$)—, —N—, —NR$_{220}$—, —N((CO)$_{0-1}$R$_{200}$ and —N(SO$_2$R$_{200}$)—; and wherein the monocyclic or bicyclic groups included within $R_{245}$ and $R_{250}$ are optionally substituted with at least one group independently selected from halogen, —(CH$_2$)$_{0-2}$—OH, —(CH$_2$)$_{0-2}$—S-alkyl, —CF$_3$, —O-alkyl, alkyl, aryl, —N($R_{220}R_{225}$), —CN, —(CH$_2$)$_{0-2}$—NH$_2$, —(CH$_2$)$_{0-2}$—NH(alkyl), —NHOH, —NH—O-alkyl, —N(alkyl)(alkyl), —NH-heteroaryl, —NH—C(O)-alkyl, and —NHS(O$_2$)-alkyl.

In another embodiment, $R_C$ is selected from formulae (Va), (Vb), (Vc), and (Vd),

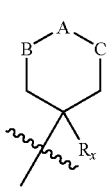

(Va)

-continued

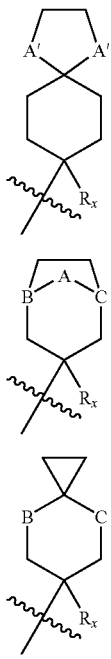

(Vb)

(Vc)

(Vd)

wherein
A, B, and C are independently selected from —CH$_2$—, —O—, —C(O)—, —S(O)$_{0-2}$—, —N((CO)$_{0-1}$R$_{200}$)—, —N(SO$_2$R$_{200}$)—, —C(=N—R$_{255}$) and —N(R$_{220}$)—;
A' at each occurence is independently selected from —CH$_2$— and —O—;
  wherein (Va), (Vb), (Vc), and (Vd) are each optionally substituted with at least one group independently selected from -alkyl, —O-alkyl, —(CH$_2$)$_{0-2}$—OH, —(CH$_2$)$_{0-2}$—S-alkyl, —CF$_3$, —CN, -halogen, —(CH$_2$)$_{0-2}$—NH$_2$, —(CH$_2$)$_{0-2}$—NH(alkyl), —NHOH, —NH—O-alkyl, —N(alkyl)(alkyl), —NH-heteroaryl, —NH—C(O)-alkyl, and —NHS(O$_2$)-alkyl.

In another embodiment, R$_C$ is selected from formulae (VIa) and (VIb),

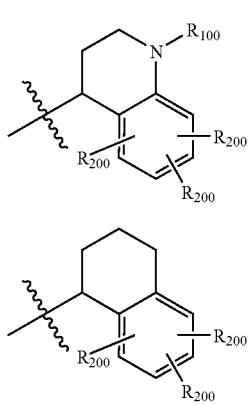

(VIa)

(VIb)

wherein at least one carbon of the heterocycloalkyl of formula (VIa) and the cycloalkyl of formula (VIb) is optionally replaced with a group independently selected from —O—, —SO$_2$—, and —C(O)—, wherein at least one carbon of the heterocycloalkyl or cycloalkyl is optionally substituted with at least one group independently selected from R$_{205}$, R$_{245}$, and R$_{250}$, wherein R$_{100}$, R$_{200}$, R$_{205}$, R$_{245}$, and R$_{250}$ are as defined herein.

In another embodiment, R$_C$ is selected from 6-isobutyl-1,1-dioxo-1λ$^6$-thiochroman-4-yl, 6-isopropyl-2,2-dioxo-2λ$^6$-isothiochroman-4-yl, 6-ethyl-2,2-dioxo-2λ$^6$-isothiochroman-4-yl, 7-ethyl-1,2,3,4-tetrahydro-naphthalen-1-yl, 1-(3-tert-Butyl-phenyl)-cyclohexyl, and 3-methoxy-benzyl.

In another embodiment, R$_2$ is selected from hydrogen, 3-Bromo-[1,2,4]thiadiazol-5-ylamino, [1,2,4]thiadiazol-5-ylamino, 4-Chloro-[1,2,5]thiadiazol-3-ylamino, [1,2,5]thiadiazol-3-ylamino, thiazol-2-ylamino, 5-Bromo-[1,3,4]thiadiazol-2-ylamino, [1,3,4]thiadiazol-2-ylamino, 5-Amino-[1,3,4]thiadiazol-2-ylamino, 2-Bromo-thiazol-5-ylamino, thiazol-5-ylamino, 5-trifluoromethyl-[1,3,4]thiadiazol-2-ylamino, 5-trifluoromethyl-[1,3,4]oxadiazol-2-ylamino, 5-Amino-[1,3,4]oxadiazol-2-ylamino, 1-trityl-1H-[1,2,4]triazol-3-ylamino, 1H-[1,2,4]triazol-3-ylamino, oxazol-2-ylamino, 5-Bromo-2-trityl-2H-[1,2,3]triazol-4-ylamino, 2-trityl-2H-[1,2,3]triazol-4-ylamino, 5-Bromo-2H-[1,2,3]triazol-4-ylamino, 2H-[1,2,3]triazol-4-ylamino, thiophen-2-ylamino, 3-methyl-5-nitro-3H-imidazol-4-ylamino, 4-Cyano-5-phenyl-isothiazol-3-ylamino, 4-phenyl-[1,2,5]thiadiazol-3-ylamino, 3,4-dioxo-cyclobut-1-enylamino, 2-methoxy-3,4-dioxo-cyclobut-1-enylamino, and 2-methylamino-3,4-dioxo-cyclobut-enylamino.

In another embodiment, R$_X$ is selected from 3-(1,1-dimethyl-propyl)-phenyl, 3-(1)-ethyl-propyl)-phenyl, 3-(1H-pyrrol-2-yl)-phenyl, 3-(1-hydroxy-1-methyl-ethyl-phenyl, 3-(1-methyl-1H-imidazol-2-yl)-phenyl, 3-(1-methyl-cyclopropyl)-phenyl, 3-(2,2-dimethyl-propyl)-phenyl, 3-(2,5-dihydro-1H-pyrrol-2-yl)-phenyl, 3-(2-Chloro-thiophen-3-yl)-phenyl, 3-(2-Cyano-thiophen-3-yl)-phenyl, 3-(2-fluoro-benzyl-phenyl, 3-(3,5-dimethyl-3H-pyrazol-4-yl)-phenyl, 3-(3,6-dimethyl-pyrazin-2-yl)-phenyl, 3-(3-Cyano-pyrazin-2-yl)-phenyl, 3-(3-formyl-furan-2-yl)-phenyl, 3-(3H-[1,2,3]triazol-4-yl)-phenyl, 3-(3H-imidazol-4-yl)-phenyl, 3-(3-methyl-butyl)-phenyl, 3-(3-methyl-pyridin-2-yl)-phenyl, 3-(3-methyl-thiophen-2-yl)-phenyl, 3-(4-Cyano-pyridin-2-yl)-phenyl, 3-(4-fluoro-benzyl)-phenyl, 3-(4H-[1,2,4]triazol-3-yl)-phenyl, 3-(4-methyl-thiophen-2-yl)-phenyl, 3-(5-Acetyl-thiophen-2-yl)-phenyl, 3-(5-Acetyl-thiophen-3-yl)-phenyl, 3-(5-formyl-thiophen-2-yl)-phenyl, 3-(5-oxo-pyrrolidin-2-yl)-phenyl, 3-(6-methyl-pyridazin-3-yl)-phenyl, 3-(6-methyl-pyridin-2-yl)-phenyl, 3-(Cyano-dimethyl-methyl)-phenyl, 3-[1-(2-tert-Butyl-pyrimidin-4-yl)-]cyclohexylamino, 3-[1,2,3]triazol-1-yl-phenyl, 3-[1,2,4]oxadiazol-3-yl-phenyl, 3-[1,2,4]oxadiazol-5-yl-phenyl, 3-[1,2,4]thiadiazol-3-yl-phenyl, 3-[1,2,4]thiadiazol-5-yl-phenyl, 3-[1,2,4]triazol-4-yl-phenyl, 3-Acetyl-5-tert-butyl-phenyl, 3'-Acetylamino-biphenyl-3-yl, 3-Adamantan-2-yl-phenyl, 3-Bromo-[1,2,4]thiadiazol-5-yl-phenyl, 3-Bromo-5-tert-butyl-phenyl, 3-Cyano-phenyl, 3-Cyclobutyl-phenyl, 3-Cyclopentyl-phenyl, 3-Cyclopropyl-phenyl, 3-ethyl-phenyl, 3-ethynyl-phenyl, 3-fluoro-5-(2-hydroxy-1,1-dimethyl-ethyl)-phenyl, 3-furan-3-yl-phenyl, 3-imidazol-1-yl-phenyl, 3-isobutyl-phenyl, 3-isopropyl-phenyl, 3-isoxazol-3-yl-phenyl, 3-isoxazol-4-yl-phenyl, 3-isoxazol-5-yl-phenyl, 3-pent-4-enyl-phenyl, 3-pentyl-phenyl, 3-Phenyl-propionic acid ethyl ester, 3-pyrazin-2-yl-phenyl, 3-pyridin-2-yl-phenyl, 3-pyrrolidin-2-yl-phenyl, 3-sec-Butyl-phenyl, 3-tert-Butyl-4-chloro-phenyl, 3-tert-Butyl-4-cyano-phenyl, 3-tert-Butyl-4-ethyl-phenyl, 3-tert-Butyl-4-methyl-phenyl, 3-tert-Butyl-4-trifluoromethyl-phenyl, 3-tert-Butyl-5-chloro-phenyl, 3-tert-Butyl-5-cyano-phenyl, 3-tert-Butyl-5-ethyl-phenyl, 3-tert- Butyl-5-fluoro-phenyl, 3-tert-Butyl-5-methyl-phenyl, 3-tert-Butyl-5-trifluoromethyl-phenyl, 3-tert-Butyl-phenyl, 3-thiazol-2-yl-phenyl, 3-thiazol-4-yl-phenyl, 3-thiophen-3-yl-phenyl, 3-trifluoromethyl-phenyl, 4-Acetyl-3-tert-butyl-phenyl, 4-tert-Butyl-pyridin-2-yl, 4-tert-Butyl-pyrimidin-2-yl, 5-tert-Butyl-pyridazin-3-yl, 6-tert-Butyl-pyridazin-4-yl, and 6-tert-Butyl-pyrimidin-4-yl.

In another embodiment, the present invention encompasses compounds of formula (I) wherein the hydroxyl substituent alpha to the —$(CHR_1)$— group, as shown in formula (I), may optionally be replaced by —$NH_2$, —$NH(R_{800})$, —$N(R_{800})(R_{800})$, —SH, and —$SR_{800}$, wherein —$R_{800}$ is alkyl optionally substituted with at least one group independently selected from $R_{200}$, $R_{205}$, $R_{210}$, $R_{215}$, $R_{220}$, and $R_{225}$.

The present invention encompasses methods of treatment using compounds with structural characteristics designed for interacting with their target molecules. Such characteristics include at least one moiety capable of interacting with at least one subsite of beta-secretase. Such characteristics also include at least one moiety capable of enhancing the interaction between the target and at least one subsite of beta-secretase.

It is preferred that the compounds of formula (I) are efficacious. For example, it is preferred that the compounds of formula (I) decrease the level of beta-secretase using low dosages of the compounds. Preferably, the compounds of formula (I) decrease the level of A-beta by at least 10% using dosages of 100 mg/kg. It is more preferred that the compounds of formula (I) decrease the level of A-beta by at least 10% using dosages of less than 100 mg/kg. It is also more preferred that the compounds of formula (I) decrease the level of A-beta by greater than 10% using dosages of 100 mg/kg. It is most preferred that the compounds of formula (I) decrease the level of A-beta by greater than 10% using dosages of less than 100 mg/kg.

Another embodiment of the present invention is to provide methods of preventing or treating conditions associated with amyloidosis using compounds with increased oral bioavailability (increased F values).

Accordingly, an embodiment of the present invention is also directed to methods for preventing or treating conditions associated with amyloidosis, comprising administering to a host a therapeutically effective amount of at least one compound of formula (I), or a pharmaceutically acceptable salt thereof, wherein $R_1$, $R_2$, and $R_C$ are as previously defined, and wherein the compound has an F value of at least 10%.

Investigation of potential beta-secretase inhibitors produced compounds with increased selectivity for beta-secretase over other aspartyl proteases such as cathepsin D (catD), cathepsin E (catE), HIV protease, and renin. Selectivity was calculated as a ratio of inhibition (IC50) values in which the inhibition of beta-secretase was compared to the inhibition of other aspartyl proteases. A compound is selective when the IC50 value (i.e., concentration required for 50% inhibition) of a desired target (e.g., beta-secretase) is less than the IC50 value of a secondary target (e.g., catD). Alternatively, a compound is selective when its binding affinity is greater for its desired target (e.g., beta-secretase) versus a secondary target (e.g., catD). Accordingly, methods of treatment include administering selective compounds of formula (I) having a lower IC50 value for inhibiting beta-secretase, or greater binding affinity for beta-secretase, than for other aspartyl proteases such as catD, catE, HIV protease, or renin. A selective compound is also capable of producing a higher ratio of desired effects to adverse effects, resulting in a safer method of treatment.

In an embodiment, the host is a cell.

In another embodiment, the host is an animal.

In another embodiment, the host is human.

In another embodiment, at least one compound of formula (I) is administered in combination with a pharmaceutically acceptable carrier or diluent.

In another embodiment, the pharmaceutical compositions comprising compounds of formula (I) can be used to treat a wide variety of disorders or conditions including Alzheimer's disease, Down's syndrome or Trisomy 21 (including mild cognitive impairment (MCI) Down's syndrome), hereditary cerebral hemorrhage with amyloidosis of the Dutch type, chronic inflammation due to amyloidosis, prion diseases (including Creutzfeldt-Jakob disease, Gerstmann-Straussler syndrome, kuru scrapie, and animal scrapie), Familial Amyloidotic Polyneuropathy, cerebral amyloid angiopathy, other degenerative dementias including dementias of mixed vascular and degenerative origin, dementia associated with Parkinson's disease, dementia associated with progressive supranuclear palsy and dementia associated with cortical basal degeneration, diffuse Lewy body type of Alzheimer's disease, and frontotemporal dementias with parkinsonism (FTDP), In another embodiment, the condition is Alzheimer's disease.

In another embodiment, the condition is dementia.

When treating or preventing these diseases, the methods of the present invention can either employ the compounds of formula (I) individually or in combination, as is best for the patient.

In treating a patient displaying any of the conditions discussed above, a physician may employ a compound of formula (I) immediately and continue administration indefinitely, as needed. In treating patients who are not diagnosed as having Alzheimer's disease, but who are believed to be at substantial risk for it, the physician may start treatment when the patient first experiences early pre-Alzheimer's symptoms, such as memory or cognitive problems associated with aging. In addition, there are some patients who may be determined to be at risk for developing Alzheimer's disease through the detection of a genetic marker such as APOE4 or other biological indicators that are predictive for Alzheimer's disease and related conditions. In these situations, even though the patient does not have symptoms of the disease or condition, administration of the compounds of formula (I) may be started before symptoms appear, and treatment may be continued indefinitely to prevent or delay the onset of the disease. Similar protocols are provided for other diseases and conditions associated with amyloidosis, such as those characterized by dementia.

In an embodiment, the methods of preventing or treating conditions associated with amyloidosis, comprising administering to a host a composition comprising a therapeutically effective amount of at least one compound of formula (I), may include beta-secretase complexed with at least one compound of formula (I), or a pharmaceutically acceptable salt thereof.

An embodiment of the present invention is a method of preventing or treating the onset of Alzheimer's disease comprising administering to a patient a therapeutically effective amount of at least one compound of formula (I), or a pharmaceutically acceptable salt thereof, wherein $R_1$, $R_2$, and $R_C$ are as previously defined.

Another embodiment of the present invention is a method of preventing or treating the onset of dementia comprising administering to a patient a therapeutically effective amount of at least one compound of formula (I), or a pharmaceutically acceptable salt thereof, wherein $R_1$, $R_2$, and $R_C$ are as previously defined.

Another embodiment of the present invention is a method of preventing or treating conditions associated with amyloidosis by administering to a host an effective amount of at least one compound of formula (I), or a pharmaceutically acceptable salt thereof, wherein $R_1$, $R_2$, and $R_C$ are as previously defined.

Another embodiment of the present invention is a method of preventing or treating Alzheimer's Disease by administering to a host an effective amount of at least one compound of formula (I), or a pharmaceutically acceptable salt thereof, wherein $R_1$, $R_2$, and $R_C$ are as previously defined.

Another embodiment of the present invention is a method of preventing or treating dementia by administering to a host an effective amount of at least one compound of formula (I), or a pharmaceutically acceptable salt thereof, wherein $R_1$, $R_2$, and $R_C$ are as previously defined.

Another embodiment of the present invention is a method of inhibiting beta-secretase activity in a cell. This method comprises administering to the cell an effective amount of at least one compound of formula (I), or a pharmaceutically acceptable salt thereof, wherein $R_1$, $R_2$, and $R_C$ are as previously defined.

Another embodiment of the present invention is a method of inhibiting beta-secretase activity in a host. This method comprises administering to the host an effective amount of at least one compound of formula (I), or a pharmaceutically acceptable salt thereof, wherein $R_1$, $R_2$, and $R_C$ are as previously defined.

Another embodiment of the present invention is a method of inhibiting beta-secretase activity in a host. This method comprises administering to the host an effective amount of at least one compound of formula (I), or a pharmaceutically acceptable salt thereof, wherein $R_1$, $R_2$, and $R_C$ are as previously defined, and wherein the host is a human.

Another embodiment of the present invention is a method of affecting beta-secretase-mediated cleavage of amyloid precursor protein in a patient, comprising administering a therapeutically effective amount of at least one compound of formula (I), or a pharmaceutically acceptable salt thereof, wherein $R_1$, $R_2$, and $R_C$ are as previously defined.

Another embodiment of the present invention is a method of inhibiting cleavage of amyloid precursor protein at a site between Met596 and Asp597 (numbered for the APP-695 amino acid isotype), or at a corresponding site of an isotype or mutant thereof, comprising administering a therapeutically effective amount of at least one compound of formula (I), or a pharmaceutically acceptable salt thereof, wherein $R_1$, $R_2$, and $R_C$ are as previously defined.

Another embodiment of the present invention is a method of inhibiting cleavage of amyloid precursor protein or mutant thereof at a site between amino acids, comprising administering a therapeutically effective amount of at least one compound of formula (I), or a pharmaceutically acceptable salt thereof, wherein $R_1$, $R_2$, and $R_C$ are as previously defined, and wherein the site between amino acids corresponds to between Met652 and Asp653 (numbered for the APP-751 isotype), between Met671 and Asp672 (numbered for the APP-770 isotype), between Leu596 and Asp597 of the APP-695 Swedish Mutation, between Leu652 and Asp853 of the APP-751 Swedish Mutation, or between Leu671 and Asp672 of the APP-770 Swedish Mutation.

Another embodiment of the present invention is a method of inhibiting production of A-beta, comprising administering to a patient a therapeutically effective amount of at least one compound of formula (I), or a pharmaceutically acceptable salt thereof, wherein $R_1$, $R_2$, and $R_C$ are as previously defined.

Another embodiment of the present invention is a method of preventing or treating deposition of A-beta, comprising administering a therapeutically effective amount of at least one compound of formula (I), or a pharmaceutically acceptable salt thereof, wherein $R_1$, $R_2$, and $R_C$ are as previously defined.

Another embodiment of the present invention is a method of preventing, delaying, halting, or reversing a disease characterized by A-beta deposits or plaques, comprising administering a therapeutically effective amount of at least one compound of formula (I), or a pharmaceutically acceptable salt thereof, wherein $R_1$, $R_2$, and $R_C$ are as previously defined.

In another embodiment, the A-beta deposits or plaques are in a human brain.

Another embodiment of the present invention is a method of preventing, delaying, halting, or reversing a condition associated with a pathological form of A-beta in a host comprising administering to a patient in need thereof an effective amount of at least one compound of formula (I), or a pharmaceutically acceptable salt thereof, wherein $R_1$, $R_2$, and $R_C$ are as previously defined.

Another embodiment of the present invention is a method of inhibiting the activity of at least one aspartyl protease in a patient in need thereof, comprising administering a therapeutically effective amount of at least one compound of formula (I), or a pharmaceutically acceptable salt thereof to the patient, wherein $R_1$, $R_2$, and $R_C$ are as previously defined.

In another embodiment, the at least one aspartyl protease is beta-secretase.

Another embodiment of the present invention is a method of interacting an inhibitor with beta-secretase, comprising administering to a patient in need thereof a therapeutically effective amount of at least one compound of formula (I), or a pharmaceutically acceptable salt thereof, wherein $R_1$, $R_2$, and $R_C$ are as previously defined, and wherein the at least one compound interacts with at least one beta-secretase subsite such as S1, S1' or S2'.

Another embodiment of the present invention is a method of selecting a compound of formula (I) wherein the pharmacokinetic parameters are adjusted for an increase in desired effect (e.g., increased brain uptake).

Another embodiment of the present invention is a method of selecting a compound of formula (I) wherein $C_{max}$, $T_{max}$ and/or half-life are adjusted to provide for maximum efficacy.

Another embodiment of the present invention is a method of treating a condition in a patient, comprising administering a therapeutically effective amount of at least one compound of formula (I), or a pharmaceutically acceptable salt, derivative or biologically active metabolite thereof, to the patient, wherein $R_1$, $R_2$, and $R_C$ are as previously defined.

In another embodiment, the condition is Alzheimer's disease.

In another embodiment, the condition is dementia.

In another embodiment of the present invention, the compounds of formula (I) are administered in oral dosage form. The oral dosage forms are generally administered to the patient 1, 2, 3, or 4 times daily. It is preferred that the compounds be administered either three or fewer times daily, more preferably once or twice daily. It is preferred that, whatever oral dosage form is used, it be designed so as to protect the compounds from the acidic environment of the stomach. Enteric coated tablets are well known to those skilled in the art. In addition, capsules filled with small spheres, each coated to be protected from the acidic stomach, are also well known to those skilled in the art.

Therapeutically effective amounts include, for example, oral administration from about 0.1 mg/day to about 1,000 mg/day, parenteral, sublingual, intranasal, intrathecal administration from about 0.2 mg/day to about 100 mg/day, depot administration and implants from about 0.5 mg/day to about 50 mg/day, topical administration from about 0.5 mg/day to about 200 mg/day, and rectal administration from about 0.5 mg/day to about 500 mg/day.

When administered orally, an administered amount therapeutically effective to inhibit beta-secretase activity, to inhibit A-beta production, to inhibit A-beta deposition, or to treat or prevent Alzheimer's disease is from about 0.1 mg/day to about 1,000 mg/day.

In various embodiments, the therapeutically effective amount may be administered in, for example, pill, tablet, capsule, powder, gel, or elixir form, and/or combinations thereof. It is understood that, while a patient may be started at one dose or method of administration, that dose or method of administration may be varied over time as the patient's condition changes.

Another embodiment of the present invention is a method of prescribing a medication for preventing, delaying, halting, or reversing disorders, conditions or diseases associated with amyloidosis. The method includes identifying in a patient symptoms associated with disorders, conditions or diseases associated with amyloidosis, and prescribing at least one dosage form of at least one compound of formula (I), or a pharmaceutically acceptable salt, to the patient, wherein $R_1$, $R_2$, and $R_C$ are as previously defined.

Another embodiment of the present invention is an article of manufacture, comprising (a) at least one dosage form of at least one compound of formula (I), or a pharmaceutically acceptable salt thereof, wherein $R_1$, $R_2$, and $R_C$ are as previously defined, (b) a package insert providing that a dosage form comprising a compound of formula (I) should be administered to a patient in need of therapy for disorders, conditions or diseases associated with amyloidosis, and (c) at least one container in which at least one dosage form bf at least one compound of formula (I) is stored.

Another embodiment of the present invention is a packaged pharmaceutical composition for treating conditions related to amyloidosis, comprising (a) a container which holds an effective amount of at least one compound of formula (I), or a pharmaceutically acceptable salt thereof, and (b) instructions for using the pharmaceutical composition.

Another embodiment of the present invention is an article of manufacture, comprising (a) a therapeutically effective amount of at least one compound of formula (I), or a stereoisomer, or pharmaceutically acceptable salt thereof, wherein $R_1$, $R_2$, and $R_C$ are as previously defined, (b) a package insert providing an oral dosage form should be administered to a patient in need of therapy for disorders, conditions or diseases associated with amyloidosis, and (c) at least one container comprising at least one oral dosage form of at least one compound of formula (I).

Another embodiment of the present invention is an article of manufacture, comprising (a) at least one oral dosage form of at least one compound of formula (I), or a pharmaceutically acceptable salt thereof, wherein $R_1$, $R_2$, and $R_C$ are as previously defined, in a dosage amount ranging from about 2 mg to about 1000 mg, associated with (b) a package insert providing that an oral dosage form comprising a compound of formula (I) in a dosage amount ranging from about 2 mg to about 1000 mg should be administered to a patient in need of therapy for disorders, conditions or diseases associated with amyloidosis, and (c) at least one container in which at least one oral dosage form of at least one compound of formula (I) in a dosage amount ranging from about 2 mg to about 1000 mg is stored.

Another embodiment of the present invention is an article of manufacture, comprising (a) at least one oral dosage form of at least one compound of formula (I) in a dosage amount ranging from about 2 mg to about 1000 mg in combination with (b) at least one therapeutically active agent, associated with (c) a package insert providing that an oral dosage form comprising a compound of formula (I) in a dosage amount ranging from about 2 mg to about 1000 mg in combination with at least one therapeutically active agent should be administered to a patient in need of therapy for disorders, conditions or diseases associated with amyloidosis, and (d) at least one container in which at least one dosage form of at least one compound of formula (I) in a dosage amount ranging from about 2 mg to about 1000 mg in combination with a therapeutically active agent is stored.

Another embodiment of the present invention is an article of manufacture, comprising (a) at least one parenteral dosage form of at least one compound of formula (I) in a dosage amount ranging from about 0.2 mg/mL to about 50 mg/mL, associated with (b) a package insert providing that a parenteral dosage form comprising a compound of formula (I) in a dosage amount ranging from about 0.2 mg/mL to about 50 mg/mL should be administered to a patient in need of therapy for disorders, conditions or diseases associated with amyloidosis, and (c) at least one container in which at least one parenteral dosage form of at least one compound of formula (I) in a dosage amount ranging from about 0.2 mg/mL to about 50 mg/mL is stored.

Another embodiment of the present invention is an article of manufacture comprising (a) a medicament comprising an effective amount of at least one compound of formula (I) in combination with active and/or inactive pharmaceutical agents, (b) a package insert providing that an effective amount of at least one compound of formula (I) should be administered to a patient in need of therapy for disorders, conditions or diseases associated with amyloidosis, and (c) a container in which a medicament comprising an effective amount of at least one compound of formula (I) in combination with a therapeutically active and/or inactive agent is stored.

In another embodiment, the therapeutically active agent is selected from an antioxidant, an anti-inflammatory, a gamma-secretase inhibitor, a neurotrophic agent, an acetyl cholinesterase inhibitor, a statin, an A-beta, and/or an anti-A-beta antibody.

Another embodiment of the present invention is a method of producing a beta-secretase complex comprising exposing beta-secretase to a compound of formula (I), or a pharmaceutically acceptable salt thereof, in a reaction mixture under conditions suitable for the production of the complex.

Another embodiment of the present invention is a manufacture of a medicament for preventing, delaying, halting, or reversing Alzheimer's disease, comprising adding an effective amount of at least one compound of formula (I) to a pharmaceutically acceptable carrier.

Another embodiment of the present invention provides a method of selecting a beta-secretase inhibitor comprising targeting at least one moiety of at least one formula (I) compound, or a pharmaceutically acceptable salt thereof, to interact with at least one beta-secretase subsite such as, but not limited to, S1, S1' or S2'.

The methods of treatment described herein include administering the compounds of formula (I) orally, parenterally (via intravenous injection (IV), intramuscular injection (IM), depo-IM, subcutaneous injection (SC or SQ), or depo-SQ), sublingually, intranasally (inhalation), intrathecally, topically, or rectally. Dosage forms known to those skilled in the art are suitable for delivery of the compounds of formula (I).

In treating or preventing the above diseases, the compounds of formula (I) are administered using a therapeutically effective amount. The therapeutically effective amount will vary depending on the particular compound used and the route of administration, as is known to those skilled in the art.

The compositions are preferably formulated as suitable pharmaceutical preparations, such as for example but not limited to, pill, tablet, capsule, powder, gel, or elixir form, and/or combinations thereof, for oral administration or in sterile solutions or suspensions for parenteral administration. Typically the compounds described above are formulated into pharmaceutical compositions using techniques and/or procedures well known in the art.

For example, a therapeutically effective amount of a compound or mixture of compounds of formula (I), or a physiologically acceptable salt is combined with a physiologically acceptable vehicle, carrier, binder, preservative, stabilizer, flavor, and the like, in a unit dosage form as called for by accepted pharmaceutical practice, and as defined herein. The amount of active substance in those compositions or preparations is such that a suitable dosage in the range indicated is obtained. The compound concentration is effective for delivery of an amount upon administration that lessens or ameliorates at least one symptom of the disorder for which the compound is administered. For example, the compositions can be formulated in a unit dosage form, each dosage containing from about 2 mg to about 1000 mg.

The active ingredient may be administered in a single dose, or may be divided into a number of smaller doses to be administered at intervals of time. It is understood that the precise dosage and duration of treatment is a function of the disease or condition being treated and may be determined empirically using known testing protocols or by extrapolation from in vivo or in vitro test data. It is to be noted that concentrations and dosage values may also vary with the severity of the condition to be alleviated. It is also to be understood that the precise dosage and treatment regimens may be adjusted over time according to the individual need and the professional judgment of the person administering or supervising the administration of the compositions, and that the concentration ranges set forth herein are exemplary only and are not intended to limit the scope or practice of the claimed compositions. A dosage and/or treatment method for any particular patient also may depend on, for example, the age, weight, sex, diet, and/or health of the patient, the time of administration, and/or any relevant drug combinations or interactions.

To prepare compositions to be employed in the methods of treatment, at least one compound of formula (I) is mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. An effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. Additionally, the active materials can also be mixed with other active materials that do not impair the desired action, or with materials that supplement the desired action, or have another action. For example, the compounds of formula (I) may be formulated as the sole pharmaceutically active ingredient in the composition or may be combined with other active ingredients.

Where the compounds exhibit insufficient solubility, methods for solubilizing may be used. Such methods, are known and include, for example, using co-solvents (such as dimethylsulfoxide), using surfactants (such as Tween®), and/or dissolution in aqueous sodium bicarbonate. Derivatives of the compounds, such as salts, metabolites, and/or pro-drugs, may also be used in formulating effective pharmaceutical compositions. Such derivatives may improve the pharmacokinetic properties of treatment administered.

The compounds of formula (I) may be prepared with carriers that protect them against rapid elimination from the body, such as time-release formulations or coatings. Such carriers include controlled release formulations, such as, for example, microencapsulated delivery systems and the like. The active compound is included in the pharmaceutically acceptable carrier in an amount sufficient to exert a therapeutically useful effect in the absence of undesirable side effects on the patient treated. Alternatively, the active compound is included in an amount sufficient to exert a therapeutically useful effect and/or minimize the severity and form of undesirable side effects. The therapeutically effective concentration may be determined empirically by testing the compounds in known in vitro and/or in vivo model systems for the treated disorder.

The tablets, pills, capsules, troches, and the like may contain a binder (e.g., gum tragacanth, acacia, corn starch, gelatin, and the like); a vehicle (e.g., microcrystalline cellulose, starch, lactose, and the like); a disintegrating agent (e.g., alginic acid, corn starch, and the like); a lubricant (e.g., magnesium stearate, and the like); a gildant (e.g., colloidal silicon dioxide, and the like); a sweetening agent (e.g., sucrose, saccharin, and the like); a flavoring agent (e.g., peppermint, methyl salicylate, and the like) or fruit flavoring; compounds of a similar nature, and/or mixtures thereof.

When the dosage unit form is a capsule, it can contain, in addition to material described above, a liquid carrier such as a fatty oil. Additionally, dosage unit forms can contain various other materials, which modify the physical form of the dosage unit, for example, coatings of sugar or other enteric agents. A method of treatment can also administer the compound as a component of an elixir, suspension, syrup, wafer, chewing gum or the like. A syrup may contain, in addition to the active compounds, sucrose as a sweetening agent, flavors, preservatives, dyes and/or colorings.

The methods of treatment may employ at least one carrier that protects the compound against rapid elimination from the body, such as time-release formulations or coatings. Such carriers include controlled release formulations, such as, for example, implants or microencapsulated delivery systems and the like, or biodegradable, biocompatible polymers such as collagen, ethylene vinyl acetate, polyanhydrides, polyglycolic acid, polyorthoesters, polylactic acid, and the like. Methods for preparation of such formulations are known to those in the art.

When orally administered, the compounds of the present invention can be administered in usual dosage forms for oral administration as is well known to those skilled in the art. These dosage forms include the usual solid unit dosage forms of tablets and capsules as well as liquid dosage forms such as solutions, suspensions, and elixirs. When solid dosage forms are used, it is preferred that they be of the sustained release type so that the compounds of the present invention need to be administered only once or twice daily. When liquid oral dosage forms are used, it is preferred that they be of about 10 mL to about 30 mL each. Multiple doses may be administered daily.

The methods of treatment may also employ a mixture of the active materials and other active or inactive materials that do not impair the desired action, or with materials that supplement the desired action.

Solutions or suspensions used for parenteral, intradermal, subcutaneous, or topical application can include a sterile diluent (e.g., water for injection, saline solution, fixed oil, and the like); a naturally occurring vegetable oil (e.g., sesame oil, coconut oil, peanut oil, cottonseed oil, and the like); a synthetic fatty vehicle (e.g., ethyl oleate, polyethylene glycol, glycerine, propylene glycol, and the like, including other synthetic solvents); antimicrobial agents (e.g., benzyl alcohol, methyl parabens, and the like); antioxidants (e.g., ascorbic acid, sodium bisulfite, and the like); chelating agents (e.g., ethylenediaminetetraacetic acid (EDTA), and the like); buffers (e.g., acetates, citrates, phosphates, and the like); and/or agents for the adjustment of tonicity (e.g., sodium chloride, dextrose, and the like); or mixtures thereof.

Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and the like, and mixtures thereof. Liposomal suspensions including tissue-targeted liposomes may also be suitable as pharmaceutically acceptable carriers. These may be prepared according to methods known, for example, as described in U.S. Pat. No. 4,522,811.

The methods of treatment include delivery of the compounds of the present invention in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The methods of treatment include administration of the compounds parenterally, for example, by IV, IM, SC, or depo-SQ. When administered parenterally, a therapeutically effective amount of about 0.2 mg/mL to about 50 mg/ml is preferred. When a depot or IM formulation is used for injection once a month or once every two weeks, the preferred dose should be about 0.2 mg/mL to about 50 mg/mL.

The methods of treatment include administration of the compounds sublingually. When given sublingually, the compounds of the present invention should be given one to four times daily in the amounts described above for IM administration.

The methods of treatment include administration of the compounds intranasally. When given by this route, the appropriate dosage forms are a nasal spray or dry powder, as is known to those skilled in the art. The dosage of the compounds of the present invention for intranasal administration is the amount described above for IM administration.

The methods of treatment include administration of the compounds intrathecally. When given by this route the appropriate dosage form can be a parenteral dosage form as is known to those skilled in the art. The dosage of the compounds of the present invention for intrathecal administration is the amount described above for IM administration.

The methods of treatment include administration of the compounds topically. When given by this route, the appropriate dosage form is a cream, ointment, or patch. When topically administered, the dosage is from about 0.2 mg/day to about 200 mg/day. Because the amount that can be delivered by a patch is limited, two or more patches may be used. The number and size of the patch is not important. What is important is that a therapeutically effective amount of a compound of the present invention be delivered as is known to those skilled in the art. The compounds can be administered rectally by suppository as is known to those skilled in the art. When administered by suppository, the therapeutically effective amount is from about 0.2 mg to about 500 mg.

The methods of treatment include administration of the compounds by implants as is known to those skilled in the art. When administering a compound of the present invention by implant, the therapeutically effective amount is the amount described above for depot administration.

Given a particular compound of the present invention and/or a desired dosage form and medium, one skilled in the art would know how to prepare and administer the appropriate dosage form and/or amount.

The methods of treatment include use of the compounds of the present invention, or acceptable pharmaceutical salts thereof, in combination, with each other or with other therapeutic agents, to treat or prevent the conditions listed above. Such agents or approaches include acetylcholinesterase inhibitors such as tacrine (tetrahydroaminoacridine, marketed as COGNEX®), donepezil hydrochloride, (marketed as Aricept®) and rivastigmine (marketed as Exelon®), gamma-secretase inhibitors, anti-inflammatory agents such as cyclooxygenase II inhibitors, anti-oxidants such as Vitamin E or ginkolides, immunological approaches, such as, for example, immunization with A-beta peptide or administration of anti-A-beta peptide antibodies, statins, and direct or indirect neurotropic agents such as Cerebrolysin®, AIT-082 (Emilien, 2000, *Arch. Neurol.* 57:454), and other neurotropic agents, and complexes with beta-secretase or fragments thereof.

Additionally, the methods of treatment also employ the compounds of the present invention with inhibitors of P-glycoprotein (P-gp). P-gp inhibitors and the use of such compounds are known to those skilled in the art. See, for example, *Cancer Research,* 53, 4595-4602 (1993), *Clin. Cancer Res.,* 2, 7-12 (1996), *Cancer Research,* 56, 4171-4179 (1996), International Publications WO 99/64001 and WO 01/10387. The blood level of the P-gp inhibitor should be such that it exerts its effect in inhibiting P-gp from decreasing brain blood levels of the compounds of formula (I). To that end the P-gp inhibitor and the compounds of formula (I) can be administered at the same time, by the same or different route of administration, or at different times. Given a particular compound of formula (I), one skilled in the art would know whether a P-gp inhibitor is desirable for use in the method of treatment, which P-gp inhibitor should be used, and how to prepare and administer the appropriate dosage form and/or amount.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as $GF_{120918}$, FK506, VX-710, LY335979, PSC-833, GF-102, 918, quinoline-3-carboxylic acid (2-[4-[2-(6,7-dimethyl-3,4-dihydro-1H-isoquinoline-2-yl)-ethyl]phenylcarbamoyl}-4, 5-dimethylphenyl)-amide (Xenova), or other compounds.

Compounds that have the same function and therefore achieve the same outcome are also considered to be useful.

The P-gp inhibitors can be administered orally, parenterally, (via IV, IM, depo-IM, SQ, depo-SQ), topically, sublingually, rectally, intranasally, intrathecally or by implant.

The therapeutically effective amount of the P-gp inhibitors is from about 0.1 mg/kg to about 300 mg/kg daily, preferably about 0.1 mg/kg to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets or capsules as well as liquid dosage forms such as solutions, suspensions or elixirs. When the solid dosage forms are used, it is preferred that they be of the sustained release type so that the P-gp inhibitors need to be administered only once or twice daily. The oral dosage forms are administered to the patient one through four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that the dosage form used, is designed to protect the P-gp inhibitors from the acidic environment of the stomach. Enteric coated tablets are well known to those skilled in the art. Capsules filled with small spheres, each coated to protect from the acidic stomach, are also well known to those skilled in the art.

In addition, the P-gp inhibitors can be administered parenterally. When administered parenterally they can be administered via IV, IM, depo-IM, SQ or depo-SQ.

The P-gp inhibitors can be given sublingually. When given sublingually, the P-gp inhibitors should be given one through four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important; what is important is that a therapeutically effective amount of the P-gp inhibitors be delivered as is known to those skilled in the art.

The P-gp inhibitors can be administered rectally by suppository or by implants, both of which are known to those skilled in the art.

It should be apparent to one skilled in the art that the exact dosage and frequency of administration will depend on the particular compounds of the present invention administered, the particular condition being treated, the severity of the condition being treated, the age, weight, or general physical condition of the particular patient, or any other medication the individual may be taking as is well known to administering physicians who are skilled in this art.

In another embodiment, the present invention provides a method of preventing or treating conditions which benefit from inhibition of at least one aspartyl-protease, comprising administering to a host a composition comprising a therapeutically effective amount of at least one compound of the formula,

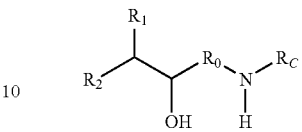

or pharmaceutically acceptable salts thereof, and wherein $R_1$, $R_2$, and $R_C$ are as defined above and $R_0$ is selected from —CH(alkyl)-, —C(alkyl)$_2$-, —CH(cycloalkyl)-, —C(alkyl)(cycloalkyl)-, and —C(cycloalkyl)$_2$-.

Exemplary compounds of formula (I) are provided in the examples below. All compound names were generated using AutoNom (AUTOmatic Nomenclature) version 2.1, AGO Namepro version 5.09, Chemdraw Ultra (versions 6.0, 8.0, 8.03, and 9.0), or were derived therefrom.

EXAMPLE 1

4-(3,5-DIFLUORO-PHENYL)-1-[7-(2,2-DIMETHYL-PROPYL)-1,2,3,4-TETRAHYDRO-NAPHTHALEN-1-YLAMINO]-3-PENTAZOL-1-YL-BUTAN-2-OL

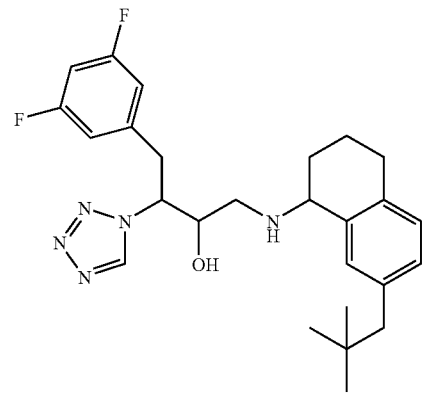

EXAMPLE 2

4-(3,5-DIFLUORO-PHENYL)-1-[6-(2,2-DIMETHYL-PROPYL)-2,2-DIOXO-2$\lambda^6$-ISOTHIOCHROMAN-4-YLAMINO]-3-PENTAZOL-1-YL-BUTAN-2-OL

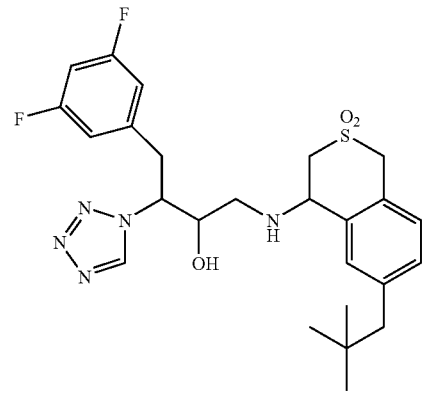

EXAMPLE 3

4-(3,5-DIFLUORO-PHENYL)-1-[6-(2,2-DIM-ETHYL-PROPYL)-CHROMAN-4-YLAMINO]-3-PENTAZOL-1-YL-BUTAN-2-OL

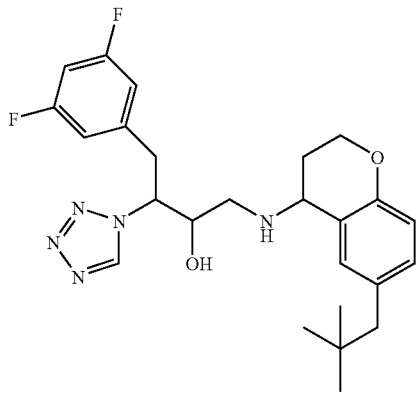

EXAMPLE 4

1-[1-(3-TERT-BUTYL-PHENYL)-CYCLOHEXY-LAMINO]-4-(3,5-DIFLUORO-PHENYL)-3-PEN-TAZOL-1-YL-BUTAN-2-OL

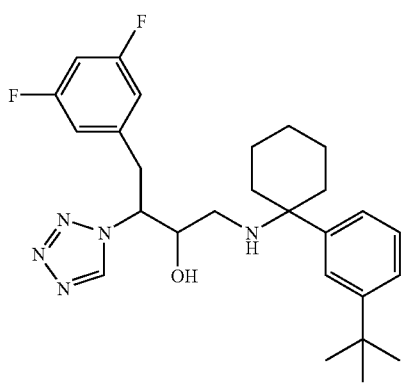

EXAMPLE 5

1-[1-(3-TERT-BUTYL-PHENYL)-CYCLOHEXY-LAMINO]-4-(3,5-DIFLUORO-PHENYL)-3-(1-PHENYL-1H-TETRAZOL-5-YL)-BUTAN-2-OL

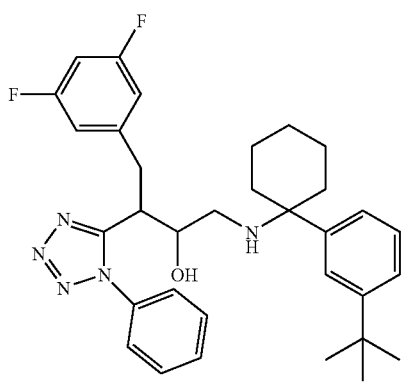

EXAMPLE 6

4-(3,5-DIFLUORO-PHENYL)-1-[5-(2,2-DIM-ETHYL-PROPYL)-2-(1H-IMIDAZOL-2-YL)-BEN-ZYLAMINO]-3-TETRAZOL-1-YL-BUTAN-2-OL

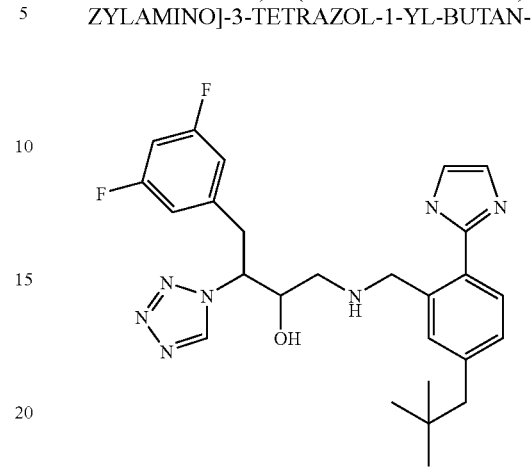

EXAMPLE 7

4-(3,5-DIFLUORO-PHENYL)-1-(7-ETHYL-1,2,3,4-TETRAHYDRO-NAPHTHALEN-1-YLAMINO)-3-PYRROL-1-YL-BUTAN-2-OL

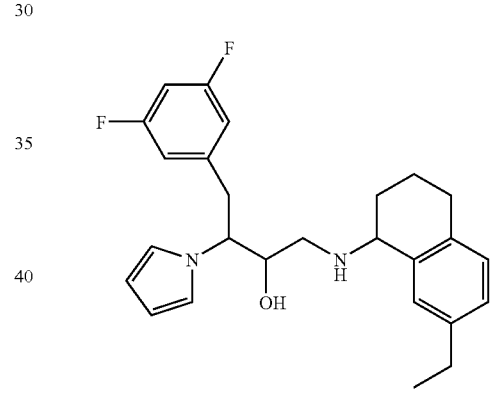

EXAMPLE 8

4-(3,5-DIFLUORO-PHENYL)-1-(7-ETHYL-1,2,3,4-TETRAHYDRO-NAPHTHALEN-1-YLAMINO)-3-IMIDAZOL-1-YL-BUTAN-2-OL

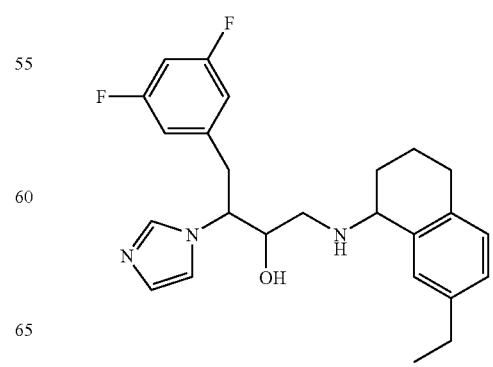

EXAMPLE 9

4-(3,5-DIFLUORO-PHENYL)-1-[7-(2,2-DIM-ETHYL-PROPYL)-1,2,3,4-TETRAHYDRO-NAPH-THALEN-1-YLAMINO]-3-(1H-IMIDAZOL-2-YL)-BUTAN-2-OL

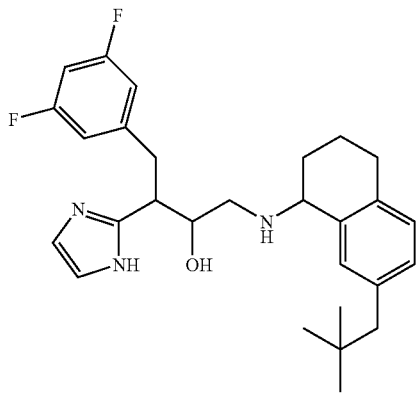

EXAMPLE 10

4-(3,5-DIFLUORO-PHENYL)-1-[6-(2,2-DIM-ETHYL-PROPYL)-2,2-DIOXO-2$\lambda^6$-ISOTHIO-CHROMAN-4-YLAMINO]-3-(1H-IMIDAZOL-2-YL)-BUTAN-2-OL

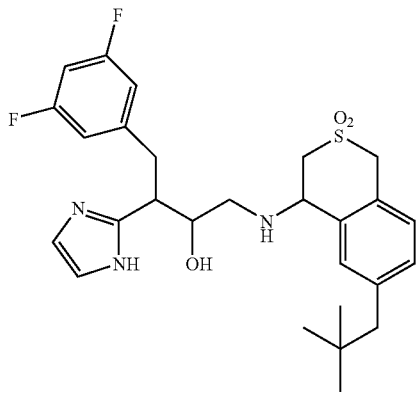

EXAMPLE 11

4-(3,5-DIFLUORO-PHENYL)-1-[6-(2,2-DIM-ETHYL-PROPYL)-CHROMAN-4-YLAMINO]-3-(1H-IMIDAZOL-2-YL)-BUTAN-2-OL

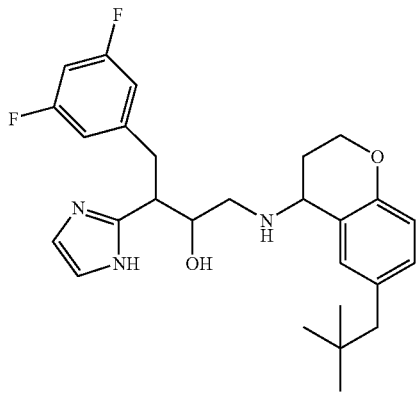

EXAMPLE 12

4-(3,5-DIFLUORO-PHENYL)-1-[6-(2,2-DIM-ETHYL-PROPYL)-1,2,3,4-TETRAHYDRO-QUINOLIN-4-YLAMINO]-3-(1H-IMIDAZOL-2-YL)-BUTAN-2-OL

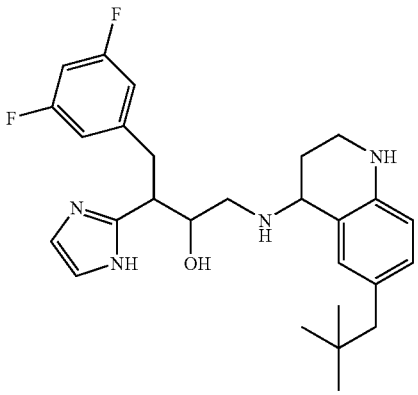

EXAMPLE 13

4-(3,5-DIFLUORO-PHENYL)-1-[5-(2,2-DIM-ETHYL-PROPYL)-2-(1H-IMIDAZOL-2-YL)-BEN-ZYLAMINO]-3-(1H-IMIDAZOL-2-YL)-BUTAN-2-OL

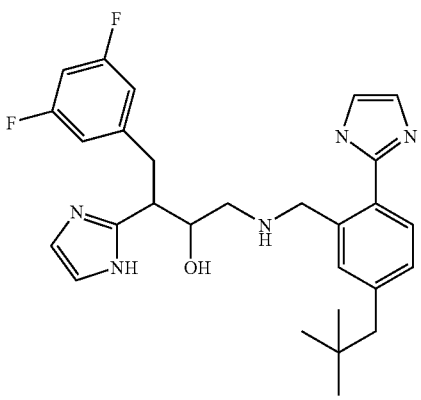

EXAMPLE 14

4-(3,5-DIFLUORO-PHENYL)-1-(6-ISOBUTYL-1,1-DIOXO-1$\lambda^6$-THIOCROMAN-4-YLAMINO)-BUTAN-2-OL

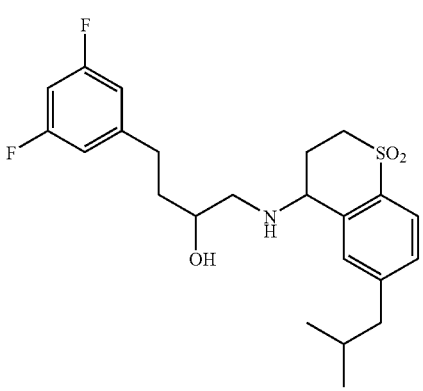

EXAMPLE 15

4-(3,5-DIFLUORO-PHENYL)-1-(6-ETHYL-2,2-DIOXO-2λ⁶-ISOTHIOCHROMAN-4-YLAMINO)-BUTAN-2-OL

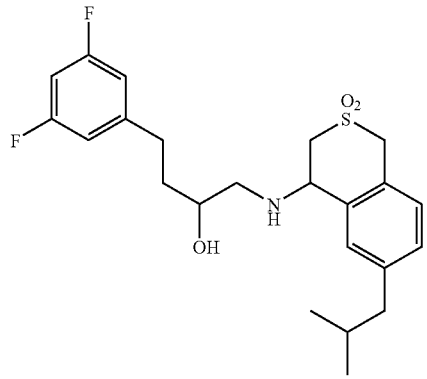

EXAMPLE 16

3-(3-BROMO-[1,2,4]THIADIAZOL-5-YLAMINO)-4-(3,5-DIFLUORO-PHENYL)-1-(6-ETHYL-2,2-DIOXO-2λ⁶-ISOTHIOCHROMAN-4-YLAMINO)-BUTAN-2-OL

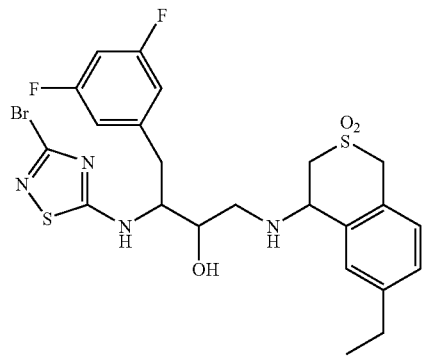

EXAMPLE 17

4-(3,5-DIFLUORO-PHENYL)-1-(6-ETHYL-2,2-DIOXO-2λ⁶-ISOTHIOCHROMAN-4-YLAMINO)-3-([1,2,4]-THIADIAZOL-5-YLAMINO)-BUTAN-2-OL

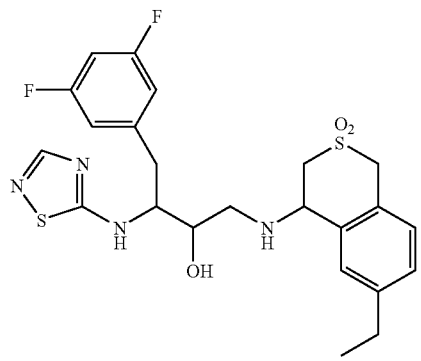

EXAMPLE 18

3-(4-CHLORO-[1,2,5]THIADIAZOL-3-YLAMINO)-4-(3,5-DIFLUORO-PHENYL)-1-(6-ETHYL-2,2-DIOXO-2λ⁶-ISOTHIOCHROMAN-4-YLAMINO)-BUTAN-2-OL

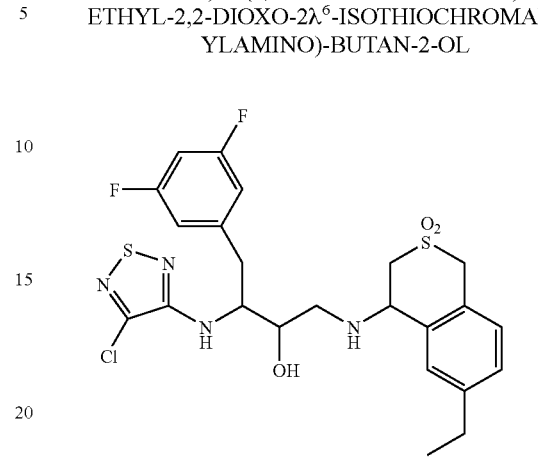

EXAMPLE 19

4-(3,5-DIFLUORO-PHENYL)-1-(6-ETHYL-2,2-DIOXO-2λ⁶-ISOTHIOCHROMAN-4-YLAMINO)-3-([1,2,5]THIADIAZOL-3-YLAMINO)-BUTAN-2-OL

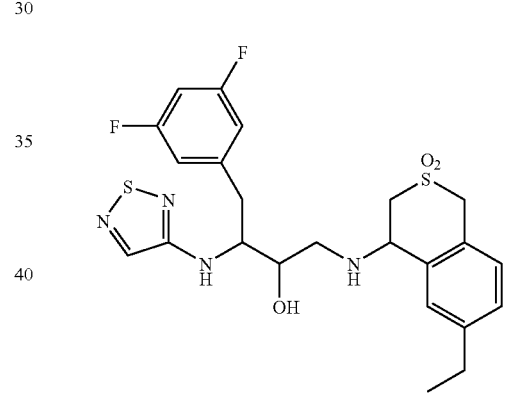

EXAMPLE 20

4-(3,5-DIFLUORO-PHENYL)-1-(6-ETHYL-2,2-DIOXO-2λ⁶-ISOTHIOCHROMAN-4-YLAMINO)-3-(THIAZOL-2-YLAMINO)-BUTAN-2-OL

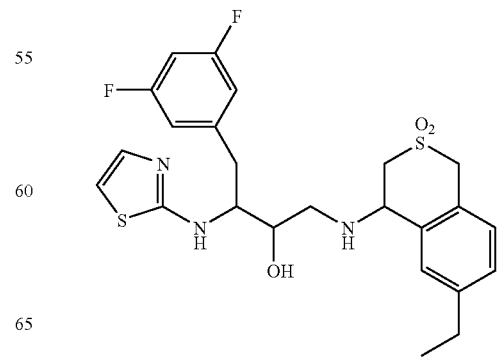

EXAMPLE 21

3-(5-BROMO-[1,3,4]THIADIAZOL-2-YLAMINO)-
4-(3,5-DIFLUORO-PHENYL)-1-(6-ETHYL-2,2-
DIOXO-2$\lambda^6$-ISOTHIOCHROMAN-4-YLAMINO)-
BUTAN-2-OL

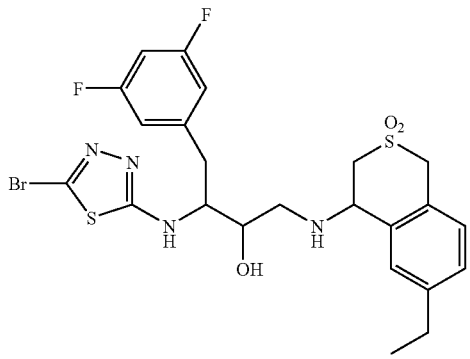

EXAMPLE 22

4-(3,5-DIFLUORO-PHENYL)-1-(6-ETHYL-2,2-
DIOXO-2$\lambda^6$-ISOTHIOCHROMAN-4-YLAMINO-
3-([1,3,4]THIADIAZOL-2-YLAMINO)-BUTAN-2-
OL

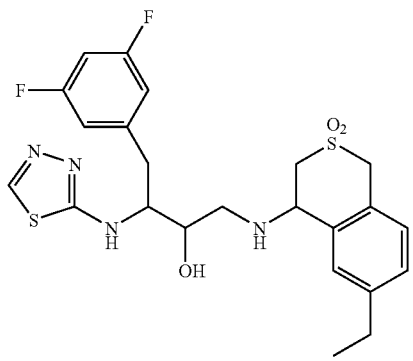

EXAMPLE 23

3-(5-AMINO-[1,3,4]THIADIAZOL-2-YLAMINO)-
4-(3,5-DIFLUORO-PHENYL)-1-(6-ETHYL-2,2-
DIOXO-2$\lambda^6$-ISOTHIOCHROMAN-4-YLAMINO)-
BUTAN-2-OL

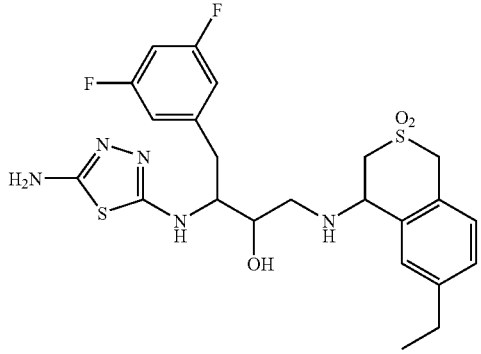

EXAMPLE 24

3-(2-BROMO-THIAZOL-5-YLAMINO)-4-(3,5-
DIFLUORO-PHENYL)-1-(6-ETHYL-2,2-DIOXO-
2$\lambda^6$-ISOTHIOCHROMAN-4-YLAMINO)-BUTAN-
2-OL

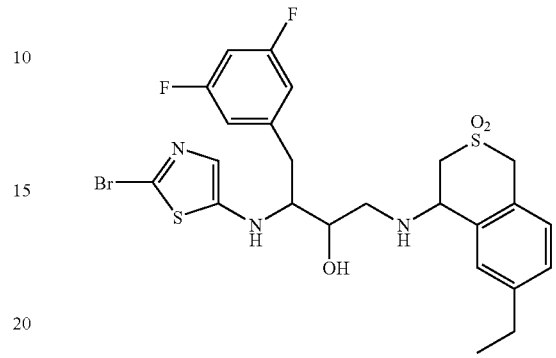

EXAMPLE 25

4-(3,5-DIFLUORO-PHENYL)-1-(6-ETHYL-2,2-
DIOXO-2$\lambda^6$-ISOTHIOCHROMAN-4-YLAMINO)-
3-(THIAZOL-5-YLAMINO)-BUTAN-2-OL

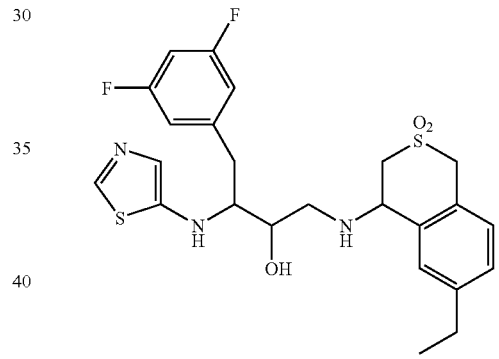

EXAMPLE 26

4-(3,5-DIFLUORO-PHENYL)-1-(6-ETHYL-2,2-
DIOXO-2$\lambda^6$-ISOTHIOCHROMAN-4-YLAMINO)-
3-(5-TRIFLUOROMETHYL-[1,3,4]THIADIAZOL-
2-YLAMINO)-BUTAN-2-OL

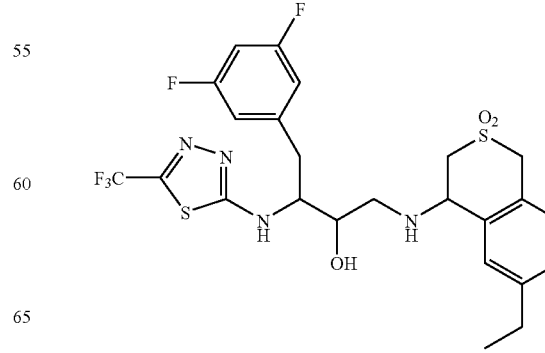

EXAMPLE 27

4-(3,5-DIFLUORO-PHENYL)-1-(6-ETHYL-2,2-DIOXO-2λ⁶-ISOTHIOCHROMAN-4-YLAMINO)-3-(5-TRIFLUOROMETHYL-[1,3,4]OXADIAZOL-2-YLAMINO)-BUTAN-2-OL

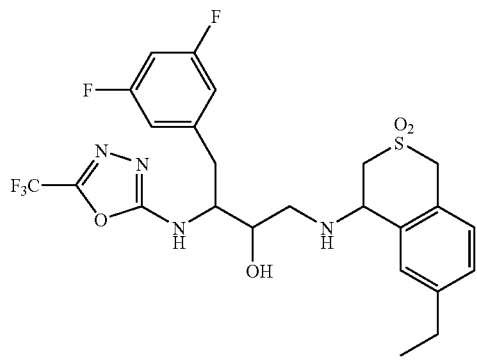

EXAMPLE 28

3-(5-AMINO-[1,3,4]-OXADIAZOL-2-YLAMINO)-4-(3,5-DIFLUORO-PHENYL)-1-(6-ETHYL-2,2-DIOXO-2λ⁶-ISOTHIOCHROMAN-4-YLAMINO)-BUTAN-2-OL

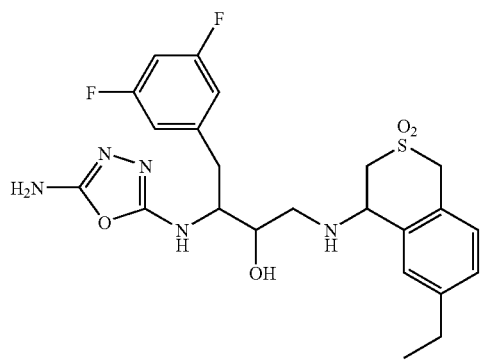

EXAMPLE 29

4-(3,5-DIFLUORO-PHENYL)-1-(6-ETHYL-2,2-DIOXO-2λ⁶-ISOTHIOCHROMAN-4-YLAMINO)-3-(1-TRITYL-1H-[1,2,4]TRIAZOL-3-YLAMINO)-BUTAN-2-OL

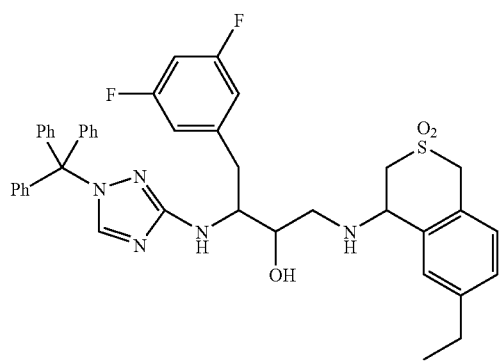

EXAMPLE 30

4-(3,5-DIFLUORO-PHENYL)-1-(6-ETHYL-2,2-DIOXO-2λ⁶-ISOTHIOCHROMAN-4-YLAMINO)-3-(1H-[1,2,4]TRIAZOL-3-YLAMINO)-BUTAN-2-OL

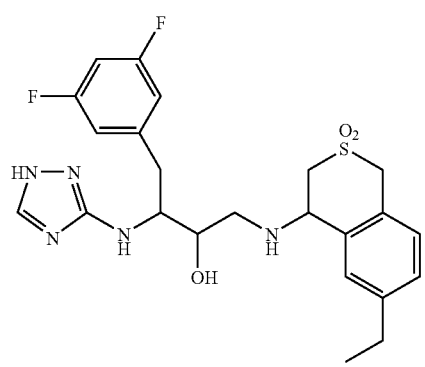

EXAMPLE 31

4-(3,5-DIFLUORO-PHENYL)-1-(6-ETHYL-2,2-DIOXO-2λ⁶-ISOTHIOCHROMAN-4-YLAMINO)-3-(OXAZOL-2-YLAMINO)-BUTAN-2-OL

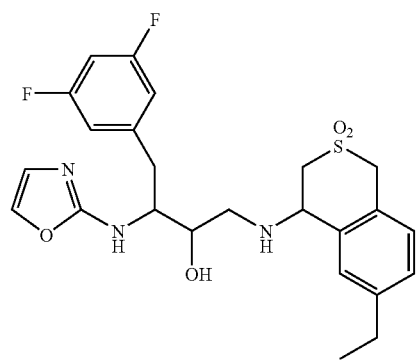

EXAMPLE 32

3-(5-BROMO-2-TRITYL-2H-[1,2,3]TRIAZOL-4-YLAMINO)-4-(3,5-DIFLUORO-PHENYL)-1-(6-ETHYL-2,2-DIOXO-2λ⁶-ISOTHIOCHROMAN-4-YLAMINO)-BUTAN-2-OL

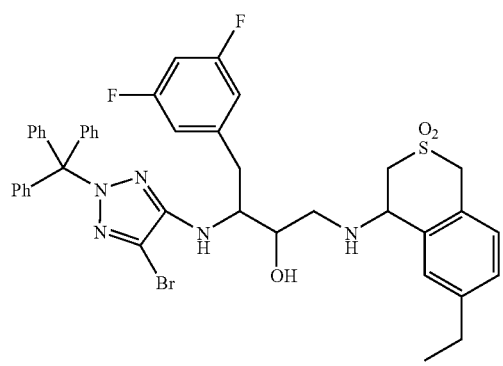

EXAMPLE 33

4-(3,5-DIFLUORO-PHENYL)-1-(6-ETHYL-2,2-DIOXO-2λ⁶-ISOTHIOCHROMAN-4-YLAMINO)-3-(2-TRITYL-2H-[1,2,3]TRIAZOL-4-YLAMINO)-BUTAN-2-OL

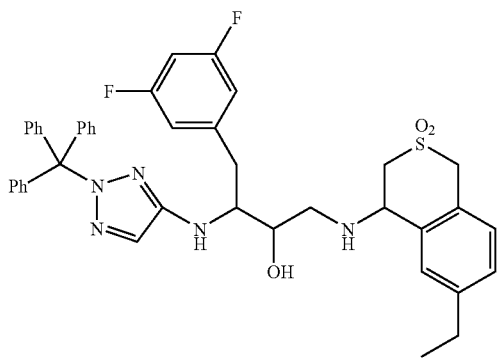

EXAMPLE 34

3-(5-BROMO-2H-[1,2,3]TRIAZOL-4-YLAMINO)-4-(3,5-DIFLUORO-PHENYL)-1-(6-ETHYL-2,2-DIOXO-2λ⁶-ISOTHIOCHROMAN-4-YLAMINO)-BUTAN-2-OL

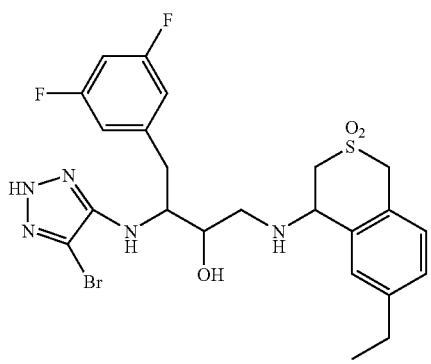

EXAMPLE 35

4-(3,5-DIFLUORO-PHENYL)-1-(6-ETHYL-2,2-DIOXO-2λ⁶-ISOTHIOCHROMAN-4-YLAMINO)-3-(2H-[1,2,3]TRIAZOL-4-YLAMINO)-BUTAN-2-OL

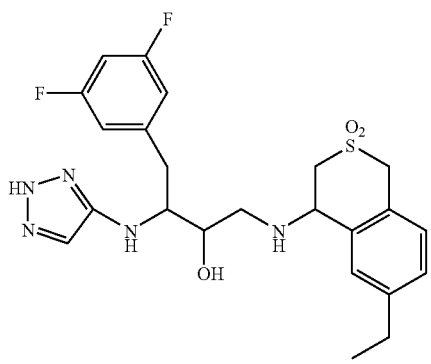

EXAMPLE 36

4-(3,5-DIFLUORO-PHENYL)-1-(6-ETHYL-2,2-DIOXO-2λ⁶-ISOTHIOCHROMAN-4-YLAMINO)-3-(THIOPHEN-2-YLAMINO)-BUTAN-2-OL

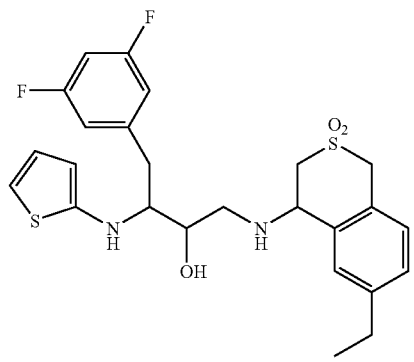

EXAMPLE 37

4-(3,5-DIFLUORO-PHENYL)-1-(6-ETHYL-2,2-DIOXO-2λ⁶-ISOTHIOCHROMAN-4-YLAMINO)-3-(3-METHYL-5-NITRO-3H-IMIDAZOL-4-YLAMINO)-BUTAN-2OL

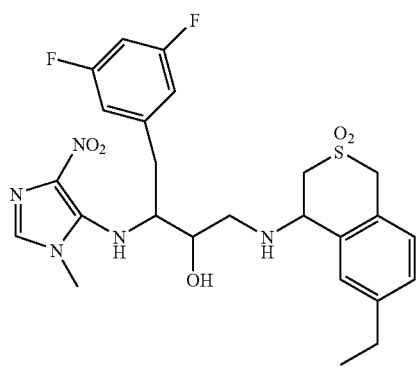

EXAMPLE 38

3-[1-(3,5-DIFLUORO-BENZYL)-3-(6-ETHYL-2,2-DIOXO-2λ⁶-ISOTHIOCHROMAN-4-YLAMINO)-2-HYDROXY-PROPYLAMINO]-5-PHENYL-ISOTHIAZOLE-4-CARBONITRILE

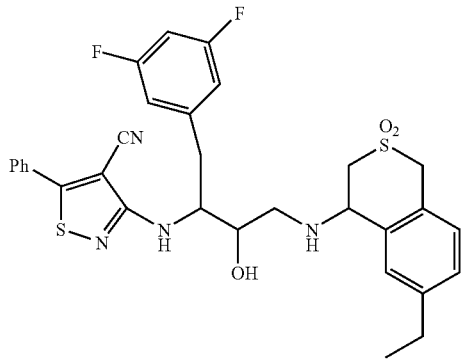

EXAMPLE 39

4-(3,5-DIFLUORO-PHENYL)-1-(6-ETHYL-2,2-DIOXO-2λ⁶-ISOTHIOCHROMAN-4-YLAMINO)-3-(4-PHENYL-[1,2,5]THIADIAZOL-3-YLAMINO)-BUTAN-2-OL

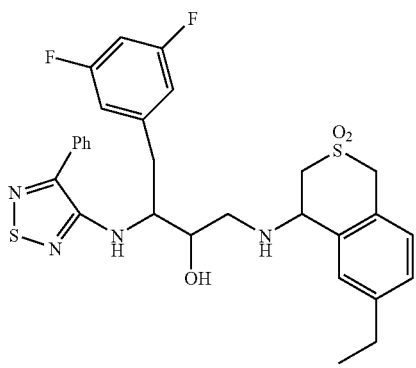

EXAMPLE 40

3-[1-(3,5-DIFLUORO-BENZYL)-3-(6-ETHYL-2,2-DIOXO-2λ⁶-ISOTHIOCHROMAN-4-YLAMINO)-2-HYDROXY-PROPYLAMINO]-CYCLOBUT-3-ENE-1,2-DIONE

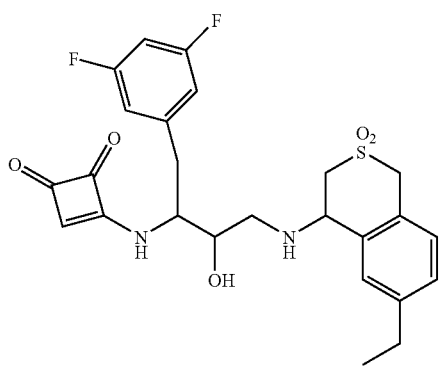

EXAMPLE 41

3-[1-(3,5-DIFLUORO-BENZYL)-3-(6-ETHYL-2,2-DIOXO-2λ⁶-ISOTHIOCHROMAN-4-YLAMINO)-2-HYDROXY-PROPYLAMINO]-4-METHOXY-CYCLOBUT-3-ENE-1,2-DIONE

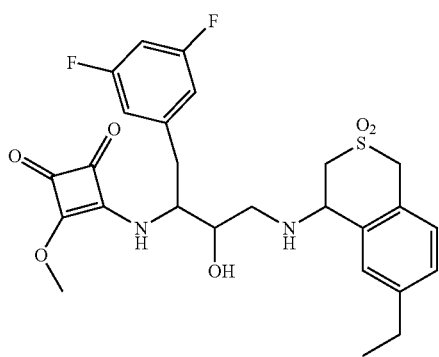

EXAMPLE 42

3-[1-(3,5-DIFLUORO-BENZYL)-3-(6-ETHYL-2,2-DIOXO-2λ⁶-ISOTHIOCHROMAN-4-YLAMINO)-2-HYDROXY-PROPYLAMINO]-4-METHYLAMINO-CYCLOBUT-3-ENE-1,2-DIONE

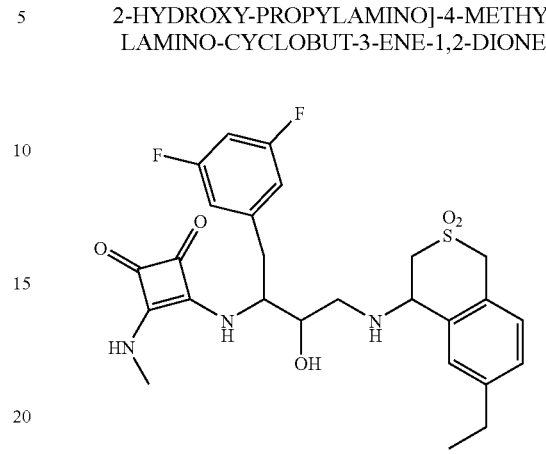

EXAMPLE 43

3-(3-BROMO-[1,2,4]THIADIAZOL-5-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

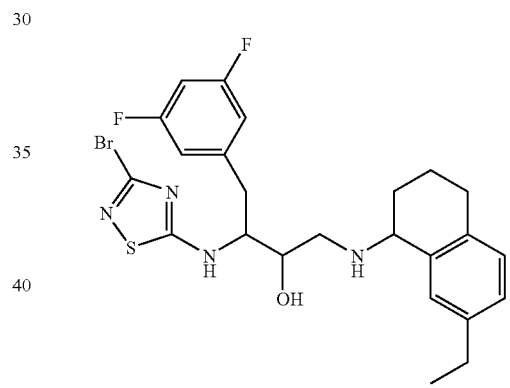

EXAMPLE 44

4-(3,5-DIFLUORO-PHENYL)-1-(7-ETHYL-1,2,3,4-TETRAHYDRO-NAPHTHALEN-1-YLAMINO)-3-([1,2,4]THIADIAZOL-5-YLAMINO)-BUTAN-2-OL

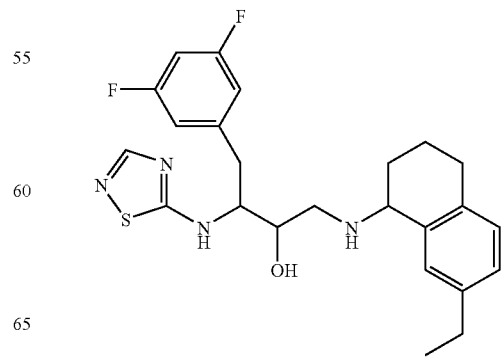

EXAMPLE 45

4-(3,5-DIFLUORO-PHENYL)-1-(7-ETHYL-1,2,3,4-TETRAHYDRO-NAPHTHALEN-1-YLAMINO)-3-(1-METHYL-1H-PYRAZOL-4-YLAMINO)-BUTAN-2-OL

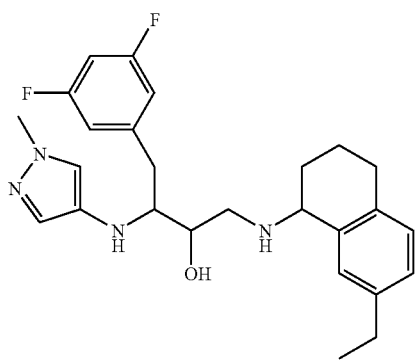

EXAMPLE 46

3-(4-CHLORO-[1,2,5]THIADIAZOL-3-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

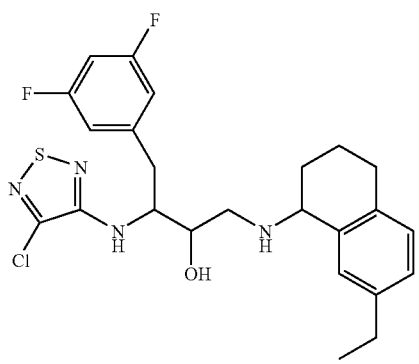

EXAMPLE 47

4-(3,5-DIFLUORO-PHENYL)-1-(7-ETHYL-1,2,3,4-TETRAHYDRO-NAPHTHALEN-1-YLAMINO)-3-([1,2,5]THIADIAZOL-3-YLAMINO)-BUTAN-2-OL

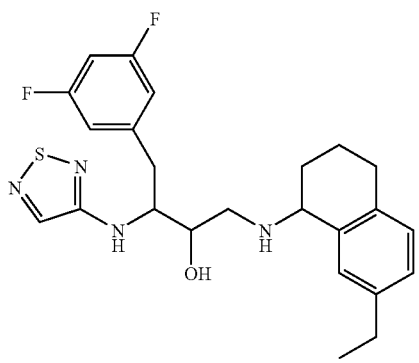

EXAMPLE 48

4-(3,5-DIFLUORO-PHENYL)-1-(7-ETHYL-1,2,3,4-TETRAHYDRO-NAPHTHALEN-1-YLAMINO)-3-(THIAZOL-2-YLAMINO)-BUTAN-2-OL

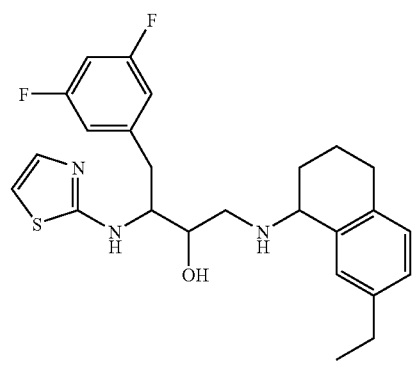

EXAMPLE 49

3-(5-BROMO-[1,3,4]-THIADIAZOL-2-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

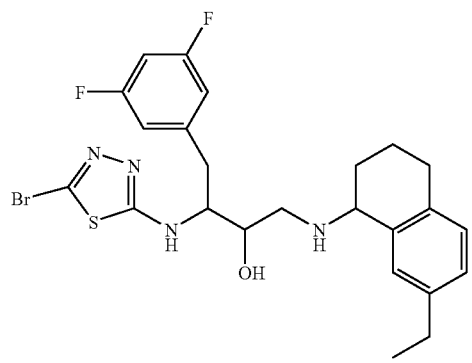

EXAMPLE 50

4-(3,5-DIFLUORO-PHENYL)-1-(7-ETHYL-1,2,3,4-TETRAHYDRO-NAPHTHALEN-1-YLAMINO)-3-([1,3,4]THIADIAZOL-2-YLAMINO)-BUTAN-2-OL

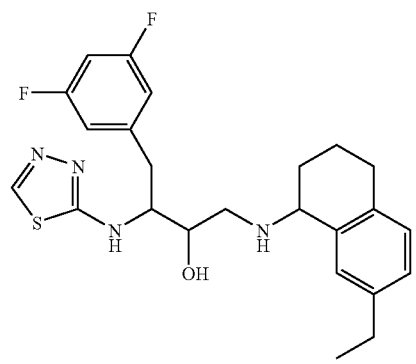

EXAMPLE 51

3-(5-AMINO-[1,3,4]THIADIAZOL-2-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

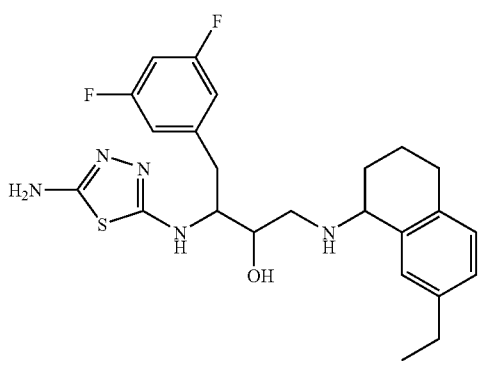

EXAMPLE 52

3-(2-BROMO-THIAZOL-5-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

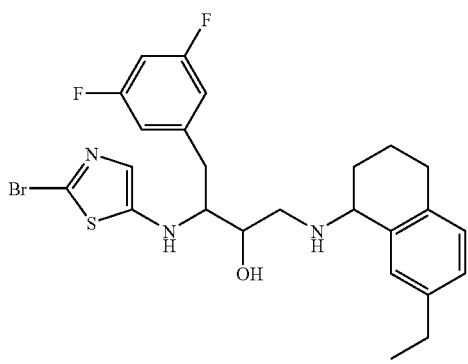

EXAMPLE 53

4-(3,5-DIFLUORO-PHENYL)-1-(7-ETHYL-1,2,3,4-TETRAHYDRO-NAPHTHALEN-1-YLAMINO)-3-(THIAZOL-5-YLAMINO)-BUTAN-2-OL

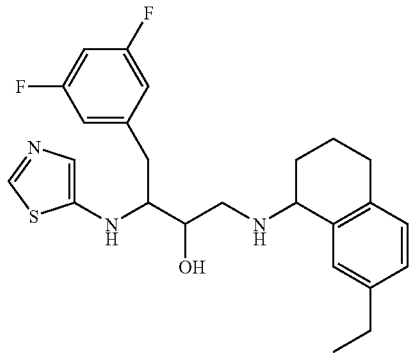

EXAMPLE 54

4-(3,5-DIFLUORO-PHENYL)-1-(7-ETHYL-1,2,3,4-TETRAHYDRO-NAPHTHALEN-1-YLAMINO)-3-(5-TRIFLUOROMETHYL-[1,3,4]THIADIAZOL-2-YLAMINO)-BUTAN-2-OL

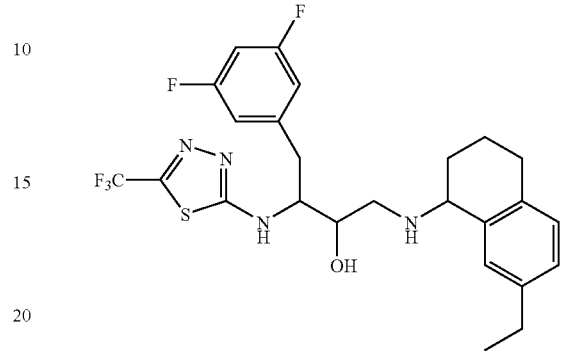

EXAMPLE 55

4-(3,5-DIFLUORO-PHENYL)-1-(7-ETHYL-1,2,3,4-TETRAHYDRO-NAPHTHALEN-1-YLAMINO)-3-(5-TRIFLUOROMETHYL-[1,3,4]OXADIAZOL-2-YLAMINO)-BUTAN-2-OL

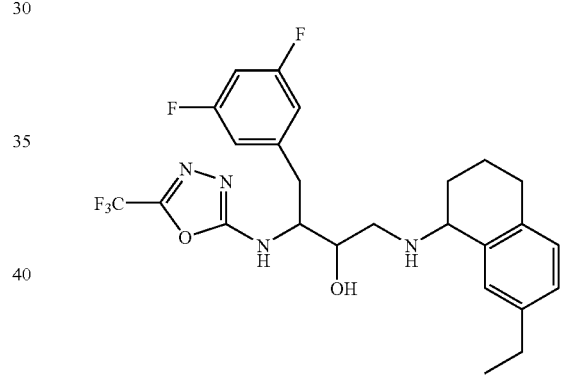

EXAMPLE 56

3-(5-AMINO-[1,3,4]OXADIAZOL-2-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

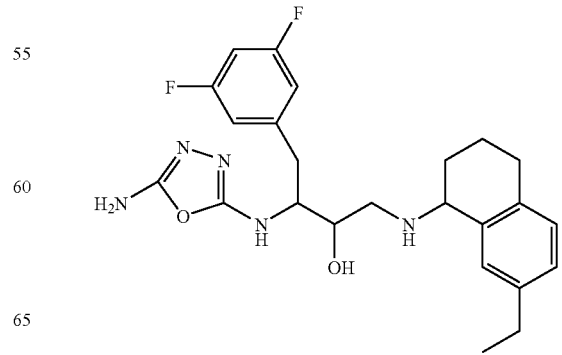

EXAMPLE 57

4-(3,5-DIFLUORO-PHENYL)-1-(7-ETHYL-1,2,3,
4-TETRAHYDRO-NAPHTHALEN-1-YLAMINO)-
3-(1-TRITYL-1H-[1,2,4]TRIAZOL-3-YLAMINO)-
BUTAN-2-OL

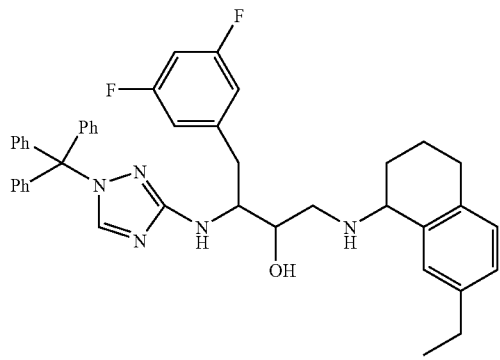

EXAMPLE 58

4-(3,5-DIFLUORO-PHENYL)-1-(7-ETHYL-1,2,3,
4-TETRAHYDRO-NAPHTHALEN-1-YLAMINO)-
3-(1H-[1,2,4]TRIAZOL-3-YLAMINO)-BUTAN-2-
OL

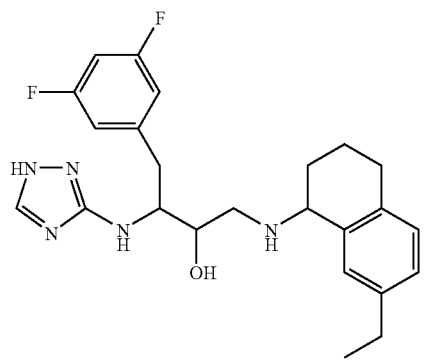

EXAMPLE 59

4-(3,5-DIFLUORO-PHENYL)-1-(7-ETHYL-1,2,3,
4-TETRAHYDRO-NAPHTHALEN-1-YLAMINO)-
3-(OXAZOL-2-YLAMINO)-BUTAN-2-OL

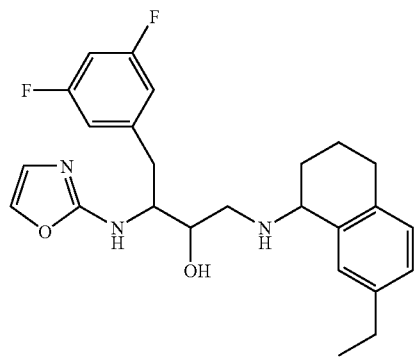

EXAMPLE 60

3-(5-BROMO-2-TRITYL-2H-[1,2,3]TRIAZOL-4-
YLAMINO)-4-(3,5-DIFLUORO-PHENYL)-1-(7-
ETHYL-1,2,3,4-TETRAHYDRO-NAPHTHALEN-
1-YLAMINO)-BUTAN-2-OL

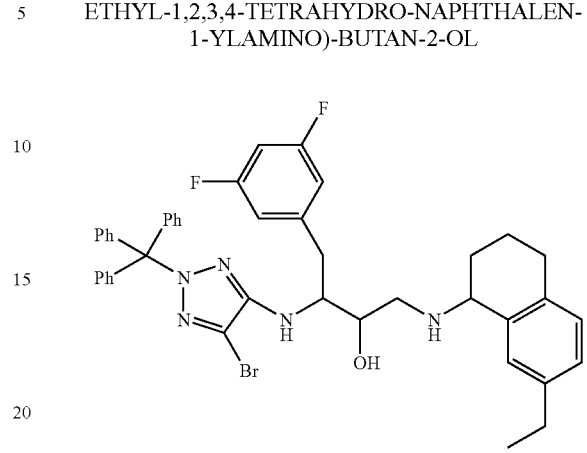

EXAMPLE 61

4-(3,5-DIFLUORO-PHENYL)-1-(7-ETHYL-1,2,3,
4-TETRAHYDRO-NAPHTHALEN-1-YLAMINO)-
3-(2-TRITYL-2H-[1,2,3]TRIAZOL-4-YLAMINO)-
BUTAN-2-OL

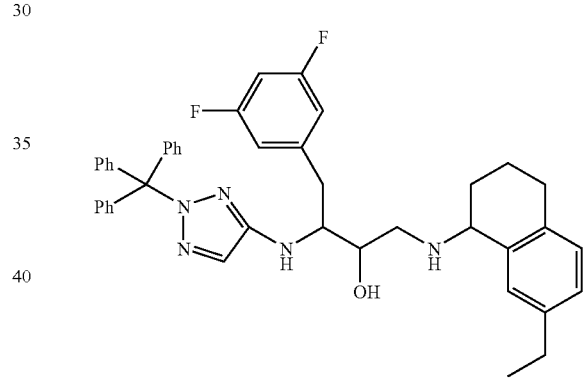

EXAMPLE 62

3-(5-BROMO-2H-[1,2,3]TRIAZOL-4-YLAMINO)-
4-(3,5-DIFLUORO-PHENYL)-1-(7-ETHYL-1,2,3,
4-TETRAHYDRO-NAPHTHALEN-1-YLAMINO)-
BUTAN-2-OL

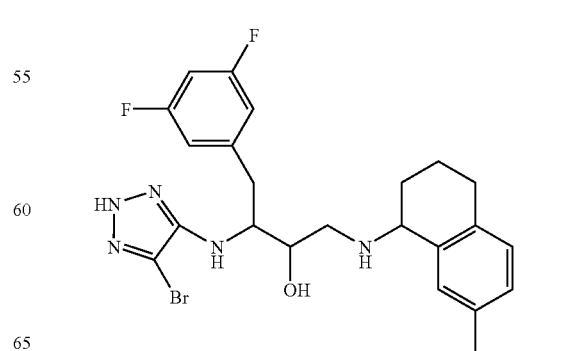

EXAMPLE 63

4-(3,5-DIFLUORO-PHENYL)-1-(7-ETHYL-1,2,3,4-TETRAHYDRO-NAPHTHALEN-1-YLAMINO)-3-(2H-[1,2,3]TRIAZOL-4-YLAMINO)-BUTAN-2-OL

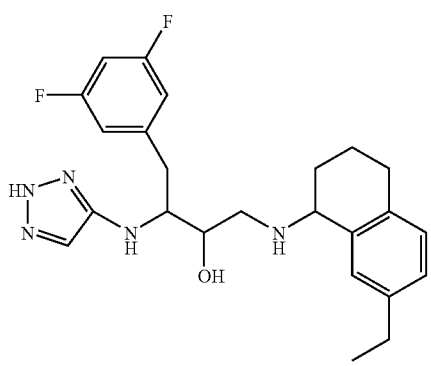

EXAMPLE 64

4-(3,5-DIFLUORO-PHENYL)-1-(7-ETHYL-1,2,3,4-TETRAHYDRO-NAPHTHALEN-1-YLAMINO)-3-(THIOPHEN-2-YLAMINO)-BUTAN-2-OL

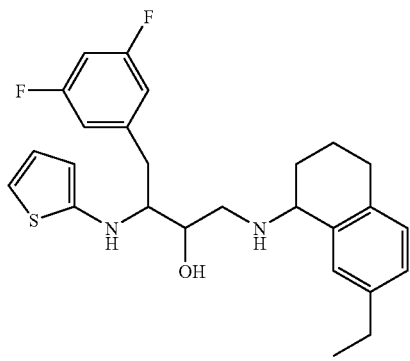

EXAMPLE 65

4-(3,5-DIFLUORO-PHENYL)-1-(7-ETHYL-1,2,3,4-TETRAHYDRO-NAPHTHALEN-1-YLAMINO)-3-(3-METHYL-5-NITRO-3H-IMIDAZOL-4-YLAMINO)-BUTAN-2-OL

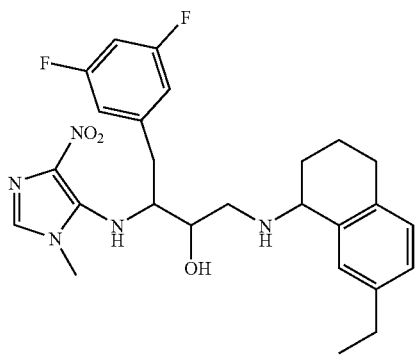

EXAMPLE 66

3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-5-PHENYL-ISOTHIAZOLE-4-CARBONITRILE

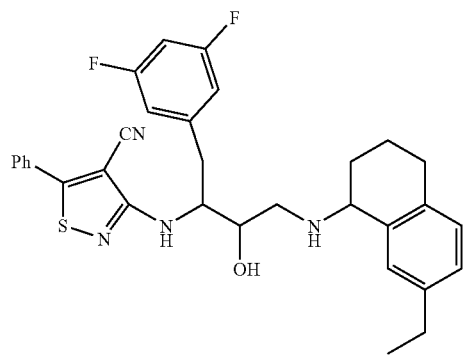

EXAMPLE 67

4-(3,5-DIFLUORO-PHENYL)-1-(7-ETHYL-1,2,3,4-TETRAHYDRO-NAPHTHALEN-1-YLAMINO)-3-(4-PHENYL-[1,2,5]THIADIAZOL-3-YLAMINO)-BUTAN-2-OL

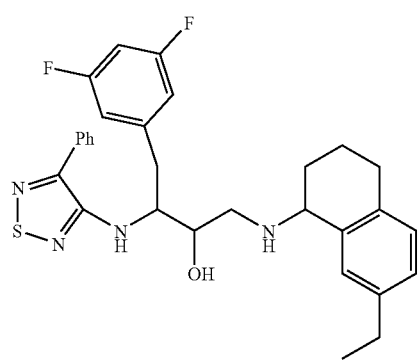

EXAMPLE 68

3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-CYCLOBUT-3-ENE-1,2-DIONE

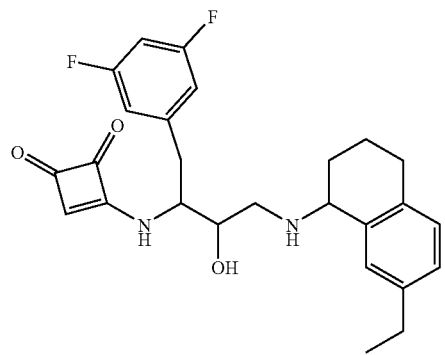

EXAMPLE 69

3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-METHOXY-CYCLOBUT-3-ENE-1,2-DIONE

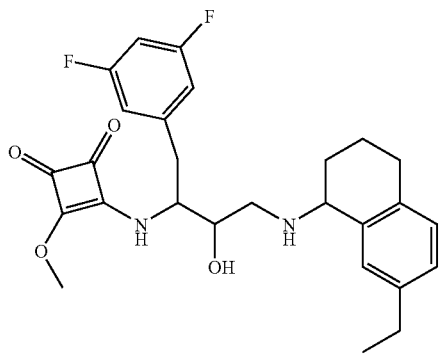

EXAMPLE 70

3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-4-METHYLAMINO-CYCLOBUT-3-ENE-1,2-DIONE

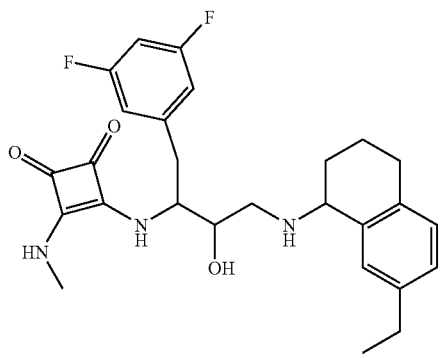

EXAMPLE 71

{3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-PHENYL}-ACETIC ACID

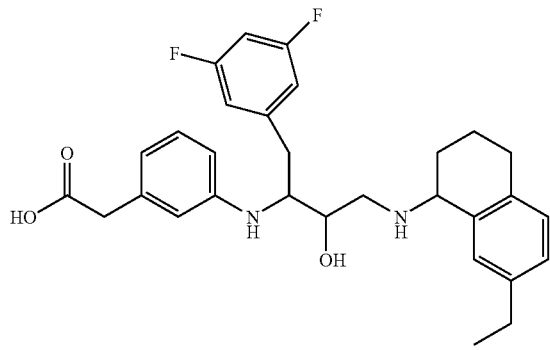

EXAMPLE 72

3-(2-CHLORO-PYRIMIDIN-4-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

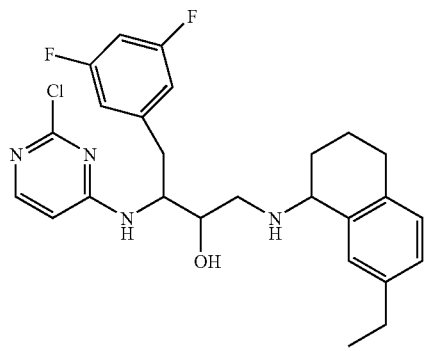

EXAMPLE 73

1-[1-(3-TERT-BUTYL-PHENYL)-CYCLOHEXYLAMINO]-4-(3,5-DIFLUORO-PHENYL)-3-([1,2,4]THIADIAZOL-5-YLAMINO)-BUTAN-2-OL

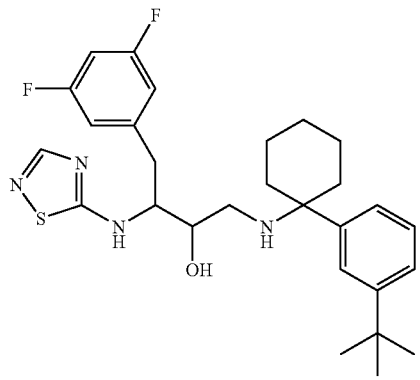

EXAMPLE 74

1-[1-(3-TERT-BUTYL-PHENYL)-CYCLOHEXYLAMINO]-3-(4-CHLORO-[1,2,5]THIADIAZOL-3-YLAMINO)-4-(3,5-DIFLUORO-PHENYL)-BUTAN-2-OL

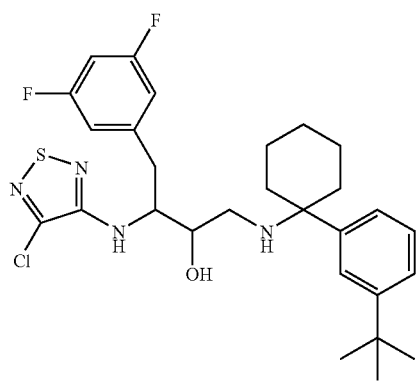

EXAMPLE 75

1-[1-(3-TERT-BUTYL-PHENYL)-CYCLOHEXY-LAMINO]-4-(3,5-DIFLUORO-PHENYL)-3-([1,2,5]THIADAZOL-3-YLAMINO)-BUTAN-2-OL

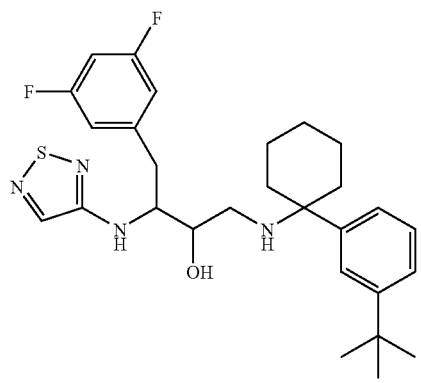

EXAMPLE 76

1-[1-(3-TERT-BUTYL-PHENYL)-CYCLOHEXY-LAMINO]-4-(3,5-DIFLUORO-PHENYL)-3-(THIAZOL-2-YLAMINO)-BUTAN-2-OL

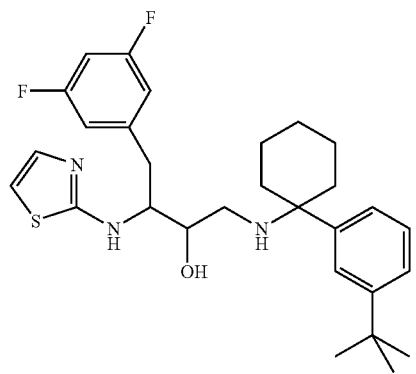

EXAMPLE 77

3-(5-BROMO-[1,3,4]THIADIAZOL-2-YLAMINO)-1-[1-(3-TERT-BUTYL-PHENYL)-CYCLOHEXY-LAMINO]-4-(3,5-DIFLUORO-PHENYL)-BUTAN-2-OL

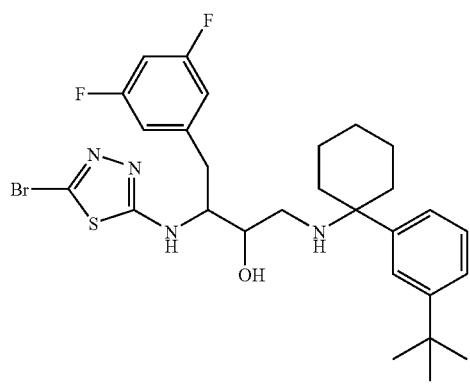

EXAMPLE 78

1-[1-(3-TERT-BUTYL-PHENYL)-CYCLOHEXY-LAMINO]-4-(3,5-DIFLUORO-PHENYL)-3-([1,3,4]THIADIAZOL-2-YLAMINO)-BUTAN-2-OL

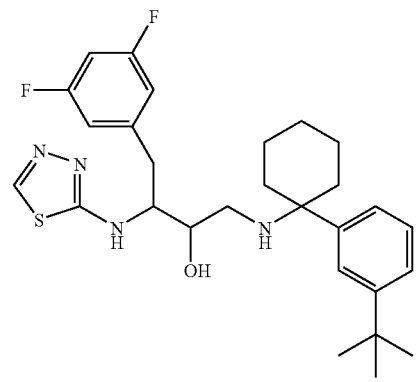

EXAMPLE 79

1-[1-(3-TERT-BUTYL-PHENYL)-CYCLOHEXY-LAMINO]-4-(3,5-DIFLUORO-PHENYL)-3-(5-METHYL-[1,3,4]THIADIAZOL-2-YLAMINO)-BUTAN-2-OL

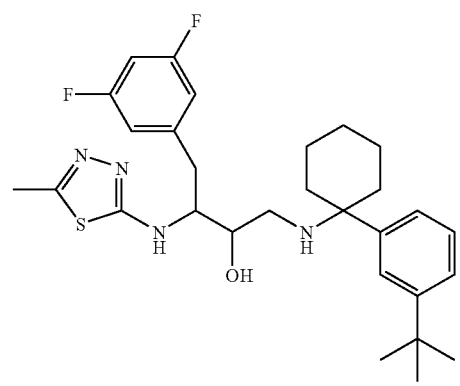

EXAMPLE 80

3-(5-AMINO-[1,3,4]THIADIAZOL-2-YLAMINO)-1-[1-(3-TERT-BUTYL-PHENYL)-CYCLOHEXY-LAMINO]-4-(3,5-DIFLUORO-PHENYL)-BUTAN-2-OL

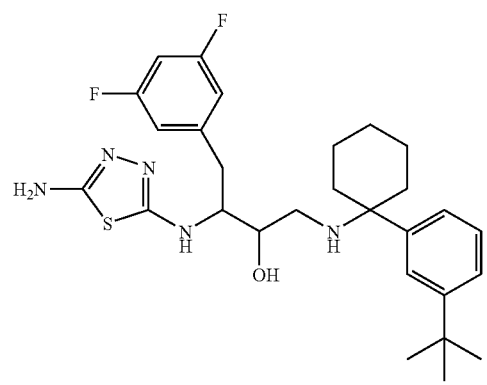

EXAMPLE 81

3-(2-BROMO-THIAZOL-5-YLAMINO)-1-[1-(3-TERT-BUTYL-PHENYL)-CYCLOHEXYLAMINO]-4-(3,5-DIFLUORO-PHENYL)-BUTAN-2-OL

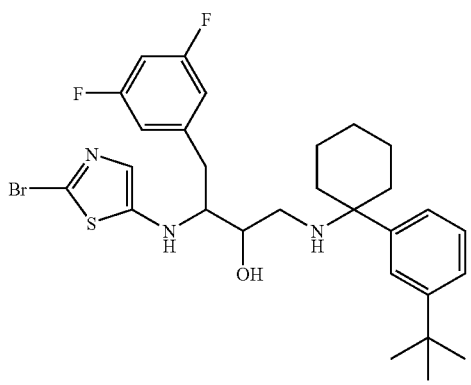

EXAMPLE 82

1-[1-(3-TERT-BUTYL-PHENYL)-CYCLOHEXYLAMINO]-4-(3,5-DIFLUORO-PHENYL)-3-(THIAZOL-5-YLAMINO)-BUTAN-2-OL

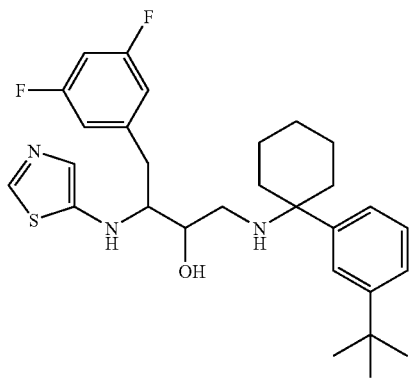

EXAMPLE 83

1-[1-(3-TERT-BUTYL-PHENYL)-CYCLOHEXYLAMINO]-4-(3,5-DIFLUORO-PHENYL)-3-(5-TRIFLUOROMETHYL-[1,3,4]THIADIAZOL-2-YLAMINO)-BUTAN-2-OL

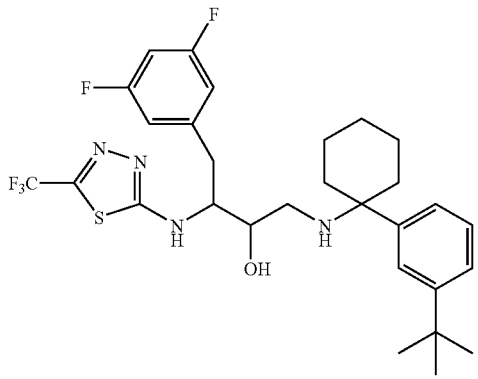

EXAMPLE 84

3-(3-BROMO-[1,2,4]THIADIAZOL-5-YLAMINO)-1-[1-(3-TERT-BUTYL-PHENYL)-CYCLOHEXYLAMINO]-4-(3,5-DIFLUORO-PHENYL)-BUTAN-2-OL

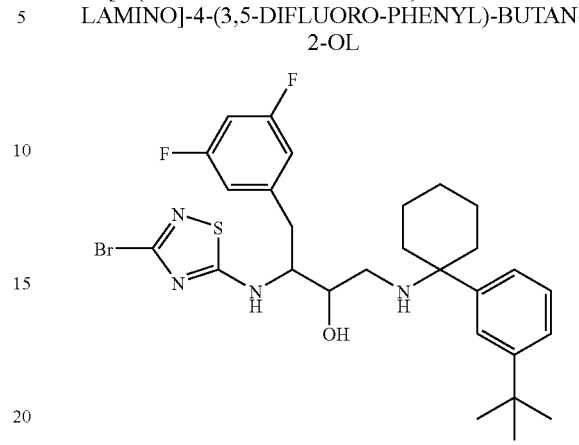

EXAMPLE 85

1-[1-(3-TERT-BUTYL-PHENYL)-CYCLOHEXYLAMINO]-4-(3,5-DIFLUORO-PHENYL)-3-(5-TRIFLUOROMETHYL-[1,3,4]OXADIAZOL-2-YLAMINO)-BUTAN-2-OL

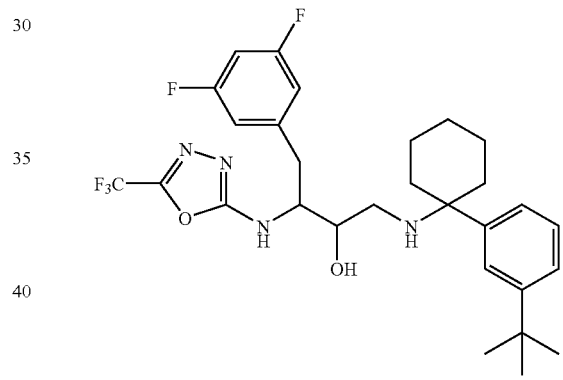

EXAMPLE 86

3-(5-AMINO-[1,3,4]OXADIAZOL-2-YLAMINO)-1-[1-(3-TERT-BUTYL-PHENYL)-CYCLOHEXYLAMINO]-4-(3,5-DIFLUORO-PHENYL)-BUTAN-2-OL

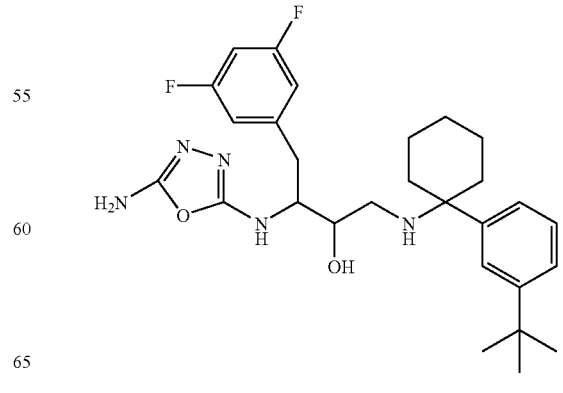

EXAMPLE 87

1-[1-(3-TERT-BUTYL-PHENYL)-CYCLOHEXY-LAMINO]-4-(3,5-DIFLUORO-PHENYL)-3-(5-METHYL-[1,3,4]OXADIAZOL-2-YLAMINO)-BUTAN-2-OL

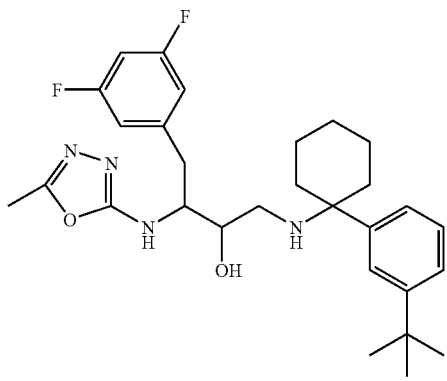

EXAMPLE 88

1-[1-(3-TERT-BUTYL-PHENYL)-CYCLOHEXY-LAMINO]-4-(3,5-DIFLUORO-PHENYL)-3-(5-PHENYL-[1,3,4]OXADIAZOL-2-YLAMINO)-BUTAN-2-OL

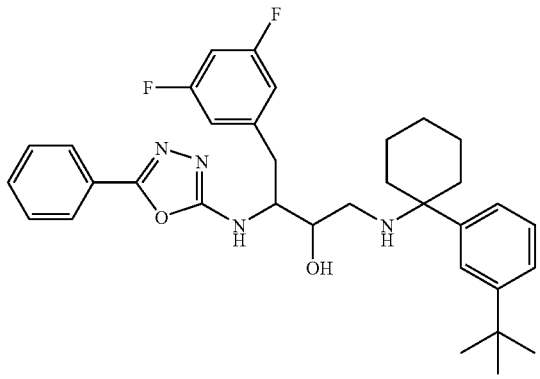

EXAMPLE 89

1-[1-(3-TERT-BUTYL-PHENYL)-CYCLOHEXY-LAMINO]-4-(3,5-DIFLUORO-PHENYL)-3-(5-PYRIDIN-4-YL-[1,3,4]OXADIAZOL-2-YLAMINO)-BUTAN-2-OL

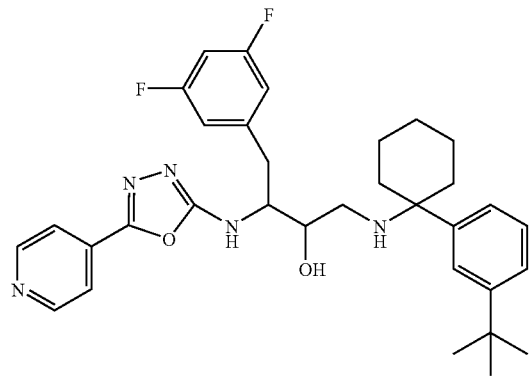

EXAMPLE 90

1-[1-(3-TERT-BUTYL-PHENYL)-CYCLOHEXY-LAMINO]-4-(3,5-DIFLUORO-PHENYL)-3-(1-TRITYL-1H-[1,2,4]TRIAZOL-3-YLAMINO)-BUTAN-2-OL

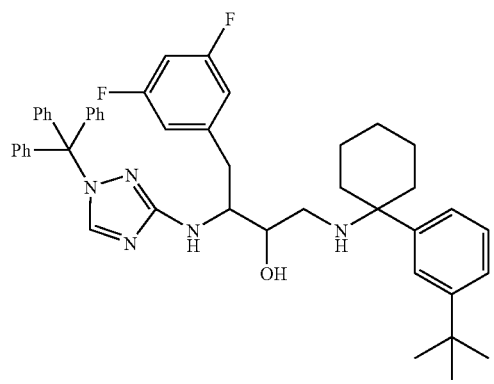

EXAMPLE 91

1-[1-(3-TERT-BUTYL-PHENYL)-CYCLOHEXY-LAMINO]-4-(3,5-DIFLUORO-PHENYL)-3-(1H-[1,2,4]TRIAZOL-3-YLAMINO)-BUTAN-2-OL

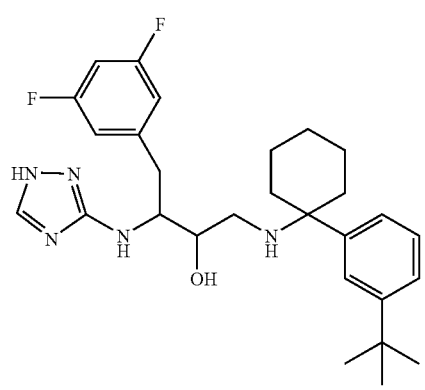

EXAMPLE 92

1-[1-(3-TERT-BUTYL-PHENYL)-CYCLOHEXY-LAMINO]-4-(3,5-DIFLUORO-PHENYL)-3-(OXAZOL-2-YLAMINO)-BUTAN-2-OL

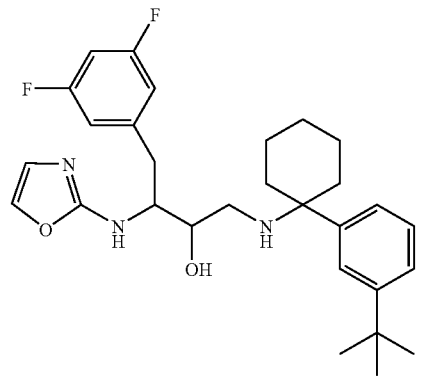

EXAMPLE 93

3-(5-BROMO-2-TRITYL-2H-[1,2,3]TRIAZOL-4-YLAMINO)-1-[1-(3-TERT-BUTYL-PHENYL)-CYCLOHEXYLAMINO]-4-(3,5-DIFLUORO-PHENYL)-BUTAN-2-OL

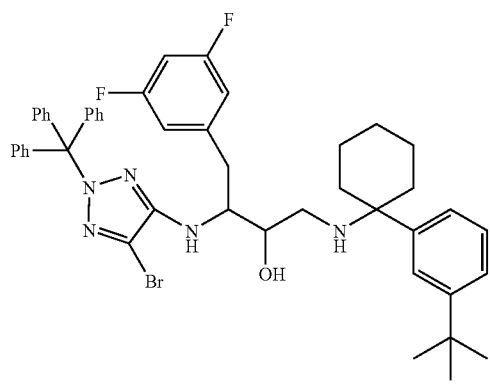

EXAMPLE 94

1-[1-(3-TERT-BUTYL-PHENYL)-CYCLOHEXYLAMINO]-4-(3,5-DIFLUORO-PHENYL)-3-(2-TRITYL-2H-[1,2,3]TRIAZOL-4-YLAMINO)-BUTAN-2-OL

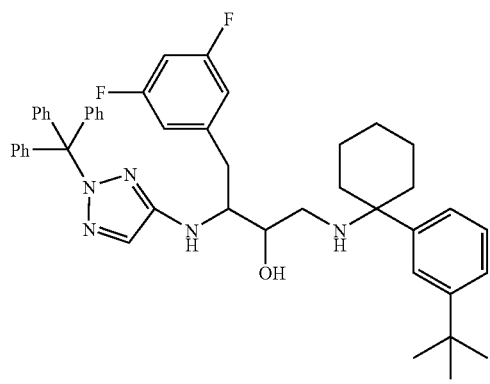

EXAMPLE 95

3-(5-BROMO-2H-[1,2,3]TRIAZOL-4-YLAMINO)-1-[1-(3-TERT-BUTYL-PHENYL)-CYCLOHEXYLAMINO]-4-(3,5-DIFLUORO-PHENYL)-BUTAN-2-OL

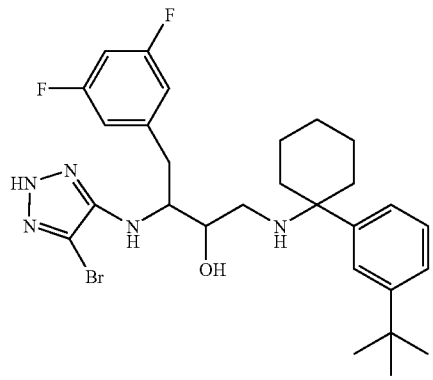

EXAMPLE 96

1-[1-(3-TERT-BUTYL-PHENYL)-CYCLOHEXYLAMINO]-4-(3,5-DIFLUORO-PHENYL)-3-(2H-[1,2,3]TRIAZOL-4-YLAMINO)-BUTAN-2-OL

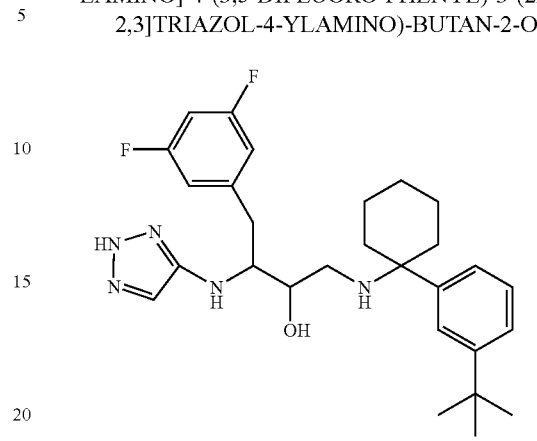

EXAMPLE 97

1-[1-(3-TERT-BUTYL-PHENYL)-CYCLOHEXYLAMINO]-4-(3,5-DIFLUORO-PHENYL)-3-(THIOPHEN-3-YLAMINO)-BUTAN-2-OL

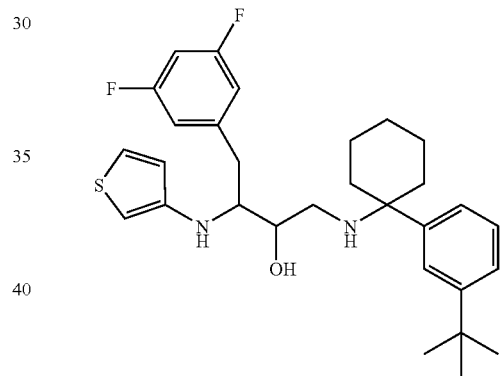

EXAMPLE 98

1-[1-(3-TERT-BUTYL-PHENYL)-CYCLOHEXYLAMINO]-4-(3,5-DIFLUORO-PHENYL)-3-(THIOPHEN-YLAMINO)-BUTAN-2-OL

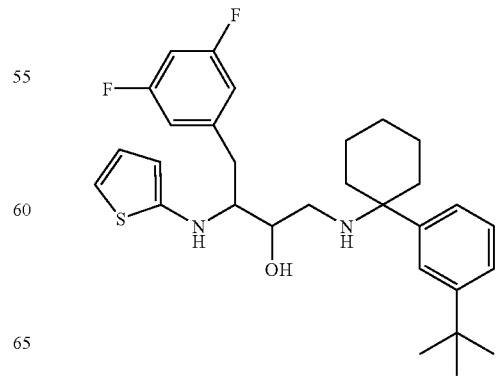

EXAMPLE 99

1-[1-(3-TERT-BUTYL-PHENYL)-CYCLOHEXY-LAMINO]-4-(3,5-DIFLUORO-PHENYL)-3-(3-NITRO-THIOPHEN-2-YLAMINO)-BUTAN-2-OL

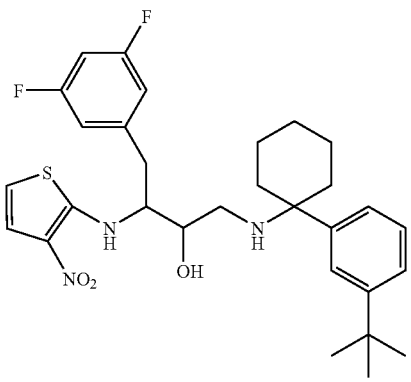

EXAMPLE 100

1-[1-(3-TERT-BUTYL-PHENYL)-CYCLOHEXY-LAMINO]-4-(3,5-DIFLUORO-PHENYL)-3-(3-METHYL-5-NITRO-3H-IMIDAZOL-4-YLAMINO)-BUTAN-2-OL

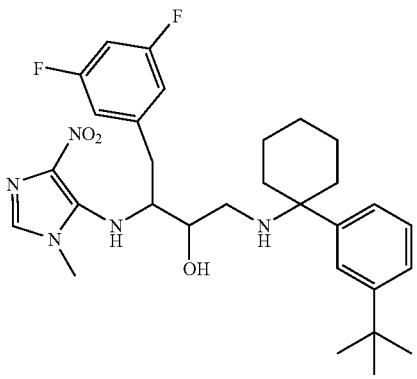

EXAMPLE 101

1-[1-(3-TERT-BUTYL-PHENYL)-CYCLOHEXY-LAMINO]-4-(3,5-DIFLUORO-PHENYL)-3-(2,5-DIMETHYL-4-NITRO-2H-PYRAZOL-3-YLAMINO)-BUTAN-2-OL

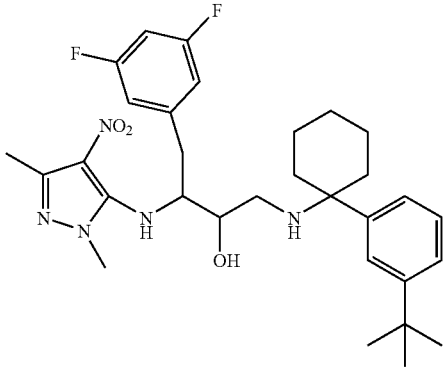

EXAMPLE 102

3-[3-[1-(3-TERT-BUTYL-PHENYL)-CYCLO-HEXYLAMINO]-1-(3,5-DIFLUORO-BENZYL)-2-HYDROXY-PROPYLAMINO]-5-PHENYL-ISOTHIAZOLE-4-CARBONITRILE

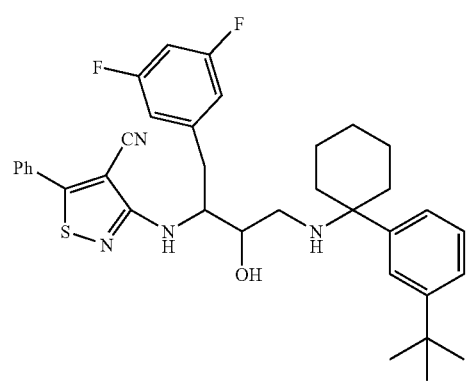

EXAMPLE 103

1-[1-(3-TERT-BUTYL-PHENYL)-CYCLOHEXY-LAMINO]-4-(3,5-DIFLUORO-PHENYL)-3-(4-PHENYL-[1,2,5]THIADIAZOL-3-YLAMINO)-BUTAN-2-OL

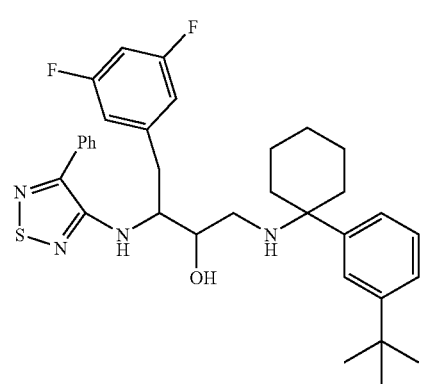

EXAMPLE 104

1-[1-(3-TERT-BUTYL-PHENYL)-CYCLOHEXY-LAMINO]-4-(3,5-DIFLUORO-PHENYL)-3-(1-METHYL-1H-PYRAZOL-4-YLAMINO)-BUTAN-2-OL

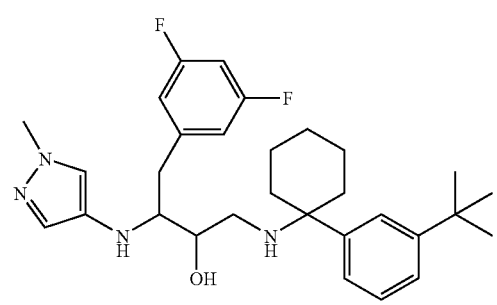

EXAMPLE 105

1-[1-(3-TERT-BUTYL-PHENYL)-CYCLOHEXY-LAMINO]-4-(3,5-DIFLUORO-PHENYL)-3-(PYRIMIDIN-4-YLAMINO)-BUTAN-2-OL

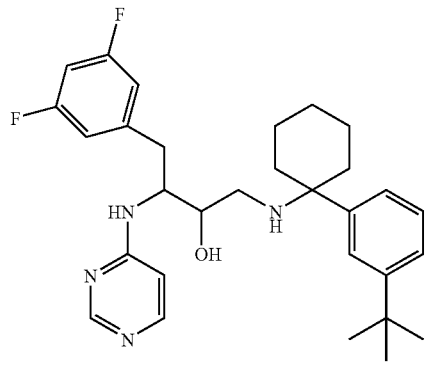

EXAMPLE 106

1-[1-(3-TERT-BUTYL-PHENYL)-CYCLOHEXY-LAMINO]-3-(2-CHLORO-PYRIMIDIN-4-YLAMINO)-4-(3,5-DIFLUORO-PHENYL)-BUTAN-2-OL

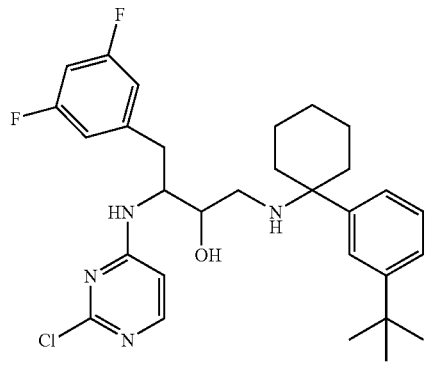

EXAMPLE 107

2-{4-[3-[1-(3-TERT-BUTYL-PHENYL)-CYCLOHEXYLAMINO]-1-(3,5-DIFLUORO-BENZYL)-2-HYDROXY-PROPYLAMINO]-PYRIMIDIN-2-YLAMINO}-N,N-DIPROPYL-ACETAMIDE

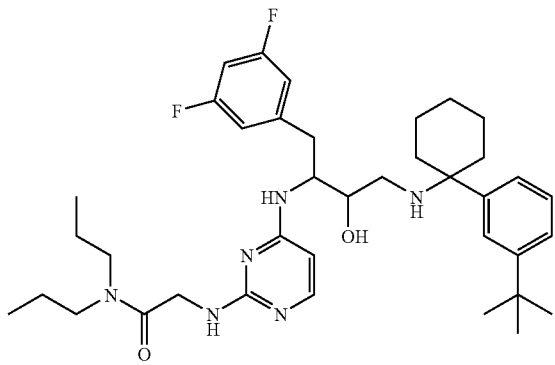

EXAMPLE 108

3-[3-[1-(3-TERT-BUTYL-PHENYL)-CYCLOHEXYLAMINO]-1-(3,5-DIFLUORO-BENZYL)-2-HYDROXY-PROPYLAMINO]-PYRIDIN-4-OL

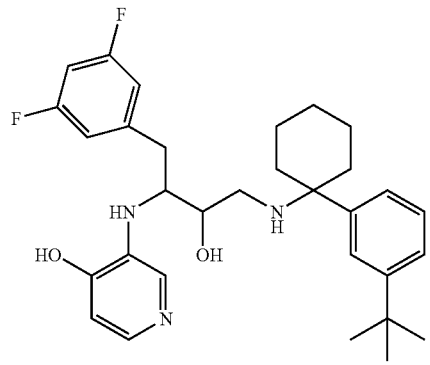

EXAMPLE 109

3-[3-[1-(3-TERT-BUTYL-PHENYL)-CYCLOHEXYLAMINO]-(3,5-DIFLUORO-BENZYL)-2-HYDROXY-PROPYLAMINO]-5-IODO-PYRIDIN-4-OL

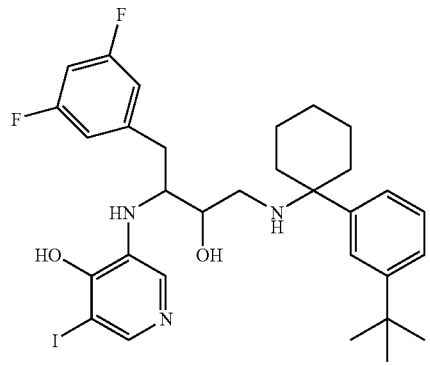

EXAMPLE 110

3-[3-[1-(3-TERT-BUTYL-PHENYL)-CYCLOHEXYLAMINO]-1-(3,5-DIFLUORO-BENZYL)-2-HYDROXY-PROPYLAMINO]-5-IODO-1-METHYL-1H-PYRIDIN-4-ONE

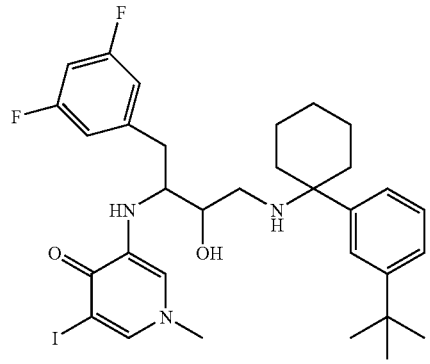

EXAMPLE 111

3-(BENZO[4,5]THIENO[3,2-D]PYRIMIDIN-4-YLAMINO)-1-[1-(3-TERT-BUTYL-PHENYL-CYCLOHEXYLAMINO]-4-(3,5-DIFLUORO-PHENYL)-BUTAN-2-OL

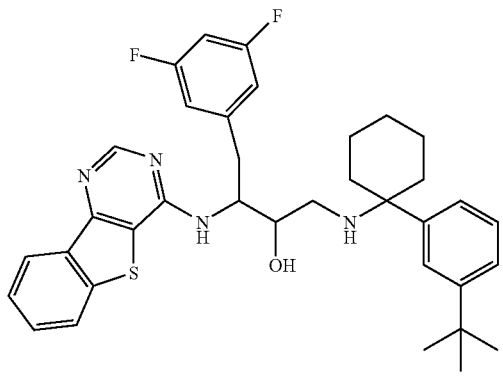

EXAMPLE 112

5-[3-[1-(3-TERT-BUTYL-PHENYL)-CYCLOHEXYLAMINO]-1-(3,5-DIFLUORO-BENZYL)-2-HYDROXY-PROPYLAMINO]-4-CHLORO-ISOTHIAZOLE-3-CARBOXYLIC ACID METHYL ESTER

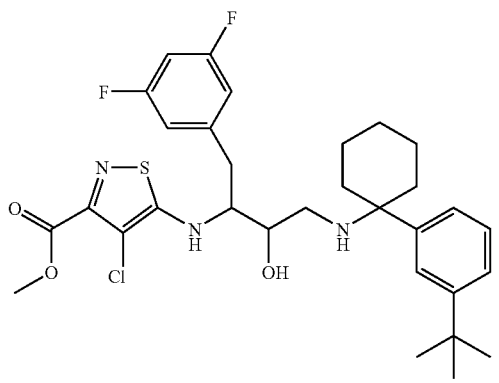

EXAMPLE 113

5-[3-[1-(3-TERT-BUTYL-PHENYL)-CYCLOHEXYLAMINO]-1-(3,5-DIFLUORO-BENZYL)-2-HYDROXY-PROPYLAMINO]-3-METHANE-SULFINYL-ISOTHIAZOLE-4-CARBONITRILE

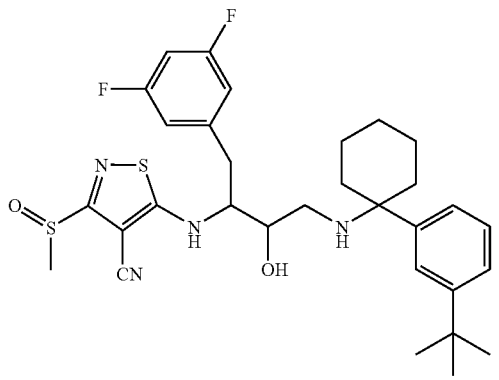

EXAMPLE 114

1-[1-(3-TERT-BUTYL-PHENYL)-CYCLOHEXYLAMINO]-4-(3,5-DIFLUORO-PHENYL)-3-(2-FLUORO-4-TRIFLUOROMETHYL-THIAZOL-5-YLAMINO)-BUTAN-2-OL

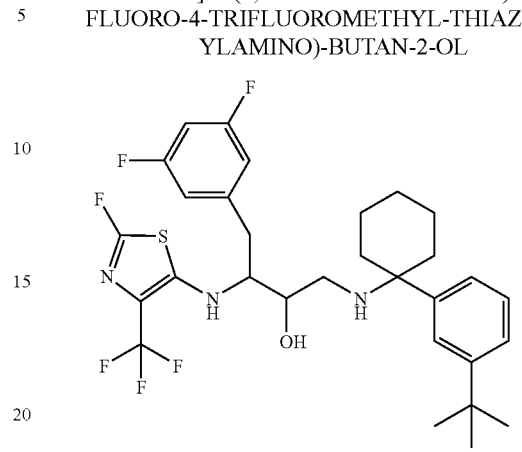

EXAMPLE 115

3-(1-BENZYL-1H-PYRAZOL-4-YLAMINO)-1-[1-(3-TERT-BUTYL-PHENYL)-CYCLOHEXYLAMINO]-4-(3,5-DIFLUORO-PHENYL)-BUTAN-2-OL

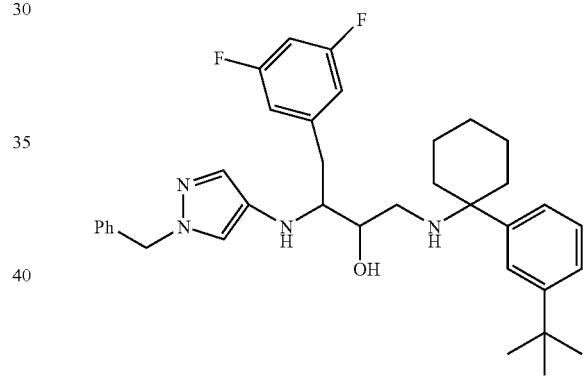

EXAMPLE 116

3-[3-[1-(3-TERT-BUTYL-PHENYL)-CYCLOHEXYLAMINO]-1-(3,5-DIFLUORO-BENZYL)-2-HYDROXY-PROPYLAMINO]-CYCLOBUT-3-ENE-1,2-DIONE

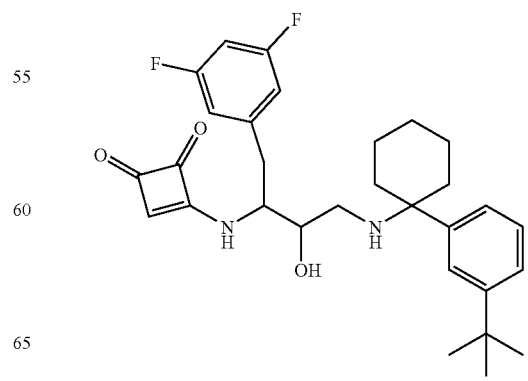

EXAMPLE 117

3-[3-[1-(3-TERT-BUTYL-PHENYL)-CYCLO-HEXYLAMINO]-1-(3,5-DIFLUORO-BENZYL)-2-HYDROXY-PROPYLAMINO]-4-METHOXY-CYCLOBUT-3-ENE-1,2-DIONE

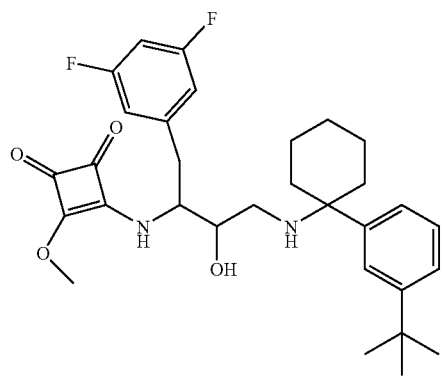

EXAMPLE 118

3-[3-[1-(3-TERT-BUTYL-PHENYL)-CYCLO-HEXYLAMINO]-1-(3,5-DIFLUORO-BENZYL)-2-HYDROXY-PROPYLAMINO]-4-METHYLAMINO-CYCLOBUT-3-ENE-1,2-DIONE

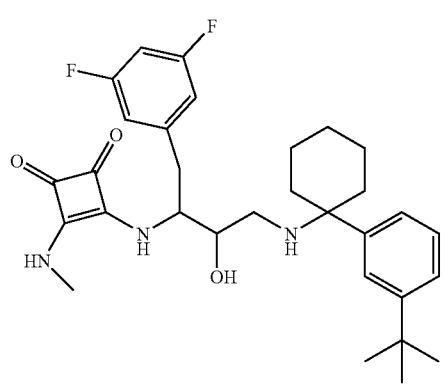

EXAMPLE 119

4-[3-[1-(3-TERT-BUTYL-PHENYL)-CYCLO-HEXYLAMINO]-1-(3,5-DIFLUORO-BENZYL)-2-HYDROXY-PROPYLAMINO]-BENZOIC ACID

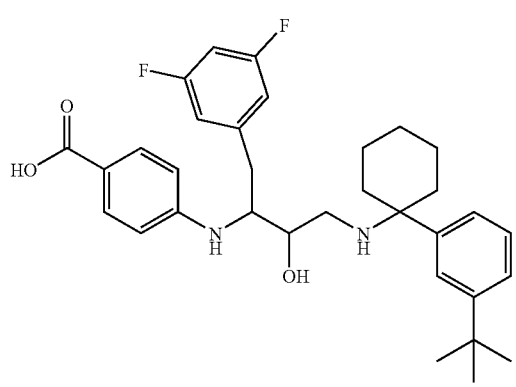

EXAMPLE 120

4-[3-[1-(3-TERT-BUTYL-PHENYL)-CYCLO-HEXYLAMINO]-1-(3,5-DIFLUORO-BENZYL)-2-HYDROXY-PROPYLAMINO]-BENZAMIDE

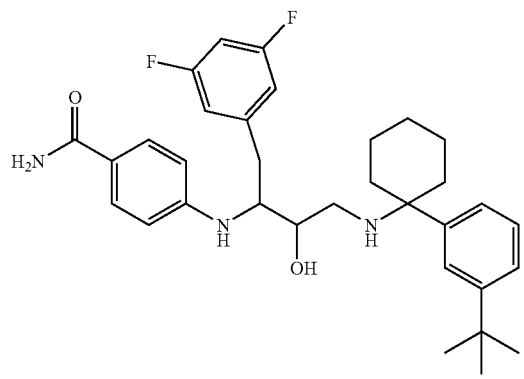

EXAMPLE 121

4-[3-[1-(3-TERT-BUTYL-PHENYL)-CYCLO-HEXYLAMINO]-1-(3,5-DIFLUORO-BENZYL)-2-HYDROXY-PROPYLAMINO]-N-METHYL-BENZAMIDE

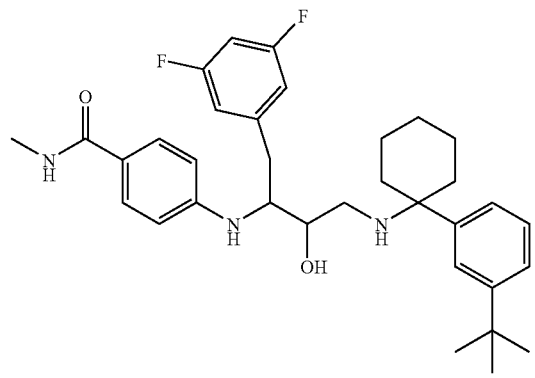

EXAMPLE 122

{4-[3-[1-(3-TERT-BUTYL-PHENYL)-CYCLO-HEXYLAMINO]-1-(3,5-DIFLUORO-BENZYL)-2-HYDROXY-PROPYLAMINO]-PHENYL}-ACETIC ACID

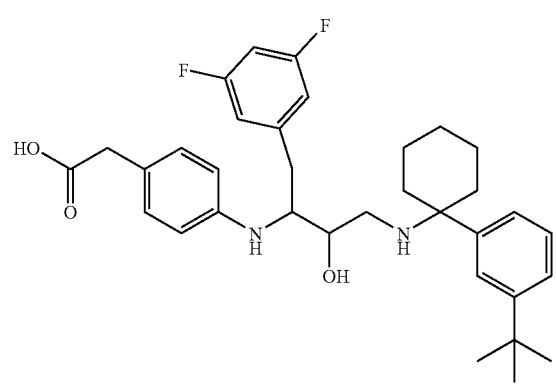

EXAMPLE 123

3-{4-[3-[1-(3-TERT-BUTYL-PHENYL)-CYCLO-HEXYLAMINO]-1-(3,5-DIFLUORO-BENZYL)-2-HYDROXY-PROPYLAMINO]-PHENYL}-PROPIONIC ACID

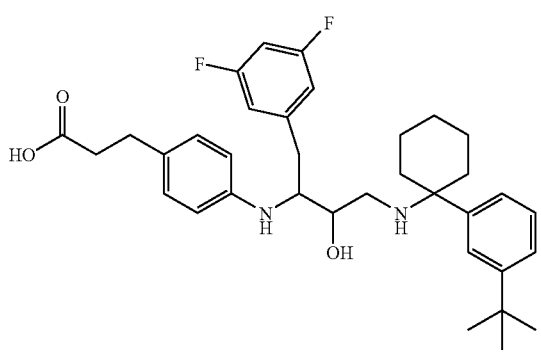

EXAMPLE 124

2-{3-[3-[1-(3-TERT-BUTYL-PHENYL)-CYCLO-HEXYLAMINO]-1-(3,5-DIFLUORO-BENZYL)-2-HYDROXY-PROPYLAMINO]-PHENYL}-N,N-DIPROPYL-ACETAMIDE

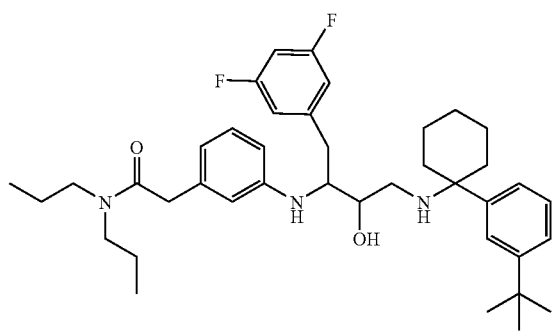

EXAMPLE 125

2-{3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-PHENYL}-N,N-DIPROPYL-ACETAMIDE

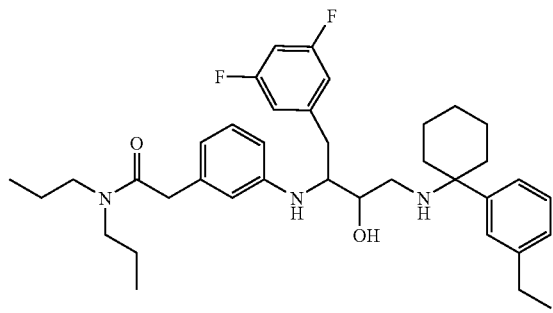

EXAMPLE 126

1-(6-BROMO-1,1-DIOXO-1$\lambda^6$-THIOCHROMAN-4-YLAMINO)-3-(3,5-DIFLUORO-PHENOXY)-PROPAN-2-OL

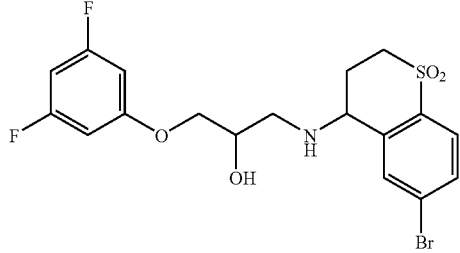

EXAMPLE 127

1-(3,5-DIFLUORO-PHENOXY)-3-(6-ISOBUTYL-1,1-DIOXO-1$\lambda^6$-THIOCHROMAN-4-YLAMINO)-PROPAN-2-OL

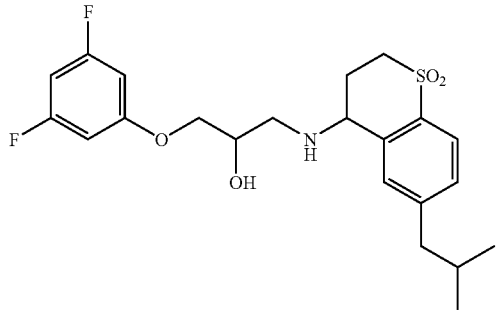

EXAMPLE 128

1-(6-TERT-BUTYL-1,1-DIOXO-1$\lambda^6$-THIOCHROMAN-4-YLAMINO)-3-(3,5-DIFLUORO-PHENOXY)-PROPAN-2-OL

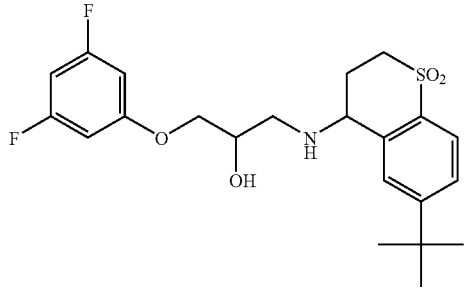

EXAMPLE 129

1-[1-(3-BROMO-PHENYL)-CYCLOHEXYLAMINO]-3-(3,5-DIFLUORO-PHENOXY)-PROPAN-2-OL

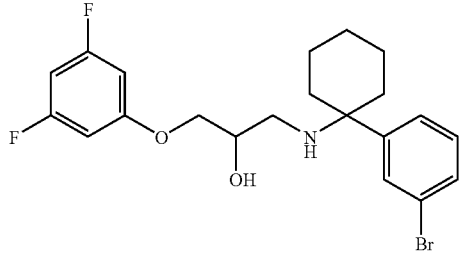

EXAMPLE 130

1-(3,5-DIFLUORO-PHENOXY)-3-[1-(3-ISOBU-TYL-PHENYL)-CYCLOHEXYLAMINO]-PROPAN-2-OL

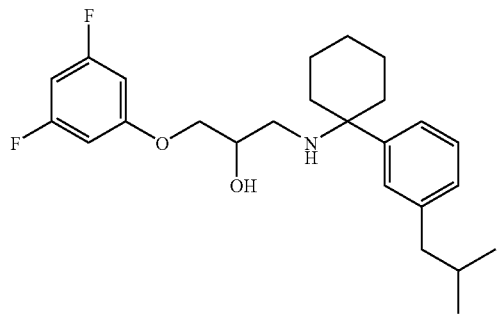

EXAMPLE 131

1-[1-(3-TERT-BUTYL-PHENYL)-CYCLOHEXY-LAMINO]-3-(3,5-DIFLUORO-PHENOXY)-PROPAN-2-OL

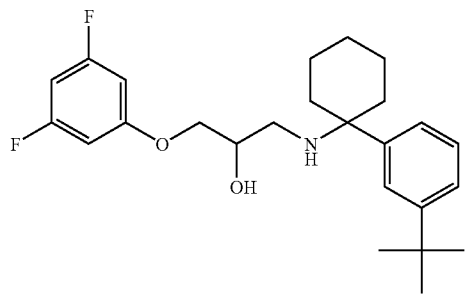

EXAMPLE 132

1-(6-BROMO-1,1-DIOXO-1λ⁶-THIOCHROMAN-4-YLAMINO)-3-(3,5-DIFLUORO-BENZENE-SULFONYL)-PROPAN-2-OL

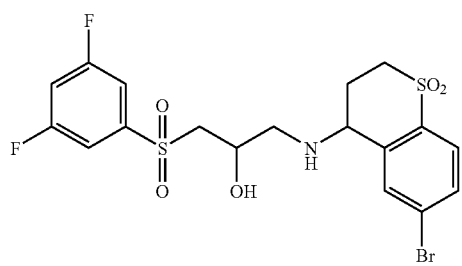

EXAMPLE 133

1-(3,5-DIFLUORO-BENZENESULFONYL)-3-(6-ISOBUTYL-1,1-DIOXO-1λ⁶-THIOCHROMAN-4-YLAMINO)-PROPAN-2-OL

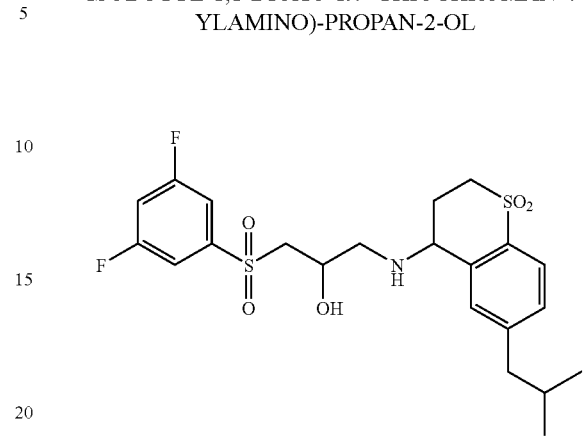

EXAMPLE 134

1-(6-TERT-BUTYL-1,1-DIOXO-1λ⁶-THIOCHRO-MAN-4-YLAMINO)-3-(3,5-DIFLUORO-BENZE-NESULFONYL)-PROPAN-2-OL

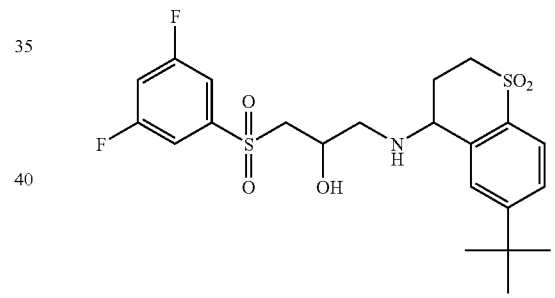

EXAMPLE 135

1-[1-(3-BROMO-PHENYL)-CYCLOHEXY-LAMINO]-3-(3,5-DIFLUORO-BENZENESULFO-NYL)-PROPAN-2-OL

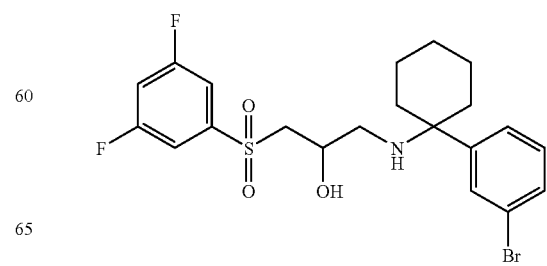

EXAMPLE 136

1-(3,5-DIFLUORO-BENZENESULFONYL)-3-[1-(3-ISOBUTYL-PHENYL)-CYCLOHEXY-LAMINO]-PROPAN-2-OL

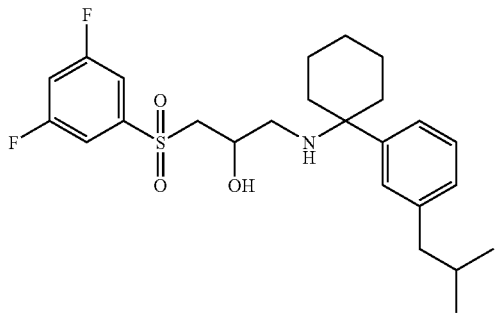

EXAMPLE 139

1-(3,5-DIFLUORO-PHENYL)-3-HYDROXY-4-(6-ISOBUTYL-1,1-DIOXO-1$\lambda^6$-THIOCHROMAN-4-YLAMINO)-BUTAN-1-ONE

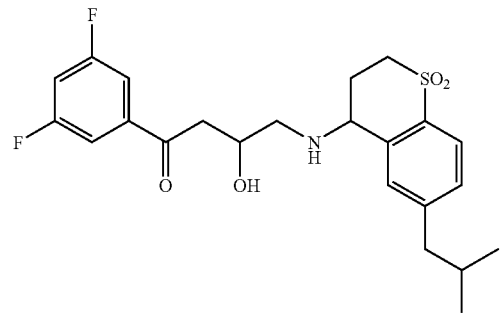

EXAMPLE 137

1-[1-(3-TERT-BUTYL-PHENYL)-CYCLOHEXY-LAMINO]-3-(3,5-DIFLUORO-BENZENESULFONYL)-PROPAN-2-OL

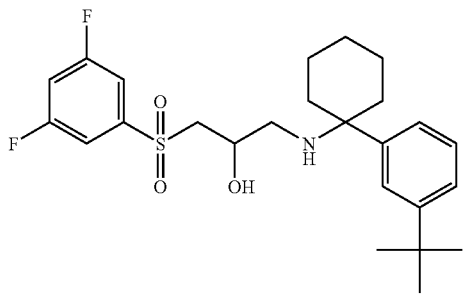

EXAMPLE 140

4-(6-TERT-BUTYL-1,1-DIOXO-1$\lambda^6$-THIOCHROMAN-4-YLAMINO)-1-(3,5-DIFLUORO-PHENYL)-3-HYDROXY-BUTAN-1-ONE

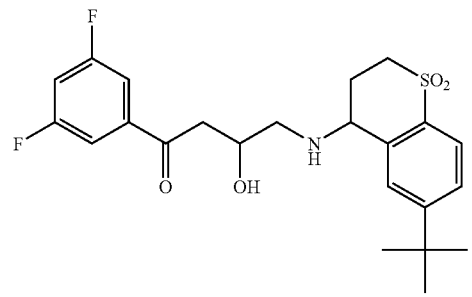

EXAMPLE 138

4-(6-BROMO-1,1-DIOXO-1$\lambda^6$-THIOCHROMAN-4-YLAMINO)-1-(3,5-DIFLUORO-PHENYL)-3-HYDROXY-BUTAN-1-ONE

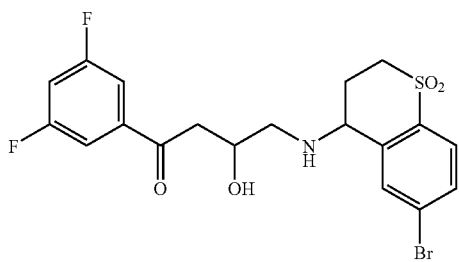

EXAMPLE 141

4-[1-(3-BROMO-PHENYL)-CYCLOHEXY-LAMINO]-1-(3,5-DIFLUORO-PHENYL)-3-HYDROXY-BUTAN-1-ONE

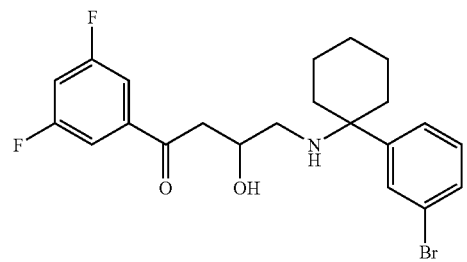

EXAMPLE 142

1-(3,5-DIFLUORO-PHENYL)-3-HYDROXY-4-[1-(3-ISOBUTYL-PHENYL)-CYCLOHEXY-LAMINO]-BUTAN-1-ONE

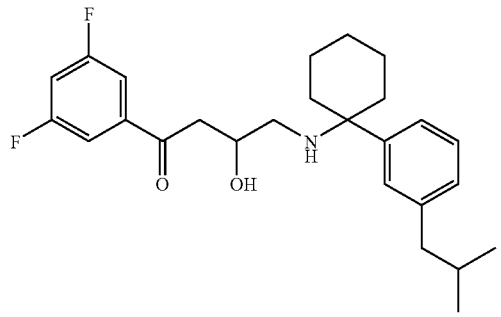

EXAMPLE 143

4-[1-(3-TERT-BUTYL-PHENYL)-CYCLOHEXY-LAMINO]-1-(3,5-DIFLUORO-PHENYL)-3-HYDROXY-BUTAN-1-ONE

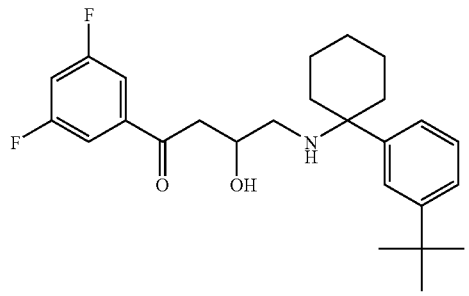

EXAMPLE 144

1-(6-BROMO-1,1-DIOXO-1λ⁶-THIOCHROMAN-4-YLAMINO)-4-(3,5-DIFLUORO-PHENYL)-PENTAN-2-OL

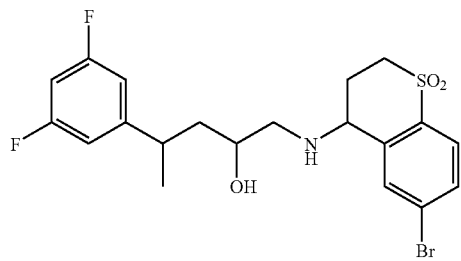

EXAMPLE 145

1-(6-BROMO-1,1-DIOXO-1λ⁶-THIOCHROMAN-4-YLAMINO)-4-(3,5-DIFLUORO-PHENYL)-4-METHYLAMINO-BUTAN-2-OL

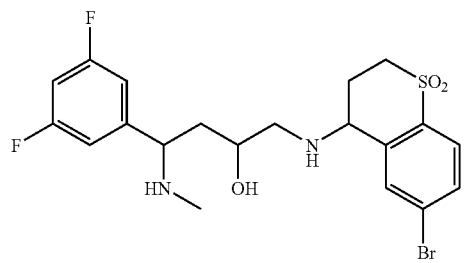

EXAMPLE 146

1-[1-(3-TERT-BUTYL-PHENYL)-CYCLOHEXY-LAMINO]-4-(3,5-DIFLUORO-PHENYL)-PENTAN-2-OL

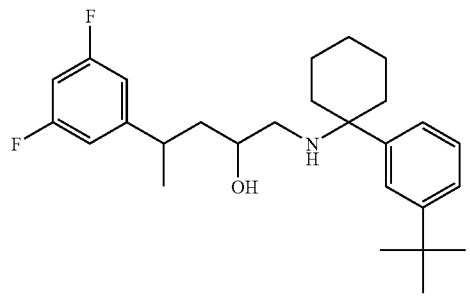

EXAMPLE 147

1-[1-(3-TERT-BUTYL-PHENYL)-CYCLOHEXY-LAMINO]-4-(3,5-DIFLUORO-PHENYL)-4-METHYLAMINO-BUTAN-2-OL

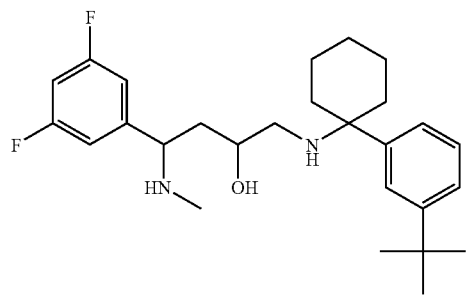

EXAMPLE 148

1-(6-TERT-BUTYL-1,1-DIOXO-1λ⁶-THIOCHRO-MAN-4-YLAMINO)-4-(3,5-DIFLUORO-PHE-NYL)-PENTAN-2-OL

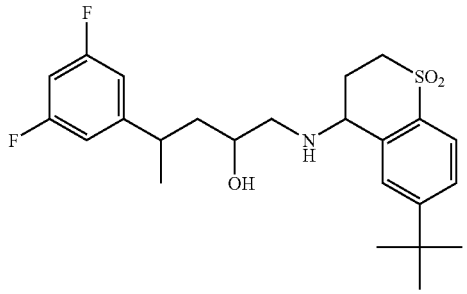

EXAMPLE 149

1-(6-TERT-BUTYL-1,1-DIOXO-1λ⁶-THIOCHRO-MAN-4-YLAMINO)-4-(3,5-DIFLUORO-PHE-NYL)-4-METHYLAMINO-BUTAN-2-OL

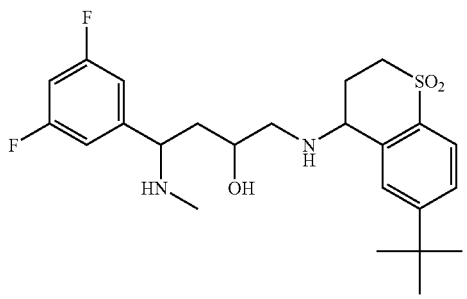

EXAMPLE 150

1-[1-(3-BROMO-PHENYL)-CYCLOHEXY-LAMINO]-4-(3,5-DIFLUORO-PHENYL)-PEN-TAN-2-OL

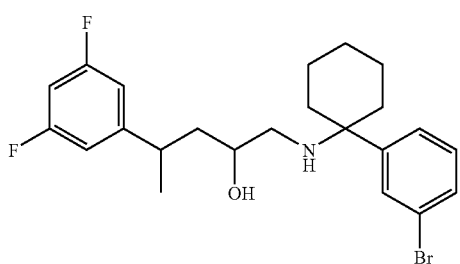

EXAMPLE 151

1-[1-(3-BROMO-PHENYL)-CYCLOHEXY-LAMINO]-4-(3,5-DIFLUORO-PHENYL)-4-ME-THYLAMINO-BUTAN-2-OL

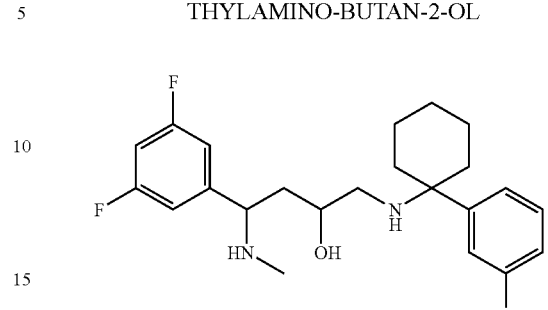

EXAMPLE 152

2-(3,5-DIFLUORO-BENZYL)-4-[7-(2,2-DIM-ETHYL-PROPYL)-1,2,3,4-TETRAHYDRO-NAPH-THALEN-1-YLAMINO]-3-HYDROXY-N-ME-THYL-BUTYRAMIDE

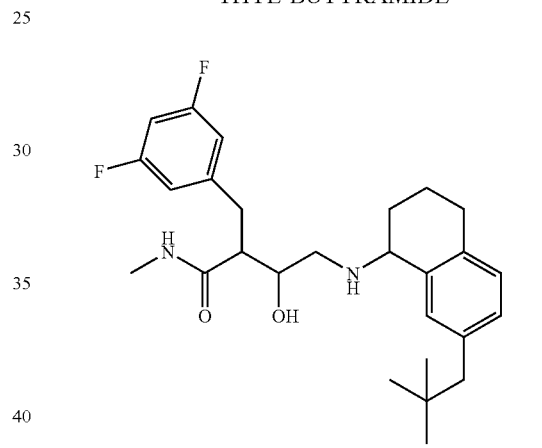

EXAMPLE 153

2-(3,5-DIFLUORO-BENZYL)-4-[6-(2,2-DIM-ETHYL-PROPYL)-2,2-DIOXO-2λ⁶-ISOTHIO-CHROMAN-4-YLAMINO]-3-HYDROXY-N-ME-THYL-BUTYRAMIDE

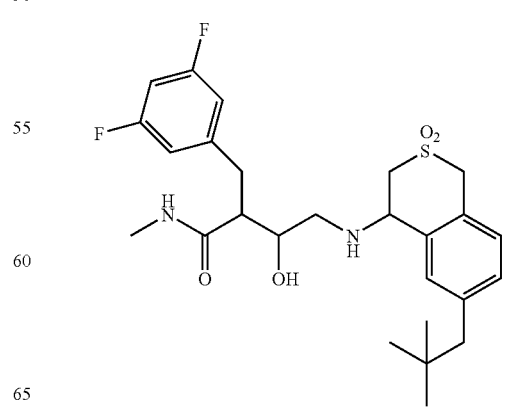

EXAMPLE 154

2-(3,5-DIFLUORO-BENZYL)-4-[6-(2,2-DIM-ETHYL-PROPYL)-1,1-DIOXO-1λ⁶-THIOCHRO-MAN-4-YLAMINO]-3-HYDROXY-N-METHYL-BUTYRAMIDE

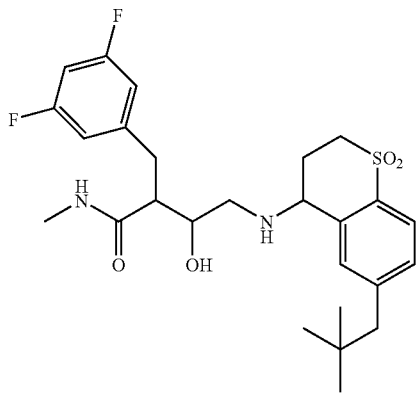

EXAMPLE 155

2-(3,5-DIFLUORO-BENZYL)-4-[6-(2,2-DIM-ETHYL-PROPYL)-CHROMAN-4-YLAMINO]-3-HYDROXY-N-METHYL-BUTYRAMIDE

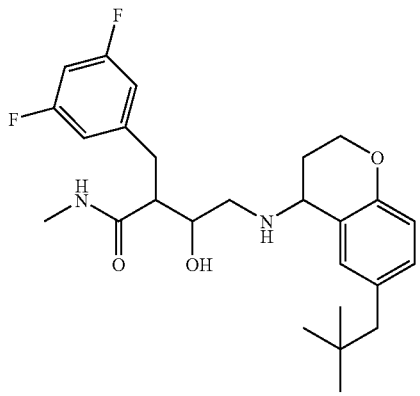

EXAMPLE 156

2-(3,5-DIFLUORO-BENZYL)-4-[6-(2,2-DIM-ETHYL-PROPYL)-1,2,3,4-TETRAHYDRO-QUINOLIN-4-YLAMINO]-3-HYDROXY-N-METHYL-BUTYRAMIDE

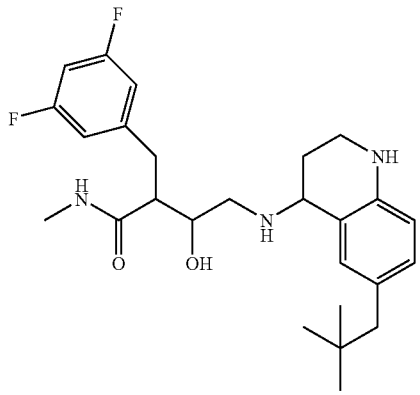

EXAMPLE 157

2-(3,5-DIFLUORO-BENZYL)-4-[5-(2,2-DIM-ETHYL-PROPYL)-2-(1H-IMIDAZOL-2-YL)-BEN-ZYLAMINO]-3-HYDROXY-N-METHYL-BU-TYRAMIDE

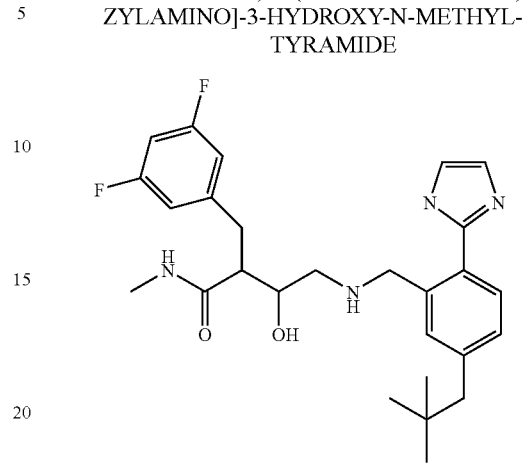

EXAMPLE 158

2-(3,5-DIFLUORO-BENZYL)-4-[7(2,2-DIM-ETHYL-PROPYL)-1,2,3,4-TETRAHYDRO-NAPH-THALEN-1-YLAMINO]-3-HYDROXY-N-PHE-NYL-BUTYRAMIDE

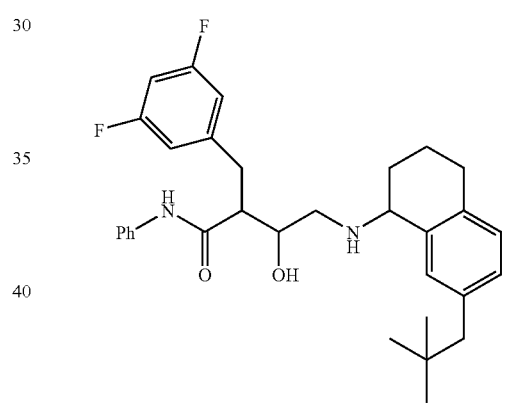

EXAMPLE 159

2-(3,5-DIFLUORO-BENZYL)-4-[6-(2,2-DIM-ETHYL-PROPYL)-2,2-DIOXO-2λ⁶-ISOTHIO-CHROMAN-4-YLAMINO]-3-HYDROXY-N-PHE-NYL-BUTYRAMIDE

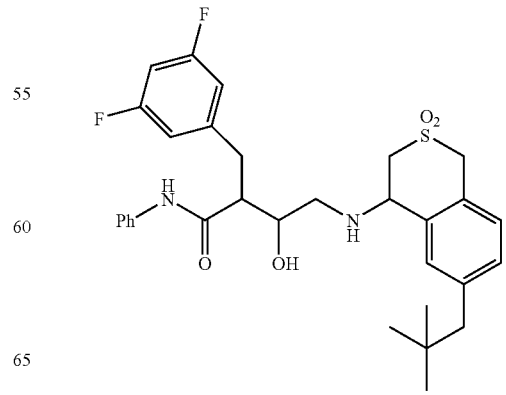

EXAMPLE 160

2-(3,5-DIFLUORO-BENZYL)-4-[6-(2,2-DIM-ETHYL-PROPYL)-1,1-DIOXO-1λ⁶-THIOCHRO-MAN-4-YLAMINO]-3-HYDROXY-N-PHENYL-BUTYRAMIDE

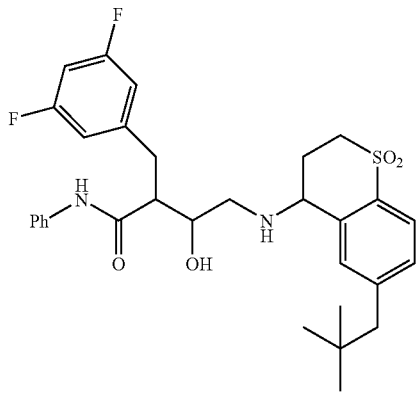

EXAMPLE 161

2-(3,5-DIFLUORO-BENZYL)-4-[6-(2,2-DIM-ETHYL-PROPYL)-CHROMAN-4-YLAMINO]-3-HYDROXY-N-PHENYL-BUTYRAMIDE

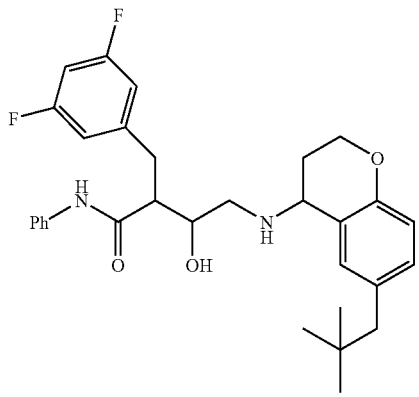

EXAMPLE 162

2-(3,5-DIFLUORO-BENZYL)-4-[6-(2,2-DIM-ETHYL-PROPYL)-1,2,3,4-TETRAHYDRO-QUINOLIN-4-YLAMINO]-3-HYDROXY-N-PHE-NYL-BUTYRAMIDE

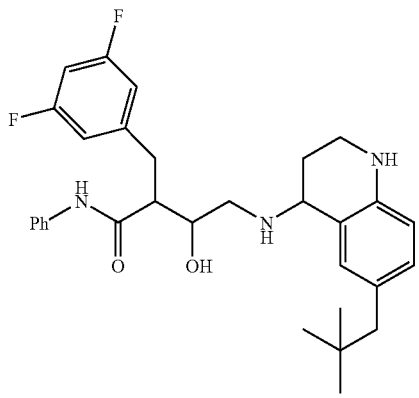

EXAMPLE 163

2-(3,5-DIFLUORO-BENZYL)-4-[5-(2,2-DIM-ETHYL-PROPYL)-2-(1H-IMIDAZOL-2-YL)-BEN-ZYLAMINO]-3-HYDROXY-N-PHENYL-BU-TYRAMIDE

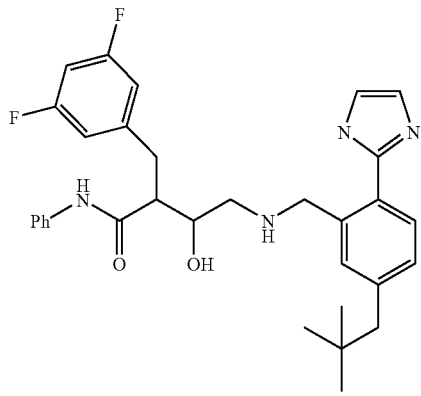

EXAMPLE 164

4-[1-(3-TERT-BUTYL-PHENYL)-CYCLOHEXY-LAMINO]-2-(3,5-DIFLUORO-BENZYL)-3-HY-DROXY-N-METHYL-BUTYRAMIDE

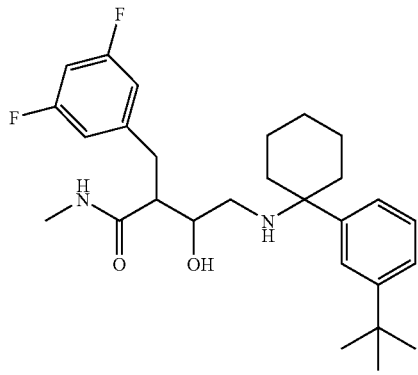

EXAMPLE 165

4-[1-(3-TERT-BUTYL-PHENYL)-CYCLOHEXY-LAMINO]-2-(3,5-DIFLUORO-BENZYL)-3-HY-DROXY-N-PHENYL-BUTYRAMIDE

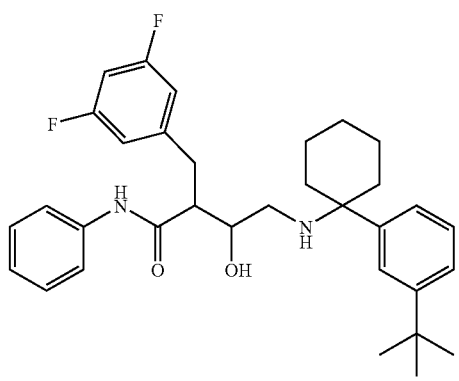

EXAMPLE 166

4-[4-(3-TERT-BUTYL-PHENYL)-TETRAHYDRO-PYRAN-4-YLAMINO]-2-(3,5-DIFLUORO-BENZYL)-3-HYDROXY-N-METHYL-BUTYRAMIDE

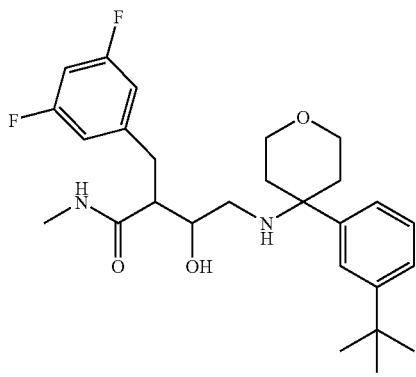

EXAMPLE 167

4-[4-(3-TERT-BUTYL-PHENYL)-TETRAHYDRO-PYRAN-4-YLAMINO]-2-(3,5-DIFLUORO-BENZYL)-3-HYDROXY-N-PHENYL-BUTYRAMIDE

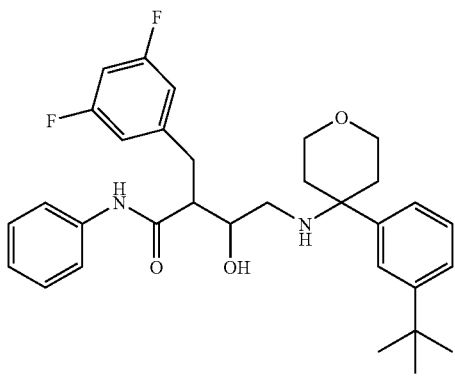

EXAMPLE 168

1-[1-(3-TERT-BUTYL-PHENYL)-CYCLOHEXYLAMINO]-4-(3,5-DIFLUORO-PHENYL)-3-ETHYLAMINO-BUTAN-2-OL

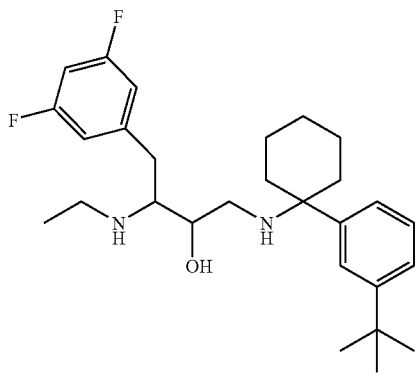

EXAMPLE 169

1-[1-(3-TERT-BUTYL-PHENYL)-CYCLOHEXYLAMINO]-4-(3,5-DIFLUORO-PHENYL)-3-PROPYLAMINO-BUTAN-2-OL

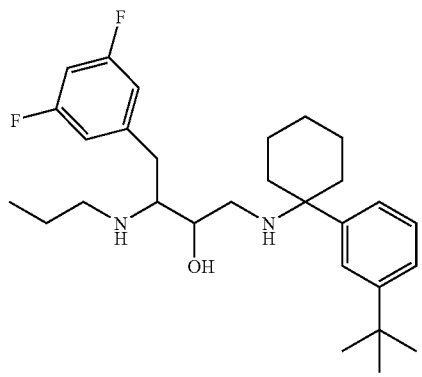

EXAMPLE 170

1-[1-(3-TERT-BUTYL-PHENYL)-CYCLOHEXYLAMINO]-3-(2,2-DIFLUORO-ETHYLAMINO)-4-(3,5-DIFLUORO-PHENYL)-BUTAN-2-OL

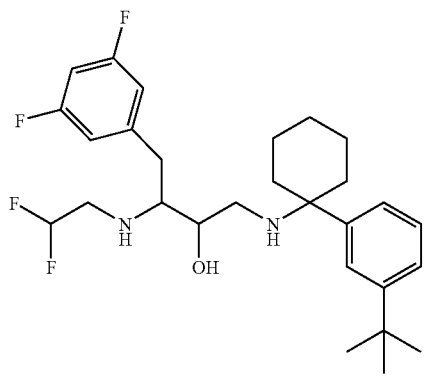

EXAMPLE 171

1-[1-(3-TERT-BUTYL-PHENYL)-CYCLOHEXYLAMINO]-4-(3,5-DIFLUORO-PHENYL)-3-(2,2,2-TRIFLUORO-ETHYLAMINO)-BUTAN-2-OL

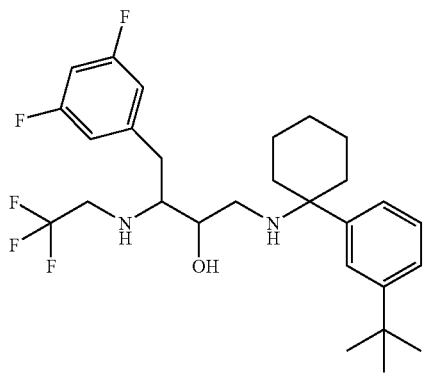

EXAMPLE 172

1-[1-(3-TERT-BUTYL-PHENYL)-CYCLOHEXY-LAMINO]-3-(CYCLOPROPYLMETHYL-AMINO)-4-(3,5-DIFLUORO-PHENYL)-BUTAN-2-OL

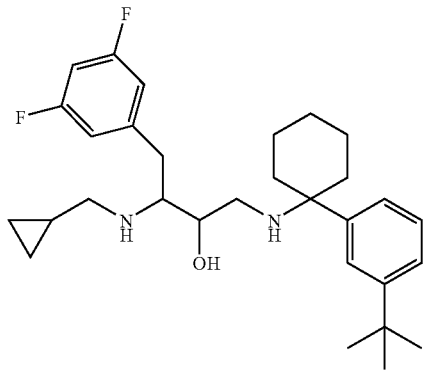

EXAMPLE 173

1-[1-(3-TERT-BUTYL-PHENYL)-CYCLOHEXY-LAMINO]-4-(3,5-DIFLUORO-PHENYL)-3-(2-HYDROXY-ETHYLAMINO)-BUTAN-2-OL

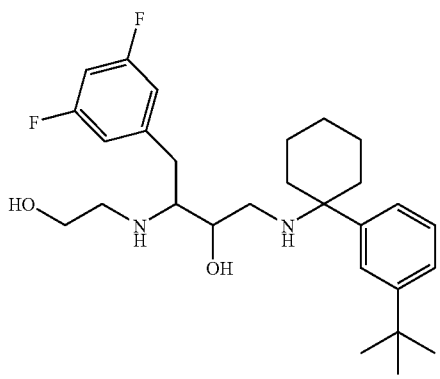

EXAMPLE 174

3-[3-[1-(3-TERT-BUTYL-PHENYL)-CYCLO-HEXYLAMINO]-1-(3,5-DIFLUORO-BENZYL)-2-HYDROXY-PROPYLAMINO]-PROPANE-1,2-DIOL

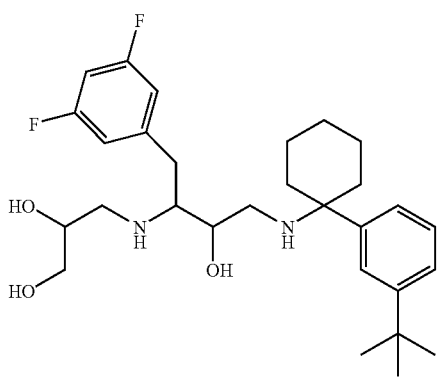

EXAMPLE 175

3-(2-AMINO-ETHYLAMINO)-1-[1-(3-TERT-BUTYL-PHENYL)-CYCLOHEXYLAMINO]-4-(3,5-DIFLUORO-PHENYL)-BUTAN-2-OL

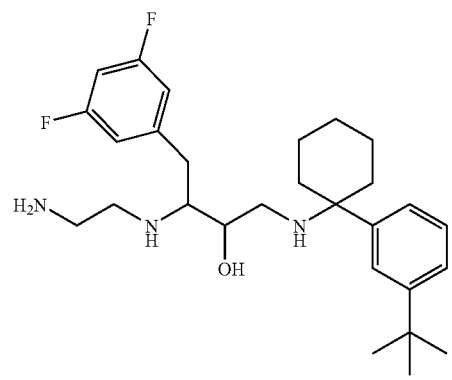

EXAMPLE 176

1-[1-(3-TERT-BUTYL-PHENYL)-CYCLOHEXY-LAMINO]-4-(3,5-DIFLUORO-PHENYL)-3-(3-METHYLSULFANYL-PROPYLAMINO)-BUTAN-2-OL

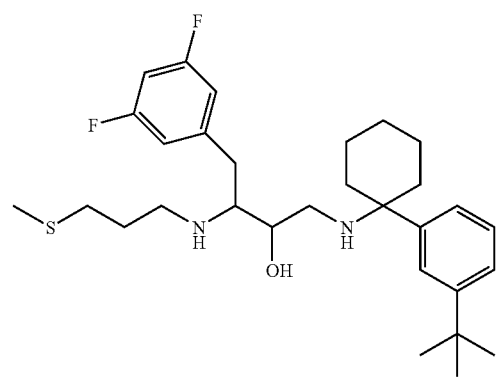

EXAMPLE 177

1-[1-(3-TERT-BUTYL-PHENYL)-CYCLOHEXY-LAMINO]-4-(3,5-DIFLUORO-PHENYL)-3-(3-HYDROXY-2,2-DIMETHYL-PROPYLAMINO)-BUTAN-2-OL

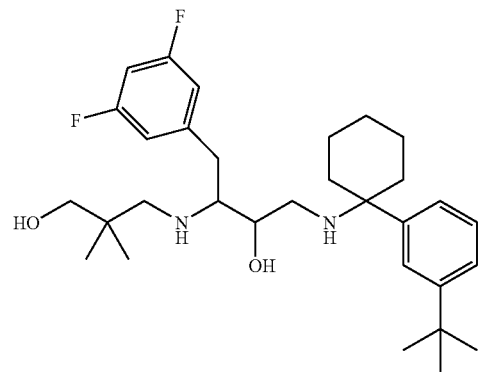

EXAMPLE 178

6-[3-[1-(3-TERT-BUTYL-PHENYL)-CYCLO-HEXYLAMINO]-1-(3,5-DIFLUORO-BENZYL)-2-HYDROXY-PROPYLAMINO]-HEXANOIC ACID METHYL ESTER

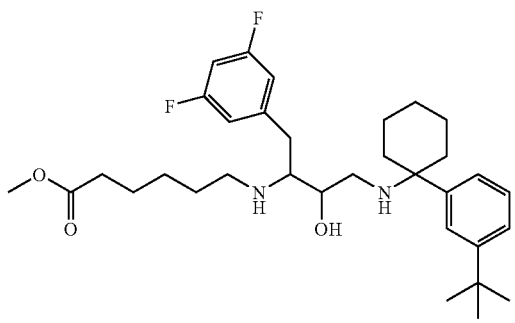

EXAMPLE 179

1-[1-(3-TERT-BUTYL-PHENYL)-CYCLOHEXY-LAMINO]-4-(3,5-DIFLUORO-PHENYL)-3-[(PYR-ROLIDIN-3-YLMETHYL)-AMINO]-BUTAN-2-OL

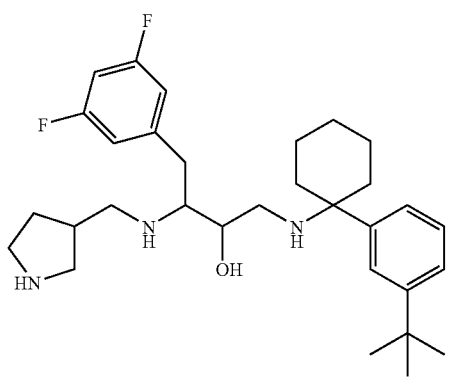

EXAMPLE 180

1-[1-(3-TERT-BUTYL-PHENYL)-CYCLOHEXY-LAMINO]-4-(3,5-DIFLUORO-PHENYL)-3-[(PIP-ERIDIN-4-YLMETHYL)-AMINO]-BUTAN-2-OL

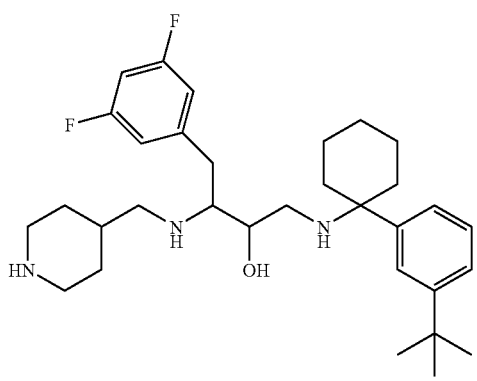

EXAMPLE 181

1-[1-(3-TERT-BUTYL-PHENYL)-CYCLOHEXY-LAMINO]-4-(3,5-DIFLUORO-PHENYL)-3-(2-PIPERIDIN-4-YL-ETHYLAMINO)-BUTAN-2-OL

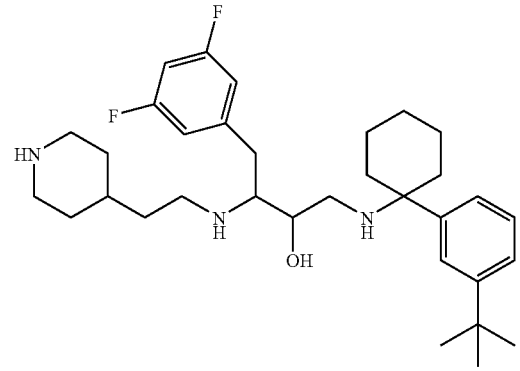

EXAMPLE 182

1-[1-(3-TERT-BUTYL-PHENYL)-CYCLOHEXY-LAMINO]-4-(3,5-DIFLUORO-PHENYL)-3-[(1-PHENYL-1H-[1,2,3]TRIAZOL-4-YLMETHYL)-AMINO]-BUTAN-2-OL

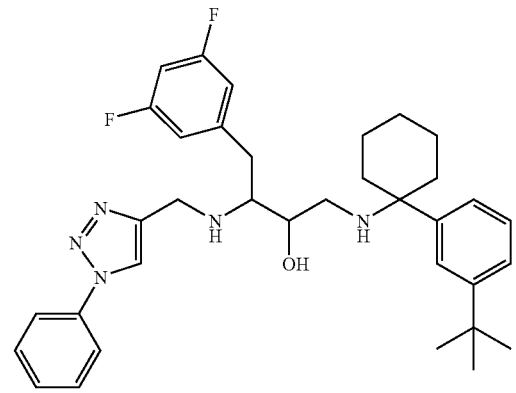

EXAMPLE 183

1-[1-(3-TERT-BUTYL-PHENYL)-CYCLOHEXY-LAMINO]-4-(3,5-DIFLUORO-PHENYL)-3-[(1H-PYRAZOL-3-YLMETHYL)-AMINO]-BUTAN-2-OL

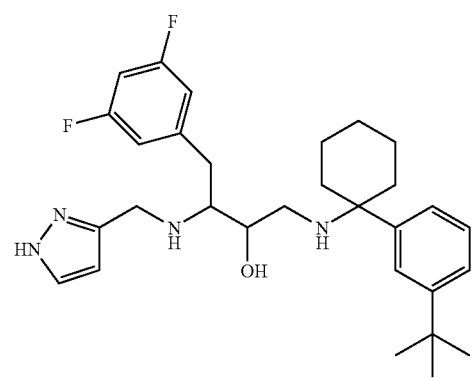

EXAMPLE 184

1-[1-(3-TERT-BUTYL-PHENYL)-CYCLOHEXY-
LAMINO]-3-[(4-CHLORO-1-METHYL-1H-PYRA-
ZOL-3-YLMETHYL)-AMINO]-4-(3,5-DIF-
LUORO-PHENYL)-BUTAN-2-OL

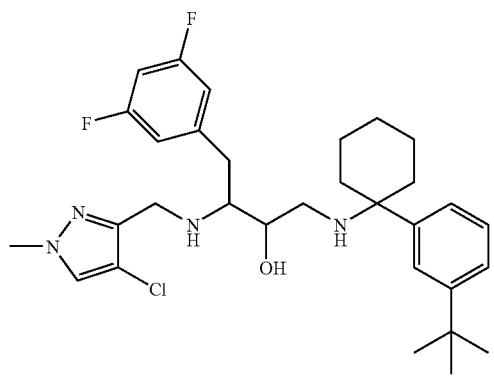

EXAMPLE 185

1-[1-(3-TERT-BUTYL-PHENYL)-CYCLOHEXY-
LAMINO]-4-(3,5-DIFLUORO-PHENYL)-3-[(FU-
RAN-2-YLMETHYL)-AMINO]-BUTAN-2-OL

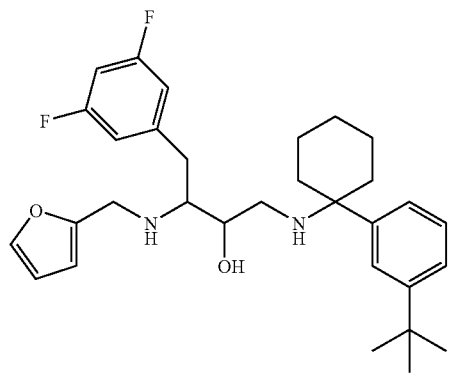

EXAMPLE 186

1-[1-(3-TERT-BUTYL-PHENYL)-CYCLOHEXY-
LAMINO]-4-(3,5-DIFLUORO-PHENYL)-3-[1,2,3]
TRIAZOL-1-YL-BUTAN-2-OL

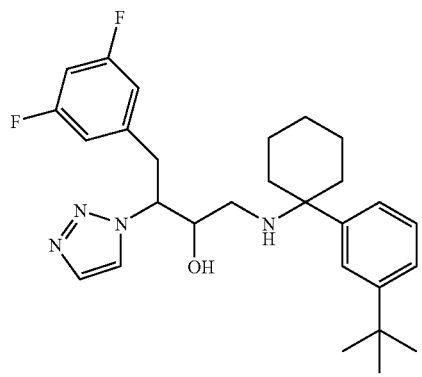

EXAMPLE 187

1-[1-(3-TERT-BUTYL-PHENYL)-CYCLOHEXY-
LAMINO]-4-(3,5-DIFLUORO-PHENYL)-3-(1-
METHYL-1H-PYRAZOL-4-YL)-BUTAN-2-OL

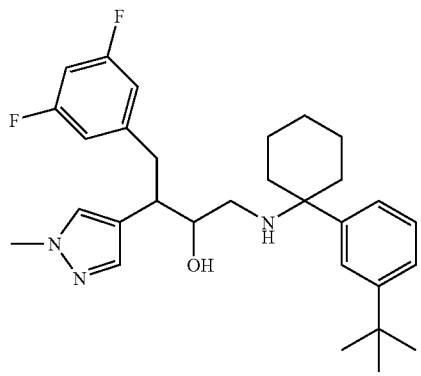

EXAMPLE 188

3-BENZYLAMINO-1-[1-(3-TERT-BUTYL-PHE-
NYL)-CYCLOHEXYLAMINO]-4-(3,5-DIF-
LUORO-PHENYL)-BUTAN-2-OL

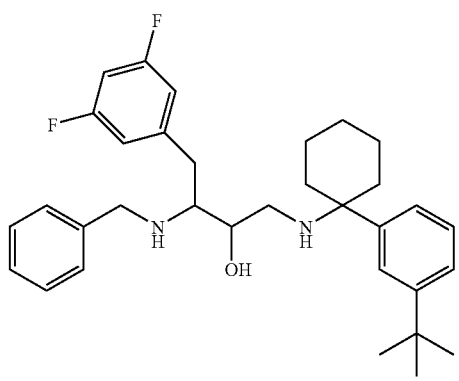

EXAMPLE 189

2-{[3-[1-(3-TERT-BUTYL-PHENYL)-CYCLO-
HEXYLAMINO]-1-(3,5-DIFLUORO-BENZYL)-2-
HYDROXY-PROPYLAMINO]-METHYL}-PHE-
NOL

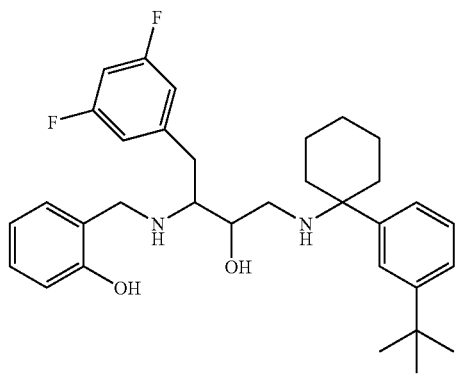

EXAMPLE 190

4-{[3-[1-(3-TERT-BUTYL-PHENYL)-CYCLO-HEXYLAMINO]-1-(3,5-DIFLUORO-BENZYL)-2-HYDROXY-PROPYLAMINO]-METHYL}-BENZENE-1,3-DIOL

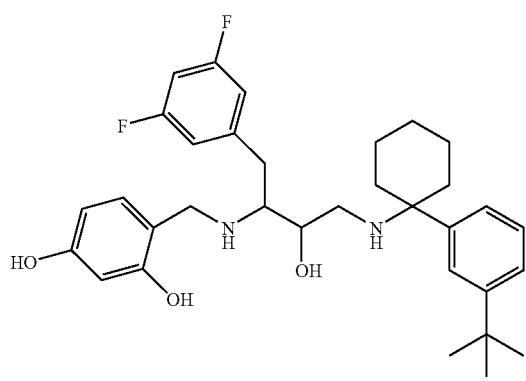

EXAMPLE 191

4-(3,5-DIFLUORO-PHENYL)-1-(7-ETHYL-1,2,3,4-TETRAHYDRO-NAPHTHALEN-1-YLAMINO)-3-(PYRIDIN-4-YLAMINO)-BUTAN-2-OL

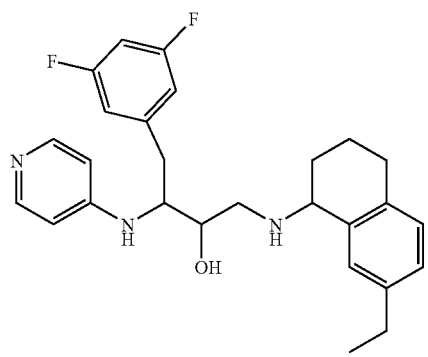

EXAMPLE 192

4-(3,5-DIFLUORO-PHENYL)-1-[6-(2,2-DIMETHYL-PROPYL)-CHROMAN-4-YLAMINO]-3-(1-METHYL-1H-PYRAZOL-4-YLAMINO)-BUTAN-2-OL

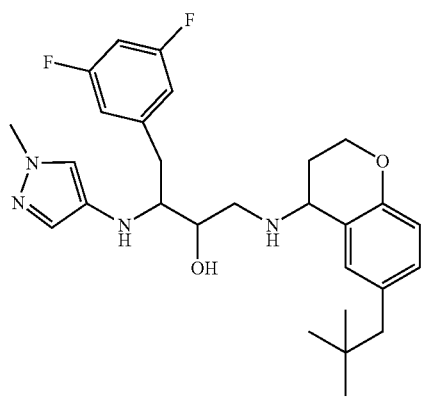

EXAMPLE 193

4-(3,5-DIFLUORO-PHENYL)-1-[5-(2,2-DIMETHYL-PROPYL)-2-IMIDAZOL-1-YL-BENZYLAMINO]-BUTAN-2-OL

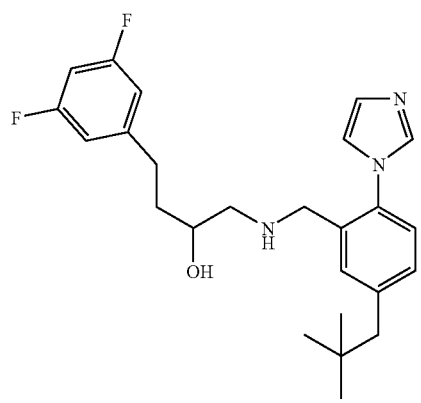

EXAMPLE 194

4-(3,5-DIFLUORO-PHENYL)-1-[5-(2,2-DIMETHYL-PROPYL)-2-(4-HYDROXYMETHYL-IMIDAZOL-1-YL)-BENZYLAMINO]-BUTAN-2-OL

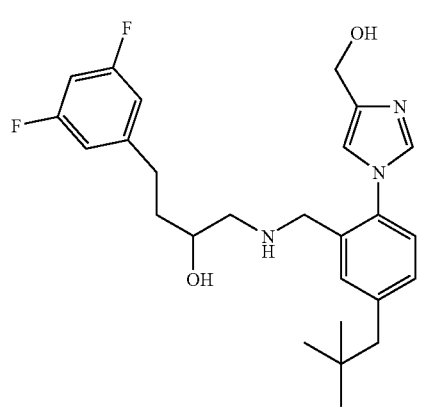

EXAMPLE 195

4-(3,5-DIFLUORO-PHENYL)-1-(3,4,5-TRIMETHOXY-BENZYLAMINO)-BUTAN-2-OL

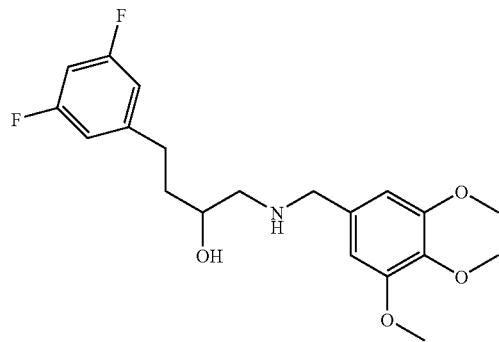

EXAMPLE 196

4-(3,5-DIFLUORO-PHENYL)-1-[2-(2-HYDROXYMETHYL-PHENYLSULFANYL)-BENZYLAMINO]-BUTAN-2-OL

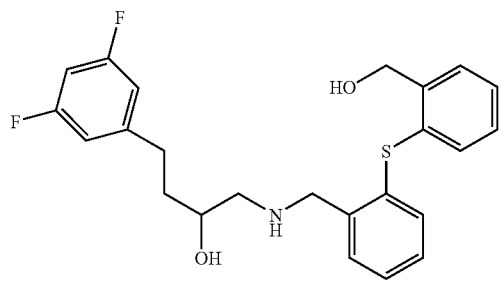

EXAMPLE 197

N-(4-{[4-(3,5-DIFLUORO-PHENYL)-2-HYDROXY-BUTYLAMINO]-METHYL}-PHENYL)-N-METHYL-ACETAMIDE

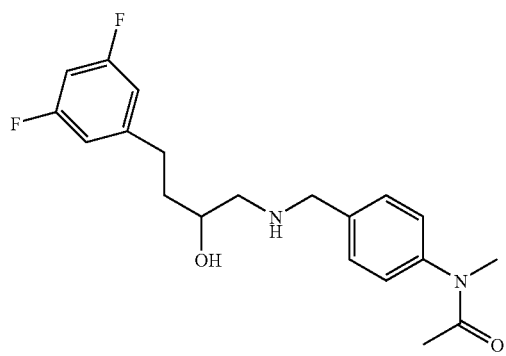

EXAMPLE 198

4-(3,5-DIFLUORO-PHENYL)-(3-IODO-BENZYLAMINO)-BUTAN-2-OL

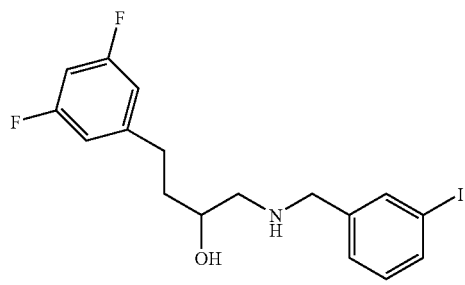

EXAMPLE 199

1-(4-AMINO-BENZYLAMINO)-4-(3,5-DIFLUORO-PHENYL)-BUTAN-2-OL

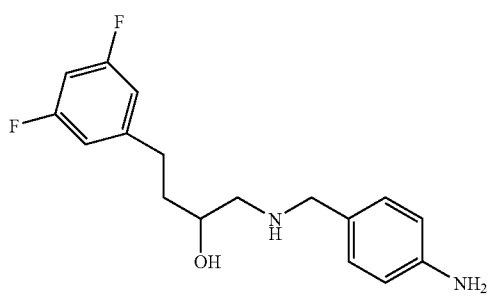

EXAMPLE 200

4-(3,5-DIFLUORO-PHENYL)-1-[1-(3-ETHYL-PHENYL)-CYCLOPROPYLAMINO]-3-(1-METHYL-1H-PYRAZOL-4-YLAMINO)-BUTAN-2-OL

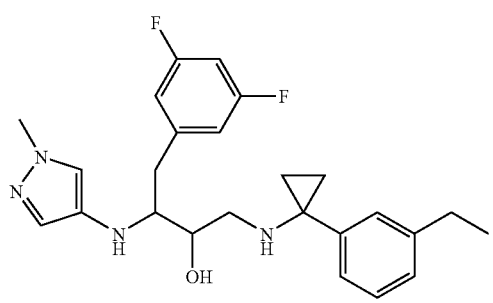

EXAMPLE 201

4-(3,5-DIFLUORO-PHENYL)-1-(3-ETHYL-BENZYLAMINO)-3-(1-METHYL-1H-PYRAZOL-4-YLAMINO)-BUTAN-2-OL

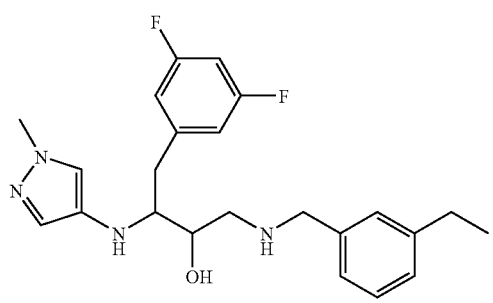

EXAMPLE 202

3-(2-CHLORO-PYRIMIDIN-4-YLAMINO)-4-(3,5-DIFLUORO-PHENYL)-1-(3-ETHYL-BENZY-LAMINO)-BUTAN-2-OL

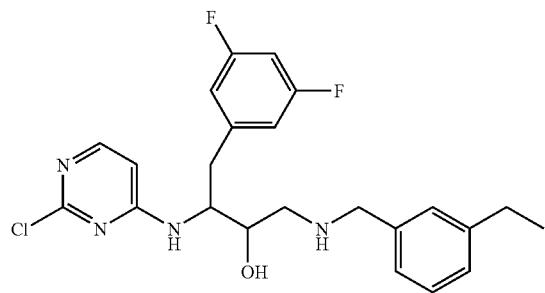

EXAMPLE 203

4-(3,5-DIFLUORO-PHENYL)-1-[(3,4-DIHYDRO-2H-BENZO[b][1,4]DIOXEPIN-6-YLMETHYL)-AMINO]-BUTAN-2-OL

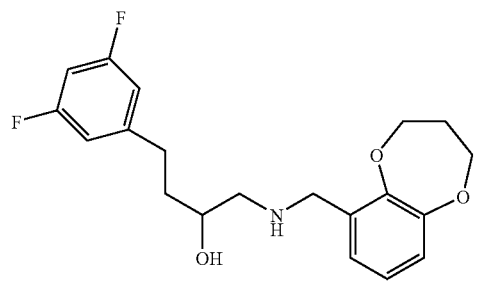

EXAMPLE 204

4-(3,5-DIFLUORO-PHENYL)-1-[(3,4-DIHYDRO-2H-BENZO[b][1,4]DIOXEPIN-7-YLMETHYL)-AMINO]-BUTAN-2-OL

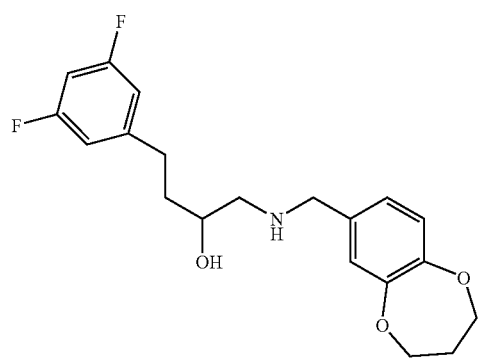

EXAMPLE 205

4-(3,5-DIFLUORO-PHENYL)-1-[(2,3-DIHYDRO-BENZO[1,4]DIOXIN-5-YLMETHYL)-AMINO]-BUTAN-2-OL

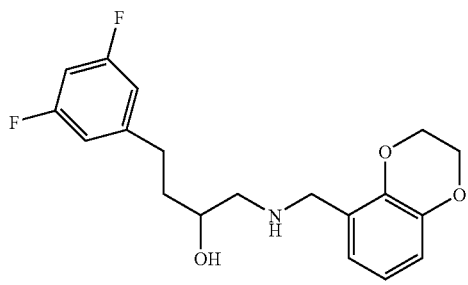

EXAMPLE 206

4-(3,5-DIFLUORO-PHENYL)-1-[(7,7-DIMETHYL-BICYCLO[3.1.1]HEPT-6-YLMETHYL)-AMINO]-BUTAN-2-OL

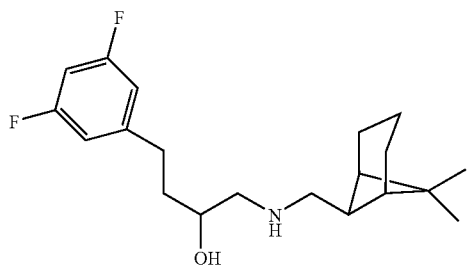

EXAMPLE 207

3-[4-(3,5-DIFLUORO-PHENYL)-2-HYDROXY-BUTYLAMINO]-5-PHENYL-1,3-DIHYDRO-BENZO[e][1,4]DIAZEPIN-2-ONE

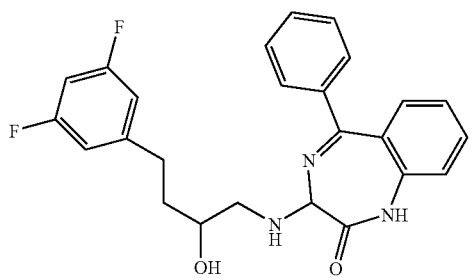

EXAMPLE 208

4-(3,5-DIFLUORO-PHENYL)-1-[1-(3-ETHYL-PHENYL)-CYCLOPROPYLAMINO]-BUTAN-2-OL

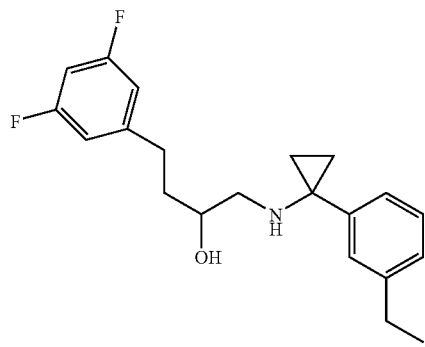

EXAMPLE 209

3-(2-CHLORO-PYRIMIDIN-4-YLAMINO)-(3,5-DIFLUORO-PHENYL)-1-[1-(3-ETHYL-PHENYL)-CYCLOPROPYLAMINO]-BUTAN-2-OL

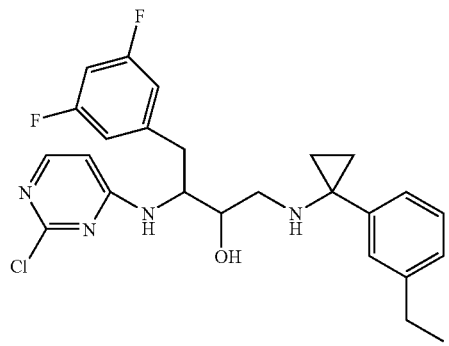

EXAMPLE 210

4-(3,5-DIFLUORO-PHENYL)-1-(1,1-DIOXO-1λ$_6$-THIOCHROMAN-4-YLAMINO)-BUTAN-2-OL

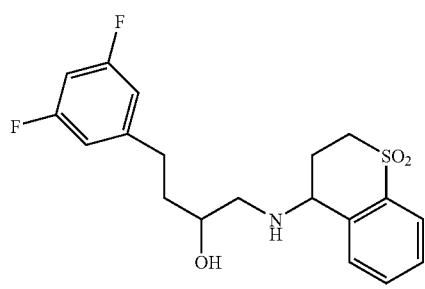

EXAMPLE 211

1-(6-BROMO-1,1-DIOXO-1λ$_6$-THIOCHROMAN-4-YLAMINO)-4-(3,5-DIFLUORO-PHENYL)-BUTAN-2-OL

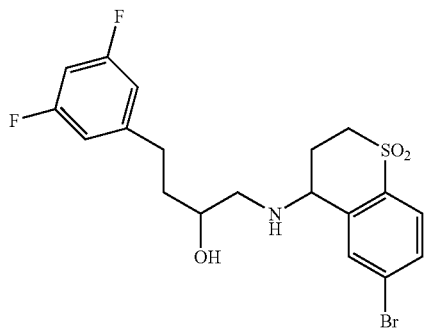

EXAMPLE 212

4-(3,5-DIFLUORO-PHENYL)-1-[6-(2,2-DIMETHYL-PROPYL)-CHROMAN-4-YLAMINO]-BUTAN-2-OL

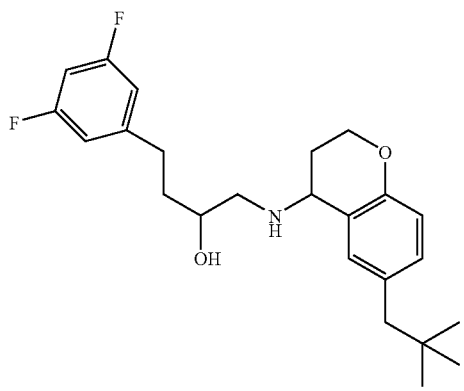

EXAMPLE 213

[4-[4-(3,5-DIFLUORO-PHENYL)-2-HYDROXY-BUTYLAMINO]-6-(2,2-DIMETHYL-PROPYL)-CHROMAN-7-YL]-CARBAMIC ACID BENZYL ESTER

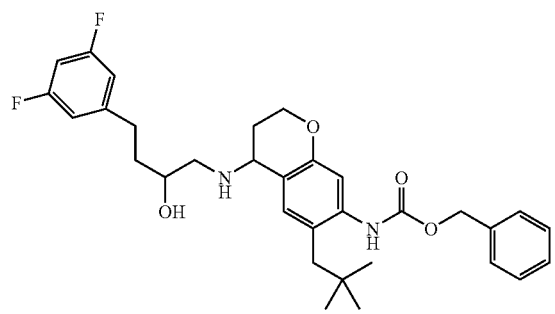

EXAMPLE 214

4-(3,5-DIFLUORO-PHENYL)-1-(7-ETHYL-1,2,3,4-TETRAHYDRO-NAPHTHALEN-1-YLAMINO)-BUTAN-2-OL

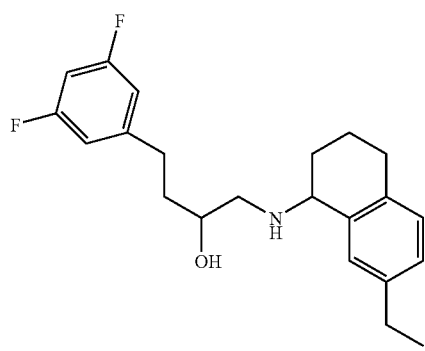

EXAMPLE 215

4-(3,5-DIFLUORO-PHENYL)-1-[7-(2,2-DIMETHYL-PROPYL)-1,2,3,4-TETRAHYDRO-NAPHTHALEN-1-YLAMINO]-BUTAN-2-OL

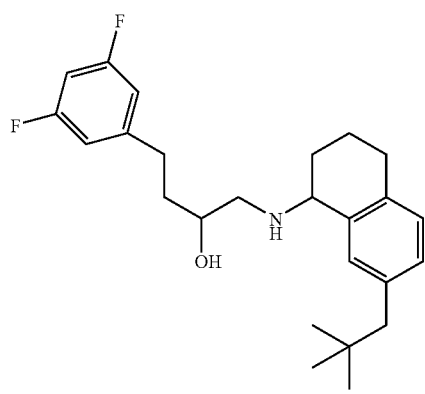

EXAMPLE 216

1-(2-BROMO-9H-FLUOREN-9-YLAMINO)-4-(3,5-DIFLUORO-PHENYL)-BUTAN-2-OL

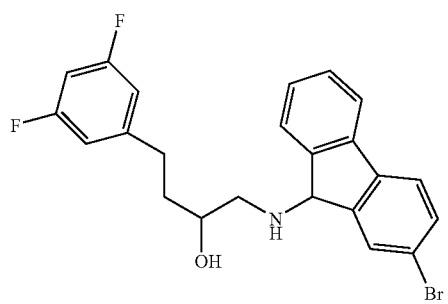

EXAMPLE 217

4-(3,5-DIFLUORO-PHENYL)-1-(2-ISOBUTYL-9H-FLUOREN-9-YLAMINO)-BUTAN-2-OL

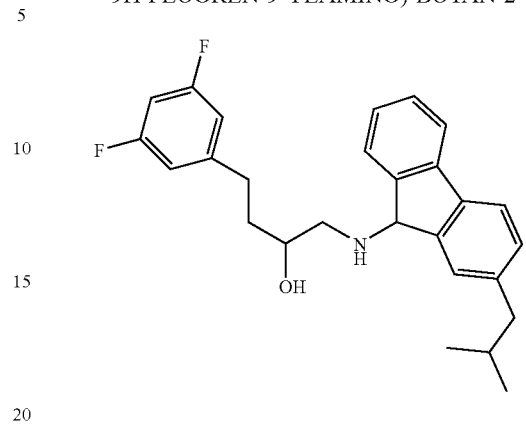

EXAMPLE 218

1-[2-BROMO-5-(2,2-DIMETHYL-PROPYL)-BENZYLAMINO]-4-(3,5-DIFLUORO-PHENYL)-BUTAN-2-OL

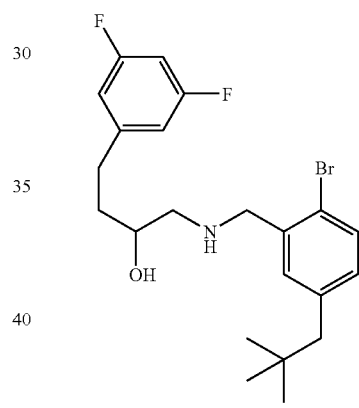

EXAMPLE 219

1-[1-(3-TERT-BUTYL-PHENYL)-CYCLOHEXYLAMINO]-4-(3,5-DIFLUORO-PHENYL)-BUTAN-2-OL

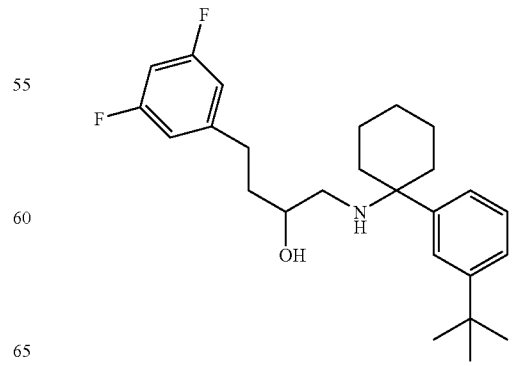

EXAMPLE 220

1-[1-(3-TERT-BUTYL-PHENYL)-4-METHYL-CYCLOHEXYLAMINO]-4-(3,5-DIFLUORO-PHENYL)-BUTAN-2-OL

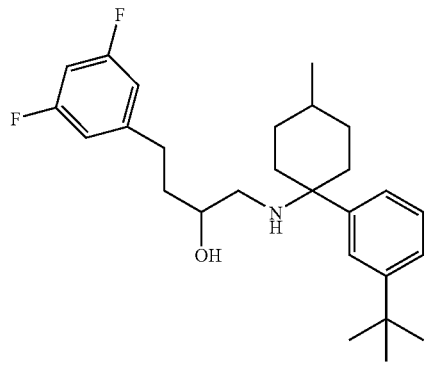

EXAMPLE 221

1-[1-(3-TERT-BUTYL-PHENYL)-HYDROXYMETHYL-CYCLOHEXYLAMINO]-4-(3,5-DIFLUORO-PHENYL)-BUTAN-2-OL

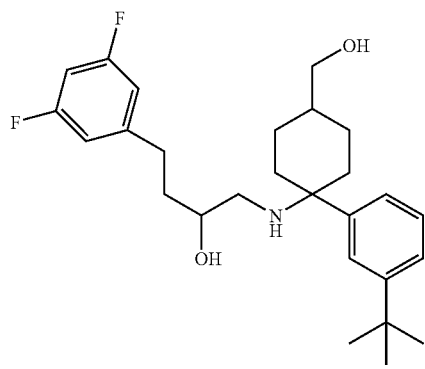

EXAMPLE 222

1-[1-(3-TERT-BUTYL-PHENYL)-3-METHYL-CYCLOHEXYLAMINO]-4-(3,5-DIFLUORO-PHENYL)-BUTAN-2-OL

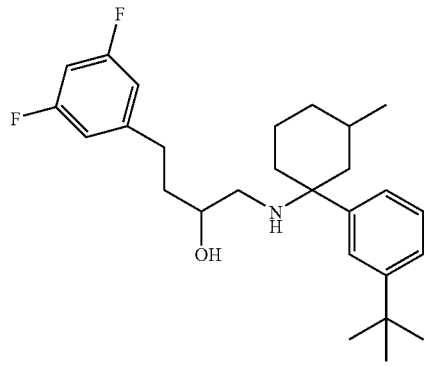

EXAMPLE 223

1-[1-(3-TERT-BUTYL-PHENYL)-2-METHYL-CYCLOHEXYLAMINO]-4-(3,5-DIFLUORO-PHENYL)BUTAN-2-OL

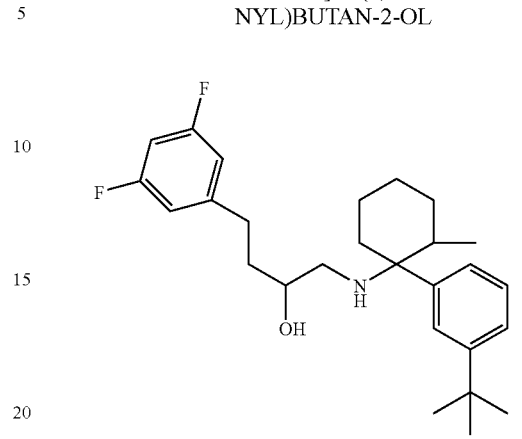

EXAMPLE 224

2-(3-TERT-BUTYL-PHENYL)-2-[4-(3,5-DIFLUORO-PHENYL)-2-HYDROXY-BUTYLAMINO]-CYCLOHEXANOL

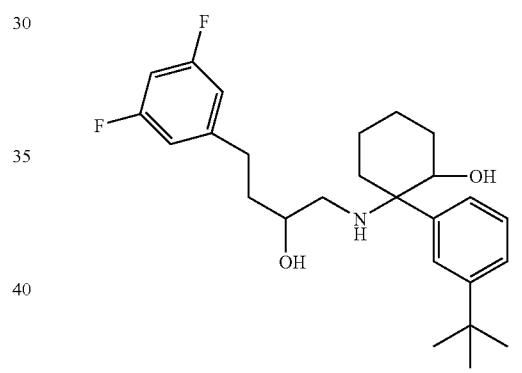

EXAMPLE 225

1-[1-(3-TERT-BUTYL-5-FLUORO-PHENYL)-CYCLOHEXYLAMINO]-4-(3,5-DIFLUORO-PHENYL)-BUTAN-2-OL

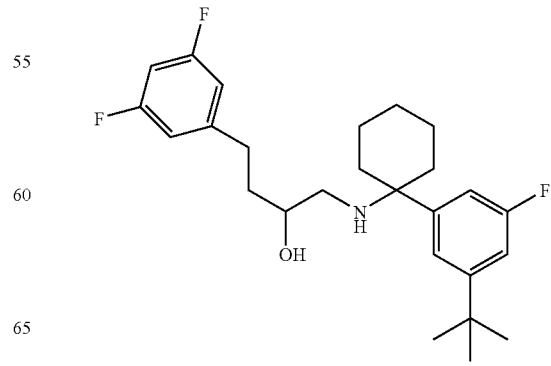

EXAMPLE 226

1-[1-(3-TERT-BUTYL-PHENYL)-METHYLSUL-FANYL-CYCLOHEXYLAMINO]-4-(3,5-DIF-LUORO-PHENYL)-BUTAN-2-OL

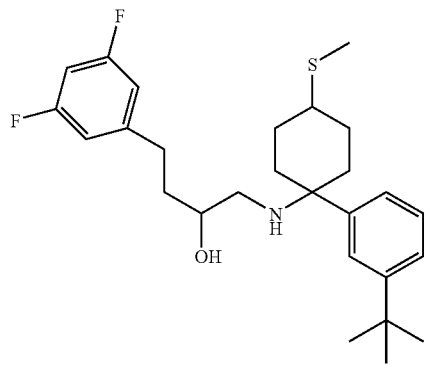

EXAMPLE 227

1-[1-(3-TERT-BUTYL-PHENYL)-4-METHOXY-CYCLOHEXYLAMINO]-4-(3,5-DIFLUORO-PHENYL)-BUTAN-2-OL

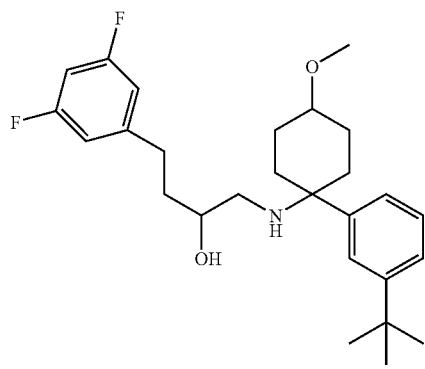

EXAMPLE 228

4-(3-TERT-BUTYL-PHENYL)-4-[4-(3,5-DIF-LUORO-PHENYL)-2-HYDROXY-BUTY-LAMINO]-CYCLOHEXANONE

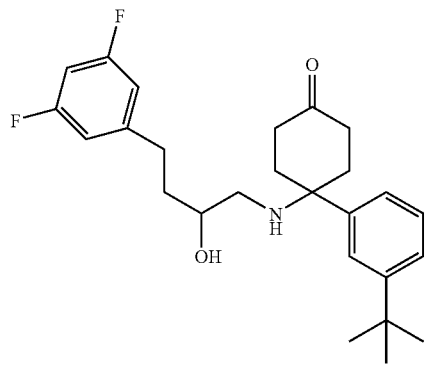

EXAMPLE 229

1-[1-(3-TERT-BUTYL-PHENYL)-4-(THIAZOL-2-YLAMINO)-CYCLOHEXYLAMINO]-4-(3,5-DIF-LUORO-PHENYL)-BUTAN-2-OL

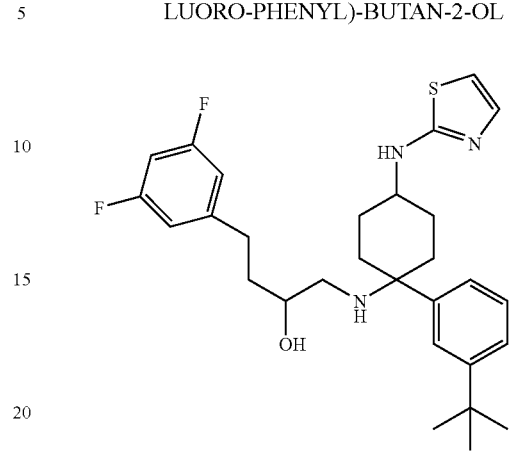

EXAMPLE 230

1-[1-(3-TERT-BUTYL-PHENYL)-4-(3-METHYL-ISOXAZOL-5-YLAMINO)-CYCLOHEXY-LAMINO]-4-(3,5-DIFLUORO-PHENYL)-BUTAN-2-OL

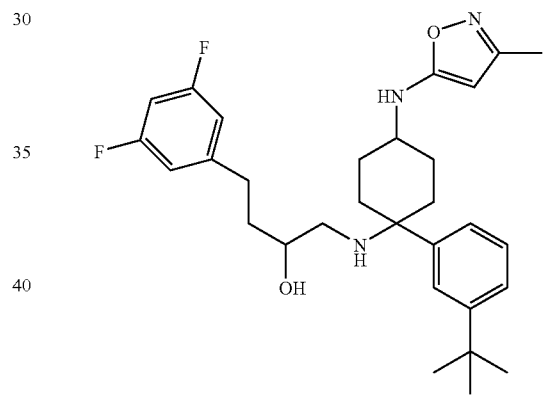

EXAMPLE 231

1-[1-(3-TERT-BUTYL-PHENYL)-4-(1H-PYRA-ZOL-3-YLAMINO)-CYCLOHEXYLAMINO]-4-(3,5-DIFLUORO-PHENYL)-BUTAN-2-OL

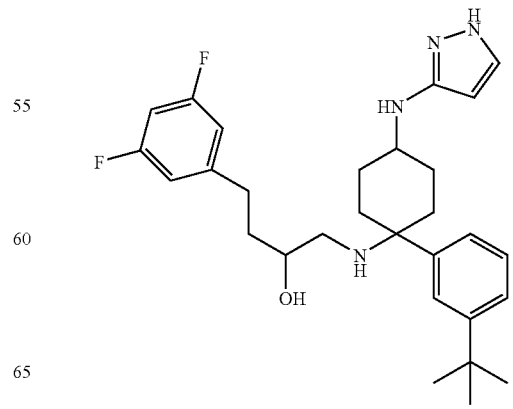

EXAMPLE 232

1-[1-(3-TERT-BUTYL-PHENYL)-4-(ISOXAZOL-3-YLAMINO)-CYCLOHEXYLAMINO]-4-(3,5-DIFLUORO-PHENYL)-BUTAN-2-OL

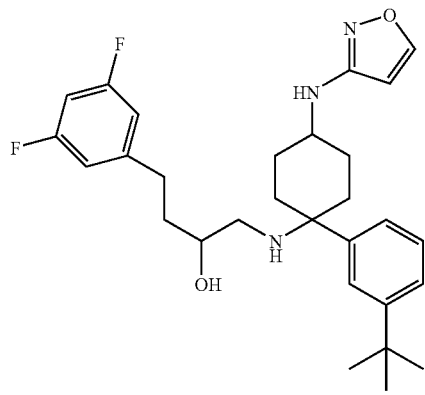

EXAMPLE 233

1-[1-(3-TERT-BUTYL-PHENYL)-4-(5-METHYL-ISOXAZOL-3-YLAMINO)-CYCLOHEXYLAMINO]-4-(3,5-DIFLUORO-PHENYL)-BUTAN-2-OL

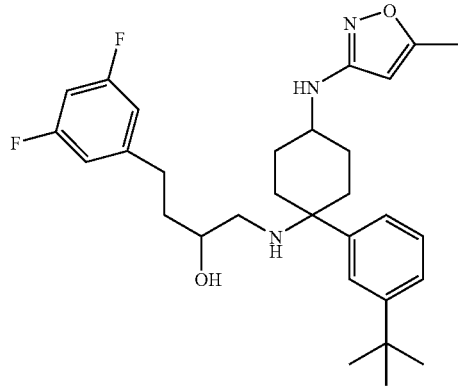

EXAMPLE 234

1-[1-(3-TERT-BUTYL-PHENYL)-4-(PYRIDIN-3-YLAMINO)-CYCLOHEXYLAMINO]-4-(3,5-DIFLUORO-PHENYL)-BUTAN-2-OL

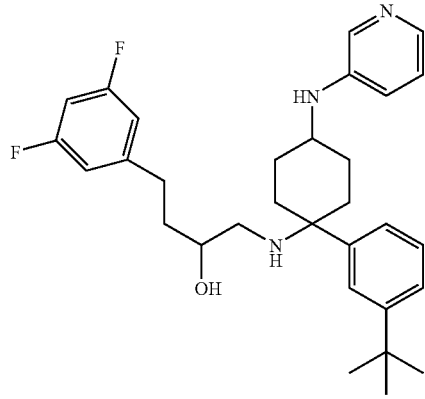

EXAMPLE 235

1-[1-(3-TERT-BUTYL-PHENYL)-4-(PYRIDIN-2-YLAMINO)-CYCLOHEXYLAMINO]-4-(3,5-DIFLUORO-PHENYL)-BUTAN-2-OL

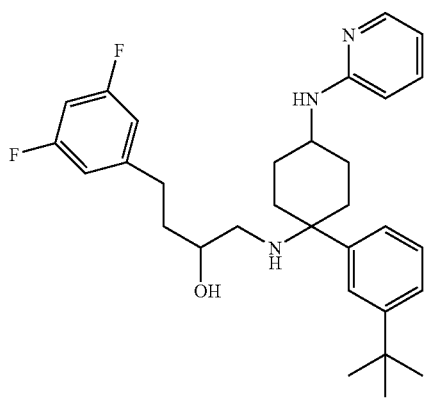

EXAMPLE 236

1-[1-(3-TERT-BUTYL-PHENYL)-4-TRIFLUOROMETHYL-CYCLOHEXYLAMINO]-4-(3,5-DIFLUORO-PHENYL)-BUTAN-2-OL

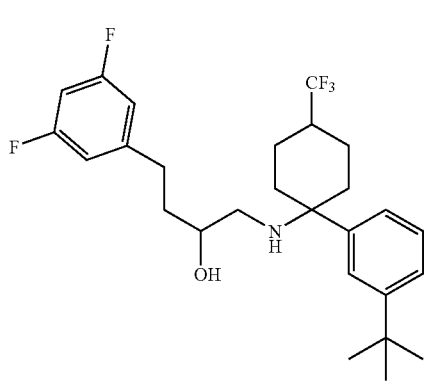

EXAMPLE 237

1-[1-(3-TERT-BUTYL-PHENYL)-4,4-DIFLUORO-CYCLOHEXYLAMINO]-4-(3,5-DIFLUORO-PHENYL)-BUTAN-2-OL

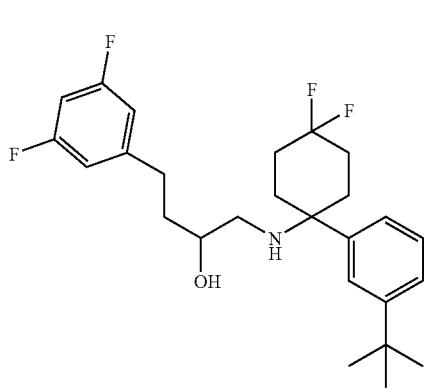

EXAMPLE 238

1-[1-(6-TERT-BUTYL-PYRIMIDIN-4-YL)-CYCLOHEXYLAMINO]-4-(3,5-DIFLUORO-PHENYL)-BUTAN-2-OL

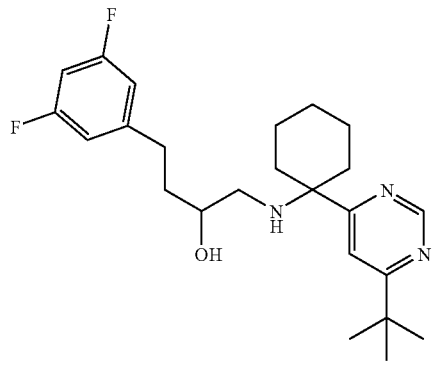

EXAMPLE 239

1-[3-(3-TERT-BUTYL-PHENYL)-PIPERIDIN-3-YLAMINO]-4-(3,5-DIFLUORO-PHENYL)-BUTAN-2-OL

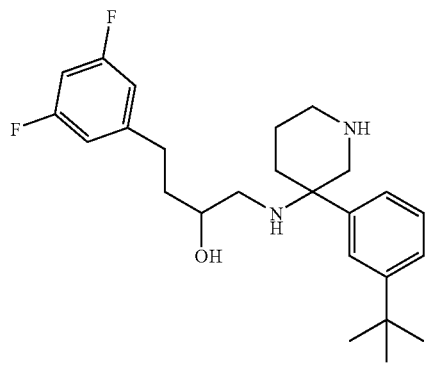

EXAMPLE 240

3-(3-TERT-BUTYL-PHENYL)-3-[4-(3,5-DIFLUORO-PHENYL)-2-HYDROXY-BUTYLAMINO]-PIPERIDIN-1-OL

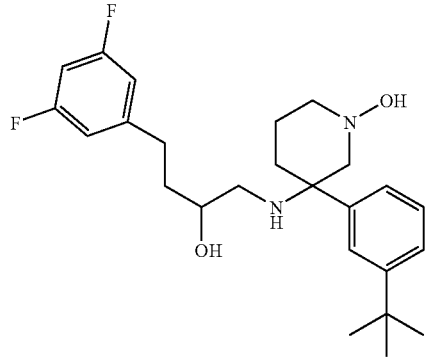

EXAMPLE 241

1-[3-(3-TERT-BUTYL-PHENYL)-1-METHYL-PIPERIDIN-3-YLAMINO]-4-(3,5-DIFLUORO-PHENYL)-BUTAN-2-OL

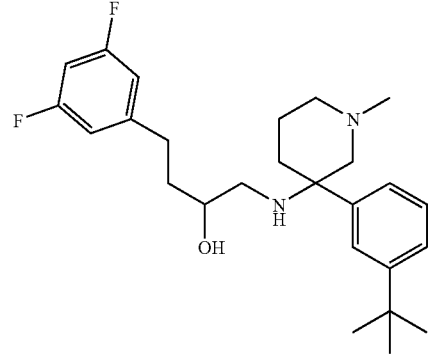

EXAMPLE 242

1-{3-(3-TERT-BUTYL-PHENYL)-3-[4-(3,5-DIFLUORO-PHENYL)-2-HYDROXY-BUTYLAMINO]-PIPERIDIN-1-YL}-ETHANONE

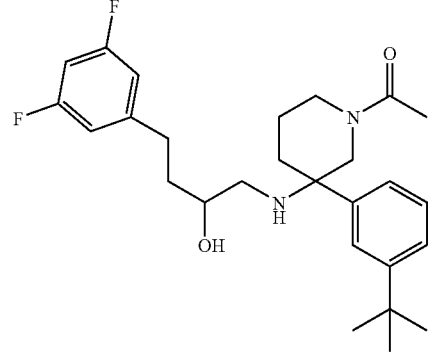

EXAMPLE 243

3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID METHYLAMIDE

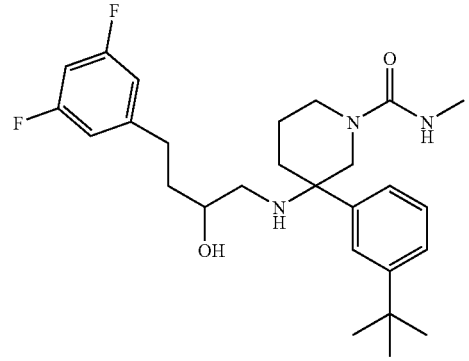

EXAMPLE 244

3-(3-TERT-BUTYL-PHENYL)-3-[4-(3,5-DIF-
LUORO-PHENYL)-2-HYDROXY-BUTY-
LAMINO]-PIPERIDINE-1-CARBOXYLIC ACID
DIMETHYLAMIDE

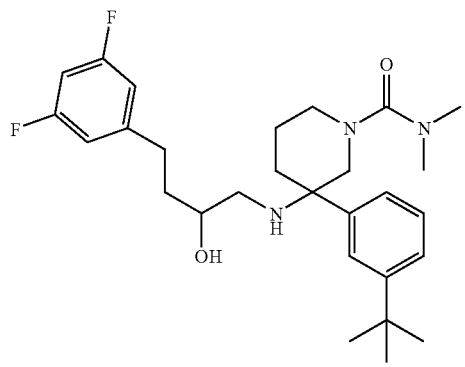

EXAMPLE 245

3-(3-TERT-BUTYL-PHENYL)-3-[4-(3,5-DIF-
LUORO-PHENYL)-2-HYDROXY-BUTY-
LAMINO]-PIPERIDINE-1-CARBOXYLIC ACID
BENZYLAMIDE

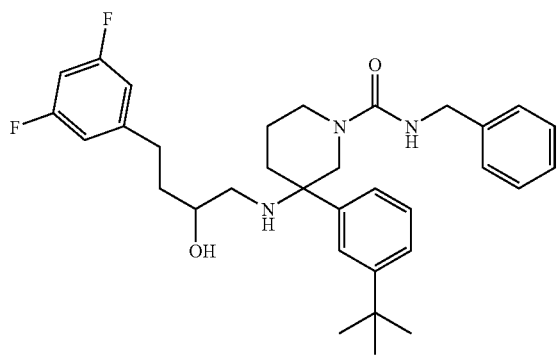

EXAMPLE 246

3-(3-TERT-BUTYL-PHENYL)-3-[4-(3,5-DIF-
LUORO-PHENYL)-2-HYDROXY-BUTY-
LAMINO]-PIPERIDINE-1-CARBOXYLIC ACID
ISOPROPYLAMIDE

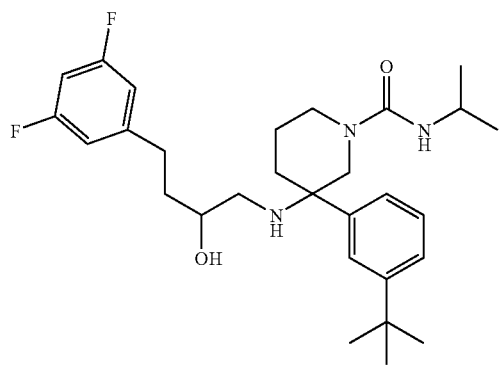

EXAMPLE 247

{3-(3-TERT-BUTYL-PHENYL)-3-[4-(3,5-DIF-
LUORO-PHENYL)-2-HYDROXY-BUTY-
LAMINO]-PIPERIDIN-1-YL}-PIPERIDIN-1-YL-
METHANONE

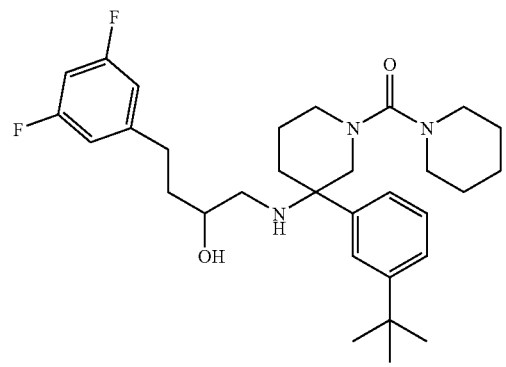

EXAMPLE 248

3-(3-TERT-BUTYL-PHENYL)-3-[4-(3,5-DIF-
LUORO-PHENYL)-2-HYDROXY-BUTY-
LAMINO]-PIPERIDINE-1-CARBOXYLIC ACID
METHYL ESTER

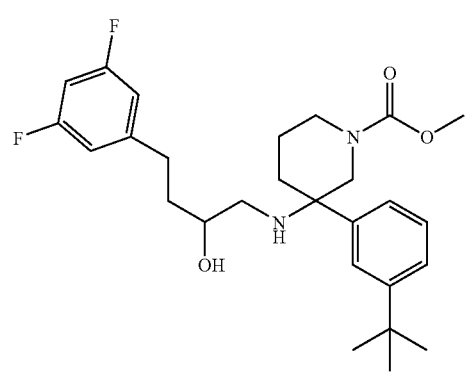

EXAMPLE 249

1-[3-(3-TERT-BUTYL-PHENYL)-1-METHANE-
SULFONYL-PIPERIDIN-3-YLAMINO]-4-(3,5-
DIFLUORO-PHENYL)-BUTAN-2-OL

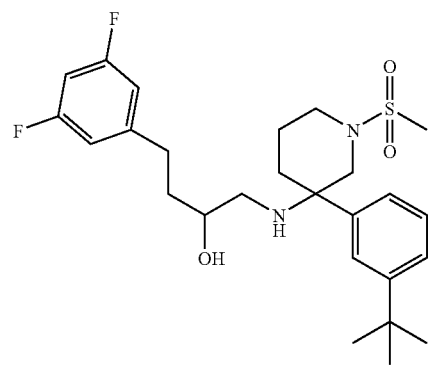

EXAMPLE 250

3-(3-TERT-BUTYL-PHENYL)-3-[4-(3,5-DIF-
LUORO-PHENYL)-2-HYDROXY-BUTY-
LAMINO]-PIPERIDINE-1-CARBOXYLIC ACID
AMIDE

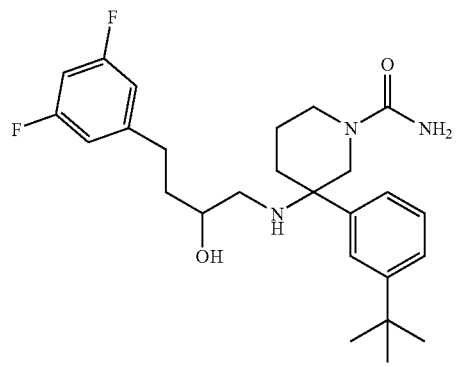

EXAMPLE 251

1-{3-(3-TERT-BUTYL-PHENYL)-3-[4-(3,5-DIF-
LUORO-PHENYL)-2-HYDROXY-BUTY-
LAMINO]-PIPERIDIN-1-YL}-3-PHENYL-PRO-
PAN-1-ONE

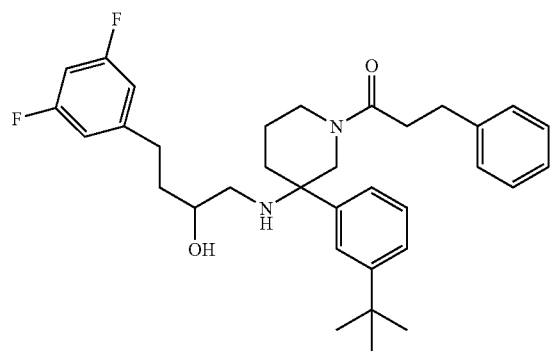

EXAMPLE 252

3-(3-TERT-BUTYL-PHENYL)-3-[4-(3,5-DIF-
LUORO-PHENYL)-2-HYDROXY-BUTY-
LAMINO]-PIPERIDINE-1-CARBOXYLIC ACID
BENZYL ESTER

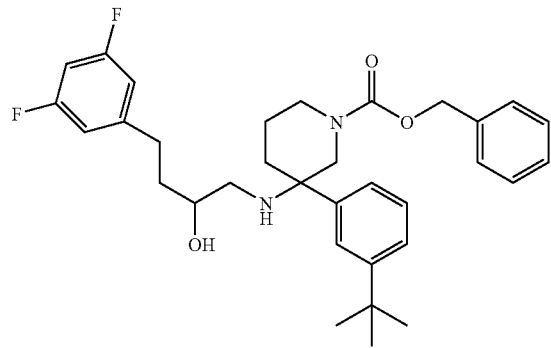

EXAMPLE 253

4-[4-(3,5-DIFLUORO-PHENYL)-2-HYDROXY-
BUTYLAMINO]-6-(2,2-DIMETHYL-PROPYL)-3,
4-DIHYDRO-2H-QUINOLINE-1-CARBOXYLIC
ACID BENZYL ESTER

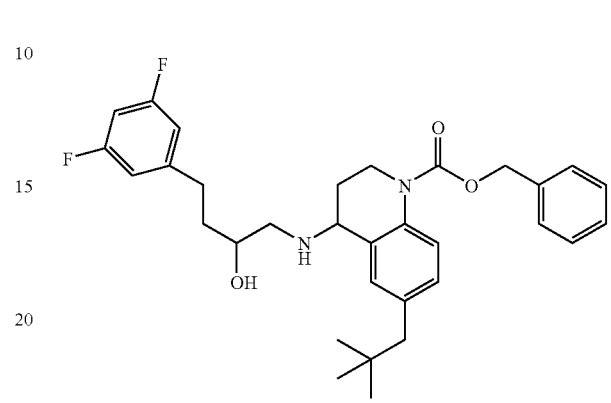

EXAMPLE 254

1-[(ADAMANTAN-1-YLMETHYL)-AMINO]-4-(3,
5-DIFLUORO-PHENYL)-BUTAN-2-OL

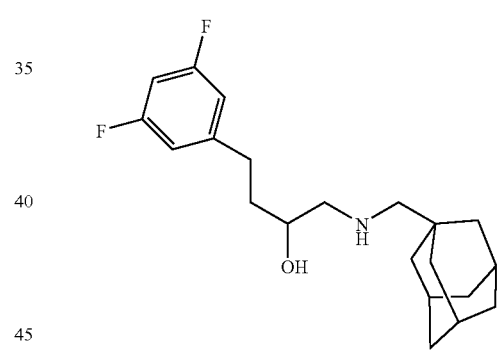

EXAMPLE 255

4-(3,5-DIFLUORO-PHENYL)-1-(1-THIOPHEN-3-
YL-CYCLOHEXYLAMINO)-BUTAN-2-OL

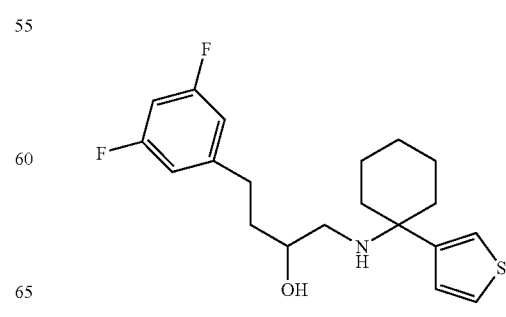

EXAMPLE 256

4-(3,5-DIFLUORO-PHENYL)-1-[1-(5-ETHYL-THIOPHEN-3-YL)-CYCLOHEXYLAMINO]-BUTAN-2-OL

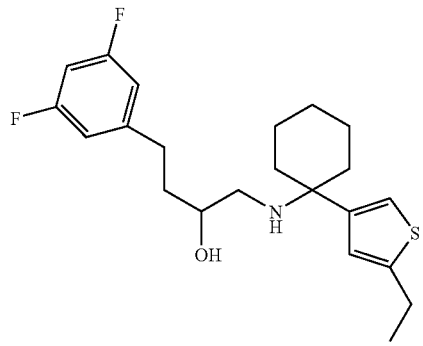

EXAMPLE 257

4-(3,5-DIFLUORO-PHENYL)-1-[1-(5-ISOPROPYL-THIOPHEN-3-YL)-CYCLOHEXYLAMINO]-BUTAN-2-OL

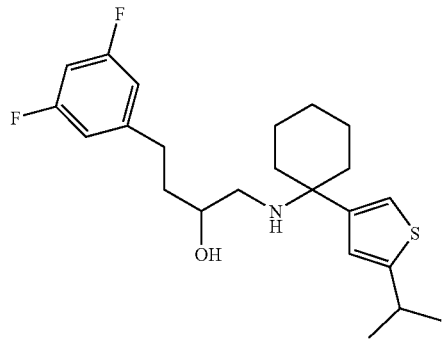

EXAMPLE 258

1-[1-(3-TERT-BUTYL-PHENYL)-CYCLOHEXYLAMINO]-4-(3,5-DIFLUORO-PHENYL)-BUTANE-2,3-DIOL

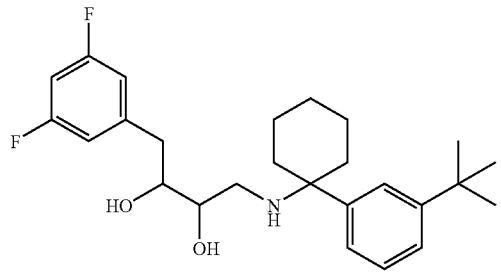

EXAMPLE 259

1-(3,5-DIFLUORO-PHENYL)-4-[7-(2,2-DIMETHYL-PROPYL)-1,2,3,4-TETRAHYDRO-NAPHTHALEN-1-YLAMINO]-BUTANE-2,3-DIOL

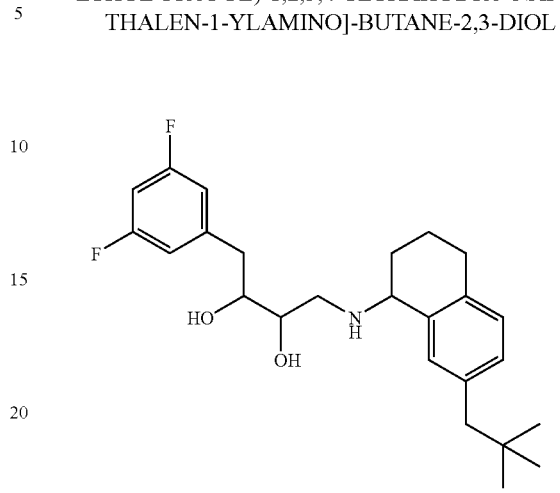

EXAMPLE 260

1-[1-(3-TERT-BUTYL-PHENYL)-CYCLOHEXYLAMINO]-4-(3,5-DIFLUORO-PHENYL)-3-METHOXY-BUTAN-2-OL

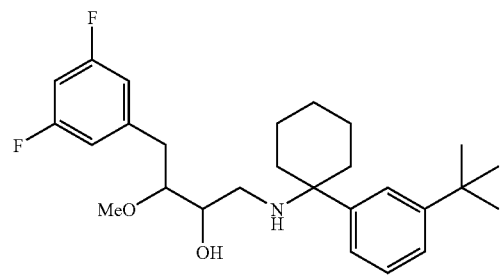

EXAMPLE 261

1-[1-(3-TERT-BUTYL-PHENYL)-CYCLOHEXYLAMINO]-4-(3,5-DIFLUORO-PHENYL)-3-PHENOXY-BUTAN-2-OL

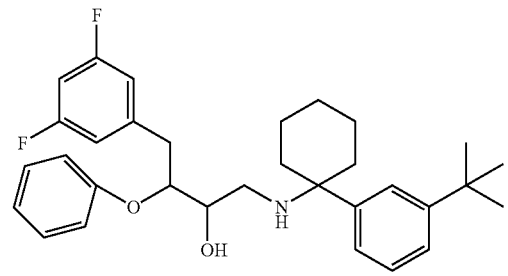

EXAMPLE 262

METHYL-CARBAMIC ACID 3-[1-(3-TERT-BUTYL-PHENYL)-CYCLOHEXYLAMINO]-1-(3,5-DIFLUORO-BENZYL)-2-HYDROXY-PROPYL ESTER

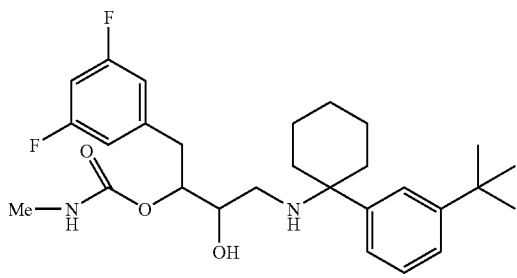

EXAMPLE 263

{1-(3,5-DIFLUORO-BENZYL)-3-[7-(2,2-DIMETHYL-PROPYL)-1,2,3,4-TETRAHYDRO-NAPHTHALEN-1-YLAMINO]-2-HYDROXY-PROPOXY}-METHANESULFONAMIDE

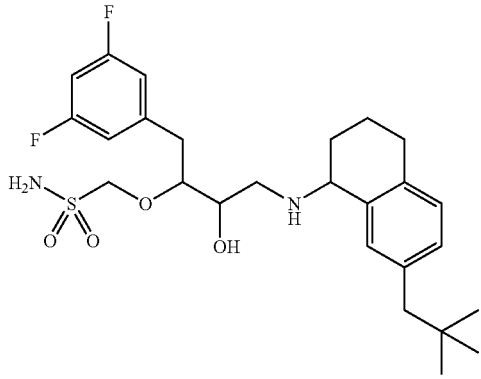

EXAMPLE 264

2-[3-[1-(3-TERT-BUTYL-PHENYL)-CYCLOHEXYLAMINO]-1-(3,5-DIFLUORO-BENZYL)-2-HYDROXY-PROPYL]-2,3,4,5-TETRAHYDRO-BENZO[C]AZEPIN-1-ONE

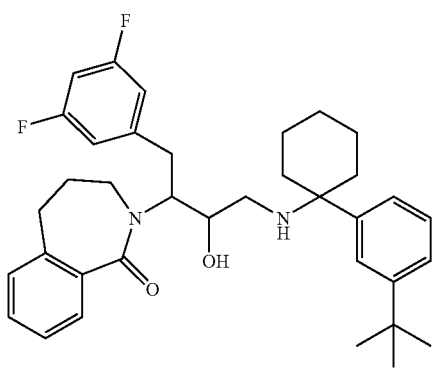

EXAMPLE 265

1-[3-[1-(3-TERT-BUTYL-PHENYL)-CYCLOHEXYLAMINO]-1-(3,5-DIFLUORO-BENZYL)-2-HYDROXY-PROPYL]-PYRROLIDIN-2-ONE

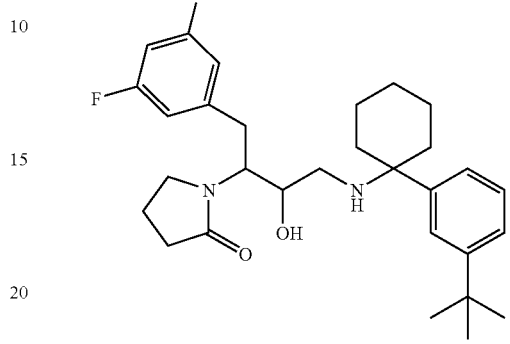

EXPERIMENTAL PROCEDURES

The compounds and the methods of treatment of the present invention can be prepared by one skilled in the art based on knowledge of the compound's chemical structure. The chemistry for the preparation of the compounds employed in the methods of treatment of this invention is known to those skilled in the art. In fact, there is more than one process to prepare the compounds employed in the methods of treatment of the present invention. Specific examples of methods of preparation can be found in the art. For examples, see Zuccarello et at, *J. Org. Chem.* 1998, 63, 4898-4906; Benedetti et al., *J. Org. Chem.* 1997, 62, 9348-9353; Kang et al., *J. Org. Chem.* 1996, 61, 5528-5531; Kempf et al., *J. Med. Chem.* 1993, 36, 320-330; Lee et al., *J. Am. Chem. Soc.* 1999, 121, 1145-1155, and references cited therein; *Chem. Pharm. Bull.* (2000), 48(11), 1702-1710; *J. Am. Chem. Soc.* (1974), 96(8), 2463-72; *Ind. J. Chem.*, Section B: Organic Chemistry Including Medicinal Chemistry (2003), 42B(4), 910-915; *J. Chem. Soc.* [Section] C: Organic (1971), (9), 1658-60, and *Tet. Lett.* (1995), 36(11), 1759-1762. See also U.S. Pat. Nos. 6,150,530, 5,892,052, 5,696,270, and 5,362,912, and references cited therein, which are incorporated herein by reference.

EXAMPLE 266

$^1$H, $^{13}$C NMR, and Mass Spec Procedures $^1$H and $^{13}$C NMR spectra were obtained on a Varian 400 MHz, Varian 300 MHz, or Bruker 300 MHz instrument. Mass spec samples analyses were performed with electron spray ionization (ESI).

EXAMPLE 267

Exemplary HPLC Procedures

Various High Pressure Liquid Chromatography (HPLC) procedures employed the following methods:
Method [1] utilizes a 20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [2] utilizes a 50% [B]: 50% [A] to 95% [B]: 5% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [3] utilizes a 5% [B]: 95% [A] to 20% [B]: 80% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [4] utilizes a 20% [B]: 80% [A] to 70% [B]: 30% [A] gradient in 2.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [5] utilizes a 50% [B]: 50% [A] to 95% [B]: 5% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [6] utilizes a 5% [B]: 95% [A] to 20% [B]; 80% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [7] utilizes a 20% [8]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

Method [8] utilizes a YMC ODS-AQ S-3 120 A 3.0×50 mm cartridge, with a standard gradient from 5% acetonitrile containing 0.01% heptafluorobutyric acid (HFBA) and 1% isopropanol in water containing 0.01% HFBA to 95% acetonitrile containing 0.01% HFBA and 1% isopropanol in water containing 0.01% HFBA over 5 min.

Method [9]: 20-70% Acetonitrile in 1.75 min; 2 mL/min; 35° C.; Column=Luna C18(2) 30 cm×4.6 mm; SN 112046-8 API-ES.

Method [10]: Column dimensions: 150 mm (long)×21.2 mm (i.d.), C-18 stationary phase, 5 micron particle size, 100 angstrom pore size. Mobile phases are 0.1% Trifluoroacetic acid in water (solvent A), and 0.1% trifluoroacetic acid in acetonitrile (solvent B). Chromatographic conditions are 25 mL/min.: 5% solvent B from 0 to 4.0 minutes, 5% to 95% solvent B from 4.0 to 22.0 minutes, 95% solvent B from 22.0 to 24.0 minutes 95% to 5% solvent B from 24.0 to 24.4 minutes, then 5% solvent B from 24.4 to 27.0 minutes.

Method [11]: Column dimensions: 50 mm (long)×3 mm (i.d.), C-18 stationary phase, 5 micron particle size, 100 angstrom pore size. Mobile phases are 0.05% trifluoroacetic acid in water (solvent A), and 0.05% trifluoroacetic acid in acetonitrile (solvent B). Chromatographic conditions are 3 mL/min.: 5% solvent B from 0 to 0.275 minutes, 5% to 95% solvent B from 0.275 to 2.75 minutes, then 95% solvent B from 2.75 to 3.50 minutes.

EXAMPLE 268

Preparation of Precursor (4) for Formula (I) Compounds

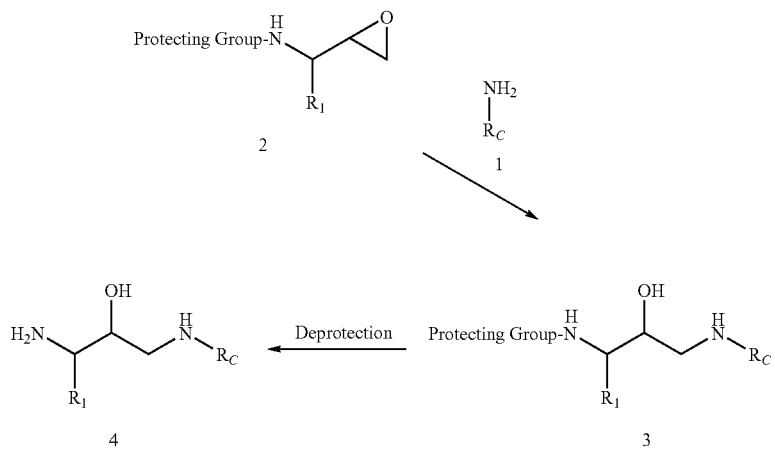

Scheme 1.

As described herein, one embodiment of the present invention provides for compounds of formula (4) as shown above in Scheme 1. These compounds can be made by methods known to those skilled in the art from starting compounds that are also known to those skilled in the art. The process chemistry is further well known to those skilled in the art. A suitable process for the preparation of compounds of formula (4) is set forth in Scheme 1 above.

EXAMPLE 269

Alternative Preparation of Precursors for Formula (I) Compounds

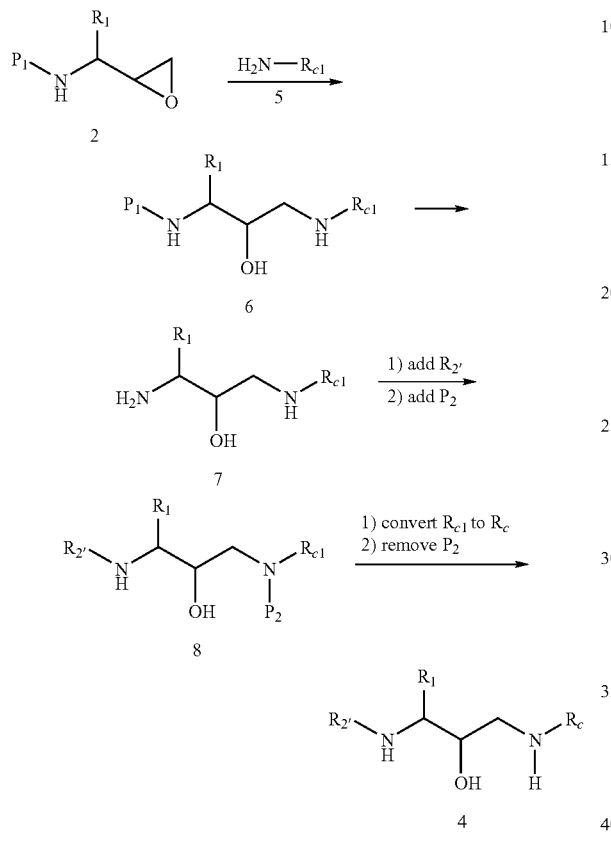

An alternative approach, shown in Scheme 2 above, was to use a common advanced intermediate 8 by which a reactive group could be converted to yield compounds (4). Epoxides (2) were treated with 1.5-5 equivalents of primary amine $H_2N$—$R_{C1}$ (5) in an alcoholic solvent, such as ethanol, isopropanol, or sec-butanol to effect ring opening of the epoxide. In an embodiment, this reaction is prepared at elevated temperatures from 40° C. to reflux. In another embodiment, this reaction is performed at reflux in isopropanol. The resulting amino alcohol (6) was then deprotected to form the free amine (7). The subsequent substitution of the free amine (7) was followed by the protection of the —NH—$R_{C1}$ moiety to give compound 8.

When $R_{C1}$ contains a labile functional group, such as an aryl iodide, aryl bromide, aryl trifluoromethanesulfonate, or aryl boronic ester, which may be converted into $R_C$ via transition metal-mediated coupling, this allows for the rapid synthesis of a variety of analogs (4). Such conversions may include Suzuki (aryl boronic acid or boronic ester and aryl halide), Negishi (arylzinc and aryl or vinyl halide), and Sonogashira (arylzinc and alkynyl halide) couplings. Subsequent to the coupling reaction, the protecting group $P_2$ is removed by methods known in the art to yield compounds (4).

The example below provides an exemplary procedure for the preparation of epoxides 2 above.

EXAMPLE 270

Preparation of [2-(3,5-DIFLUORO-PHENYL)-1-OXIRANYL-ETHYL]-CARBAMIC ACID TERT-BUTYL ESTER

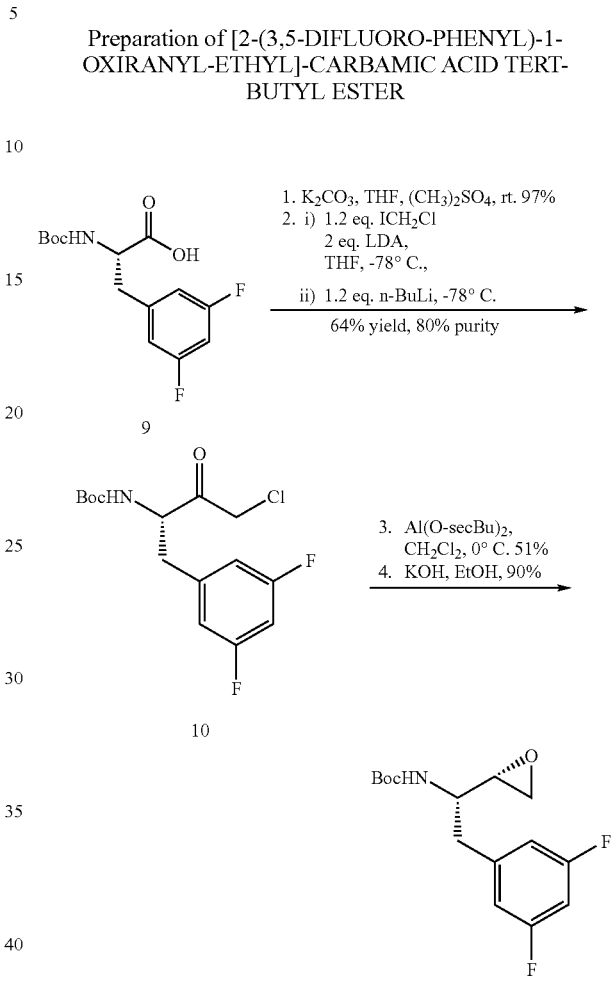

The synthesis of tert-butyl (1S)-2-(3,5-difluorophenyl)-1-[(2S)-oxiranyl]ethylcarbamate (11) was carried out using the procedure described by Reeder, M. R., WO 2002085877. (2S)-2-[(tert-butoxycarbonyl)amino]-3-(3,5-difluorophenyl) propionic acid (9) was purchased from Chem Impex and converted to the methyl ester without incident. Conversion of the methyl ester to the chloroketone 10 was carried out on a 50 g scale and repeatedly gave yields between 60-65% of an impure product. The chlorohydrin was obtained via a diastereoselective Meerwein-Ponndorf-Verley reduction. The product was washed with octane to remove some, but not all of the impurities. Conversion of the chlorohydrin to the epoxide 11 occurred with potassium hydroxide in ethanol with the product being isolated from the reaction mixture by precipitation after the addition of water. The epoxide 11 could be recrystallized from hexanes/isopropanol, although some batches of epoxide contained an unidentified impurity.

Step 1: Preparation of (2S)-2-[(tert-Butoxycarbonyl)amino]-3-(3,5-difluorophenyl)propionic Acid Methyl Ester.

A solution of (2S)-2-[(tert-butoxycarbonyl)amino]-3-(3,5-difluorophenyl)propionic acid (9) (138 g, 458 mmol) was dissolved in THF (1000 mL) and cooled to 0° C. Potassium carbonate (69.6 g, 503.8 mmol) was added followed by the dropwise addition of dimethyl sulfate (45.5 mL, 480.9 mmol). The reaction was removed from the ice bath and allowed to stir at room temperature overnight after which HPLC analysis shows the complete consumption of starting material. The reaction was quenched by the addition of 10% ammonium hydroxide (150 mL). The aqueous layer was removed and extracted with ethyl acetate (500 mL). The combined organics were washed with brine (500 mL), dried over magnesium sulfate and concentrated to give a yellow solid. The solid was recrystallized from hexanes to give the product as an off white solid (140.3 g, 445.0 mmol, 97%).

Step 2: tert-Butyl (1S)-3-chloro-1-(3,5-difluorobenzyl)-2-oxopropylcarbamate.

A solution of LDA was prepared by adding n-BuLi (26 mL, 260 mmol) to a solution of diisopropylamin(e) (26.3 g, 260 mmol) in THF (200 mL) at −78° C. After the addition was complete, the reaction was allowed by warm to 0° C. This light yellow solution was added dropwise to a solution of (2S)-2-[(tert-butoxycarbonyl)amino]-3-(3,5-difluorophenyl)propionic acid methyl ester (40 g, 127 mmol) and chloroiodomethane (11.1 mL, 152 mmol) keeping the temperature below −65° C. After the addition, the solution was stirred for 30 minutes at —78° C. n-BuLi (15 mL, 150 mmol) was added dropwise keeping the internal temperature below −62° C. The reaction was stirred for 30 minutes at −78° C. then quenched into 500 mL of 1N HCl at 0° C. The product was extracted into EtOAc (500 mL), washed with brine (300 mL), dried over magnesium sulfate and concentrated. Octane (400 mL) was added to the product and the resulting solid collected by filtration and dried. The octane was cooled to −78° C. then allowed to warm until the octane melted. The resulting solid was collected and added to the previously collected solid. Drying of the combined solid gave the title compound 10 as an off-white solid (33.9 g, 101.5 mmol, 64.5%).

Step 3: tert-Butyl (1S, 2S)-3-chloro-1-(3,5-difluorobenzyl)-2-hydroxypropylcarbamate.

A solution of tert-butyl (1S)-3-chloro-1-(3,5-difluorobenzyl)-oxopropylcarbamate (67.4 g, 202 mmol) (10) was dissolved in DCM (500 mL) and cooled to 0° C. Tri(sec-butoxy) aluminum (54.7 g, 222.1 mmol, 1.1 eq) in DCM (50 mL) was added dropwise. After stirring for 2 h at 0° C., the reaction was complete by HPLC. The reaction was quenched with 1N HCl (750 mL) and the product extracted into ethyl acetate (2×400 mL). The combined organics were washed with brine (500 mL), dried over magnesium sulfate and concentrated to give an oily yellow solid. Octane (300 mL) was added and the resulting solid was collected by filtration and washed with octane (100 mL). Drying overnight gave a white solid. The octane layers were collected and concentrated to about 100 mL of volume, then placed in the freezer for 48 h to yield a second crop of the title compound (35 g, 104 mmol, 51%).

Step 4: tert-Butyl (1S)-2-(3,5-difluorophenyl)-1-[(2S)-oxiranyl]ethylcarbamate.

A solution of tert-butyl (1S, 2S)-3-chloro-1-(3,5-difluorobenzyl)-2-hydroxypropylcarbamate in ethanol (150 mL) was cooled to 0° C. A solution of KOH in EtOH (25 mL) was added. The reaction was removed from the ice bath and stirred for 2 h. The reaction was diluted with 300 mL of water and placed into an ice bath. The resulting solid was collected by filtration and washed with cold water (100 mL). Drying overnight gave an off-white solid (11) (6.74 g, 22.51 mmol, 90%).

EXAMPLE 271

Alternative Procedure for the Preparation of Formula (I) Compounds

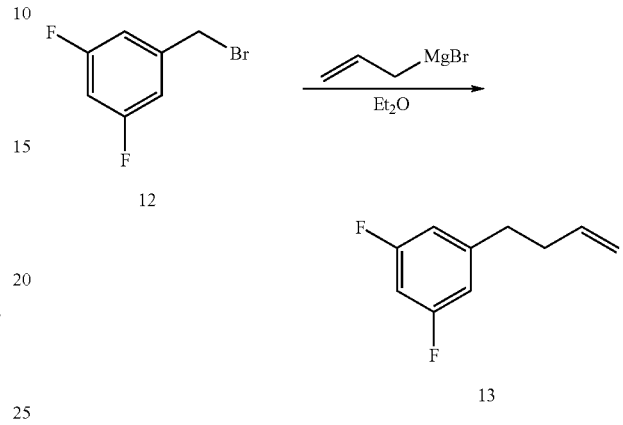

1-But-3-enyl-3,5-difluorobenzene

1-Bromomethyl-3,5-difluorobenzene (12) (10.75 g, 51.9 mmol) was added dropwise slowly to a stirring solution of allylmagnesium bromide (Aldrich, 1.0 M solution in diethyl ether, 78 mL, 78 mmol) at rt. Upon complete addition, the reaction mixture was stirred at rt for 2.5 h. The reaction was quenched by slow addition of 1 N HCl (40 mL). Diethyl ether (30 mL) was added, and the organics were separated, washed (brine), dried (MgSO$_4$), filtered and concentrated. Fractional distillation (55-60° C. at 13 torr) afforded product 13 as a clear, colorless liquid (5.3 g, 60%): R$_f$=0.77 (hexanes).

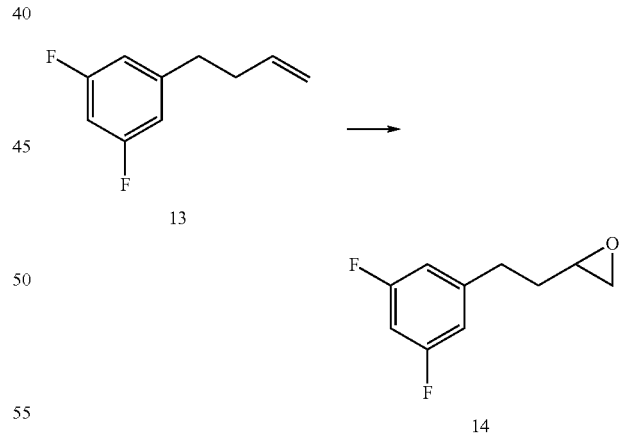

2-[2-(3,5-Difluorophenyl)ethyl]oxirane m-Chloroperbenzoic acid (22 g, Lancaster, 50-55 wt %, 64 mmol) was dissolved in dichloromethane (150 mL), and cooled to 0° C. 1-But-3-enyl-3,5-difluorobenzene (13) (5.3 g, 31.5 mmol) in dichloromethane (10 mL) was added, and the mixture was allowed to warm to rt overnight. The reaction was quenched with saturated Na$_2$SO$_3$ (70 mL) and saturated NaHCO$_3$ (70 mL), and the resulting mixture was stirred for 2 h. The organics were separated, washed with saturated NaHCO$_3$ (40 mL), brine (50 mL), dried (MgSO$_4$), filtered and concentrated. The residue was dissolved in minimal cold hexanes and filtered. The filtrate was concentrated to give desired product 14 (4.0 g, 70%): retention time (min)=1.977; $^{13}$C NMR (75 MHz, CDCl$_3$) δ 162.9 (dd, J=246.4, 12.9 Hz, 2C), 145.0 (t, J=8.9 Hz, 1C), 111.0 (dd, J=16.7, 7.4 Hz, 2C), 101.4 (t, J=25.1 Hz, 1C), 51.2, 47.0, 33.5, 31.9; MS (ESI) 167.

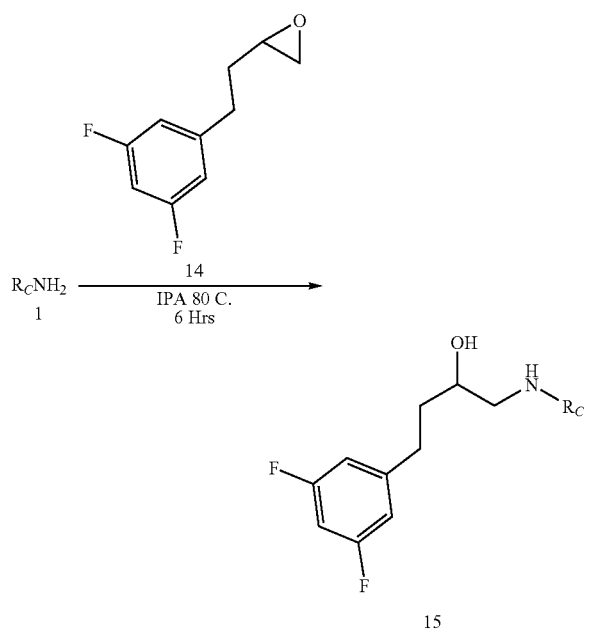

Amine 1 (1 eq.) and 2-[2-(3,5-Difluorophenyl)ethyl]oxirane 14 (1 eq.) were dissolved in isopropanol and the reaction mixture heated at 80° C. for 6 hours. The solvent was evaporated and product 15 was purified by flash chromatography and further purified by HPLC.

EXAMPLE 272

Preparation of 4(S)-(3,5-DIFLUORO-PHENYL)-1-[6-(2,2-DIMETHYL-PROPYL)-CHROMAN-4-YLAMINO]-BUTAN-2-OL

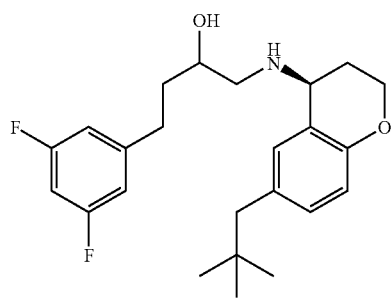

The title compound was prepared according to the method described in EXAMPLE 271. Characterization: MH+ 426.1, retention time=2.0 min, Method [9].

EXAMPLE 273

Preparation of 1-(2-BROMO-9H-FLUOREN-9-YLAMINO)-4-(3,5-DIFLUORO-PHENYL)-BUTAN-2-OL

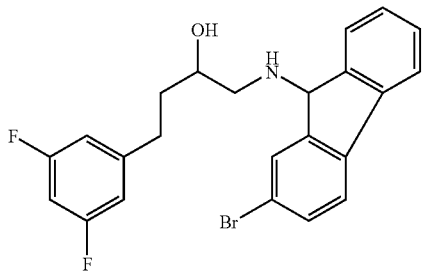

The title compound was prepared according to the method described in EXAMPLE 271. Characterization: MH+ 446.0, retention time=2.1 min, Method [9].

EXAMPLE 274

Preparation of 4-(3,5-DIFLUORO-PHENYL)-1-[2-(2,2-DIMETHYL-PROPYL)-9H-FLUOREN-9-YLAMINO]-BUTAN-2-OL

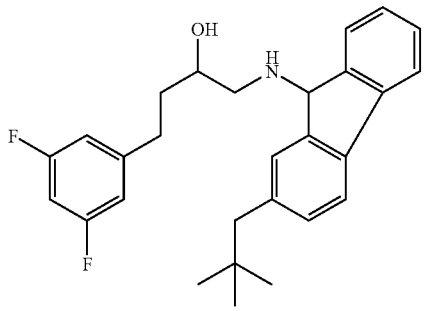

The title compound was prepared according to the method described in EXAMPLE 271. Characterization: MH+ 422.1, retention time=2.2 min, Method [9].

EXAMPLE 275

Preparation of 4-(3,5-DIFLUORO-PHENYL)-1-(6-ISOBUTYL-1,1-DIOXO-1λ$^6$-THIOCHROMAN-4-YLAMINO)-BUTAN-2-OL

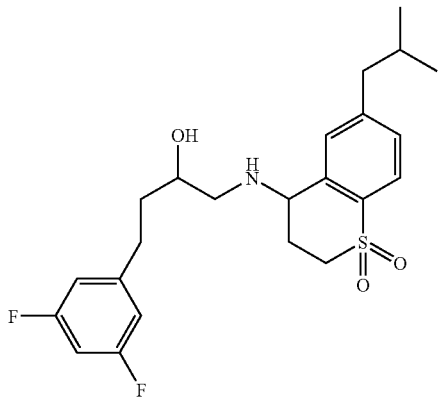

The title compound was prepared according to the method described in EXAMPLE 271. Characterization: MH+ 437.8, retention time=1.9 min, Method [9].

EXAMPLE 276

Preparation of 1-(6-BROMO-1,1-DIOXO-1λ⁶-THIOCHROMAN-4-YLAMINO)-4-(3,5-DIFLUORO-PHENYL)-BUTAN-2-OL

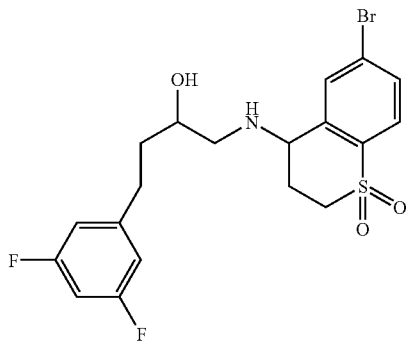

The title compound was prepared according to the method described in EXAMPLE 271. Characterization: MH+ 460.0, retention time=1.6 min, Method [9].

EXAMPLE 277

Preparation of 4-(3,5-DIFLUORO-PHENYL)-1-(1,1-DIOXO-1λ⁶-THIOCHROMAN-4-YLAMINO)-BUTAN-2-OL

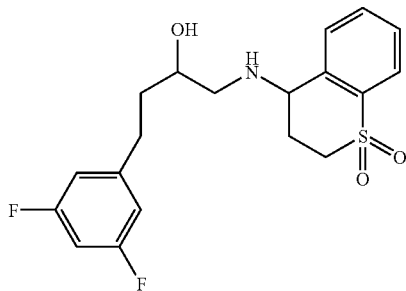

The title compound was prepared according to the method described in EXAMPLE 271. Characterization: MH+ 382.1, retention time=1.4 min, Method [9].

EXAMPLE 278

Preparation of 1-[1-(3-TERT-BUTYL-PHENYL)-4-METHYLSULFANYL-CYCLOHEXYLAMINO]-(3,5-DIFLUORO-PHENYL)-BUTAN-2-OL

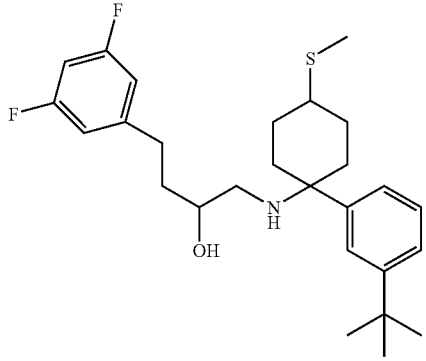

Synthesis of 4-METHYLSULFANYL-CYCLOHEXANONE (20)

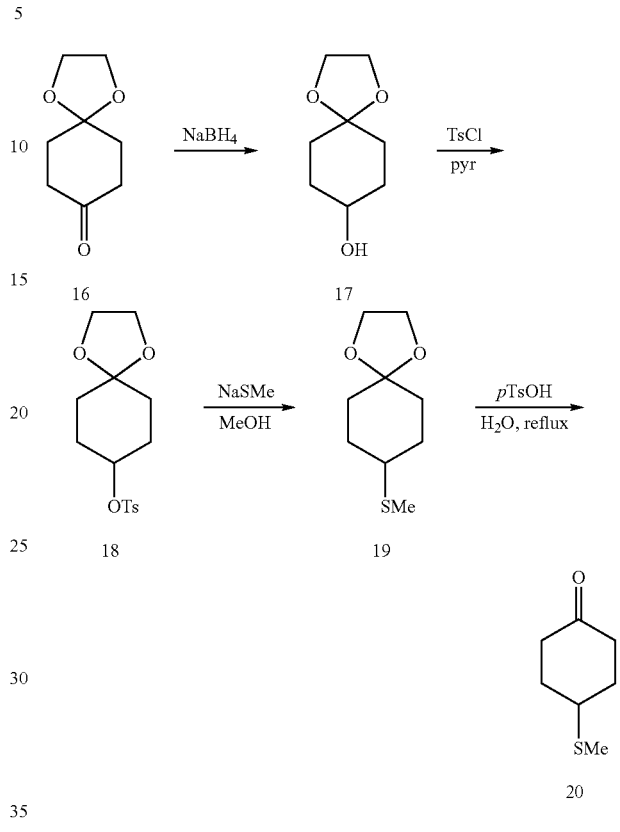

1,4-Dioxa-spiro[4.5]decan-8-ol (17) from 1,4-Dioxa-spiro[4.5]decan-8-one (16)

To a solution of 1,4-dioxa-spiro[4.5]decan-8-one (16) (Aldrich, 10.0 g, 64.0 mmol) in anhydrous methanol (250 mL) at 0° C. was added solid sodium borohydride (4.6 g, 121 mmol). The reaction mixture was allowed to warm to rt over 1 h, whereupon TLC analysis indicated complete reaction. Water (60 mL) was added, and the methanol was removed under reduced pressure. The aqueous residue was partitioned between ethyl acetate (200 mL) and saturated aqueous brine (50 mL). The layers were separated, and the aqueous extracted with addition ethyl acetate (200 mL). The combined organic layers were dried (MgSO₄), filtered and concentrated under reduced pressure to afford the crude alcohol 17 (9.3 g, 92%): $R_f$=0.2 (CH$_2$Cl$_2$); ¹H NMR (300 MHz, CDCl$_3$) δ3.95 (s, 4H), 3.85-3.75 (m, 1H), 2.00-1.75 (m, 4H), 175-1.50 (m, 4H).

8-Methylsulfanyl-1,4-dioxa-spiro[4.5]decane (18) from 1,4-Dioxa-spiro[4,5]decan-8-ol (17)

Ref.: *J. Org. Chem.* 1986, 51, 2386-2388. To a solution of 1,4-dioxa-spiro[4.5]decan-8-ol (17) (8.6 g, 54 mmol) in chloroform (54 mL) at 0° C. was added pyridine (13.2 mL, 163 mmol). To this stirring solution was added p-toluenesulfonyl chloride (20.7 g, 108 mmol) in portions. This was stirred at 0° C. for 7 h, whereupon the mixture was partitioned between diethyl ether (150 mL) and water (50 mL). The organic layer was washed with 3 N NCl (50 mL), saturated sodium bicarbonate (50 mL), and water (50 mL). The organic layer was dried (MgSO₄), filtered and concentrated under reduced pressure to give crude toluene-4-sulfonic acid 1,4-dioxa-spiro [4.5]dec-8-yl ester (18) as a crystalline solid, contaminated with p-toluenesulfonic acid: $R_f$=0.31 (CH₂Cl₂).

Crude toluene-4-sulfonic acid 1,4-dioxa-spiro[4.5]dec-8-yl ester (18) (18 g) in ethanol (25 mL) was added to a solution of sodium thiomethoxide (12.1 g, 173 mmol) in dry methanol (75 mL). This mixture was heated to 80° C. for 4 h. The mixture was partitioned between ethyl acetate (100 mL) and water (100 mL). The aqueous layer was extracted with additional ethyl acetate (100 mL). The combined organic layers were concentrated under reduced pressure. The residue was partitioned between CH₂Cl₂ (75 mL) and saturated NaHCO₃ (100 mL). The aqueous layer was extracted with additional CH₂Cl₂ (50 mL). The combined organic layers were dried (Na₂SO₄), filtered and concentrated under reduced pressure to give crude 8-methylsulfanyl-1,4-dioxa-spiro[4.5]decane (19) (6.6 g, 77% over two steps): $R_f$=0.45 (CH₂Cl₂); ¹H NMR (300 MHz, CDCl₃) δ 3.94 (s, 4H), 3.67-3.53 (m, 1H), 2.09 (s, 3H), 2.05-1.92 (m, 2H), 1.90-1.50 (m, 6H).

4-Methylsulfanyl-cyclohexanone (20) from 8-Methylsulfanyl-1,4-dioxa-spiro[4.5]decane (19).

8-Methylsulfanyl-1,4-dioxa-spiro[4.5]decane (19) (6.6 g, 35 mmol) was combined with p-toluenesulfonic acid (6.65 g, 35 mmol) in water (75 mL), and heated to reflux for 5 h, and was subsequently allowed to stir at rt overnight. The aqueous reaction mixture was extracted with Et₂O (3×100 mL). The combined organic layers were washed successively with 3 N HCl (2×25 mL), saturated NaHCO₃ (2×25 mL), and water (2×25 mL), The organics were then dried (Na₂SO₄), filtered and concentrated under reduced pressure. The residue was purified by flash chromatography (CH₂Cl₂ elution) to give 4-methylsulfanyl-cyclohexanone (20) (3.0 g, 60%): $R_f$=0.21 (3:1 CH₂Cl₂/hexanes); ¹H NMR (300 MHz, CDCl₃) δ 3.01-2.98 (m, 1H), 2.52-2.38 (m, 2H), 2.35-2.22 (m, 2H), 2.22-2.08 (m, 2H), 2.06 (s, 3H), 1.88-1.72 (m, 2H).

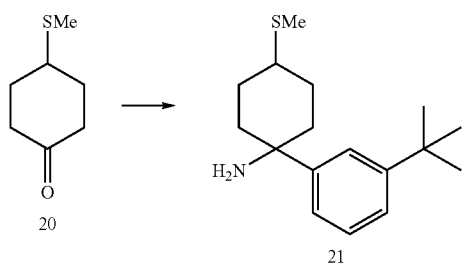

1-(3-tert-Butyl-phenyl)-4-methylsulfanyl-cyclohexylamine from 4-Methylsulfanyl-cyclohexanone 4-Methylsulfanyl-cyclohexanone (20) was converted into 1-(3-tert-Butyl-phenyl)-4-methylsulfanyl-cyclohexylamine (21) in the manner described in EXAMPLE 361 below, except using 1-bromo-3-tert-butyl-benzene in the first step.

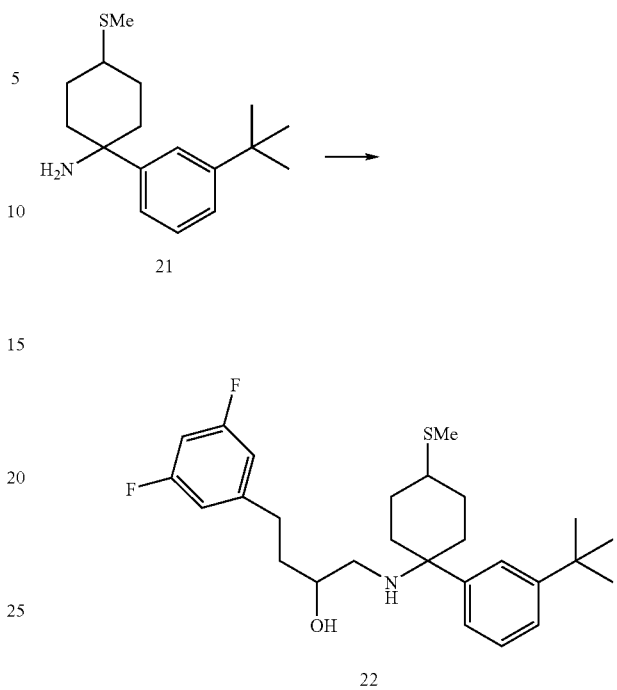

1-[1-(3-tert-Butyl-phenyl)-4-methylsulfanyl-cyclohexylamino]-4-(3,5-difluoro-phenyl)-butan-2ol from 1-(3-tert-Butyl-phenyl)-4-methylsulfanyl-cyclohexylamine 1-[1-(3-tert-Butyl-phenyl)-4-methylsulfanyl-cyclohexylamino]-4-(3,5-difluoro-phenyl)-butan-2-ol (22) was synthesized from 1-(3-tert-Butyl-phenyl)-4-methylsulfanyl-cyclohexylamine (21) according to the procedure described in EXAMPLE 271.

EXAMPLE 279

Preparation of 1-[1-(3-TERT-BUTYL-PHENYL)-4-METHOXY-CYCLOHEXYLAMINO]-4-(3,5-DIFLUORO-PHENYL)-BUTAN-2-OL

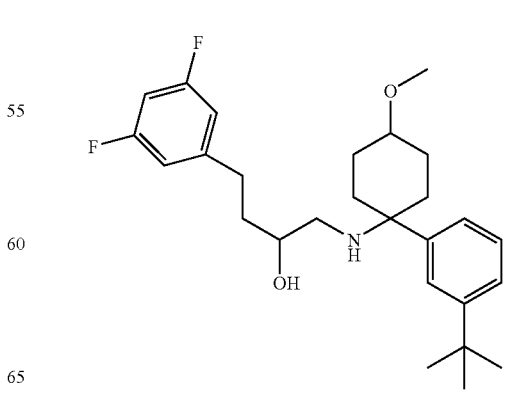

1-(3-tert-Butyl-phenyl)-4-methoxy-cyclohexylamine from 4-methoxycyclohexanone

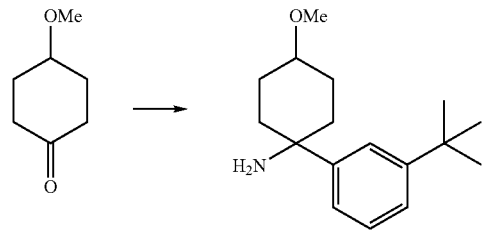

4-Methoxycyclohexanone was synthesized according to the procedure described in Kaiho, T. et al. *J. Med. Chem.* 1989, 32, 351-357. The ketone was converted to the 1-(3-tert-Butyl-phenyl)-4-methoxy-cyclohexylamine in the manner described in EXAMPLE 361, except using 1-bromo-3-tert-butyl-benzene in the first step to give a 1:1 mixture of isomers: retention time (min)=1.33 and 1.42 (diastereomers), method [1], MS(ESI) 213.2 (M−NH$_2$); MS(ESI) 213.2 (M−NH$_2$).

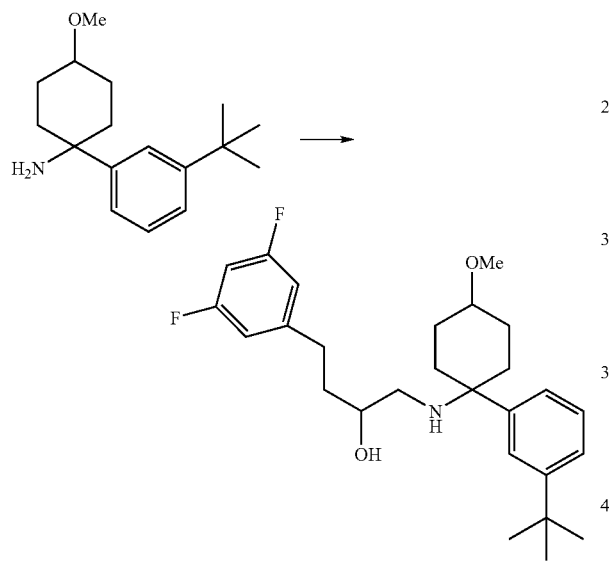

The amine was converted into 1-[1-(3-tert-Butyl-phenyl)-4-methoxy-cyclohexylamino]-4-(3,5-difluoro-phenyl)-butan-2-ol according to the procedure described in EXAMPLE 271.

EXAMPLE 280
Preparation of 1-[1-(3-TERT-BUTYL-PHENYL)-4-TRIFLUOROMETHYL-CYCLOHEXYLAMINO]-4-(3,5-DIFLUORO-PHENYL)-BUTAN-2-OL

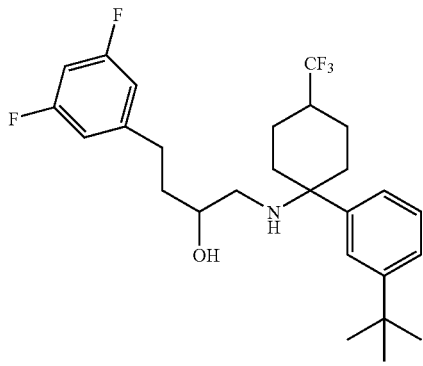

1-(3-tert-Butyl-phenyl)-4-trifluoromethyl-cyclohexylamine from 4-Trifluoromethyl-cyclohexanone

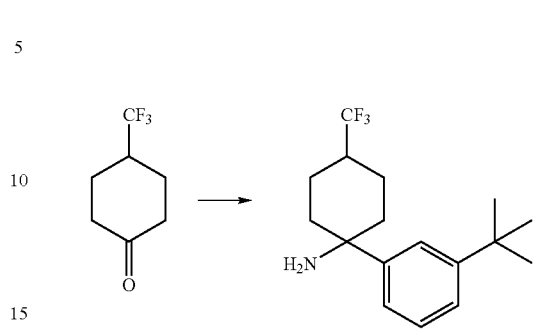

4-Trifluoromethylcyclohexanone (Matrix Scientific) was converted to the titled amine by the method described in EXAMPLE 361: retention time (min)=1.64 and 1.69 (diastereomers), method [1]; $^1$H NMR (300 MHz, CDCl$_3$) δ 7.55 (s, 0.5H), 7.47 (s, 0.5H), 7.40-7.20 (m, 3H), 2.54 (d, J=13.2 Hz, 1H), 2.15 (br s, 2H), 2.00-1.80 (m, 4H), 1.75-1.50 (m, 4H), 1.34 (s, 9H); MS(ESI) 283.1 (M−NH$_2$).

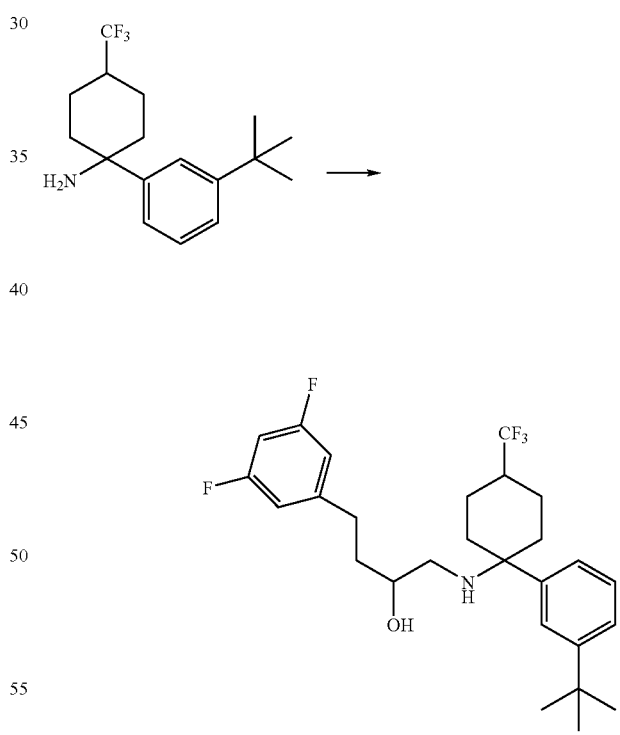

1-[1-(3-tert-Butyl-phenyl)-4-trifluoromethyl-cyclohexylamino]-4-(3,5-difluoro-phenyl)-butan-2-ol from 1-(3-tert-Butyl-phenyl)-4-trifluoromethyl-cyclohexylamine The titled compound can be synthesized from the intermediate amine by the route described in EXAMPLE 271.

EXAMPLE 281

Preparation of 1-[1-(6-TERT-BUTYL-PYRIMIDIN-4-YL)-CYCLOHEXYLAMINO]-4-(3,5-DIFLUORO-PHENYL)-BUTAN-2-OL

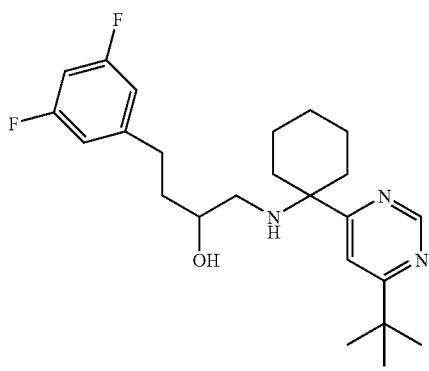

Synthesis of 1-(6-tert-Butyl-pyrimidin-4-yl)-cyclohexylamine

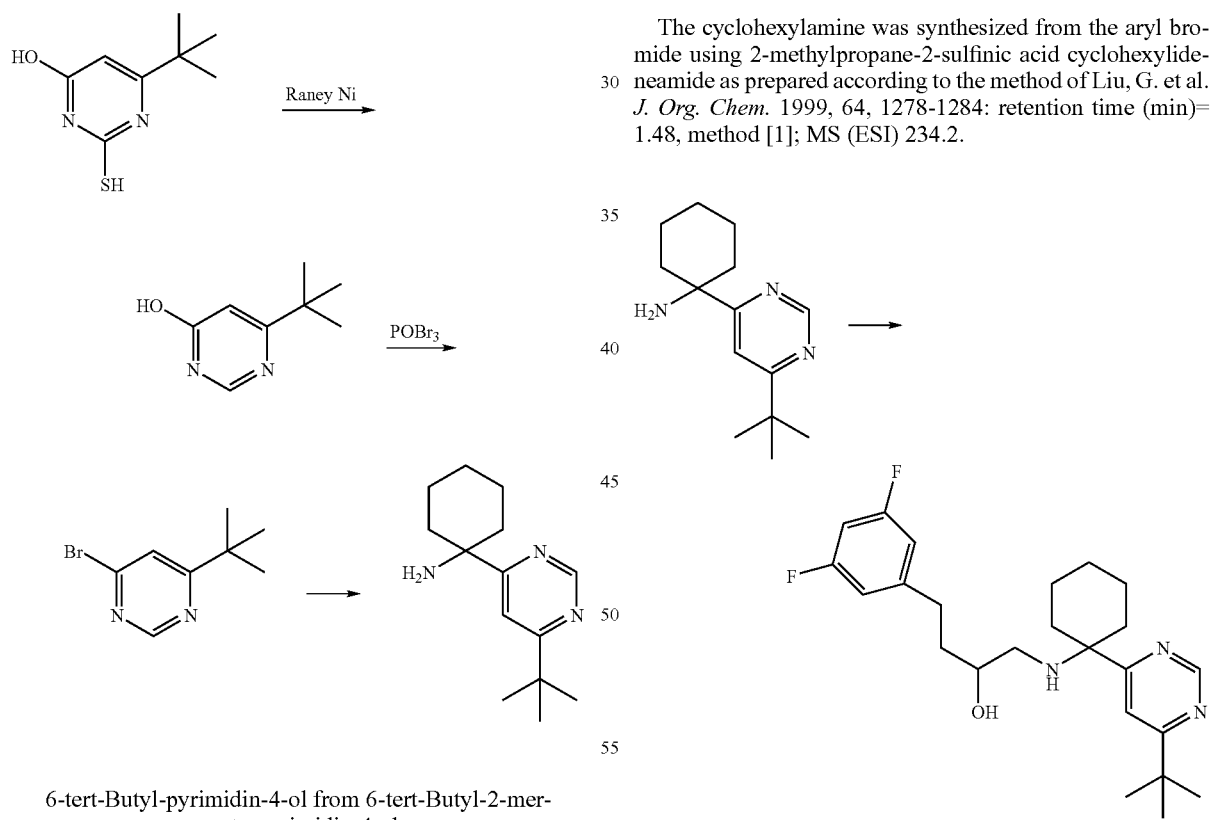

6-tert-Butyl-pyrimidin-4-ol from 6-tert-Butyl-2-mercapto-pyrimidin-4-ol

Procedure adapted from: *J. Med. Chem.* 2002, 45, 1918-1929. 6-tert-Butyl-2-mercapto-pyrimidin-4-ol (1.0 g, 5.4 mmol), synthesized according to the procedure described in *J. Am. Chem. Soc.* 1945, 67, 2197, was dissolved in boiling EtOH (30 mL). Raney Ni 2800 slurry (Aldrich) was added to the mixture dropwise until starting material had been determined by TLC to be completely consumed (approx. 5 mL of slurry over 3h). The mixture was filtered through diatomaceous earth, washed with EtOH (50 mL). The filtrate was concentrated under reduced pressure to give 794 mg, 96% of desired product: $R_f$=0.13 (1:1 EtOAc/hexanes); [1] H NMR (300 MHz, MeOD-$d_4$) δ8.14 (s, 1H), 6.37 (s, 1H), 1.29 (s, 9H), 4-Bromo-6-tert-butyl-pyrimidine from 6-tert-Butyl-pyrimidin-4-ol Procedure adapted from: Kim, J. T. *Org. Lett*, 2002, 4, 4697-4699. Phosphorus oxybromide (14.9 g, 51.9 mmol) was added to a solution of 6-tert-Butyl-pyrimidin-4-ol (5.2 g, 34 mmol) and N,N-dimethylaniline (1.25 g, 10 mmol) in anhydrous benzene (150 mL). The mixture was then heated to reflux for 3 h. The reaction mixture was then allowed to cool to rt, and saturated $Na_2CO_3$ (200 mL) was added. The layers were separated, and the aqueous further extracted with EtOAc (300 mL). The combined organic layers were washed (sat'd NaCl), dried ($Na_2SO_4$), filtered and concentrated under reduced pressure. Flash chromatography (0-20% EtOAc/hexanes gradient elution) afforded pure product (3 g, 40%): $R_f$=0.84 (1:4 EtOAc/hexanes); [1] H NMR (300 MHz, $CDCl_3$) δ8.82 (d, J=0.6 Hz, 1H), 7.74 (d, J=0.6 Hz, 1H), 1.35 (s, 9H).

1-(6-tert-Butyl-pyrimidin-4-yl)-cyclohexylamine from 4-Bromo-6-tert-butyl-pyrimidine The cyclohexylamine was synthesized from the aryl bromide using 2-methylpropane-2-sulfinic acid cyclohexylideneamide as prepared according to the method of Liu, G. et al. *J. Org. Chem.* 1999, 64, 1278-1284: retention time (min)= 1.48, method [1]; MS (ESI) 234.2.

1-[1-(6-tert-Butyl-pyrimidin-4-yl)-cyclohexylamino]-4-(3,5-difluoro-phenyl)-butan-2-ol from 1-(8-tert-Butyl-pyrimidin-4-yl)-cyclohexylamine The title compound can be synthesized from the intermediate amine according to methods described in EXAMPLE 271.

EXAMPLE 282

Preparation of 1-[1-(3-TERT-BUTYL-5-FLUORO-PHENYL)-CYCLOHEXYLAMINO]-4-(3,5-DIFLUORO-PHENYL)-BUTAN-2-OL Scheme

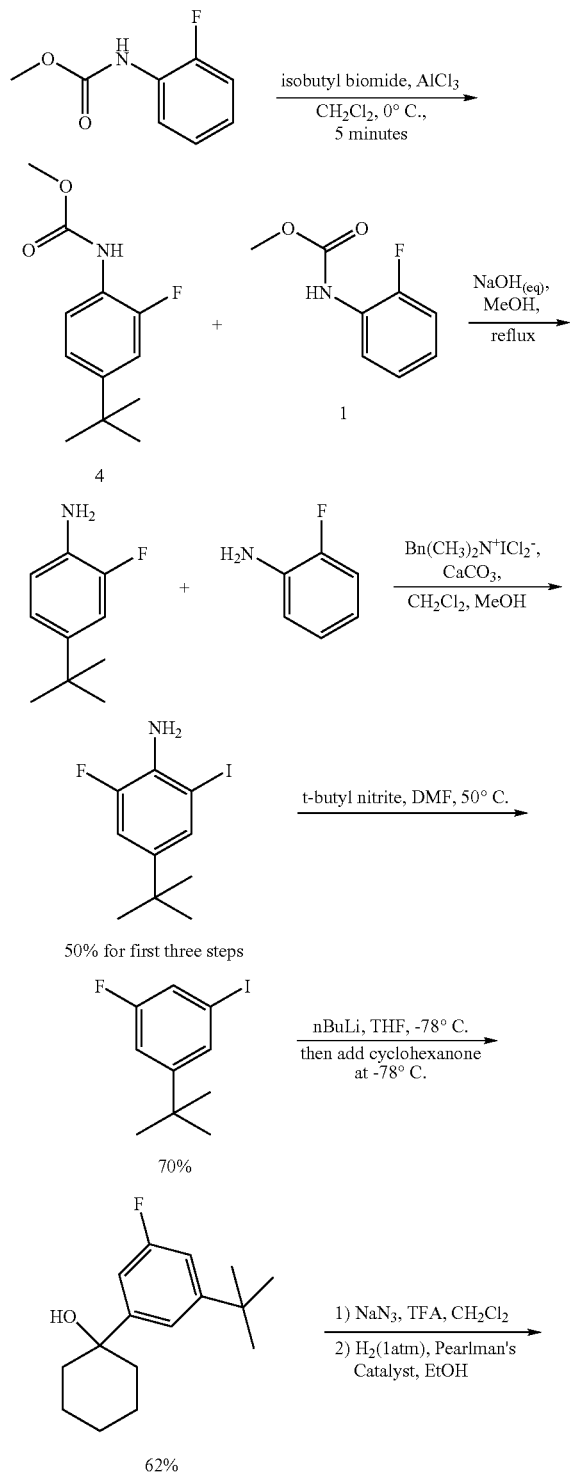

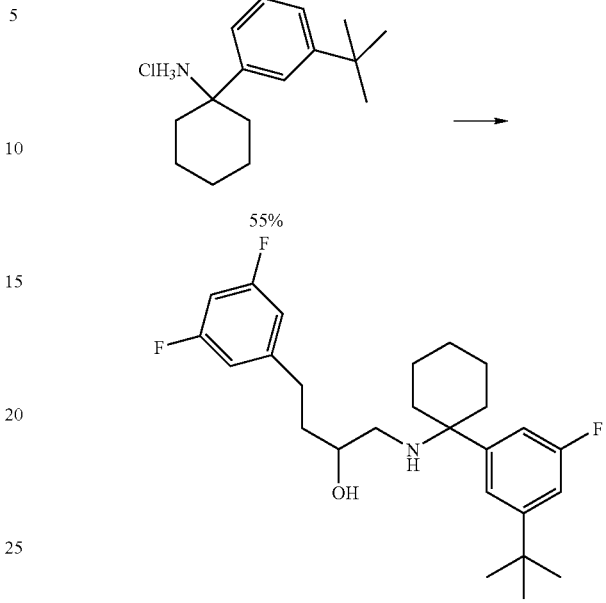

(4-tert-Butyl-2-fluoro-phenyl)-carbamic acid methyl ester:

To a stirred solution of the carbamate (12.2 g, 72 mmol) in 144 mL dichloromethane at 0° C. under a drying tube was added aluminum trichloride (28.85 gm, 216 mmol) carefully portion wise as a solid (some exotherm). The suspension was allowed to cool back to 0° C. for about 5 minutes and then isobromobutane (39.22 mL, 360 mmol) was added carefully by syringe at a rate that avoided reflux. The reaction was stirred for 5 minutes. HPLC shows near complete conversion at this time (retention time (min)=3.60, method [8]), The reaction was carefully poured into rapidly stirring ice water (500 mL) and diluted with 400 mL $CH_2Cl_2$. The mixture was stirred for about 5 minutes and the layers separated. The organics were washed 2×100 mL with $H_2O$, 1×200 mL with saturated $NaHCO_3$ and 1×100 mL with brine. The organics were dried ($MgSO_4$), filtered and concentrated to a brown oil that was used crude in the next reaction.

4-tert-Butyl-2-fluoro-phenylamine:

To a stirred solution of the crude carbamate (18.4 gm, 81.7 mmol) in 163 mL MeOH at room temperature under nitrogen was added 2N NaOH (81.7 mL, 163.4 mmol). The reaction was warmed to 75° C. and stirred overnight. 40 mL of 2N NaOH was added and the reaction stirred at 75° C. overnight again. HPLC showed the reaction has gone to completion (retention time=3.59, 3.65, method [8]). The reaction was cooled to room temperature and most of the MeOH was removed by rotovap. The residual aqueous mixture was cooled on ice and neutralized to pH=8 with conc. HCl. The solution was then extracted 2×100 mL with $CH_2Cl_2$ and the organics combined, dried ($MgSO_4$), filtered and concentrated to a brown oil which was taken into the iodination as is.

4-tert-Butyl-2-fluoro-6-iodo-phenylamine:

To a stirred solution of the crude aniline (12.8 g, 76.54 mmol) in 240 mL CH$_2$Cl$_2$ and 80 mL MeOH at room temperature under nitrogen was added calcium carbonate (15.32 gm, 153.1 mmol) followed by the iodinating reagent, benzyltrimethylammonium iododichloride (67.28 g, 153.1 mmol). The reaction was allowed to proceed overnight at room temperature. HPLC showed complete consumption of starting material and a new late eluting peak. The reaction was diluted to 500 mL with CH$_2$Cl$_2$ and poured into ice cold 10% NaHSO$_3$ with rapid stirring. The layers were separated and the organics washed 1×500 mL with 10% NaHSO$_3$, 1×500 mL with H$_2$O and 1×500 mL with saturated NaHCO$_3$. The organics were dried (MgSO$_4$), filtered and concentrated to a brown oil which was diluted in CH$_2$Cl$_2$ and absorbed onto silica gel. After rotovap and thorough high vacuum drying the silica was loaded into a ZIF module in line with a Biotage 75S column and eluted first with pure hexanes and then 98/2 hexanes/Et$_2$O. The product was isolated and concentrated to a brown oil (11.72 gm, 52% for three steps): retention time (min)=4.45, method [8]; $^1$H NMR (400 MHz, CDCl$_3$) δ 7.38 (s, 1H), 7.00 (d, J=10.8 Hz, 1H), 3.99 (s, 2H), 1.25 (s, 9H).

1-tert-Butyl-3-fluoro-5-iodo-benzene:

To a stirred solution of t-butyl nitrite 7.13 mL, 60 mmol) in 80 mL DMF at 60° C. under nitrogen was added a solution of the iodoaniline (11.72 gm, 40 mmol) in 80 mL DMF dropwise by cannulation. The reaction began to evolve gas. After complete addition the reaction was stirred for 1 hour and then cooled to room temperature. HPLC showed complete consumption of starting material and a new late eluting peak. The reaction was diluted with 1 L EtOAc and washed 4×800 mL with H$_2$O and then 1×800 mL with brine. The organics were dried (MgSO$_4$), filtered and concentrated to a brown oil that was loaded onto a Biotage 65 column with hexane and eluted with the same solvent. The product containing fractions were pooled and partially concentrated to about 100 mL. The solution of combined fractions was washed 1×100 mL with 10% NaHSO$_3$, 1×100 mL with H$_2$O and 1×100 mL with NaHCO$_3$. The clear organics were dried (MgSO$_4$), filtered and concentrated to a clear oil (6.8 gm, 61%): $^1$H NMR (400 MHz, CDCl$_3$) δ7.48 (s, 1H), 7.27-7.22 (m, 1H), 7.04 (d, J=10.5 Hz, 1H), 1.26 (s, 9H).

1-(3-tert-Butyl-5-fluoro-phenyl)-cyclohexanol:

To a stirred solution of the iodobenzene derivative (2.3 gm, 8.27 mmol) in 16 mL THF at −78° C. under nitrogen was added n-BuLi (2.5 M in hexanes, 3.31 mL, 8.27 mmol) dropwise by syringe. After 2 hours, a solution of cyclohexanone (1.03 mL, 9.92 mmol) in 8 mL THF was added dropwise by cannulation at −78° C. After 1 hour TLC in 4/1 hexanes/EtOAc shows a major spot at r$_f$=0.4. The reaction was poured into 50 mL saturated NH$_4$Cl and then the solution was extracted 3×50 mL with EtOAc. The combined organics were dried (MgSO$_4$), filtered and concentrated. The crude product was loaded onto a. Biotage 40M column with hexanes and eluted with 4/96 EtOAc/hexanes. Product containing fractions were pooled and concentrated to a clear oil which solidified upon storage in the freezer overnight (1.3 gm, 63%): R$_f$=0.2 (9:1 hexanes: EtOAc); $^1$H NMR (400 MHz, CDCl$_3$) δ7.31 (s, 1H), 7.01 (d, J=10.5 Hz, 1H), 6.95 (d, J=10.4 Hz, 1H), 1.86-1.56 (m, 10H), 1.31 (s, 9H).

1-(1-Azido-cyclohexyl)-3-tert-butyl-5-fluoro-benzene:

To a stirred solution of the tertiary alcohol (1.3 gm, 5.2 mmol) in 11 mL CH$_2$Cl$_2$ at 0° C. under nitrogen was added sodium azide (1.01 gm, 15.6 mmol) as a solid. A solution of TFA (1.2 mL, 15.6 mmol) in 5 mL CH$_2$Cl$_2$ was then added dropwise by syringe. Immediately a solid began to precipitate. The cooling bath was removed and after 1 hour, TLC in 9/1 hexanes/EtOAc showed near complete consumption of starting material. The reaction was allowed to proceed overnight. The reaction was partitioned between CH$_2$Cl$_2$ (50 mL) and H$_2$O (50 mL) and the organics washed 2×50 mL with 3N NH$_4$OH and 1×50 mL with brine. The organics were dried (MgSO$_4$), filtered and concentrated to a yellow oil. The material was taken crude into the Staudinger Reduction.

1-(3-tert-Butyl-5-fluoro-phenyl)-cyclohexylamine hydrochloride salt:

To a stirred solution of the azide (800 mg, 2.9 mmol) in 9 mL 95% EtOH at room temperature was added Pearlman's Catalyst. The suspension was put through a vacuum/purge cycle three times with hydrogen gas and then held under 1 atm hydrogen. After 2 hours the reaction appeared to be complete by TLC in 9/1 EtOAc/MeOH. The suspension was filtered through GF/F filter paper with 95% EtOH and the filtrate concentrated to a crude oil. The oil was loaded onto a Biotage 40M cartridge with EtOAc and eluted on the Horizon system with a gradient of EtOAc to 10% MeOH in EtOAc. Product containing fractions were pooled and concentrated to a clear oil (540 mg, 75%). The free base was dissolved in 5 mL Et$_2$O and cooled to 0° C. and treated with 1M HCl in Et$_2$O (2 eq). A white precipitate formed that was filtered off with hexane rinse and dried under high vacuum: retention time (min)= 2.73, method [8]; $^1$H NMR (400 MHz, DMSO-d$_6$) δ8.44 (s, 2H), 7.49 (s, 1H), 7.28-7.20 (m, 2H), 2.32-2.20 (m, 2H), 1.99-1.87 (m, 2H), 1.79-1.65 (m, 2H), 1.50-1.27 (m, 4H), 1.30 (s, 9H); MS (ESI) 249.8.

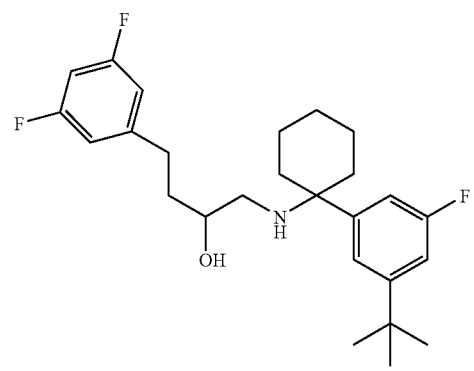

1-[1-(3-tert-Butyl-5-fluoro-phenyl)-cyclohexylamino]-4-(3,5-difluoro-phenyl)-butan-2-ol The title compound can be synthesized from 1-(3-tert-Butyl-5-fluoro-phenyl)-cyclohexylamine using methods described in EXAMPLE 271.

EXAMPLE 283

Preparation of 4-AMINO-4-(3-TERT-BUTYL-PHENYL)-CYCLOHEXANONE

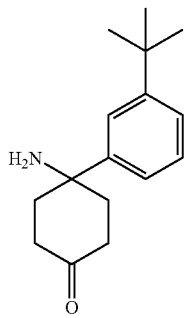

This amine was synthesized from 8-(3-tert-Butyl-phenyl)-1,4-dioxa-spiro[4.5]dec-8-ylamine, TsOH, and ethylene glycol in refluxing benzene. Retention time (min)=1.34, method [4]; MS (ESI) 229.1 (100), 246.1 (40).

EXAMPLE 284

Preparation of 1-[1-(3-TERT-BUTYL-PHENYL)-4,4-DIFLUORO-CYCLOHEXYLAMINO]-4-(3,5-DIFLUORO-PHENYL)-BUTAN-2-OL from 1-(3-TERT-BUTYL-PHENYL)-4,4-DIFLUORO-CYCLOHEXYLAMINE

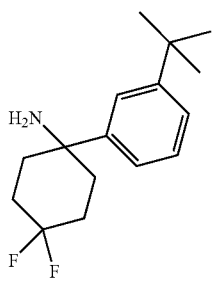

To 4-amino-4-(3-tert-butyl-phenyl)-cyclohexanone (200 mg, 0.82 mmol) was added a solution of bis(2-methoxyethyl)amino-sulfur trifluoride (360 mg, 1.6 mmol) and ethanol (12 µL) In $CH_2Cl_2$ (1 mL). This was stirred overnight at rt. The reaction mixture was quenched, with saturated $NaHCO_3$ (5 mL), and extracted with EtOAc (2×5 mL). The organic extracts were dried ($Na_2SO_4$), filtered and concentrated under reduced pressure, The residue was purified by flash chromatography (10% MeOH/$CH_2Cl_2$ elution) to give 20 mg (9%) of material as an oil; $R_f$=0.33 (10% MeOH/$CH_2Cl_2$); retention time (min)=1.51, method [1]; MS (ESI) 251.1.

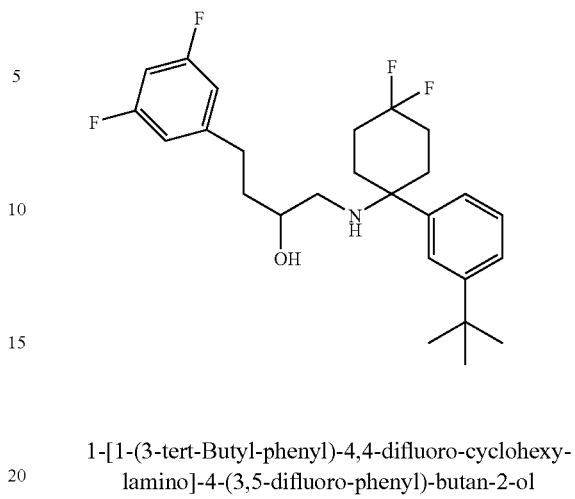

1-[1-(3-tert-Butyl-phenyl)-4,4-difluoro-cyclohexylamino]-4-(3,5-difluoro-phenyl)-butan-2-ol The title compound can be synthesized from 1-(3-tert-Butyl-phenyl)-4,4-difluoro-cyclohexylamine according to the method described in EXAMPLE 271.

EXAMPLE 285

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID BENZYL ESTER

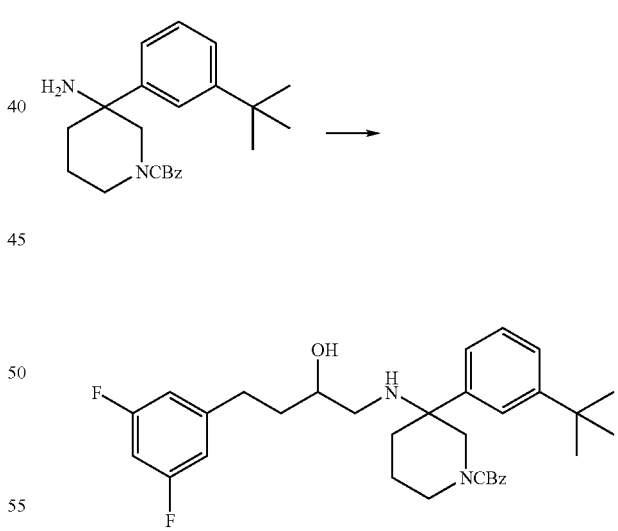

3-(3-tert-Butyl-phenyl)-3-[4-(3,5-difluoro-phenyl)-2-hydroxy-butylamino]-piperidine-1-carboxylic acid benzyl ester from 3-amino-3-(3-tert-butyl-phenyl)-piperidine-1-carboxylic acid benzyl ester The titled compound was prepared according to the procedure described in EXAMPLE 271 from 3-amino-3-(3-tert-butyl-phenyl)-piperidine-1-carboxylic acid benzyl ester.

EXAMPLE 286

Preparation of 1-[3-(3-TERT-BUTYL-PHENYL)-1-METHYL-PIPERIDIN-3-YLAMINO]-4-(3,5-DIFLUORO-PHENYL)-BUTAN-2-OL and 1-[3-(3-TERT-BUTYL-PHENYL)-PIPERIDIN-3-YLAMINO]-4-(3,5-DIFLUORO-PHENYL)-BUTAN-2-OL

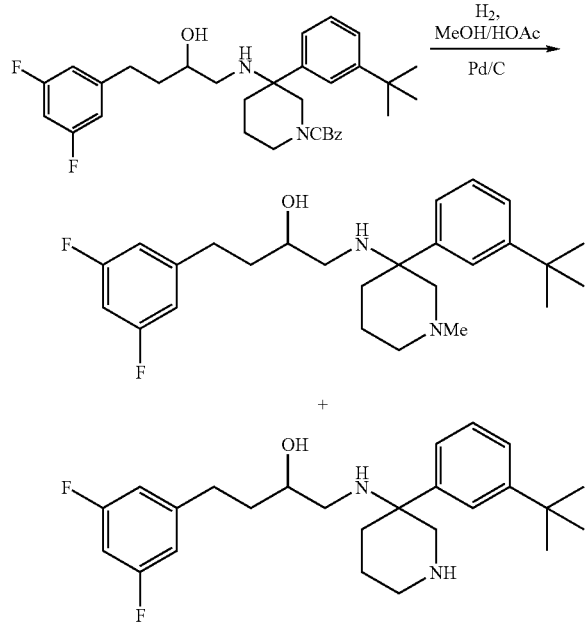

To a stirring solution of 3-(3-tert-Butyl-phenyl)-3-[4-(3,6-difluoro-phenyl)-2-hydroxy-butylamino]-piperidine-1-carboxylic acid benzyl ester in MeOH and HOAc was added 10% palladium-carbon. The resulting mixture was stirred at room temperature under an atmospheric pressure of hydrogen for 2 days. The mixture was then filtered through a plug of Celite. The Celite plug was washed several times with 10% MeOH/EtOAc. The filtrate was concentrated under reduced pressure to give a crude mixture, which was subjected to silica gel chromatography, and further purified via HPLC to give the title compounds.

EXAMPLE 287

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID METHYL ESTER

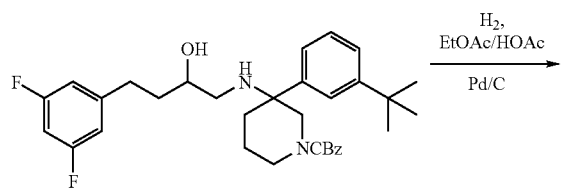

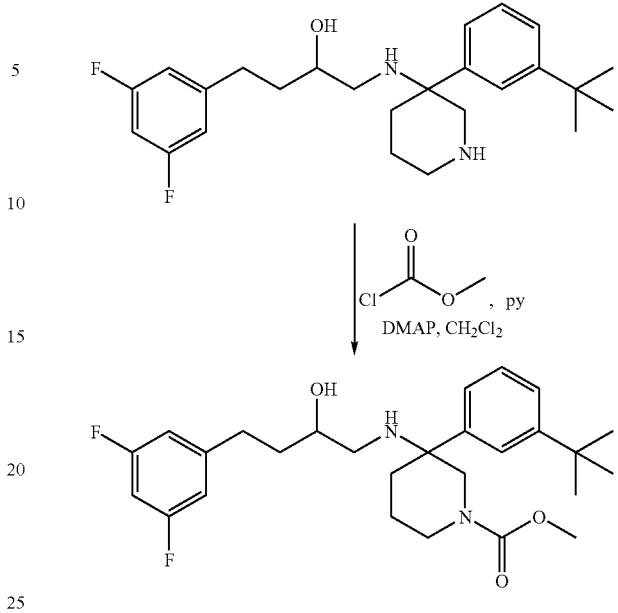

To a stirring solution of 3-(3-tert-Butyl-phenyl)-3-[4-(3,5-difluoro-phenyl)-2-hydroxy-butylamino]-piperidine-1-carboxylic acid benzyl ester in EtOAc and HOAc was added 10% palladium-carbon. The resulting mixture was stirred at room temperature under an atmospheric pressure of hydrogen for 2 days. The mixture was then filtered through a plug of Celite. The Celite plug was washed several times with 10% MeOH/EtOAc. The filtrate was concentrated under reduced pressure to give a crude mixture, which was subjected to silica gel chromatography to give 1-[3-(3-tert-Butyl-phenyl)-piperidin-3-ylamino]-4-(3,5-difluoro-phenyl)-butan-2-ol.

To a stirring solution of 1-[3-(3-tert-Butyl-phenyl)-piperidin-3-ylamino]-4-(3,5-difluoro-phenyl)-butan-2-ol in $CH_2Cl_2$ was successively added pyridine, DMAP, and methyl chloroformate. The resulting mixture was allowed to react overnight at room temperature. The reaction was quenched with a saturated $NaHCO_3$ solution and extracted with EtOAc (2×20 mL). The organic layers were washed with brine, dried over $Na_2SO_4$, and filtered. The combined organic layers were evaporated under reduced pressure. The crude mixture was purified via silica gel chromatography to give the title compound.

EXAMPLE 288

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID BENZYL ESTER

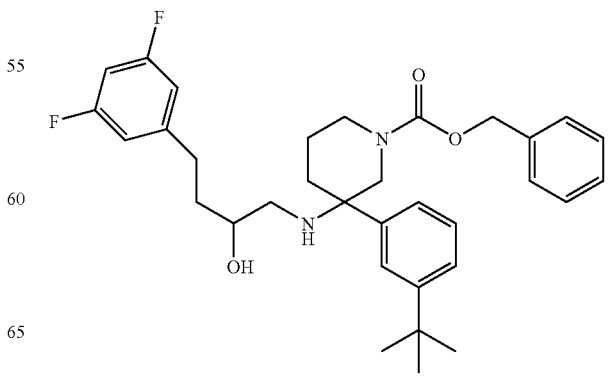

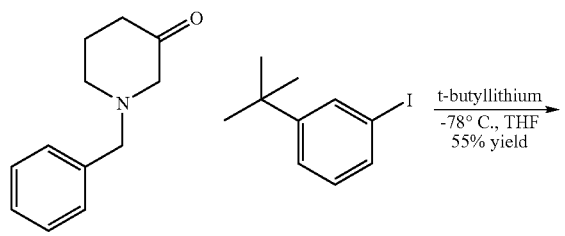

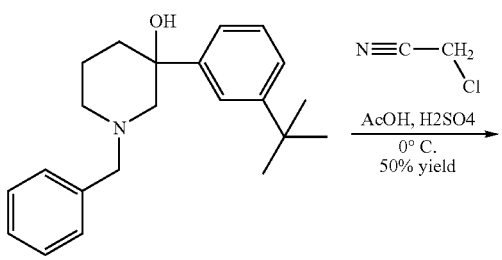

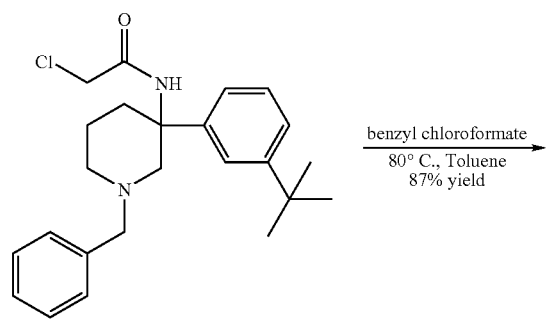

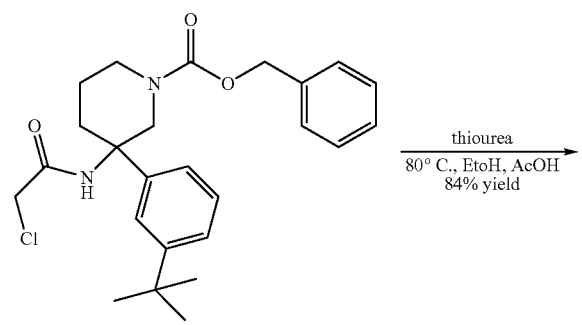

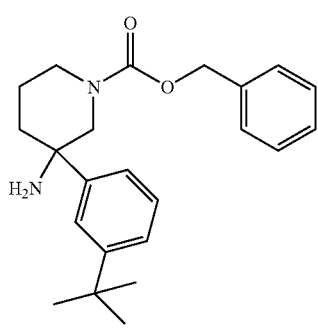

1-Benzyl-3-(3-tert-butyl-phenyl)-piperidin-3-ol. Iodo t-butyl benzene (2.46 g, 9.44 mmol) was taken up in 10 mL of THF, placed under $N_2$ and cooled to −78° C. T-Butyl lithium (11.06 mL, 1.7M solution, 18.8 mmol) was added dropwise over 5 minutes. The reaction was allowed to stir for 1 hour. The 1-benzyl-piperidin-3-one (1.5 g, 8.0 mmol) was added and the reaction was stirred for 3 hours warming to r.t. The reaction was quenched with water and extracted with ether. The ether layer was dried over MgSO4, filtered and concentrated under reduced pressure. The material was purified using a biotage 40M eluting with hexanes: ethyl acetate (70:30) to yield 1.4 g (54% yield) of a clear oil: $^1$H NMR (400 MHz, CDCl$_3$) δ 7.57 (t, J=1.3 Hz, 1H), 7.36-7.22 (m, 8H), 3.95 (s, 1H), 3.58 (s, 2H), 2.91 (d, J=10.4 Hz, 1H), 2.76 (d, J=10.8 Hz, 1H), 2.34 (d, J=10.8 Hz, 1H), 2.10-1.90 (m, 3H), 1.85-1.62 (m, 4H), 1.32 (s, 9H).

N-[1-Benzyl-3-(3-tert-butyl-phenyl)-piperidin-3-yl]-2-chloro-acetamide. To 1-benzyl-3-(3-tert-butyl-phenyl)-piperidin-3-ol (517 mg, 1.6 mmol) and chloroacetonitrile (241 mg, 3.2 mmol) was added 300 uL of AcOH. This mixture was placed under nitrogen and cooled to 0° C. Sulfuric acid (300 uL) was added dropwise keeping the temp below 10° C., The reaction was stirred for 12 hours warming to r.t. The reaction was diluted with ethyl acetate (75 mL) and 10% aq sodium carbonate (75 mL). The layers were separated and the organic layer was dried over MgSO$_4$, filtered and concentrated under reduced pressure. The material was purified using a biotage 40S cartridge eluting with hexanes:ethyl acetate (70:30) to afford 247 mg (40% yield) of a clear oil: $^1$H NMR (400 MHz, CDCl$_3$) δ 7.73 (s, 1H), 7.37-7.20 (m, 7H), 7.12 (dt, J=7.1, 1.8 Hz, 1H), 4.02 (s, 2H), 3.55 (d, J=13.4 Hz, 1H), 3.48 (d, J=13.4 Hz, 1H), 2.95 (d, J=9.8 Hz, 1H), 2.80 (d, J=11.8 Hz, 1H), 2.71 (d, J=9.9 Hz, 1H), 2.10-2.00 (m, 2H), 1.91 (dt, J=12.8, 4.6 Hz, 1H), 1.85-1.65 (m, 2H), 1.29 (s, 9H).

3-(3-tert-Butyl-phenyl)-3-(2-chloro-acetylamino)-piperidine-1-carboxylic acid benzyl ester. To a stirred solution of N-[1-Benzyl-3-(3-tert-butyl-phenyl)-piperidin-3-yl]-2-chloro-acetamide (247 mg, 0.620 mmol) in Toluene (2 mL) was added benzylchloroformate (177 uL, 1.24 mmol). The reaction was heated to 80° C. and stirred for 4 hours. An additional 2 eq was added and the reaction was stirred at r.t. for 3 days. The reaction was diluted with ethyl acetate (50 mL) and 10% aq sodium carbonate (50 mL). The layers were separated and the organic layer was dried over MgSO$_4$, filtered and concentrated under reduced pressure. The material was purified using a biotage 12i cartridge, eluting with hexanes:ethyl acetate (70:30) to afford 240 mg (84% yield) of a clear oil: $^1$H NMR (400 MHz, CDCl$_3$) δ 7.45-7.22 (m, 9H), 5.23 (d, J=12.3 Hz, 1H), 5.17 (d, J=12.3 Hz, 1H), 4.44-4.30 (m, 1H), 4.30-4.10 (m, 1H), 3.95-3.80 (m, 2H), 3.20-3.00 (m, 1H), 3.00-2.80 (m, 2H), 2.10-1.90 (m, 1H), 1.80-1.60 (m, 2H), 1.30 (s, 9H).

3-Amino-3-(3-tert-butyl-phenyl)-piperidine-1-carboxylic acid benzyl ester. The 3-(3-tert-butyl-phenyl)-3-(2-chloroacetylamino)-piperidine-1-carboxylic acid benzyl ester (239 mg, 0.540 mmol) was taken up in ethanol (1 mL) and AcOH (200 uL) followed by the addition of thiourea (50 mg, 0.648 mmol). The reaction was heated to 80° C. and stirred for 12 hours. The reaction was diluted with ethyl acetate (50 mL) and 10% aq sodium carbonate (50 mL). The layers were separated and the organic layer was dried over MgSO4, filtered and concentrated under reduced pressure. The material was purified using a biotage 12i cartridge eluting with ethyl acetate: methanol (92:8) to afford 166 mg (84% yield) of a clear oil: retention time (min)=1.71, method [1]; MS(ESI) 367.4 (31), 350.4 (100).

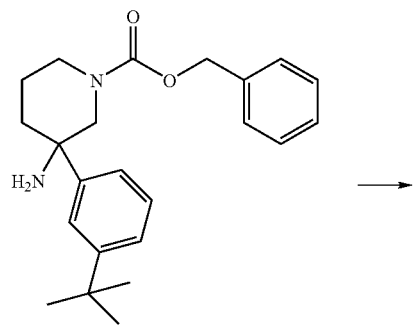

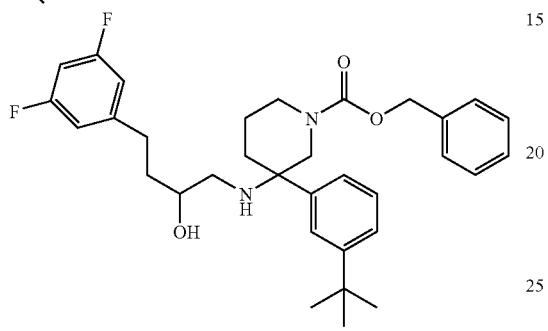

3-(3-tert-Butyl-phenyl)-3-[4-(3,5-difluoro-phenyl)-2-hydroxy-butylamino]-piperidine-1-carboxylic acid benzyl ester was synthesized from 3-Amino-3-(3-tert-butyl-phenyl)-piperidine-1-carboxylic acid benzyl ester according to the procedure described in EXAMPLE 271.

EXAMPLE 289

Preparation of 1-{3-(3-TERT-BUTYL-PHENYL)-3-[4-(3,5-DIFLUORO-PHENYL)-2-HYDROXY-BUTYLAMINO]-PIPERIDIN-1-YL}-ETHANONE

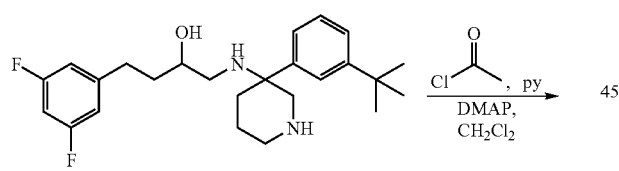

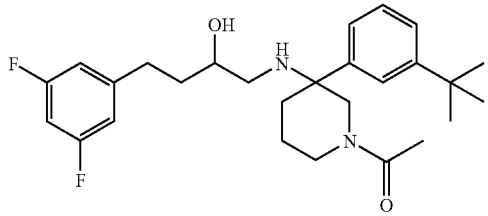

The free amine was converted into 1-{3-(3-tert-Butyl-phenyl)-3-[4-(3,5-difluoro-phenyl)-2-hydroxy-butylamino]-piperidin-1-yl}-ethanone according to EXAMPLE 288.

EXAMPLE 290

Preparation of 1-[3-(3-TERT-BUTYL-PHENYL)-1-METHANESULFONYL-PIPERIDIN-3-YLAMINO]-4-3,5-DIFLUORO-PHENYL)-BUTAN-2-OL

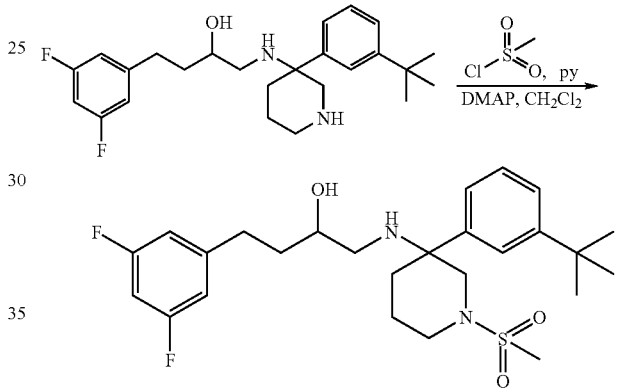

The free amine was converted into 1-[3-(3-tert-Butyl-phenyl)-1-methanesulfonyl-piperidin-3-ylamino]-4-(3,5-difluoro-phenyl)-butan-2-ol according to EXAMPLE 288.

EXAMPLE 291

Preparation of 1-{3-(3-TERT-BUTYL-PHENYL)-3-[4-(3,5-DIFLUORO-PHENYL)-2-HYDROXY-BUTYLAMINO]-PIPERIDIN-1-YL}-3-PHENYL-PROPAN-1-ONE

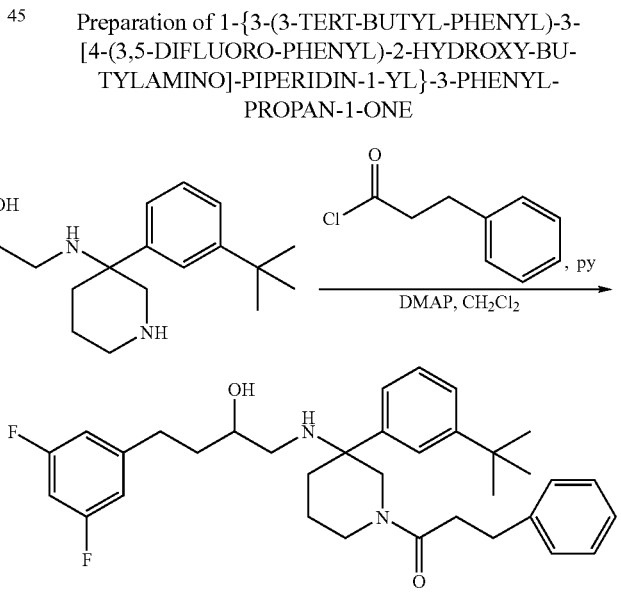

The free amine was converted into 1-{3-(3-tert-Butyl-phenyl)-3-[4-(3,5-difluoro-phenyl)-2-hydroxy-butylamino]-piperidin-1-yl}-3-phenyl-propan-1-one according to EXAMPLE 288.

EXAMPLE 292

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID AMIDE

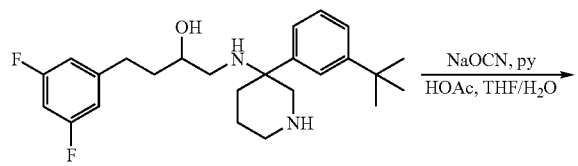

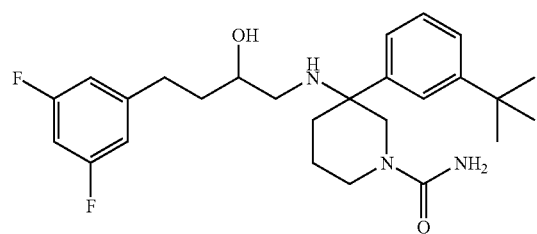

To a stirring solution of the free amine (0.074 mmol) in THF/H$_2$O (0.6 mL each) was added pyridine, acetic acid (2 drops each) and NaOCN (3.7 mmol). The resulting mixture was allowed to react for 24 h. The mixture was then quenched with CH$_2$Cl$_2$ (10 ml) and saturated NaHCO$_3$ solution (10 mL). The layers were separated and the aqueous layer was extracted with EtOAc (2×10 mL). The layers were dried over NaSO$_4$, filtered, and concentrated under reduced pressure. The crude mixture was purified via a silica gel chromatography to give 3-(3-tert-Butyl-phenyl)-3-[4-(3,5-difluoro-phenyl)-2-hydroxy-butylamino]-piperidine-1-carboxylic acid amide.

EXAMPLE 293

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID AMIDE

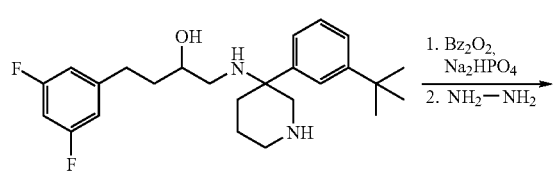

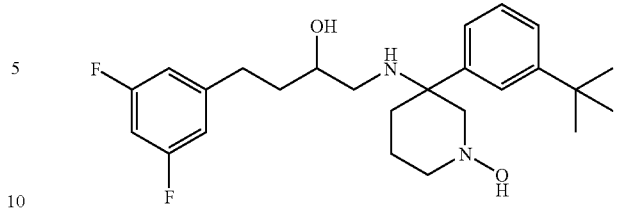

To a stirring mixture of the amine (0.158 mmol) and NaHPO$_4$ (0.80 mmol) in THF (1 mL) was added dibenzoylperoxide (0.182 mmol) in THF (0.2 mL) dropwise. After 15 h of stirring, the resulting mixture was then filtered and the solid was washed with 50 ml of CH$_2$Cl$_2$. The organic layer was then concentrated under reduced pressure. The insoluble material was then dissolved in 10% NaHCO$_3$ and CH$_2$Cl$_2$ (20 mL, each). The layers were separated and the aqueous layer was extracted with CH$_2$Cl$_2$. The combined organic layers were dried over Na$_2$SO$_4$, filtered, and concentrated under reduced pressure. This crude mixture was directly taken to the next reaction without any further purification.

To a stirring solution of N—OBz in THF (1 mL) was added hydrazine (200 µL) dropwise at room temperature. After 15 h of stirring, the mixture was then concentrated under reduced pressure. The crude mixture was purified via silica chromatography to give 3-(3-tert-Butyl-phenyl)-3-[4-(3,5-difluoro-phenyl)-2-hydroxy-butylamino]-piperidine-1-carboxylic acid amide.

EXAMPLE 294

Preparation of {3-(3-TERT-BUTYL-PHENYL)-3-[4-(3,5-DIFLUORO-PHENYL)-2-HYDROXY-BUTYLAMINO]-PIPERIDIN-1-YL}-PIPERIDIN-1-YL-METHANONE

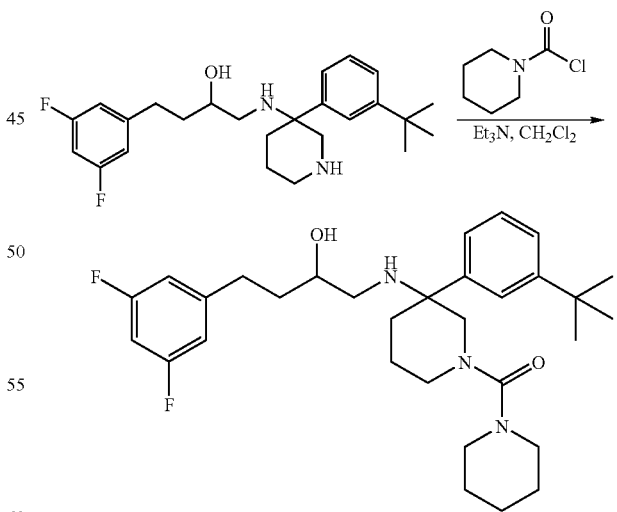

To a stirring solution of the free amine (0.74 mmol) in CH$_2$Cl$_2$ (1 mL) was added Et$_3$N and 1-piperidinecarbonyl chloride (1.4 mmol). The resulting mixture was allowed to react at room temperature overnight. The reaction mixture was then quenched with a saturated NaHCO$_3$ solution. The layers were separated and the aqueous layer was extracted with CH$_2$Cl$_2$ (2×10 mL). The combined organic layers were dried over Na$_2$SO$_4$, filtered, and concentrated under reduced pressure. The crude mixture was purified via silica gel chromatography and then further purified via HPLC to give {3-(3-tert-Butyl-phenyl)-3-[4-(3,5-difluoro-phenyl)-2-hydroxy-butylamino]-piperidin-1-yl}-piperidin-1-yl-methanone.

EXAMPLE 295

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID DIMETHYLAMIDE

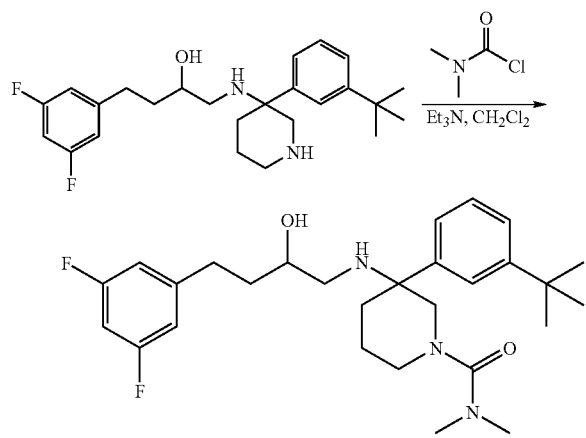

3-(3-tert-Butyl-phenyl)-(3-[4-(3,5-difluoro-phenyl)-2-hydroxy-butylamino]-piperidine-1-carboxylic acid dimethylamide was synthesized analogous to EXAMPLE 294.

EXAMPLE 296

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID ISOPROPYLAMIDE

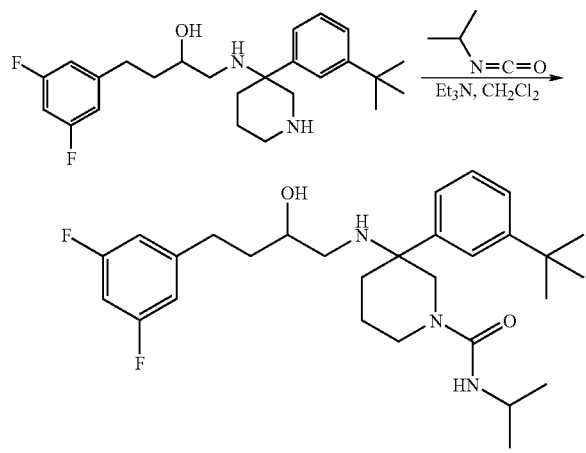

3-(3-tert-Butyl-phenyl)-3-[4-(3,5-difluoro-phenyl)-2-hydroxy-butylamino]-piperidine-1-carboxylic acid isopropylamide was synthesized analogous to EXAMPLE 294.

EXAMPLE 297

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID METHYLAMIDE

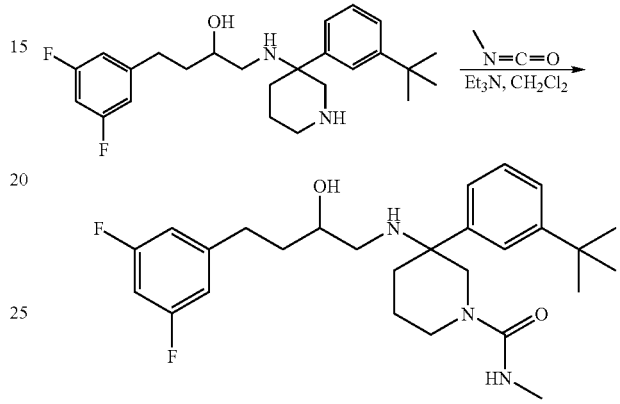

3-(3-tert-Butyl-phenyl)-3-[4-(3,5-difluoro-phenyl)-2-hydroxy-butylamino]-piperidine-1-carboxylic acid methylamide was synthesized analogous to EXAMPLE 294.

EXAMPLE 298

Preparation of 3-(3-TERT-BUTYL-PHENYL)-3-[4-(3,5-DIFLUORO-PHENYL)-2-HYDROXY-BUTYLAMINO]-PIPERIDINE-1-CARBOXYLIC ACID BENZYLAMIDE

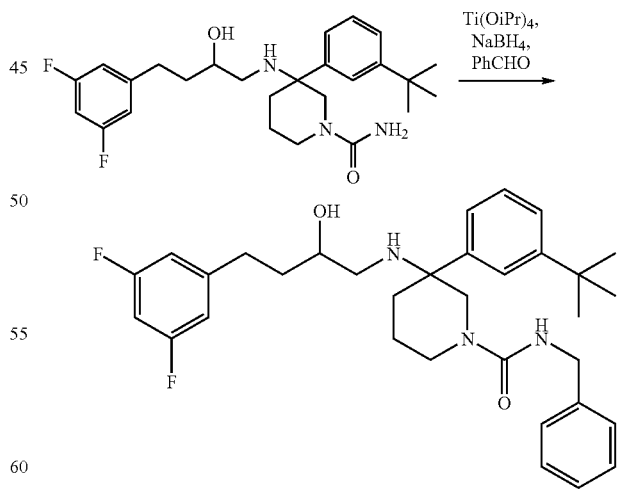

To a stirring solution of 3-(3-tert-Butyl-phenyl)-3-[4-(3,5-difluoro-phenyl)-2-hydroxy-butylamino]-piperidine-1-carboxylic acid amide (0.14 mmol) in THF (1 mL) at 0° C. was added Ti(O$^i$Pr)$_4$ (48 mmol), followed by the addition of benzaldehyde (0.2 mmol) and NaBH$_4$ (4 mg). The reaction was then allowed to warm to room temperature overnight. After 48 h, the reaction mixture was quenched with a saturated NH₄Cl solution (5 mL). The reaction mixture was then diluted with CH₂Cl₂ (10 mL). The layers were separated and the aqueous layer was extracted with CH₂Cl₂ (2×10 mL). The combined organic layers were washed brine, dried over Na₂SO₄, filtered, and concentrated under- reduced pressure to give crude product. This crude mixture was then purified via silica gel chromatography to give 3-(3-tert-Butyl-phenyl)-3-[4-(3,5-difluoro-phenyl)-2-hydroxy-butylamino]-piperidine-1-carboxylic acid benzylamide which was further purified by HPLC.

EXAMPLE 299

Preparation of 4-(3,5-DIFLUORO-PHENYL)-1-[7-(2,2-DIMETHYL-PROPYL)-1,2,3,4-TETRAHYDRO-NAPHTHALEN-1-YLAMINO]-BUTAN-2-OL

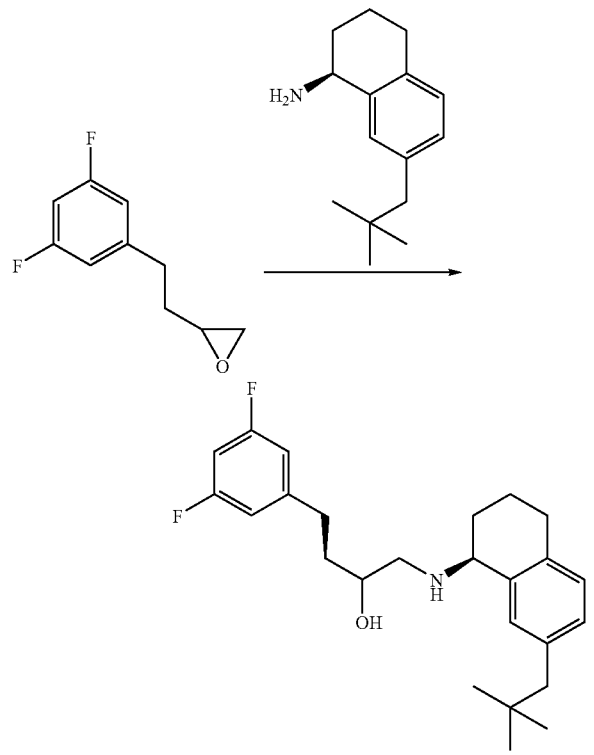

The amine (mono-trifluoroacetate salt, 0.25 mmol, 54.4 mg) and epoxide (0.25 mmol, 46 mg) were dissolved in isopropanol (1 mL) and heated at 80° C. for 12 hours, when LCMS was performed. The product was purified by injection of the reaction mixture onto preparative RP-HPLC [Method 10].

LCMS: Column dimensions: 50 mm (long)×3 mm (i.d.), C-18 stationary phase, 5 micron particle size, 100 angstrom pore size. Mobile phases are 0.05% trifluoroacetic acid in water (solvent A), and 0.05% trifluoroacetic acid in acetonitrile (solvent B). The program gradient is 10% solvent B from 0 to 0.25 minutes, 10% to 90% solvent B from 0.25 to 9.50 minutes, then 90% solvent B from 9.50 to 10.25 minutes. Ret. time (min): 4.72; [M+H]=401.74.

EXAMPLE 300

Preparation of 4-[4-(3,5-DIFLUORO-PHENYL)-2-HYDROXY-BUTYLAMINO]-6-(2,2-DIMETHYL-PROPYL)-DIHYDRO-2H-QUINOLINE-1-CARBOXYLIC ACID BENZYL ESTER

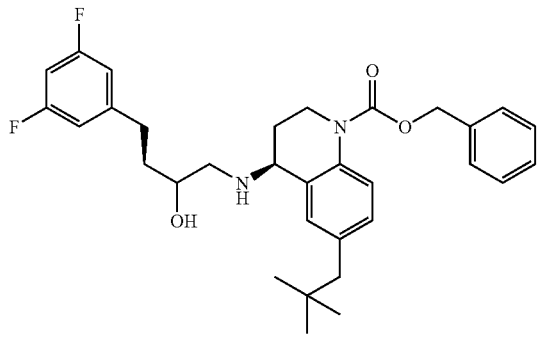

The title compound was prepared according to the procedure described in Example 299 from the amine prepared in EXAMPLE 383. LCMS ret. time (min): 5.17; [M+H]= 536.70.

EXAMPLE 301

Preparation of 1-[2-BROMO-5-(2,2-DIMETHYL-PROPYL)-BENZYLAMINO]-4-(3,5-DIFLUORO-PHENYL)-BUTAN-2-OL

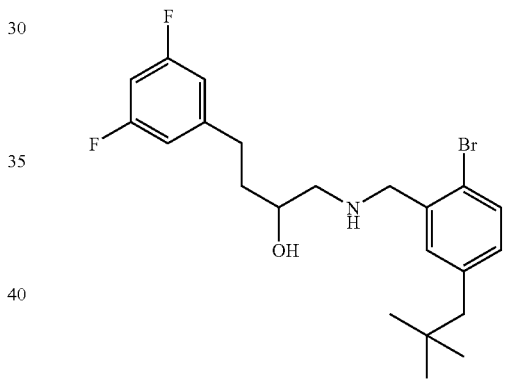

The title compound was prepared according to the procedure described in Example 299 from the amine prepared in Example 385. LCMS ret. time (min): 4.68; [M+H]=439.86.

EXAMPLE 302

Preparation of 4-(3,5-DIFLUORO-PHENYL)-1-[5-(2,2-DIMETHYL-PROPYL)-2-IMIDAZOL-1-YL-BENZYLAMINO]-BUTAN-2-OL

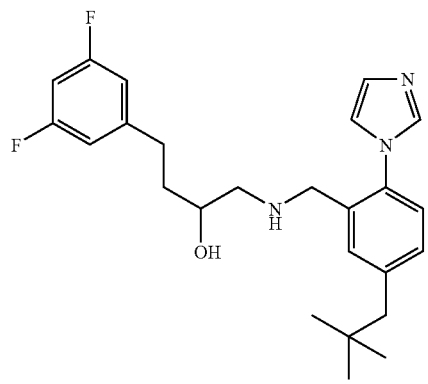

The title compound was prepared according to the procedure described in Example 299 from the amine prepared in EXAMPLE 369. LCMS ret. time (min): 3.20; [M+H]= 428.05.

EXAMPLE 303

4-(3,5-DIFLUORO-PHENYL)-1-[5-(2,2-DIMETHYL-PROPYL)-2-(4-HYDROXYMETHYL-IMIDAZOL-1-YL)-BENZYLAMINO]-BUTAN-2-OL

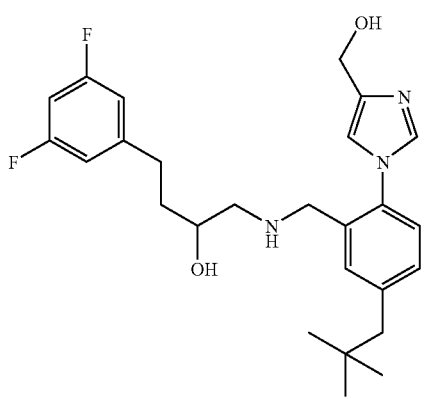

The title compound was prepared according to the procedure described in Example 299. LCMS ret. time (min): 3.27; [M+H]=457.95.

EXAMPLE 304

Representative Procedure for 4-HETEROARYL Compounds Made via Reductive Amination

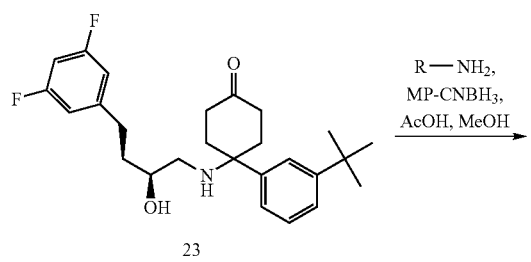

23

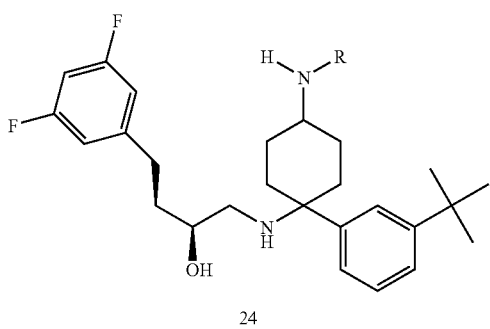

24

To 0.2 mmol of compound 23 in 1.5 mL of methanol is added 0.24 mmol of heteroaryl amine. The mixture is stirred for 15 minutes at room temperature. 0.15 mL of glacial acetic acid is then added to the reaction mixture. The mixture is stirred for an additional 30 minutes. 2.5 equivalents of Argonaut MP-Cyanoborohydride is then added to the reaction vial. Each reaction vial is placed on a J-Kem Orbit Shaker block. The reaction temperature is raised to 60° C. The reaction mixture is stirred for 60 h. The resins are filtered out of the reaction mixture. The reaction mixture is then concentrated and isolated via preparative HPLC utilizing a Varian ProStar Preparative HPLC system to leave compounds with general structure 24. LC/MS analysis is conducted utilizing method [1].

EXAMPLE 305

Representative Procedure for Preparation of Heteroaryl Analogs via Nucleophilic Displacement

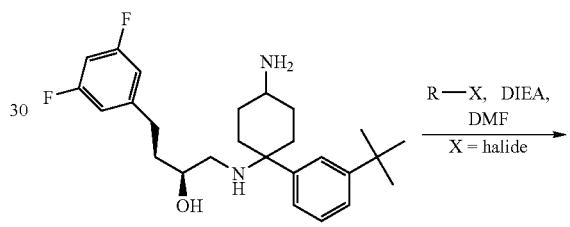

25

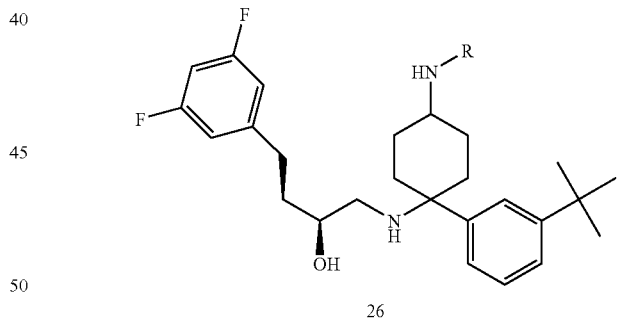

26

To 0.1 mmol of 1-[4-Amino-1-(3-tert-butyl-phenyl)-cyclohexylamino]-4-(3,5-difluoro-phenyl)-butan-2-ol (25) in 1 mL DMF is added 0.15 mmol of heteroaryl halide. 0.1 mL of diisopropylethylamine is added to each reaction vial. Each reaction vial is placed on a J-Kem Orbit Shaker block. The reaction temperature is then raised to 80° C. The reaction mixture is then stirred for 16 h. The reaction mixture is then concentrated and isolated via preparative HPLC utilizing a Varian ProStar Preparative HPLC system to leave compounds with general structure 26. LC/MS analysis is conducted utilizing method [1].

EXAMPLE 306

Preparation of 1-[1-(3-TERT-BUTYL-PHENYL)-4-(PYRIDIN-2-YLAMINO)-CYCLOHEXY-LAMINO]-4-(3,5-DIFLUORO-PHENYL)-BUTAN-2-OL

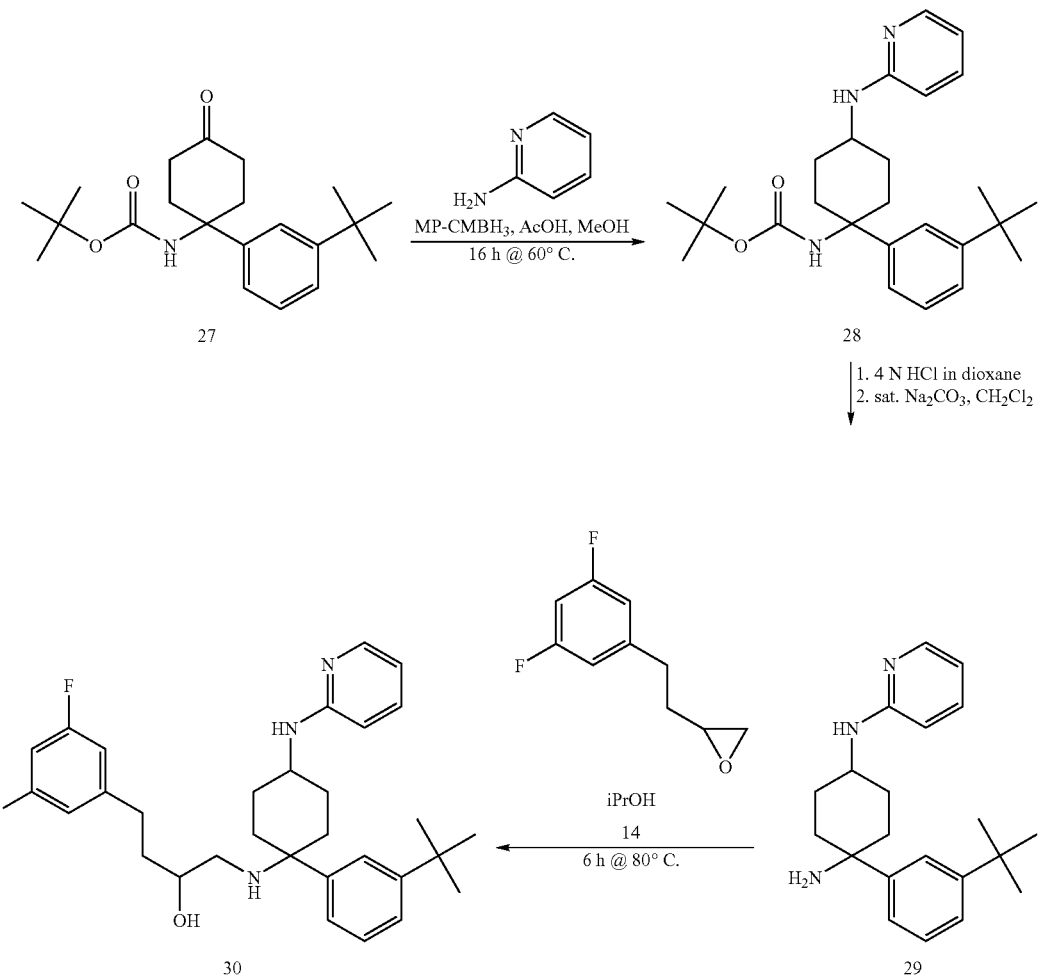

To 125 mgs (0.33 mmol) of [1-(3-tert-Butyl-phenyl)-4-oxo-cyclohexyl]-carbamic acid tert-butyl ester (27) in 1 mL methanol in a 4-mL reaction vial was added 0.4 mmol of 2-aminopyridine. 0.1 mL of glacial acetic acid was added to each reaction vial. 2.5 equivalents (0.825 mequivalents., 323 mgs) of MP-cyanoborohydride was then added to the reaction vial. The reaction mixture was stirred for 16 hours at 60° C. to yield [1-(3-tert-Butyl-phenyl)-4-(pyridin-2-ylamino)-cyclohexyl]-carbamic acid tert-butyl ester (28). 1.5 mL of 4 N HCl in dioxane was added to remove the BOC-group. The reaction mixture was stirred for 1 hour at room temperature to yield 1-(3-tert-Butyl-phenyl)-N'-pyridin-2-yl-cyclohexane-1,4-diamine (29).

To 0.25 mmol of 29 in 1 mL of isopropanol was added 1 eq (0,25 mmol) of 2-[2-(3,5-Difluoro-phenyl)-ethyl]-oxirane (14). The reaction mixture was then stirred for 6 hours at 80° C. to yield 1-[1-(3-tert-Butyl-phenyl)-4-(pyridin-2-ylamino)-cyclohexylamino]-4-(3,5-difluoro-phenyl)-butan-2-ol (30). Isolation of 30 was accomplished via preparative HPLC utilizing a Varian ProStar Preparative HPLC. LC/MS analysis is conducted utilizing method [1].

1-[1-(3-tert-Butyl-phenyl)-4-(pyridin-2-ylamino)-cyclohexylamino]-4-(3,5-difluoro-phenyl)-butan-2-ol. $^1$H NMR (CD$_3$OD) 8.07-7.80 (m, 1H), 7.79-7.64 (m, 1H), 7.64-7.42 (m, 3H), 7.35-7.14 (m, 1H), 6.94-6.65 (m, 3H), 3.95-3.76 (m, 1H), 3.70-3.48 (m, 1H), 2.91-2.76 (m, 2H), 2.76-2.61 (m, 2H), 2.52-2.34 (m, 2H), 2.25-2.07 (m, 1H), 2.07-1.89 (m, 2H), 1.89-1.70 (m, 2H), 1.70-1.52 (m, 2H). HPLC ret. time 1.662.

EXAMPLE 307

Preparation of 4-(6-TERT-BUTYL-1,1-DIOXO-1λ⁶-THIOCHROMAN-4-YLAMINO)-1-(3,5-DIFLUORO-PHENYL)-3-HYDROXY-BUTAN-1-ONE

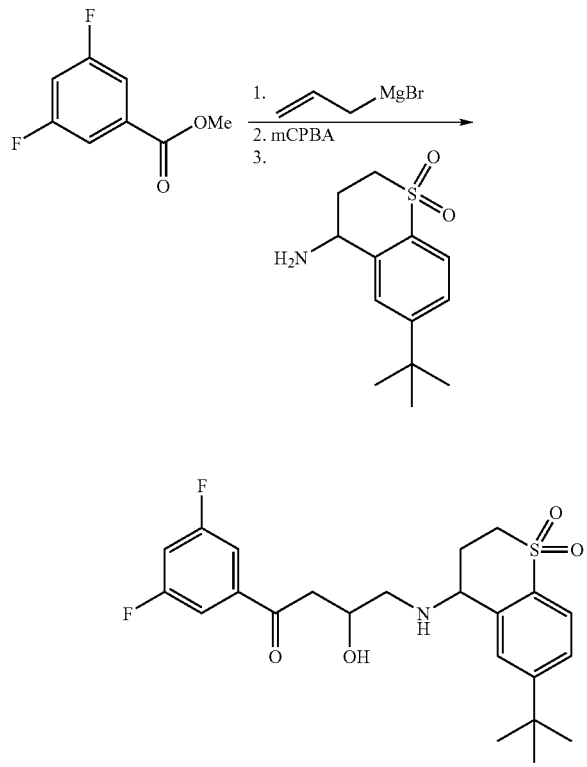

EXAMPLE 308

Preparation of 1-(6-TERT-BUTYL-2,2-DIOXO-2λ⁶-ISOTHIOCHROMAN-4-YLAMINO)-3-METHYL-4-PHENYL-BUTAN-2-OL

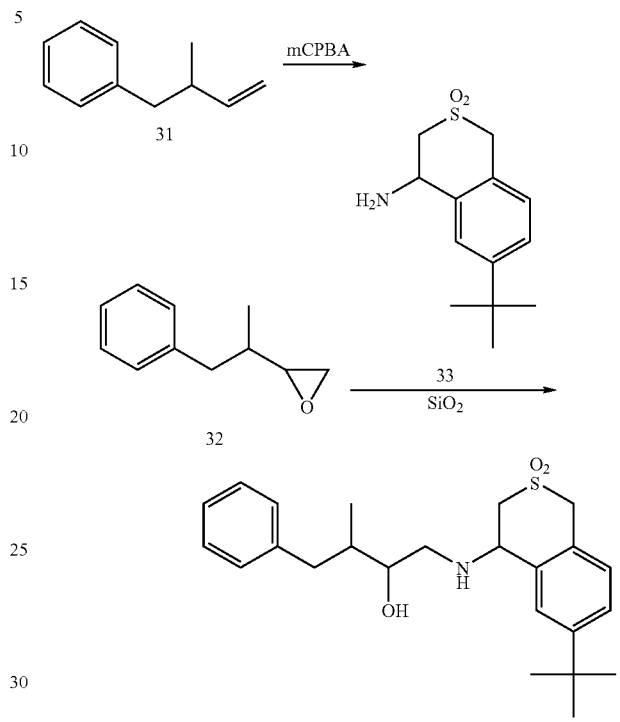

Epoxidation of olefin 31 with m-chloroperbenzoic acid gives epoxide 32. Nucleophilic opening of epoxide 32 with amine 33 affords 34.

EXAMPLE 309

Preparation of 4-(3,5-DIFLUORO-PHENYL)-1-(6-ISOBUTYL-1,1-DIOXO-1λ⁶-THIOCHROMAN-4-YLAMINO)-PENTAN-2-OL

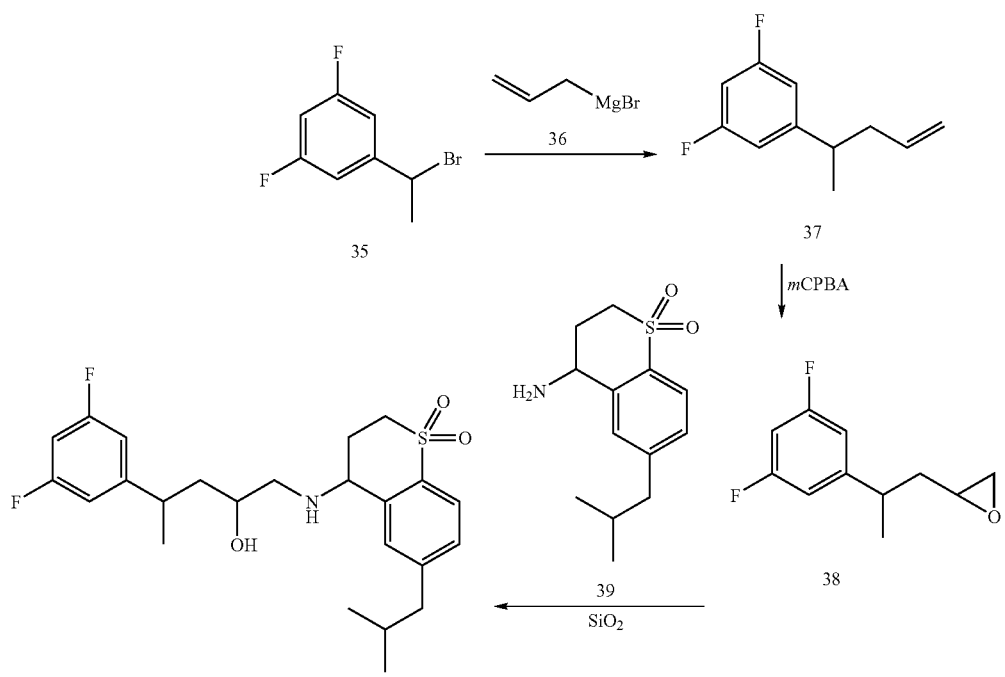

1-(1-Bromo-ethyl)-3,5-difluoro-benzene (35) is treated with allylmagnesium bromide (36) to give intermediate 37. Epoxidation of intermediate 37 with m-chloroperbenzoic acid affords epoxide 38. Nucleophilic opening of epoxide 38 with amine 39 affords 1-(6-tert-Butyl-1,1-dioxo-1$\lambda^6$-thio-chroman-4-ylamino)-4-(3,5-difluoro-phenyl)-pentan-2-ol (40).

Further examples of compounds that can be made according to the present invention are found in Example 310 below.

EXAMPLE 310

General Procedure for the Preparation of Compounds of Formula (I) via Nucleophilic Displacement

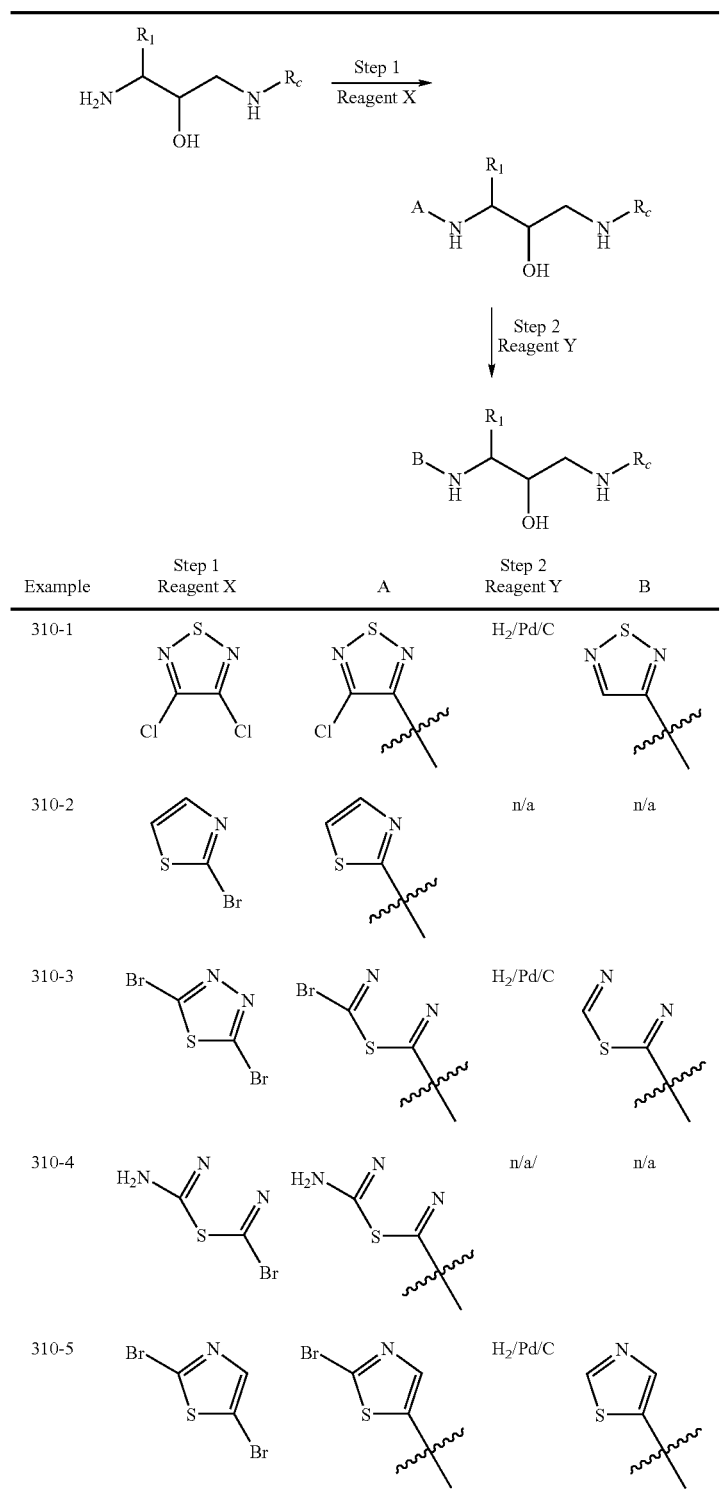

-continued

| | | | | |
|---|---|---|---|---|
| 310-6 | F₃C-C(=N)-S-C(=N)-Cl | F₃C-C(=N)-S-C(=N)- | n/a | n/a |
| 310-7 | HS-[1,3,4-oxadiazole]-CF₃ | F₃C-C(=N)-O-C(=N)- | n/a | n/a |
| 310-8 | H₂N-C(=N)-O-C(=N)-NO₂ | H₂N-C(=N)-O-C(=N)- | n/a | n/a |
| 310-9 | 1-trityl-3-iodo-1,2,4-triazole, I, cat. Cu | Ph₃C-N(H)-CH=N-C(=N)- | n/a | n/a |
| 310-10 | n/a | Ph₃C-N(H)-CH=N-C(=N)- | TFA | H-N=CH-N=C- |
| 310-11 | 2-chlorooxazole | 2-oxazolyl- | n/a | n/a |
| 310-12 | Ph₃C-NH-N=C(Br)-C(Br)=N | Ph₃C-NH-N=C(Br)-C(=N)- | H₂Pd/C | Ph₃C-NH-N=CH-C(=N)- |

-continued
| | | | | |
|---|---|---|---|---|
| 310-13 | n/a | 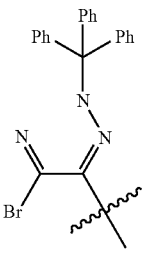 | TFA | 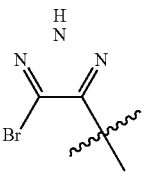 |
| 310-14 | n/a | 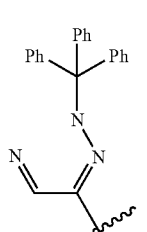 | TFA | 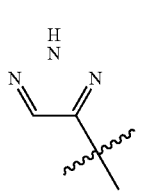 |
| 310-15 | 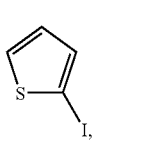, cat. Cu | 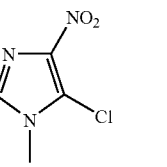 | n/a | n/a |
| 310-16 | 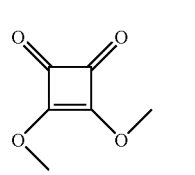 | 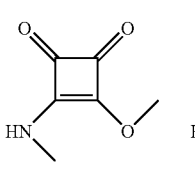 | n/a | n/a |
| 310-17 | 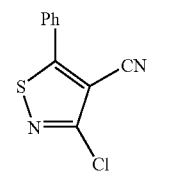 | 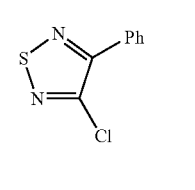 | n/a | n/a |
| 310-18 | | | n/a | n/a |
| 310-19 | | | n/a | n/a |
| 310-20 | | | n/a | n/a |

Representative Procedure for Nucleophilic Displacement

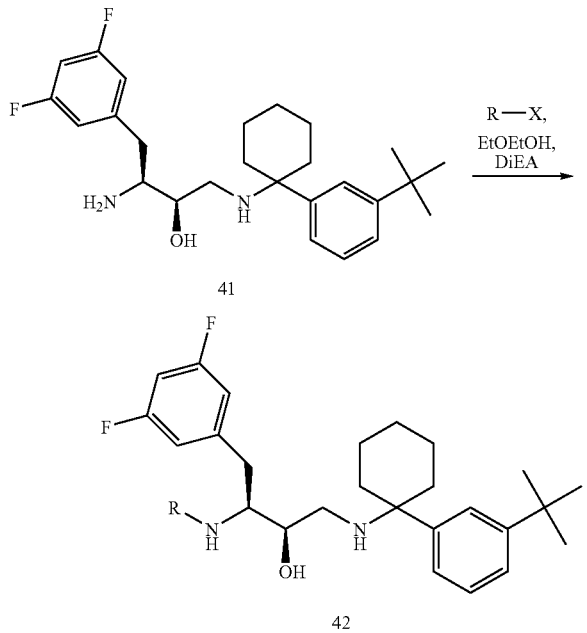

To 43 mgs (0.1 mmol) of 3-Amino-1-[1-(3-tert-butyl-phenyl)-cyclohexylamino]-4-(3,5-difluoro-phenyl)-butan-2-ol (41) in 1 mL of ethoxyethanol in a 4-mL reaction vial is added 0.4 mmol of diisopropylethylamine and 0.1 mmol of the halide. The reaction mixture is stirred for 18 hours at various temperatures (25-150° C.) to yield compounds of general structure 42. Isolation of final products is accomplished via preparative HPLC utilizing a Varian ProStar Preparative HPLC system. LC/MS analysis is conducted utilizing method (described below).

For compounds 3-(3-Bromo-[1,2,4]thiadiazol-5-ylamino)-4-(3,5-difluoro-phenyl)-1-(6-ethyl-2,2-dioxo-2l6-isothiochroman-4-ylamino)-butan-2-ol and 3-(3-Bromo-[1,2,4]thiadiazol-5-ylamino)-4-(3,5-difluoro-phenyl)-1-(7-ethyl-1,2,3,4-tetrahydro-naphthalen-1-ylamino)-butan-2-ol, 3-Amino-4-(3,5-difluoro-phenyl)-1-(6-ethyl-2,2-dioxo-2l6-isothiochroman-4-ylamino)-butan-2-ol and 3-Amino-4-(3,5-difluoro-phenyl)-1-(7-ethyl-1,2,3,4-tetrahydro-naphthalen-1-ylamino)-butan-2-ol are used as starting materials instead of 1.

LC/MS method Column dimensions: 50 mm (long)×2 mm (i.d.), C-18 stationary phase, 5 micron particle size, 100 angstrom pore size. Mobile phases: 0.05% trifluoroacetic acid in water (solvent A), 0.05% trifluoroacetic acid in acetonitrile (solvent B).

Chromatographic conditions: 3 mL/min., 5% to 95% solvent B from 0.00 to 2.40 minutes, 95% solvent B from 2.40 to 3.00 minutes, 95% to 5% solvent B from 3.00 to 3.10 minutes, 5% solvent B from 3.10 to 3.50 minutes.

The compounds in the chart below were made according to the procedure above.

| Compound | M + H | Ret. time |
| --- | --- | --- |
| 3-(3-Bromo-[1,2,4]thiadiazol-5-ylamino)-4-(3,5-difluoro-phenyl)-1-(6-ethyl-2,2-dioxo-2λ$^6$-isothiochroman-4-ylamino)-butan-2-ol | 588.7 | 1.55 |
| 3-(3-Bromo-[1,2,4]thiadiazol-5-ylamino)-4-(3,5-difluoro-phenyl)-1-(7-ethyl-1,2,3,4-tetrahydro-naphthalen-1-ylamino)-butan-2-ol | 538.6 | 1.67 |
| 3-(3-Bromo-[1,2,4]thiadiazol-5-ylamino)-1-[1-(3-tert-butyl-phenyl)-cyclohexylamino]-4-(3,5-difluoro-phenyl)-butan-2-ol | 593.6 | 1.98 |
| 1-[1-(3-tert-Butyl-phenyl)-cyclohexylamino]-4-(3,5-difluoro-phenyl)-3-([1,2,4]thiadiazol-5-ylamino)-butan-2-ol | 514.8 | 1.89 |
| 3-[3-[1-(3-tert-Butyl-phenyl)-cyclohexylamino]-1-(3,5-difluoro-benzyl)-2-hydroxy-propylamino]-4-methoxy-cyclobut-3-ene-1,2-dione | 540.7 | 1.84 |
| 1-[1-(3-tert-Butyl-phenyl)-cyclohexylamino]-4-(3,5-difluoro-phenyl)-3-(3-nitro-thiophen-2-ylamino)-butan-2-ol | 559.8 | 2.81 |
| 1-[1-(3-tert-Butyl-phenyl)-cyclohexylamino]-4-(3,5-difluoro-phenyl)-3-(2,5-dimethyl-4-nitro-2H-pyrazol-3-ylamino)-butan-2-ol | 571.8 | 2.79 |
| 1-[1-(3-tert-Butyl-phenyl)-cyclohexylamino]-4-(3,5-difluoro-phenyl)-3-(3-methyl-5-nitro-3H-imidazol-4-ylamino)-butan-2-ol | 557.7 | 2.76 |
| 3-(Benzo[4,5]thieno[3,2-d]pyrimidin-4-ylamino)-1-[1-(3-tert-butyl-phenyl)-cyclohexylamino]-4-(3,5-difluoro-phenyl)-butan-2-ol | 614.9 | 2.64 |
| 5-[3-[1-(3-tert-Butyl-phenyl)-cyclohexylamino]-1-(3,5-difluoro-benzyl)-2-hydroxy-propylamino]-4-chloro-isothiazole-3-carboxylic acid methyl ester | 606.8 | 2.15 |
| 1-[1-(3-tert-Butyl-phenyl)-cyclohexylamino]-4-(3,5-difluoro-phenyl)-3-(2-fluoro-4-trifluoromethyl-thiazol-5-ylamino)-butan-2-ol | 600.9 | 2.21 |
| 1-[1-(3-tert-Butyl-phenyl)-cyclohexylamino]-4-(3,5-difluoro-phenyl)-3-(5-pyridin-4-yl-[1,3,4]oxadiazol-2-ylamino)-butan-2-ol | 575.2 | 2.59 |
| 3-(5-Amino-[1,3,4]thiadiazol-2-ylamino)-1-[1-(3-tert-butyl-phenyl)-cyclohexylamino]-4-(3,5-difluoro-phenyl)-butan-2-ol | 529.8 | 1.71 |
| 1-[1-(3-tert-Butyl-phenyl)-cyclohexylamino]-4-(3,5-difluoro-phenyl)-3-(1-phenyl-1H-tetrazol-5-ylamino)-butan-2-ol | 574.8 | 2.83 |

-continued

| Compound | M + H | Ret. time |
|---|---|---|
| 3-[3-[1-(3-tert-Butyl-phenyl)-cyclohexylamino]-1-(3,5-difluoro-benzyl)-2-hydroxy-propylamino]-5-iodo-1-methyl-1H-pyridin-4-one | 663.8 | 1.73 |
| 3-[3-[1-(3-tert-Butyl-phenyl)-cyclohexylamino]-1-(3,5-difluoro-benzyl)-2-hydroxy-propylamino]-5-iodo-pyridin-4-ol | 649.8 | 1.74 |
| 1-[1-(3-tert-Butyl-phenyl)-cyclohexylamino]-4-(3,5-difluoro-phenyl)-3-(5-methyl-[1,3,4]oxadiazol-2-ylamino)-butan-2-ol | 512.9 | 2.02 |
| 1-[1-(3-tert-Butyl-phenyl)-cyclohexylamino]-4-(3,5-difluoro-phenyl)-3-(5-phenyl-[1,3,4]oxadiazol-2-ylamino)-butan-2-ol | 574.9 | 2.17 |

EXAMPLE 311

Preparation of 4-(3,5-DIFLUORO-PHENYL)-1-(6-ETHYL-2,2-DIOXO-2λ⁶-ISOTHIOCHROMAN-4-YLAMINO)-3-([1,2,4]THIADIAZOL-5-YLAMINO)-BUTAN-2-OL.

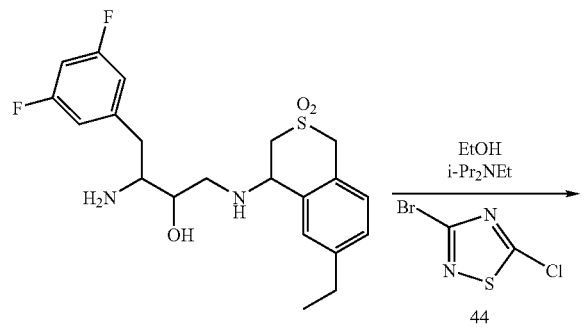

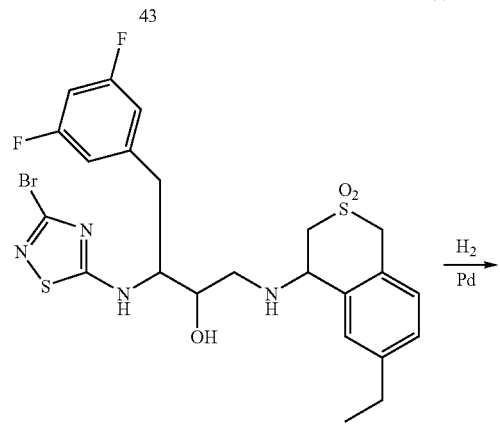

Combined 3-Amino-4-(3,5)-difluoro-phenyl)-1-(6)-ethyl-2,2-dioxo-2+²-isothiochroman-4-ylamino)-butan-2-ol (43) (0.1 mmol) with diisopropylamine (0.4 mmol) in ethanol. 3-bromo-5-chloro-[1,2,4]-thiadiazole (44) (0.1 mmol) was added. The reaction mixture was allowed to stir at room temperature for 16 hours. Purification of the resulting reaction mixture by HPLC afforded 3-(3-Bromo-[1,2,4]thiadiazol-5-ylamino)-4-(3,5-difluoro-phenyl)-1-(6-ethyl-2,2-dioxo-2α⁶-isothiochroman-4-ylamino)-butan-2-ol (45), m/z=586.8. 45 was added to methanol, followed by the addition of a catalytic amount of Pd on carbon, and subjected to 50 psi of H₂, affording 4-(3,5-Difluoro-phenyl)-1-(6-ethyl-2,2-dioxo-2λ⁶-isothiochroman-4-ylamino)-3-([1,2,4]thiadiozol-5-ylamino)-butan-2-ol (46), m/z=508.9.

Synthetic Procedures for Examples 312, 314-317, AND 319-323

General Procedure A

The amine (1 mmol) and 2,4-dichloropyrimidine (1.5 mmol) were dissolved in DMF (2 mL). DIPEA (5 mmol) was added and the resulting mixture was stirred at 90° C. for 20 h under an atmosphere of N₂. The solution was cooled to room temperature and diluted with Et₂O (10 mL). The solution was washed with brine (2×5 mL), dried over Na₂SO₄, filtered and concentrated under vacuum.

General Procedure B

The amine (1 mmol), 1-methyl-4-iodopyrazole (1 mmol), CuI (0.05 mmol) and KOH (4 mmol) were placed in a vial. The vial was evacuated and purged with N₂ three times. DMSO/H₂O (2 mL, 1/1, v/v) was added and the resulting mixture was stirred at 90° C. for 20 h under an atmosphere of N₂. The solution was cooled to room temperature, diluted with CH₂Cl₂ (10 mL) and washed with H₂O (5 mL). The organic layer was dried over Na₂SO₄, filtered and concentrated under vacuum.

General Procedure C

The amine (1 mmol), 2-(3-iodo-phenyl)-N,N-dipropyl-acetamide (1 mmol), CuI (0.05 mmol) and KOH (4 mmol) were placed in a vial. The vial was evacuated and purged with N₂ three times. DMSO/H₂O (2 mL, 1/1, v/v) was added and the resulting mixture was stirred at 90° C. for 20 h under an atmosphere of N₂. The solution was cooled to room temperature, diluted with CH₂Cl₂ (10 mL) and washed with H₂O (5 mL). The organic layer was dried over Na₂SO₄, filtered and concentrated under vacuum.

EXAMPLE 312

Preparation of 1-[1-(3-TERT-BUTYL-PHENYL)-CYCLOHEXYLAMINO]-3-(2-CHLORO-PYRIMIDIN-4-YLAMINO)-4-(3,5-DIFLUORO-PHENYL)-BUTAN-2-OL

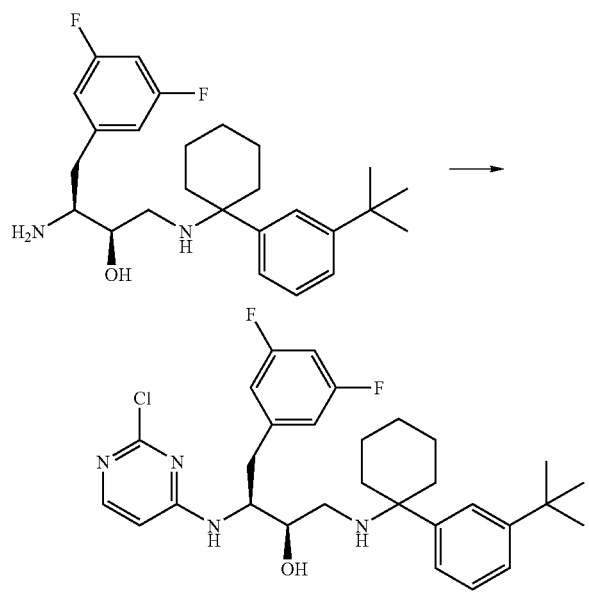

Following procedure A, 3-Amino-1-[1-(3-tert-butyl-phenyl)-cyclohexylamino]-4-(3,5-difluoro-phenyl)-butan-2-ol was converted to 1-[1-(3-tert-Butyl-phenyl)-cyclohexylamino]-3-(2-chloro-pyrimidin-4-ylamino)-4-(3,5-difluoro-phenyl)-butan-2-ol which was purified using flash chromatography ($CH_2Cl_2/CH_3OH/NH_4OH$, 98/2/0.2) and HPLC.

Retention time (min)=2.18, method [1], MS(ESI) 543.4 (M+H); $^1$H NMR (300 MHz, $CDCl_3$) δ7.94 (d, J=5.9 Hz, 1 H), 7.45 (s, 1 H), 7.20-7.11 (m, 5 H), 6.75-6.55 (m, 3 H), 6.12 (bs, 1 H), 5.32 (bs, 1 H), 4.42 (bs, 1 H), 3.41-3.32 (m, 1 H), 2.85-2.71 (m, 2 H), 2.45-2.21 (m, 2 H), 2.05-1.83 (m, 4 H), 1.77-1.50 (m, 5 H), 1.34 (s, 9 H); $^{13}$C NMR (75 MHz, $CDCl_3$) δ150.9, 127,8, 123.5, 123.3, 123.2, 112.5, 112.0, 101.6, 77.1, 57.3, 42.9, 36.3, 36.2, 35.9, 34.6, 31.3, 25.6, 22.2

EXAMPLE 313

Preparation of 1-[1-(3-TERT-BUTYL-PHENYL)-CYCLOHEXYLAMINO]-4-(3,5-DIFLUORO-PHENYL)-3-(PYRIMIDIN-4-YLAMINO)-BUTAN-2-OL

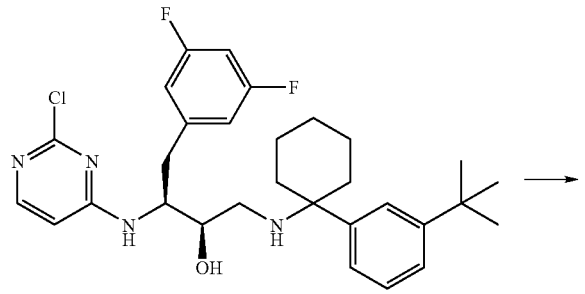

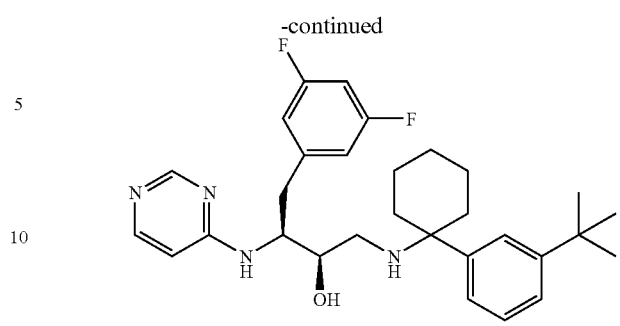

1-[1-(3-tert-Butyl-phenyl)-cyclohexylamino]-3-(2-chloro-pyrimidin-4-ylamino)-4-(3,5-difluoro-phenyl)-butan-2-ol (101 mg, 0.186 mmol) was dissolved in EtOAc (1 mL) containing Pd/C (20 mg) and triethylamine (38 μL, 0.279 mmol). The mixture was shaken under a 45 psi hydrogen atmosphere for 40 hours. The mixture was filtered through a pad of Celite and concentrated to give 1-[1-(3-tert-Butyl-phenyl)-cyclohexylamino]-4-(3,5-difluoro-phenyl)-3-(pyrimidin-4-ylamino)-butan-2-ol which was purified using flash chromatography ($CH_2Cl_2/CH_3OH/NH_4OH$, 99/1/0.1) and HPLC.

Retention time (min)=1.68, method [1], MS(ESI) 509.5 (M+H); $^1$H NMR (300 MHz, $CDCl_3$) δ8.33 (s, 1 H), 7.81 (d, J=5.2 Hz, 1 H), 7.62 (s, 1 H). 7.45-7.29 (m, 2 H), 7.29-7.20 (m, 1 H), 6.65-6.53 (m, 3 H), 4.45 (bs, 1 H), 4.09 (bs, 1 H), 2.81-2.79 (m, 2 H), 2.70-2.61 (m, 4 H), 2.13-2.03 (m, 4 H), 1.80-1.59 (m, 4 H), 1.35 (s, 9 H).

EXAMPLE 314

Preparation of 4-(3,5-DIFLUORO-PHENYL)-1-(7-ETHYL-1,2,3,4-TETRAHYDRO-NAPHTHALEN-1-YLAMINO)-3-(1-METHYL-1H-PYRAZOL-4-YLAMINO)-BUTAN-2-OL

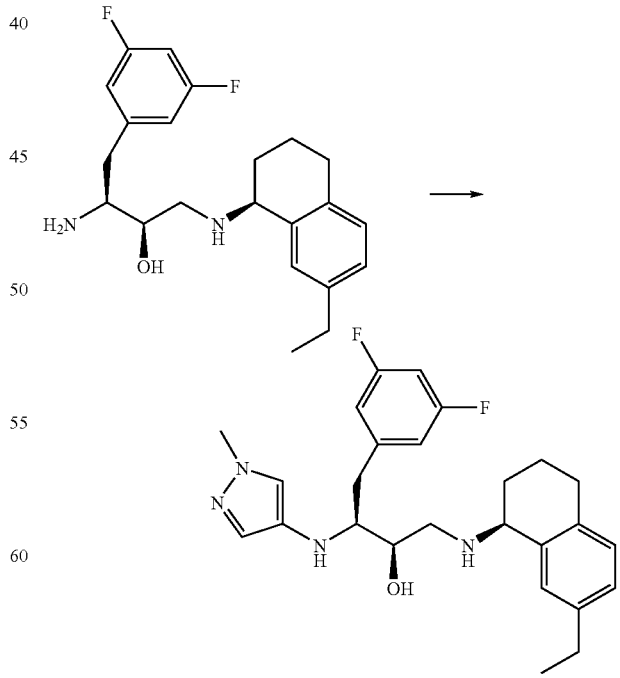

Following procedure B, 3-Amino-4-(3,5-difluoro-phenyl)-1-(7-ethyl-1,2,3,4-tetrahydro-naphthalen-1-ylamino)- butan-2-ol was converted to 4-(3,5-Difluoro-phenyl)-1-(7-ethyl-1,2,3,4-tetrahydro-naphthalen-1-ylamino)-3-(1-methyl-1H-pyrazol-4-ylamino)-butan-2-ol which was purified using flash chromatography (CH$_2$Cl$_2$/CH$_3$OH/NH$_4$OH, 98/2/0.2) and HPLC.

Retention time (min)=1.64, method [1], MS(ESI) 455.4 (M+H); $^1$H NMR (300 MHz, CDCl$_3$) δ7.30-6.95 (m, 5 H), 6.60-6.51 (m, 1 H), 6.50-6.42 (m, 2 H), 4.51-4.29 (m, 2 H), 3.85 (s, 3 H), 3.45-3.30 (m, 1 H), 3.08-2.91 (m, 2 H), 2.84 (dd, J=14.4, 5.1 Hz, 1 H), 2.71-2.65 (m, 3 H), 2.55 (q, J=7.5 Hz, 2 H), 2.15-1.70 (m, 4 H), 1.18 (t, J=7.5 Hz, 3H); $^{13}$C NMR (75 MHz, CDCl$_3$) δ 142.9, 140.6, 135.4, 131.0, 129.7, 128.9, 128.2, 127.9, 111.9, 102.5 (t, J=25 Hz, 1C), 77.1, 66.7, 63.7, 55.7, 74.3, 39.2, 32.6, 28.1, 27.9, 25.1, 18.7, 15.2.

EXAMPLE 315

Preparation of 4-(3,5-DIFLUORO-PHENYL)-1-[1-(3-ETHYL-PHENYL)-CYCLOPROPYLAMINO]-3-(1-METHYL-1H-PYRAZOL-4-YLAMINO)-BUTAN-2-OL

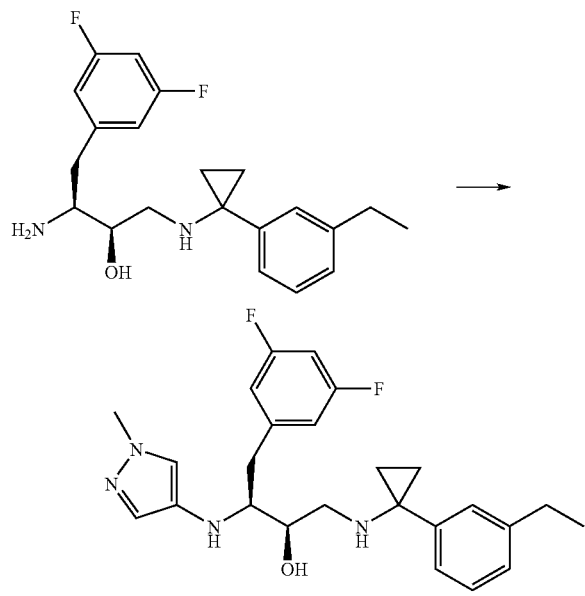

Following procedure B, 3-Amino-4-(3,5-difluoro-phenyl)-1-[1-(3-ethyl-phenyl)-cyclopropylamino]-butan-2-ol was converted to 4-(3,5-Difluoro-phenyl)-1-[1-(3-ethyl-phenyl)-cyclopropylamino]-3-(1-methyl-1H-pyrazol-4-ylamino)-butan-2-ol which was purified using flash chromatography (CH$_2$Cl$_2$/CH$_3$OH/NH$_4$OH, 98/2/0.2) and HPLC.

Retention time (min)=1.57, method [1], MS(ESI) 441.4 (M+H); $^1$H NMR (300 MHz, CDCl$_3$) δ7.30-7.05 (m, 6 H), 6.71-6.41 (m, 3 H), 4.10-4.01 (m, 1 H), 3.82 (s, 3 H), 3.32-3.20 (m, 1 H), 3.10-2.75 (m, 4 H), 2.67 (q, 7.5 Hz, 2 H), 1.53 (bs, 2 H), 1.23 (t, J=7.5 Hz, 3 H), 1.20-1.09 (m, 2 H); $^{13}$C NMR (75 MHz, CDCl$_3$) δ 145.5, 140.7, 140.6, 133.6, 130.6, 129.3, 129.0, 127.0, 120.9, 118.1, 114.3, 112.1, 111.9, 102.2 (t, J=25 Hz, 1C), 77.1, 66.9, 62.9, 49.3, 44.1, 39.1, 33.4, 28.6, 15.1, 11.5, 10.8.

EXAMPLE 316

Preparation of 4-(3,5-DIFLUORO-PHENYL)-1-(3-ETHYL-BENZYLAMINO)-3-(1-METHYL-1H-PYRAZOL-4-YLAMINO)-BUTAN-2-OL from 3-AMINO-4-(3,5-DIFLUORO-PHENYL)-1-(3-ETHYL-BENZYLAMINO)-BUTAN-2-OL

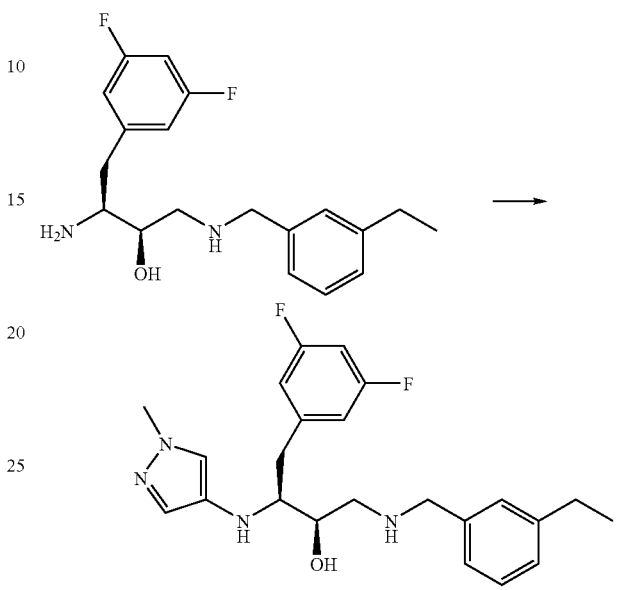

Following procedure B, 3-Amino-4-(3,5-difluoro-phenyl)-1-(3-ethyl-benzylamino)-butan-2-ol was converted to 4-(3,5-Difluoro-phenyl)-1-(3-ethyl-benzylamino)-3-(1-methyl-1H-pyrazol-4-ylamino)-butan-2-ol which was purified using flash chromatography (CH$_2$Cl$_2$/CH$_3$OH/NH$_4$OH, 98/2/0.2) and HPLC.

Retention time (min)=1.46, method [1], MS(ESI) 415.4 (M+H); $^1$H NMR (300 MHz, CDCl$_3$) δ7.30-6.85 (m, 6 H), 6.69-6.51 (m, 3 H), 4.10-3.87 (m, 3 H), 3.72 (s, 3 H), 3.30-3.05 (m, 2 H), 2.95-2.68 (m, 3 H), 2.56 (q, J=7.5 Hz, 2 H), 1.20 (t, J=7.5 Hz, 3 H); $^{13}$C NMR (75 MHz, CDCl$_3$) δ 145.5, 129.9, 129.7, 129.2, 129.2, 129.1, 126.8, 119.1, 112.2, 111.8, 102.4 (t, J=25 Hz, 1C), 77.1, 67.2, 61.8, 51.5, 50.1. 38.9, 34.4, 28.3, 15.1.

EXAMPLE 317

Preparation of 4-(3,5-DIFLUORO-PHENYL)-1-[6-(2,2-DIMETHYL-PROPYL)-CHROMAN-4-YLAMINO]-3-(1-METHYL-1H-PYRAZOL-4-YLAMINO)-BUTAN-2-OL

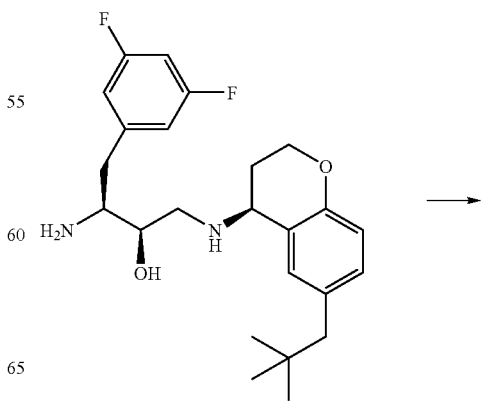

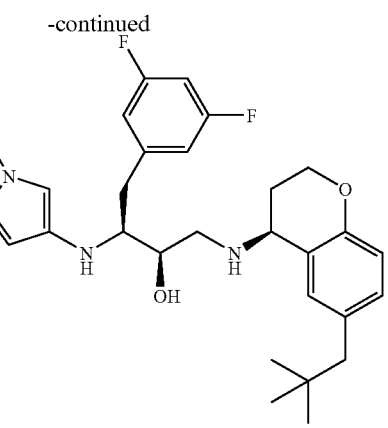

Following procedure B, 3-amino-4-(3,5-difluoro-phenyl)-1-[6-(2,2-dimethyl-propyl)-chroman-4-ylamino]-butan-2-ol was converted to 4-(3,5-Difluoro-phenyl)-1-[6-(2,2-dimethyl-propyl)-chroman-4-ylamino]-3-(1-methyl-1H-pyrazol-4-ylamino)-butan-2-ol which was purified using flash chromatography (CH$_2$Cl$_2$/CH$_3$OH/NH$_4$OH, 99/1/0.1) and HPLC.

Retention time (min)=1.84, method [1], MS(ESI) 499.5 (M+H); $^1$H NMR (300 MHz, CDCl$_3$) δ7.32-7.15 (m, 2 H), 7.10-7.01 (m, 2 H), 6.75 (d, J=8.3 Hz, 1 H), 6.65 (t, J=8.9 Hz, 1 H), 6.54 (d, J=5.9 Hz, 2 H), 4.45-4.30 (m 2 H), 4.18-4.08 (m, 2 H), 3.84 (s, 3 H), 3.43 (bs, 1 H), 3.08-2.85 (m, 2 H), 2.85 (dd, J=14.2, 5.3, 1 H), 2.71 (dd, J=9.2, 5.3, 1 H), 2.46-2.10 (m, 4 H), 1.27 (s, 9 H); $^{13}$C NMR (75 MHz, CDCl$_3$) δ 153.5, 133.3, 130.7, 117.2, 113.4, 112.1, 111.8, 102.5, 77.3, 66.8, 63.0, 61.5, 51.6, 48.8, 47.9, 39.0, 33.3, 31.5, 29.6, 28.9, 24.6.

EXAMPLE 318

Preparation of 1-[1-(3-TERT-BUTYL-PHENYL)-CYCLOHEXYLAMINO]-3-(2-DIETHYLAMINO-PYRIMIDIN-4-YLAMINO)-4-(3,5-DIFLUORO-PHENYL)-BUTAN-2-OL

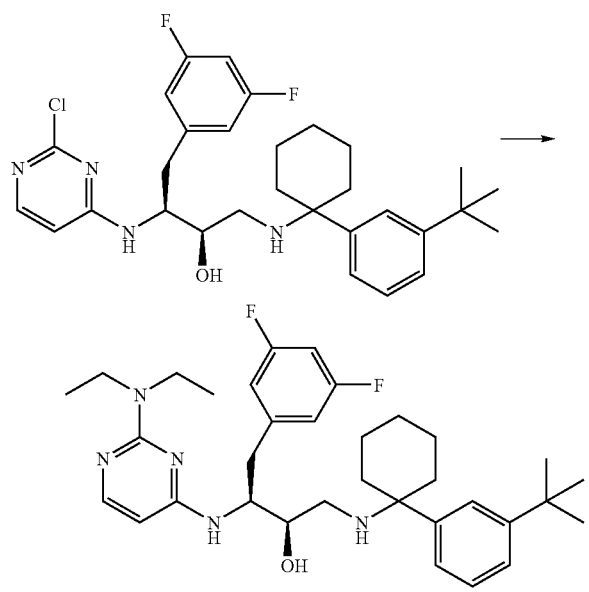

1-[1-(3-tert-Butyl-phenyl)-cyclohexylamino]-3-(2-diethylamino-pyrimidin-4-ylamino)-4-(3,5-difluorophenyl)-butan-2-ol from 1-[1-(3-tert-Butyl-phenyl)-cyclohexylamino]-3-(2-chloro-pyrimidin-4-ylamino)-4-(3,5-difluoro-phenyl)-butan-2-ol (78 mg, 0.144 mmol) was dissolved in DMF (0.5 mL) containing diethylamine (74 µL, 0.718 mmol) and potassium carbonate (100 mg, 0.718 mmol). The reaction mixture was heated in a seated tube at 90° C. for 48 h. The resulting solution was diluted with Et$_2$O (10 mL), washed with brine (3×5 mL), dried over Na$_2$SO$_4$ and purified using flash chromatography (CH$_2$Cl$_2$/CH$_3$OH/NH$_4$OH, 98/2/0.2) and HPLC to give 1-[1-(3-tert-Butyl-phenyl)-cyclohexylamino]-3-(2-diethylamino-pyrimidin-4-ylamino)-4-(3,5-difluoro-phenyl)-butan-2-ol.

Retention time (min)=1.85, method [1], MS(ESI) 580.6 (M+H); $^1$H NMR (300 MHz, CDCl$_3$) δ9.99 (bs, 1 H), 8.56 (d, J=8.2 Hz, 1 H), 8.13 (bs, 1 H), 7.67 (s, 1 H), 4.43-7.25 (m, 3 H), 7.11 (d, J=6.9 Hz, 1 H), 6.65-6.50 (m, 3 H), 5.95 (d, J=7.2 Hz, 1 H), 4.30-4.15 (m, 2 H), 3.59-3.30 (m, 5 H), 2.89-2.48 (m, 7 H), 2.18-1.99 (m, 4 H), 1.85-4.52 (m, 2 H), 1.35 (s, 9 H), 1.15 (bs, 6 H); $^{13}$C NMR (75 MHz, CDCl$_3$) δ 152.5, 151.6, 141.6, 139.8, 133.9, 128.6, 125.8, 124.8, 124.7, 111.5 (d, J=24 Hz), 101.6 (t, J=24 Hz), 97.7, 77.1, 67.9, 64.1, 54.5, 45.1, 42.6, 34.7, 34.6, 32.9, 31.0, 24.8, 21.9, 12.3.

EXAMPLE 319

Preparation of 2-(3-{1-(3,5-DIFLUORO-BENZYL)-3-[1-(3-ETHYL-PHENYL)-CYCLOPROPYLAMINO]-2-HYDROXY-PROPYLAMINO}-PHENYL)-N,N-DIPROPYL-ACETAMIDE

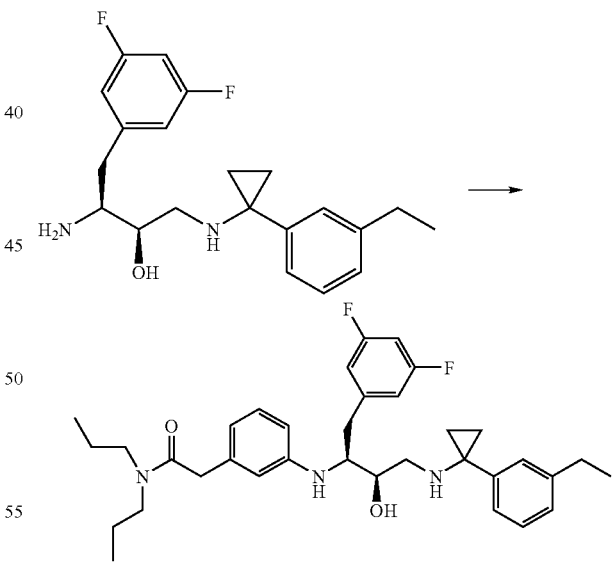

Following procedure C, 3-Amino-4-(3,5-difluoro-phenyl)-1-[1-(3-ethyl-phenyl)-cyclopropylamino]-butan-2-ol was converted to 2-(3-{1-(3,5-Difluoro-benzyl)-3-[1-(3-ethyl-phenyl)-cyclopropylamino]-2-hydroxy-propylamino}-phenyl)-N,N-dipropyl-acetamide which was purified using flash chromatography (CH$_2$Cl$_2$/CH$_3$OH/NH$_4$OH, 99/1/0.1) and HPLC.

2-(3-{1-(3,5-Difluoro-benzyl)-3-[1-(3-ethyl-phenyl)-cyclopropylamino]-2-hydroxy-propylamino}-phenyl)-N,N- dipropyl-acetamide retention time (min)=2.13, method [1], MS(ESI) 578.3 (M+H); $^1$H NMR (300 MHz, CD$_3$OD) δ7.22-6.98 (m, 5 H), 6.80-6.60 (m, 3 H), 6.48-6.32 (m, 3 H), 3.65-3.45 (m, 3 H), 3.29-3.15 (m, 3 H), 3.04 (dd, J=13.7, 3.6, 1 H), 2.87-2.54 (m, 5 H), 1.62-1.39 (m, 4 H), 1.18 (t, J=13.7 Hz, 3 H), 0.99-0.78 (m, 10 H); $^{13}$C NMR (75 MHz, CD$_3$OD) δ 172.1, 148.2, 143.9, 143.8, 143.7, 143.6, 142.3, 135.7, 128.9, 127.7, 126.8, 125.5, 124.7, 116.0, 112.1, 1211.9, 111.8, 111.7, 110.8, 100.4 (t, J=24 Hz), 72.0, 56.8, 49.7, 49.3, 46.5, 41.8, 40.6, 35.8, 28.2, 21.3, 20.1, 14.7, 14.1, 13.3, 10.1, 9.8.

EXAMPLE 320

Preparation of 2-{3-[1-(3,5-DIFLUORO-BENZYL)-3-(3-ETHYL-BENZYLAMINO)-2-HYDROXY-PROPYLAMINO]-PHENYL}-N,N-DIPROPYL-ACETAMIDE

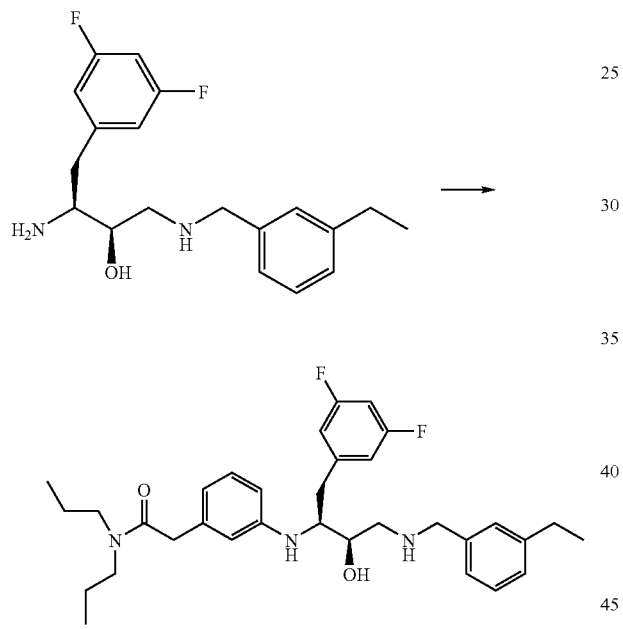

Following procedure C, 3-Amino-4-(3,5-difluoro-phenyl)-1-(3-ethyl-benzylamino)-butan-2-ol was converted to 2-{3-[1-(3,5-Difluoro-benzyl)-3-(3-ethyl-benzylamino)-2-hydroxy-propylamino]-phenyl}-N,N-dipropyl-acetamide which was purified using flash chromatography (CH$_2$Cl$_2$/CH$_3$OH/NH$_4$OH, 99/1/0.1) and HPLC.

Retention time (min)=2.03 min, method [1], MS(ESI) 552.3 (M+H); $^1$H NMR (300 MHz, CD$_3$OD) δ7.36-7.18 (m, 4 H), 6.98 (t, J=7.6 Hz, 1 H), 6.81 (d, 6.4 Hz, 2 H), 6.71-6.62 (m, 1 H), 6.49-6.43 (m, 3 H), 4.18 (s, 2 H), 3.89-3.75 (m, 1 H), 3.70-3.61 (m 1 H), 3.58 (s, 2 H), 3.30-3.08 (m, 6 H), 3.01 (dd, J=14.2, 12.4, 1 H), 2.75 (dd, J=8.8, 13.7 Hz, 1 H), 2.71-2.62 (m, 2 H), 1.60-1.41 (m, 4 H), 1.22 (t, J=7.6 Hz, 3 H), 0.92-0.75 (m, 6 H); $^{13}$C NMR (75 MHz, CD$_3$OD) δ 171.9, 147.7, 145.1, 143.0, 142.9, 142.8, 135.9, 130.6, 129.0, 128.7, 128.6, 126.8, 116.8, 112.7, 112.0, 111.7, 111.1, 100.7 (t, J=24 Hz), 69.0, 57.1, 50.6, 48.0, 40.4, 35,9, 28.1, 21.4, 20.2, 14.5, 10.1, 9.8.

EXAMPLE 321

Preparation of 3-(2-CHLORO-PYRIMIDIN-4-YLAMINO)-4-(3,5-DIFLUORO-PHENYL)-1-[6-(2,2-DIMETHYL-PROPYL)-CHROMAN-4-YLAMINO]-BUTAN-2-OL

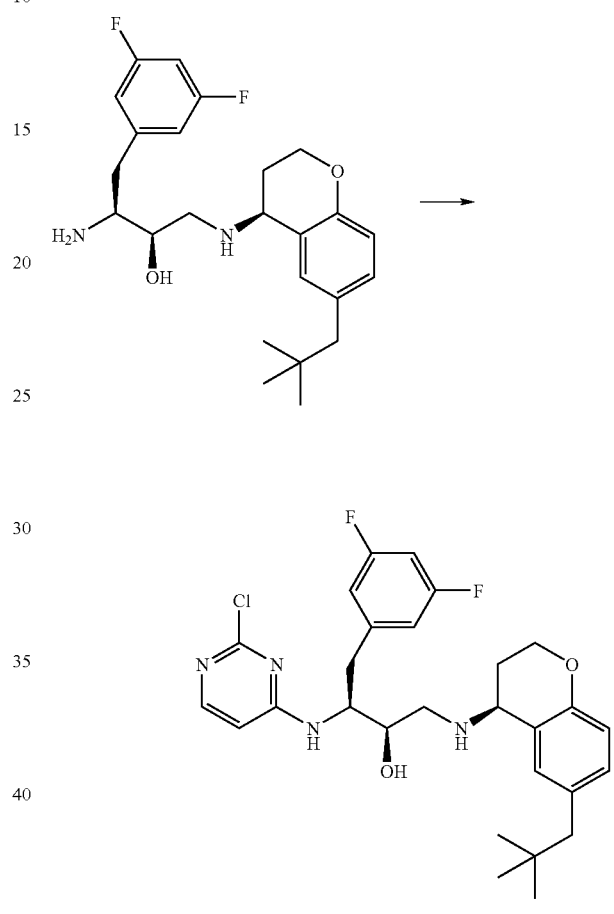

Following procedure A, 3-Amino-4-(3,5-difluoro-phenyl)-1-[6-(2,2-dimethyl-propyl)-chroman-4-ylamino]-butan-2-ol was converted to 3-(2-Chloro-pyrimidin-4-ylamino)-4-(3,5-difluoro-phenyl)-1-[6-(2,2-dimethyl-propyl)-chroman-4-ylamino]-butan-2-ol which was purified using flash chromatography (CH$_2$Cl$_2$/CH$_3$OH/NH$_4$OH, 98/2/0.2) and HPLC.

Retention time (min)=1.90, method [1], MS(ESI) 531.2 (M+H); $^1$H NMR (300 MHz, CO$_3$OD) δ7.82 (d, J=6.1 Hz, 1 H), 7.12-7.08 (m, 2 H), 6.89-6.68 (m, 4 H), 6.37 (d, J=6.1 Hz, 1 H), 4.62-4.58 (m, 1 H), 4.49-4.41 (bs, 1 H), 4.30-4.25 (m, 2 H), 3.97 (dd, J=6.0, 7.3 Hz, 1 H), 3.39-3.12 (m, 3 H), 2.75 (dd, J=13.7, 11.3 Hz, 1 H), 2.41-2.35 (m, 4 H), 0.91 (s, 9 H); $^{13}$C NMR (75 MHz, CD$_3$OD) δ 154.8, 153.6, 142.3, 132.9, 131.9, 130.7, 116.6, 114.3, 111.7, 111.4, 101.5, 100.8 (t, J=24 Hz), 68.5, 61.1, 54.5, 51.5, 48.5, 35.3, 30.9, 28.2, 24.2.

EXAMPLE 322

Preparation of 3-(2-CHLORO-PYRIMIDIN-4-YLAMINO)-4-(3,5-DIFLUORO-PHENYL)-1-(7-ETHYL-1,2,3,4-TETRAHYDRO-NAPHTHALEN-1-YLAMINO)-BUTAN-2-OL

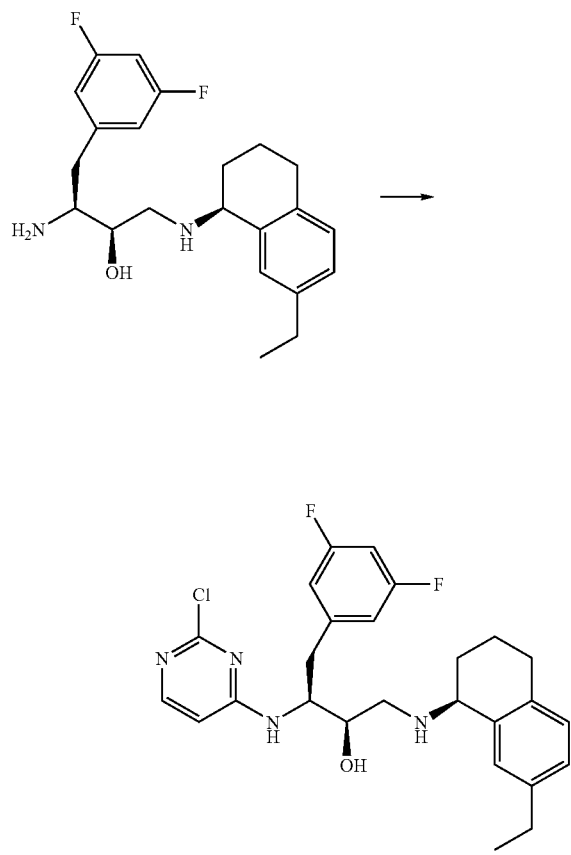

Following procedure A, 3-Amino-4-(3,5-difluoro-phenyl)-1-(7-ethyl-1,2,3,4-tetrahydro-naphthalen-1-ylamino)-butan-2-ol was converted to 3-(2-Chloro-pyrimidin-4-ylamino)-4-(3,5-difluoro-phenyl)-1-(7-ethyl-1,2,3,4-tetrahydro-naphthalen-1-ylamino)-butan-2-ol which was purified using flash chromatography (CH$_2$Cl$_2$/CH$_3$OH/NH$_4$OH, 98/2/0.2) and HPLC.

Retention time (min)=1.79, method [1], MS(ESI) 487.4 (M+H); $^1$H NMR (300 MHz, CD$_3$OD) δ7.81 (d, J=6.0 Hz, 1 H), 7.27-7.09 (m, 3 H), 6.82 (d, J=7.9 Hz, 2 H), 6.71 (t, J=9.2 Hz), 1 H), 6.38 (d, J=6.0 Hz, 1 H), 4.55-4.40 (m, 1 H), 4.40 (bs, 1 H), 3.99 (dd, J=7.1, 7.6, 1 H), 3.30-3.21 (m, 2 H), 3.05 (dd, J=10.8, 12.2, 1 H), 2.90-2.71 (m, 3 H), 2.60 (q, J=7.5, 2 H), 2.21-2.07 (m, 2 H), 2.01-1.87 (m, 2 H), 1.98 (t J=7.5 Hz, 3 H); $^{13}$C NMR (75 MHz, CD$_3$OD) δ 154.8, 142.4, 135.6, 129.5, 129.1, 128.5, 127.8, 111.7, 111.4, 104.3, 101.1 (t, J=24 Hz), 68.4, 55.3, 54.9, 47.6, 47.1, 27.8, 27.6, 24.7, 18.1, 14.5.

EXAMPLE 323

Preparation of 3-(2-CHLORO-PYRIMIDIN-4-YLAMINO)-4-(3,5-DIFLUORO-PHENYL)-1-[1-(3-ETHYL-PHENYL)-CYCLOPROPYLAMINO]-BUTAN-2-OL

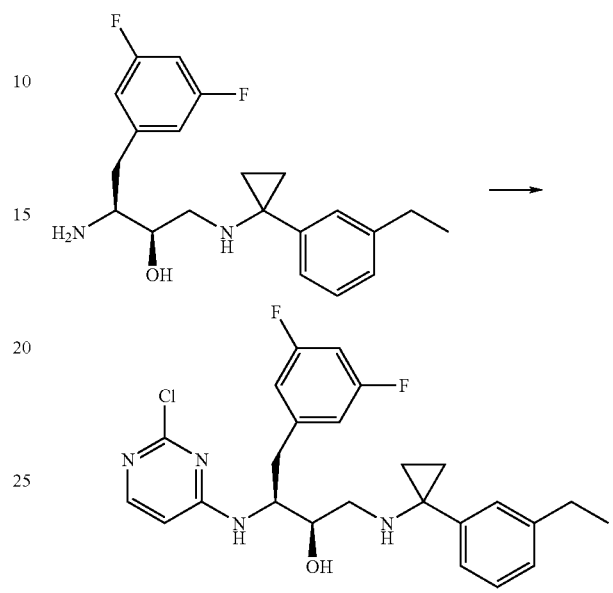

Following procedure A, 3-Amino-4-(3,5-difluoro-phenyl)-1-[1-(3-ethyl-phenyl)-cyclopropylamino]-butan-2-ol was converted to 3-(2-Chloro-pyrimidin-4-ylamino)-4-(3,5-difluoro-phenyl)-1-[1-(3-ethyl-phenyl)-cyclopropylamino]-butan-2-ol which was purified using flash chromatography (CH$_2$Cl$_2$/CH$_3$OH/NH$_4$OH, 98/2/0.2) and HPLC.

Retention time (min)=1.72, method [1], MS(ESI) 473.4 (M+H); $^1$H NMR (300 MHz, CD$_3$OD) δ7.80 (d, J=6.0 Hz, 1 H), 7.42-7.21 (m, 4 H), 6.81 (d, J=6.1 Hz, 2 H), 6.72 (t, J=9.1 Hz, 1 H), 6.28 (d, J=6.0 Hz, 1 H), 4.38-4.25 (m, 1 H), 3.19 (dd, J=3.2, 14.0 Hz, 1 H), 3.15-3.08 (m, 1 H), 2.95 (dd, J=10.2, 10.4, 1 H), 2.81-2.58 (m, 4 H), 1.60-1.25 (m, 4 H), 1.21 (t, J=7.6 Hz, 3 H); $^{13}$C NMR (75 MHz, CD$_3$OD) δ 154.5, 145.3, 133.6, 129.1, 128.8, 128.7, 127.0, 111.7, 111.4, 104.2, 101.1, 68.6, 54.3, 48.8, 43.2, 35.3, 28.1, 14.4, 10.7, 10.0.

EXAMPLE 324

Preparation of 2-{4-[3-[1-(3-TERT-BUTYL-PHENYL)-CYCLOHEXYLAMINO]-1-(3,5-DIFLUORO-BENZYL)-2-HYDROXY-PROPYLAMINO]-PYRIMIDIN-2-YLAMINO}-N,N-DIPROPYL-ACETAMIDE

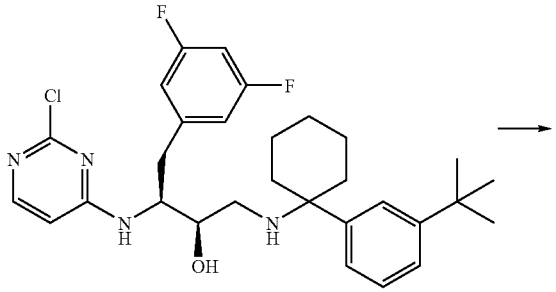

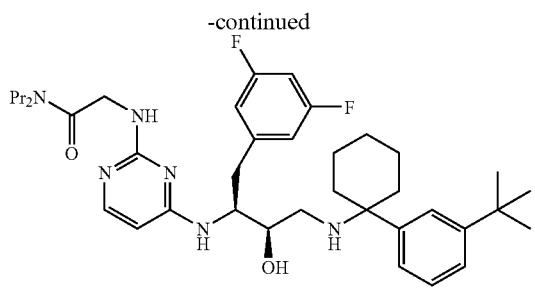

1-[1-(3-tert-Butyl-phenyl)-cyclohexylamino]-3-(2-chloro-pyrimidin-4-ylamino)-4-(3,5-difluoro-phenyl)-butan-2-ol (27 mg, 49.7 μmol) and 2-amino-N,N-dipropyl-acetamide (15 mg, 74.5 μmol) were dissolved in DMF (100 μL) containing potassium carbonate (21 mg, 149.1 μmol). The reaction mixture was heated at 90° C. for 48 h. The resulting solution was diluted with brine (5 mL), extracted with Et$_2$O (5 mL), dried over Na$_2$SO$_4$ and purified using flash chromatography (CH$_2$Cl$_2$/CH$_3$OH/NH$_4$OH, 98/2/0.2) and HPLC to give 2-{4-[3-[1-(3-tert-Butyl-phenyl)-cyclohexylamino]-1-(3,5-difluoro-benzyl)-2-hydroxy-propylamino]-pyrimidin-2-ylamino}-N,N-dipropyl-acetamide.

Retention time (min)=1.95, method [1], MS(ESI) 665.6 (M+H); $^1$H NMR (300 MHz, CD$_3$OD) δ 7.64 (s, 1 H), 7.58 (d, J=7.2 Hz, 1 H), 7.48-7.35 (m, 3 H), 6.81-6.71 (m, 3 H), 5.86 (d, J=7.1 Hz, 1 H), 4.35-4.11 (m, 3 H), 3.75 (bs, 1 H), 3.18 (dd, J=14, 3.4 Hz, 1 H), 2.95-2.51 (m, 8 H), 2.05-1.59 (m, 12 H), 1.34 (s, 9 H), 1.01 (t, J=7.5 Hz, 3 H), 0.95 (t, J=7.5 Hz, 3 H).

EXAMPLE 325

Preparation of {4-[3-[1-(3-TERT-BUTYL-PHENYL)-CYCLOHEXYLAMINO]-1-(3,5-DIFLUORO-BENZYL)-2-HYDROXY-PROPYLAMINO]-PHENYL}-ACETIC ACID

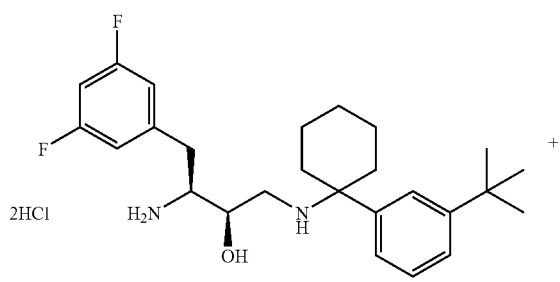

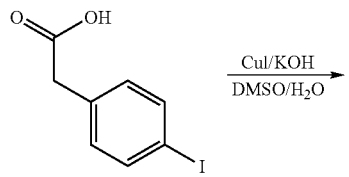

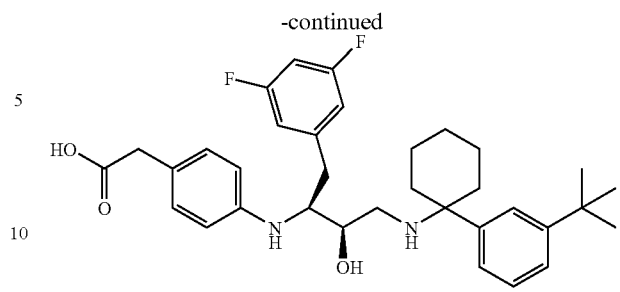

3-Amino-1-[1-(3-tert-butyl-phenyl)-cyclohexylamino]-4-(3,5-difluoro-phenyl)-butan-2-ol dihydrochloride salt (1 mmol), 4-iodophenylacetic acid (1 mmol), and potassium hydroxide (5 mmol) were added to around bottom flask equipped with stirbar. DMSO (5 mL) and H$_2$O (5 mL) were added and the mixture dissolved. Copper iodide (10%) was added and the mixture was heated for 16 hours at 90° C. The reaction was extracted with DCM (2×10 mL), then neutralized with 1M HCl and extracted with 4:1 CHCl$_3$/IPA. Both organic fractions were combined, dried with sodium sulfate, and concentrated to give a brown oil. This residue was purified by reverse-phase HPLC.

Retention time (min)=2.274, method [1]; $^1$H NMR (300 MHz, CD$_3$OD) δ 7.54 (s, 1H), 7.46-7.27 (m, 3H), 6.94 (d, 2H, J=7.8 Hz), 6.76-6.59 (m, 3H), 6.36 (d, 2H, J=7.8 Hz), 3.58-3.43 (m, 2H), 3.41 (s, 2H), 3.03 (d, 1H, J=13.7 Hz), 2.87 (d, 1H, J=13.7 Hz), 2.76-2.45 (m, 4H), 1.95-1.54 (m, 4H), 1.39-1.06 (m, 11H). $^{13}$C NMR (75 MHz, CD$_3$OD) 174.7, 182.7 (dd, 2C, J=248.2, 13.5 Hz), 158.2, 152.2, 146.0, 142.6 (t, 1C, J=9.7 Hz), 133.1, 129.6, 128.9, 126.0, 124.6, 124.3, 123.0, 112.6, 111.8 (dd, 2C, J=17.1, 7.4 Hz), 100.9 (t, 1C, J=25.7 Hz), 69.7, 64.0, 57.3, 45.1, 39.5, 35.9, 34.3, 32.6, 32.5, 30.0, 24.6, 21.7; MS (ESI) 565.2.

EXAMPLE 326

Preparation of 3-{4-[3-[1-(3-TERT-BUTYL-PHENYL)-CYCLOHEXYLAMINO]-1-(3,5-DIFLUORO-BENZYL)-2-HYDROXY-PROPYLAMINO]-PHENYL}-PROPIONIC ACID

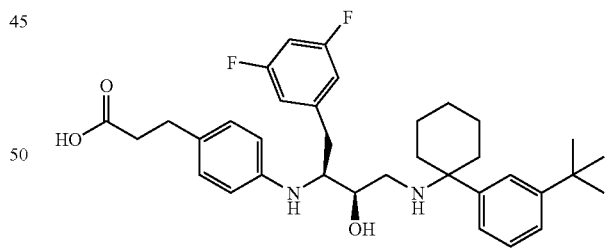

The title compound was prepared in an identical manner to Example 325 using 3-(4-iodo-phenyl)-propionic acid as the coupling species. Retention time (min)=2.106, method [1]; $^1$H NMR (300 MHz, CD$_3$OD) δ 7.55 (s, 1H), 7.46-7.27 (m, 3H), 6.90 (d, 2H, J=7.8 Hz), 6.76-6.59 (m, 3H), 6.36 (d, 2H, J=7.8 Hz), 3.58-3.43 (m, 2H), 3.02 (dd, 1H, J=14.0, 4.0 Hz), 2.88 (dd, 1H, J=13.0, 2.7 Hz), 2.76-2.46 (m, 6H), 1.95-1.54 (m, 4H), 1.39-1.06 (m, 11H). $^{13}$C NMR (75 MHz, CD$_3$OD) 175.4, 162.7 (dd, 2C, J=248.2, 13.5 Hz). 159.4, 152.2, 147.5, 145.0, 142.6 (t, 1C, J=9.7 Hz), 133.3, 129.6, 128.9, 126.0, 124.6, 124.3, 123.0, 112.6, 111.8 (dd, 2C, J=17.1, 7.4 Hz), 100.9 (t, 1C, J=25.7 Hz), 69.7, 64.0, 57.3, 45.1, 39.5, 35.9, 35.5, 34.3, 32.6, 32.5, 30.1, 29.6, 24.6, 21.7; MS (ESI) 579.3.

EXAMPLE 327

Preparation of 2-{3-[3-[1-(3-TERT-BUTYL-PHENYL)-CYCLOHEXYLAMINO]-1-DIFLUORO-BENZYL)-2-HYDROXY-PROPYLAMINO]-PHENYL}-N,N-DIPROPYL-ACETAMIDE

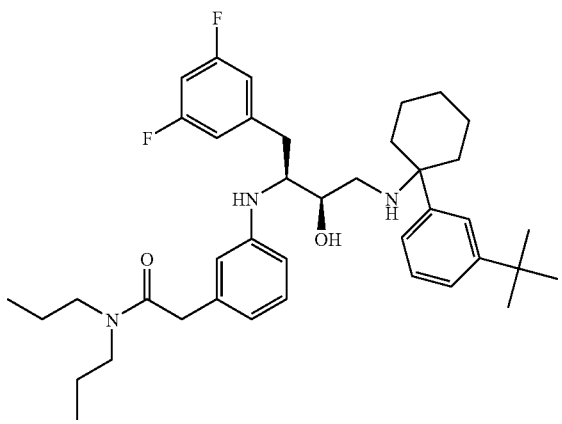

The title compound was prepared in an identical manner to Example 325 using 2-(3-iodo-phenyl)-N,N-dipropyl-acetamide as the coupling species. Retention time (min)=2.529, method [1]; $^1$H NMR (300 MHz, CD$_3$OD) δ 7.56 (s, 1H), 7.46-7.27 (m, 3H), 6.96 (t, 1H, J=7.6 Hz), 6.76-6.59 (m, 3H), 6.46 (d, 1H, J=7.2 Hz), 6.33 (s, 1H), 6.29 (d, 1H, J=7.9 Hz), 3.57 (s, 2H), 3.55-3.45 (m, 2H), 3.31-3.17 (m, 5H), 3.01 (dd, 1H, J=13.8, 3.8), 2.87 (dd, 1H, J=12.6, 2.1 Hz), 2.79-2.51 (m, 4H), 1.96-1.30 (m, 12H), 1.28 (s, 9H); MS (ESI) 648.3.

EXAMPLE 328

Preparation of 4-[3-[1-(3-TERT-BUTYL-PHENYL)-CYCLOHEXYLAMINO]-1-(3,5-DIFLUORO-BENZYL)-2-HYDROXY-PROPYLAMINO]-BENZOIC ACID

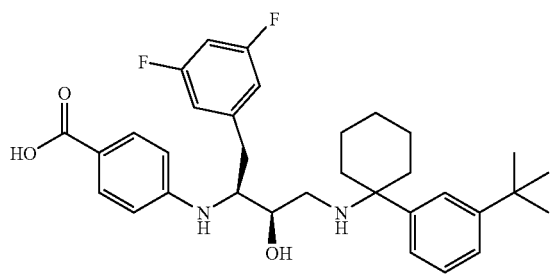

The title compound was prepared in an identical manner to Example 325 using 4-iodo-benzoic acid as the coupling species. Retention time (min)=1.966, method [1]; MS (ESI) 551.2.

EXAMPLE 329

Preparation of 4-[3-[1-(3-TERT-BUTYL-PHENYL)-CYCLOHEXYLAMINO]-1-(3,5-DIFLUORO-BENZYL)-2-HYDROXY-PROPYLAMINO]-N-METHYL-BENZAMIDE

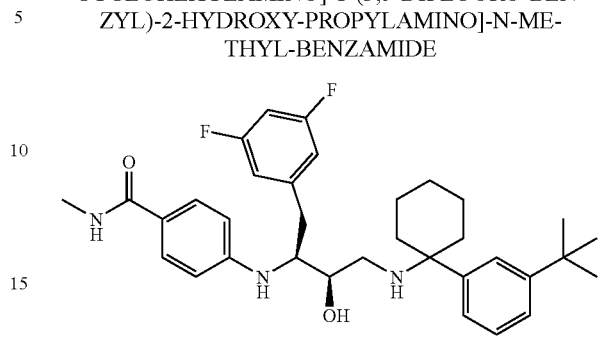

The title compound was prepared in an identical manner to Example 325 using 4-iodo-N-methyl-benzamide as the coupling species. Retention time (min)=1.949, method [1]; MS (ESI) 564.3.

EXAMPLE 330

Preparation of 4-[3-[1-(3-TERT-BUTYL-PHENYL)-CYCLOHEXYLAMINO]-1-(3,5-DIFLUORO-BENZYL)-2-HYDROXY-PROPYLAMINO]-BENZAMIDE

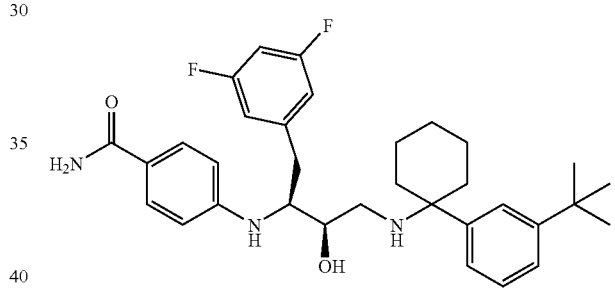

The title compound was prepared in an identical manner to Example 325 using 4-iodo-benzamide as the coupling species. Retention time (min)=1.977, method [1]; MS (ESI) 551.2.

EXAMPLE 331

Preparation of 4-(3,5-DIFLUORO-PHENYL)-1-(7-ETHYL-1,2,3,4-TETRAHYDRO-NAPHTHALEN-1-YLAMINO)-3-(2-FLUORO-PHENYLAMINO)-BUTAN-2-OL

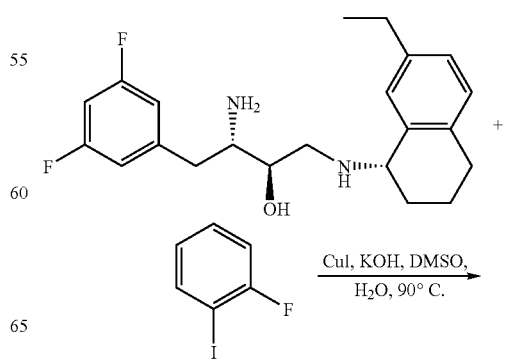

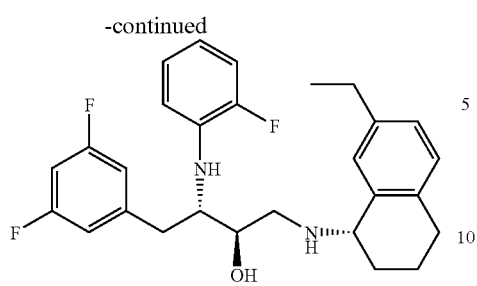

Cuprous iodide (17 mg, 89.3 μmol), 3-amino-4-(3,5-difluoro-phenyl)-1-(7-ethyl-1,2,3,4-tetrahydro-naphthalen-1-ylamino)-butan-2-ol dihydrochloride (91 mg, 203 μmol), 1-fluoro-2-iodo-benzene (56 mg, 252 μmol), and powdered potassium hydroxide (48 mg, 855 umol) were placed into a culture tube, evacuated, and refilled with nitrogen. Dimethylsulfoxide (0.20 mL) and water (0.10 mL) were added and the heterogenous mixture was placed into a preheated oil bath at 90° C. After stirring for 20 h, the heterogeneous mixture was flash chromatographed with 99:1:0.1, 49:1:0.1, 24:1:0.1, and 23:2:0.2, methylene chloride:methanol:concentrated ammonium hydroxide as the eluant to yield 4-(3,5-Difluoro-phenyl)-1-(7-ethyl-1,2,3,4-tetrahydro-naphthalen-1-ylamino)-3-(2-fluoro-phenylamino)-butan-2-ol.

Method [4] Retention time 2.99 min by HPLC and 3.08 min by MS (M+=469).

EXAMPLE 332

Preparation of 4-(3,5-DIFLUORO-PHENYL)-1-(7-ETHYL-1,2,3,4-TETRAHYDRO-NAPHTHALEN-1-YLAMINO)-3-(4-TRIFLUOROMETHYL-PHENYLAMINO)-BUTAN-2-OL

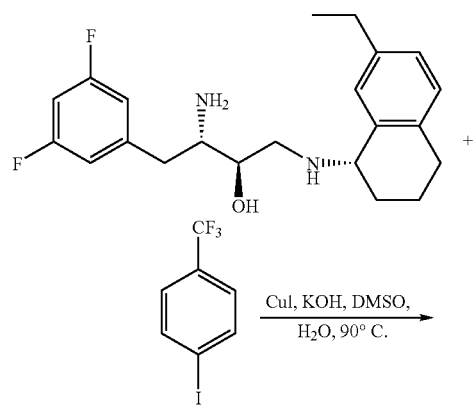

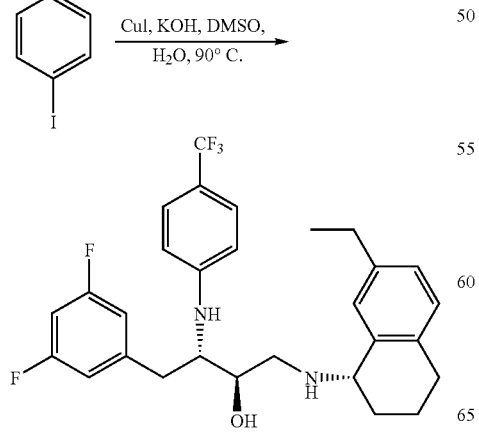

The title compound was prepared according to the procedure described in Example 331. Method [4] Retention time 3.22 min by HPLC and 3.31 min by MS (M+=519).

EXAMPLE 333

Preparation of 4-(3,5-DIFLUORO-PHENYL)-1-(7-ETHYL-1,2,3,4-TETRAHYDRO-NAPHTHALEN-1-YLAMINO)-3-(3-TRIFLUOROMETHYL-PHENYLAMINO)-BUTAN-2-OL

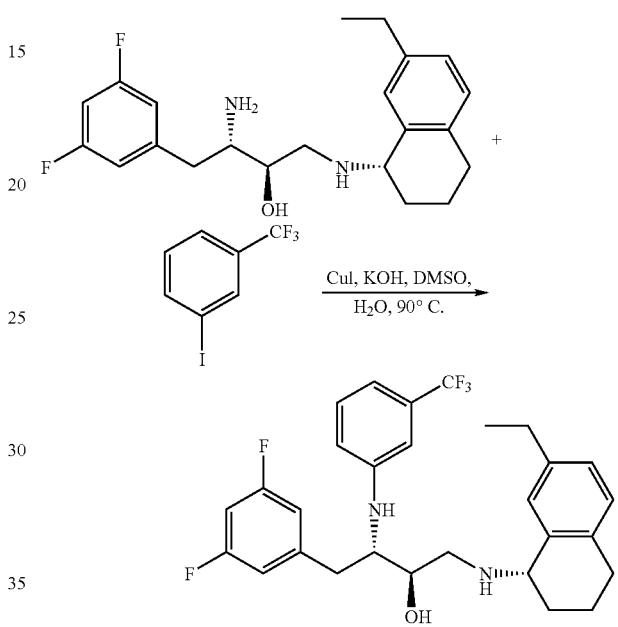

The title compound was prepared according to the procedure described in Example 331. Method [4] Retention time 3.16 min by HPLC and 3.24 min by MS (M+=519).

EXAMPLE 334

Preparation of 4-(3,5-DIFLUORO-PHENYL)-1-(7-ETHYL-1,2,3,4-TETRAHYDRO-NAPHTHALEN-1-YLAMINO)-3-3-HYDROXYMETHYL-PHENYLAMINO)-BUTAN-2-OL

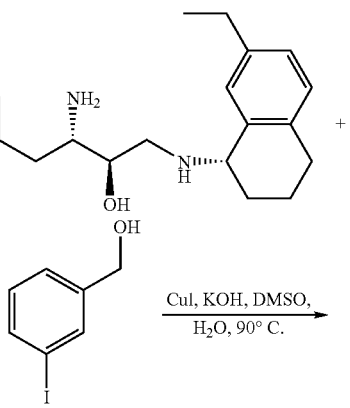

-continued

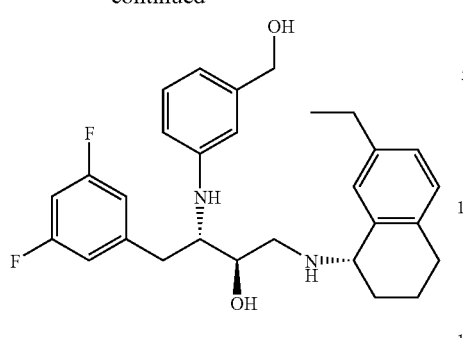

The title compound was prepared according to the procedure described in Example 331. Method [4] Retention time 2.64 min by HPLC and 2.73 min by MS (M+=481).

EXAMPLE 335

Preparation of 3-(4-AMINO-PHENYLAMINO)-4-(3,5-DIFLUORO-PHENYL)-1-(7-ETHYL-1,2,3,4-TETRAHYDRO-NAPHTHALEN-1-YLAMINO)-BUTAN-2-OL

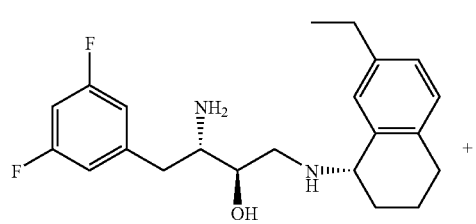

The title compound was prepared according to the procedure described in Example 331. Method [1] Retention time 1.37 min by HPLC and 1.43 min by MS (M+=466).

EXAMPLE 336

Preparation of 3-(3-AMINO-PHENYLAMINO)-4-(3,5-DIFLUORO-PHENYL)-1-(7-ETHYL-1,2,3,4-TETRAHYDRO-NAPHTHALEN-1-YLAMINO)-BUTAN-2-OL

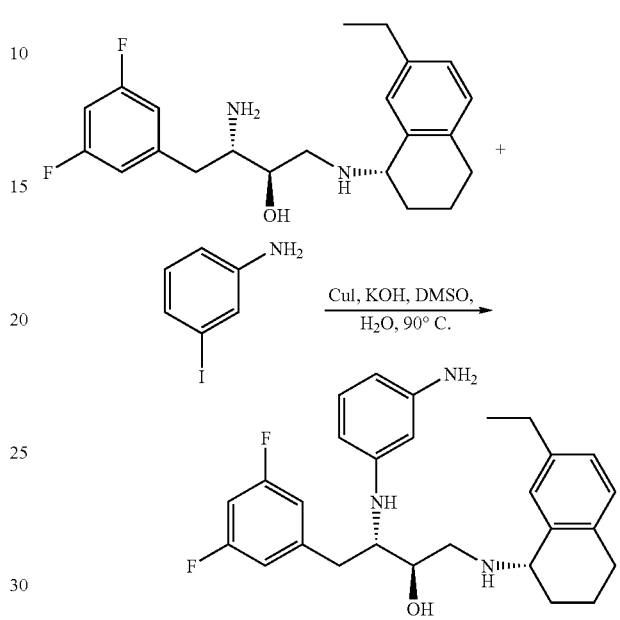

The title compound was prepared according to the procedure described in Example 331. Method [4] Retention time 2.19 min by HPLC and 2.28 min by MS (M+=466).

EXAMPLE 337

Preparation of 4-(3,5-DIFLUORO-PHENYL)-1-(7-ETHYL-1,2,3,4-TETRAHYDRO-NAPHTHALEN-1-YLAMINO)-3-(PYRIDIN-2-YLAMINO)-BUTAN-2-OL

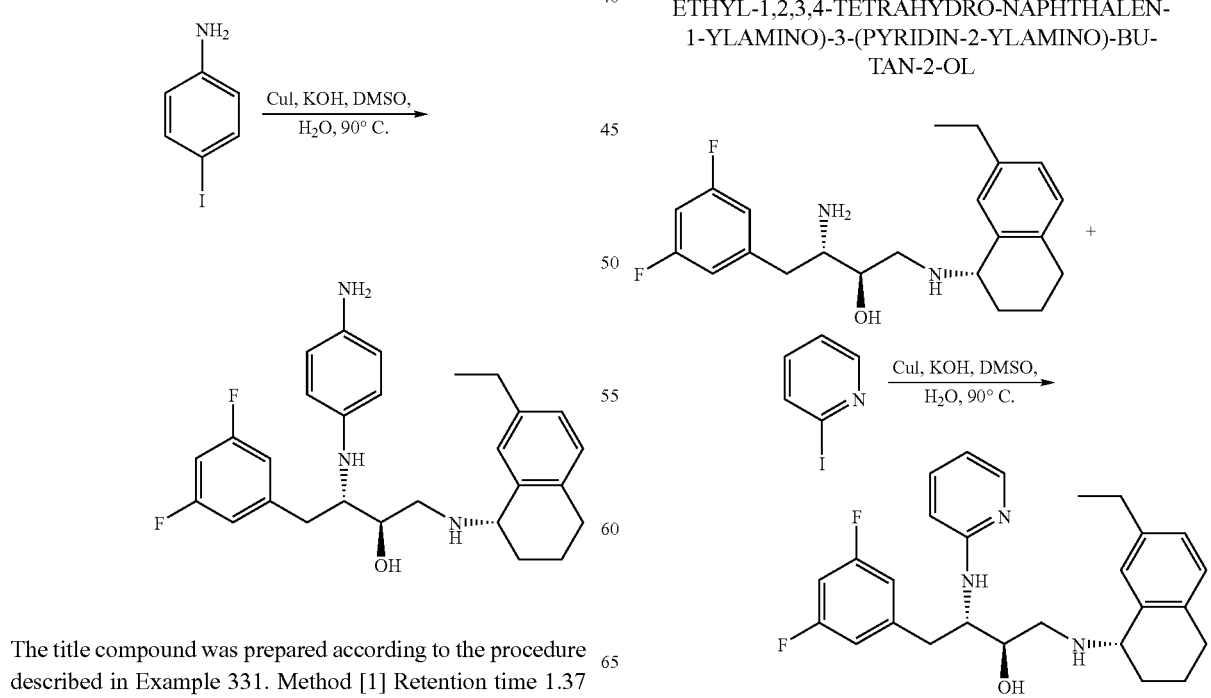

The title compound was prepared according to the procedure described in Example 331. Method [4] Retention time 2.32 min by HPLC and 2.41 min by MS (M+=452).

EXAMPLE 338

Preparation of 4-(3,5-DIFLUORO-PHENYL)-1-(7-ETHYL-1,2,3,4-TETRAHYDRO-NAPHTHALEN-1-YLAMINO)-3-(PYRIDIN-3-YLAMINO)-BUTAN-2-OL

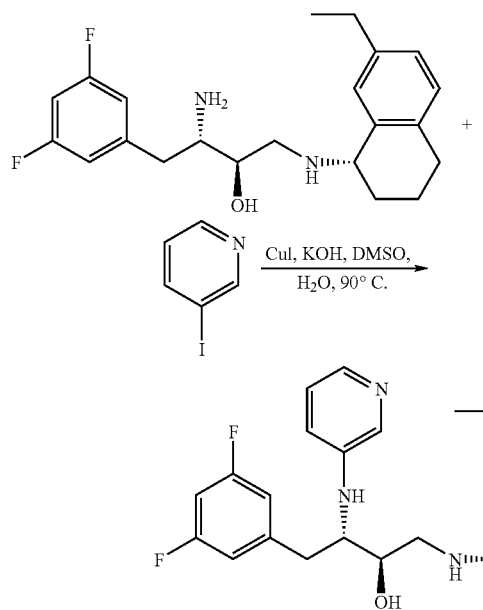

The title compound was prepared according to the procedure described in Example 331. Method [1] Retention time 1.35 min by HPLC and 1.42 min by MS (M+=452).

EXAMPLE 339

Preparation of 4-(3,5-DIFLUORO-PHENYL)-1-(7-ETHYL-1,2,3,4-TETRAHYDRO-NAPHTHALEN-1-YLAMINO)-3-(PYRIDIN-4-YLAMINO)-BUTAN-2-OL

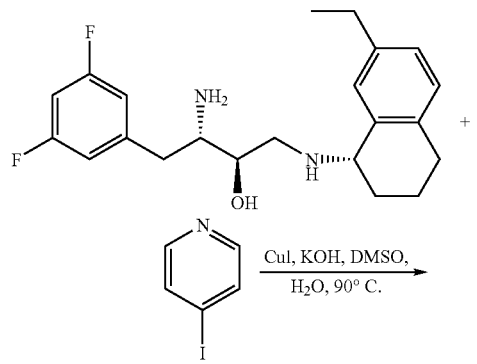

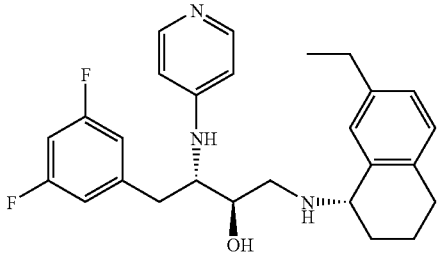

The title compound was prepared according to the procedure described in Example 331. Method [1] Retention time 1.34 min by HPLC and 1.40 min by MS (M+=452).

EXAMPLE 340

Preparation of {3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-PHENYL}-ACETIC ACID

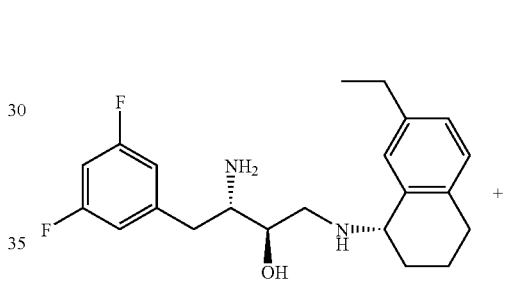

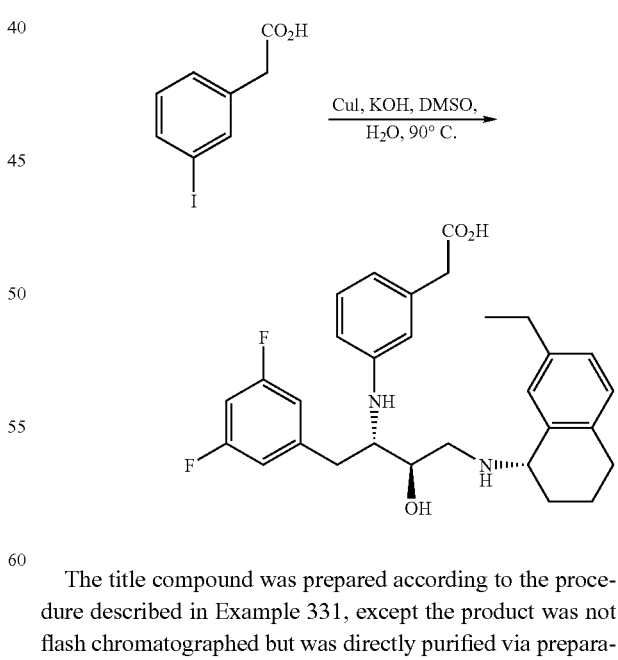

The title compound was prepared according to the procedure described in Example 331, except the product was not flash chromatographed but was directly purified via preparative HPLC.

Method [1] Retention time 1.74 min by HPLC and 1.83 min by MS (M+=509).

EXAMPLE 341

Preparation of 2-{3-[1-(3,5-DIFLUORO-BENZYL)-3-(7-ETHYL-1,2,3,4-TETRAHYDRO-NAPHTHALEN-1-YLAMINO)-2-HYDROXY-PROPYLAMINO]-PHENYL}-N,N-DIPROPYL-ACETAMIDE Step 1: Preparation of 2-(3-Iodo-phenyl)-N,N-dipropyl-acetamide

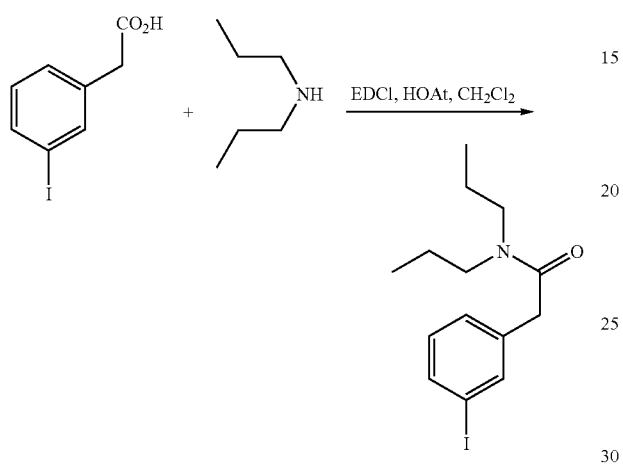

Dipropylamine (0.18 mL, 1.31 mmol), 3-iodophenylacetic acid (269 mg, 1.03 mmol), 1-(3-dimethylaminopropyl)-3-ethylcarbodiimide hydrochloride (237 mg, 1.24 mmol), and 1-hydroxyazabenzotriazole (22 mg, 162 umol) in methylene chloride (10 mL) were stirred for 20 h. The solution was concentrated and the residue was flash chromatographed with 9:1, 4:1, and 7:3 hexane:ethyl acetate as the eluant to afford 350 mg (99% yield) of 2-(3-iodo-phenyl)-N,N-dipropyl-acetamide as a colorless oil.

Step 2: Preparation of 2-{3-[1-(3,5-Difluoro-benzyl)-3-(7-ethyl-1,2,3,4-tetrahydro-naphthalen-1-ylamino)-2-hydroxypropylamino]-phenyl}-N,N-dipropyl-acetamide

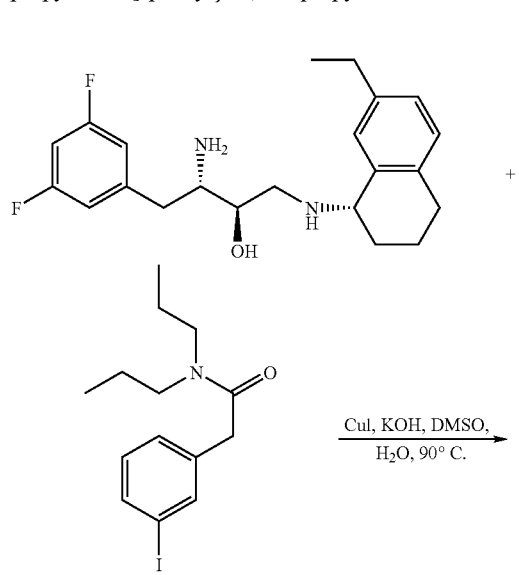

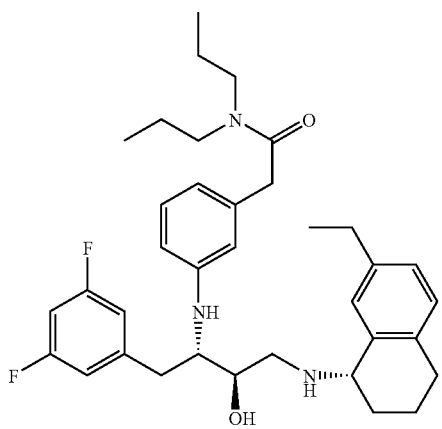

The title compound was prepared according to the procedure described in Example 331. Method [1] Retention time 2.18 min by HPLC and 2.25 min by MS (M+=592).

EXAMPLE 342

Preparation of 1-[1-(3-TERT-BUTYL-PHENYL)-CYCLOHEXYLAMINO]-4-(3,5-DIFLUORO-PHENYL)-3-(1-METHYL-1H-PYRAZOL-4-YLAMINO)-BUTAN-2-OL

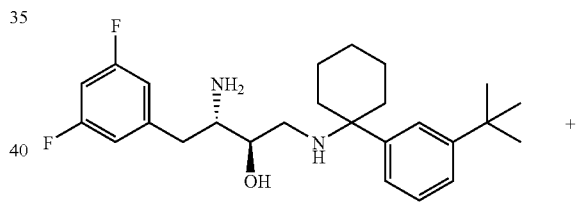

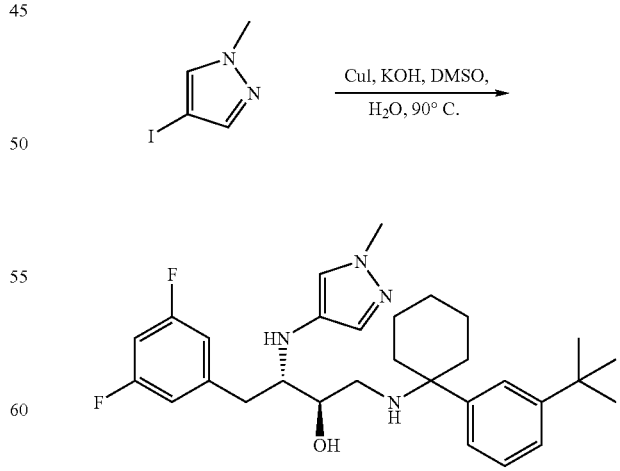

The title compound was prepared according to the procedure described in Example 331. Method [1] Retention time 1.86 min by HPLC and 1.92 min by MS (M+=511).

EXAMPLE 343

Preparation of 4-(3,5-DIFLUORO-PHENYL)-1-(7-ETHYL-1,2,3,4-TETRAHYDRO-NAPHTHALEN-1-YLAMINO)-3-(PYRIMIDIN-2-YLAMINO)-BUTAN-2-OL

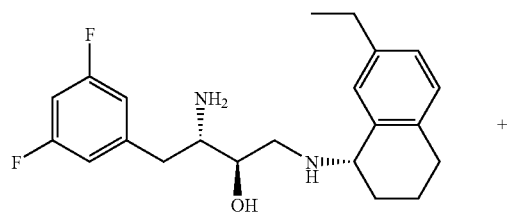

+

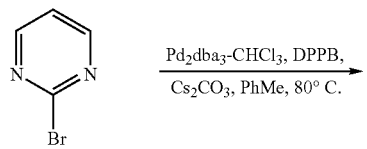

-continued

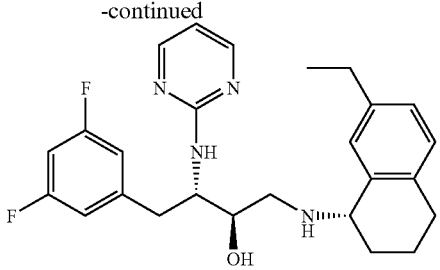

Powdered cesium carbonate (420 mg, 1.29 mmol), 3-amino-4-(3,5-difluoro-phenyl)-1-(7-ethyl-1,2,3,4-tetrahydro-naphthalen-1-ylamino)-butan-2-ol dihydrochloride (93 mg, 208 μmol), 1,4-bis(diphenylphosphino)butane (27 mg, 63.3 μmol), tris(dibenzylideneacetone)dipalladium(0)-chloroform adduct (22 mg, 21.3 μmol), and 2-bromopyrimidine (38 mg, 239 μmol) were placed into a flask. The flask was evacuated and refilled with nitrogen three times. Toluene (2.0 mL) was added and the heterogenous mixture was placed into a preheated oil bath at 80° C. After stirring for 18 h, the heterogeneous mixture was flash chromatographed with 49:1:0.1, 24:1:0.1, and 23:2:0.2, methylene chloride:methanol:concentrated ammonium hydroxide as the eluant to yield 4-(3,5-difluoro-phenyl)-1-(7-ethyl-1,2,3,4-tetrahydro-naphthalen-1-ylamino)-3-(pyrimidin-2-ylamino)-butan-2-ol. Method [4] Retention time 2.50 min by HPLC and 2.58 min by MS (M+=453).

EXAMPLE 344

Preparation of N-Substituted Compounds Via Reductive Animation

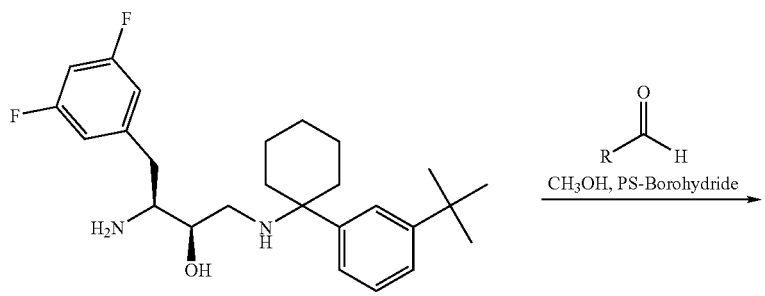

47

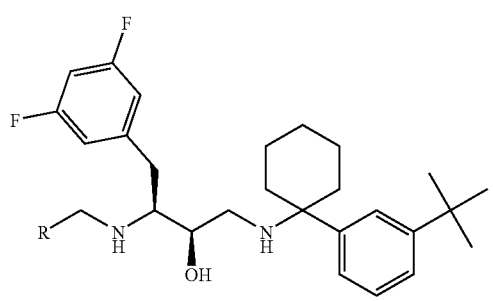

48

To 50 mgs (0.12 mmol) of 3-Amino-1-[1-(3-tert-butyl-phenyl)-cyclohexylamino]-4-(3,5-difluoro-phenyl)-butan-2-ol (47) in 1.0 mL of methanol in a 4-mL reaction vial was added 1 equivalent (0.12 mmol) of R-aldehyde. The mixture was stirred for 15 minutes at room temperature. After stirring, 2 equivalents (48 mg) of polymer-supported borohydride was added to the reaction mixture. The reaction mixture was allowed to stir overnight at room temperature. The borohydride resins were filtered out of the reaction mixture. The reaction mixture was then concentrated and isolated via preparative HPLC utilizing a Varian ProStar Preparative HPLC system to leave compounds with general structure 48. LC/MS analysis is conducted utilizing method [1].

The compounds in the chart below were made according to the procedure above.

| Compound | M + H | Ret. time |
|---|---|---|
| 1-[1-(3-tert-Butyl-phenyl)-cyclohexylamino]-4-(3,5-difluoro-phenyl)-3-ethylamino-butan-2-ol | 459.5 | 1.754 |
| 1-[1-(3-tert-Butyl-phenyl)-cyclohexylamino]-4-(3,5-difluoro-phenyl)-3-propylamino-butan-2-ol | 473.5 | 1.781 |
| 1-[1-(3-tert-Butyl-phenyl)-cyclohexylamino]-3-(cyclopropylmethyl-amino)-4-(3,5-difluoro-phenyl)-butan-2-ol | 485.5 | 1.800 |
| 1-[1-(3-tert-Butyl-phenyl)-cyclohexylamino]-4-(3,5-difluoro-phenyl)-3-[(1-phenyl-1H-[1,2,3]triazol-4-ylmethyl)-amino]-butan-2-ol | 588.5 | 2.052 |
| 2-{[3-[1-(3-tert-Butyl-phenyl)-cyclohexylamino]-1-(3,5-difluoro-benzyl)-2-hydroxy-propylamino]-methyl}-phenol | 537.5 | 1.852 |
| 3-(2-Amino-ethylamino)-1-[1-(3-tert-butyl-phenyl)-cyclohexylamino]-4-(3,5-difluoro-phenyl)-butan-2-ol | 474.5 | 1.633 |
| 1-[1-(3-tert-Butyl-phenyl)-cyclohexylamino]-4-(3,5-difluoro-phenyl)-3-[(pyrrolidin-3-ylmethyl)-amino]-butan-2-ol | 514.5 | 1.566 |
| 1-[1-(3-tert-Butyl-phenyl)-cyclohexylamino]-4-(3,5-difluoro-phenyl)-3-(2-piperidin-4-yl-ethylamino)-butan-2-ol | 542.5 | 1.559 |
| 1-[1-(3-tert-Butyl-phenyl)-cyclohexylamino]-4-(3,5-difluoro-phenyl)-3-[(piperidin-4-ylmethyl)-amino]-butan-2-ol | 528.5 | 1.560 |
| 3-Benzylamino-1-[1-(3-tert-butyl-phenyl)-cyclohexylamino]-4-(3,5-difluoro-phenyl)-butan-2-ol | 521.5 | 1.948 |
| 1-[1-(3-tert-Butyl-phenyl)-cyclohexylamino]-3-[(4-chloro-1-methyl-1H-pyrazol-3-ylmethyl)-amino]-4-(3,5-difluoro-phenyl)-butan-2-ol | 559.5 | 1.874 |
| 1-[1-(3-tert-Butyl-phenyl)-cyclohexylamino]-4-(3,5-difluoro-phenyl)-3-[(furan-2-ylmethyl)-amino]-butan-2-ol | 511.5 | 1.861 |
| 4-{[3-[1-(3-tert-Butyl-phenyl)-cyclohexylamino]-1-(3,5-difluoro-benzyl)-2-hydroxy-propylamino]-methyl}-benzene-1,3-diol | 553.5 | 1.769 |
| 1-[1-(3-tert-Butyl-phenyl)-cyclohexylamino]-4-(3,5-difluoro-phenyl)-3-[(1H-pyrazol-3-ylmethyl)-amino]-butan-2-ol | 511.5 | 1.701 |
| 3-(1-Benzyl-1H-pyrazol-4-ylamino)-1-[1-(3-tert-butyl-phenyl)-cyclohexylamino]-4-(3,5-difluoro-phenyl)-butan-2-ol | 587.5 | 2.227 |
| 3-[3-[1-(3-tert-Butyl-phenyl)-cyclohexylamino]-1-(3,5-difluoro-benzyl)-2-hydroxy-propylamino]-propane-1,2-diol | 505.5 | 1.646 |
| 1-[1-(3-tert-Butyl-phenyl)-cyclohexylamino]-4-(3,5-difluoro-phenyl)-3-(3-methylsulfanyl-propylamino)-butan-2-ol | 519.5 | 1.907 |
| 1-[1-(3-tert-Butyl-phenyl)-cyclohexylamino]-4-(3,5-difluoro-phenyl)-3-(3-hydroxy-2,2-dimethyl-propylamino)-butan-2-ol | 517.5 | 1.815 |
| 1-[1-(3-tert-Butyl-phenyl)-cyclohexylamino]-4-(3,5-difluoro-phenyl)-3-(2-hydroxy-ethylamino)-butan-2-ol | 475.5 | 1.649 |

EXAMPLE 345

Preparation of 4-(3,5-DIFLUORO-PHENYL)-1-{1-[3-(2,2-DIMETHYL-PROPYL)-PHENYL]-CYCLOHEXYLAMINO}-3-(2,2,2-TRIFLUORO-ETHYLAMINO)-BUTAN-2-OL Step 1:

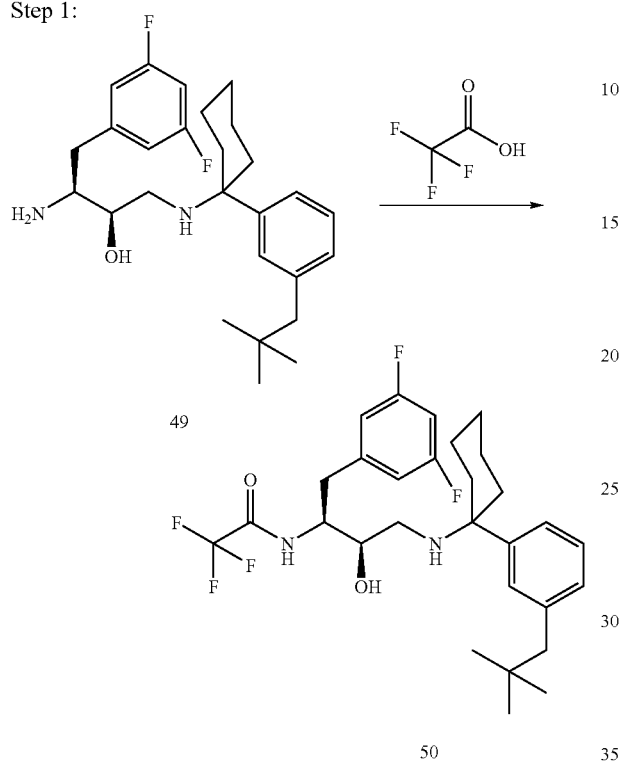

1-[3-(Dimethylamino)propyl]-3-ethylcarbodiimide hydrochloride was added to a THF (anhydrous) solution (500 μL) of amine 49 (0.186 mmol, 80 mg), trifluoroacetic acid (0.186 mmol, 18 mg), diisopropylethylamine (0.386 mmol, 48 mg) and hydroxybenzotriazole (0.2 mmol, 27.6 mg). The reaction was capped and allowed to shake at room temperature for 12 hours at which time LCMS indicated complete reaction. The reaction was evaporated of THF by N₂ stream, acidified with 1N HCl in ethanol (100 μL), diluted (400 μL ethanol), and filtered. The solution was injected onto a preparative RP-HPLC [Method 10] for purification to provide amide 50.

LCMS Method [11]: ret. time (min): 2.77; [M+H]=526.80.

Step 2:

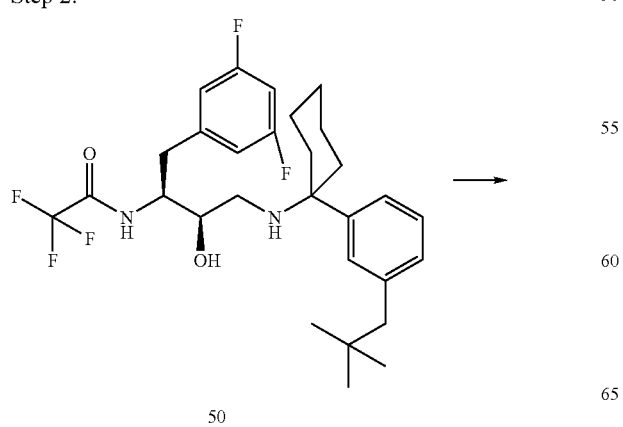

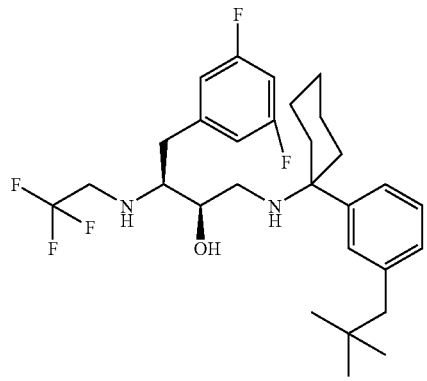

Amide 50 (15 mg, 0.0285 mmol) was dissolved in BH₃ dimethylsulfide complex (2M in THF, 100 μL, 0.2 mmol), and the reaction was capped and heated with shaking at 80° C. for 4 hours. At this time, LCMS was performed showing a complete reaction, The reaction was quenched with a few drops of isopropanol, then evaporated of volatiles by N₂ stream, acidified with 1N HCl in ethanol (100 μL), diluted (400 μl ethanol), and filtered. This solution was injected onto a preparative RP-HPLC [Method 10] for purification to give 4-(3,5-Difluoro-phenyl)-1-{1-[3-(2,2-dimethyl-propyl)-phenyl]-cyclohexylamino}-3-(2,2,2-trifluoro-ethylamino)-butan-2-ol (51).

LCMS Method [11]: Ret. time (min); 2.37; [M+H]= 512.90.

EXAMPLE 346

Preparation of 3-(2,2-DIFLUORO-ETHYLAMINO)-4-(3,5-DIFLUORO-PHENYL)-1-{1-[3-(2,2-DIMETHYL-PROPYL)-PHENYL]-CYCLOHEXYLAMINO}-BUTAN-2-OL

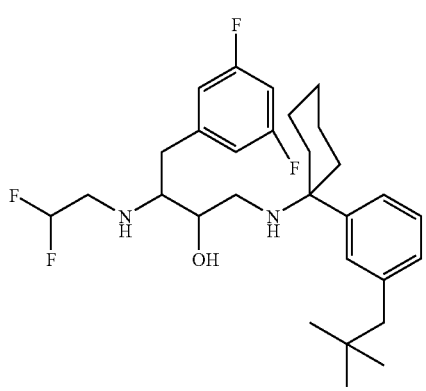

The title compound was prepared according to the procedure described in Example 345. LCMS ret. time (min): 2.03; [M+H]=494.90.

EXAMPLE 347

Alternative Preparation of Formula (I) Compounds

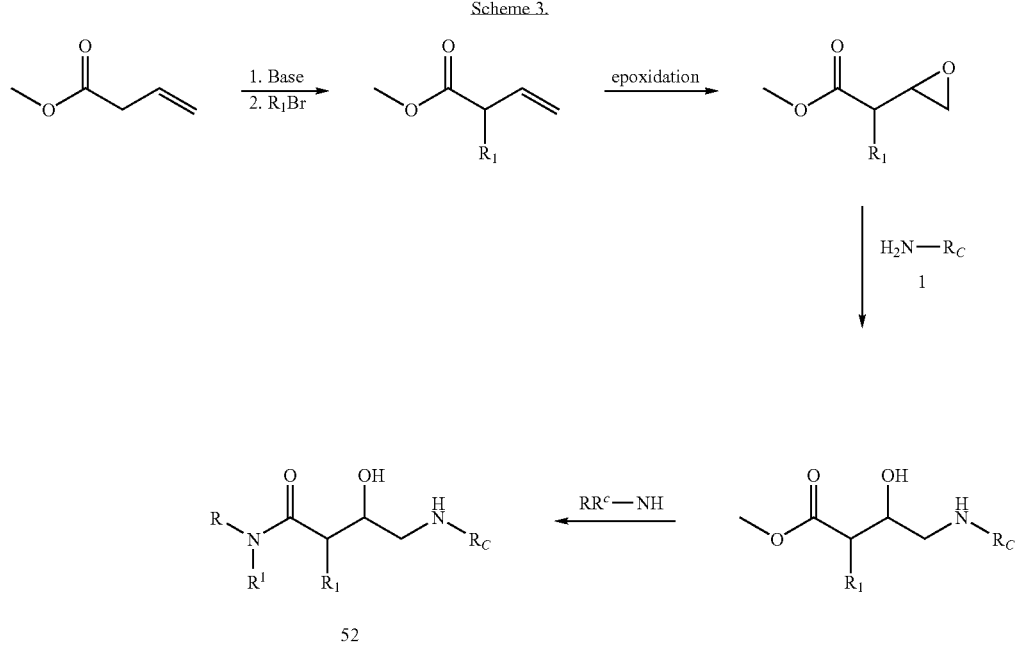

As described above and below, an embodiment of the present invention provides for compounds with structure 52 as shown above in Scheme 4. These compounds can be made by methods known to those skilled in the art from starting compounds that are also known to those skilled in the art. The process chemistry is further well known to those skilled in the art. A suitable process for the preparation of compounds with structure 52 is set forth in EXAMPLE 348 below.

EXAMPLE 348

Preparation of 2-(3,5-DIFLUORO-BENZYL)-4-(6-ETHYL-2,2-DIOXO-2$\alpha^6$-ISOTHIOCHROMAN-4-YLAMINO)-3-HYDROXY-N-METHYL-BU-TYRAMIDE

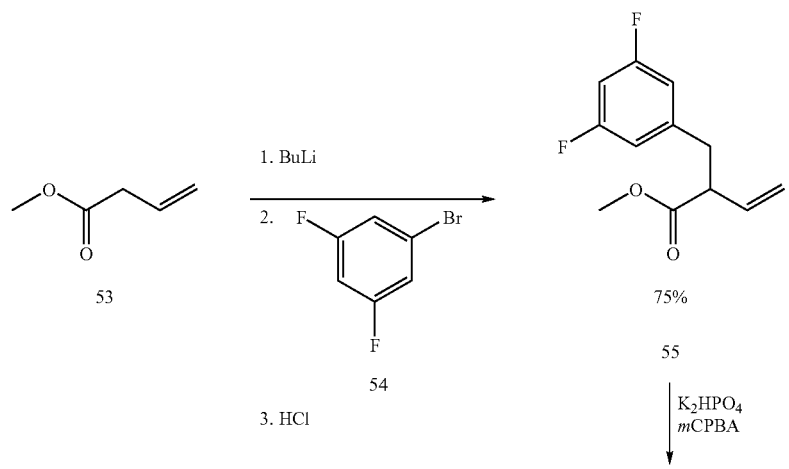

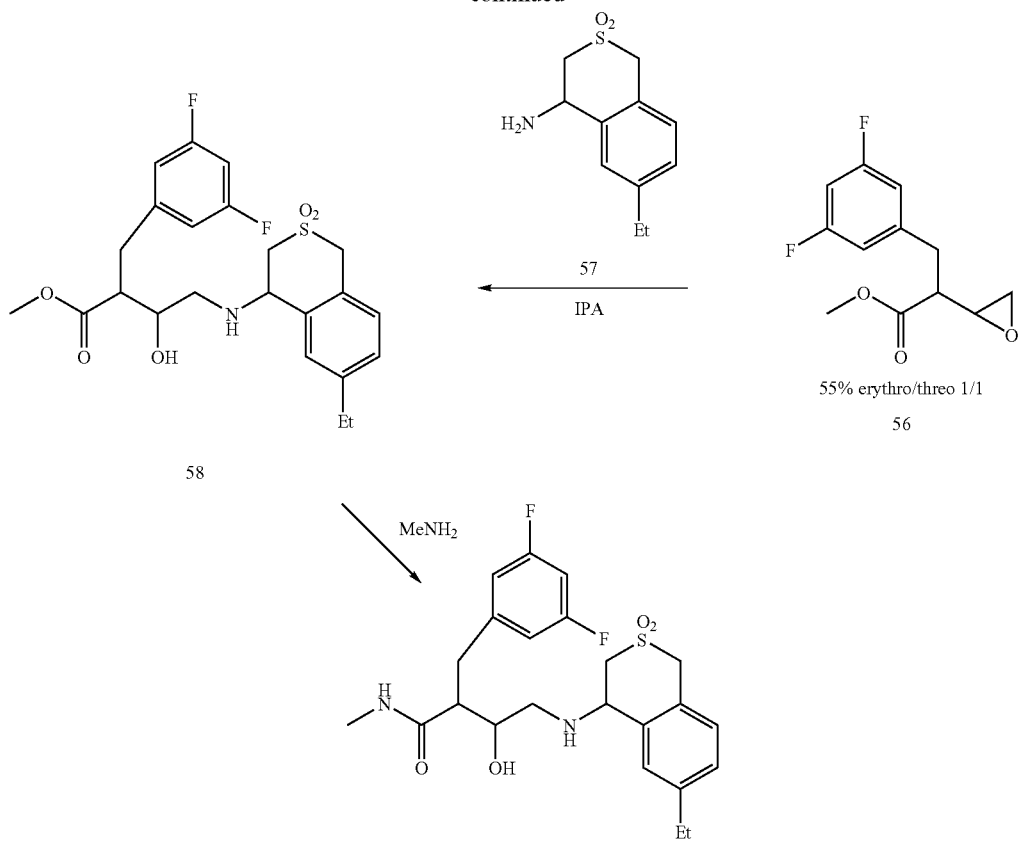

Alkylation of ester 53 with bromide 54 affords the aryl substituted ester 55. Intermediate 55 is epoxidized with m-chloroperbenzoic acid to give epoxide 56. Nucleophilic opening of epoxide 56 with amine 57 affords intermediate 58. Treatment of intermediate 58 with methylamine affords 2-(3, 5-Difluoro-benzyl)-4-(6-ethyl-2,2-dioxo-2λ$^6$-isothiochroman-4-ylamino)-3-hydroxy-N-methyl-butyramide (59).

Further examples of compounds that can be made according to the present invention are found in the examples below.

EXAMPLE 349

Preparation of 4-(3,5-DIFLUORO-PHENYL)-1-(7-ETHYL-1,2,3,4-TETRAHYDRO-NAPHTHALEN-1-YLAMINO)-3—OXAZOL-2-YL-BUTAN-2-OL

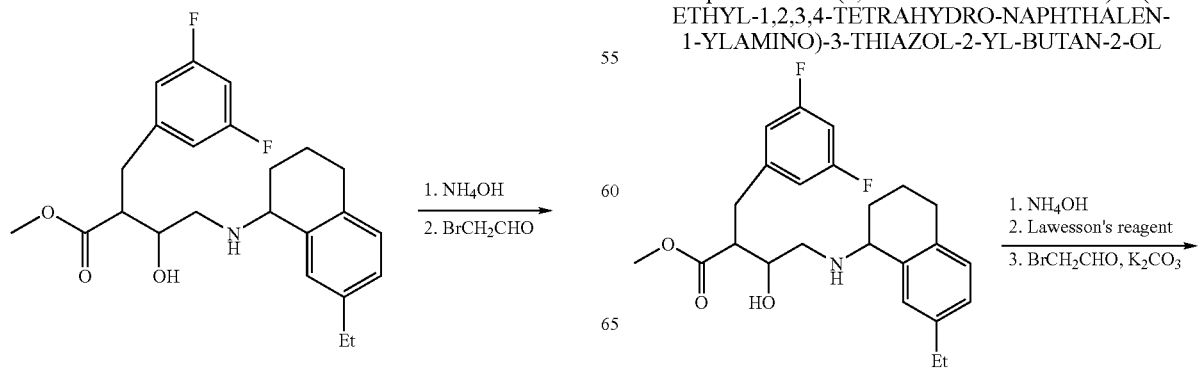

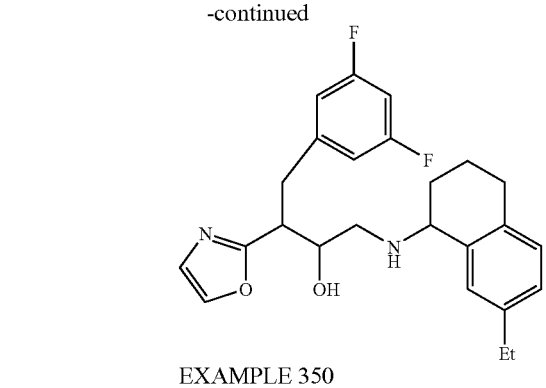

EXAMPLE 350
Preparation of 4-(3,5-DIFLUORO-PHENYL)-1-(7-ETHYL-1,2,3,4-TETRAHYDRO-NAPHTHALEN-1-YLAMINO)-3-THIAZOL-2-YL-BUTAN-2-OL

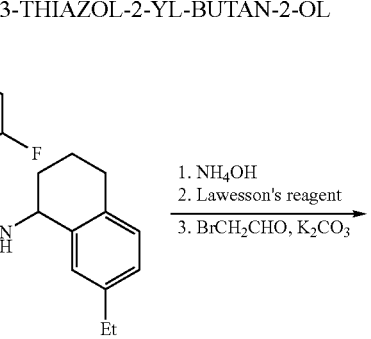

-continued

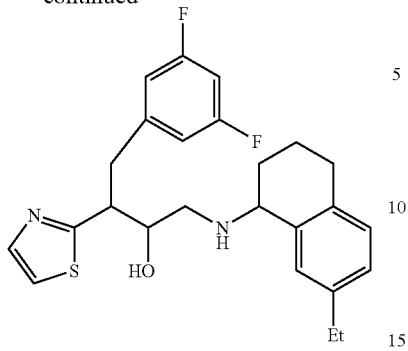

EXAMPLE 351

4-(3,5-DIFLUORO-PHENYL)-1-(7-ETHYL-1,2,3,4-TETRAHYDRO-NAPHTHALEN-1-YLAMINO)-3-(1H-IMIDAZOL-2-YL)-BUTAN-2-OL

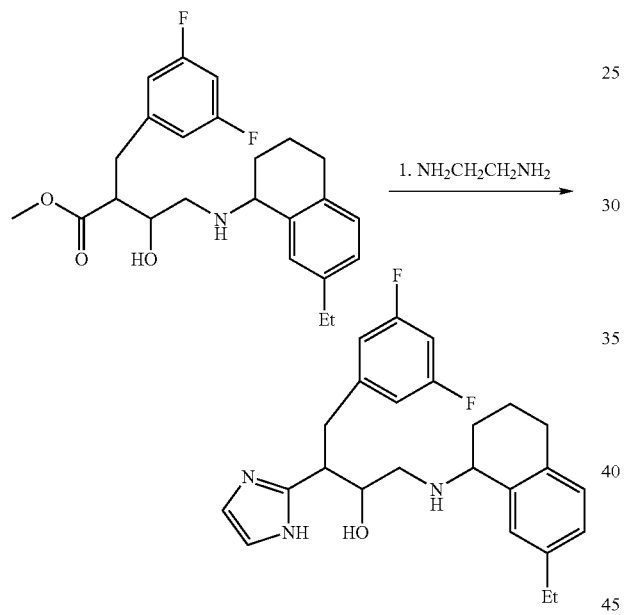

EXAMPLE 352

Preparation of 4-(3,5-DIFLUORO-PHENYL)-1-(7-ETHYL-1,2,3,4-TETRAHYDRO-NAPHTHALEN-1-YLAMINO)-3-(5-ETHYL-2H-[1,2,4]TRIAZOL-3-YL)-BUTAN-2-OL

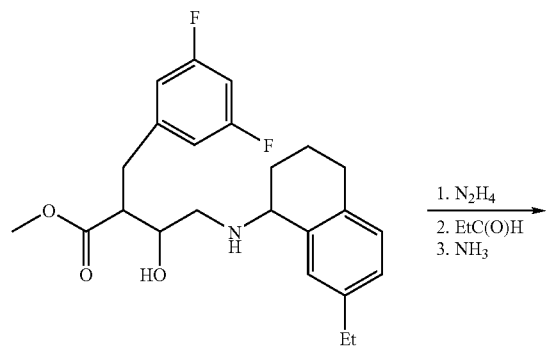

-continued

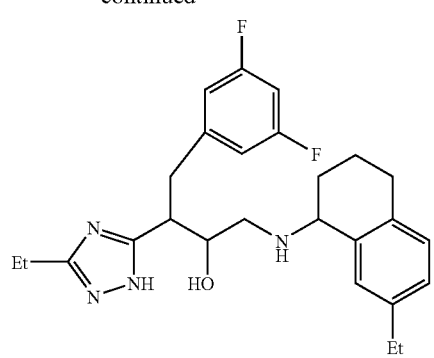

EXAMPLE 353

Preparation of 4-(3,5-DIFLUORO-PHENYL)-1-(7-ETHYL-1,2,3,4-TETRAHYDRO-NAPHTHALEN-1-YLAMINO)-3-(5-METHYL-2H-PYRAZOL-3-YL)-BUTAN-2-OL

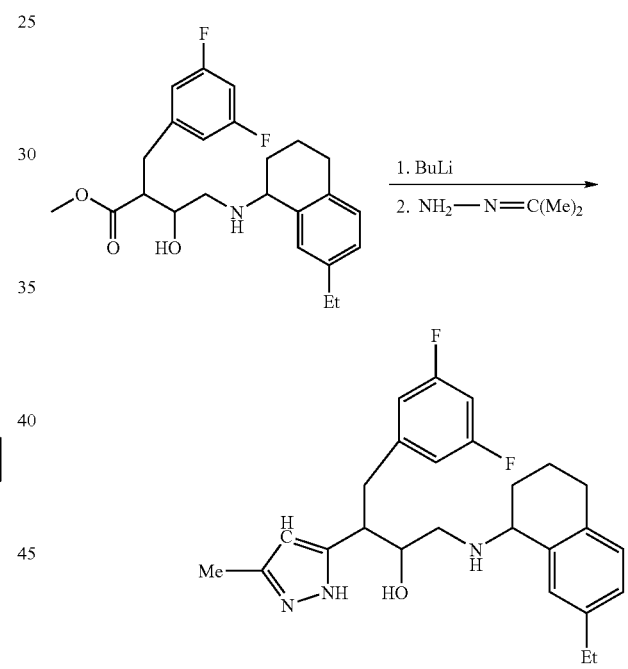

EXAMPLE 354

Preparation of 1-[1-(3-TERT-BUTYL-PHENYL)-CYCLOHEXYLAMINO]-4-(3,5-DIFLUORO-PHENYL)-3-TETRAZOL-1-YL-BUTAN-2-OL

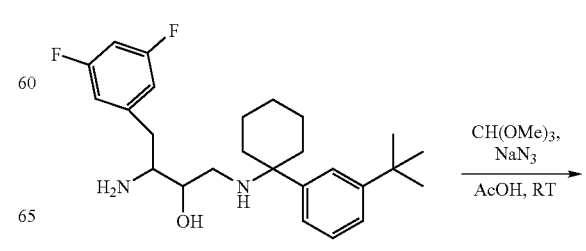

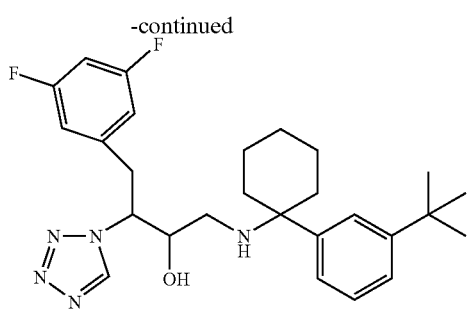

EXAMPLE 355

Preparation of 1-[1-(3-tert-Butyl-phenyl)-cyclohexylamino]-4-(3,5-difluoro-phenyl)-3-[1,2,3]triazol-1-yl-butan-2-ol (3)

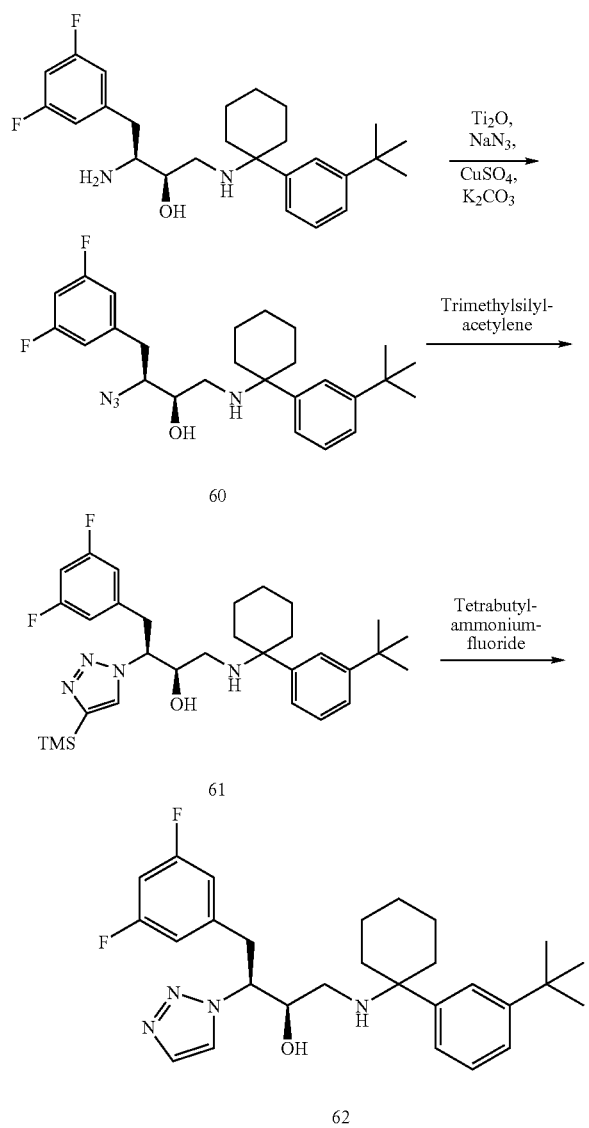

Step 1: Preparation of 3-Azido-1-[1-(3-tert-butyl-phenyl)-cyclohexylamino]-4-(3,5-difluoro-phenyl)-butan-2-ol (60)

Preparation of the Trifylazide Solution: $NaN_3$ (0.262 g, 4.028 mmol., 9.8 eq) was added to a round bottom flask, and dissolved in 0.68 mL of de-ionized water and 1.2 mL of $CH_2Cl_2$. The reaction was cooled to 0° C. using an ice bath. To the round bottom flask was added $Tf_2O$ (0.231 g, 0.13 mL, 0.818 mmol., 1.99 eq.) slowly. The reaction stirred for 2 hours at 0° C., and then was warmed to room temperature. The $CH_2Cl_2$ layer was extracted and the water layer was rinsed with $CH_2Cl_2$ (twice with 6 mL). All organic layers were combined and washed with sat. $NaHCO_3$.

To a separate round bottom flask, 3-Amino-1-[1-(3-tert-butyl-phenyl)-cyclohexylamino]-4-(3,5-difluoro-phenyl)-butan-2-ol (0.177 g, 0.411 mmol., 1 eq), $K_2CO_3$ (0.085 g, 0.6165 mmol., 1.5 eq), $CuSO_4$ (0.001 g, 0.0041 mmol., 0.01 eq), de-ionized water (1.35 mL), and methanol (2.7 mL) were added. The trifylazide solution above was added to the round bottom flask and stirred at room temperature over night. The organic layer was concentrated under reduced pressure. The wafer layer was diluted with 7.5 mL de-ionized water. The pH of the solution was lowered to about 6 using a pH 6.2 0.25M phosphate buffer. The water layer was extracted with EtOAc (three times, 10 mL each). The pH of the water layer was lowered to pH 2. The solution was rinsed with EtOAc (three times, 10 mL each). The EtOAc layers were combined and dried with $MgSO_4$, filtered, and concentrated under reduced pressure to provide 0.211 grams of compound 60. MS m/z 457.2 (M–H) (retention time: 2.254, method; [1]).

Step 2: Preparation of 1-[1-(3-tert-Butyl-phenyl)-cyclohexylamino]-4-(3,5-difluoro-phenyl)-3-(4-trimethylsilanyl-[1,2,3]triazol-1-yl)-butan-2-ol (61)

Compound 60 (0.211 grams, 0.463 mmol.) was dissolved in trimethylsilylacetylene (5 mL) and stirred at room temperature for fourteen days. The reaction gave 0.17 grams of compound 61. MS m/z 555.3 (M–H) (retention time: 2.385, method: [1]).

Step 3: Preparation of 1-[1-(3-tert-Butyl-phenyl)-cyclohexylamino]-4-(3,5-difluoro-phenyl)-3-[1,2,3]triazol-1-yl-butan-2-ol (62)

Compound 61 (0.17 g, 0.306 mmol., 1.0 eq) was dissolved in 5 mL dry THF and added to a round bottom flask. Tetrabutylammoniumfluoride (1.0 M in THF) (0.46 mL, 0.460 mmol.) was added slowly to the round bottom flask. The reaction was then heated to reflux (70° C.) for three hours. The reaction mixture was then concentrated in vacuo and the product 62 isolated after flash chromatographic purification.

$^1$H NMR ($CD_3OD$) δ 7.68 (s, 1H), 7.54 (s, 1H), 7.45 (s, 1H), 7.27-7.22 (m, 3H), 6,69 (t, J=9 Hz, 1H), 6.56-6.54 (d, J=6 Hz, 2H), 3.99 (m, 1H), 3.37-3.20 (m, 5H), 2.16-2.05 (m, 4H), 1.81-1.66 (m, 4H), 1.51-1.40 (m, 2H), 1.30 (s, 9H)

MS m/z 483.3 (M–H) (retention time: 2.045, method: [1]).

EXAMPLE 356

Preparation of 2-(3,5-DIFLUOROPHENYL)-1-OXIRANYLETHANOL (67) and 2-[2-(3,5-DIFLUOROPHENYL)-1-METHOXYETHYL]OXIRANE (68)

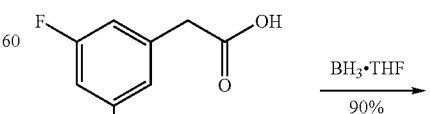

63

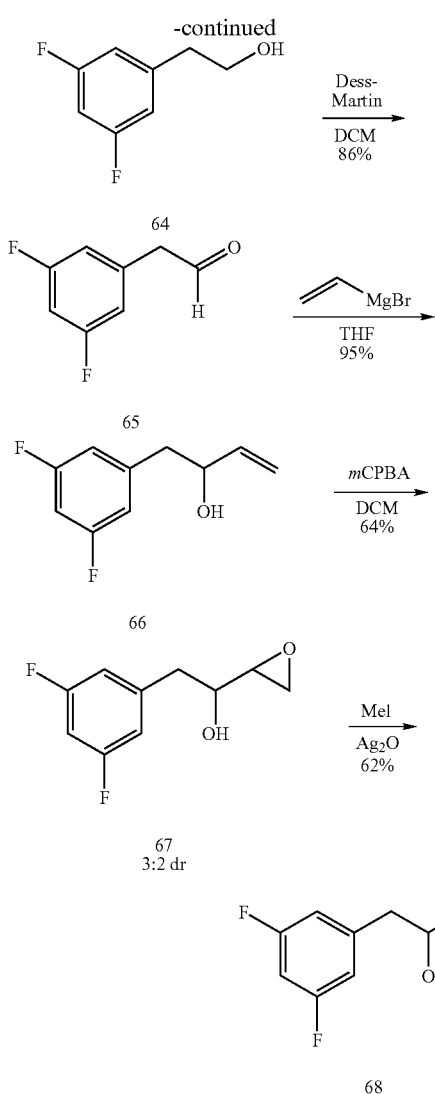

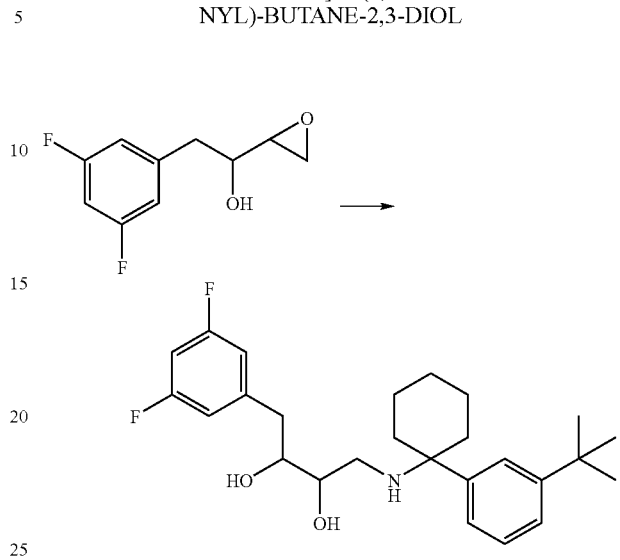

The synthesis of 2-(3,5-Difluorophenyl)-1-oxiranylethanol (67) followed that reported in Kurihara, M. et al. *Tetrahedron Lett*, 1999, 40, 3183-3184 for the synthesis of 2-phenyl-1-oxiranylethanol. 2-(3,5-Difluorophenyl)-1-oxiranylethanol: $R_f$=0.42 (30% EtOAc/hexanes); retention time (min)=1.350 (method [1]); MS(ESI) 242.3 (84), 201.3 (26), 183.3 (100).

The synthesis of 2-[2-(3,5-Difluorophenyl)-1-methoxyethyl]oxirane (68) followed the method of Boeckman, R. K. Jr.; Liu, X. *Synthesis* 2002, 2138-2142. 2-(3,5-Difluorophenyl)-1-oxiranylethanol (67) (411 mg, 2.05 mmol) was combined with silver(I) oxide (1.934 g, 8.34 mmol) in iodomethane (5.2 mL, 83.3 mmol), and heated to gentle reflux (45° C. bath) for 20 h. The mixture was then diluted with diethyl ether, filtered through diatomaceous earth, and the filtrate concentrated under reduced pressure to give 68. Flash chromatography (10% EtOAc/hexanes elution) afforded 273 mg (63%) of the product as an oil: $R_f$=0.26 (10% EtOAc/hexanes); retention time (min)=1.895 (major), 1.951 (minor), method [1]; MS (ESI) 256.3 (100), 237.3 (22), 215.3 (26).

EXAMPLE 357

Preparation of 1-[1-(3-TERT-BUTYLPHENYL)CYCLOHEXYLAMINO]-4-(3,5-DIFLUOROPHENYL)-BUTANE-2,3-DIOL A solution of 1-(3-tert-Butylphenyl)cyclohexylamine (266 mg, 1.15 mmol) in isopropanol (2 mL) was added to 2-(3,5-Difluorophenyl)-1-oxiranylethanol (67) (209 mg, 1.05 mmol) in a sealed tube. The flask was sealed and heated to 90° C. for 7 h. The reaction mixture was concentrated under vacuum, and purified by flash chromatography (0-5% MeOH/CH$_2$Cl$_2$ elution) to give a white foam as product (260 mg, 57%): $R_f$=0.53 in 10% MeOH/CH$_2$Cl$_2$; retention time (min)=1.95, method [1]; MS (ESI) 432.4.

EXAMPLE 358

Preparation of 1-[1-(3-TERT-BUTYLPHENYL)CYCLOHEXYLAMINO]-4-(3,5-DIFLUOROPHENYL)-3-METHOXY-BUTAN-2-OL

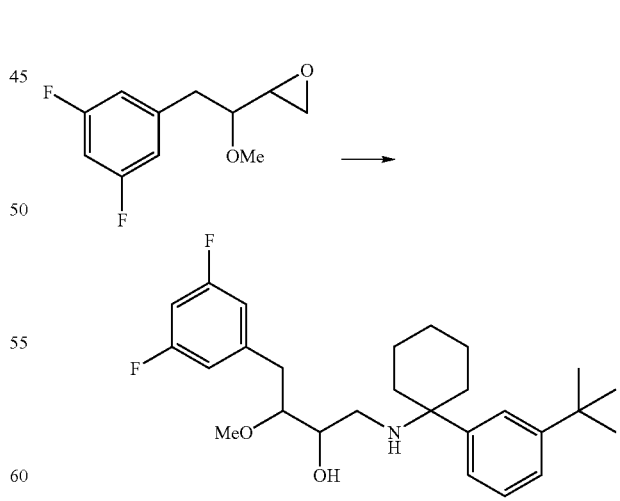

This procedure follows that for the synthesis of 1-[1-(3-tert-butylphenyl)cyclohexylamino]-4-(3,5-difluorophenyl)-butane-2,3-diol in EXAMPLE 357, except 2-[2-(3,5-Difluorophenyl)-1-methoxyethyl]oxirane (68) is used instead of 2-(3,5-Difluorophenyl)-1-oxiranylethanol (67) to give the title compound. Yield: 168 mg (55%). Retention time (min)= 2.11, method [1]; MS (ESI) 446.5.

Other analogs of this type include:

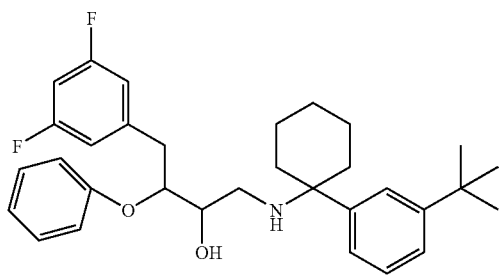

1-[1-tert-Butyl-phenyl)-cyclohexylamino]-4-(3,5-difluoro-phenyl)-3-phenoxy-butan-2-ol

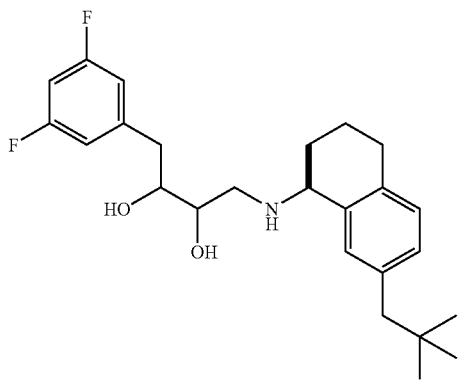

1-(3,5-Difluoro-phenyl)-4-[7-(2,2-dimethyl-propyl)-1,2,3,4-tetrahydro-naphthalen-1-ylamino]-butane-2,3-diol

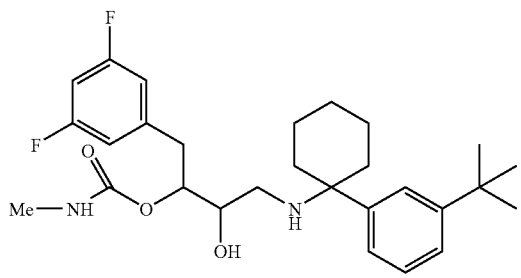

Methyl-carbamic acid 3-[1-(3-tert-butyl-phenyl)-cycloheylamino]-1-(3,5-difluoro-benzyl)-2-hydroxypropyl ester

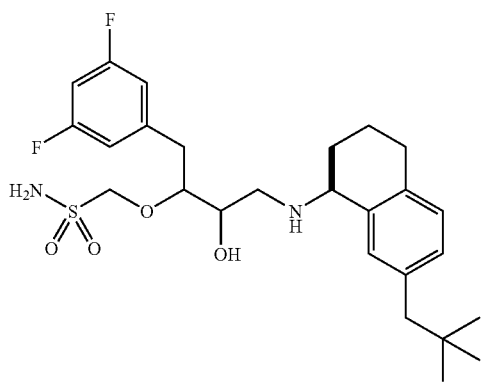

{1-(3,5-Difluoro-benzyl)-3-[7-(2,2-dimethyl-propyl)-1,2,3,4-tetrahydro-naphthalen-1-ylamino]-2-hydroxy-propoxy}-methanesulfonamide

EXAMPLE 359

Preparation of 1-[3-[1-(3-TERT-BUTYL-PHENYL)-CYCLOHEXYLAMINO]-1-(3,5-DIFLUORO-BENZYL)-2-HYDROXY-PROPYL]-AZEPAN-2-ONE (74) and 1-[3-[1-(3-TERT-BUTYL-PHENYL)-CYCLOHEXYLAMINO]-1-(3,5-DIFLUORO-BENZYL)-2-HYDROXY-PROPYL]-PYRROLIDIN-2-ONE (75).

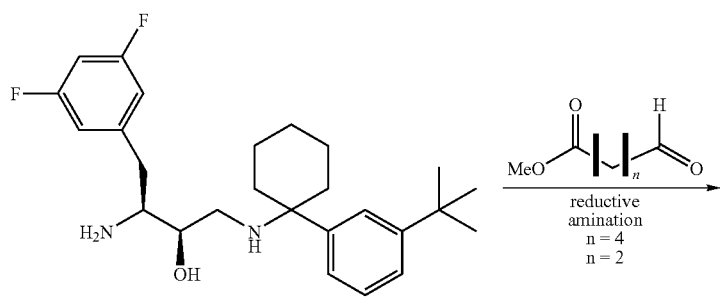

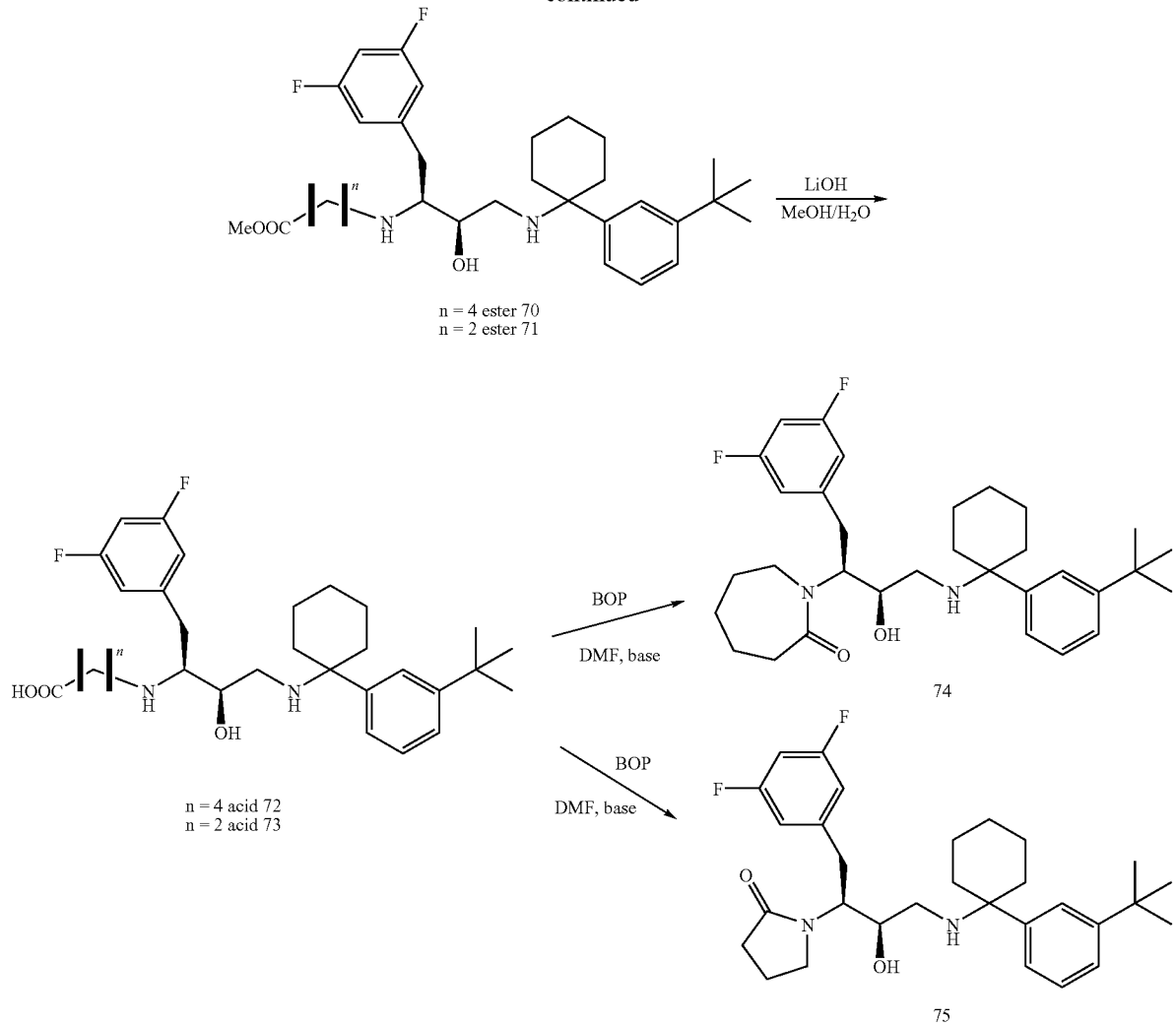

n = 4 ester 70
n = 2 ester 71 n = 4 acid 72
n = 2 acid 73

74

75

Preparation of Ester (70):

The amine (68) (0.1 g, 0.23 mM), adipic semialdehyde methyl ester (0.05 mL, 0.35 mM), and polymer supported borohydride (2.5 M/g, 0.19 g, 0.46 mM) in MeOH (10 mL) was stirred overnight at RT. Polymer supported borohydride was filtered off, filtrate was concentrated and purified on Biotage (eluted with 4% MeOH in $CH_2Cl_2$). Yield 0.12 g (92%) of ester (70).

Retention time (min)=1.91, method [1]; MS (ESI) 559.5

Hydrolysis of Ester (70):

An ester (70) (0.12 g, 0.22 mM) treated with LiOH hydride (0.05 g) in water (0.25 mL) and MeOH (0.25 mL) was stirred overnight at RT. The solvent was stripped and aq. citric acid was added until pH 3, The acid (72) was extracted with $CH_2Cl_2$ (4×). Yield 0.105 g.

Retention time (min)=4.20, Method [3]; MS (ESI) 545.5

Preparation of 1-[3-[1-(3-tert-Butyl-phenyl)-cyclohexylamino]-1-(3,5-difluoro-benzyl)-2-hydroxy-propyl]-azepan-2-one (74):

An acid (72) (0.10 g, 0.18 mM) in 10 mL of DMF was treated with BOP (0.09 g, 0.20 mM) and $NaHCO_3$ (0.09 g, 1.08 mM). The reaction mixture was stirred o/n at RT and then poured into water (100 mL) and extracted with EtOAc (3×20 mL). The organic layer was combined, washed with brine, dried and concentrated. Crude yield 0.08 g. The product was purified by HPLC. Final yield 0.009 g (9.4%).

Retention time (min)=2.28, method [1]; MS (ESI) 527.3.

Preparation of 1-[3-[1-(3-tert-Butyl-phenyl)-cyclohexylamino]-1-(3,5-difluoro-benzyl)-2-hydroxy-propyl]-pyrrolidin-2-one (75):

Lactam (75) was synthesized according to the procedure described above for lactam (74).

Retention time (min)=2.06, method [1]; $^1H$ NMR (300 MHz, $CDCl_3$) δ 7.69 (s, 1H), 7.50-7.25 (m, 3H), 6.65 (m, 3H), 4.17 (m, 1H), 3.93 (m, 1H), 3.28 (m, 1H), 3.15 (m, 1H), 2.88 (m, 1H), 2.76-2.57 (m, 5H), 2.17-1.95 (m, 4H), 1.80-1.61 (m, 5H), 1.45 (m, 2H), 1.35 (s, 9H); $^{13}C$ NMR (75 MHz, $CDCl_3$); δ 176.4, 152.8, 134.1, 128.7, 126.1, 124.6, 124.5, 11.1, 102.1, 67.5, 64.3, 54.5, 44.4, 44.0, 34.9, 34.0, 33.1, 32.3, 31.1, 30.7, 24.8, 21.9, 18.2; MS (ESI) 499.3.

EXAMPLE 360

Preparation of 2-[3-[1-(3-TERT-BUTYL-PHENYL)-CYCLOHEXYLAMINO]-1-(3,5-DIFLUORO-BENZYL)-2-HYDROXY-PROPYL]-2,3,4,5-TETRAHYDRO-BENZO[C]AZEPIN-1-ONE (81)

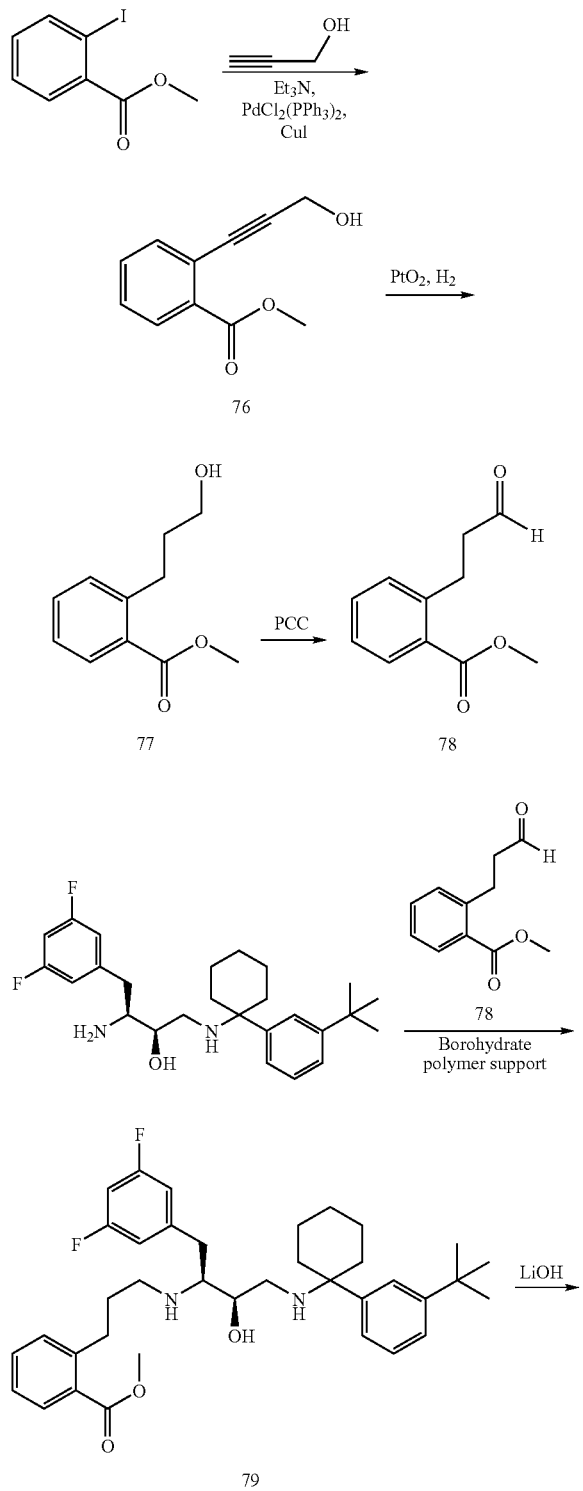

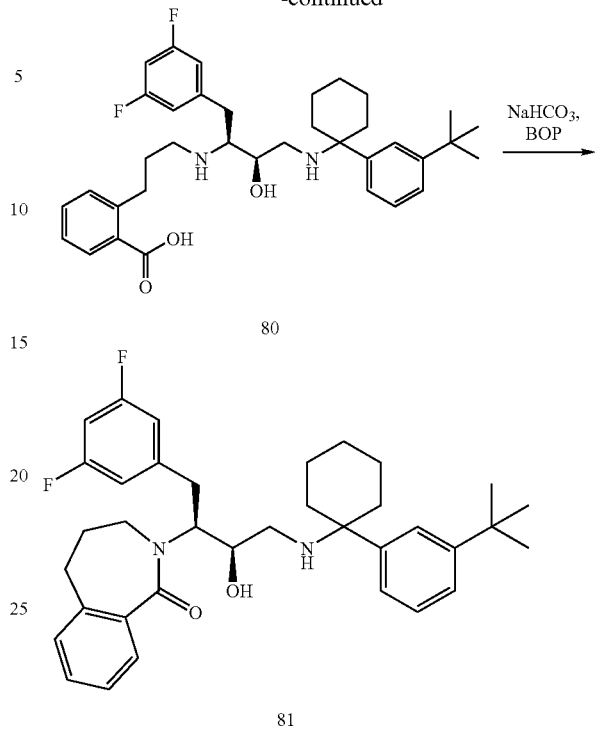

Step 1: Preparation of 2-(3-Hydroxy-prop-1-ynyl)-benzoic acid methyl ester (76)

2-Iodo-benzoic acid methyl ester (2.0 g, 7.632 mmol., 1 eq) with propargyl alcohol (0.513 g, 9.158 mmol, 1.2 eq), triethylamine (25 mL), PdCl$_2$(PPh$_3$)$_2$ (0.121 g, 0.153 mmol., 0.02 eq), and copper(I) iodide (0.014 g, 0.076 mmol., 0.01 eq) were added to a round bottom flask. The reaction mixture was heated to 75° C. for three days. For the workup, the reaction was tittered through Celite and concentrated. The crude compound was purified by silica column: (10% EtOAc:Hexanes, (250 mL), then 50% EtOAc:Hexanes, (500 mL)). The reaction provided 0.59 grams of pure compound (76). MS m/z 173.3 (M−OH) (retention time: 1.349, method: [1]).

Step 2: Preparation of 2-(3-Hydroxy-propyl)-benzoic acid methyl ester (77)

Compound (76) (0.59 g, 3.10 mmol.) was dissolved in 5 mL EtOAc and placed in a hydrogenation bottle. To the bottle, PtO$_2$ (0.06 g, 10.2% of the grams of compound (76)) was added. The bottle was sealed and 50 psi of hydrogen was added. It was then placed on the shaker for 2 hours. The reaction mixture was filtered with Celite and concentrated. The reaction provided 0.53 g of compound (77).

$^1$H NMR (CDCl$_3$) δ 7.88-7.86 (d, J=6 Hz, 1H), 7.44-7.41 (d, J=9 Hz, 1H), 7.28 (t, J=9 Hz 1H), 7.25 (t, J=6 Hz, 1H), 3.89 (s, 3H), 3.63 (t, J=9 Hz, 2H), 3.06 (t, J=9 Hz 2H), 1.96-1.85 (m, 2H).

Step 3: Preparation of 2-(3-Oxo-propyl)-benzoic acid methyl ester (78)

Added to a round bottom flask was PCC (0.788 g, 3.66 mmol., 1.3 eq) and CH$_2$Cl$_2$ (35 mL). The reaction was cooled to 0° C. Compound (77) (0.53 g, 2.72 mmol.) dissolved in 5 mL CH$_2$Cl$_2$, was added slowly to the round bottom flask. The reaction stirred over night (0° C. to room temperature), was filtered through Celite, and was rinsed with 50 mL of diethyl ether. The filtrate was concentrated under reduced pressure. The reaction provided 0.79 g of compound (78).

$^1$H NMR (CDCl$_3$) δ 9.58 (s, 1H), 7.97-7.94 (d, J=9 Hz, 1H), 7.47-7.45 (d, J=6 Hz, 1H), 7.30-7.25 (bs, 2H), 3.91 (s, 3H), 3.30 (t, J=6 Hz, 2H), 2.84 (t, J=6 Hz, 2H)

MS m/z 161.1 (M–O$_2$) (retention time; 1.665, method: [1]).

Step 4: Preparation of 2-{3-[3-[1-(3-tert-Butyl-phenyl)-cyclohexylamino]-1-(3,5-difluoro-benzyl)-2-hydroxy-propylamino]-propyl}-benzoic acid methyl ester (79)

3-Amino-1-[1-(3-tert-butyl-phenyl)-cyclohexylamino]-4-(3,5-difluoro-phenyl)-butan-2-ol (0.1 g, 0.23 mmol, 1.0 eq), compound (78) (0.066 g, 0.345 mmol, 1.5 eq), Borohydrate (polymer support, 2.5 mmol/g) (0.184 g, 0.46 mmol, 2.0 eq), and 10 mL methanol were added to a round bottom flask. The reaction stirred at room temperature over night. The reaction was then filtered through Celite and rinsed with 5 mL methanol. The filtrate was concentrated under reduced pressure to provide 0.136 g of crude product. The crude material was purified using a silica column (100% EtOAc (150 mL), then 10% methanol in CH$_2$Cl$_2$ (150 mL)) to provide 0.052 g of pure compound (79). MS m/z 607.5 (M–H) (retention time: 2.21, method: [1]).

Step 5: Preparation of 2-{3-[3-[1-(3-tert-Butyl-phenyl)-cyclohexylamino]-1-(3,5-difluoro-benzyl)-2-hydroxy-propylamino]-propyl}-benzoic acid (80)

Compound (79) (0.052 g, 0.0856, 1.0 eq), lithium hydroxide monohydrate (0.0198 g, 0.471 mmol, 5.5 eq) and one mL each of wafer and methanol were added to a round bottom flask, and stirred at room temperature overnight. The reaction was then treated with 0.05 g of KOH, stirred at 40° C. for one hour, and concentrated under reduced pressure. The solution was treated with 0.5 M citric acid until the pH was 3. The solution was rinsed four times with 3 mL CH$_2$Cl$_2$. All CH$_2$Cl$_2$ washes were combined and dried with MgSO$_4$. The MgSO$_4$ was removed by filtration, and the compound was concentrated by reduced pressure. The reaction gave 0.036 grams of compound (80).

MS m/z 593.5 (M–H) (retention time: 1.92, method; [1]).

Step 6: Preparation of 2-[3-[1-(3-tert-Butyl-phenyl)-cyclohexylamino]-1-(3,5-difluoro-benzyl)-2-hydroxy-propyl]-2,3,4,5-tetrahydro-benzo[c]azepin-1-one (81)

Compound (80) (0.036 g, 0.061 mmol, 1.0 eq) was added to a round bottom flask with NaHCO$_3$ (0.031 g, 0.3642 mmol, 6.0 eq), (benzotriazol-1-yloxy)tris(dimethylamine) phosphonium hexafluorophosphate (BOP) (0.0295 g, 0.067 mmol, 1.1 eq), and 5 mL of DMF. The reaction stirred at room temperature overnight. The reaction was poured into 25 mL water and extracted with EtOAc three times, 20 mL each. The EtOAc was treated with brine (30 mL) and dried with MgSO$_4$. The MgSO$_4$ was removed by filtration, and the solvent was removed by reduced pressure. The reaction gave 0.04 g of crude product. The reaction was purified by reversed phase HPLC providing 4.5 mg of pure compound (81).

$^1$H NMR (CDCl$_3$) δ 7.68 (s, 1H), 7.40-7.32 (m, 6H), 7.06-7.03 (d, J=6 Hz, 1H), 6.75-6.72 (d, J=9 Hz, 2H), 6.63 (t, J=9 Hz, 1H), 4.15-4.05 (bs, 2H), 3.55-3.35 (bs, 2H), 2.90-2.80 (m, 2H), 2.70-2.55 (m, 2H), 2.45-2.35 (m, 2H), 2.15-2.05 (m, 2H), 1.85-1.75 (m, 4H), 1.65-1.45 (m, 6H), 1.29 (s, 9H)

MS m/z 575.3 (M–H) (retention time: 2.40, method; [1]).

Various amines that may be used for the preparation of compounds of formula (I) are described in the Examples below.

EXAMPLE 361

Preparation of 1-(3-ISOPROPYLPHENYL)CYCLO HEXANAMINE HYDROCHLORIDE

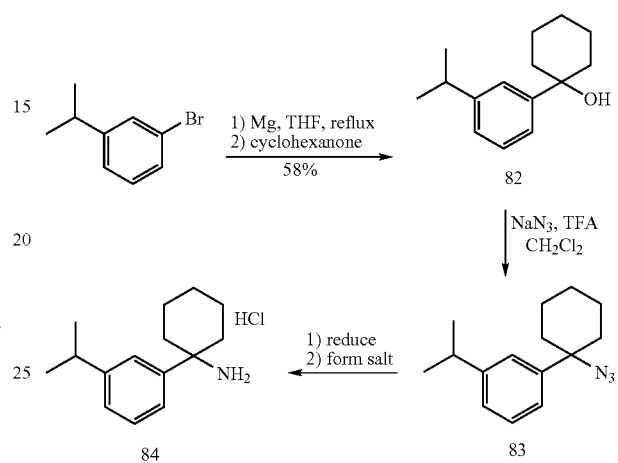

Step 1. Preparation of 1-(3-isopropylphenyl)cyclohexanol (82).

To 1.2 g (50 mmol) of magnesium turnings in 15 mL of dry THF is added a small crystal of iodine followed by 40 μL of dibromoethane. This mixture is placed in a water bath at 50° C. and 3-isopropylbromobenzene (5.0 g, 25 mmol) in 15 mL of dry tetrahydrofuran (THF) is added dropwise over 20 min, while the bath temperature is raised to 70° C. The mixture is stirred and refluxed for 40 additional min. The solution is cooled in an ice-water bath and cyclohexanone (2.0 mL, 19 mmol) in 10 mL of dry THF is added dropwise over 15 min. The ice bath is removed and the mixture is allowed to warm to ambient temperature over 1 h. The solution is decanted into aqueous saturated NH$_4$Cl and combined with an ether wash of the residual magnesium turnings. The organic phase is washed twice more with aqueous NH$_4$Cl, dried over anhydrous Na$_2$SO$_4$, filtered, and concentrated. Chromatography on silica gel, eluting with 10% ethyl acetate in heptane, affords 2.7 g (12 mmol, 60%) of 1-(3-isopropylphenyl)cyclohexanol 82 as an oil: $^1$H NMR (CDCl$_3$) δ 7.39 (m, 1 H), 7.3 (m, 2 H), 7.12 (m, 1 H), 2.92 (m, 1 H), 1.84-1.54 (m, 10 H), 1.26 (d, J=7 Hz, 6 H).

Step 2. Preparation of 1-(3-isopropylphenyl)cyclohexylazide (83).

To 3.20 g (14.7 mmol) of 1-(3-isopropylphenyl)cyclohexanol 82 in 60 mL of CH$_2$Cl$_2$ under nitrogen is added 2.10 g (32.3 mmol) of sodium azide. The stirred suspension is cooled to –5° C. and a solution of trifluoroacetic acid (9.0 mL, 120 mmol) in 35 mL of dichloromethane is added dropwise over 1 h. The resulting suspension is stirred at 0° C. for an additional hour. 10 mL of water is added dropwise to the cold, vigorously stirred mixture, followed by dropwise addition of a mixture of 10 mL of water and 10 mL of concentrated ammonium hydroxide. After 30 min the mixture is poured into a separatory funnel containing 350 mL of a 1:1 mixture of heptane and ethyl acetate, and 100 mL of water. The organic phase is washed with an additional portion of water, followed successively by 1 N KH$_2$PO$_4$, water, and brine. It is then dried over anhydrous Na$_2$SO$_4$, filtered and concentrated to afford 3.6 g (14.7 mmol, 100%) of 83 as a pale yellow oil: $^1$H NMR (CDCl$_3$) δ 7.3 (m, 2 H), 7.25 (m, 1 H), 7.16 (m, 1 H), 2.92 (m, 1 H), 2.01 (m, 2 H), 1.83 (m, 2 H), 1.73-1.64 (m, 5 H), 1.3 (m, 1 H), 1.26 (d, J=7 Hz, 6 H).

Step 3. Preparation of 1-(3-isopropylphenyl)cyclohexanamine hydrochloride (84).

To 1-(3-isopropylphenyl)cyclohexylazide 83 (2.7 g, 11 mmol) in 200 mL of ethanol is added 20 mL of glacial acetic acid and 0.54 g of 10% palladium on carbon. The mixture is evacuated and placed under 16 psi of hydrogen, with shaking, for 2.5 h. The reaction mixture is filtered, the catalyst is washed with ethanol, and the solvents are removed in vacuo. Residual acetic acid is removed by chasing the residue with toluene. The acetate salt is dissolved in ethyl acetate and 1 N NaOH is added. The organic phase is washed with more 1 N NaOH and then with water, dried over Na$_2$SO$_4$, filtered and concentrated. The residue is dissolved in ether and ethereal HCl (concentrated HCl in ether which has been stored over MgSO$_4$) is added to afford a white solid. This is filtered, washed with ether, collected as a solution in dichloromethane, and concentrated to afford 2.1 g (8.3 mmol, 75%) of hydrochloride 84 as a white solid: $^1$H NMR (CDCl$_3$) δ 8.42 (br s, 3 H), 7.43 (m, 2 H), 7.25 (m, 1 H), 7.15 (m, 1 H), 2.92 (hept, J=7 Hz, 1 H), 2.26 (m, 2 H), 2.00 (m, 2 H), 1.69 (m, 2 H), 1.45-1.3 (m, 4 H), 1.24 (d, J=7 Hz, 6 H); IR (diffuse reflectance) 2944, 2864, 2766, 2707, 2490, 2447, 2411, 2368, 2052, 1599, 1522, 1455, 1357, 796, 704 cm$^{-1}$. MS (EI)m/z (relative intensity) 217 (M+,26), 200 (13), 175 (18), 174 (99), 157 (15), 146 (23), 132 (56), 131 (11), 130 (16), 129 (18). HRMS (ESI) calculated for C$_{15}$H$_{23}$N+H$_1$ 218.1909, found 218.1910. Anal. Calculated for C$_{15}$H$_{23}$N.HCl: C, 70.98; H, 9.53; N, 5.52; Cl, 13.97. Found: C, 70.98; H, 9.38; N, 5.49.

EXAMPLE 362

Preparation of 1-(3-ETHYL-PHENYL)-CYCLO-HEXYLAMINE from 1-(1-AZIDO-CYCLO-HEXYL)-3-ETHYL-BENZENE.

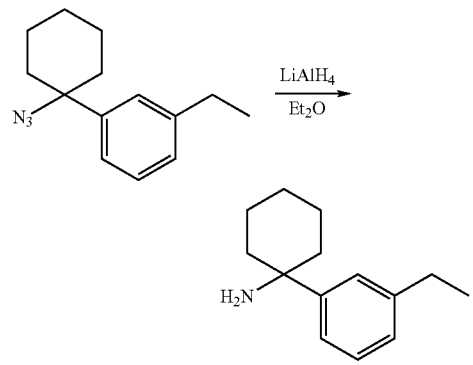

A solution of 1-(1-azido-cyclohexyl)-3-ethyl-benzene (1.94 g, 8.39 mmol) in Et$_2$O (8 mL) was added dropwise to a suspension of lithium aluminum hydride (0.31 g, 8.17 mmol) in THF (30 mL). This was stirred at room temperature under N$_2$ (g) inlet for 3 h, whereupon the reaction was quenched with 1.0N NaOH. The reaction mixture was then partitioned between EtO$_2$ and 1N HCl, The aqueous layer was collected and basified with 2N NH$_4$OH and extracted with CHCl$_3$. The organic layer was separated, dried (Na$_2$SO$_4$), filtered, and concentrated under reduced pressure. The crude product was used without further purification: mass spec (Cl) 187.1 (M−16).

Scheme 4.
PREPARATION OF 8-(3-ISOPROPYLPHENYL)-1,4-DIOXA-SPIRO[4.5]DECANE-8-AMINE ACETATE

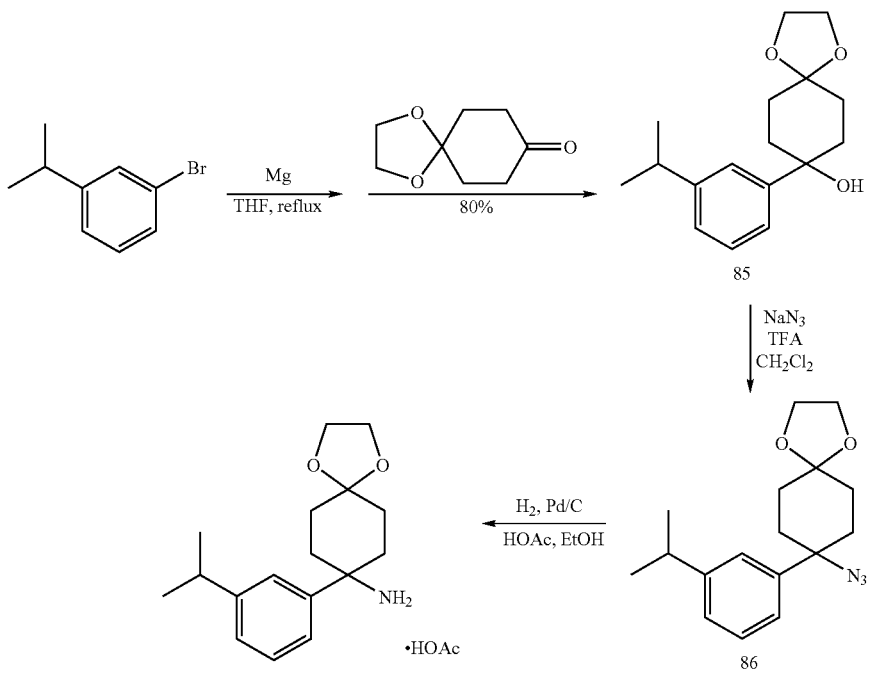

Step 1. Preparation of 8-(3-isopropylphenyl)-1,4-dioxa-spiro[4.5]decane-8-alcohol (85).

A solution of 3-bromoisopropylbenzene (25 mmol) in 20 mL of dry THF is added dropwise over 20 min to 1.22 g (50 mmol) of magnesium turnings in 10 mL of refluxing THF under nitrogen and the mixture is refluxed for an additional 25 min to form the Grignard reagent. The Grignard solution is cooled and added by cannula to a suspension of CuBr-dimethylsulfide complex (0.52 g, 2.5 mmol) in dry THF at −25° C. The suspension is stirred at −25° C. for 20 min, and then a solution of 1,4 cyclohexanedione, monoethylene ketal (3.9 g, 25 mmol) in 15 mL of THF is added dropwise over 5 min. The mixture is allowed to gradually warm to ambient temperature. After chromatography over silica gel, eluting with 20% to 30% ethyl acetate in heptane, alcohol 85 (5.6 g, 20 mmol, 80%) as a colorless oil which crystallizes to a white solid on cooling: $^1$H NMR (CDCl$_3$) δ 7.39 (s, 1 H), 7.33 (m, 1 H), 7.28 (t, J=7.5 Hz, 1 H), 7.13 (d, J=7.5 Hz, 1 H), 4.0 (m, 4 H), 2.91 (hept, J=7 Hz, 1 H), 2.15 (m, 4 H), 1.82 (br d, J=11.5 Hz, 2 H), 1.70 (br d, J=11.5 Hz, 2 H), 1.25 (d, J=7 Hz, 6 H); MS (Cl) m/z 259.2 (M−OH).

Step 2. Preparation of 8-(3-isopropylphenyl)-1,4-dioxa-spiro[4.5]decane-8-azide (86).

8-(3-isopropylphenyl)-1,4-dioxa-spiro[4.5]decane-8-alcohol 85 (5.5 g, 20 mmol) is reacted, with sodium azide (2.9 g, 45 mmol) and trifluoroacetic acid (TFA, 13 mL, 170 mmol) in 120 mL of CH$_2$Cl$_2$ at 0° C., allowing the reaction to stir 2 h after dropwise addition of the TFA. The reaction is quenched by dropwise addition of 18 mL of concentrated NH$_4$OH.

The mixture is taken up in water, ethyl acetate, and heptane, and the organic phase is washed three more times with water and once with brine. The solution is dried (Na$_2$SO$_4$), filtered, concentrated, and chromatographed over silica gel, eluting with 3% acetone in heptane. Concentration of the product-containing fractions affords 2.2 g (7.3 mmol, 36%) of 86 as a colorless oil: $^1$H NMR (CDCl$_3$) δ 7.33-7.26 (m, 3 H), 7.17 (m, 1 H), 3.98 (m, 4 H), 2.92 (hept, J=7 Hz, 1 H), 2.2-2.12 (m, 2 H), 2.07-1.95 (m, 4 H), 1.72 (m, 2 H), 1.26 (d, J=7 Hz, 6 H).

Step 3. Preparation of 8-(3-isopropylphenyl)-1,4-dioxa-spiro[4.5]decane-8-amine acetate (87).

2.2 g (7.3 mmol) of 8-(3-isopropylphenyl)-1,4-dioxa-spiro[4.5]decane-8-azide 86in 200 mL of ethanol is reduced under 16 psi of hydrogen in the presence of 0.7 g of 10% palladium on carbon for 4.5 h. Filtration and removal of solvents with a toluene azeotrope affords a white solid which is triturated with pentane to yield 2.14 g (6.4 mmol, 87%) of 87 as a white solid: $^1$H NMR (CDCl$_3$) δ 7.37-7.33 (m, 2 H), 7.30-7.26 (m, 1 H), 7.13 (d, J=7.5 Hz, 1 H), 5.91 (br, 3 H), 3.96 (m, 4 H), 2.90 (dept., J=7 Hz, 1 H), 2.32 (m, 2 H), 2.03 (s, 3 H), 2.0-1.85 (m, 4 H), 1.63 (m, 2 H), 1.25 (d, J=7 Hz, 6 H); MS (Cl) m/z 259.2 (M−NH$_2$).

EXAMPLE 363

Preparation of 1-TERT-BUTYL-3-IODO-BENZENE from 3-(TERT-BUTYL) ANILINE 3-(tert-Butyl)aniline (Oakwood, 8.0 g, 40.21 mmol) was slowly added to a cold solution of 12 N HCl (24.5 mL) white stirring over an ice/acetone bath in a three-neck round bottom flask equipped with a thermometer. A 2.9 M solution of sodium nitrite (16 mL) was added via addition funnel to the reaction flask at a rate so as maintain the temperature below 2° C. The solution was stirred for 30 min prior to being added to a reaction flask containing a 4.2 M solution of potassium iodide (100 mL), The reaction mixture was allowed to stir overnight while warming to RT. The mixture was then extracted with a hexane/ether solution (1:1) followed by washing with H$_2$O (2×), 0.2N citric acid (2×) and sat. NaCl. The organic phase was separated, dried (Na$_2$SO$_4$) and concentrated under reduced pressure. The residue was purified by flash chromatography (100% Hexane) to give the desired iodo intermediate (8.33 g, 80%): $^1$H NMR (CDCl$_3$, 300 MHz) δ 1.34 (s, 9H), 7.07 (t, J=8.0 Hz, 1H), 7.39 (d, J=8.0 Hz, 1H), 7.55 (d, J=8.0 Hz, 1H), 7.77 (t, J=2.0 Hz, 1H).

EXAMPLE 364

Preparation of 1-(3-TERT-BUTYL-PHENYL)-CYCLO HEXANOL from 1-TERT-BUTYL-3-IODO-BENZENE

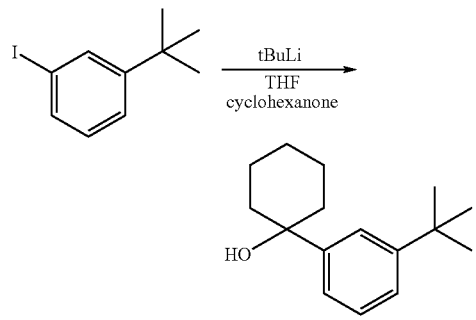

1-tert-Butyl-3-iodo-benzene (8.19 g, 31.49 mmol) in anhydrous THF (35 mL) was cooled to −78° C. A solution of 1.7M tert-butyl lithium was added and the reaction mixture was allowed to stir while under N$_2$ (g) inlet for 2 h. A solution of cyclohexanone in anhydrous THF (5 mL) was added and the reaction mixture was stirred for 1 h before transferring to a 0° C. bath for 1 h and warming to room temperature for 1 h. The reaction was quenched with H$_2$O and extracted with ether. The organic layer was separated, dried (NaSO$_4$) and concentrated under reduce pressure. The residue was purified by flash chromatography (100% CHCl$_3$) to give the desired alcohol (4.73 g, 65%): mass spec (Cl) 215.2 (M−OH).

EXAMPLE 365

Preparation of 1-(1-AZIDO-CYCLOHEXYL)-3-TERT-BUTYL-BENZENE from 1-(3-TERT-BUTYL-PHENYL)-CYCLO HEXANOL 1-(3-tert-Butyl-phenyl)-cyclohexanol (3.33 g, 14.34 mmol) in dry chloroform (75 mL) was cooled to 0° C. under N$_2$ (g) inlet. Sodium azide (2.89 g, 44.45 mmol) was added followed by dropwise addition of trifluoroacetic acid (5.5 mL, 71.39 mmol). The reaction mixture was allowed to stir at room temperature overnight and then partitioned between H$_2$O and ether. The aqueous layer was removed and the mixture was washed with H$_2$O followed by 1.0 N NH$_4$OH, The organic layer was separated, dried (Na$_2$SO$_4$), and concentrated under reduced pressure. The residue was purified by flash chromatography (100% hexane) to give the desired azide (0.50 g, 14%):mass spec (Cl) 215.2 (M−N$_3$).

EXAMPLE 366

Preparation of 1-(3-TERT-BUTYL-PHENYL)-CYCLOHEXYLAMINE from 1-(1-AZIDO-CYCLOHEXYL)3-TERT-BUTYL-BENZENE

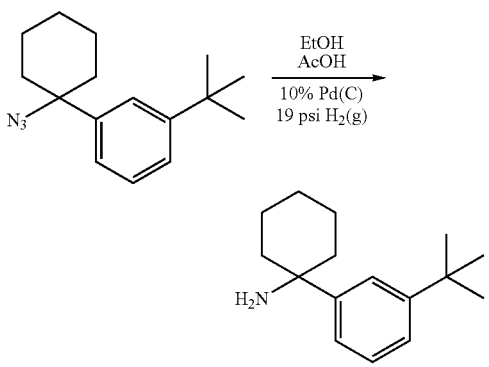

To a solution of 1-(1-Azido-cyclohexyl)-3-tert-butylbenzene dissolved in ethanol (5 mL) was added acetic acid (0.5 mL) and 10% palladium on carbon (0.10 g, 0.94 mmol). The reaction mixture was placed on the hydrogenator at 19 psi for 3.5 h and then filtered through Celite and rinsed with ethanol. The filtrate was collected and concentrated under reduced pressure. This was then partitioned between EtOAc and 1N NaOH. The aqueous layer was removed and the mixture was washed with H$_2$O. The organic layer was separated, dried (Na$_2$SO$_4$), and concentrated under reduced pressure. The crude product was used without further purification; mass spec (CI) 215.2 (M−NH$_2$).

EXAMPLE 367

Preparation of 1-(3-isopropylphenyl)cyclohexanamine hydrochloride

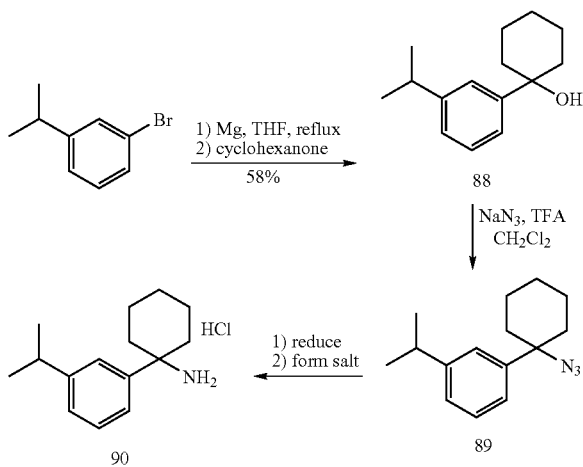

Step 1. Preparation of 1-(3-isopropylphenyl)cyclohexanol (88).

To 1.2 g (50 mmol) of magnesium turnings in 15 mL of dry THF is added a small crystal of iodine followed by 40 μL of dibromoethane. This mixture is placed in a water bath at 50° C. and 3-isopropylbromobenzene (5.0 g, 25 mmol) in 15 mL of dry tetrahydrofuran (THF) is added dropwise over 20 min, while the bath temperature is raised to 70° C. The mixture is stirred and refluxed for 40 additional min. The solution is cooled in an ice-water bath and cyclohexanone (2.0 mL, 19 mmol) in 10 mL of dry THF is added dropwise over 15 min. The ice bath is removed and the mixture is allowed to warm to ambient temperature over 1 h. The solution is decanted into aqueous saturated NH$_4$Cl and combined with an ether wash of the residual magnesium turnings. The organic phase is washed twice more with aqueous NH$_4$Cl, dried over anhydrous sodium sulfate, filtered and concentrated. Chromatography on silica gel, eluting with. 10% ethyl acetate in heptane, affords 2.7 g (12 mmol, 60%) of 1-(3-isopropylphenyl)cyclohexanol 88 as an oil: $^1$H NMR (CDCl$_3$) δ 7.39 (m, 1 H), 7.3 (m, 2 H), 7.12 (m, 1 H), 2.92 (m, 1 H), 1.84-1.54 (m, 10 H), 1.26(d, J=7 Hz, 6 H).

Step 2. Preparation of 1-(3-isopropylphenyl)cyclohexylazide (89).

To 3.20 g (14.7 mmol) of 1-(3-isopropylphenyl)cyclohexanol 88 in 60 mL of CH$_2$Cl$_2$ under nitrogen is added 2.10 g (32.3 mmol) of sodium azide. The stirred suspension is cooled to −5° C. and a solution of trifluoroacetic acid (9.0 mL, 120 mmol) in 35 mL of dichloromethane is added dropwise over 1 h. The resulting suspension is stirred at 0° C. for an additional 1 h. 10 mL of water is added dropwise to the cold, vigorously stirred mixture, followed by dropwise addition of a mixture of 10 mL of water and 10 mL of concentrated ammonium hydroxide. After 30 min the mixture is poured into a separatory funnel containing 350 mL of a 1:1 mixture of heptane and ethyl acetate, and 100 mL of water. The organic phase is washed with an additional portion of water, followed successively by 1 N KH$_2$PO$_4$, water, and brine. It is then dried over anhydrous sodium sulfate, filtered and concentrated to afford 3.6 g (14.7 mmol, 100%) of 89 as a pale yellow oil: $^1$H NMR (CDCl$_3$) δ 7.3 (m, 2 H), 7.25 (m, 1 H), 7.16 (m, 1 H), 2.92 (m, 1 H), 2.01 (m, 2 H), 1.83 (m, 2 H), 1.73-1.64 (m, 5 H), 1.3 (m, 1 H), 1.26 (d, J=7 Hz,6 H).

Step 3. Preparation of 1-(3-isopropylphenyl)cyclohexanamine hydrochloride (90).

To 1-(3-isopropylphenyl)cyclohexylazide 89 (2.7 g, 11 mmol) in 200 mL of ethanol is added 20 mL of glacial acetic acid and 0.54 g of 10% palladium on carbon. The mixture is evacuated and placed under 16 psi of hydrogen, with shaking, for 2.5 h. The reaction mixture is filtered, the catalyst is washed with ethanol, and the solvents are removed in vacuo. Residual acetic acid is removed by chasing the residue with toluene. The acetate salt is dissolved in ethyl acetate and 1 N NaOH is added. The organic phase is washed with more 1 N NaOH and then with water, dried over sodium sulfate, filtered and concentrated. The residue is dissolved in ether and ethereal HCl (concentrated HCl in ether which has been stored over magnesium sulfate) is added to afford a white solid. This is filtered, washed with ether, collected as a solution In dichloromethane, and concentrated to afford 2.1 g (8.3 mmol, 75%) of hydrochloride 90 as a white solid: $^1$H NMR (CDCl$_3$) δ 8.42 (br s, 3 H), 7.43 (m, 2 H), 7.25 (m, 1 H), 7.15 (m, 1 H), 2.92 (hept, J=7 Hz, 1 H), 2.26 (m, 2 H), 2.00 (m, 2 H), 1.69 (m, 2 H), 1.45-1.3 (m, 4 H), 1.24 (d, J=7 Hz, 6 H); IR (diffuse reflectance) 2944, 2864, 2766, 2707, 2490, 2447, 2411, 2368, 2052, 1599, 1522, 1455, 1357, 796, 704 cm$^{-1}$. MS (EI)m/z (relative intensity) 217 (M+,26), 200 (13), 175 (18), 174 (99), 157 (15), 146 (23), 132 (56), 131 (11), 130 (16), 129 (18). HRMS (ESI) calculated for C$_{15}$H$_{23}$N+H$_1$ 218.1909, found 218.1910. Anal. Calculated for C$_{15}$H$_{23}$N.HCl: C, 70.98; H, 9.53; N, 5.52; Cl, 13.97.

Found: C, 70.98; H, 9.38; N, 5.49.

EXAMPLE 368

Preparation of 5-(2,2-DIMETHYL-PROPYL)-2-IMIDAZOL-1-YL-BENZYLAMINE

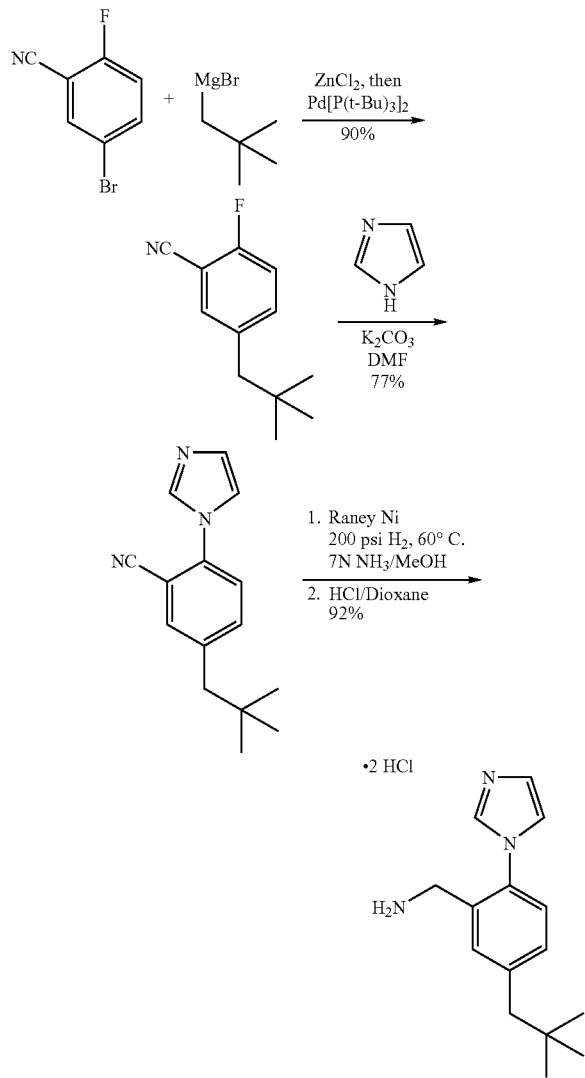

Incorporation of the neopentyl group was performed using a Negishi coupling with the neopentyl zinc species generated from the commercially available neopentylmagnesium chloride. The in situ generated neopentyl zinc reagent underwent cross-coupling reaction with the aryl bromide using the Fu catalyst at room temperature. Displacement of the aryl fluoride with imidazole occurred in DMF with heating. Reduction of the nitrile was carried out with Raney Ni. During the reduction, a significant amount of dimer was seen when Boc anhydride was used instead of ammonia. The reaction was found to proceed to completion at 200 psi of hydrogen at 60° C. Reduction of the temperature to either 20° C. or 40° C. or reducing the pressure of hydrogen significantly reduced the rate of the reduction. The product was an oil, but treating with hydrogen chloride in dioxane gave the salt as a free flowing solid.

Step 1: Preparation of 5-neopentyl-2-fluoro-benzonitrile.

To a solution of zinc chloride (50 mL, 1.0M in diethyl ether, 50 mmol) was added neopentylmagnesium chloride (50 mL, 1.0M in THF, 50 mmol) dropwise at 0° C. During the addition, the generated magnesium salts formed a white precipitate. The reaction was removed from the ice bath and allowed to stir for in, then 1-bromo-2-fluorobenzonitrile (5 g, 25 mmol) was added followed by bis(tri-tert-butytphosphine) palladium (0.127 g, 0.25 mmol, 1%). The reaction began to reflux and was placed back into the ice bath. After 1 h, the reaction was diluted with 200 mL of diethyl ether and washed with 1N HCl (2×100 mL), brine (100 mL), dried over magnesium sulfate and concentrated to give an oily solid (4.3 g, 22 mmol, 90%). $^1$H NMR (400 MHz, CDCl$_3$) δ 7.38-7.30 (m, 2H), 7.11 (dt, J=8.5, 1.4 Hz, 1H), 2.49 (s, 2H), 0.90 (s, 9H).

Step 2: Preparation of 5-neopentyl-2-imidazol-1-yl-benzonitrile.

A solution of 5-neopentyl-2-fluoro-benzonitrile (4.3 g, 22.5 mmol), imidazole (1.68 g, 24.73 mmol) and potassium carbonate (6.25 g, 44.97 mmol) were stirred in DMF (50 mL) at 90° C. The reaction was stopped after 4 h and worked up, but LCMS and HNMR show starting material remaining. The crude product was resubmitted to reaction conditions and stirred overnight. The reaction was diluted with ethyl acetate (100 mL) and washed with water (2×75 mL) and brine (75 mL). The organic layer was dried over magnesium sulfate and concentrated to give a white solid (4.16 g, 17.4 mmol, 77%); MH+ 240.2.

Step 3: Preparation of 5-neopentyl-2-fluoro-benzylamine.

To a solution 5-neopentyl-2-imidazol-1-yl-benzonitrile (10.00 g, 41.79 mmol) in ammonia in methanol solution (~7N, 350 mL) was added a slurry of Raney nickel (10 mL). The reaction was sealed in a parr bomb and placed under H$_2$ (200 psi) then heated to 60° C. As the pressure dropped, H$_2$ was added to adjust the pressure to 200 psi. After 8 h, the pressure had stabilized. The vessel was cooled, the hydrogen was removed and the reaction was placed under N$_2$(g). The reaction was filtered, washed with methanol and concentrated. The resulting oil was dried for 48 h. The oil was dissolved in 50 mL of diethyl ether and 4N HCl in dioxane (32 mL) was added which caused a precipitate to form. This precipitate was collected by filtration, washed with diethyl ether (100 mL) and methylene chloride (100 mL). Drying under high vacuum gave a white solid (12.1 g, 38.3 mmol, 92%); MH+ 244.2.

EXAMPLE 369

Preparation of 1-(3-TERT-BUTYL-PHENYL)-4-METHYL-CYCLOHEXYLAMINE

Step 1:

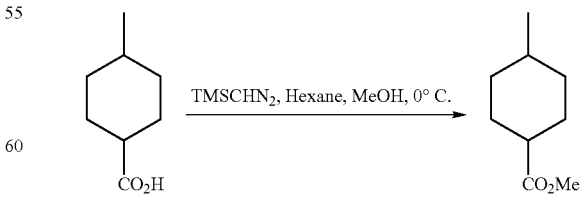

A 2.0M solution of trimethylsilyldiazomethane in hexanes (11.0 mL, 22.0 mmol) was added to a solution of a mixture of cis/trans isomers of 4-methyl-cyclohexanecarboxylic acid (2.0 mL, 14.1 mmol) in methanol (14 mL) and hexane (14 mL). The clear solution turned yellow following the addition of the trimethylsilyldiazomethane. The solution was concentrated to yield a mixture of cis/trans isomers of 4-methyl-cyclohexanecarboxylic acid methyl ester.

$^1$H NMR (300 MHz, CDCl$_3$) δ 3.68 and 3.66 (s, 3 H), 2.51 and 2.21 (m and tt, J=3.6 Hz, and 12.2 Hz, 1 H), 1.96 (m, 3 H), 1.74-1.15 (broad m, 6 H), 0.89 (m, 3 H).

Step 2:

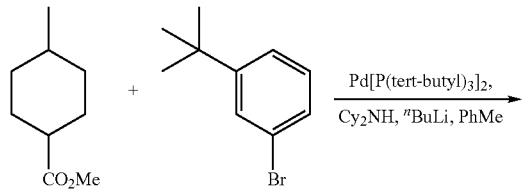

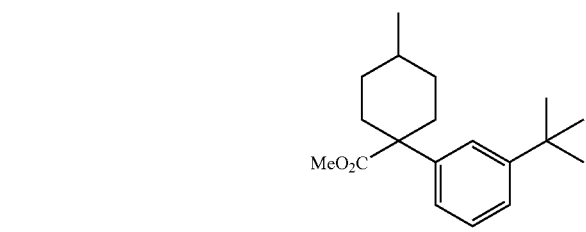

A 1.6M solution of "butyllithium (1.7 mL, 2.72 mmol) was added to a solution of dicyclohexylamine (0.52 mL, 2.61 mmol) in toluene (10 mL). After stirring for 5 min, a mixture of cis/trans isomers of 4-methyl-cyclohexanecarboxylic acid methyl ester (342 mg, 2.19 mmol) was added. After stirring for 10 min, 1-bromo-3-tert-butyl-benzene (428 mg, 2.01 mmol) and bis(tri-tert-butylphosphine)palladium(0) (52 mg, 102 umol) was sequentially added. After stirring for 20 h, the solution was diluted with 10% aqueous hydrochloric acid, and extracted with diethyl ether. The combined organic extracts were dried over magnesium sulfate, filtered, and concentrated. The residue was flash chromatographed with 49:1, 24:1, and 23:2 hexanes:ethyl acetate as the eluant to yield 484 mg (84% yield) of a mixture of cis/trans isomers of 1-(3-tert-butyl-phenyl)-4-methyl-cyclohexanecarboxylic acid methyl ester as a Sight yellow oil.

$^1$H NMR (300 MHz, CDCl$_3$) δ 7.51 and 7.40 (t and m, J=1.9 Hz, 1H), 7.33-7.13 (m, 3 H), 3.65 (s, 3 H), 2.62 (m, 2H), 1.77-1.02 (broad m, 7 H), 1.30 (s, 9H), 0.91 (d, J=6.5 Hz, 3H).

Step 3:

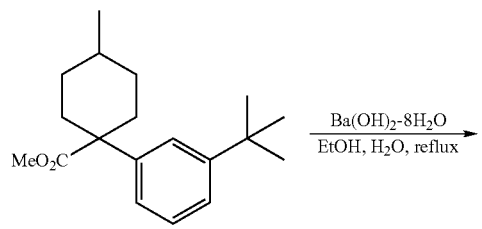

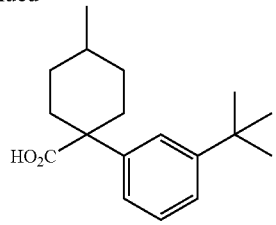

Barium hydroxide-octahydrate (968 mg, 3.07 mmol), and a mixture of cis/trans isomers of 1-(3-tert-butyl-phenyl)-4-methyl-cyclohexanecarboxylic acid methyl ester in ethanol (10 mL) and water (10 mL) was placed into a preheated oil bath at 85° C. After heating at reflux for 18 h, the solution was diluted with 10% aqueous hydrochloric acid, and extracted with methylene chloride. The combined organic extracts were dried over magnesium sulfate, filtered, and concentrated to yield 285 mg (69% yield) of a mixture of cis/trans isomers of 1-(3-tert-butyl-phenyl)-4-methyl-cyclohexanecarboxylic acid as a light yellow oil.

$^1$H NMR (300 MHz, CDCl$_3$) δ 7.51 and 7.48 (t and s, J=1.9 Hz, 1H), 7.33-7.14 (m, 3 H), 2.65 (d, J=12.6 Hz, 2H), 1.77-1.10 (broad m, 7 H), 1.31 (s, 9H), 0.92 and 0.88 (both d, both J=6.4 Hz, 3 H).

Step 4:

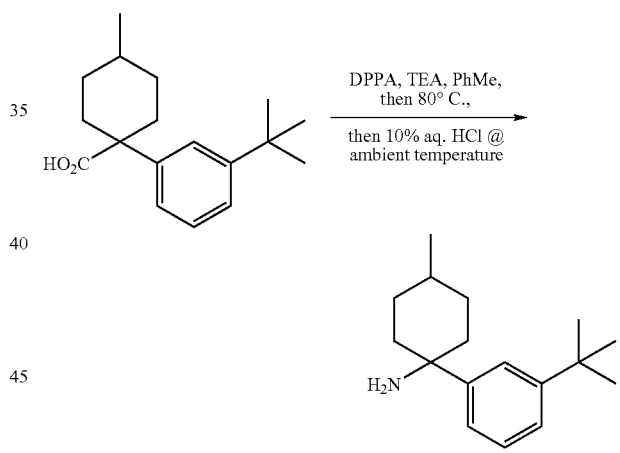

Diphenylphosphoryl azide (0.26 mL, 1.20 mmol) was added to a solution of a mixture of cis/trans 1-(3-tert-butyl-phenyl)-4-methyl-cyclohexanecarboxylic acid (275 mg, 1.00 mmol) and triethylamine (0.19 mL, 1.36 mmol) in toluene (5 mL). After stirring at ambient temperature for 1.6 h, the solution was placed into a preheated oil bath at 80° C. Bubbling was observed. After stirring for 1 h at 80° C., the bubbling had ceased and the solution was cooled to ambient temperature. Dioxane (2.5 mL) and 10% aqueous hydrochloric acid (2.5 mL) was added and stirred vigorously for 18 h. The aqueous layer was made alkaline with aqueous 3N NaOH and extracted with methylene chloride. The combined organic extracts were dried over magnesium sulfate, filtered, and concentrated. The residue was flash chromatographed with 19:1:0.1, 9:1:0.1, 17:3:0.3, and 4:1:0.1 methylene chloride:methanol:concentrated ammonium hydroxide as the eluant to yield 75 mg (30% yield) of a single isomer of 1-(3-tert-butyl-phenyl)-4-methyl-cyclohexylamine.

$^1$H NMR (300 MHz, CDCl$_3$) δ 7.51 (d, J=1.9 Hz, 1H), 7.37-7.27 (m, 3 H), 1.77-1.10 (broad m, 9 H), 1.34 (s, 9H), 0.98 (d, J=5.7 Hz, 3 H).

Method [1] Retention time 1.55 min by HPLC and 1.62 min by MS (M−NH$_2$=229).

EXAMPLE 370

Preparation of
1-THIOPHEN-3-YL-CYCLOHEXYLAMINE

Step 1:

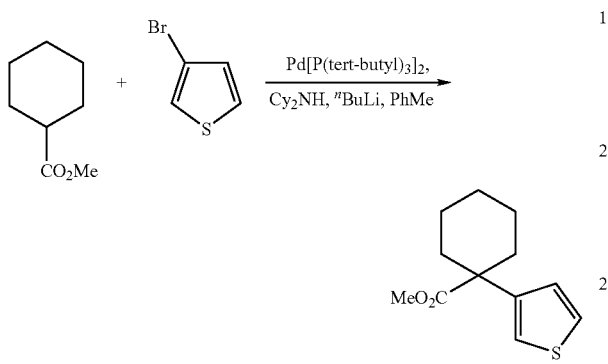

A 1.6M solution of $^n$butyllithium (25.0 mL, 40.0 mmol) was added to a solution of dicyclohexylamine (7.8 mL, 39.1 mmol) in toluene (60 mL). After stirring for 5 min, cyclohexanecarboxylic acid methyl ester (4.8 mL, 33.6 mmol) was added. After stirring for 10 min, 1-bromo-thiophene (2.8 mL, 29.6 mmol) and bis(tri-tert-butylphosphine)palladium(0) (312 mg, 610 μmol) was sequentially added. After stirring for 24 h, the solution was diluted with 10% aqueous hydrochloric acid, filtered through a Buchner funnel, and the solid was washed with diethyl ether. The aqueous layer was extracted with diethyl ether, the combined organic extracts were dried over magnesium sulfate, filtered, and concentrated. The residue was flash chromatographed with 99:1, 49:1, and 24:1 hexanes:ethyl acetate as the eluant to yield 4.93 g (74% yield) of 1-thiophen-3-yl-cyclohexanecarboxylic acid methyl ester as a light yellow oil.

$^1$H NMR (300 MHz, CDCl$_3$) δ 7.24 (m, 1H), 7.10 (m, 2H), 3.65 (s, 3H), 2.48 (d, J=6.7 Hz, 2H), 1.78-1.28 (broad m, 8H).

Step 2:

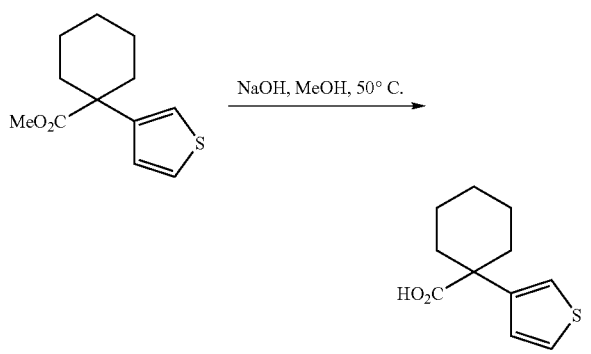

A 3 N solution of aqueous sodium hydroxide (5.0 mL, 15.0 mmol) was added to a solution of 1-thiophen-3-yl-cyclohexanecarboxylic acid methyl ester (500 mg, 2.23 mmol) in methanol (10 mL) and was placed into a preheated oil bath at 50° C. After stirring for 18 h, the solution was concentrated, diluted with 10% aqueous hydrochloric acid, and extracted with methylene chloride. The combined organic extracts were dried over magnesium sulfate, filtered, and concentrated to yield 450 mg (96% yield) of 1-thiophen-3-yl-cyclohexanecarboxylic acid as a white solid.

$^1$H NMR (300 MHz, CDCl$_3$) δ 7.24 (m, 1H), 7.10 (m, 2H), 2.46 (d, J=6.7 Hz, 2H), 1.78-1.26 (broad m, 8H).

Step 3:

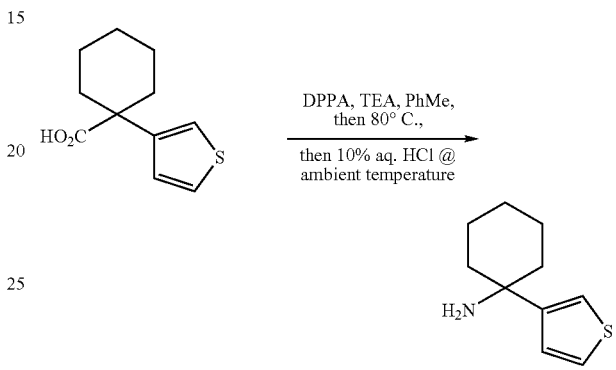

Diphenylphosphoryl azide (1.0 mL, 4.63 mmol) was added to a solution of 1-thiophen-3-yl-cyclohexanecarboxylic acid (450 mg, 2.14 mmol) and triethylamine (1.00 mL, 7.17 mmol) in toluene (10 mL). After stirring at ambient temperature for 16 h, the solution was placed into a preheated oil bath at 80° C. Bubbling was observed. After stirring for 1 h at 80° C., the bubbling had ceased and the solution was cooled to ambient temperature. Dioxane (5 mL) and 10% aqueous hydrochloric acid (5 mL) was added and stirred vigorously for 18 h. The aqueous layer was made alkaline with aqueous 3N NaOH and extracted with methylene chloride. The combined organic extracts were dried over magnesium sulfate, filtered, and concentrated. The residue was flash chromatographed with 19:1:0.1, 9:1:0.1, 17:3:0.3, and 4:1:0.1 methylene chloride:methanol:concentrated ammonium hydroxide as the eluant to yield 1-thiophen-3-yl-cyclohexylamine as an impure product.

Method [1] Retention time 0.43 min by HPLC and 0.50 min by MS (M−NH$_2$=165).

EXAMPLE 371

Preparation of CIS/TRANS 1-(3-TERT-BUTYL-PHENYL)-3-METHYL-CYCLOHEXYLAMINE

Step 1:

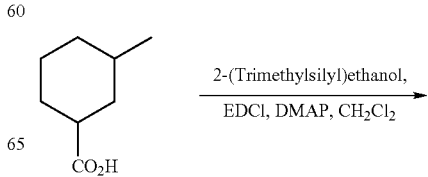

-continued

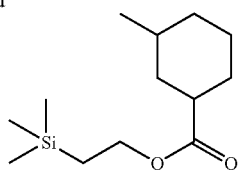

A mixture of cis/trans isomers of 3-methyl-cyclohexanecarboxylic acid (1.44 g, 10.1 mmol), 2-trimethylsilylethanol (1.30 g, 11.0 mmol), 4-dimethylaminopyridine (128 mg, 1.05 mmol), and 1-(3-dimethylaminopropyl)-3-ethylcarbodiimide hydrochloride (2.12 g, 11.1 mmol) in methylene chloride (10 mL) was stirred for 36 h. The solution was diluted with 10% aqueous hydrochloric acid and extracted with methylene chloride. The combined organic extracts were dried over magnesium sulfate, filtered, and concentrated to yield 2.45 g (100% yield) of a mixture of cis/trans isomers of 3-methyl-cyclohexanecarboxylic acid 2-trimethylsilanyl-ethyl ester as a clear oil.

$^1$H NMR (300 MHz, CDCl$_3$) δ 4.15 (m, 2H), 2.59 and 2.26 (m and tt, J=3.5 Hz, and 12.1 Hz, 1H), 1.98-1.19 (broad m, 8H), 1.12-0.93 (broad m, 3H), 0.90 (d and d, J=6.5 Hz and 6.7 Hz, 3H), 0.04 (s, 9H).

Step 2:

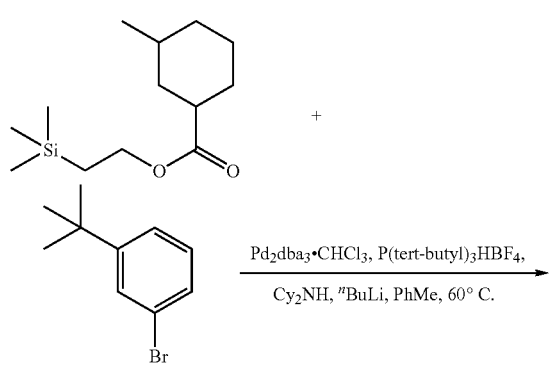

A 1.6M solution of $^n$butyllithium (0.85 mL, 1.36 mmol) was added to a solution of dicyclohexylamine (0.27 mL, 1.36 mmol) in toluene (5 mL). After stirring for 5 min, a mixture of cis/trans isomers of 3-methyl-cyclohexanecarboxylic acid 2-trimethylsilanyl-ethyl ester (269 mg, 1.11 mmol) was added. After stirring for 30 min, 1-bromo-3-tert-butyl-benzene (250 mg, 1.17 mmol) was added followed by the simultaneous addition of tri-tert-butylphosphonium tetrafluoroborate (31 mg, 107 μmol) and tris(dibenzylideneacetone)dipalladium(0)-chloroform adduct (54 mg, 52.2 μmol). The solution was placed into a preheated oil bath at 60° C. After stirring for 20 h, the solution was diluted with 10% aqueous hydrochloric acid, and extracted with diethyl ether. The combined organic extracts were dried over magnesium sulfate, filtered, and concentrated. The residue was flash chromatographed with 49:1, 24:1, and 23:2 hexanes:ethyl acetate as the eluant to yield 250 mg (62% yield) of a mixture of cis/trans isomers of 1-(3-tert-butyl-phenyl)-3-methyl-cyclohexanecarboxylic acid 2-trimethylsilanyl-ethyl ester as a yellow oil.

Method [2] Retention time 3.64 min by HPLC and 3.68 min by MS (M+Na=397).

Step 3:

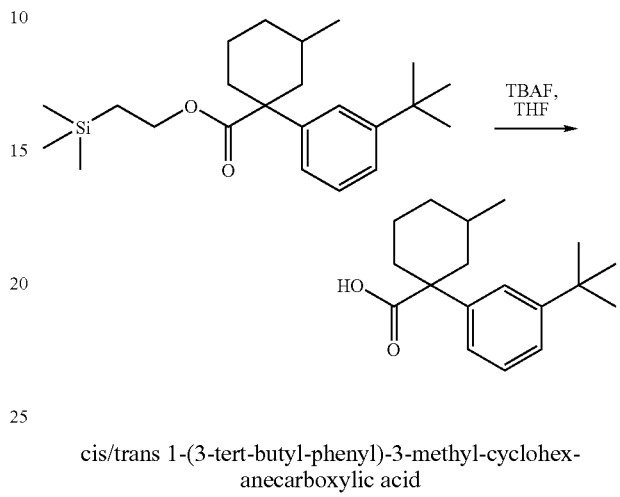

cis/trans 1-(3-tert-butyl-phenyl)-3-methyl-cyclohexanecarboxylic acid

A 1.0 M solution of tetrabutylammonium fluoride in tetrahydrofuran (2.5 mL, 2.5 mmol) was added to a solution of a mixture of cis/trans isomers of 1-(3-tert-butyl-phenyl)-3-methyl-cyclohexanecarboxylic acid 2-trimethylsilanyl-ethyl ester (500 mg, 1.34 mmol) in tetrahydrofuran (10 mL). After stirring for 24 h, the solution was diluted with 10% aqueous hydrochloric acid, and extracted with diethyl ether. The combined organic extracts were dried over magnesium sulfate, filtered, and concentrated to yield 419 mg (impure) of a mixture of cis/trans isomers of 1-(3-tert-butyl-phenyl)-3-methyl-cyclohexanecarboxylic acid as a brown viscous oil.

Step 4:

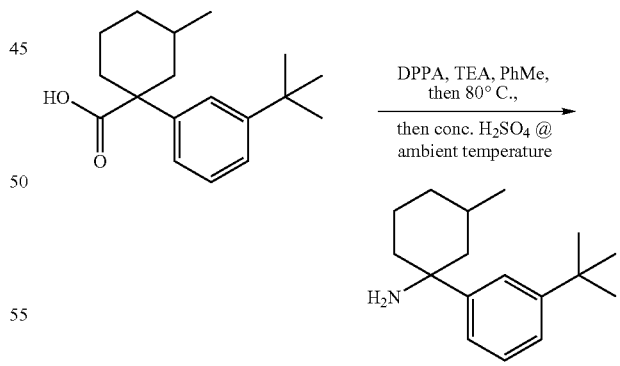

Diphenylphosphoryl azide (0.34 mL, 1.57 mmol) was added to a solution of a mixture of cis/trans isomers of 1-(3-tert-butyl-phenyl)-3-methyl-cyclohexanecarboxylic acid (ca. 1.34 mmol) and triethylamine (0.24 mL, 1.72 mmol) in toluene (6 mL). After stirring at ambient temperature for 16 h, the solution was placed into a preheated oil bath at 80° C. Bubbling was observed. After stirring for 1 h at 80° C., the bubbling had ceased and the solution was cooled to ambient temperature. Concentrated sulfuric acid was added and stirred vigorously for 2 min. The aqueous layer was made alkaline with aqueous 3N NaOH and extracted with methylene chloride. The combined organic extracts were dried over magnesium sulfate, filtered, and concentrated. The residue was flash chromatographed with 99:1:0.1, 49:1:0.1, 24:1:0.1, 23:2:0.2, 22:3:0.3, 21:4:0.4, and 4:1:0.1 methylene chloride:methanol:concentrated ammonium hydroxide as the eluant to yield 185 mg (impure) of a mixture of cis/trans isomers of 1-(3-tert-butyl-phenyl)-3-methyl-cyclohexylamine.

Method [1] Retention time 1.75 min by HPLC and 1.82 min by MS (M−NH$_2$=229).

EXAMPLE 372

Preparation of CIS/TRANS 1-(3-TERT-BUTYL-PHENYL)-2-METHYL-CYCLOHEXYLAMINE

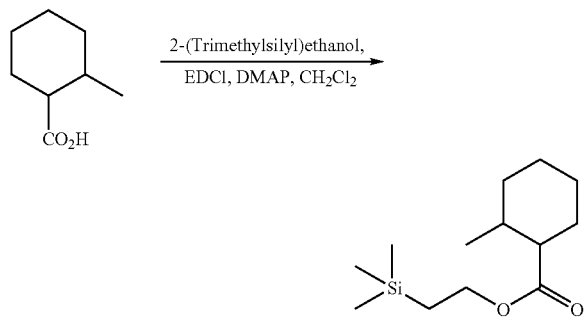

Step 1:

A mixture of cis/trans isomers of 2-methyl-cyclohexanecarboxylic acid (1.44 g, 10.1 mmol), 2-trimethylsilylethanol (1.31 g, 11.1 mmol), 4-dimethylaminopyridine (123 mg, 1.01 mmol), and 1-(3-dimethylaminopropyl)-3-ethylcarbodiimide hydrochloride (2.11 g, 11.0 mmol) in methylene chloride (10 mL) was stirred for 36 h. The solution was diluted with 10% aqueous hydrochloric acid and extracted with methylene chloride. The combined organic extracts were dried over magnesium sulfate, filtered, and concentrated to yield 2.45 g (100% yield) of a mixture of cis/trans isomers of 2-methyl-cyclohexanecarboxylic acid 2-trimethylsilanyl-ethyl ester as a clear oil.

$^1$H NMR (300 MHz, CDCl$_3$) δ 4.16 (m, 2H), 2.47 (m, 1H), 2.14 (m, 1H), 1.77-1.20 (broad m, 8H), 0.98 (m, 5H), 0.04 (s, 9H).

Step 2:

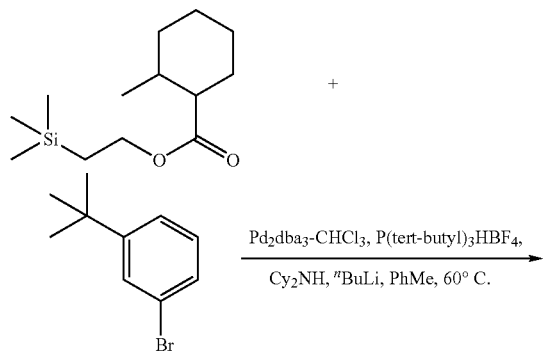

-continued

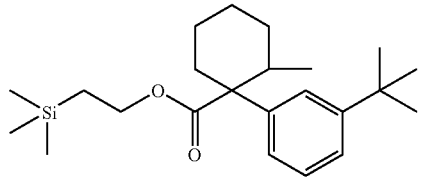

A 1.6M solution of $^n$butyllithium (0.85 mL, 1.36 mmol) was added to a solution of dicyclohexylamine (0.27 mL, 1.36 mmol) in toluene (5 mL). After stirring for 5 min, a mixture of cis/trans isomers of 2-methyl-cyclohexanecarboxylic acid 2-trimethylsilanyl-ethyl ester (269 mg, 1.11 mmol) was added. After stirring for 30 min, 1-bromo-3-tert-butyl-benzene (248 mg, 1.16 mmol) was added followed by the simultaneous addition of tri-tert-butylphosphonium tetrafluoroborate (31 mg, 107 umol) and tris(dibenzylideneacetone)dipalladium(0)-chloroform adduct (51 mg, 49.3 umol). The solution was placed info a preheated oil bath at 60° C. After stirring for 20 h, the solution was diluted with 10% aqueous hydrochloric acid, and extracted with diethyl ether. The combined organic extracts were dried over magnesium sulfate, filtered, and concentrated. The residue was flash chromatographed with 49:1, 24:1, and 23:2 hexanes:ethyl acetate as the eluant to yield 375 mg (90% yield) of a mixture of cis/trans isomers of 1-(3-tert-butyl-phenyl)-2-methyl-cyclohexanecarboxylic acid 2-trimethylsilanyl-ethyl ester as a yellow oil.

Method [2] Retention time 3.67 min by HPLC and 3.75 min by MS (M+Na=397).

Method [2] Retention time 3.77 min by HPLC and 3.85 min by MS (M+Na=397).

Step 3:

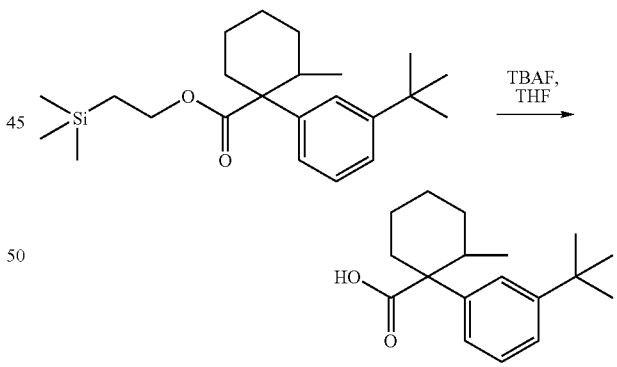

A 1.0 M solution of tetrabutylammonium fluoride in tetrahydrofuran (4.0 mL, 4.00 mmol) was added to a solution of a mixture of cis/trans isomers of 1-(3-tert-butyl-phenyl)-2-methyl-cyclohexanecarboxylic acid 2-trimethylsilanyl-ethyl ester (610 mg, 1.63 mmol) in tetrahydrofuran (10 mL). After stirring for 24 h, the solution was diluted with 10% aqueous hydrochloric acid, and extracted with diethyl ether. The combined organic extracts were dried over magnesium sulfate, filtered, and concentrated to yield. 360 mg (80% yield) of a mixture of cis/trans isomers of 1-(3-tert-butyl-phenyl)-2-methyl-cyclohexanecarboxylic acid as a yellow oil.

Step 4:

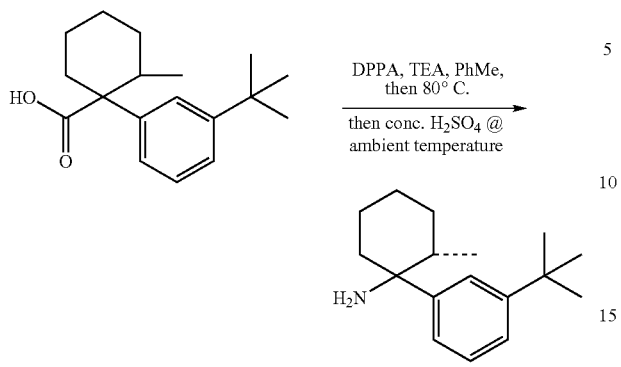

Diphenylphosphoryl azide (0.34 mL, 1.57 mmol) was added to a solution of a mixture of cis/trans isomers of 1-(3-tert-butyl-phenyl)-2-methyl-cyclohexanecarboxylic acid (ca. 1.34 mmol) and triethylamine (0.24 mL, 1.72 mmol) in toluene (6 mL). After stirring at ambient temperature for 16 h, the solution was placed into a preheated oil bath at 80° C. Bubbling was observed. After stirring for 1 h at 80° C., the bubbling had ceased and the solution was cooled to ambient temperature. Concentrated sulfuric acid was added and stirred vigorously for 2 min. The aqueous layer was made alkaline with aqueous 3N NaOH and extracted with methylene chloride. The combined organic extracts were dried over magnesium sulfate, filtered, and concentrated. The residue was flash chromatographed with 99:1:0.1, 49:1:0.1, 24:1:0.1, 23:2:0.2, 22:3:0.3, 21:4:0.4, and 4:1:0.1 methylene chloride: methanol:concentrated ammonium hydroxide as the eluant to yield 95 mg (30% yield) of a mixture of cis/trans isomers of 1-(3-tert-butyl-phenyl)-2-methyl-cyclohexylamine.

Method [1] Retention time 1.72 min by HPLC and 1.79 min by MS (M+=229).

EXAMPLE 373

Preparation of 1-(5-ETHYL-THIOPHEN-3-YL)-CYCLOHEXYLAMINE

Step 1:

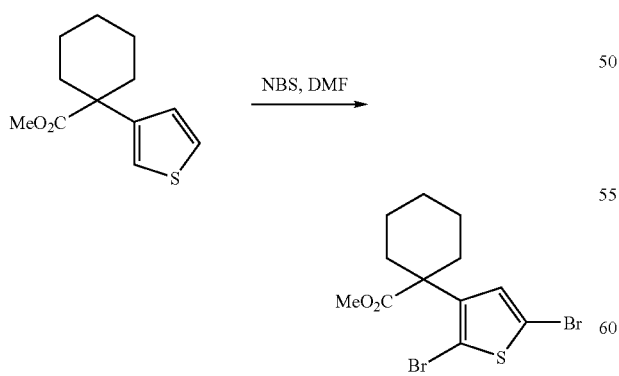

A solution of N-bromosuccinimde (5.58 g, 31.4 mmol) and 1-thiophen-3-yl-cyclohexanecarboxylic acid methyl ester (3.19 g, 14.2 mmol) in dimethylformamide (60 mL) was stirred for 72 h. The solution was diluted with 10% aqueous hydrochloric acid and extracted with diethyl ether. The combined organic extracts were dried over magnesium sulfate, filtered, and concentrated. The residue was flash chromatographed with 99:1, 49:1, and 24:1 hexanes:ethyl acetate as the eluant to yield 4.30 g (79% yield) of 1-(2,5-dibromo-thiophen-3-yl)-cyclohexanecarboxylic acid methyl ester as a yellow oil.

$^1$H NMR (300 MHz, CDCl$_3$) δ 6.93 (s, 1H), 3.67 (s, 3H), 2.34 (m, 2H), 1.90 (m, 2H), 1.60 (m, 5H), 1.36 (m, 1H).

Step 2:

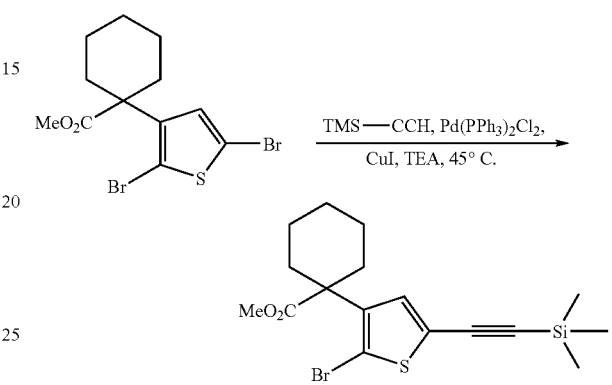

Trimethylsilylacetylene (487 mg, 4.96 mmol), cuprous iodide (55 mg, 289 umol), dichlororbis(triphenylphosphine) palladium(II) (310 mg, 442 umol), and 1-(2,5-dibromo-thiophen-3-yl)-cyclohexanecarboxylic acid methyl ester (1.71 g, 4.48 mmol) in triethylamine (20 mL) was placed into a preheat oil bath at 45° C. After stirring for 18 h, the solution was diluted with 10% aqueous hydrochloric acid and extracted with diethyl ether. The combined organic extracts were dried over magnesium sulfate, filtered, and concentrated. The residue was flash chromatographed with 99:1, 49:1, and 24:1 hexanes:ethyl acetate as the eluant to yield 1.66 g (93% yield) of 1-(2-bromo-5-trimethylsilanylethynyl-thiophen-3-yl)-cyclohexanecarboxylic acid methyl ester as a yellow solid.

$^1$H NMR (300 MHz, CDCl$_3$) δ 7.09 (s, 1H), 3.67 (s, 3H), 2.34 (m, 2H), 1.93 (m, 2H), 1.58 (m, 5H), 1.35 (m, 1H), 0.23 (s, 9H).

Step 3:

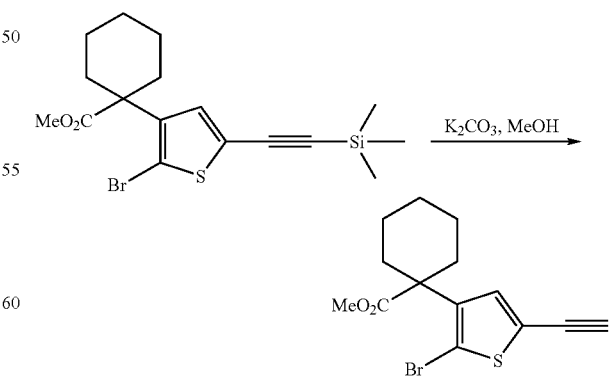

A heterogeneous mixture of potassium carbonate (1.42 g, 10.3 mmol) and 1-(2-bromo-5-trimethylsilanylethynyl-thiophen-3-yl)-cyclohexanecarboxylic acid methyl ester (1.66 g, 4.16 mmol) in methanol (10 mL) was stirred for 24 h. The solution was diluted with water and extracted with methylene chloride. The combined organic extracts were dried over magnesium sulfate, filtered, and concentrated. The residue was flash chromatographed with 99:1, 49:1, and 24:1 hexanes:ethyl acetate as the eluant to yield 1.17 g (74% yield) of 1-(2-bromo-5-ethynyl-thiophen-3-yl)-cyclohexanecarboxylic acid methyl ester as a yellow oil.

$^1$H NMR (300 MHz, CDCl$_3$) δ 7.12 (s, 1H), 3.68 (s, 3H), 3.36 (s, 1H), 2.34 (m, 2H), 1.92 (m, 2H), 1.53 (m, 5H), 1.37 (m, 1H).

Step 4:

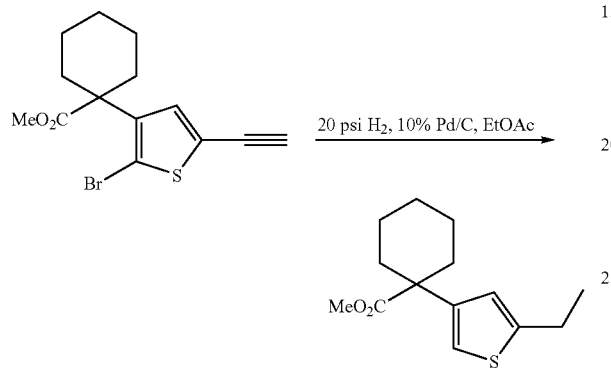

A solution 1-(2-bromo-5-ethynyl-thiophen-3-yl)-cyclohexanecarboxylic acid methyl ester (1.17 g, 3.58 mmol) of in ethyl acetate (20 mL) was added to a heterogeneous mixture of 10% palladium on carbon (1.16 g) and triethylamine (1.5 mL, 10.8 mmol) in ethyl acetate (20 mL) in a parr bottle. The parr bottle was filled with hydrogen (20 psi) and evacuated three times. The parr bottle was refilled with hydrogen (20 psi) and shook for 1.5 h, filtered through celite, and concentrated. The residue was flash chromatographed with 49:1 and 24:1 hexanes:ethyl acetate to yield 813 mg (90% yield) of 1-(5-ethyl-thiophen-3-yl)-cyclohexanecarboxylic acid methyl ester as a clear oil.

$^1$H NMR (300 MHz, CDCl$_3$) δ 6.86 (d, J=1.5 Hz, 1H), 6.76 (d, J=1.0 Hz, 1H), 3.66 (s, 3H), 2.79 (dq, J=1.0 Hz and 7.5 Hz, 2H), 2.44 (m, 2H), 1.78-1.19 (broad m, 8H), 1.28 (t, J=7.5 Hz, 3H).

Step 5:

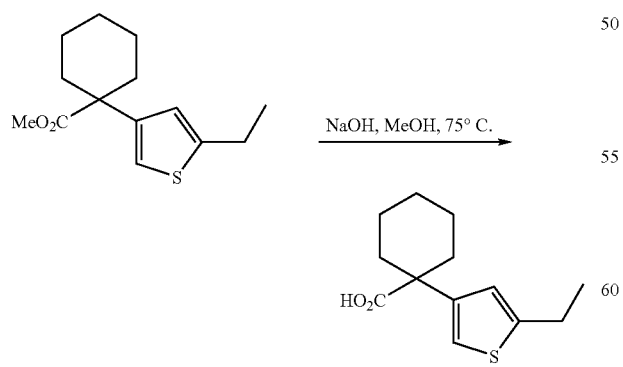

A 3N solution of aqueous sodium hydroxide (8.0 mL, 18.0 mmol) was added to a solution of 1-(5-ethyl-thiophen-3-yl)-cyclohexanecarboxylic acid methyl ester (813 mg, 3.22 mmol) in methanol (12 mL) and was placed into a preheated oil bath at 75° C. After heating at reflux for 24 h, the solution was concentrated, diluted with 10% aqueous hydrochloric acid, and extracted with methylene chloride. The combined organic extracts were dried over magnesium sulfate, filtered, and concentrated to yield 771 mg (100% yield) of 1-(5-ethyl-thiophen-3-yl)-cyclohexanecarboxylic acid as a white solid.

$^1$H NMR (300 MHz, CDCl$_3$) δ 6.92 (d, J=1.5 Hz, 1H), 6.82 (d, J=1.2 Hz, 1H), 2.81 (dq, J=1.2 Hz and 7.5 Hz, 2H), 2.42 (m, 2H), 1.61 (m, 8H), 1.29 (t, J=7.5 Hz, 3H).

Step 6:

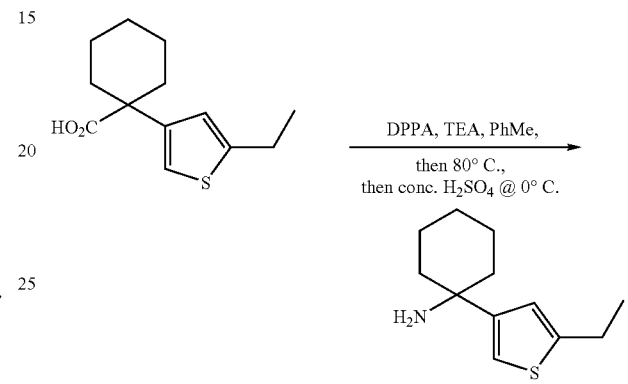

Diphenylphosphoryl azide (0.83 mL, 3.85 mmol) was added to a solution of a 1-(5-ethyl-thiophen-3-yl)-cyclohexanecarboxylic acid and triethylamine (0.67 mL, 4.81 mmol) in toluene (6 mL). After stirring at ambient temperature for 18 h, the solution was placed into a preheated oil bath at 80° C. Bubbling was observed. After stirring for 3 h at 80° C., the bubbling had ceased and the solution was cooled to ambient temperature. Concentrated sulfuric acid was added and stirred vigorously for 2 min. The aqueous layer was made alkaline with aqueous 3N NaOH and extracted with methylene chloride. The combined organic extracts were dried over magnesium sulfate, filtered, and concentrated. The residue was flash chromatographed with 49:1:0.1, 24:1:0.1, 23:2:0.2, and 22:3:0.3 methylene chloride:methanol:concentrated ammonium hydroxide as the eluant to yield 105 mg of a 1-(5-ethyl-thiophen-3-yl)-cyclohexylamine.

Method [1] Retention time 1.23 min by HPLC and 1.29 min by MS (M–NH$_2$=193).

EXAMPLE 374

Preparation of 1-(2,5-DIBROMO-THIOPHEN-3-YL)-CYCLOHEXYLAMINE

Step 1:

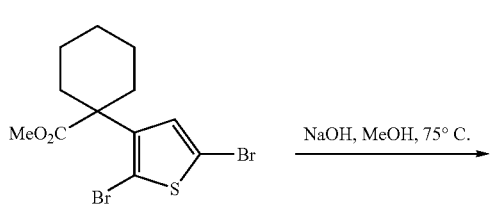

-continued

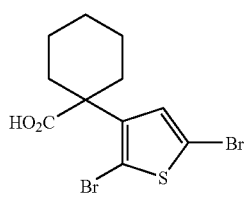

A 3N solution of aqueous sodium hydroxide (10.0 mL, 30.0 mmol) was added to a solution of 1-(2,5-dibromo-thiophen-3-yl)-cyclohexanecarboxylic acid methyl ester (1.23 g, 3.22 mmol) in methanol (30 mL) and was placed into a preheated oil bath at 75° C. After heating at reflux for 24 h, the solution was concentrated, diluted with 10% aqueous hydrochloric acid, and extracted with methylene chloride. The combined organic extracts were dried over magnesium sulfate, filtered, and concentrated to yield 1.18 mg (100% yield) of 1-dibromo-thiophen-3-yl)-cyclohexanecarboxylic acid as a yellow oil.

Step 2:

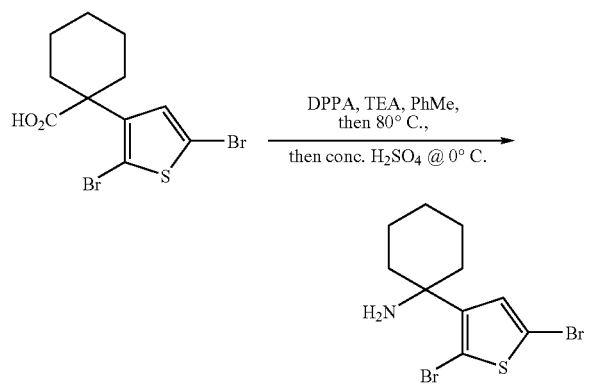

Diphenylphosphoryl azide (0.84 mL, 3.89 mmol) was added to a solution of a 1-(2,5-dibromo-thiophen-3-yl)-cyclohexanecarboxylic acid (1.18 g, 3.21 mmol) and triethylamine (0.68 mL, 4.88 mmol) in toluene (6 mL). After stirring at ambient temperature for 18 h, the solution was placed into a preheated oil bath at 80° C. Bubbling was observed. After stirring for 3 h at 80° C., the bubbling had ceased and the solution was cooled to ambient temperature. Concentrated sulfuric acid was added and stirred vigorously for 2 min. The aqueous layer was made alkaline with aqueous 3N NaOH and extracted with methylene chloride. The combined organic extracts were dried over magnesium sulfate, filtered, and concentrated. The residue was flash chromatographed with 49:1:0.1, 24:1:0.1, 23:2:0.2, and 22:3:0.3 methylene chloride:methanol:concentrafed ammonium hydroxide as the eluant to yield 610 mg (56% yield) of a 1-(2,5-dibromo-thiophen-3-yl)-cyclohexylamine as a brown oil.

Method [1] Retention time 1.31 min by HPLC and 1.37 min by MS (M+=321, 323, and 325).

EXAMPLE 375

Preparation of 1-(5-ISOPROPYL-THIOPHEN-3-YL)-CYCLOHEXYLAMINE

Step 1:

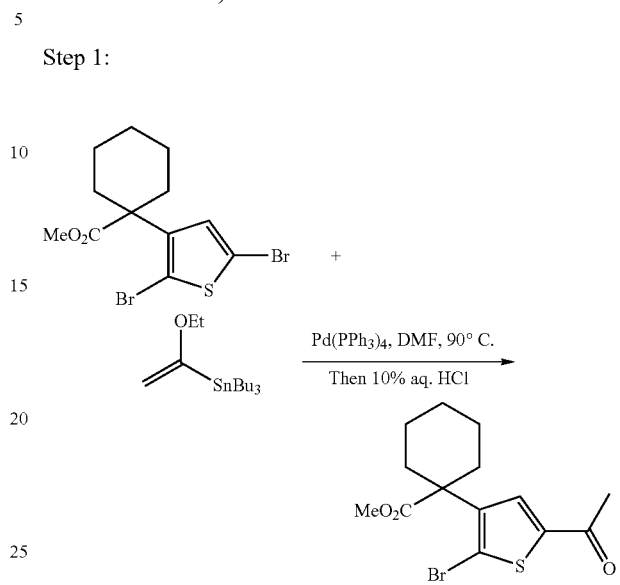

Tetrakis(triphenylphosphine)palladium(0) (380 mg, 329 mmol) was added to a solution of 1-(2,5-dibromo-thiophen-3-yl)-cyclohexanecarboxylic acid methyl ester (1.21 g, 3.17 mmol) and tributyl-(1-ethoxy-vinyl)-stannane (1.33 mg, 3.68 mmol) in dimethylformamide (15 mL) and placed into a preheated oil bath at 90° C. After stirring for 18 h, the solution was cooled to ambient temperature and 10% aqueous hydrochloric acid was added. After stirring for 4 h, the solution was extracted with diethyl ether, the combined organic extracts were dried over magnesium sulfate, filtered, and concentrated. The residue was flash chromatographed with 99:1, 49:1, 24:1, 23:2, 22:3, 21:4, and 4:1 hexanes:ethyl acetate as the eluant to yield 391 mg (impure) of 1-(5-acetyl-2-bromo-thiophen-3-yl)-cyclohexanecarboxylic acid methyl ester.

Method [2] Retention time 2.53 min by HPLC and 2.59 min by MS (M+=345 and 347).

Step 2:

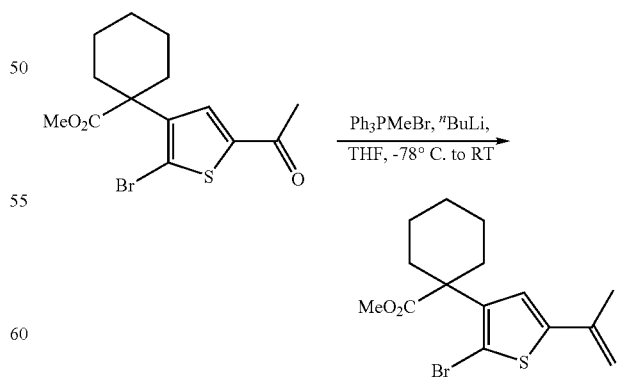

A solution of 1.6M $^n$butyllithium in hexanes (2.0 mL, 3.2 mmol) was added to a heterogeneous mixture of methyltriphenylphosphonium bromide (1.14 g, 3.19 mmol) in tetrahydrofuran (10 mL) at −10° C. After stirring for 30 min at −10°

C., the yellow slurry was cooled to −78° C. and 1-(5-acetyl-2-bromo-thiophen-3-yl)-cyclohexanecarboxylic acid methyl ester (391 mg, <1.13 mmol, impure) was added. After stirring for 10 min at −78° C., the dry ice/acetone bath was removed and the heterogeneous mixture was stirred for 3 h, during which time the solution warmed to ambient temperature. The heterogeneous mixture was concentrated and the residue was flash chromatographed with 99:1, 49:1, 24:1, and 23:2 hexanes:etheyl acetate as the eluant to yield 268 mg (impure) of 1-(2-bromo-5-isopropenyl-thiophen-3-yl)-cyclohexanecarboxylic acid methyl ester.

Step 3:

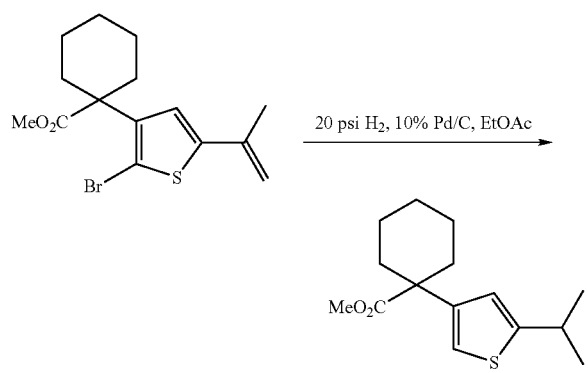

A solution 1-(2-bromo-5-isopropenyl-thiophen-3-yl)-cyclohexanecarboxylic acid methyl ester (268 mg g, (781 μmol, impure) of in ethyl acetate (5 mL) was added to a heterogeneous mixture of 10% palladium on carbon (100 mg) in ethyl acetate (5 mL) in a parr bottle. The parr bottle was filled with hydrogen (20 psi) and evacuated three times. The parr bottle was refilled with hydrogen (20 psi) and shook for 1.5 h, filtered through celite, and concentrated. The residue was flash chromatographed with 49:1 and 24:1 hexanes:ethyl acetate to yield 220 mg (impure) of 1-(5-isopropyl-thiophen-3-yl)-cyclohexanecarboxylic acid methyl ester as a clear oil.

$^1$H NMR (300 MHz, CDCl$_3$) δ 6.86 (d, J=1.5 Hz, 1H), 6.76 (m, 1H), 3.66 (s, 3H), 3.11 (m, 1H), 2.44 (m, 2H), 1.68 (m, 8H), 1.32 (d, J=6.8 Hz, 6H).

Step 4:

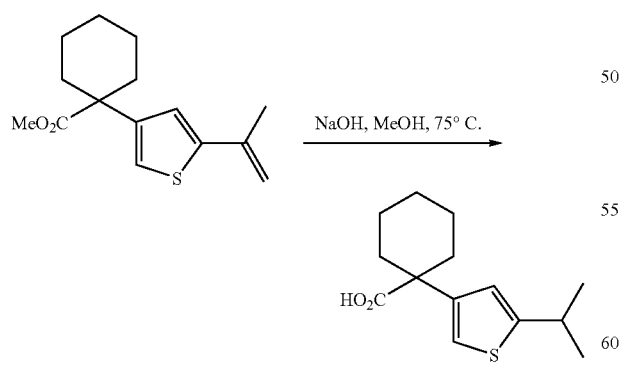

A 3N solution of aqueous sodium hydroxide (3.0 mL, 9.00 mmol) was added to a solution of 1-(5-isopropyl-thiophen-3-yl)-cyclohexanecarboxylic acid methyl ester (212 mg, <796 μmol, impure) in methanol (10 mL) and was placed into a preheated oil bath at 75° C. After heating at reflux for 24 h, the solution was concentrated, diluted with 10% aqueous hydrochloric acid, and extracted with methylene chloride. The combined organic extracts were dried over magnesium sulfate, filtered, and concentrated to yield 204 mg (impure) of 1-(5-isopropyl-thiophen-3-yl)-cyclohexanecarboxylic acid.

Step 5:

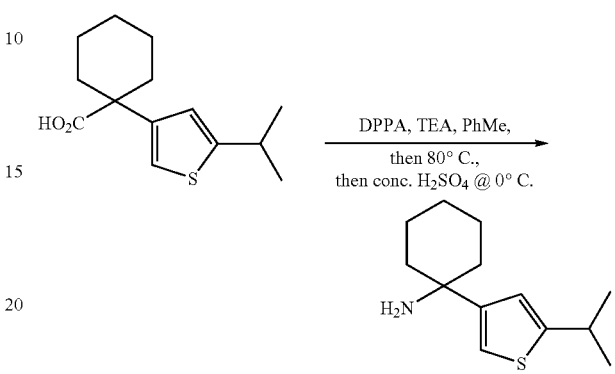

Diphenylphosphoryl azide (0.22 mL, 1.02 mmol) was added to a solution of a 1-(5-isopropyl-thiophen-3-yl)-cyclohexanecarboxylic acid (204 mg, <808 μmol, impure) and triethylamine (0.17 mL, 1.22 mmol) in toluene (2 mL). After stirring at ambient temperature for 18 h, the solution was placed into a preheated oil bath at 80° C. Bubbling was observed. After stirring for 3 h at 80° C., the bubbling had ceased and the solution was cooled to ambient temperature. Concentrated sulfuric acid was added and stirred vigorously for 2 min. The aqueous layer was made alkaline with aqueous 3N NaOH and extracted with methylene chloride. The combined organic extracts were dried over magnesium sulfate, filtered, and concentrated. The residue was flash chromatographed with 49:1:0.1, 24:1:0.1, 23:2:0.2, and 22:3:0.3 methylene chloride:methanol:concentrated ammonium hydroxide as the eluant to yield 28 mg (16% yield) of a 1-(5-isopropyl-thiophen-3-yl)-cyclohexylamine.

Method [1] Retention time 1.41 min by HPLC and 1.47 min by MS (M−NH$_2$=207).

EXAMPLE 376

Preparation of CIS/TRANS 2-AMINO-2-(3-TERT-BUTYL-PHENYL)-CYCLOHEXANOL

Step 1:

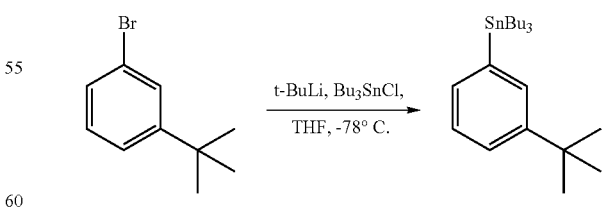

A 1.7M solution of tert-butyllithium in pentane (2.60 mL, 4.42 mmol) was added to a solution of 1-bromo-3-tert-butyl-benzene (426 mg, 2.00 mmol) in tetrahydrofuran (5 mL) at −78° C. After stirring for 1 h, tributyltin chloride (0.57 mL, 2.10 mmol) was added at −78° C. After stirring for 18 h, during which time the solution warmed to ambient temperature, the solution was diluted with water and extracted with methylene chloride. The combined organic extracts were dried over magnesium sulfate, filtered, and concentrated to yield 976 mg (115% yield) of tributyl-(3-tert-butyl-phenyl)-stannane as a impure light yellow oil.

Step 2:

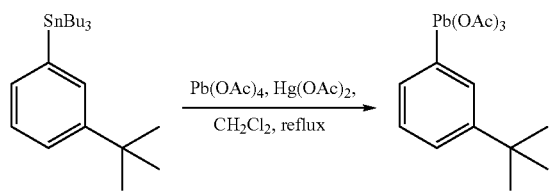

Lead tetraacetate (902 mg, 2.03 mmol) and mercuric acetate (15 mg, 47.1 mmol) was simultaneously added to a solution of tributyl-(3-tert-butyl-phenyl)-stannane (ca. 2.00 mmol) in methylene chloride (4 mL) and was placed into a preheated oil bath at 45° C. After heating at reflux for 24 h, the solution was cooled to ambient temperature and filtered through celite. The celite was washed with chloroform and the filtrate was concentrated to yield the triacetoxy-(3-tert-butyl-phenyl)-lead as an off white/light yellow solid.

Step 3:

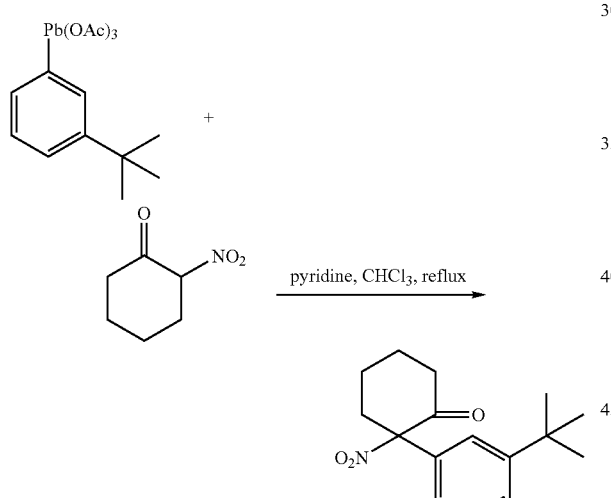

Pyridine (1.8 mL, 22.3 mmol) and 2-nitro-cyclohexanone (630 mg, 4.40 mmol) in chloroform (5 mL) was stirred for 15 min. Triacetoxy-(3-tert-butyl-phenyl)-lead (<2.00 mmol) in chloroform (5 mL) was added and the solution was placed into a preheated oil bath at 85° C. After heating at reflux for 16 h, the solution was concentrated and the residue was flash chromatographed with 19:1, 9:1, and 17:3 hexanes:ethyl acetate as the eluant to yield 160 mg (28% over three steps) of 2-(3-tert-butyl-phenyl)-2-nitro-cyclohexanone as a yellow oil.

$^1$H NMR (300 MHz, CDCl$_3$) δ 7.48 (d, J=7.7 Hz, 1H), 7.39 (m, 1H), 7.34 (s, 1H), 7.15 (d, J=7.2 Hz, 1H), 3.06 (m, 1H), 2.94 (m, 1H), 2.54 (m, 2H), 1.95 (m, 3H), 1.74 (m, 1H), 1.32 (s, 9H).

Method [2] Retention time 1.74 min by HPLC and 1.79 min by MS (M+Na=298).

Step 4:

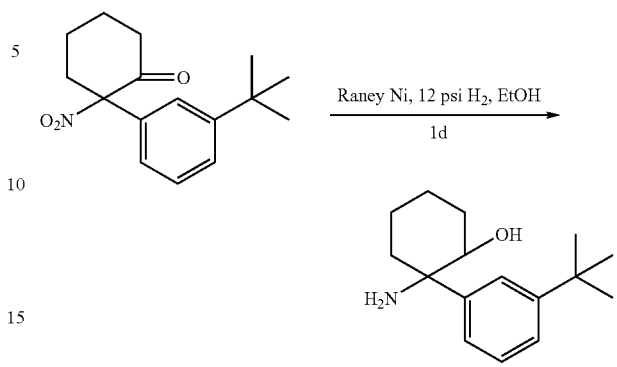

Raney 2800 nickel slurry in water (2 mL) was added to a solution of 2-(3-tert-butyl-phenyl)-2-nitro-cyclohexanone (40 mg, 145 umol) in ethanol (10 mL) in a parr bottle. The parr bottle was filled with hydrogen (12 psi) and evacuated three times. The parr bottle was refilled with hydrogen (12 psi) and shook for 18 h. The heterogeneous mixture was filtered through celite and concentrated to yield a mixture of cis/trans isomers of 2-amino-2-(3-tert-butyl-phenyl)-cyclohexanol.

Method [1] Retention time 1.38 min by HPLC and 1.43 min by MS (M−NH$_2$=231).

EXAMPLE 377

Preparation of 1-(5-BROMO-THIOPHEN-2-YL)-CYCLOHEXYLAMINE

Step 1:

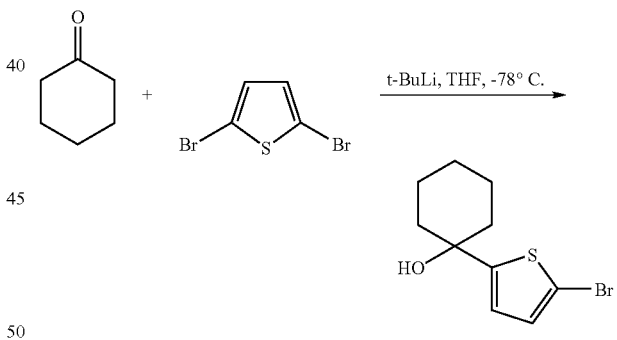

A solution of 1.7M tert-butyllithium in pentane (14.0 mL, 23.8 mmol) was added to a solution of 2,5-dibromothiophene (2.67 g, 11.0 mmol) in tetrahydrofuran (20 mL) at −78° C. After stirring for 1 h, cyclohexanone (1.4 mL, 13.5 mmol) was added. After stirring for 18 h, during which time the solution warmed to ambient temperature, the solution was diluted with saturated aqueous ammonium chloride and extracted with methylene chloride. The combined organic extracts were dried over magnesium sulfate, filtered, and concentrated. The residue was flash chromatographed with 19:1, 9:1, 17:3, 4:1 and 3:1 hexanes:ethyl acetate as the eluant to yield 2.58 g (90% yield) of 1-(5-bromo-thiophen-2-yl)-cyclohexanol as a light orange oil.

$^1$H NMR (300 MHz, CDCl$_3$) δ 6.89 (d, J=3.8 Hz, 1H), 6.72 (d, J=3.8 Hz, 1H), 2.34 (m, 2H), 1.95-1.62 (m, 6H), 1.28 (m, 2H).

Step 2:

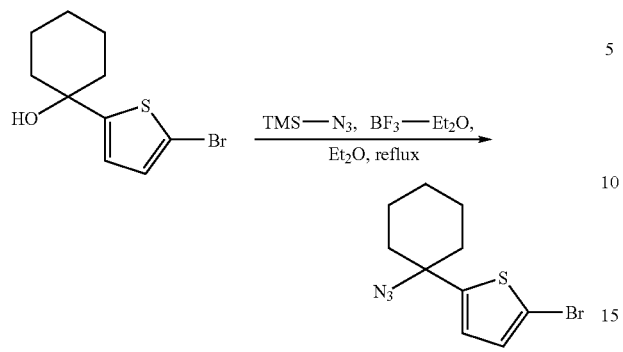

Borontrifluoride-etherate (1.3 mL, 10.3 mmol) was added to a solution of 1-(5-bromo-thiophen-2-yl)-cyclohexanol (2.57 g, 9.84 mmol) and azidotrimethylsilane (2.6 mL, 19.6 mmol) in diethyl ether (20 mL) and placed into a preheated oil bath at 45° C. After heating at reflux for 1.5 h, the solution was diluted with water and extracted with diethyl ether. The combined organic extracts were dried over magnesium sulfate, filtered, and concentrated. The residue was flash chromatographed with 99:1, 49:1, and 24:1 hexanes:ethyl acetate as the eluant to yield 1.29 g (46% yield) of 2-(1-Azido-cyclohexyl)-5-bromo-thiophene as a light yellow oil.

$^1$H NMR (300 MHz, CDCl$_3$) δ 6.95 (d, J=3.8 Hz, 1H), 6.79 (d, J=3.8 Hz, 1H), 2.00 (m, 2H), 1.87 (m, 2H), 1.62 (m, 5H), 1.34 (m, 1H).

Step 3:

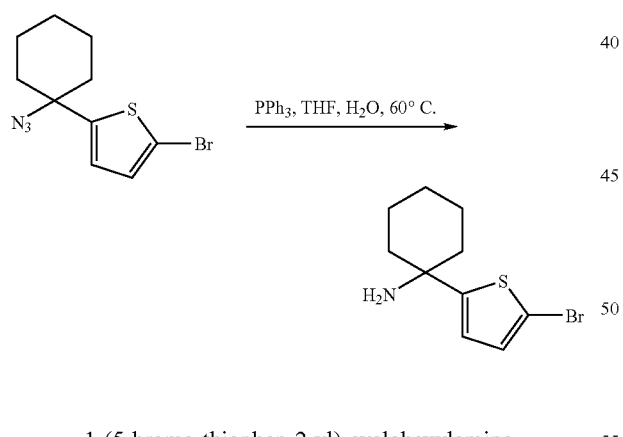

1-(5-bromo-thiophen-2-yl)-cyclohexylamine

A solution of triphenylphosphine (550 mg, 2.10 mmol) and 2-(1-Azido-cyclohexyl)-5-bromo-thiophene (289 mg, 1.01 mmol) in tetrahydrofuran (5 mL) and water (1 mL) was placed into a preheated oil bath at 60° C. After stirring for 24 h, the solution was concentrated and the residue was flash chromatographed w/49:1:0.1, 24:1:0.1, 23:2:0.2, and 22:3: 0.3 methylene chloride:methanol:concentrated ammonium hydroxide as the eluant to yield 1-(5-bromo-thiophen-2-yl)-cyclohexylamine impure with triphenylphosphine oxide.

Method [1] Retention time 1.20 min by HPLC and 1.26 min by MS (M–NH$_2$=243 and 245)

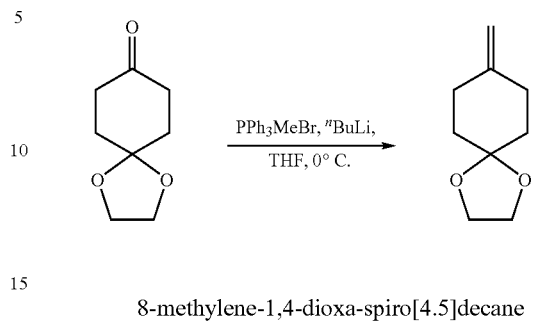

8-methylene-1,4-dioxa-spiro[4.5]decane

A solution of 1.6M $^n$butyllithium in hexanes (46 mL, 73.6 mmol) was slowly added to a heterogeneous mixture of methyltriphenylphosphonium bromide (28.07 g, 78.6 mmol) in tetrahydrofuran (150 mL) at –10° C. After stirring for 1 h, 1,4-dioxa-spiro[4.5]decan-8-one (8.01 g, 51.3 mmol) was added. After stirring for 3 h, during which time the solution warmed to ambient temperature, acetone was added and the heterogeneous mixture was concentrated. The residue was diluted with 1:1 methylene chloride:ethyl ether, filtered and concentrated. The residue was flash chromatographed with 49:1, 24:1, and 23:2 hexanes:etheyl acetate as the eluant to yield 6.22 g (79% yield) of 8-methylene-1,4-dioxa-spiro[4.5] decane as a yellow oil.

$^1$H NMR (300 MHz, CDCl$_3$) δ 4.67 (s, 2H), 3.96 (s, 4H), 2.29 (m, 4H), 1.70 (m, 4H).

EXAMPLE 378

Preparation of CIS/TRANS [4-AMINO-4-(3-TERT-BUTYL-PHENYL)-CYCLOHEXYL]-METHANOL

Step 1:

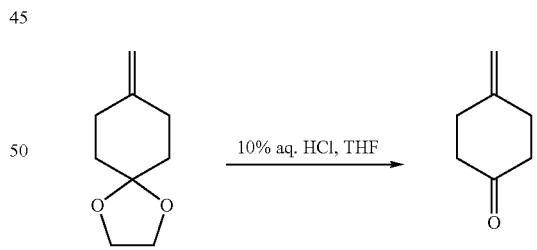

A solution of 8-methylene-1,4-dioxa-spiro[4.5]decane (6.22 g, 40.3 mmol) was stirred in tetrahydrofuran (100 mL) and 10% aqueous hydrochloric acid (100 mL) for 18 h. The solution was extracted with ethyl ether and the combined organic extracts were dried over magnesium sulfate. The combined organic extracts were filtered and concentrated to yield 3.89 g (88% yield) of 4-methylene-cyclohexanone as a yellow oil.

$^1$H NMR (300 MHz, CDCl$_3$) δ 4.89 (s, 2H), 2.47 (m, 8H).

Step 2:

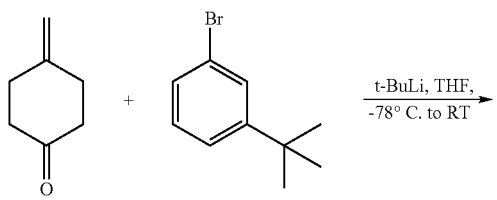

A solution of 1.7M tert-butyllithium in pentane (32.0 mL, 54.4 mmol) was added to a solution of 1-bromo-3-tert-butyl-benzene (5.54 g, 26.0 mmol) in tetrahydrofuran (60 mL) at −78° C. After stirring for 1 h, cyclohexanone (2.00 g, 18.2 mmol) in tetrahydrofuran (15 mL) was added. After stirring for 18 h, during which time the solution warmed to ambient temperature, the solution was diluted with saturated aqueous ammonium chloride and extracted with methylene chloride. The combined organic extracts were dried over magnesium sulfate, filtered, and concentrated. The residue was flash chromatographed with 49:1, 24:1, 23:2 hexanes:ethyl acetate as the eluant to yield 3.61 g (81% yield) of 1-(3-tert-butyl-phenyl)-4-methylene-cyclohexanol as a yellow oil.

$^1$H NMR (300 MHz, CDCl$_3$) δ 7.56 (s, 1H), 7.30 (m, 3H), 4.72 (s, 2H), 2.60 (m, 2H), 2.27 (m, 2H), 1.93 (m, 4H), 1.33 (s, 9H).

Step 3:

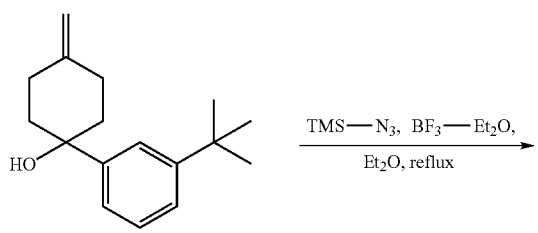

Borontrifluoride-etherate (2.0 mL, 15.7 mmol) was added to a solution of 1-(3-tert-butyl-phenyl)-4-methylene-cyclohexanol (3.60 g, 14.7 mmol) and azidotrimethylsilane (4.0 mL, 30.1 mmol) in diethyl ether (30 mL) and placed into a preheated oil bath at 45° C. After heating at reflux for 4 h, the solution was diluted with saturated aqueous ammonium chloride and extracted with diethyl ether. The combined organic extracts were dried over magnesium sulfate, filtered, and concentrated. The residue was flash chromatographed with 99:1, 49:1, and 24:1 hexanes:ethyl acetate as the eluant to yield 1.46 g (37% yield) of 1-(1-azido-4-methylene-cyclohexyl)-3-tert-butyl-benzene as a clear oil.

$^1$H NMR (300 MHz, CDCl$_3$) δ 7.47 (s, 1H), 7.36-7.23 (broad m, 3H), 4.72 (s, 2H), 2.48 (m, 2H), 2.28 (m, 2H), 2.13 (m, 2H), 1.96 (m, 2H), 1.34 (s, 9H).

Step 4:

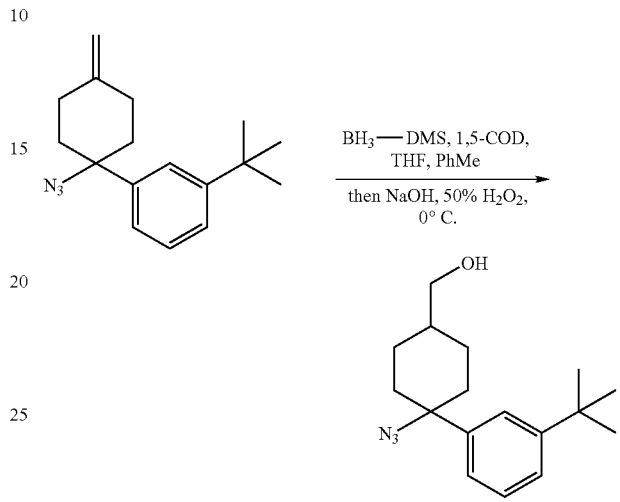

A solution of 2.0 M borane-dimethyl sulfide complex in toluene (1.1 mL, 2.2 mmol) was added to a solution of 1,5-cyclooctadiene (0.28 mL, 2.28 mmol) in tetrahydrofuran (5 mL) and was placed into a preheated oil bath at 70° C. After heating at reflux for 1 h, the solution was cooled to ambient temperature and 1-(1-azido-4-methylene-cyclohexyl)-3-tert-butyl-benzene (559 mg, 2.08 mmol) was added. After stirring for 18 h, the solution was cooled to 0° C. and 3N aqueous solution of sodium hydroxide (5.0 mL, 15.0 mmol) was added followed by the slow dropwise addition of 50% aqueous hydrogen peroxide (2.0 mL, 34.7 mmol). After stirring for 4 h, during which time the biphasic solution warmed to ambient temperature, the biphasic solution was extracted with methylene chloride. The combined organic extracts were dried over magnesium sulfate, filtered, and concentrated. The residue was flash chromatographed with 9:1, 4:1, and 7:3 hexanes:ethyl acetate as the eluant to yield 469 mg (79% yield) of a mixture of cis/trans isomers of [4-azido-4-(3-tert-butyl-phenyl)-cyclohexyl]-methanol as a clear oil.

$^1$H NMR (300 MHz, CDCl$_3$) δ 7.48 (s, 1H), 7.36-7.23 (broad m, 3H), 3.57 and 3.45 (t and m, J=5.5 Hz, 2H), 2.15 (m, 2H), 1.81 (m, 4H), 1.60-1.13 (broad m 3H), 1.34 (s, 9H).

Step 5:

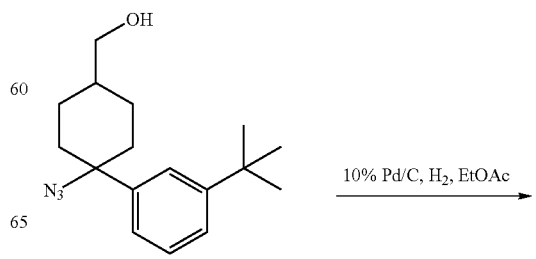

-continued

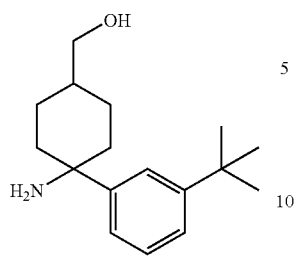

A solution of a mixture of cis/trans isomers of [4-azido-4-(3-tert-butyl-phenyl)-cyclohexyl]-methanol in ethyl acetate (10 mL) was added to a heterogeneous mixture of 10% palladium on carbon (400 mg) in ethyl acetate (10 mL) in a parr bottle. The parr bottle was filled with hydrogen (20 psi) and evacuated three times. The parr bottle was refilled with hydrogen (20 psi) and shook for 1 h, filtered through celite, and concentrated to yield a mixture of cis/trans isomers of [4-amino-4-(3-tert-butyl-phenyl)-cyclohexyl]-methanol.

Method [1] Retention time 1.18 min by HPLC and 1.26 min by MS (M−NH$_2$=245).

Method [1] Retention time 1.28 min by HPLC and 1.37 min by MS (M−NH$_2$=245).

EXAMPLE 379

Preparation of 1-[2-AMINOMETHYL-4-(2,2-DIMETHYL-PROPYL)-PHENYL]-PYRROLIDIN-3-OL

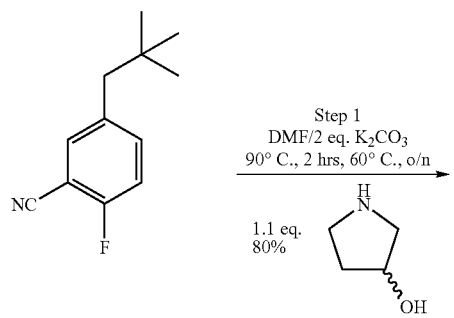

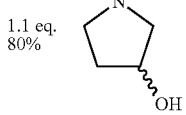

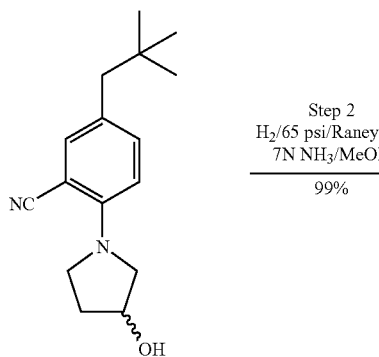

-continued

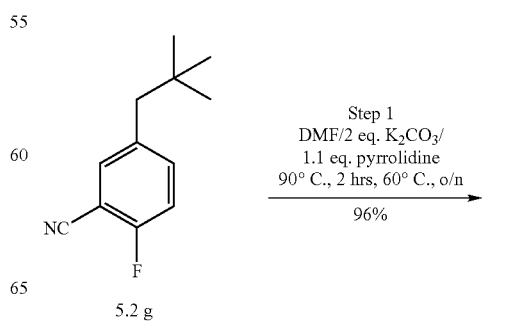

Step 1: 5-(2,2-Dimethyl-propyl)-2-(3-hydroxy-pyrrolidin-1-yl)-benzonitrile

To 0.76 g (4 mmole) of 5-(2,2-Dimethyl-propyl)-2-fluoro-benzonitrile in 15 mL of DMF was added 1.11 g (8 mmole, 2 eq.) of potassium carbonate and 0.43 mL (5.2 mmole, 1.3 eq.) of 3-pyrrolidinol and heated to 90-100° C. overnight. The reaction was monitored by HPLC/MS, Rt=1.349 min (method[2]), m/e=259.2/281.2. The reaction was allowed to cool to r. t., and quenched with ice/water/DCM, extracted and washed with brine, dried, concentrated, and purified by flash column to give 0.82 g of 5-(2,2-Dimethyl-propyl)-2-(3-hydroxy-pyrrolidin-1-yl)-benzonitrile (80% yield). Structure was confirmed by NMR.

TLC (30% EtOAc/Hexane). Rf=0.16 where s. m. at Rf=0.84. LCMS m/e=259.2(M+H), Rt (retention time, minutes)=1.349 (method[2]).

Step 2: 1-[2-Aminomethyl-4-(2,2-dimethyl-propyl)-phenyl]-pyrrolidin-3-ol

To 0.8 g (3.1 mmole) of 5-(2,2-Dimethyl-propyl)-2-(3-hydroxy-pyrrolidin-1-yl)-benzonitrile in 27 mL of 7 M NH$_3$/methanol was added 1 g of Raney 2800 Ni/water in a Parr bottle, saturated with hydrogen to 65 psi and shaken overnight. The reaction mixture was filtered through a cake of celite and solvents/ammonia stripped off to give 0.82 g of 1-[2-Aminomethyl-4-(2,2-dimethyl-propyl)-phenyl]-pyrrolidin-3-ol. (99% yield)

LCMS m/e=246.2(M−NH$_2$), Rt (retention time, minutes)=1.324 (method [1]).

EXAMPLE 380

Preparation of 5-(2,2-DIMETHYL-PROPYL)-2-PYRROLIDIN-1-YL-BENZYLAMINE

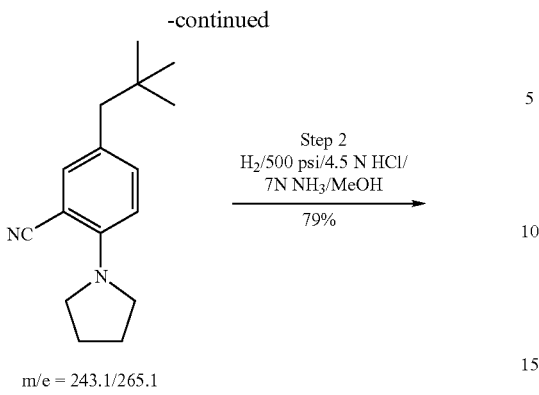

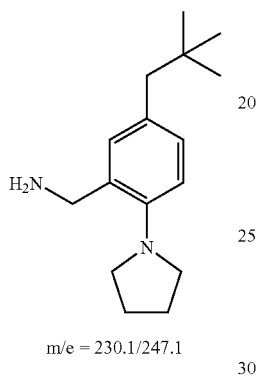

Step A: 5-(2,2-Dimethyl-propyl)-2-pyrrolidin-1-yl-benzonitrile

The title compound was prepared according to the method in EXAMPLE 379, Step 1. LCMS m/e=243.1/265.1 (M+H), Rt (retention time, minutes)=2.436 (method [1]).

Step B: 5-(2,2-Dimethyl-propyl)-2-pyrrolidin-1-yl-benzylamine

The title compound was prepared according to the method in EXAMPLE 379, Step 2.

LCMS m/e=230.1/247.1 (M+H), Rt (retention time, minutes)=1.528 (method [1]).

EXAMPLE 381

Preparation of 5-(2,2-DIMETHYL-PROPYL)-2-PIPERIDIN-1-YL-BENZYLAMINE

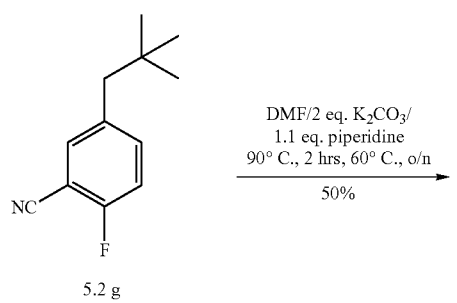

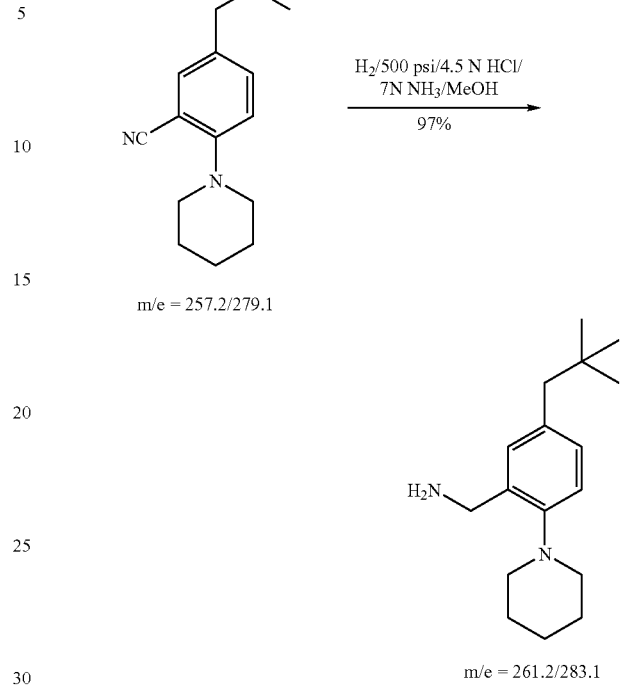

Step 1: 5-(2,2-Dimethyl-propyl)-2-piperidin-1-yl-benzonitrile

The title compound was prepared according to the method in EXAMPLE 379, Step 1.

LCMS m/e=257.1/279.1 (M+H), Rt (retention time, minutes)=2.599 (method [1]).

Step 2: 5-(2,2-Dimethyl-propyl)-2-piperidin-1-yl-benzylamine

The title compound was prepared according to the method in EXAMPLE 379, Step 2.

LCMS m/e=261.2/283.1 (M+H), Rt (retention time, minutes)=1.358 (method [1]).

EXAMPLE 382

Preparation of 4-AMINO-6-(2,2-DIMETHYL-PROPYL)-3,4-DIHYDRO-2H-QUINOLINE-1-CARBOXYLIC ACID BENZYL ESTER

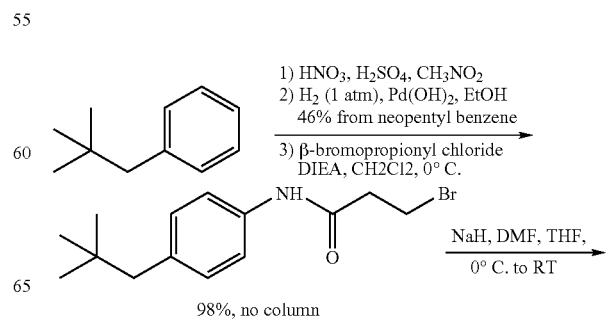

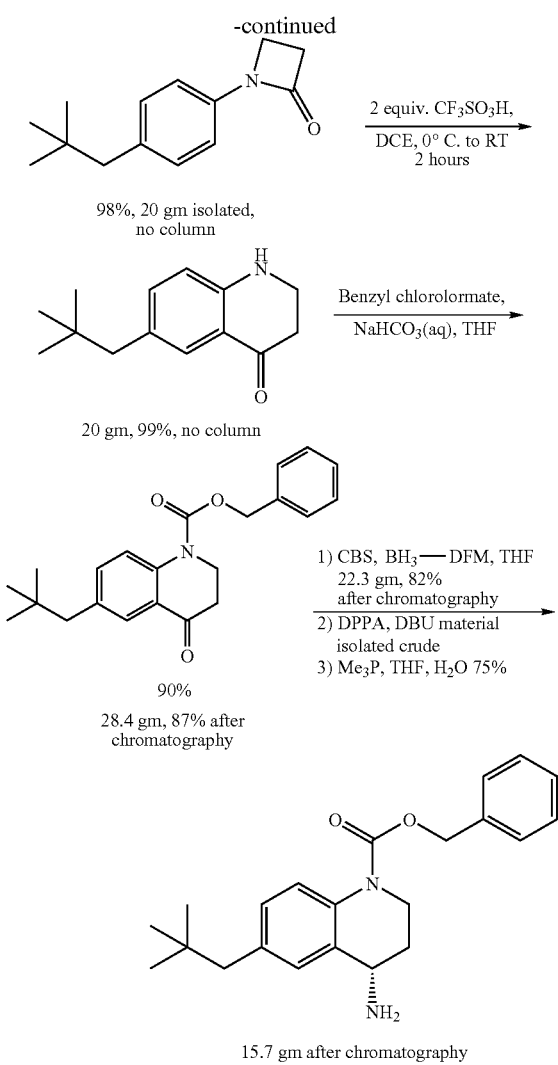

1-(2,2-Dimethyl-propyl)-4-nitro-benzene and 1-(2,2-Dimethyl-propyl)-2-nitro-benzene. To a stirred solution of concentrated sulfuric acid (13.8 mL) at 0° C. in an open flask was added concentrated HNO₃ (11.6 mL) dropwise by addition funnel. The sulfuric/nitric acid mix was then transferred to an addition funnel and added dropwise to a solution of neopentyl benzene (17.2 g, 116 mmol) in nitromethane (90 mL) stirring at 0° C. The temperature warmed to about 3° C. during the dropwise addition of the acid mixture. After complete addition, TLC in 9/1 hexanes/EtOAc showed the nitrated materials had begun forming. After warming to room temperature and stirring overnight the reaction was poured into 400 mL ice water and extracted 3×150 mL with CH₂Cl₂. The combined organics were washed 1×400 mL with H₂O, 2×400 mL with saturated NaHCO₃, and 1×400 mL with brine. The organics were dried (magnesium sulfate), filtered and concentrated to a yellow oil, which appears to be about a 1:1 mixture of regioisomers. This mixture was used crude in the subsequent reduction.

4-(2,2-Dimethyl-propyl)-phenylamine. To a stirred solution of the mixture of nitro compounds (22.4 g, 116 mmol) in 300 mL 95% EtOH was added Pearlman's catalyst (4 g). The suspension was put through a vacuum/purge cycle 3 times with hydrogen gas and then held under 1 atm H₂ overnight TLC in 9/1 hexanes/EtOAc showed two new lower rf spots. The nitro compounds had been completely consumed. The reaction was filtered through GF/F filter paper with 95% EtOH and the filtrate concentrated. The crude material was loaded onto a Biotage 75 L column with 5/95EtOAc/hexanes and eluted first with 5/95 EtOAc/hexanes (4 L) followed by 1/9 EtOAc/hexanes (6 L). The two regioisomeric anilines separated nicely and were concentrated to give the undesired high rf aniline as an orange oil and the desired lower rf aniline as a tan solid (8.7 g, 46% from neopentyl benzene).

3-Bromo-N-[4-(2,2-dimethyl-propyl)-phenyl]-propionamide. To a stirred solution of the aniline (15.3 g, 93.78 mmol) in CH₂Cl₂ (300 mL) at 0° C. under nitrogen was added dimethylaniline (12.5 g, 103 mmol) followed by β-bromopropionyl chloride (17.68 g, 103 mmol). After 2 h, the reaction was diluted to 400 mL with CH₂Cl₂ and washed 3×300 mL with 2 N HCl, 3×300 mL with saturated NaHCO₃, and 1×300 mL with brine. The organics were dried (magnesium sulfate), filtered and concentrated to a white solid (27.5 g, 98%).

1-[4-(2,2-Dimethyl-propyl)-phenyl]-azetidin-2-one. To a stirred solution of DMF (115 mL) at 0° C. under nitrogen was added sodium hydride (60% oil dispersion, 4.61 g, 115 mmol). The β-bromoamide 27.5 g, 92 mmol) was then added dropwise by cannulation in 270 mL THF, Gas evolution was observed and the cooing bath was allowed to slowly melt and the reaction stirred at room temperature overnight. The white suspension was then partitioned between EtOAc (400 mL) and brine (300 mL), The organics were isolated and washed 3×300 mL with brine. The organics were dried (magnesium sulfate), filtered and concentrated to an off white solid (20 g, 100%).

6-(2,2-Dimethyl-propyl)-2,3-dihydro-1H-quinolin-4-one. To a stirred solution of the β-lactam (20.1 g, 92.5 mmol) in 300 mL dichloroethane at 0° C. under nitrogen was added triflic acid (27.76 g, 185 mmol) dropwise by syringe. The reaction was allowed to warm to room temperature and allowed to react for 4 h. Afterward, the reaction mixture was poured into 1 L of rapidly stirred 1:1 CH₂Cl₂: ice cold saturated NaHCO₃. After stirring for a few minutes the organics were isolated and the aqueous solution extracted 1×200 mL with CH₂Cl₂. The combined organics were dried (magnesium sulfate), filtered and concentrated to a yellow oil (20.1 g, 100%).

6-(2,2-Dimethyl-propyl)-4-oxo-3,4-dihydro-2H-quinoline-1-carboxylic acid benzyl ester. To a stirred solution of the tetrahydroquinolone (20.1 g, 92.5 mmol) in 300 mL CH₂Cl₂ at 0° C. under nitrogen was added DIEA (23.9 g, 185 mmol) by syringe followed by benzyl chloroformate (23.7 g, 139 mmol) dropwise by addition funnel. The reaction was allowed to warm to room temperature overnight. TLC showed near complete consumption of starting material. The reaction was transferred to a 1 L sep funnel and washed 3×300 mL with 2 N HCl and 3×300 mL with saturated NaHCO₃. The organics were dried (magnesium sulfate), filtered and concentrated to a brown oil which was loaded directly onto a Biotage 75 L column and eluted with 9/1 hexanes/EtOAc. Product containing fractions were pooled and concentrated to a pale yellow oil that solidified upon standing (28.4 g, 87% from the aniline).

6-(2,2-Dimethyl-propyl)-4-(R)-hydroxy-3,4-dihydro-2H-quinoline-1-carboxylic acid benzyl ester. To a stirred solution of the ketone (27.5 g, 79 mmol) in 79 mL THF at −25° C. (CCl4/dry ice bath) under nitrogen was added the CBS reagent (1 M in toluene, 7.9 mL, 7.9 mmol,) followed by dropwise addition of borane dimethylsulfide complex (2 M in THF, 39.5 mL, 79 mmol) diluted with 95 mL THF by addition funnel, keeping the internal temperature below −20° C. After 1 h at −25° C., TLC in 3/7 EtOAc/hexanes showed some residual starting material with a new major lower rf spot dominating. The reaction was then allowed to warm to room temperature and stirred overnight. TLC showed the reaction had gone to completion. The reaction was recooled to 0° C. and quenched by addition of 190 mL MeOH via addition funnel. After removal of the cooling bath and stirring at room temperature for 2 h, the reaction was concentrated to dryness by rotovap and high vacuum and then loaded onto a Biotage 75 M column with 4/1 hexanes/EtOAc and eluted. Product containing fractions were pooled and concentrated to a pale yellow oil that solidified upon standing (22.3 g, 80 mmol).

column but a precipitate formed. The precipitate was filtered off and was shown to be not UV active on TLC and was thought to be trimethylphosphine oxide and was discarded. The crude product filtrate was loaded onto a Biotage 75M column with EtOAc and eluted with the same solvent. Product containing fractions were pooled and concentrated to a pate yellow oil (15.7 g, 77%).

EXAMPLE 383

Preparation of 4-(3-TERT-BUTYLPHENYL)-TETRAHYDRO-2H-PYRAN-4-AMINE

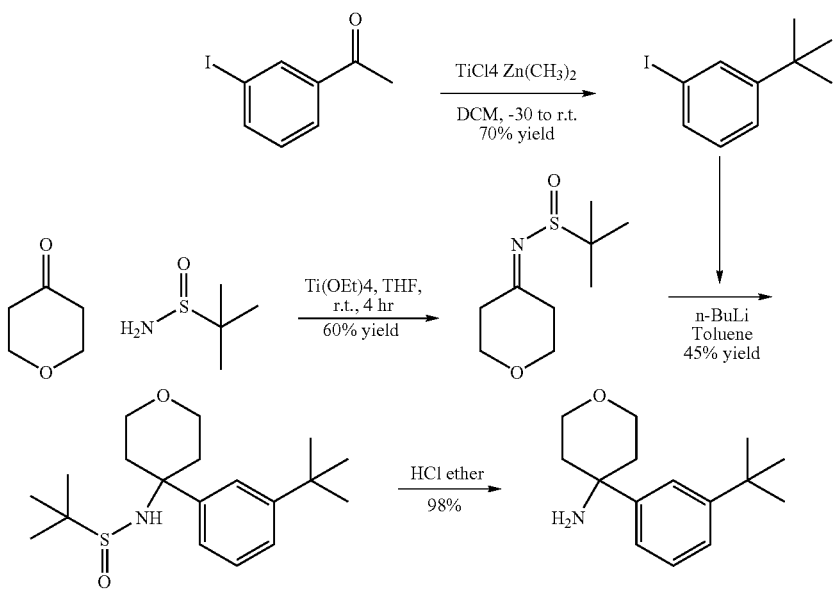

4-(S)-Azido-6-(2,2-dimethyl-propyl)-3,4-dihydro-2H-quinoline-1-carboxylic acid benzyl ester. To a stirred solution of the alcohol (22.3 g, 63 mmol) in 126 mL toluene at 0° C. under nitrogen was added DPPA (20.84 g, 75.7 mmol) neat by syringe. DBU (11.53 g, 75.7 mmol) was then added dropwise by addition funnel in 100 mL toluene. After complete addition the reaction was allowed to warm to room temperature and stir overnight. The crude reaction looked good by TLC in 4/1 hexanes/EtOAc with starting material completely consumed and a clean new higher rf spot. The reaction was reduced to about 100 mL by rotovap and was then loaded onto a Biotage 75 M column with minimum $CH_2Cl_2$ and eluted with 5/95 EtOAc/hexanes. The product containing fractions were pooled and concentrated to a clear oil which solidified upon standing (22 g, 92%).

4-(S)-Amino-6-(2,2-dimethyl-propyl)-3,4-dihydro-2H-quinoline-1-carboxylic acid benzyl ester. To a stirred solution of the azide (22 g, 58 mmol) in 580 mL THF at room temperature under nitrogen was added $H_2O$ (1.26 g, 70 mmol) followed by trimethylphosphine (1 M in toluene, 67 mL, 67 mmol) dropwise by addition funnel. After complete addition the reaction was allowed to stir overnight. TLC in EtOAc showed a trace of starting azide left with the majority of the material at the baseline. The reaction was concentrated to a yellow oil by rotary evaporation followed by high vacuum. The crude material was dissolved in EtOAc to load onto a 1-tert-Butyl-3-iodo-benzene. To a cooled (−40° C.) stirred solution of $TiCl_4$ (11 mL of a 1.0 M sol in DCM, 11 mmol) in 5 mL of DCM was added dimethyl zinc (5.5 mL of a 2 N sol. in toluene, 11 mmol). After stirring for 10 min Iodoacetophenone (1.23 g, 5.0 mmol) was added. After 2 h the reaction was warmed to 0° C. and stirred for an additional 1 h. The reaction was poured onto ice and extracted with ether. The organic phase was washed with water and sat $NaHCO_3$. The organic phase was dried over magnesium sulfate, filtered, and dried under reduced pressure. The material was distilled using a kugelrohr (80° C. at 0.1 mm) to obtain 1.0 g (76% yield) of a clear oil; $^1H$ NMR (300 MHz, $CDCl_3$) δ 7.71 (t, J=2.0 Hz, 1H), 7.51 (dt, J=7.7, 1.3 Hz, 1H), 7.35 (app d, J=7.7 Hz, 1H), 7.03 (f, J=7.9 Hz, 1H), 1.29 (s, 9H).

2-Methyl-propane-2-sulfinic acid (tetrahydro-pyran-4-ylidene)-amide. To a stirred solution of tetrahydro-pyran-4-one (1.2 g, 12 mmol) in 20 mL THF at room temperature under nitrogen was added titanium (IV) ethoxide (4.8 g, 21 mmol) followed by 2-Methyl-propane-2-sulfinic acid amide (1.29 g, 10 mmol). The reaction was stirred at room temperature for 3 h. The reaction was quenched by pouring it into 20 mL of saturated sodium bicarb, stirring rapidly. The formed precipitate was filtered off by filtration through GF/F filter paper and rinsed with EtOAc. The aqueous layer was washed once with EtOAc. The combined organics dried (magnesium sulfate), filtered and concentrated to a yellow oil. The material was purified using a biotage 40 M cartridge eluting with hexanes:ethyl acetate (60:40) to yield 1.25 g (62% yield) of a clear oil.

2-Methyl-propane-2-sulfinic acid [4-(3-tert-butyl-phenyl)-tetrahydro-pyran-4-yl]-amide. Iodo t-butyl benzene (14 g, 54.6 mmol) was taken up in 50 mL of Toulene under $N_2$ and cooled to 0° C. Butyl lithium (34 mL, 1.6 M sol. in hexanes) was added dropwise over 15 min. The reaction was stirred at 0° C. for 3 h. In a separate flask the imine (5.28 g, 26 mmoles) was taken up in 30 mL of Toluene and cooled to −78° C. Trimethyl aluminum (14.3 mL, 2.0 mmol sol. in toluene) was added dropwise over 10 min. The imine solution was stirred for 10 min and then cannuiated into the phenyl lithium over 30 min. The reaction was allowed to warm to room temperature and stirred for 4 h. The reaction was quenched with sodium sulfate decahydrate until the bubbling stopped. Magnesium sulfate was added to the reaction and stirred for 30 min. The reaction was filtered, rinsed with EtOAc and concentrated down onto silica gel. The material was purified using a biotage 75S cartridge eluting with ethyl acetate to yield 4.0 g (45% yield) of desired product.

4-(3-tert-Butyl-phenyl)-tetrahydro-pyran-4-ylamine. To a stirred solution of 2-methyl-propane-2-sulfinic acid [4-(3-tert-butyl-phenyl)-tetrahydro-pyran-4-yl]-amide (3.7 g, 11.0 mmol) in ether (10 mL) was added HCl (33 mL, 1 M sol. in ether). The reaction was stirred for 30 min and then concentrated under reduced pressure; LC rt=2.07 min; MS(ESI) 233.7.

EXAMPLE 384

Preparation of 4-AMINO-4-(3-TERT-BUTYLPHENYL)-PIPERIDINE-1-CARBOXYLIC ACID BENZYL ESTER

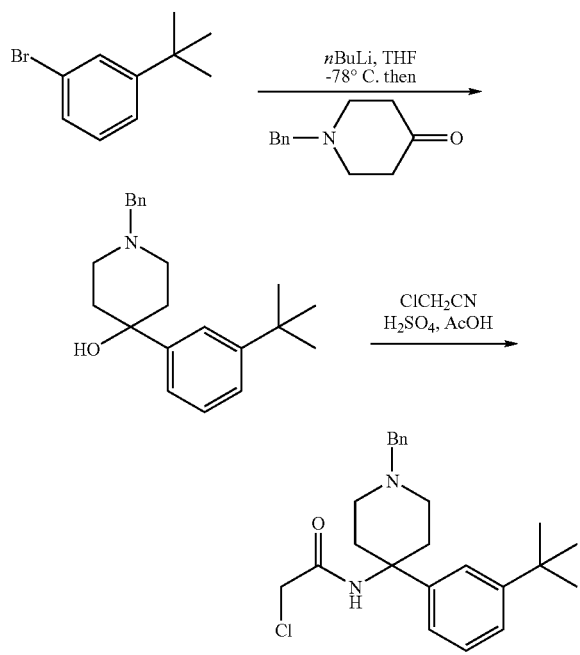

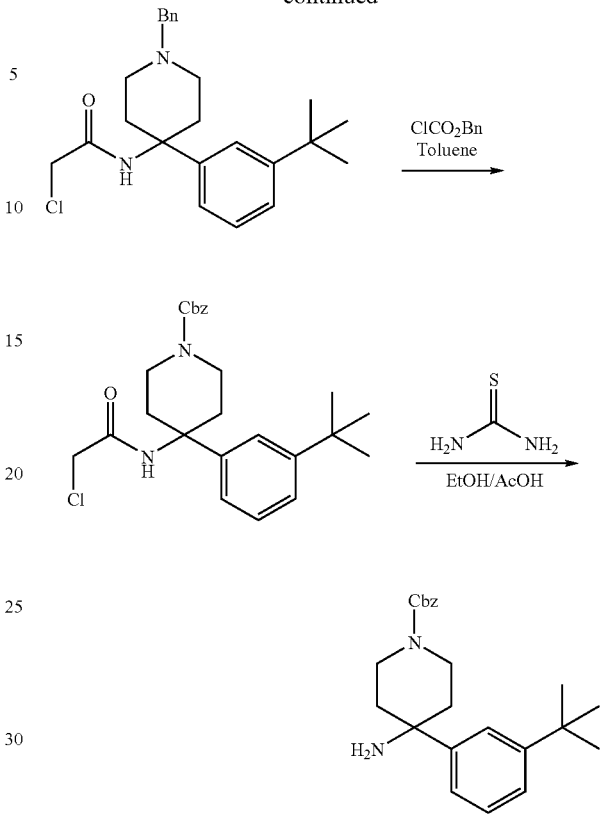

1-Benzyl-4-(3-tert-butylphenyl)-piperidin-4-ol. A solution of bromo-tert-butylbenzene (4.62 g, 21.68 mmol) in THF (50 mL) was cooled to −78° C. then n-BuLi (2.5M, 9.1 mL) was added dropwise. The reaction was stirred for 30 min then a solution of 1-benzyl-piperidin-4-one (3.69 g, 19.5 mmol) in THF (10 mL) was added dropwise. After stirring for 30 min at −78° C., the reaction was warmed to 0° C. then quenched with water (50 mL). The reaction was diluted with ethyl acetate (100 mL); the organic layer was separated, washed with brine (50 mL), dried over magnesium sulfate and concentrated to give an oil (6.94 g, 21.5 mmol), which was used in the next step without further purification; LC rt=2.98 min; MS(ESI) 306.2.

N-[1-Benzyl-4-(3-tert-butylphenyl)-piperidin-4-yl]-2-chloroacetamide. To 1-benzyl-4-(3-tert-butylphenyl)-piperidin-4-ol (6.94 g, 21.45 mmol) and chloroacetonitrile (3.24 g, 75.50 mmol) was added acetic acid (3.5 mL) then sulfuric acid (3.5 mL) and the reaction stirred at room temperature overnight. The reaction was diluted with ethyl acetate (100 mL), washed with ammonium chloride (100 mL), wafer (50 mL), brine (50 mL), then dried over magnesium sulfate and concentrated. Silica gel chromatography eluting with 100% ethyl acetate gave an oil (2.75 g, 6.89 mmol); MS(ESI) 399.3.

4-(3-tert-Butylphenyl)-4-(2-chloroacetylamino)-piperidine-1-carboxylic acid benzyl ester. To a solution of N-[1-benzyl-4-(3-tert-butylphenyl)-piperidin-4-yl]-2-chloroacetamide (2.65 g, 6.664 mmol) in toluene (20 mL) was added benzyl chloroformate (1.90 mL, 7.00 mmol) and the reaction was heated to 80° C. The reaction was concentrated, placed onto silica gel and eluted with hexane/ethyl acetate (2:1). Isolated an oil (2.82 g, 6.37 mmol); MS(ESI) 442.9.

4-Amino-4-(3-tert-butylphenyl)-piperidine-1-carboxylic acid benzyl ester. A solution of 4-(3-tert-butylphenyl)-4-(2-chloroacetylamino)-piperidine-1-carboxylic acid benzyl ester (2.82 g, 6.37 mmol) and thiourea (0.53 g, 7.00 mmol) in 10 mL of ethanol and 2 mL of acetic acid was heated to 80° C. overnight. The reaction was cooled, diluted with ethyl acetate (50 mL), washed with 1 N NaOH (50 mL), brine (50 mL), dried over magnesium sulfate and concentrated. Silica gel chromatography eluting with 5% MeOH/DCM gave some product and some mixed fractions. The mixed fractions were chromatographed over silica gel eluting with 3% MeOH/DCM and again gave some product and some mixed fractions. Finally, the mixed fractions were chromatographed over silica gel eluting with 8% MeOH/EtOAc and all impurities were removed. The batches of pure product were combined and dried to give a colorless oil (1.60 g, 4.44 mmol, 69%); LC rt=3.15 min; MS(ESI) 350.0.

EXAMPLE 385

Preparation of 2-BROMO-5-(2,2-DIMETHYL-PROPYL)-BENZYLAMINE

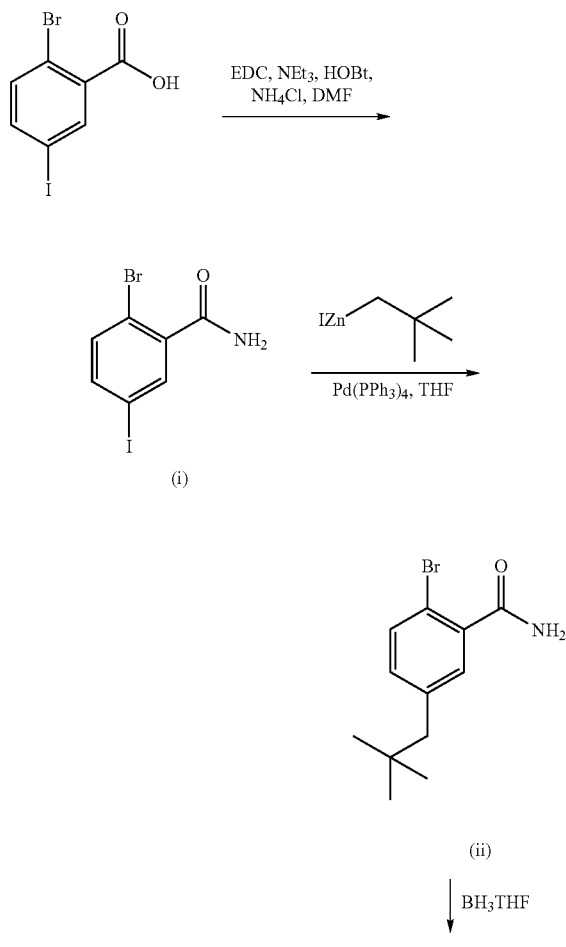

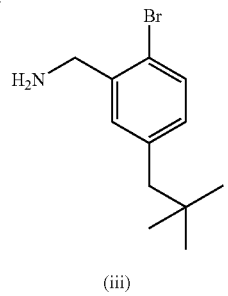

To commercially available 2-bromo-5-iodobenzoic acid (76.5 mmol, 25 g), hydroxybenzotriazole (HOBt, 76.5 mmol, 10.4 g), triethylamine (TEA, 153 mmol, 21.3 mL) and ammonium chloride (84.1 mmol, 4.50 g), is added DMF (anhydrous, 300 mL). After dissolution of solids by stirring, 1-[3-(Dimethylamino)propyl]-3-ethylcarbodiimide hydrochloride (EDC-HCl, 84.1 mmol, 16.08 g) is added. Stirring continues with the reaction capped for 16 hours. The reaction is concentrated to half the original volume via roto-evaporation, then 1 L ethyl acetate is added and the subsequent solution Is washed once with 1 M HCl (300 mL), then once with saturated NaHCO₃ (300 mL), then twice with H₂O, and then once with saturated NaCl (100 mL). A white solid resulted on drying the ethyl acetate phase with MgSO₄, filtering through celite, and evaporation of volitiles.

LCMS: Method [11]: Retention time at 220 nm detection is 1.51 minutes and $[M=1]^+$=325.8. LCMS shows nearly quantitative product (i) at >95% purity.

To a THF (anhydrous, 300 mL) solution of amide ((I), 76.5 mmol) and tetrakis)triphenylphosphine)palladium(0) (3.825 mmol, 4.42 g), is slowly added neopentylzinc iodide (commercially available 0.5M in THF, 95.6 mmol, 190 mL), The mixture is capped and allowed to stir at 40° C. (in a temperature controlled water bath) for 12 hours. The reaction solution is then quenched by adding 1M HCl in ethanol (100 mL), and then evaporated of volitiles via roto-evaporation. The resulting brown solid mass is partially taken up in ethyl acetate (500 mL), filtered, and the filtrate evaporated of volitiles via roto-evaporation. LCMS (method [11]) of the crude residue shows a complex mixture, and the product can be purified by passing a concentrated ethyl acetated solution through a silica column with hexanes/ethyl acetate eluent and fractionation. Pure fractions containing (ii) are determined by LCMS (method [11], retention 2.19 minutes, [M +1]=269.83). The pure fractions are evaporated of solvent via roto-evaporation and high vacuum.

The bromo amide ((ii), 3.7 mmol, 1.0 g) is dissolved in a 2M BH₃ (dimethylsulfide complex) solution in THF (55 mmol, 27.8 mL) then refluxed (reaction flask equipped with a water cooled condenser) for 24 h. At the end of reflux and after cooling, the mixture is quenced with the slow addition of isopropanol (50 mL). The reaction is removed of volitiles via roto-evaporation, the resulting oil is taken up in ethyl acetate (75 mL) and washed once with aqueous HCl (1M, 25 mL), the organic layer is dried with MgSO4, filtered, evaporated via roto-evaporation, and traces of volitiles removed with high vacuum. LCMS (method [11]) of the crude work-up residue shows 85% HPLC pure desired amine iii (retention 2.17 minutes, [M+1]=255.67).

EXAMPLE 386

NH$_2$ Replacement of Hydroxyl Alpha to the
—(CHR$_1$)-Group of Compounds of Formula (I)

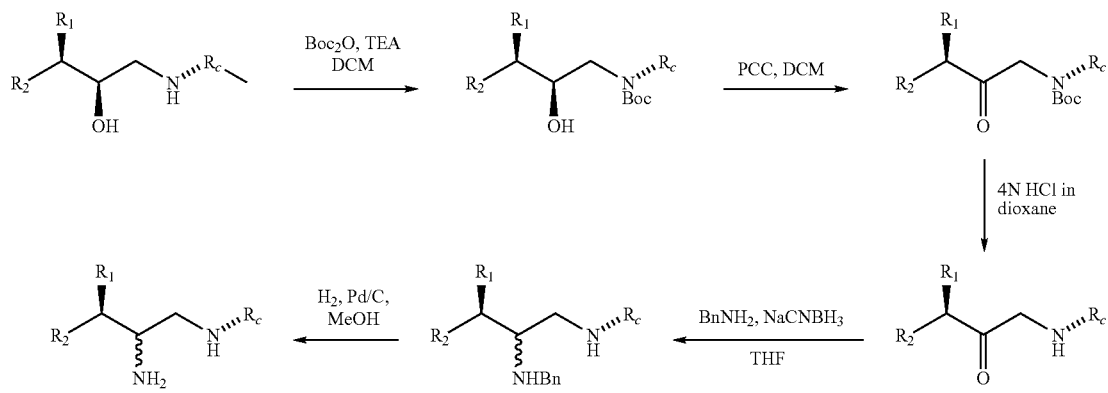

EXAMPLE 387

SH Replacement of Hydroxyl Alpha to the
—(CHR$_1$)-Group of Compounds of Formula (I)

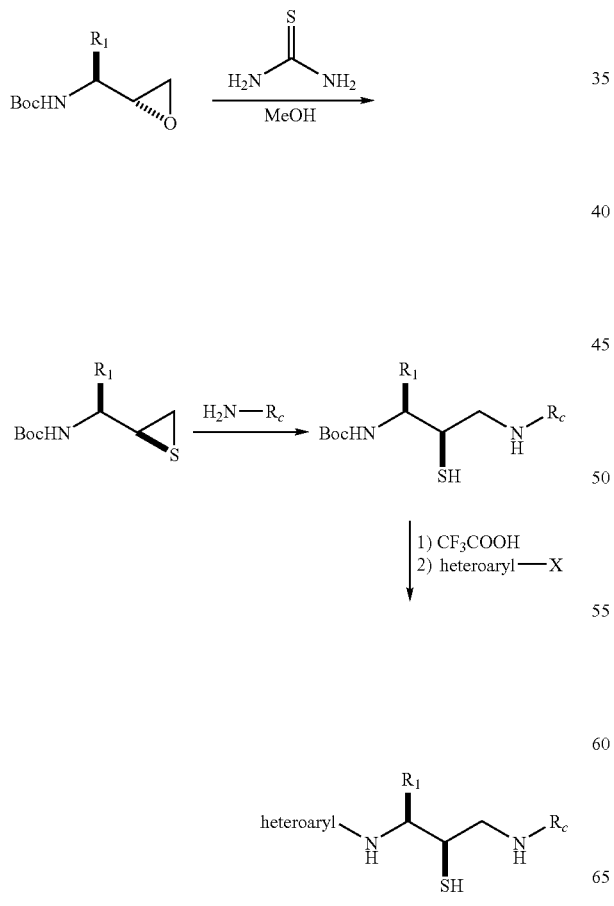

Additional Exemplary Compounds

EXAMPLE 388

1-[1-(3-TERT-BUTYL-PHENYL)-CYCLOHEXY-LAMINO]-4-(3,5-DIFLUORO-PHENYL)-3-(2-METHYLAMINO-PYRIMIDIN-4-YLAMINO)-BUTAN-2-OL

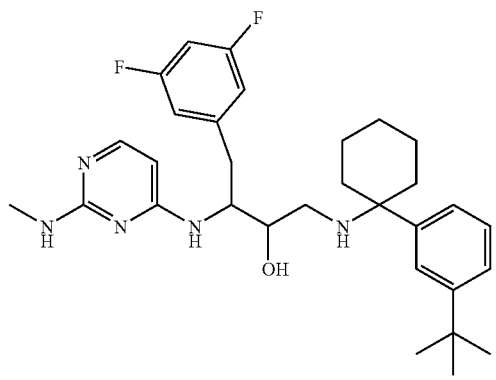

EXAMPLE 389

1-[1-(3-TERT-BUTYL-PHENYL)-CYCLOHEXY-LAMINO]-4-(3,5-DIFLUORO-PHENYL)-3-(4-METHOXY-BENZYLOXYMETHYL)-BUTAN-2-OL

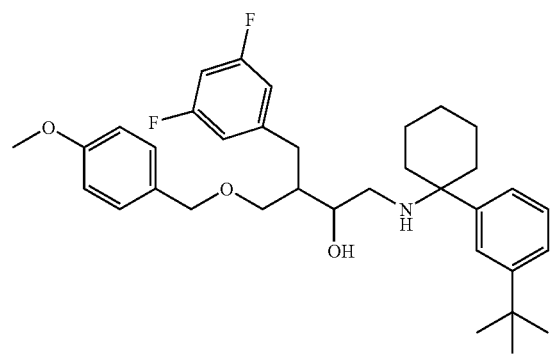

Generally, the protection of amines is conducted, where appropriate, by methods known to those, skilled, in the art. See, for example, *Protecting Groups in Organic Synthesis*, John Wiley and Sons, New York, N.Y., 1981, Chapter 7; *Protecting Groups In Organic Chemistry*, Plenum Press, New York, N.Y., 1973, Chapter 2. When the amino protecting group is no longer needed, it is removed by methods known to those skilled in the art. By definition the amino protecting group must be readily removable. A variety of suitable methodologies are known to those skilled in the art, see also T. W. Green and P. G. M. Wuts in *Protective Groups in Organic Chemistry*, John Wiley and Sons, 3$^{rd}$ edition, 1999. Suitable amino protecting groups include t-butoxycarbonyl, benzyloxycarbonyl, formyl, trityl, phthalimido, trichloro-acetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxy-carbonyl, cyclopentanyloxycarbonyl, 1-methylcyclo-pentanyloxycarbonyl, cyclohexanyloxycarbonyl, 1-methyl-cyclohexanyloxycarbonyl, 2-methylcyclohexanyloxycarbonyl, 2-(4-toluylsulfonyl)ethoxycarbonyl, 2-(methylsulfonyl)-ethoxycarbonyl, 2-(triphenylphosphino)ethoxycarbonyl, fluorenylmethoxycarbonyl, 2-(trimethylsilyl)ethoxy-carbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl, 1-piperidyloxycarbonyl, 9-fluoroenylmethyl carbonate, —CH—CH=CH$_2$, and the like.

In an embodiment, the protecting group is t-butoxycarbonyl (Boc) and/or benzyloxycarbonyl (CBZ). In another embodiment, the protecting group is Boc. One skilled in the art will recognize suitable methods of introducing a Boc or CBZ protecting group and may additionally consult *Protective Groups in Organic Chemistry*, for guidance.

The compounds of the present invention may contain geometric or optical isomers as tautomers. Thus, the present invention includes all tautomers and pure geometric isomers, such as the E and Z geometric isomers, as mixtures thereof. Further, the present invention includes pure enantiomers, diastereomers and/or mixtures thereof, including racemic mixtures. The individual geometric isomers, enantiomers or diastereomers may be prepared or isolated by methods known to those in the art, including, for example chiral chromatography, preparing diastereomers, separating the diastereomers and then converting the diastereomers into enantiomers.

Compounds of the present invention with designated stereochemistry can be included in mixtures, including racemic mixtures, with other enantiomers, diastereomers, geometric isomers or tautomers. in a preferred embodiment, compounds of the present invention are typically present in these mixtures in diastereomeric and/or enantiomeric excess of at least 50%. Preferably, compounds of the present invention are present in these mixtures in diastereomeric and/or enantiomeric excess of at least 80%. More preferably, compounds of the present invention with the desired stereochemistry are present in diastereomeric and/or enantiomeric excess of at least 90%. Even more preferably, compounds of the present invention with the desired stereochemistry are present in diastereomeric and/or enantiomeric excess of at least 99%. Preferably the compounds of the present invention have the "S" configuration at position 1. Also preferred are compounds that have the "R" configuration at position 2. Most preferred are compounds that have the "1S,2R" configuration.

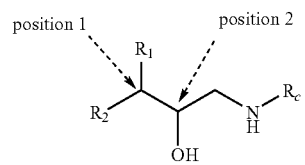

Several of the compounds of formula (I) are amines, and as such form salts when reacted with acids, Pharmaceutically acceptable salts are preferred over the corresponding amines since they produce compounds, which are more water soluble, stable and/or more crystalline.

EXAMPLE 390

Biological Examples

Properties such as efficacy, oral bioavailability, selectivity or blood-brain barrier penetration can be assessed by techniques and assays known to one skilled in the art. Exemplary assays for determining such properties are found below.

Inhibition of App Cleavage

The methods of treatment and compounds of the present invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While many theories exist, inhibition of beta-secretase activity is thought to inhibit production of A-beta.

Inhibitory activity is demonstrated in one of a variety of inhibition assays, whereby cleavage of an APP substrate in the presence of beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compounds of formula (I) are known. Representative assay systems are described, for example, in U.S. Pat. Nos. 5,942,400 and 5,744,346, as well as in the Examples below.

The enzymatic activity of beta-secretase and the production of A-beta can be analyzed in vitro or in vivo, using natural, mutated, and/or synthetic APP substrates, natural, mutated, and/or synthetic enzyme, and the compound employed in the particular method of treatment. The analysis can involve primary or secondary cells expressing native, mutant, and/or synthetic APP and enzyme, animal models expressing native APP and enzyme, or can utilize transgenic animal models expressing the substrate and enzyme. Detection of enzymatic activity can be by analysis of at least one of the cleavage products, for example, by immunoassay, fluorometric or chromogenic assay, HPLC, or other means of detection. Inhibitory compounds are determined as those able to decrease the amount of beta-secretase cleavage product produced in comparison to a control, where beta-secretase mediated cleavage in the reaction system is observed and measured in the absence of inhibitory compounds.

Efficacy reflects a preference for a target tissue. For example, efficacy values yield information regarding a compound's preference for a target tissue by comparing the compound's effect on multiple (i.e., two) tissues. See, for example, Dovey et al., *J. Neurochemistry*, 2001, 76:173-181. Efficacy reflects the ability of compounds to target a specific tissue and create the desired result (e.g., clinically). Efficacious compositions and corresponding methods of treatment are needed to prevent or treat conditions and diseases associated with amyloidosis.

Efficacious compounds of the present invention are those able to decrease the amount of A-beta produced compared to a control, where beta-secretase mediated cleavage is observed and measured in the absence of the compounds. Detection of efficacy can be by analysis of A-beta levels, for example, by Immunoassay, fluorometric or chromogenic assay, HPLC, or other means of detection. The efficacy of the compounds of formula (I) was determined as a percentage inhibition corresponding to A-beta concentrations for tissue treated and untreated with compound.

Beta-Secretase

Various forms of beta-secretase enzyme are known, are available, and useful for assaying enzymatic activity and inhibition of enzyme activity. These include native, recombinant, and synthetic forms of the enzyme. Human beta-secretase is known as Beta Site APP Cleaving Enzyme (BACE), BACE1, Asp2, and memapsin 2, and has been characterized, for example, in U.S. Pat. No. 5,744,346 and published PCT patent applications WO 98/22597, WO 00/03819, WO 01/23533, and WO 00/17369, as well as in literature publications (Hussain et al., 1999, *Mol. Cell. Neurosci.*, 14:419-427; Vassar et al., 1999, *Science*, 286:735-741; Yan et al., 1999, *Nature*, 402:533-537; Sinha et al., 1999, *Nature*, 40:537-540; and Lin et al., 2000, *Proceedings Natl. Acad. Sciences USA*, 97:1456-1460). Synthetic forms of the enzyme have also been described in, for example, WO 98/22597 and WO 00/17369. Beta-secretase can be extracted and purified from human brain tissue and can be produced in cells, for example mammalian cells expressing recombinant enzyme.

APP Substrate

Assays that demonstrate inhibition of beta-secretase-mediated cleavage of APP can utilize any of the known forms of APP, including the 695 amino acid "normal" isotype described by Kang et al., 1987, *Nature*, 325:733-6, the 770 amino acid isotype described by Kitaguchi et. al., 1981, *Nature*, 331:530-532, and variants such as the Swedish Mutation (KM670-1NL) (APP-SW), the London Mutation (V7176F), and others. See, for example, U.S. Pat. No. 5,766, 846 and also Hardy, 1992, *Nature Genet* 1:233-234, for a review of known variant mutations. Additional useful substrates include the dibasic amino acid modification, APP-KK, disclosed, for example, in WO 00/17369, fragments of APP, and synthetic peptides containing the beta-secretase cleavage site, wild type (WT) or mutated form, (e.g., SW), as described, for example, in U.S. Pat. No. 5,942,400 and WO 00/03819.

The APR substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety can be an antigenic epitope for antibody binding, a label or other defection moiety, a binding substrate, and the like.

Antibodies

Products characteristic of APR cleavage can be measured by immunoassay using various antibodies, as described, for example, in Pirttila et at, 1999, *Neuro. Lett.*, 249:21-4, and in U.S. Pat. No. 5,612,486. Useful antibodies to defect A-beta include, for example, the monoclonal antibody 6E10 (Senetek, St. Louis, Mo.) that specifically recognizes an epitope on amino acids 1-16 of the A-beta peptide, antibodies 162 and 164 (New York State institute for Basic Research, Staten Island, N.Y.) that are specific for human A-beta 1-40 and 1-42, respectively, and antibodies that recognize the junction region of A-beta, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APR and Its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the present invention are described, for example, in WO 00/17369, WO 00/03819, and U.S. Pat. Nos. 5,942,400 and 5,744,346. Such assays can be performed in cell-free incubations or in cellular incubations using cells expressing A-beta-secretase and an APP substrate having A-beta-secretase cleavage site.

An APP substrate containing the beta-secretase cleavage site of APP, for example, a complete APP or variant, an APR fragment, or a recombinant or synthetic APP substrate containing the amino acid sequence KM-DA or NL-DA is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that can be fusion proteins or peptides that contain the substrate peptide and a modification useful to facilitate the purification or detection of the peptide or its beta-secretase cleavage products. Useful modifications include the insertion of a known antigenic epitope for antibody binding, the linking of a label or detectable moiety, the linking of a binding substrate, and the like.

Suitable incubation conditions for a cell-free in vitro assay include, for example, approximately 200 nM to 10 µM substrate, approximately 10 pM to 200 pM enzyme, and approximately 0.1 nM to 10 µM inhibitor compound, in aqueous solution, at an approximate pH of 4-7, at approximately 37° C., for a time period of approximately 10 min to 3 h.

These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by an anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A-beta. Contact of an APP substrate with A-beta-secretase enzyme within the cell and in the presence or absence of a compound inhibitor of the present invention can be used to demonstrate beta-secretase inhibitory activity of the compound, it is preferred that the assay in the presence of a useful inhibitory compound provides at least about 10% inhibition of the enzymatic activity, as compared with a non-inhibited control.

In an embodiment, cells that naturally express beta-secretase are used. Alternatively, cells are modified to express a recombinant beta-secretase or synthetic variant enzyme as discussed above. The APP substrate can be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A-beta from APP provide useful means to assay inhibitory activities of the compounds employed in the methods of treatment of the present invention. Production and release of A-beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of at least one cleavage product of the APP substrate. For example, inhibition of beta-secretase activity against the substrate APR would be expected to decrease the release of specific beta-secretase induced APP cleavage products such as A-beta.

Although both neural and non-neural cells process and release A-beta, levels of endogenous beta-secretase activity are low and often difficult to detect by EIA. The use of cell types known to have enhanced beta-secretase activity, enhanced processing of APP to A-beta, and/or enhanced production of A-beta are therefore preferred. For example, transfection of cells with the Swedish Mutant form of APR (APP-SW), with APP-KK, or with APP-SW-KK provides cells having enhanced beta-secretase activity and producing amounts of A-beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor employed in the methods of treatment, the amount of A-beta released into the medium and/or the amount of $CTF_{99}$ fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release A-beta, as described above. For example, transgenic animals expressing APP substrate and beta-secretase enzyme can be used to demonstrate inhibitory activity of the compounds of the present invention. Certain transgenic animal models have been described, for example, in U.S. Pat. Nos. 5,877,399, 5,612,486, 5,387,742, 5,720,936, 5,850,003, 5,877,015, and 5,811,633, and in Games et al., 1995, *Nature,* 373:523. Animals that exhibit characteristics associated with the pathophysiology of Alzheimer's disease are preferred. Administration of the compounds of the present invention to the transgenic mice described herein provides an alternative method for demonstrating the inhibitory activity of the compounds. Administration of the compounds of the present invention in a pharmaceutically effective carrier and via an administrative route that reaches the target tissue in an appropriate therapeutic amount is also preferred.

Inhibition of beta-secretase mediated cleavage of APP at the beta-secretase cleavage site and of A-beta release can be analyzed in these animals by measuring cleavage fragments in the animal's body fluids such as cerebral fluid or tissues. Analysis of brain tissues for A-beta deposits or plaques is preferred.

A: Enzyme Inhibition Assay

The methods of treatment and compounds of the present invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942, 400. Briefly, the substrate is a fusion peptide formed of MBP and the carboxy terminal 125 amino acids of APP-SW, the Swedish mutation. The beta-secretase enzyme is derived from human brain tissue as described in Sinha et al., 1999, *Nature,* 40:537-540 or recombinantly produced as the full-length enzyme (amino acids 1-501), and can be prepared, for example, from 293 cells expressing the recombinant cDNA, as described in WO 00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu596 at the substrate's APP-SW 751 mutation site.

Specific Assay Procedure

Compounds of formula (I) are diluted in a 1:1 dilution series to a six-point concentration curve (two wells per concentration) in one row of a 96-well plate per compound tested. Each of the test compounds is prepared in DMSO to make up a 10 mM stock solution. The stock solution is serially diluted in DMSO to obtain a final compound concentration of 200 µM at the high point of a 6-point dilution curve. 10 µL of each dilution is added to each of two wells on row C of a corresponding V-bottom plate to which 190 µL of 52 mM NaOAc, 7.9% DMSO, pH 4.5 are pre-added. The NaOAc diluted compound plate is spun down to pellet precipitant and 20 µL/well is transferred to a corresponding flat-bottom plate to which 30 µL of ice-cold enzyme-substrate mixture (2.5 µl MBP-C125SW substrate, 0.03 µL enzyme and 24.5 µL ice cold 0.09% TX100 per 30 µL) is added. The final reaction mixture of 200 µM compound at the highest curve point is in 5% DMSO, 20 mM NaOAc, 0.06% TX100, at pH 4.5.

Warming the plates to 37° C. starts the enzyme reaction. After 90 min at 37° C., 200 µL/well cold specimen diluent is added to stop the reaction and 20 µL/well was transferred to a corresponding anti-MBP antibody coated ELISA plate for capture, containing 80 µL/well specimen diluent. This reaction is incubated overnight at 4° C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a 50% reduction in detected signal ($IC_{50}$) compared to the enzyme reaction signal in the control wells with no added compound, in this assay, preferred compounds of the present invention exhibit an $IC_{50}$ of less than 50 µM.

B: FP Bace Assay: Cell Free Inhibition Assay Utilizing a Synthetic APP Substrate A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds employed in the present invention. Useful substrates include
Biotin-SEVNL-DAEFRC[oregon green]KK,
Biotin-SEVKM-DAEFRC[oregon green]KK,
Biotin-GLNIKTEEISEISY-EVEFRC[oregon green]KK,
Biotin-ADRGLTTRPGSGLTNIKTEEISEVNL-DAE-FRC[oregon green]KK, and
Biotin-FVNQHLCoxGSHLVEALY-LVCoxGERGFFYT-PKAC[oregon green]KK.

The enzyme (0.1 nM) and test compounds (0.001-100 µM) are incubated in pre-blocked, low affinity, black plates (384 well) at 37° C. for 30 min. The reaction is initiated by addition of 150 mM substrate to a final volume of 30 µL/well. The final assay conditions are 0.001-100 µM compound inhibitor, 0.1 molar sodium acetate (pH 4.5), 150 nM substrate, 0.1 nM soluble beta-secretase, 0.001% Tween 20, and 2% DMSO. The assay mixture is incubated for 3 h at 37° C., and the reaction is terminated by the addition of a saturating concentration of immunopure streptavidin. After incubation with streptavidin at room temperature for 15 min, fluorescence polarization is measured, for example, using a LJL Acqurest (Ex485 nm/Em530 nm).

The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, preferred compounds of the present invention exhibit an $IC_{50}$ of less than 50 µM. More preferred compounds of the present invention exhibit an $IC_{50}$ of less than 10 µM. Even more preferred compounds of the present invention exhibit an $IC_{50}$ of less than 5 µM.

C: Beta-Secretase Inhibition: P26-P4'SW Assay

Synthetic substrates containing the beta-secretase cleavage site of APP are used to assay beta-secretase activity, using the methods described, for example, in published PCX application WO 00/47618. The P26-P4'SW substrate is a peptide of the sequence (biotin) CGGADRGLTTRPGSGLTNIK-TEEISEVNLDAEF. The P26-P1 standard has the sequence (biotin) CGGADRGLTTRPGSGLTNIKTEEISEVNL.

Briefly, the biotin-coupled synthetic substrates are incubated at a concentration of from about 0 to about 200 µM in this assay. When testing inhibitory compounds, a substrate concentration of about 1.0 µM is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 pM to 2000 pM, after dilution.

The reaction mixture also includes 20 mM sodium acetate, pH 4.5, 0.06% Triton X100, and is incubated at 37° C. for about 1 to 3 h. Samples are then diluted in assay buffer (for example, 145.4 nM sodium chloride, 9.51 mM sodium phosphate, 7.7 mM sodium azide, 0.05% Triton X405, 6 g/L bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 h at 4° C. After washing in TTBS buffer (150 mM sodium chloride, 25 mM Tris, 0.05% Tween 20, pH 7.5), the samples are incubated with streptavidin-AP according to the manufacturer's instructions. After a 1 h incubation at room temperature, the samples are washed in TTBS and incubated with fluorescent substrate solution A (31.2 g/L 2-amino-2-methyl-1-propanol, 30 mg/L, pH 9.5). Reaction with streptavidin-alkaline phosphate permits detection by fluorescence. Compounds that are effective inhibitors of beta-secretase activity demonstrate reduced cleavage of the substrate as compared to a control.

D: Assays Using Synthetic Oligopeptide-Substrates

Synthetic oligopeptides are prepared incorporating the known cleavage site of beta-secretase, and optionally include detectable tags, such as fluorescent or chromogenic moieties. Examples of such peptides, as well as their production and detection methods, are described in U.S. Pat. No. 5,942,400. Cleavage products can be detected using high performance liquid chromatography, or fluorescent or chromogenic detection methods appropriate to the peptide to be detected, according to methods well known in the art.

By way of example, one such peptide has the sequence SEVNL-DAEF, and the cleavage site is between residues 5 and 6. Another preferred substrate has the sequence ADRGLTTRPGSGLTNIKTEEISEVNL-DAEF, and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of a compound inhibitor to control results provides a measure of the compound's inhibitory activity.

E: Inhibition of Beta-Secretase Activity-Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met852 to Asn651Leu652 (numbered for APP751), commonly called the Swedish mutation and shown to overproduce A-beta (Citron et al., 1992, *Nature*, 360:672-674), as described in U.S. Pat. No. 5,604,102.

The cells are incubated in the presence/absence of the inhibitory compound (diluted in DMSO) at the desired concentration, generally up to 10 μg/mL. At the end of the treatment period, conditioned media is analyzed for beta-secretase activity, for example, by analysis of cleavage fragments. A-beta can be analyzed by immunoassay, using specific detection antibodies. The enzymatic activity is measured in the presence and absence of the compound inhibitors to demonstrate specific inhibition of beta-secretase mediated cleavage of APR substrate.

F: Inhibition of Beta-Secretase in Animal Models of Alzheimer's Disease

Various animal models can be used to screen for inhibition of beta-secretase activity. Examples of animal models useful in the present invention include mouse, guinea pig, dog, and the like. The animals used can be wild type, transgenic, or knockout models. In addition, mammalian models can express mutations in APP, such as APP895-SW and the like described herein. Examples of transgenic non-human mammalian models are described in U.S. Pat. Nos. 5,804,102, 5,912,410 and 5,811,633.

PDAPP mice, prepared as described in Games et at, 1995, *Nature*, 373:523-527 are useful to analyze in vivo suppression of A-beta release in the presence of putative inhibitory compounds. As described in U.S. Pat. No. 6,191,166, 4 month old PDAPP mice are administered a compound of formula (I) formulated in vehicle, such as corn oil. The mice are dosed with compound (1-30 mg/mL, preferably 1-10 mg/mL). After time, e.g., 3-10 h, the brains are analyzed.

Transgenic animals are administered an amount of a compound formulated in a carrier suitable for the chosen mode of administration. Control animals are untreated, treated with vehicle, or treated with an inactive compound. Administration can be acute, (i.e. single dose or multiple doses in one day), or can be chronic, (i.e. dosing is repeated daily for a period of days). Beginning at time 0, brain tissue or cerebral fluid is obtained from selected animals and analyzed for the presence of APP cleavage peptides, including A-beta, for example, by immunoassay using specific antibodies for A-beta detection. At the end of the test period, brain tissue or cerebral fluid is analyzed for the presence of A-beta and/or beta-amyloid plaques. The tissue is also analyzed for necrosis.

Reduction of A-beta in brain tissues or cerebral fluids and reduction of beta-amyloid plaques in brain tissue are assessed by administering the compounds of formula (I), or pharmaceutical compositions comprising compounds of formula (I) to animals and comparing the data with that from non-treated controls.

G: Inhibition of A-beta Production in Human Patients

Patients suffering from Alzheimer's disease demonstrate an increased amount of A-beta in the brain. Alzheimer's disease patients are subjected to a method of treatment of the present invention, (i.e. administration of an amount of the compound inhibitor formulated in a carrier suitable for the chosen mode of administration). Administration is repeated daily for the duration of the test period. Beginning on day 0, cognitive and memory tests are performed, for example, once per month.

Patients administered the compounds of formula (I) are expected to demonstrate slowing or stabilization of disease progression as analyzed by a change in at least one of the following disease parameters: A-beta present in cerebrospinal fluid or plasma, brain or hippocampal volume, A-beta deposits in the brain, amyloid plaque in the brain, or scores for cognitive and memory function, as compared with control, non-treated patients.

H: Prevention of A-beta Production in Patients at Risk for Alzheimer's Disease Patients predisposed or at risk for developing Alzheimer's disease can be identified either by recognition of a familial inheritance pattern, for example, presence of the Swedish Mutation, and/or by monitoring diagnostic parameters. Patients identified as predisposed or at risk for developing Alzheimer's disease are administered an amount of the compound inhibitor formulated in a carrier suitable for the chosen mode of administration. Administration is repeated daily for the duration of the test period. Beginning on day 0, cognitive and memory tests are performed, for example, once per month.

Patients subjected to a method of treatment of the present invention (i.e., administration of a compound inhibitor) are expected to demonstrate slowing or stabilization of disease progression as analyzed by changes in at least one of the following disease parameters: A-beta present in cerebrospinal fluid or plasma, brain or hippocampal volume, amyloid plaque in the brain, or scores for cognitive and memory function, as compared with control, non-treated patients.

I: Efficacy of Compounds to Inhibit A-beta Concentration

The invention encompasses compounds of formula (I) that are efficacious. Efficacy is calculated as a percentage of concentrations as follows:

$$\text{Efficacy} = (1 - (\text{total A-beta in dose group}/\text{total A-beta in vehicle control}) * 100\%$$

wherein the "total A-beta in dose group" equals the concentration of A-beta in the tissue, (e.g., rat brain) treated with the compound, and the "total A-beta in vehicle control" equals the concentration of A-beta in the tissue, yielding a % inhibition of A-beta production. Statistical significance is determined by p-value<0.05 using the Mann Whitney t-test. See, for example, Dovey et al., *J. Neurochemistry*, 2001, 76:173-181.

J: Selectivity of Compounds for Inhibiting BACE over Aspartyl Proteases

The compounds of formula (I) can be selective for beta-secretase versus catD. Wherein the ratio of catD: beta-secretase is greater than 1, selectivity is calculated as follows:

Selectivity=($IC_{50}$ for *catD*/$IC_{50}$ for beta-secretase) *100% wherein IC50 is the concentration of compound necessary to decrease the level of catD or beta-secretase by 50%. Selectivity is reported as the ratio of $IC_{50}$(catD):$IC_{50}$(BACE).

The compounds of formula (I) can be selective for beta-secretase versus catE. Wherein the ratio of catE:beta-secretase is greater than 1, selectivity is calculated as follows:

Selectivity=($IC_{50}$ for *catE*/$IC_{50}$ for beta-secretase) *100% wherein $IC_{50}$ is the concentration of compound necessary to decrease the level of catE or beta-secretase by 50%. Selectivity is reported as the ratio of $IC_{50}$(catE):$IC_{50}$(BACE).

Pharmacokinetic parameters were calculated by a non-compartmental approach See, for example, Gibaldi, M. and Perrier, D., *Pharmacokinetics*, Second Edition, 1982, Marcel Dekker Inc., New York, N.Y., pp 409-418.

In the following examples, each value is an average of four experimental runs. Unless otherwise indicated, specific formula (I) compound examples represent a mixture of diastereomers.

EXAMPLE 391

Selectivity of Exemplary Formula (I) Compounds

| Example No. | Compound | $IC_{50}$ (catD): $IC_{50}$ (BACE) |
|---|---|---|
| 391-1 | 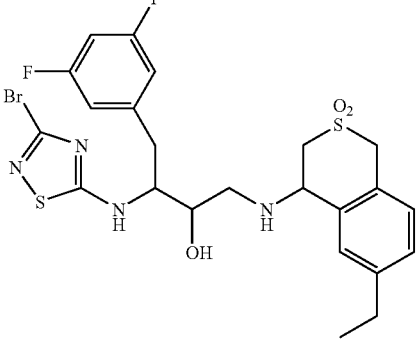 3-(3-Bromo-[1,2,4]thiadiazol-5-ylamino)-4-(3,5-difluoro-phenyl)-1-(6-ethyl-2,2-dioxo-2$\lambda^6$-isothiochroman-4-ylamino)-butan-2-ol | 3.8 |
| 391-2 | 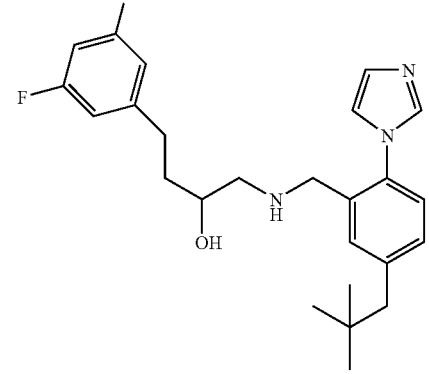 4-(3,5-Difluoro-phenyl)-1-[5-(2,2-dimethyl-propyl)-2-imidazol-1-yl-benzylamino]-butan-2-ol | 1.1 |

EXAMPLE 392

Selectivity of Exemplary Formula (I) Compounds

| Example No. | Compound | $IC_{50}$ (catE): $IC_{50}$ (BACE) |
|---|---|---|
| 392-1 | 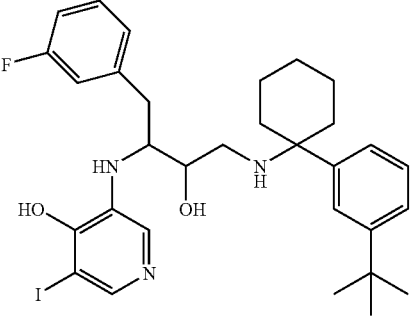 3-[3-[1-(3-tert-Butyl-phenyl)-cyclohexylamino]-1-(3,5-difluoro-benzyl)-2-hydroxy-propylamino]-5-iodo-pyridin-4-ol | 1.2 |

-continued

| Example No. | Compound | IC$_{50}$ (catE): IC$_{50}$ (BACE) |
|---|---|---|
| 392-2 | 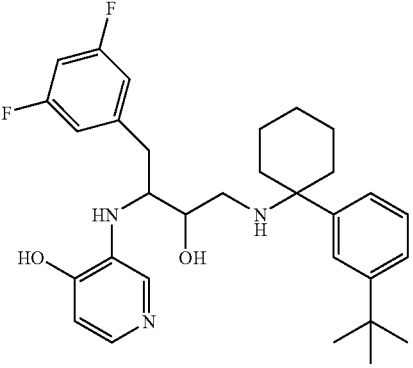3-[3-[1-(3-tert-Butyl-phenyl)-cyclohexylamino]-1-(3,5-difluoro-benzyl)-2-hydroxy-propylamino]-pyridin-4-ol | 1.9 |

K: Oral Bioavailability of Compounds for Inhibiting Amyloidosis

The invention encompasses compounds of formula (I) that are orally bioavailable. Oral bioavailability can be determined following both the an intravenous (IV) and oral (PO) administration of a test compound.

Oral Bioavailability was determined in the male Sprague-Dawley rat following both IV and PO administration of test compound. Two month-old male rats (250-300 g) were surgically implanted with polyethylene (PE-50) cannula in the jugular vein while under isoflurane anesthesia the day before the in-life phase. Animals were fasted overnight with water ad libitum, then dosed the next day. The dosing regime consisted of either a 5 mg/kg (2.5 mL/kg) IV dose (N=3) administered to the jugular vein cannula, then flushed with saline, or a 10 mg/kg (5 mL/kg) PO dose (N=3) by esophageal gavage. Compounds were formulated with 10% Solutol in 5% dextrose at 2 mg/mL. Subsequent to dosing, blood was collected at 0.016 (IV only), 0.083, 0.25, 0.5, 1, 3, 6, 9, and 24 h post administration, and heparinized plasma was recovered following centrifugation.

Compounds were extracted from samples following precipitation of the plasma proteins by methanol. The resulting supernatants were evaporated to dryness and reconstituted with chromatographic mobile phase (35% acetonitrile in 0.1% formic acid) and injected onto a reverse phase C18 column (2×50 mm, 5 µm, BDS Hypersil). Detection was facilitated with a multi-reaction-monitoring experiment on a tandem triple quadrupole mass spectrometer (LC/MS/MS) following electrospray ionization, Experimental samples were compared to calibration curves prepared in parallel with aged match rat plasma and quantitated with a weighted 1/x linear regression. The lower limit of quantization (LOQ) for the assay was typically 0.5 ng/mL.

Oral bioavailability (% F) was calculated from the dose normalized ratio of plasma exposure following oral administration to the intravenous plasma exposure in the rat by the following equation $$\% F = (AUC_{po}/AUC_{iv}) \times (D_{iv}/D_{po}) \times 100\%$$

where D is the dose and AUG is the area-under-the-plasma-concentration-time-curve from 0 to 24 h. AUG subsequently calculated from the linear trapezoidal rule by $AUC = ((C_2 + C_1)/2) \times (T_2 - T_1)$ where C is concentration and T is time.

Pharmacokinetic parameters were calculated by a non-compartmental approach See, for example, Gibaldi, M. and Perrier, D., *Pharmacokinetics*, Second Edition, 1982, Marcel Dekker Inc., New York, N.Y., pp 409-418.

L: Brain Uptake

The invention encompasses beta-secretase inhibitors that can readily cross the blood-brain barrier. Factors that affect a compound's ability to cross the blood-brain barrier include a compound's molecular weight, Total Polar Surface Area (TPSA), and log P (lipophilicity). See, e.g., Lipinski, C. A., et al., *Adv. Drug Deliv. Reviews*, 23:3-25 (1997). One of ordinary skill in the art will be aware of methods for determining characteristics allowing a compound to cross the blood-brain barrier. See, for example, Murcko et al., *Designing Libraries with CNS Activity, J. Med. Chem.*, 42 (24), pp. 4942-51 (1999). Calculations of log P values were performed using the Daylight clogP program (Daylight Chemical Information Systems, Inc.). See, for example, Hansen, C., et al., Substituent Constants for Correlation Analysis in Chemistry and Biology, Wiley, New York (1979); Rekker, R., The Hydrophobic Fragmental Constant, Elsevier, Amsterdam (1977); Fujita, T., et al., *J. Am. Chem. Soc.*, 88, 5157 (1964).

The following assay is employed to determine the brain penetration of compounds encompassed by the present invention.

In-life phase: Test compounds are administered to CF-1 (20-30 g) mice at 10 µmol/kg (4 to 7 mg/kg) following IV administration in the tail vein. Two time-points, 5 and 60 minutes, are collected post dose. Four mice are harvested for heparinized plasma and non-perfused brains at each time-point for a total of 8 mice per compound.

Analytical phase: Samples are extracted and evaporated to dryness, then reconstituted and injected onto a reverse phase chromatographic column while monitoring the effluent with a triple quadrupole mass spectrometer. Quantitation is then performed with a $1/x^2$ weighted fit of the least-squares regression from calibration standards prepared in parallel with the in vivo samples. The LOQ is generally 1 ng/mL and 0.5 ng/g for the plasma and brain respectively. Data is reported in micromolar (µM) units. Brain levels are corrected for plasma volumes (16 µL/g), Results: Comparison of a compound's brain concentration level to two marker compounds, Indinavir and Diazepam, demonstrates the ability in which the compounds of the present invention can cross the blood-brain barrier. Indinavir (HIV protease inhibitor) is a poor brain penetrant marker and Diazepam is a blood flow limited marker. The concentration levels of Indinavir in the brain at 5 and 60 min were 0.165 µM and 0.011 µM, respectively. The concentration levels of Diazepam at 5 and 60 min were 5.481 µM and 0.176 µM, respectively.

The present invention has been described with reference to various specific and preferred embodiments and techniques. However, it should be understood that many variations and modifications may be made while remaining within the spirit and scope of the present invention.

Unless defined otherwise, all scientific and technical terms used herein have the same meaning as commonly understood by one of skill in the art to which this invention belongs. Although methods and materials similar or equivalent to those described herein can be used in the practice or testing of the present invention, suitable methods and materials are described above. Additionally, the materials, methods, and examples are illustrative only and not intended to be limiting. All publications, patent applications, patents, and other references mentioned herein are incorporated by reference in their entirety. In case of conflict, the present specification, including definitions, will control.

The invention claimed is:

1. A compound of formula (I),

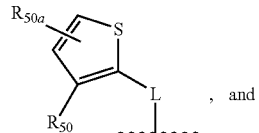
(I)

or a pharmaceutically acceptable salt thereof, wherein $R_1$ is selected from

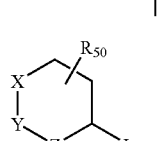
(IIa)

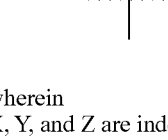
(IIb)

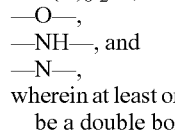
(IIc)

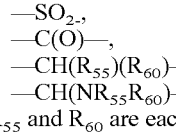
(IId)

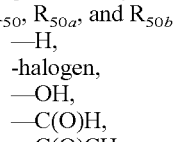
(IIe)

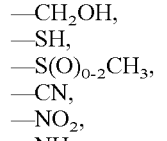
(IIf)

wherein
X, Y, and Z are independently, selected from
—C(H)$_{0-2}$—,
—O—,
—NH—, and
—N—,
wherein at least one bond of the (IIf) ring may optionally be a double bond;
L is selected from
—SO$_2$-,
—C(O)—,
—CH(R$_{55}$)(R$_{60}$)—, and
—CH(NR$_{55}$R$_{60}$)—;
R$_{55}$ and R$_{60}$ are each independently selected from hydrogen and alkyl;
R$_{50}$, R$_{50a}$, and R$_{50b}$ are independently selected from
—H,
-halogen,
—OH,
—C(O)H,
—C(O)CH$_3$,
—CH$_2$OH,
—SH,
—S(O)$_{0-2}$CH$_3$,
—CN,
—NO$_2$,
—NH$_2$,
—NHCH$_3$,
—N(CH$_3$)$_2$
—C$_1$—C$_2$ alkyl,
—OCH$_3$,
—OCF$_3$, and
—CF$_3$;
R$_2$ is selected from
—H,
wherein when R$_1$ is benzyl, and R$_c$ is 6-Isopropyl-2,2-dioxo-2$\lambda^6$-isothiochroman-4-yl, R$_2$ is not —H;
wherein, when R$_1$ is 3,5-difluorobenzyl, and R$_c$ is 6-Ethyl-2,2-dioxo-2$\lambda^6$-isothiochroman -4-yl, R$_2$ is not —H;
wherein when R$_1$ is 3,5-difluorobenzyl, and R$_c$ is 7-ethyl-1,2,3,4-tetrahydro-naphthalen-1-yl, R$_2$ is not —H;
—OH,
—O-alkyl, optionally substituted with at least one group independently selected from R$_{200}$;
—O-aryl, optionally substituted with at least one group independently selected from R$_{200}$;

-alkyl, optionally substituted with at least one group independently selected from $R_{200}$;
—NH-alkyl, optionally substituted with at least one group independently selected from $R_{200}$;
-heterocycloalkyl, (wherein at least one carbon is optionally replaced with a group independently selected from —$(CR_{245}R_{250})$—, —O—, —C(O)—, —C(O)C(O)—, —$N(R_{200})_{0-1}$-, and —$S(O)_{0-2}$-, and wherein the heterocycloalkyl is optionally substituted with at least one group independently selected from $R_{200}$);
—NH-heterocycloalkyl, wherein at least one carbon is optionally replaced with a group independently selected from —$(CR_{245}R_{250})$—, —O—, —C(O)—, —C(O)C(O)—, —$N(R_{200})_{0-2}$-, and —$S(O)_{0-2}$-, and wherein the heterocycloalkyl is optionally substituted with at least one group independently selected from $R_{200}$;
—C(O)—$N(R_{315})(R_{320})$,
 wherein $R_{315}$ and $R_{320}$ are each independently selected from —H, -alkyl, and phenyl,
 wherein when $R_1$ is 3,5-difluorobenzyl, and $R_c$ is 7-ethyl-1,2,3,4-tetrahydro-naphthalen-i -yl, $R_2$ is not methylcarbamoyl;
—O—C(O)—$N(R_{315})(R_{320})$,
—NH—$R_{400}$,
—$R_{400}$,
—NH—$R_{500}$,
—$R_{500}$
—NH—$R_{600}$,
—$R_{600}$, and
—NH—$R_{700}$;
$R_{400}$ is

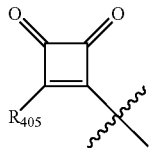

wherein $R_{405}$ is selected from —H, —$N(R_{515})_2$, and O-alkyl;
$R_{500}$ is a heteroaryl selected from III(a) and III(b),

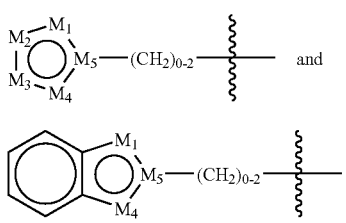

wherein
$M_1$ and $M_4$ are independently selected from
 —$C(R_{505})$—,
 —N—,
 —$N(R_{515})$—,
 —S—, and
 —O—;
$M_2$ and $M_3$ are independently selected from
 —$C(R_{510})$—,
 —N—,
 —$N(R_{520})$—,
 —S—, and
 —O—;
$M_5$ is selected from —C— and —N—;
$R_{505}$ is independently selected from
 —H,
 -alkyl,
 -halogen,
 —$NO_2$,
 —CN,
 —$R_{200}$, and
 phenyl;
$R_{510}$ is independently selected from
 —H,
 -alkyl,
 -halogen,
 -amino,
 —$CF_3$,
 —$R_{200}$, and
 -phenyl;
$R_{515}$ is independently selected from
 —H,
 -alkyl, and
 -phenyl;
$R_{520}$ is independently selected from
 —H,
 -alkyl,
 —$(CH_2)_{0-2}$-phenyl, and
 —$C(Ph)_3$
$R_{600}$ is a monocyclic, bicyclic, or tricyclic heteroaryl ring system of 6,7,8,9, 10, 11, 12, 13, or 14 atoms, optionally substituted with at least one group independently selected from $R_{605}$;
 $R_{605}$ is selected from -hydrogen, -halogen, -alkyl, -phenyl, alkyl-O—C(O)—, -nitro, —CN, -amino, —$NR_{220}R_{225}$, -thioalkyl, —$CF_3$, —OH, —O-alkyl, and -heterocycloalkyl;
 wherein when $R_1$ is 3,5-difluoro-benzyl, and $R_c$ is 6-ethyl-2,2-dioxo-$28^6$-isothiochroman-4-yl, $R_2$ is not Benzothiazol-2-ylamino, or Benzooxazol-2-ylamino;
$R_{700}$ is aryl optionally substituted with at least one $R_{205}$;
$R_c$ is selected from
 —$R_x$, and
 -formulae (IVa), (IVc), (IVe), and (IVf);
$R_X$ is selected from
 —$R_{xa}$—$R_{xb}$, wherein $R_{xa}$ is cycloalkyl and $R_{xb}$ is aryl;
 wherein the aryl of $R_{xb}$ is optionally substituted with at least one group independently selected from $R_{200}$;
 wherein the cycloalkyl of $R_{xa}$ is optionally substituted with at least one group independently selected from $R_{210}$ and —$(CR_{245}R_{250})_{0-4}$—$R_{200}$;
$R_{245}$ and $R_{250}$ at each occurrence are independently selected from
 —H,
 —$(CH_2)_{0-4}C(O)$—OH,
 —$(CH_2)_{0-4}C(O)$—O-alkyl,
 —$(CH_2)_{0-4}C(O)$-alkyl,
 -alkyl,
 -hydroxyalkyl,
 —O-alkyl,
 -haloalkoxy, —$(CH_2)_{0-4}$-cycloalkyl,
—$(CH_2)_{0-4}$-aryl,
—$(CH_2)_{0-4}$-heteroaryl, and
—$(CH_2)_{0-4}$-heterocycloalkyl; or $R_{245}$ and $R_{250}$ are taken together with the carbon to which they are attached to form a monocyclic or bicyclic ring system of 3, 4, 5, 6, 7, 8, 9, or 10 carbon atoms, wherein at least one bond in the monocyclic or bicyclic ring system is optionally a double bond, wherein the bicyclic ring system is optionally a fused or spiro ring system, wherein at least one carbon atom in the monocyclic or bicyclic ring system is optionally replaced by a group independently selected from
—O—,
—C(O)—,
—S(O)$_{0-2}$—,
—C(=N—$R_{255}$)—,
—N—,
—$NR_{220}$—,
—$N((CO)_{0-1}R_{200})$—, and
—$N(SO_2R_{200})$—, wherein the aryl, heteroaryl, and heterocycloalkyl groups included in $R_{245}$ and $R_{250}$ are optionally substituted with at least one group independently selected from -halogen, -alkyl, —$N(R_{220})(R_{225})$, —CN, and —OH;

wherein the monocyclic and bicyclic groups included in $R_{245}$ and $R_{250}$ are optionally substituted with at least one group independently selected from halogen, —$(CH_2)_{0-2}$—OH, —O-alkyl, alkyl, —$(CH_2)_{0-2}$—S-alkyl, —$CF_3$, aryl, —$N(R_{200})(R_{225})$, —CN, —$(CH_2)_{0-2}$—$NH_2$, —$(CH_2)_{0-2}$—NH(alkyl), —NHOH, —NH—O-alkyl, —N(alkyl)(alkyl), —NH-heteroaryl, —NH—C(O)-alkyl, and NHS$(O_2)$-alkyl;

formula (IVa) is

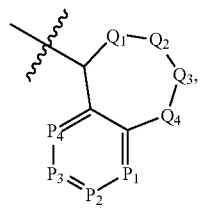

(IVa)

wherein $Q_1$ is selected from (—$CH_2$—)$_{0-1}$, —CH($R_{200}$)—, —C($R_{200}$)2-, and —C(O)—;

$Q_2$ and $Q_3$ each are independently selected from (—$CH_2$—)$_{0-1}$, —CH($R_{200}$)—, —C($R_{200}$)$_2$—, —O—, —C(O)—, —S—, —S(O)$_2$—, —NH—, and —N($R_7$)—;

$Q_4$ is selected from a bond, (—$CH_2$—)$_{0-1}$, —CH($R_{200}$)—, —C($R_{200}$)$_2$—, —O—, —C(O)—, —S—, —S(O)$_2$—, —NH—, and —N($R_7$); and $P_1$, $P_2$, $P_3$, and $P_4$ each are independently selected from —CH—, —C($R_{200}$)—, and —N—;

formula (IVc) is

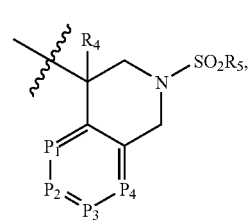

(IVc)

wherein $R_4$ is selected from —H and -alkyl; and
$P_1$, $P_2$, $P_3$, and $P_4$ at each occurrence are independently selected from —CH—, —CR$_{200}$—, and —N—;

formula (IVe) is

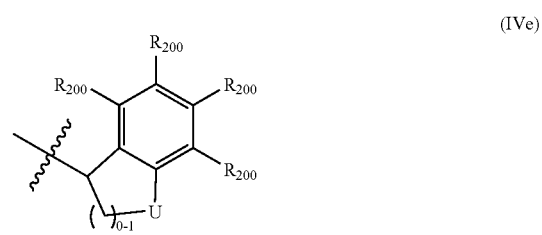

(IVe)

wherein
U is selected from —$CH_2$—$CR_{100}R_{101}$—, —$CH_2$—S—, —$CH_2$—S(O)—, —$CH_2$—$S(O)_2$—, —$CH_2$—N($R_{100}$)—, —$CH_2$—C(O)—, —$CH_2$—O—, —C(O)—C($R_{100}$)($R_{101}$)—, —$SO_2$— N($R_{100}$)—, —C(O)—N($R_{55}$)—, —N($R_{55}$)—C(O)—N($R_{55}$)—, —O—C(O)—O—, —N($R_{55}$)—C(O)—O—, and —C(O)—O—;

wherein $R_{100}$ and $R_{101}$ at each occurrence are independently selected from —H, -alkyl, -aryl, —C(O)-alkyl, —(CO)$_{0-1}R_{215}$, —(CO)$_{0-1}R_{220}$, and —S(O)$_2$-alkyl;

formula (IVf) is

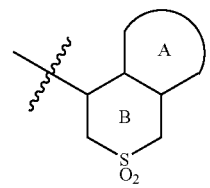

(IVf)

wherein the B ring is optionally substituted with at least one group independently selected from -alkyl, -halogen, —OH, —SH, —CN, —$CF_3$, —O-alkyl, —$N(R_5)C(O)H$, —C(O)H, —$C(O)N(R_5)(R_6)$, —$NR_5R_5$, $R_{250}$, $R_{285}$, -aryl, and -heteroaryl;

wherein $R_{280}$ and $R_{285}$, and the carbon to which they are attached form a $C_3$—$C_7$ spirocycle which is optionally substituted with at least one group independently selected from -alkyl, —O-alkyl, -halogen, —$CF_3$, and —CN;

wherein the A ring is aryl or heteroaryl, each optionally substituted with at least one group independently selected from $R_{290}$ and $R_{295}$;

wherein $R_{290}$ and $R_{295}$ at each occurrence are independently selected from -alkyl optionally substituted with at least one group selected from -alkyl, -halogen, —OH, —SH, —CN, —CF$_3$, —O-alkyl, and —NR$_5$R$_6$,
—OH,
—NO$_2$,
-halogen,
—CO$_2$H,
—CN,
—(CH$_2$)$_{0-4}$—C(O)—NR$_{21}$R$_{22}$,
—(CH$_2$)$_{0-4}$—CO$_2$R$_{20}$,
—(CH$_2$)$_{0-4}$—SO$_2$—NR$_{21}$R$_{22}$,
—(CH$_2$)$_{0-4}$S(O)-alkyl),
—(CH$_2$)$_{0-4}$—S(O)$_2$(alkyl),
—(CH$_2$)$_{0-4}$—S(O)$_2$-(cycloalkyl),
—(CH$_2$)$_{0-4}$—N(H or R$_{20}$)—C(O)—O—R$_{20}$,
—(CH$_2$)$_{0-4}$—N(H or R$_{20}$)—C(O)—N(R$_{20}$)$_2$,
—(CH$_2$)$_{0-4}$—N—C(S)—N(R$_{20}$)$_2$,
—(CH$_2$)$_{0-4}$—N(H or R$_{20}$)—CO—R$_{21}$,
—(CH$_2$)$_{0-4}$—NR$_{21}$R$_{22}$,
—(CH$_2$)$_{0-4}$—R$_{11}$,
—(CH$_2$)$_{0-4}$—O—C(O)—(alkyl),
—(CH$_2$)$_{0-4}$—O—P(O)—(OR$_5$)$_2$,
—(CH$_2$)$_{0-4}$—O—C(O)—N(R$_{20}$)$_2$,
—(CH$_2$)$_{0-4}$—O—C(S)—N(R$_{20}$)$_2$,
—(CH$_2$)$_{0-4}$—O—(R$_{20}$)$_2$,
—(CH$_2$)$_{0-4}$—O—(R$_{20}$)—CO$_2$H,
—(CH$_2$)$_{0-4}$—S—(R$_{20}$),
—(CH$_2$)$_{0-4}$-(alkyl optionally substituted with at least one halogen),
-cycloalkyl,
—(CH$_2$)$_{0-4}$—N(H or R$_{20}$)—S(O)$_2$—R$_{21}$, and
—(CH$_2$)$_{0-4}$-cycloalkyl;
R$_{21}$ and R$_{22}$ each independently are selected from
—H,
-alkyl optionally substituted with at least one group independently selected from —OH, amino, -halogen, -alkyl, -cycloalkyl, -(alkyl-cycloalkyl), -alkyl-O-alkyl), —R$_{17}$, and —R$_{18}$,
—(CH$_2$)$_{0-4}$—C(O)-(alkyl),
—(CH$_2$)$_{0-4}$—C(O)-(cycloalkyl),
—(CH$_2$)$_{0-4}$—C(O)—R$_{17}$,
—(CH$_2$)$_{0-4}$—C(O)—R$_{18}$,
—(CH$_2$)$_{0-4}$—C(O)—R$_{19}$, and
—(CH$_2$)$_{0-4}$—C(O)—R$_{11}$;
R$_{17}$ at each occurrence is aryl optionally substituted with at least one group independently selected from
-alkyl optionally substituted with at least one group independently selected from -alkyl, -halogen, —OH, —SH, —NR$_5$R$_6$, —CN, —CF$_3$, and —O-alkyl,
-halogen,
—O-alkyl optionally substituted with at least one group independently selected from halogen, —NR$_{21}$R$_{22}$, —OH, —CN, and -cycloalkyl optionally substituted with at least one group independently selected from -halogen, —OH, —SH, —CN, —CF$_3$, —O-alkyl, and —NR$_5$R$_6$,
—C(O)-(alkyl),
—S(O)—O—NR$_5$R$_6$,
—C(O)—NR$_5$R$_6$, and
—S(O)$_2$-(alkyl);
R$_{18}$ at each occurrence is heteroaryl optionally substituted with at least one group independently selected from
-alkyl optionally substituted with at least one group independently selected from -alkyl, -halogen, —OH, —SH, —CN, —CF$_3$, —O-alkyl, and —NR$_5$R$_6$,
-halogen,
—O-alkyl optionally substituted with at least one group independently selected from -halogen, —NR$_{21}$R$_{22}$, —OH, and —CN,
-cycloalkyl optionally substituted with at least one group independently selected from -halogen, —OH, —SH, —CN, CF$_3$, —O-alkyl, and —NR$_5$R$_6$,
—C(O)-(alkyl),
—S(O)$_2$—NR$_5$R$_6$,
—C(O)—NR$_5$R$_6$, and
—S(O)$_2$-(alkyl);
R$_{19}$ at each occurrence is heterocycloalkyl wherein at least one carbon is optionally replaced with —C(O)—, —S(O)—, and —S(O)r, wherein the heterocycloalkyl is optionally substituted with at least one group independently selected from
-alkyl optionally substituted with at least one group independently selected from -alkyl, -halogen, —OH, —SH, —CN, —CF$_3$, —O-alkyl, and —NR$_5$R$_6$,
-halogen,
—O-alkyl optionally substituted with at least one group independently selected from -halogen, —OH, —CN, —NR$_{21}$R$_{22}$, and -cycloalkyl optionally substituted with at least one group independently selected from -halogen, —OH, —SH, —CN, —CF$_3$, —O-alkyl, and —NR$_5$R$_6$,
—C(O)-(alkyl),
—S(O)$_2$—NR$_5$R$_6$,
—C(O)—NR$_5$R$_6$, and
—S(O)$_2$-(alkyl);
R$_{11}$ at each occurrence is heterocycloalkyl
wherein at least one carbon of the heterocycloalkyl is optionally replaced with —C(O)—, —S(O)—, and —S(O)$_2$—,
wherein the heterocycloalkyl is optionally substituted with at least one group independently selected from -alkyl, —O-alkyl, and -halogen;
R$_{20}$ is selected from -alkyl, -cycloalkyl, —(CH$_2$)$_{0-2}$—(R$_{17}$), and —(CH$_2$)$_{0-2}$—(R$_{18}$);
R$_{200}$ at each occurrence is independently selected from
-alkyl optionally substituted with at least one group independently selected from R$_{205}$,
—OH,
—NO$_2$,
—NH$_2$,
-halogen,
—CN,
—CF$_3$,
—OCF$_3$,
—(CO$_2$)$_{0-4}$—C(O)H,
—(CO)$_{0-1}$R$_{215}$,
—(CO)$_{0-1}$R$_{220}$,
—(CH$_2$)$_{0-4}$—C(O)—NR$_{220}$R$_{225}$,
—(CH$_2$)$_{0-4}$—(C(O))$_{0-1}$R$_{215}$,
—(CH$_2$)$_{0-4}$—(C(O))$_{0-1}$—R$_{220}$,
—(CH$_2$)$_{0-4}$—C(O)-alkyl,
—(CH$_2$)$_{0-4}$—(C(O))$_{0-1}$-cycloalkyl,
—(CH$_2$)$_{0-4}$—(C(O))$_{0-1}$-heterocycloalkyl,
—(CH$_2$)$_{0-4}$—(C(O))$_{0-1}$-aryl,
—(CH$_2$)$_{0-4}$—(C(O))0-1-heteroaryl,
—(CH$_2$)$_{0-4}$—C(O)—O—R$_{215}$ —$(CH_2)_{0-4}$—$S(O)_{0-2}$—$NR_{220}R_{225}$,
—$(CH_2)_{0-4}$—$S(O)_{0-2}$-alkyl,
—$(CH_2)_{0-4}$—$S(O)_{0-2}$-cycloalkyl,
—$(CH_2)_{0-4}$—N(H or $R_{15}$)—C(O)—O—$R_{215}$,
—$(CH_2)_{0-4}$—N(H or $R_{215}$)—$S(O)_{1-2}$—$R_{220}$,
—$(CH2)_{0-4}$—N(H or $R_{215}$)—C(O)—$R_{220}$,
—$(CH_2)_{0-4}$—$NR_{220}R_{225}$,
—$(CH_2)_{0-4}$—O—C(O)-alkyl,
—$(CH_2)_{0-4}$—O—$(R_{215})$,
—$(CH_2)_{0-4}$—S—$(R_{215})$,
—$(CH_2)_{0-4}$—C(O)H,
—$(CH_2)_{0-4}$—O-(alkyl optionally substituted with at least one halogen), and
-adamantane,
  wherein each aryl and heteroaryl group included within $R_{200}$ is optionally substituted with at least one group independently selected from —$R_{205}$, —$R_{210}$, and
    -alkyl optionally substituted with at least one group independently selected from $R_{205}$ and $R_{210}$;
  wherein each cycloalkyl or heterocycloalkyl group included within $R_{200}$ is optionally substituted with at least one group independently selected from
    —$R_{205}$,
    —$R_{210}$, and
    -alkyl optionally substituted with at least one group independently selected from $R_{205}$ and $R_{210}$;
$R_{205}$ at each occurrence is independently selected from
-alkyl,
-heteroaryl,
-heterocycloalkyl,
-aryl,
-haloalkoxy,
—$(CH_2)_{0-3}$-cycloalkyl,
-halogen,
—O—phenyl,
—SH,
—$(CH_2)_{0-4}$—$C(O)CH_3$
—$(CH_2)_{0-4}$—C(O)—H
—$(CH_2)_{0-4}$—$CO_2H$,
—$(CH_2)_{0-6}$—CN,
—$(CH_2)_{0-6}$—C(O)—$NR_{235}R_{240}$,
—$(CH_2)_{0-8}$—C(O)—$R_{235}$,
—$(CH_2)_{0-4}$—N(H or $R_{215}$)—$SO_2$—$R_{235}$,
—$CF_3$,
—CN,
—$OCF_3$,
—$C(O)_2$-benzyl,
—O-alkyl,
—$C(O)_2$-alkyl, and
—$NR_{235}R_{240}$;
$R_{210}$ at each occurrence is independently selected from
—OH,
—CN,
—$(CH_2)_{0-4}$—C(O)H,
  -alkyl wherein a carbon atom is optionally replaced with —C(O)—, and a carbon atom is optionally substituted with at least one group independently selected from $R_{205}$,
—S-alkyl,
-halogen,
—O-alkyl,
-haloalkoxy,
—$NR_{220}R_{225}$,
  -cycloalkyl optionally substituted with at least one group independently selected from $R_{205}$,
—C(O)-alkyl,
—$S(O)_2$—$NR_{235}R_{240}$,
—C(O)—$NR_{235}R_{240}$, and
—$S(O)_2$-alkyl;
$R_{215}$ at each occurrence is independently selected from
-alkyl,
—$(CH_2)_{0-2}$-aryl,
—$(CH_2)_{0-2}$-cycloalkyl,
—$(CH_2)_{0-2}$-heteroaryl, and
—$(CH_2)_{0-2}$-heterocycloalkyl;
  wherein the aryl groups included within $R_{215}$ are optionally substituted with at least one group independently selected from $R_{205}$ or $R_{210}$;
  wherein the heterocycloalkyl and heteroaryl groups included within $R_{215}$ are optionally substituted with at least one group independently selected from $R_{210}$;
$R_{220}$ and $R_{225}$ at each occurrence are independently selected from
—H,
—OH,
-alkyl,
—$(CH_2)_{0-4}$—C(O)H,
-alkyl-OH,
—$(CH_2)_{0-4}$—$CO_2$-alkyl, wherein alkyl is optionally substituted with at least one group independently selected from $R_{205}$,
-aminoalkyl,
—$S(O)_2$-alkyl,
—$(CH_2)_{0-4}$—C(O)-alkyl, wherein alkyl is optionally substituted with at least one group independently selected from $R_{205}$,
—$(CH_2)_{0-4}$—C(O)—$NH_2$,
—$(CH_2)_{0-4}$—C(O)-(alkyl), wherein alkyl is optionally substituted with at least one group independently selected from $R_{205}$,
—$(CH_2)_{0-4}$—C(O)—$NH_2$,
—$(CH_2)_{0-4}$—C(O)—NH(alkyl), wherein alkyl is optionally substituted with at least one group independently selected from $R_{205}$,
$(CH_2)_{0-4}$—C(O)—N(alkyl)alkyl),
-haloalkyl,
—$(CH_2)_{0-2}$-cycloalkyl,
-alkyl-O-alkyl,
—O-alkyl,
-aryl,
-heteroaryl, and
-heterocycloalkyl;
  wherein the aryl, heteroaryl and heterocycloalkyl groups included within $R_{220}$ and $R_{225}$ are each optionally substituted with at least one group independently selected from $R_{270}$;
$R_{270}$ at each occurrence is independently selected from
  —$R_{205}$,
  -alkyl optionally substituted with at least one group independently selected from $R_{205}$,
  -phenyl,
  -halogen,
  —O-alkyl,
  -haloalkoxy,
  —$NR_{235}R_{240}$,
  —OH,
  —CN,
  -cycloalkyl optionally substituted with at least one group independently selected from $R_{205}$,
  —C(O)-alkyl,
  —$S(O)_2$—$NR_{235}R_{240}$,
  —CO—$NR_{235}R_{240}$,
  —$S(O)_2$-alkyl, and

—(CH$_2$)$_{0-4}$—C(O)H;

R$_{235}$ and R$_{240}$ at each occurrence are independently selected from
—H,
-alkyl,
—C(O)-alkyl,
—OH,
—CF$_3$,
—OCH$_3$,
—NH—CH$_3$,
—N(CH$_3$)$_2$,
—(CH$_2$)$_{0-4}$—C(O)—(H or alkyl),
—SO$_2$-alkyl, and
-phenyl;

R$_{255}$ is selected from -hydrogen, —OH, —N(R$_{220}$)(R$_{225}$), and —O-alkyl;

R$_5$ and R$_6$ are independently selected from —H and -alkyl, or

R$_5$ and R$_6$, and the nitrogen to which they are attached, form a 5 or 6 membered heterocycloalkyl ring; and R$_7$ is independently selected from
—H,
-alkyl optionally substituted with at least one group independently selected from —OH, amino, and halogen,
-cycloalkyl, and
-alkyl-O-alkyl.

2. The compound according to claim 1, wherein R$_1$ is selected from —CH$_2$-phenyl, wherein the phenyl ring is optionally substituted with at least one group independently selected from -halogen, —C$_1$—C$_2$ alkyl, -0-methyl, and —OH.

3. The compound according to claim 1, wherein R$_1$ is selected from 4-hydroxy-benzyl, 3-hydroxy-benzyl, 5-chloro-thiophen-2-yl-methyl, 5-chloro-3-ethyl-thiophen-2-yl-methyl, 3,5-difluoro-2-hydroxy-benzyl, piperidin-4-yl-methyl, 2-oxo-piperidin-4-yl-methyl, 2-oxo-1,2-dihydro-pyridin-4-yl-methyl, 5-hydroxy-6-oxo-6H-pyran-2-yl-methyl, 3,5-difluoro-4-hydroxy-benzyl, 3,5-difluoro-benzyl, 3-fluoro-4-hydroxy-benzyl, 3- luoro-5-hydroxy-benzyl, and 3-fluoro-benzyl.

4. The compound according to claim 1, wherein R$_c$ is selected from formulae (VIa) and (VIb)

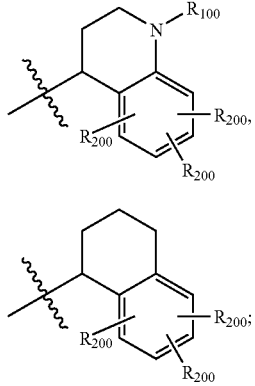

(VIa)

(VIb)

wherein at least one carbon of the heterocycloalkyl of formula (VIa) is optionally replaced with —SO$_2$- and the cycloalkyl of formula (VIb) is optionally replaced with a group independently selected from —O—, —SO$_2$—, and —C(O)—, wherein R$_{100}$, R$_{200}$, R$_{205}$, R$_{245}$, and R$_{250}$ are as defined in claim 1.

5. The compound according to claim 1, wherein R$_c$ is selected from 6-isobutyl-1,1-dioxo-1λ$^6$-thiochroman-4-yl, 6-Isopropyl-2,2-dioxo-2λ$^6$-isothiochroman-4-yl, 6-ethyl-2,2-dioxo-2λ$^6$-isothiochroman-4-yl, 7-ethyl-1,2,3,4-tetrahydro-naphthalen-1-yl, and 1-(3-tert-Butyl-phenyl)-cyclohexyl.

6. The compound according to claim 1, wherein R$_2$ is selected from hydrogen, 3-Bromo-[1,2,4]thiadiazol-5-ylamino, [1,2,4]thiadiazol-5-ylamino, 4-Chloro-[1,2,5]thiadiazol-3-ylamino, [1,2,5]thiadiazol-3-ylamino, thiazol-2-ylamino, 5-Bromo-[1,3,4]thiadiazol-2-ylamino, [1,3,4]thiadiazol-2-ylamino, 5-Amino-[1,3,4]thiadiazol-2-ylamino, 2-Bromo-thiazol-5-ylamino, thiazol-5-ylamino, 5-trifluoromethyl-[1,3,4]thiadiazol-2-ylamino, 5-trifluoromethyl-[1,3,4]oxadiazol-2-ylamino, 5-Amino-[1,3,4]oxadiazol-2-ylamino, 1-trityl-1H-[1,2,4]triazol-3-ylamino, 1H-[1,2,4]triazol-3-ylamino, oxazol-2-ylamino, 5-Bromo-2-trityl-2Hl-[1,2,3]triazol-4-ylamino, 2-trityl-2H-[1,2,3]triazol-4-ylamino, 5-Bromo-2H-[1,2,3]triazol-4-ylamino, 2H-[1,2,3]triazol-4-ylamino, thiophen-2-ylamino, 3-methyl-5-nitro-3H-imidazol-4-ylamino, 4-Cyano-5-phenyl-isothiazol-3-ylamino, 4-phenyl-[1,2,5]thiadiazol-3-ylamino, 3,4-dioxo-cyclobut-1-enylamino, 2-methoxy-3,4-dioxo-cyclobut-1-enylamino, and 2-methylamino-3,4-dioxo-cyclobut-1-enylamino.

7. A method of treating at least one condition selected from Alzheimer's disease, dementia associated with Alzheimer's disease, Parkinson's disease and dementia associated with Parkinson's disease, comprising:

administering to a host a composition comprising a therapeutically effective amount of at least one compound of formula (I),

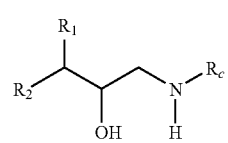

(I)

or pharmaceutically acceptable salts thereof, wherein
R$_1$ is selected from

(IIa)

(IIb)

-continued

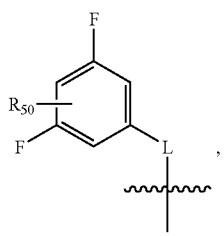
(IIc)

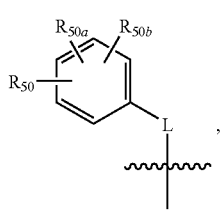
(IId)

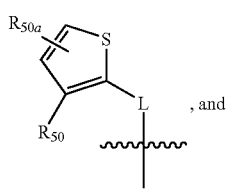
(IIe)
, and

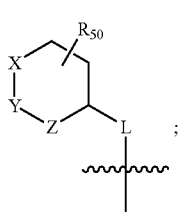
(IIf)

wherein
X, Y, and Z are independently, selected from
— $C(H)_{0-2}$—,
—O—,
—C(O)—,
—NH—, and
—N—,
wherein at least one bond of the (IIf) ring may optionally be a double bond;
L is selected from
—$SO_2$—,
—C(O)—,
—$C(R_{55})(R_{60})$—, and
—$CH(NR_{55}R_{60})$—;
$R_{55}$ and $R_{60}$ are each independently selected from hydrogen and alkyl;
$R_{50}$, $R_{50a}$, and $R_{50b}$ are independently selected from
—H
-halogen,
—OH,
—C(O)H,
—C(O)$CH_3$,
—$CH_2OH$,
—SH,
—$S(O)_{0-2}CH_3$,
—CN,
—$NO_2$,
—$NH_2$,
—$NHCH_3$,
—$N(CH_3)_2$ —$C_1$—$C_2$ alkyl,
—$OCH_3$,
—$OCF_3$, and
—$CF_3$;
$R_2$ is selected from
—H,
wherein when $R_1$ is benzyl, and $R_c$ is 6-Isopropyl-2,2-dioxo-$28^6$-isothiochroman-4-yl, $R_2$ is not —H;
wherein, when $R_1$ is 3,5-difluorobenzyl, and $R_c$ is 6-Ethyl-2,2-dioxo-$28^6$-isothiochroman-4-yl, $R_2$ is not —H;
wherein when $R_1$ is 3,5-difluorobenzyl, and $R_c$ is 7-ethyl-1,2,3,4-tetrahydro-naphthalen-1-yl, $R_2$ is not —H;
—OH,
—O-alkyl, optionally substituted with at least one group independently selected from $R_{200}$;
—O-aryl, optionally substituted with at least one group, independently selected from $R_{200}$;
-alkyl, optionally substituted with at least one group independently selected from $R_{200}$;
—NH-alkyl, optionally substituted with at least one group independently selected from $R_{200}$;
-heterocycloalkyl, (wherein at least one carbon is optionally replaced with a group independently selected from —$(CR_{245}R_{250})$—, —O—, —C(O)—, —C(O)C(O)—, —$N(R_{200})_{0-1}$-, and —$S(O)_{0-2}$—, and wherein the heterocycloalkyl is optionally substituted with at least one group independently selected from $R_{200}$);
—NH-heterocycloalkyl, wherein at least one carbon is optionally replaced with a group independently selected from —$(CR_{245}R_{250})$—, —O—, —C(O)—, —C(O)C(O)—, —$N(R_{200})_{0-2}$—, and —$S(O)_{0-2}$—, and wherein the heterocycloalkyl is optionally substituted with at least one group Independently selected from $R_{200}$;
—C(O)—N($R_{315}$)($R_{320}$),
wherein $R_{315}$ and $R_{320}$ are each independently selected from —H, -alkyl, and phenyl,
wherein when $R_1$ is 3,5-difluorobenzyl, and $R_c$ is 7-ethyl-1,2,3,4-tetrahydro-naphthalen-1-yl, $R_2$ is not methylcarbamoyl;
—O—C(O)—N($R_{315}$)($R_{320}$),
—NH—$R_{400}$,
—$R_{400}$,
—NH—$R_{500}$,
—$R_{500}$
—NH—$R_{600}$,
—$R_{600}$, and
—NH—$R_{700}$,
$R_{400}$ is wherein $R_{405}$ is selected from —H, —N($R_{515}$)$_2$, and O-alkyl;

$R_{500}$ is a heteroaryl selected from III(a) and III(b),

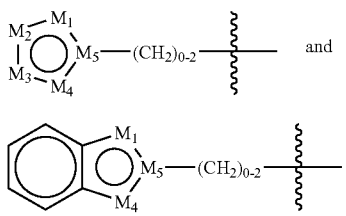

(IIIa)

(IIIb)

wherein
$M_1$ and $M_4$ are independently selected from
  —C($R_{505}$)—,
  —N—,
  —N($R_{515}$)—,
  —S—, and
  —O—;
$M_2$ and $M_3$ are independently selected from
  —C($R_{510}$)—,
  —N—,
  —N($R_{520}$)—,
  —S—, and
  —O—;
$M_5$ is selected from —C— and —N—;
$R_{505}$ is independently selected from
  —H,
  -alkyl,
  -halogen,
  —NO$_2$,
  —CN,
  —R$_{200}$, and
  phenyl;
$R_{510}$ is independently selected from
  —H,
  -alkyl,
  -halogen,
  -amino,
  —CF$_3$,
  —R$_{200}$, and
  -phenyl;
$R_{515}$ is independently selected from
  —H,
  -alkyl, and
  -phenyl;
$R_{520}$ is independently selected from
  —H,
  -alkyl,
  —(CH$_2$)$_{0-2}$-phenyl, and
  —C(Ph)$_3$;
$R_{600}$ is a monocyclic, bicyclic, or tricyclic heteroaryl ring system of 6, 7, 8, 9, 10, 11, 12, 13, or 14 atoms, optionally substituted with at least one group independently selected from $R_{605}$;
  $R_{605}$ is selected from -hydrogen, -halogen, -alkyl, -phenyl, alkyl-O—C(O)—, -nitro, —CN, -amino, —NR$_{220}$R$_{225}$, -thioalkyl, —CF$_3$, —OH, —O-alkyl, and -heterocycloalkyl;
    wherein when $R_1$ is 3,5-difluoro-benzyl, and $R_c$ is 6-ethyl-2,2-dioxo-286-isothiochroman-4-yl, R2 is not Benzothiazol-2-ylamino, or Benzooxazol-2-ylamino;
$R_{700}$ is aryl optionally substituted with at least one $R_{205}$;

$R_c$ is selected from
  $R_x$, and
  -formulae (IVa), (IVc), (IVe), and (IVf);
$R_x$ is selected from
  —$R_{xa}$—$R_{xb}$, wherein $R_{xa}$ is cycloalkyl and $R_{xb}$ is aryl;
    wherein the aryl of $R_{xb}$ is optionally substituted with at least one group independently selected from $R_{200}$;
    wherein the cycloalkyl of $R_{xa}$ is optionally substituted with at least one group independently selected from $R_{210}$ and —(CR$_{245}$R$_{250}$)$_{0-4}$—R$_{200}$;
$R_{245}$ and $R_{250}$ at each occurrence are independently selected from
  —H,
  —(CH$_2$)$_{0-4}$C(O)—O—OH,
  —(CH$_2$)$_{0-4}$C(O)—O-alkyl,
  —(CH$_2$)$_{0-4}$C(O)-alkyl,
  -alkyl,
  -hydroxyalkyl,
  —O-alkyl,
  -haloalkoxy,
  —(CH$_2$)$_{0-4}$-cycloalkyl,
  —(CH$_2$)$_{0-4}$-aryl,
  —(CH$_2$)$_{0-4}$-heteroaryl, and
  —(CH$_2$)$_{0-4}$-heterocycloalkyl; or
$R_{245}$ and $R_{250}$ are taken together with the carbon to which they are attached to form a monocyclic or bicyclic ring system of 3, 4, 5, 6, 7, 8, 9, or 10 carbon atoms, wherein at least one bond in the monocyclic or bicyclic ring system is optionally a double bond,
  wherein the bicyclic ring system is optionally a fused or spiro ring system,
  wherein at least one carbon atom in the monocyclic or bicyclic ring system is optionally replaced by a group independently selected from
    —O—,
    —C(O)—,
    —S(O)$_{0-2}$—,
    —(=N—R$_{255}$)—,
    —N—,
    —NR$_{220}$—,
    —NR((CO)$_{0-1}$R$_{200}$)—, and
    —N(SO$_2$R$_{200}$)—;
  wherein the aryl, heteroaryl, and heterocycloalkyl groups included in $R_{245}$ and $R_{250}$ are optionally substituted with at least one group independently selected from -halogen, -alkyl, —N(R$_{220}$)(R$_{225}$), —CN, and —OH;
  wherein the monocyclic and bicyclic groups included in $R_{245}$ and $R_{250}$ are optionally substituted with at least one group independently selected from halogen, —(CH$_2$)$_{0-2}$—OH, —O-alkyl, alkyl, —(CH$_2$)$_{0-2}$—S-alkyl, —CF$_3$, aryl, —N(R$_{220}$)(R$_{225}$), —CN, —(CH$_2$)$_{0-2}$—NH$_2$, —(CH$_2$)$_{0-2}$—NH(alkyl), —NHOH, —NH—O-alkyl, —N(alkyl)(alkyl), —NH—C(O)-alkyl, and —NHS(O$_2$)-alkyl;

formula (IVa) is

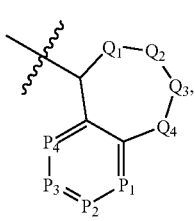

(IVa)

wherein $Q_1$ is selected from $(-CH_2-)_{0-1}$, $-CH(R_{200})-$, $-C(R_{200})_2-$, and $-C(O)-$;

$Q_2$ and $Q_3$ each are independently selected from $(-CH_2-)_{0-1}$, $-CH(R_{200})-$, $-C(R_{200})_2-$, $-O-$, $-C(O)-$, $-S-$, $-S(O)_2-$, $-NH-$, and $-N(R_7)-$;

$Q_4$ is selected from a bond, $(-CH_2-)_{0-1}$, $-CH(R_{200})-$, $-C(R_{200})2-$, $-O-$, $-C(O)-$, $-S-$, $-S(O)_2-$, $-NH-$, and $-N(R_7)$; and $P_1$, $P_2$, $P_3$, and $P_4$ each are independently selected from $-CH-$, $-C(R_{200})-$, and $-N-$;

formula (IVc) is

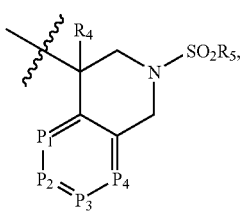

(IVc)

wherein $R_4$ is selected from $-H$ and -alkyl; and $P_1$, $P_2$, $P_3$, and $P_4$ at each occurrence are independently selected from $-CH-$, $-CR_{200}-$, and $-N-$;

formula (IVe) is

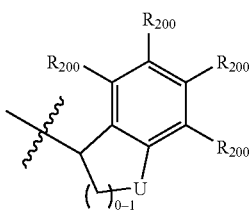

(IVe)

wherein

U is selected from $-CH_2-CR_{100}R_{101}-$, $-CH_2-S-$, $-CH_2-S(O)-$, $-CH_2-S(O)_2-$, $-CH_2-N(R_{100})-$, $-CH_2-C(O)-$, $-CH_2-O-$, $-C(O)-C(R_{100})(R_{101})-$, $-SO_2-N(R_{100})-$, $-C(O)-N(R_{55})-$, $-N(R_{55})-C(O)-N(R_{55})-$, $-O-C(O)-O-$, $-N(R_{55})-C(O)-O-$, and $-C(O)-O-$;

wherein $R_{100}$ and $R_{101}$ at each occurrence are independently selected from $-H$, -alkyl, -aryl, $-C(O)$-alkyl, $-(CO)_{0-1}R_{215}$, $-(CO)_{0-1}R_{220}$, and $-S(O)_2$-alkyl;

formula (IVf) is

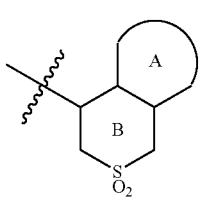

(IVf)

wherein the B ring is optionally substituted with at least one group independently selected from -alkyl, -halogen, $-OH$, $-SH$, $-CN$, $-CF_3$, $-O$-alkyl, $-N(R_5)C(O)H$, $-C(O)H$, $-C(O)N(R_5)(R_6)$, $-NR_5R_5$, $R_{280}$, $R_{285}$, -aryl, and -heteroaryl;

wherein $R_{280}$ and $R_{285}$, and the carbon to which they are attached form a $C_3-C_7$ spirocycle which is optionally substituted with at least one group independently selected from -alkyl, $-O$-alkyl, -halogen, $-CF_3$, and $-CN$;

wherein the A ring is aryl or heteroaryl, each optionally substituted with at least one group independently selected from $R_{290}$ and $R_{295}$;

wherein $R_{290}$ and $R_{295}$ at each occurrence are independently selected from -alkyl optionally substituted with at least one group selected from -alkyl, -halogen, $-OH$, $-SH$, $-CN$, $-CF3$, $-O$-alkyl, and $-NR_5R_6$, $-OH$,
$-NO_2$,
-halogen,
$-CO_2H$,
$-CN$,
$-(CH_2)_{0-4}-C(O)-NR_{21}R_{22}$,
$-(CH_2)_{0-4}-CO_2R_{20}$,
$-(CH_2)_{0-4}-SO_2NR_{21}R_{22}$,
$-(CH_2)_{0-4}-S(O)$-alkyl),
$-(CH2)_{0-4}-S(O)_2$-(alkyl),
$-(CH2)_{0-4}-S(O)_2$-(cycloalkyl),
$-(CH2)_{0-4}-N(H$ or $R_{20})-C(O)-O-R_{20}$,
$-(CH2)_{0-4}-N(H$ or $R_{20})-C(O)-N(R_{20})_2$,
$-(CH2)_{0-4}-N-C(S)-N(R_{20})_2$,
$-(CH2)_{0-4}-N(H$ or $R_{20})-CO-R_{21}$,
$-(CH2)_{0-4}-NR_{21}R_{22}$,
$-(CH2)_{0-4}-R_{11}$,
$-(CH2)_{0-4}-O-C(O)$-(alkyl),
$-(CH2)_{0-4}-O-P(O)-(OR_5)_2$,
$-(CH2)_{0-4}-O-C(O)-N(R_{20})_2$,
$-(CH2)_{0-4}-O-C(S)-N(R_{20})_2$,
$-(CH2)_{0-4}-O-(R_{20})_2$,
$-(CH2)_{0-4}-O-(R_{20})-CO_2H$,
$-(CH2)_{0-4}-S-(R_{20})$,
$-(CH_2)_{0-4}-O$-(alkyl optionally substituted with at least one halogen),
-cycloalkyl,
$-(CH_2)_{0-4}-N(H$ or $R_{20})-S(O)_2-R_{21}$, and
$-(CH_2)_{0-4}$-cycloalkyl;

$R_{21}$ and $R_{22}$ each independently are selected from
$-H$,
-alkyl optionally substituted with at least one group independently selected from $-OH$, amino, -halogen, -alkyl, -cycloalkyl, -(alkyl-cycloalkyl), -alkyl-O-alkyl, $-R_{17}$, and $-R_{18}$, —$(CH_2)_{0-4}$—C(O)-(alkyl),
—$(CH_2)_{0-4}$—C(O)-(cycloalkyl),
—$(CH_2)_{0-4}$—C(O)—$R_{17}$,
—$(CH_2)_{0-4}$—C(O)—$R_{18}$,
—$(CH_2)_{0-4}$—C(O)—$R_{19}$, and
—$(CH_2)_{0-4}$—C(O)—$R_{11}$;

$R_{17}$ at each occurrence is aryl optionally substituted with at least one group independently selected from
- -alkyl optionally substituted with at least one group independently selected from -alkyl, -halogen, —OH, —SH, —$NR_5R_6$, —CN, —$CF_3$, and —O-alkyl,
- -halogen,
- —O-alkyl optionally substituted with at least one group independently selected from halogen, —$NR_{21}R_{22}$, —OH, —CN, and -cycloalkyl optionally substituted with at least one group independently selected from -halogen, —OH, —SH, —CN, —$CF_3$, —O-alkyl, and —$NR_5R_6$,
- —C(O)-(alkyl),
- —S(O)—O—$NR_5R_5$,
- —C(O)—$NR_5R_5$, and
- —$S(O)_2$-(alkyl);

$R_{18}$ at each occurrence is heteroaryl optionally substituted with at least one group independently selected from
- -alkyl optionally substituted with at least one group independently selected from -alkyl, -halogen, —OH, —SH, —CN, —$CF_3$, —O-alkyl, and —$NR_5R_6$,
- -halogen,
- —O-alkyl optionally substituted with at least one group independently selected from -halogen, —$NR_{21}R_{22}$, —OH, and —CN,
- -cycloalkyl optionally substituted with at least one group independently selected from -halogen, —OH, —SH, —CN, $CF_3$, —O —alkyl, and —$NR_5R_6$,
- —C(O)-alkyl),
- —$S(O)_2$—$NR_5R_5$,
- —C(O)—$NR_5R_6$, and
- —$S(O)_2$-(alkyl);

$R_{19}$ at each occurrence is heterocycloalkyl wherein at least one carbon is optionally replaced with —C(O)—, —S(O)—, and —$S(O)_2$—, wherein the heterocycloalkyl is optionally substituted with at least one group independently selected from
- -alkyl optionally substituted with at least one group independently selected from -alkyl, -halogen, —OH, —SH, —CN, —$CF_3$, —O-alkyl, and —$NR_5R_6$,
- -halogen,
- —O-alkyl optionally substituted with at least one group independently selected from -halogen, —OH, —CN, —$NR_{21}R_{22}$, and -cycloalkyl optionally substituted with at least one group independently selected from -halogen, —OH, —SH, —CN, —$CF_3$, —O-alkyl, and —$NR_5R_6$,
- —C(O)-(alkyl),
- —$S(O)_2$—$NR_5R_6$,
- —C(O)—$NR_5R_6$, and
- —$S(O)_2$-(alkyl);

$R_{11}$ at each occurrence is heterocycloalkyl
wherein at least one carbon of the heterocycloalkyl is optionally replaced with —C(O)—, —S(O)—, and —$S(O)_2$—,
wherein the heterocycloalkyl is optionally substituted with at least one group independently selected from -alkyl, —O-alkyl, and -halogen;

$R_{20}$ is selected from -alkyl, -cycloalkyl, —$(CH_2)_{0-2}$—$(R_{17})$, and —$(CH_2)_{0-2}$—$(R_{18})$;

$R_{200}$ at each occurrence is independently selected from
- -alkyl optionally substituted with at least one group independently selected from $R_{205}$,
- —OH,
- —$NO_2$,
- —$NH_2$,
- -halogen,
- —CN,
- —$CF_3$,
- —$OCF_3$,
- —$(CH_2)_{0-4}$—C(O)H,
- —$(CO)_{0-1}R_{215}$,
- —$(CO)_{0-1}R_{220}$,
- —$(CH_2)_{0-4}C(O)NR_{220}R_{225}$,
- —$(CH_2)_{0-4}$—$(C(O))_{0-1}$—$R_{215}$,
- —$(CH_2)_{0-4}$—$(C(O))_{0-1}$—$R_{220}$,
- —$(CH_2)_{0-4}$—C(O)-alkyl,
- —$(CH_2)_{0-4}$—$(C(O))_{0-1}$-cycloalkyl,
- —$(CH_2)_{0-4}$—$(C(O))_{0-1}$-heterocycloalkyl,
- —$(CH_2)_{0-4}$—$(C(O))_{0-1}$-heteroaryl,
- —$(CH_2)_{0-4}$—C(O)—O—$R_{215}$,
- —$(CH_2)_{0-4}$—$S(O)_{0-2}$—$NR_{220}R_{225}$,
- —$(CH_2)_{0-4}$—$S(O)_{0-2}$-alkyl,
- —$(CH_2)_{0-4}S(O)_{0-2}$-cycloalkyl,
- —$(CH_2)_{0-4}$—N(H or $R_{215}$)—C(O)—O—$R_{215}$,
- —$(CH_2)_{0-4}$—N(H or $R_{215}$)—$S(O)_{1-2}$—$R_{220}$,
- —$(CH_2)_{0-4}$—N(H or $R_{215}$)—C(O)—$N(R_{215})_2$,
- —$(CH_2)_{0-4}$—N(H or $R_{215}$)—C(O)—$R_{220}$,
- —$(CH_2)_{0-4}$—$NR_{220}R_{225}$,
- —$(CH_2)_{0-4}$—O—C(O)-alkyl,
- —$(CH_2)_{0-4}$—O—$(R_{215})$,
- —$(CH_2)_{0-4}$—S—$(R_{215})$,
- —$(CH_2)_{0-4}$—C(O)H,
- —$(CH_2)_{0-4}$—O-(alkyl optionally substituted with at least one halogen), and
- -adamantane, wherein each aryl and heteroaryl group included within $R_{200}$ is optionally substituted with at least one group independently selected from —$R_{205}$, —$R_{210}$, and
- -alkyl optionally substituted with at least one group independently selected from $R_{205}$ and $R_{210}$;

wherein each cycloalkyl or heterocycloalkyl group included within $R_{200}$ is optionally substituted with at least one group independently selected from
- —$R_{205}$,
- —$R_{210}$, and
- -alkyl optionally substituted with at least one group independently selected from $R_{205}$ and $R_{210}$;

$R_{205}$ at each occurrence is independently selected from
- -alkyl,
- -heteroaryl,
- -heterocycloalkyl,
- -aryl,
- -haloalkoxy,
- —$(CH_2)_{0-3}$-cycloalkyl,
- -halogen,
- —O-phenyl,
- —SH,
- —$(CH_2)_{0-4}$—$C(O)CH_3$
- —$(CH_2)_{0-4}$—C(O)H
- —$(CH_2)_{0-4}$—$CO_2H$,
- —$(CH_2)_{0-6}$—CN, —$(CH_2)_{0-6}$—C(O)—$NR_{235}R_{240}$,
—$(CH_2)_{0-6}$—C(O)—$R_{235}$,
—$(CH_2)_{0-4}$—N(H or $R_{215}$)—$SO_2$—$R_{235}$,
—$CF_3$,
—CN,
—$C(O)_2$-benzyl,
—O-alkyl,
—$C(O)_2$-alkyl, and
—$NR_{235}R_{240}$;

$R_{210}$ at each occurrence is independently selected from
—OH,
—CN,
—$(CH_2)_{0-4}$—C(O)H,
-alkyl wherein a carbon atom is optionally replaced with —C(O)—, and a carbon atom is optionally substituted with at least one group independently selected from $R_{205}$,
—S-alkyl,
-halogen,
—O-alkyl,
-haloalkoxy,
—$NR_{220}R_{225}$,
-cycloalkyl optionally substituted with at least one group independently selected from $R_{205}$,
—C(O)-alkyl,
—S(O)2—$NR_{235}R_{240}$,
—C(O)—N $R_{235}R_{240}$, and
—$S(O)_2$-alkyl;

$R_{215}$ at each occurrence is independently selected from
-alkyl,
—$(CH_2)_{0-2}$-aryl,
—$(CH_2)_{0-2}$-cycloalkyl,
—$(CH_2)_{0-2}$-heteroaryl, and
—$(CH_2)_{0-2}$-heterocycloalkyl;
wherein the aryl groups included within $R_{215}$ are optionally substituted with at least one group independently selected from $R_{205}$ or $R_{210}$;
wherein the heterocycloalkyl and heteroaryl groups included within $R_{215}$ are optionally substituted with at least one group independently selected from $R_{210}$;

$R_{220}$ and $R_{225}$ at each occurrence are independently selected from
—H,
—OH,
-alkyl,
—$(CH_2)_{0-4}$—C(O)H,
-alkyl-OH,
—$(CH_2)_{0-4}CO_2$-alkyl, wherein alkyl is optionally substituted with at least one group independently selected from $R_{205}$,
-aminoalkyl,
—$S(O)_2$-alkyl,
—$(CH_2)_{0-4}$—C(O)-alkyl, wherein alkyl is optionally substituted with at least one group independently selected from $R_{205}$,
—$(CH_2)_{0-4}$—C(O)—$NH_2$,
—$(CH_2)_{0-4}$—C(O)—NH(alkyl), wherein alkyl is optionally substituted with at least one group independently selected from $R_{205}$,
—$(CH_2)_{0-4}$—C(O)—N(alkyl)(alkyl),
-haloalkyl,
—$(CH_2)_{0-2}$-cycloalkyl,
-alkyl-O-alkyl,
—O-alkyl,
-aryl,
-heteroaryl, and
-heterocycloalkyl;

wherein the aryl, heteroaryl and heterocycloalkyl groups included within $R_{220}$ and $R_{225}$ are each optionally substituted with at least one group independently selected from $R_{270}$;

$R_{270}$ at each occurrence is independently selected from
—$R_{205}$,
-alkyl optionally substituted with at least one group independently selected from $R_{205}$,
-phenyl,
-halogen,
—O-alkyl,
-haloalkoxy,
—$NR_{235}R_{240}$,
—OH,
—CN,
-cycloalkyl optionally substituted with at least one group independently selected from $R_{205}$,
—C(O)-alkyl,
—$S(O)_2$—$NR_{235}R_{240}$,
—CO—$NR_{235}R_{240}$,
—$S(O)_2$-alkyl, and
—$(CH_2)_{0-4}$—C(O)H;

$R_{235}$ and $R_{240}$ at each occurrence are independently selected from
—H,
-alkyl,
—C(O)-alkyl,
—OH,
—$CF_3$,
—$OCH_3$,
—NH—$CH_3$,
—$N(CH_3)_2$,
—$(CH_2)_{0-4}$—C(O)—(H or alkyl),
—$SO_2$-alkyl, and
-phenyl;

$R_{255}$ is selected from -hydrogen, —OH, —$N(R_{220})(R_{225})$, and —O-alkyl;

$R_5$ and $R_6$ are independently selected from —H and -alkyl, or $R_5$ and $R_6$, and the nitrogen to which they are attached, form a 5 or 6 membered heterocycloalkyl ring; and $R_7$ is independently selected from
—H,
-alkyl optionally substituted with at least one group independently selected from —OH, amino, and halogen,
-cycloalkyl, and
-alkyl-O-alkyl.

8. The method according to claim 7, wherein $R_1$ is selected from —$CH_2$-phenyl, wherein the phenyl ring is optionally substituted with at least one group independently selected from -halogen, —$C_1$—$C_2$ alkyl, —O-methyl, and —OH.

9. The method according to claim 7, wherein $R_1$ is selected from 4-hydroxy-benzyl, 3-hydroxy-benzyl, 5-chloro-thiophen-2-yl-methyl, 5-chloro-3-ethyl-thiophen-2-yl-methyl, 3,5-difluoro-2-hydroxy-benzyl, piperidin-4-yl-methyl, 2-oxo-piperidin-4-yl-methyl, 2-oxo-1,2-dihydro-pyridin-4-yl-methyl, 5-hydroxy-6-oxo-6H-pyran-2-yl-methyl, 3,5-difluoro-4-hydroxy-benzyl, 3,5-difluoro-benzyl, 3-fluoro-4-hydroxy-benzyl, 3- fluoro-5-hydroxy-benzyl, and 3-fluoro-benzyl.

10. The method according to claim 7, wherein $R_c$ is selected from formulae (VIa) and (VIb),

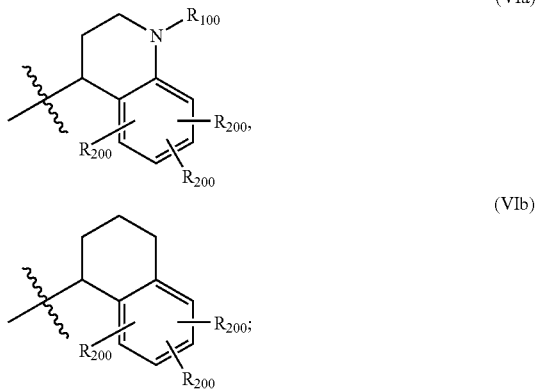

wherein at least one carbon of the heterocycloalkyl of formula (VIa) is optionally replaced with $—SO_2—$ and the cycloalkyl of formula (VIb) is optionally replaced with a group independently selected from $—O—$, $—SO_2—$, and $—C(O)—$, wherein $R_{100}$, $R_{200}$, $R_{205}$, $R_{245}$, and $R_{250}$ are as defined in claim 7.

11. The method according to claim 7, wherein $R_c$ is selected from 6-isobutyl-1,1-dioxo-$1\lambda^6$-thiochroman-4-yl, 6-4-yl, 7-ethyl-1,2,3,4-tetrahydronaphthalen-1-yl, and 1-(3-tert-Butyl-phenyl)-cyclohexyl.

12. The method according to claim 7, wherein $R_2$ is selected from hydrogen, 3-Bromo-[1,2,4]thiadiazol-5-ylamino, [1,2,4]thiadiazol-5-ylamino, 4-Chloro-[1,2,5]thiadiazol-3-ylamino, [1,2,5]thiadiazol-3-ylamino, thiazol-2-ylamino, 5-Bromo-[1,3,4]thiadiazol-2-ylamino, [1,3,4]thiadiazol-2-ylamino, 5-Amino-[1,3,4]thiadiazol-2-ylamino, 2-Bromo-thiazol-5-ylamino, thiazol-5-ylamino, 5-trifluoromethyl-[1,3,4]thiadiazol-2-ylamino, 5-trifluoromethyl-[1,3,4]oxadiazol-2-ylamino, 5-Amino-[1,3,4]oxadiazol-2-ylamino, 1-trityl-1H-[1,2,4]triazol-3-ylamino, 1H-[1,2,4]triazol-3-ylamino, oxazol-2-ylamino, 5-Bromo-2-trityl-2H-[1,2,3]triazol-4-ylamino, 2-trityl-2H-[1,2,3]triazol-4-ylamino, 5-Bromo-2H-[1,2,3]triazol-4-ylamino, 2H-[1,2,3]triazol-4-ylamino, thiophen-2-ylamino, 3-methyl-5-nitro-3H-imidazol-4-ylamino, 4-Cyano-5-phenyl-isothiazol-3-ylamino, 4-phenyl-[1,2,5]thiadiazol-3-ylamino, 3,4-dioxocyclobut-1-enylamino, 2-methoxy-3,4-dioxo-cyclobut-1-enylamino, and 2-methylamino-3,4-dioxo-cyclobut-1-enylamino.

13. The method according to claim 7, wherein the condition is Alzheimer's disease.

14. A method of treating at least one condition selected from Alzheimer's disease, dementia associated with Alzheimer's disease, Parkinson's disease and dementia associated with Parkinson's disease, comprising:
administering to a host a composition comprising a therapeutically effective amount of at least one beta-secretase inhibitor of formula (I) according to claim 1,
further comprising a composition comprising a beta-secretase complexed with at least one compound of formula (I), or pharmaceutically acceptable salt thereof.

15. A method or treating the onset of dementia associated with Alzheimer's disease, or dementia associated with Parkinson's disease comprising: administering to a patient a therapeutically effective amount of at least one compound of formula (I), or a pharmaceutically acceptable salt thereof according to claim 1 to the patient.

16. A method of inhibiting beta-secretase activity in a cell, the method comprising the step of adding to the cell an effective amount of at least one compound of formula (I) or a pharmaceutically acceptable salt thereof, wherein $R_1$, $R_2$, and $R_c$ are defined as in claim 1.

17. A method of prescribing a medication for Alzheimer's disease, dementia associated with Alzheimer's disease, Parkinson's disease or dementia associated with Parkinson's disease comprising: identifying in a patient symptoms associated with at least one disorder, condition or disease associated with amyloidosis; and prescribing at least one dosage form of at least one compound of formula (I),

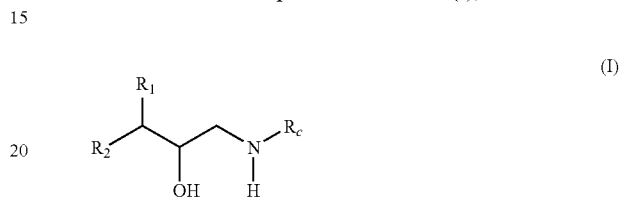

or a pharmaceutically acceptable salt, derivative or biologically active metabolite thereof according to claim 1, to the patient.

18. An article of manufacture, comprising:
(a) at least one dosage form of at least one compound of formula (I),
or a stereoisomer, or pharmaceutically acceptable salt thereof, according to claim 1;
(b) a package insert providing that a dosage form comprising a compound of formula (I) should be administered to a patient in need of therapy for at least one disorder, condition selected from Alzheimer's disease, dementia associated with Alzheimer's disease, Parkinson's disease and dementia associated with Parkinson's disease; and
(c) at least one container in which at least one dosage form of at least one compound of formula (I) is stored.

19. An article of manufacture, comprising:
(a) at least one oral dosage form of at least one compound of formula (I)
or a stereoisomer, or pharmaceutically acceptable salt thereof, according to claim 1;
in a dosage amount ranging from about 2 mg to about 1000 mg;
(b) a package insert providing that an oral dosage form comprising: a compound of formula (I) in a dosage amount ranging from about 2 mg to about 1000 mg should be administered to a patient in need of therapy for at least one disorder, condition or disease selected from Alzheimer's disease, dementia associated with Alzheimer's disease, Parkinson's disease and dementia associated with Parkinson's disease; and
(c) at least one container In which at least one oral dosage form of at least one compound of formula (I) in a dosage amount ranging from about 2 mg to about 1000 mg is stored.

20. An article of manufacture, comprising:
(a) at least one oral dosage form of at least one compound of formula (I)
according to claim 1, in a dosage amount ranging from about 2 mg to about 1000 mg in combination with
(b) at least one therapeutically active agent; associated with
(c) a package insert providing that an oral dosage form comprising: a compound of formula (I) in a dosage amount ranging from about 2 mg to about 1000 mg in combination with at least one therapeutically active agent should be administered to a patient in need of therapy for at least one disorder, condition or diseases selected from Alzheimer's disease, dementia associated with Alzheimer's disease, Parkinson's disease and dementia associated with Parkinson's disease; and (d) at least one container in which at least one dosage form of at least one compound of formula (I) in a dosage amount ranging from about 2 mg to about 1000 mg in combination with a therapeutically active agent is stored.

21. The article of manufacture according to claim 20 wherein the therapeutically active agent, is selected from an antioxidant, an anti-inflammatory, a gamma-secretase inhibitor, a neurotrophic agent, an acetyl cholinesterase inhibitor, a statin, an A-beta, and an anti-A-beta antibody.

22. An article of manufacture, comprising:
(a) at least one parenteral dosage form of at least one compound of formula (I) according to claim 1, in a dosage amount ranging from about 0.2 mg/mL to about 50 mg/mL;

(b) a package insert providing that a parenteral dosage form comprising: a compound of formula (I) in a dosage amount ranging from about 0.2 mg/mL to about 50 mg/mL should be administered to a patient in need of therapy for at least one disorder, condition or disease selected from Alzheimer's disease, dementia associated with Alzheimer's disease, Parkinson's disease and dementia associated with Parkinson's disease; and (c) at least one container in which at least one parenteral dosage form of at least one compound of formula (I) in a dosage amount ranging from about 0.2 mg/mL to about 50 mg/mL is stored.

23. A kit comprising:
(a) at least one dosage form of at least one compound according to claim 1; and
(b) at least one container in which at least one dosage form of at least one compound according to claim 1 is stored.

24. A method of manufacture of a medicament for treating Alzheimer's disease, comprising: adding an effective amount of at least one compound of formula (I) as defined in claim 1, to a pharmaceutically acceptable carrier.

* * * * *